(12) United States Patent
Mead et al.

(10) Patent No.: US 11,994,512 B2
(45) Date of Patent: May 28, 2024

(54) SINGLE-CELL GENOMIC METHODS TO GENERATE EX VIVO CELL SYSTEMS THAT RECAPITULATE IN VIVO BIOLOGY WITH IMPROVED FIDELITY

(71) Applicants: Massachusetts Institute of Technology, Cambridge, MA (US); The Brigham and Women's Hospital, Inc., Boston, MA (US)

(72) Inventors: Benjamin E. Mead, Cambridge, MA (US); Jose Ordovas-Montanes, Cambridge, MA (US); Alexander K. Shalek, Cambridge, MA (US); Jeffrey Karp, Boston, MA (US); Robert Langer, Cambridge, MA (US)

(73) Assignees: Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 725 days.

(21) Appl. No.: 16/240,361

(22) Filed: Jan. 4, 2019

(65) Prior Publication Data
US 2019/0204299 A1 Jul. 4, 2019

Related U.S. Application Data

(60) Provisional application No. 62/613,710, filed on Jan. 4, 2018, provisional application No. 62/702,168, filed on Jul. 23, 2018.

(51) Int. Cl.
| | |
|---|---|
| *A61K 38/17* | (2006.01) |
| *A61K 35/17* | (2015.01) |
| *C12N 5/071* | (2010.01) |
| *C12N 15/00* | (2006.01) |
| *C12Q 1/6881* | (2018.01) |
| *C40B 30/06* | (2006.01) |
| *G01N 33/50* | (2006.01) |
| *C12Q 1/6869* | (2018.01) |
| *C12Q 1/6883* | (2018.01) |
| *C12Q 1/6886* | (2018.01) |

(52) U.S. Cl.
CPC ......... *G01N 33/5023* (2013.01); *A61K 35/17* (2013.01); *C12N 5/068* (2013.01); *C12Q 1/6881* (2013.01); *C40B 30/06* (2013.01); *G01N 33/5008* (2013.01); *G01N 33/5011* (2013.01); *C12N 2501/11* (2013.01); *C12N 2501/40* (2013.01); *C12N 2501/998* (2013.01); *C12N 2501/999* (2013.01); *C12Q 1/6869* (2013.01); *C12Q 1/6883* (2013.01); *C12Q 1/6886* (2013.01); *C12Q 2600/158* (2013.01); *G01N 2800/52* (2013.01)

(58) Field of Classification Search
None
See application file for complete search history.

(56) References Cited

U.S. PATENT DOCUMENTS

| | | |
|---|---|---|
| 5,686,281 A | 11/1997 | Roberts |
| 5,843,728 A | 12/1998 | Seed et al. |
| 5,851,828 A | 12/1998 | Seed et al. |
| 5,858,358 A | 1/1999 | June et al. |
| 5,869,326 A | 2/1999 | Hofmann |
| 5,883,223 A | 3/1999 | Gray |
| 5,906,936 A | 5/1999 | Eshhar et al. |
| 5,912,170 A | 6/1999 | Seed et al. |
| 5,912,172 A | 6/1999 | Eshhar et al. |
| 6,004,811 A | 12/1999 | Seed et al. |
| 6,040,177 A | 3/2000 | Riddell et al. |
| 6,284,240 B1 | 9/2001 | Seed et al. |
| 6,352,694 B1 | 3/2002 | June et al. |
| 6,392,013 B1 | 5/2002 | Seed et al. |
| 6,410,014 B1 | 6/2002 | Seed et al. |
| 6,479,626 B1 | 11/2002 | Kim et al. |
| 6,489,458 B2 | 12/2002 | Hackett et al. |
| 6,534,055 B1 | 3/2003 | June et al. |
| 6,534,261 B1 | 3/2003 | Cox et al. |

(Continued)

FOREIGN PATENT DOCUMENTS

| | | |
|---|---|---|
| EP | 2 771 468 B1 | 2/2015 |
| EP | 2 784 162 B1 | 4/2015 |

(Continued)

OTHER PUBLICATIONS

Xian et al HMGA1 amplifies Wnt signalling and expands the intestinal stem cell compartment and Paneth cell niche Nature Communications Published Apr. 28, 2017 pp. 1-15.*

(Continued)

*Primary Examiner* — Maria G Leavitt
(74) *Attorney, Agent, or Firm* — F. Brent Nix, Esq.; Johnson, Marcou, Isaacs & Nix, LLC

(57) ABSTRACT

Disclosed here is a generally applicable framework that utilizes massively-parallel single-cell RNA-seq to compare cell types/states found in vivo to those of in vitro models. Furthermore, Applicants leverage identified discrepancies to improve model fidelity. Applicants uncover fundamental gene expression differences in lineage-defining genes between in vivo systems and in vitro systems. Using this information, molecular interventions are identified for rationally improving the physiological fidelity of the in vitro system. Applicants demonstrated functional (antimicrobial activity, niche support) improvements in Paneth cell physiology using the methods.

12 Claims, 41 Drawing Sheets
Specification includes a Sequence Listing.

(56) References Cited

U.S. PATENT DOCUMENTS

| | | |
|---|---|---|
| 6,607,882 B1 | 8/2003 | Cox et al. |
| 6,746,838 B1 | 6/2004 | Choo et al. |
| 6,753,162 B1 | 6/2004 | Seed et al. |
| 6,794,136 B1 | 9/2004 | Eisenberg et al. |
| 6,797,514 B2 | 9/2004 | Berenson et al. |
| 6,824,978 B1 | 11/2004 | Cox et al. |
| 6,866,997 B1 | 3/2005 | Choo et al. |
| 6,867,041 B2 | 3/2005 | Berenson et al. |
| 6,887,466 B2 | 5/2005 | June et al. |
| 6,903,185 B2 | 6/2005 | Kim et al. |
| 6,905,680 B2 | 6/2005 | June et al. |
| 6,905,681 B1 | 6/2005 | June et al. |
| 6,905,874 B2 | 6/2005 | Berenson et al. |
| 6,933,113 B2 | 8/2005 | Case |
| 6,979,539 B2 | 12/2005 | Cox et al. |
| 7,013,219 B2 | 3/2006 | Case et al. |
| 7,030,215 B2 | 4/2006 | Liu et al. |
| 7,144,575 B2 | 12/2006 | June et al. |
| 7,148,203 B2 | 12/2006 | Hackett et al. |
| 7,160,682 B2 | 1/2007 | Hackett et al. |
| 7,175,843 B2 | 2/2007 | June et al. |
| 7,220,719 B2 | 5/2007 | Case et al. |
| 7,232,566 B2 | 6/2007 | June et al. |
| 7,241,573 B2 | 7/2007 | Choo et al. |
| 7,241,574 B2 | 7/2007 | Choo et al. |
| 7,446,190 B2 | 11/2008 | Sadelain et al. |
| 7,572,631 B2 | 8/2009 | Berenson et al. |
| 7,585,849 B2 | 9/2009 | Liu et al. |
| 7,595,376 B2 | 9/2009 | Kim et al. |
| 7,741,465 B1 | 6/2010 | Eshhar et al. |
| 7,985,739 B2 | 7/2011 | Kay et al. |
| 8,021,867 B2 | 9/2011 | Smith et al. |
| 8,034,334 B2 | 10/2011 | Dudley et al. |
| 8,088,379 B2 | 1/2012 | Robbins et al. |
| 8,119,361 B2 | 2/2012 | Smith et al. |
| 8,119,381 B2 | 2/2012 | Smith et al. |
| 8,124,369 B2 | 2/2012 | Smith et al. |
| 8,129,134 B2 | 3/2012 | Smith et al. |
| 8,133,697 B2 | 3/2012 | Smith et al. |
| 8,163,514 B2 | 4/2012 | Smith et al. |
| 8,211,422 B2 | 7/2012 | Eshhar et al. |
| 8,227,432 B2 | 7/2012 | Hackett et al. |
| 8,399,645 B2 | 3/2013 | Campana et al. |
| 8,440,431 B2 | 5/2013 | Voytas et al. |
| 8,440,432 B2 | 5/2013 | Voytas et al. |
| 8,450,471 B2 | 5/2013 | Voytas et al. |
| 8,637,307 B2 | 1/2014 | June et al. |
| 8,697,359 B1 | 4/2014 | Zhang |
| 8,697,854 B2 | 4/2014 | Schendel et al. |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,906,682 B2 | 12/2014 | June et al. |
| 8,911,993 B2 | 12/2014 | June et al. |
| 8,916,381 B1 | 12/2014 | June et al. |
| 8,932,814 B2 | 1/2015 | Cong et al. |
| 8,945,839 B2 | 2/2015 | Zhang |
| 8,975,071 B1 | 3/2015 | June et al. |
| 8,993,233 B2 | 3/2015 | Zhang et al. |
| 8,999,641 B2 | 4/2015 | Zhang et al. |
| 9,101,584 B2 | 8/2015 | June et al. |
| 9,102,760 B2 | 8/2015 | June et al. |
| 9,102,761 B2 | 8/2015 | June et al. |
| 9,181,527 B2 | 11/2015 | Sentman |
| 9,233,125 B2 | 1/2016 | Davila et al. |
| 2004/0171156 A1 | 9/2004 | Hartley et al. |
| 2004/0224402 A1 | 11/2004 | Bonyhadi et al. |
| 2006/0013842 A1 | 1/2006 | Matkin et al. |
| 2010/0104509 A1 | 4/2010 | King et al. |
| 2011/0091433 A1 | 4/2011 | Abuljadayel |
| 2011/0265198 A1 | 10/2011 | Gregory et al. |
| 2012/0017290 A1 | 1/2012 | Cui et al. |
| 2012/0244133 A1 | 9/2012 | Rosenberg et al. |
| 2013/0071414 A1 | 3/2013 | Dotti et al. |
| 2013/0236946 A1 | 9/2013 | Gouble |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0310830 A1 | 10/2014 | Zhang et al. |
| 2015/0184139 A1 | 7/2015 | Zhang et al. |
| 2015/0368342 A1 | 12/2015 | Wu et al. |
| 2015/0368360 A1 | 12/2015 | Liang et al. |
| 2016/0129109 A1 | 5/2016 | Davila et al. |
| 2016/0166613 A1 | 6/2016 | Spencer et al. |
| 2016/0175359 A1 | 6/2016 | Spencer et al. |
| 2017/0306335 A1 | 10/2017 | Zhang et al. |
| 2018/0100201 A1* | 4/2018 | Garraway ............ C12Q 1/6886 |
| 2019/0085324 A1* | 3/2019 | Regev ................ C12N 15/1093 |
| 2019/0094223 A1* | 3/2019 | Shen-Orr .......... G01N 33/5047 |
| 2020/0176080 A1* | 6/2020 | Newman ............. C12Q 1/6881 |

FOREIGN PATENT DOCUMENTS

| | | |
|---|---|---|
| EP | 2 764 103 B1 | 8/2015 |
| EP | 3 009 511 A2 | 4/2016 |
| WO | 92/15322 A1 | 9/1992 |
| WO | 97/49450 A1 | 12/1997 |
| WO | 98/52609 A1 | 11/1998 |
| WO | 03/020763 A2 | 3/2003 |
| WO | 03/057171 A2 | 7/2003 |
| WO | 2004/033685 A1 | 4/2004 |
| WO | 2004/044004 A2 | 5/2004 |
| WO | 2004/074322 A1 | 9/2004 |
| WO | 2005/113595 A2 | 12/2005 |
| WO | 2005/114215 A2 | 12/2005 |
| WO | 2006/000830 A2 | 1/2006 |
| WO | 2006/125962 A2 | 11/2006 |
| WO | 2008/038002 A2 | 4/2008 |
| WO | 2008/039818 A2 | 4/2008 |
| WO | 2011/146862 A1 | 11/2011 |
| WO | 2012/079000 A1 | 6/2012 |
| WO | 2013/039889 A1 | 3/2013 |
| WO | 2013/040371 A2 | 3/2013 |
| WO | 2013/044225 A1 | 3/2013 |
| WO | 2013/166321 A1 | 11/2013 |
| WO | 2013/176915 A1 | 11/2013 |
| WO | 2014/011987 A1 | 1/2014 |
| WO | 2014/018423 A2 | 1/2014 |
| WO | 2014/018863 A1 | 1/2014 |
| WO | 2014/059173 A2 | 4/2014 |
| WO | 204/093635 A1 | 6/2014 |
| WO | 2014/083173 A1 | 6/2014 |
| WO | 2014/093595 A1 | 6/2014 |
| WO | 2014/093622 A2 | 6/2014 |
| WO | 2014/093655 A2 | 6/2014 |
| WO | 2014/093661 A2 | 6/2014 |
| WO | 2014/093694 A1 | 6/2014 |
| WO | 2014/093701 A1 | 6/2014 |
| WO | 2014/093709 A1 | 6/2014 |
| WO | 2014/093712 A1 | 6/2014 |
| WO | 2014/093718 A1 | 6/2014 |
| WO | 2014/133567 A1 | 9/2014 |
| WO | 2014/133568 A1 | 9/2014 |
| WO | 2014/134165 A1 | 9/2014 |

(56) References Cited

FOREIGN PATENT DOCUMENTS

| | | |
|---|---|---|
| WO | 2014/159356 A1 | 10/2014 |
| WO | 2014/172606 A1 | 10/2014 |
| WO | 2014/184744 A1 | 11/2014 |
| WO | 2014/191128 A1 | 12/2014 |
| WO | 2014/204723 A1 | 12/2014 |
| WO | 2014/204724 A1 | 12/2014 |
| WO | 2014/204725 A1 | 12/2014 |
| WO | 2014/204726 A1 | 12/2014 |
| WO | 2014/204727 A1 | 12/2014 |
| WO | 2014/204728 A1 | 12/2014 |
| WO | 2014/204729 A1 | 12/2014 |
| WO | 2014/210353 A2 | 12/2014 |
| WO | 2015/057834 A1 | 4/2015 |
| WO | 2015/057852 A1 | 4/2015 |
| WO | 2015/058052 A1 | 4/2015 |
| WO | 2015/070083 A1 | 5/2015 |
| WO | 2015/089351 A1 | 6/2015 |
| WO | 2015/089354 A1 | 6/2015 |
| WO | 2015/089364 A1 | 6/2015 |
| WO | 2015/089419 A2 | 6/2015 |
| WO | 2015/089427 A1 | 6/2015 |
| WO | 2015/089462 A1 | 6/2015 |
| WO | 2015/089465 A1 | 6/2015 |
| WO | 2015/089473 A1 | 6/2015 |
| WO | 2015/089486 A2 | 6/2015 |
| WO | 2015/120096 A2 | 8/2015 |
| WO | 2015/142675 A2 | 9/2015 |
| WO | 2015/187528 A1 | 12/2015 |
| WO | 2016/000304 A1 | 1/2016 |
| WO | 2016/011210 A2 | 1/2016 |
| WO | 2016/028682 A1 | 2/2016 |
| WO | 2016/040476 A1 | 3/2016 |
| WO | 2016/049258 A2 | 3/2016 |
| WO | 2016/069591 A2 | 5/2016 |
| WO | 2016/070061 A1 | 5/2016 |
| WO | 2016/094867 A1 | 6/2016 |
| WO | 2016/094872 A1 | 6/2016 |
| WO | 2016/094874 A1 | 6/2016 |
| WO | 2016/106236 A1 | 6/2016 |
| WO | 2016/106244 A1 | 6/2016 |
| WO | 2016/168584 A1 | 10/2016 |
| WO | 2016/191756 A1 | 12/2016 |
| WO | 2016/196388 A1 | 12/2016 |
| WO | 2016/205749 A1 | 12/2016 |
| WO | 2016/205759 A1 | 12/2016 |
| WO | 2017/004916 A1 | 1/2017 |
| WO | 2017/011804 A1 | 1/2017 |
| WO | 2017/070395 A1 | 4/2017 |
| WO | 2017/164936 A1 | 9/2017 |
| WO | 2018/035250 A1 | 2/2018 |
| WO | 2019/089803 A1 | 5/2019 |

OTHER PUBLICATIONS

Yin et al., "Niche-Independent High-Purity Cultures of Lgr5+ Intestinal Stem Cells and their Progeny", Nature Methods, vol. 11, No. 1, Jan. 2014, 17 pages.

Basak et al., "Induced Quiescence of Lgr5+ Stem Cells in Intestinal Organoids Enables Differentiation of Hormone-Producing Enteroendocrine Cells", Cell Stem Cell, vol. 20, No. 2, Feb. 2, 2017, 177-190.

Clevers et al., "Modeling Development and Disease with Organoids", Cell, vol. 165, No. 7, Jun. 16, 2016, 1586-1597.

Drost et al., "Use of CRISPR-Modified Human Stem Cell Organoids to Study the Origin of Mutational Signatures in Cancer", Science, vol. 358, No. 6360, Oct. 13, 2017, 11 pages.

Farin et al., "Paneth Cell Extrusion and Release of Antimicrobial Products is Directly Controlled by Immune Cell-Derived IFN-γ", Journal of Experimental Medicine, vol. 211, No. 7, Jun. 30, 2014, 1393-1405.

Foulke-Abel et al., "Human Enteroids as a Model of Upper Small Intestinal Ion Transport Physiology and Pathophysiology", Gastroenterology, vol. 150, No. 3, Mar. 2016, 638-649.

Gjorevski et al., "Designer Matrices for Intestinal Stem Cell and Organoid Culture", Nature, vol. 539, Nov. 24, 2016, 560-564.

Grun et al., "Single-Cell Messenger RNA Sequencing Reveals Rare Intestinal Cell Types", Nature, vol. 525, No. 7568, Sep. 10, 2015, 251-255.

Haber et al., "A Single-cell Survey of The Small Intestinal Epithelium", Nature, vol. 551, No. 7680, Nov. 16, 2017, 40 pages.

McLean et al., "Clonal Expansion of Lgr5-Positive Cells from Mammalian Cochlea and High-Purity Generation of Sensory Hair Cells", Cell Reports, vol. 18, No. 8, Feb. 21, 2017, 1917-1929.

Moon et al., "Development of a Primary Mouse Intestinal Epithelial Cell Monolayer Culture System to Evaluate Factors That Modulate IgA Transcytosis", Mucosal Immunology, vol. 7, No. 4, Jul. 2014, 818-828.

Mou et al., "Dual SMAD Signaling Inhibition Enables Long-Term Expansion of Diverse Epithelial Basal Cells", Cell Stem Cell, vol. 19, Issue 2, Aug. 4, 2016, 217-231.

Rodriguez-Colman, "Interplay between Metabolic Identities in the Intestinal Crypt Supports Stem Cell Function", Nature, vol. 543, No. 7645, Mar. 16, 2017, 13 pages.

Satija et al., "Heterogeneity in Immune Responses: From Populations to Single Cells", Trends in Immunology, vol. 35, No. 5, May 2014, 219-229.

Schwank et al., "Functional Repair of CFTR by CRISPR/Cas9 in Intestinal Stem Cell Organoids of Cystic Fibrosis Patients", Cell Stem Cell, vol. 13, No. 6, Dec. 5, 2013, 653-658.

Stockinger et al., "Interleukin-13-mediated Paneth Cell Degranulation and Antimicrobial Peptide Release", Journal of Innate Immunity, vol. 6, No. 4, Feb. 19, 2014, 530-541.

Tan et al., "Down-Regulation of Human Enteric Antimicrobial Peptides by NOD2 during Differentiation of the Paneth Cell Lineage", Scientific Reports, vol. 5, No. 8383, Feb. 11, 2015, 6 pages.

Tanay et al., "Scaling Single-cell Genomics from Phenomenology to Mechanism", Nature, vol. 541, Jan. 19, 2017, 331-338.

Tian et al., "Opposing Activities of Notch and Wnt Signaling Regulate Intestinal Stem Cells and Gut Homeostasis", Cell Reports, vol. 11, Issue 1, Apr. 7, 2015, 33-42.

Van Es et al., "Wnt Signalling Induces Maturation of Paneth Cells in Intestinal Crypts", Nature Cell Biology, vol. 7, No. 4, Apr. 2005, 381-386.

Vandussen et al., "Development of an Enhanced Human Gastrointestinal Epithelial Culture System to Facilitate Patient-Based Assays", Gut, vol. 64, Issue 6, Jun. 2015, 23 pages.

Vandussen et al., "Notch Signaling Modulates Proliferation and Differentiation of Intestinal Crypt Base Columnar Stem Cells", Development and Stem Cells, vol. 139, No. 3, Feb. 2012, 488-497.

Wilson et al., "A Small Intestinal Organoid Model of Non-Invasive Enteric Pathogen-Epithelial Cell Interactions", Mucosal Immunology, vol. 8, No. 2, Mar. 2015, 352-361.

Yan et al., "Non-equivalence of Wnt and R-spondin Ligands During Lgr5 + Intestinal Stem-Cell Self-Renewal", Nature, vol. 545, No. 7653, May 11, 2017, 36 pages.

Yin et al., "Engineering Stem Cell Organoids", Cell Stem Cell, vol. 18, Issue 1, Jan. 7, 2016, 25-38.

* cited by examiner

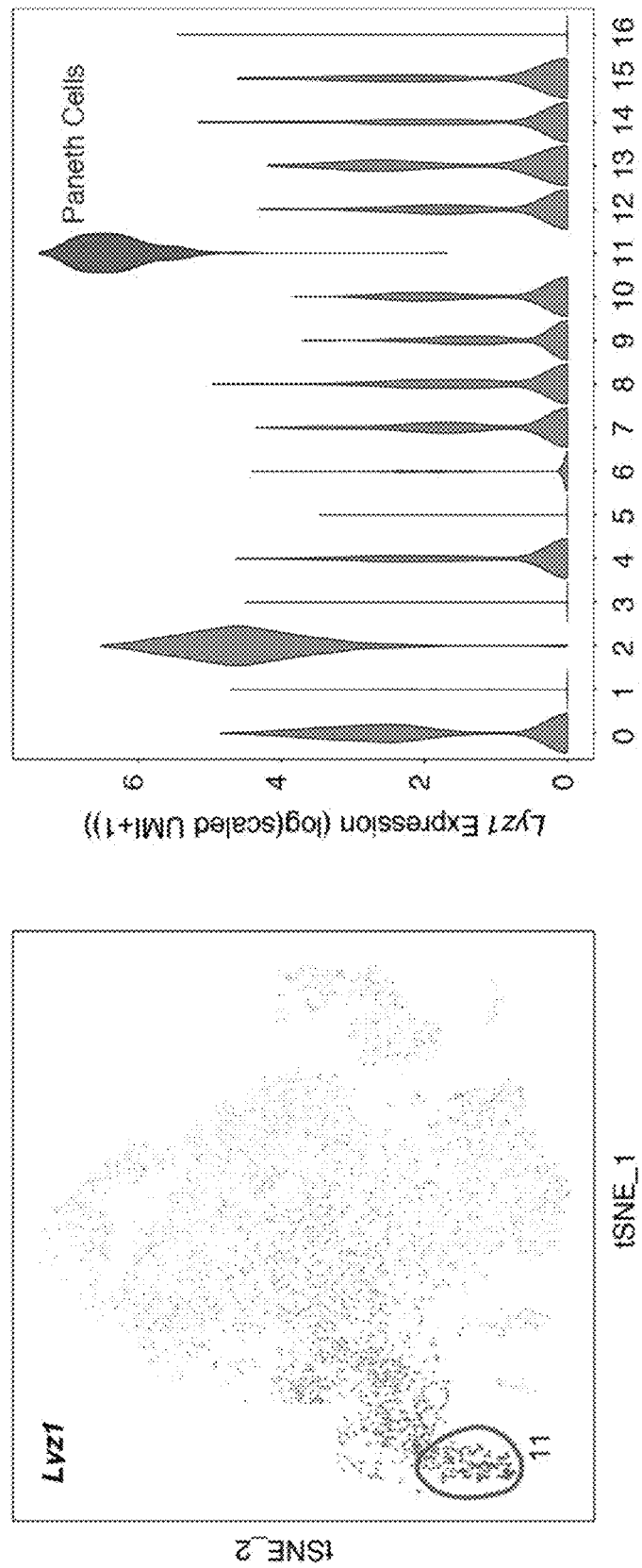

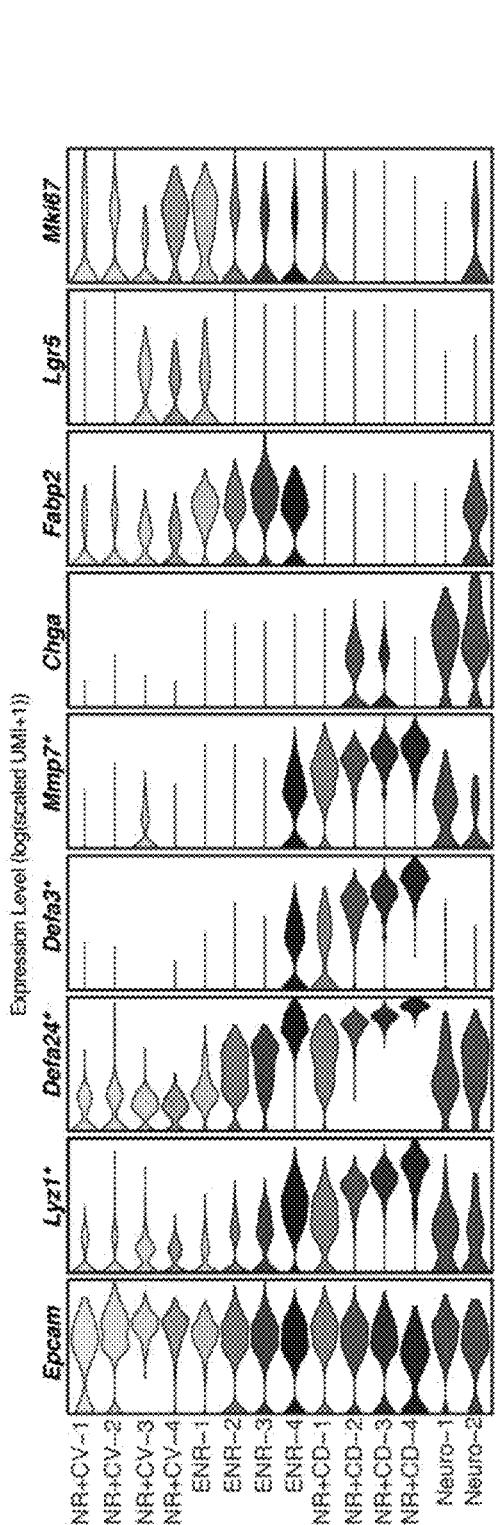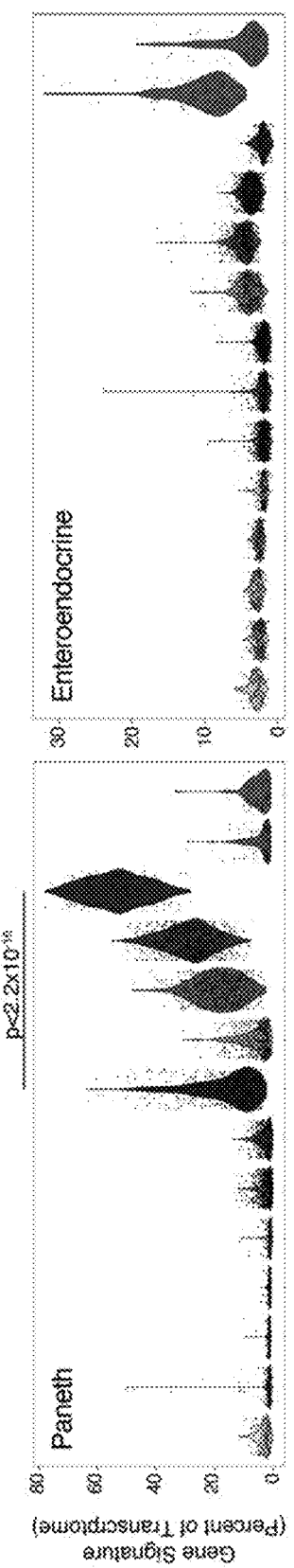
FIG. 5A
FIG. 5B

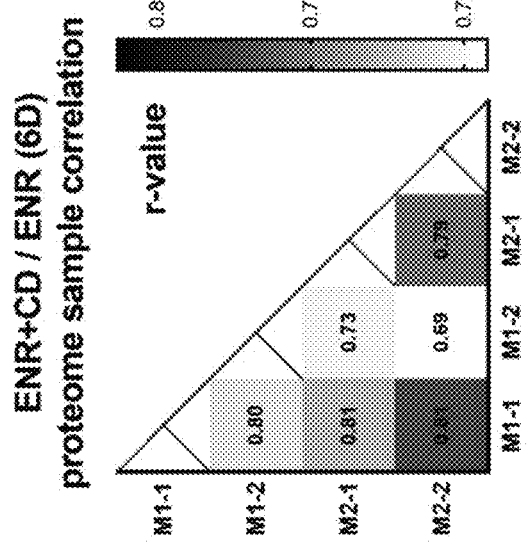
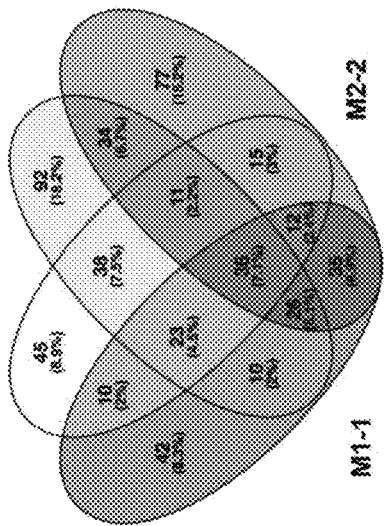
FIG. 9B
FIG. 9C
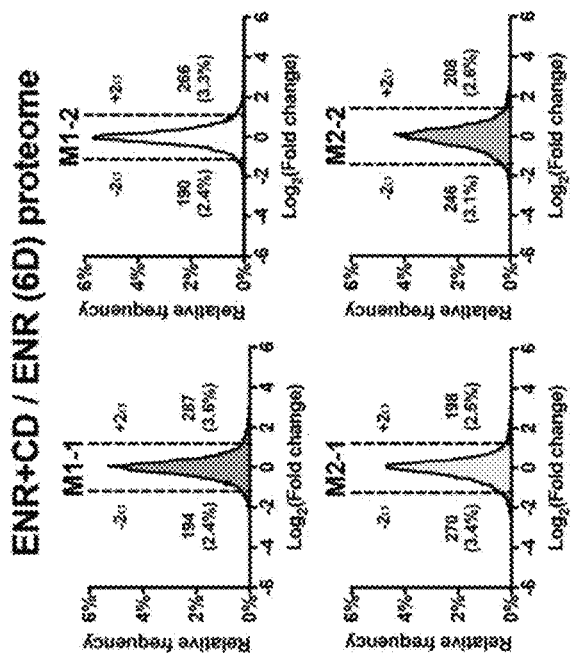
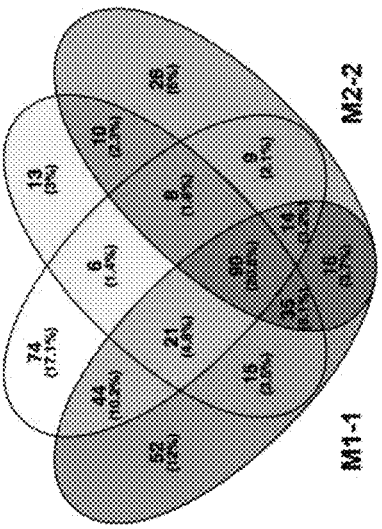
FIG. 9D
FIG. 9E

SINGLE-CELL GENOMIC METHODS TO GENERATE EX VIVO CELL SYSTEMS THAT RECAPITULATE IN VIVO BIOLOGY WITH IMPROVED FIDELITY

CROSS-REFERENCE TO RELATED APPLICATIONS

This application claims the benefit of U.S. Provisional Application Nos. 62/613,710, filed Jan. 4, 2018, and 62/702,168, filed Jul. 23, 2018. The entire contents of the above-identified applications are hereby fully incorporated herein by reference.

STATEMENT REGARDING FEDERALLY SPONSORED RESEARCH

This invention was made with government support under Grant Nos. DE013023, HL095722, OD020839, AI089992, CA217377, AI039671, AI118672, HG006193, CA202820, and CA184956 awarded by the National Institutes of Health. The government has certain rights in the invention.

REFERENCE TO AN ELECTRONIC SEQUENCE LISTING

The contents of the electronic sequence listing (BROD-2417.ST25.txt"; Size is 8 Kilobytes and it was created on Jan. 2, 2019) is herein incorporated by reference in its entirety.

TECHNICAL FIELD

The subject matter disclosed herein is generally directed to ex vivo cell-based systems that faithfully recapitulate an in vivo phenotype of interest and methods of generating and using the cell-based systems.

BACKGROUND

Intestinal organoids, derived from intestinal stem cells (ISCs) and composed of ISCs, Paneth cells (PCs), enteroendocrine cells (EECs), goblet cells and absorptive enterocytes, have been invaluable to the study of intestinal biology [1]. Recent advances in massively-parallel single-cell RNA-sequencing (scRNA-seq) have enabled [2] the cataloging of cell types and states of the murine small intestinal epithelium [3] and intestinal organoids [4], offering extensive insight into tissue heterogeneity; specifically within subsets of rare secretory cell populations. Indeed, the generation of comprehensive cellular atlases has become a major focus of a global effort seeking to map tissues in humans, model organisms, and derived organoids at single-cell resolution [5]. The ability to reconstruct tissues with a "bottom-up" unbiased approach will undoubtedly yield key insights into their cellular constituents [6,7].

To improve the representation of specific cell types in organoids, investigators have utilized cellular engineering approaches starting with ISCs to derive multiple enriched or specialized models. These include enterocytes with improved intestinal ion transport [8], epithelial monolayers capable of secretion and IgA transcytosis [9], and organoids enriched for the rare secretory EEC population [10]. However, there has been no formal comparison of the extent to which conventional intestinal organoids, or further specialized models, recapitulate defined in vivo cell types and states. Moving beyond the generation of in vivo tissue maps towards mechanistic insights, particularly in disease settings, will require an understanding of how the in vitro organoid models utilized for such studies represent the cell types and states identified.

Recent work has demonstrated the utility of organoids in assessing how genetic mutations impact the overall regenerative and/or tumorigenic capacity of ISCs [11,12]. However, their application to the study of polygenic inflammatory disease has been more complex. While cancer-causing mutations appear as a readily visible phenotype in organoids derived from stem cells which uniformly harbor these mutations [12], subtler phenotypes, such as those present in inflammatory bowel disease (IBD), may not manifest if the correct cell state present in vivo is not accurately represented within an organoid. This challenge is particularly clear in IBD [13], where loci identified through genome wide association study (GWAS) have proven difficult to efficiently examine through the use of in vivo animal models.

PC dysfunction is implicated in Crohn's disease, a subset of IBD typically afflicting the small bowel [14]. Co-localized with, LGR5$^+$ ISCs of the small intestinal crypts, long-lived PCs support maintenance of the ISC niche, producing the Wnt and Notch signaling ligands WNT3, WNT3A, and DLL4 and are potent modulators of the gut microflora through secretion of multiple antimicrobials including lysozyme (LYZ), phospholipase A2 group 1B (PLA2G1B), angiogenin ribonuclease A family member 5 (ANGS), and alpha-defensins (DEFAs), amongst others [17]. Allelic variants of NOD2, ATGI6L1, and XBP1, are associated with inflammation, barrier dysfunction, and microbial dysbiosis in IBD through altered function in PCs [18-21]. Risk variants of NOD2 result in lower DEFA expression [22], murine knockout (KO) or alteration of autophagy gene ATGI6L1 leads to defects in autophagy, granule formation, and secretion [21,23], and KO of the ER stress response gene XBP1 results in a total absence of PCs due to uncompensated ER stress [24]. While in vivo models currently provide the most physiologically-representative system to probe PC biology, they are inherently complex and poorly scaled, hindering basic research and therapeutic lead identification.

Existing in vitro models have also proven inherently limited. Ex vivo fresh crypt isolates, which were used to identify the secretion of antimicrobials in response to host stimuli [25,26], are unstable and as such restricted to brief experimental windows. A more sustainable and scalable approach using Caco2 cells differentiated to a PC proxy, has elucidated the role of NOD2 in antimicrobial production [27]. However, the phenotype of these induced PCs is not established. Recently, conventional intestinal organoids were used to describe the dynamics of PC degranulation in response to multiple agonists and to assess PC suppression of enteric pathogens [29]. While these organoid studies are arguably more representative than other in vitro systems, the question of physiological fidelity of this heterogeneous system remains unanswered.

Thus, in vitro systems that faithfully recapitulate an in vivo phenotype and methods of obtaining such systems are needed.

SUMMARY

Single-cell genomic methods provide unprecedented resolution for characterizing the component cell types/states of tissues, such as the epithelial subsets of the gastrointestinal tract. Nevertheless, functional studies of these subsets at scale require faithful ex vivo and in vitro models of identified in vivo biology. While organoids have been invaluable in providing mechanistic insights in vitro, the extent to which organoid-derived cell types, and other ex vivo models, recapitulate their in vivo counterparts remains untested, with no systematic approach for improving model fidelity.

Here, Applicants present a generally applicable framework that utilizes massively-parallel single-cell RNA-seq to identify discrepancies in cell types/states of ex vivo cell-based systems, such as organoids, to those found in vivo models that the ex vivo cell-based systems are intended to emulate. Furthermore, Applicants leverage those identified discrepancies to improve model fidelity. Using the Paneth cell (PC), which supports the stem cell niche and produces the largest diversity of antimicrobials in the small intestine, as an exemplar, Applicants uncover fundamental gene expression differences in lineage-defining genes between in vivo PCs and those of the current in vitro organoid model. Using this information, Applicants nominated molecular interventions for rationally improving the biological fidelity of the in vitro PCs. Applicants then performed transcriptomic, cytometric, morphologic, and proteomic characterization, and demonstrated functional (antimicrobial activity, niche support) improvements in Paneth cell physiology.

This systematic approach provides a workflow for identifying the limitations of ex vivo models and enhancing their biological fidelity. Using adult stem cell-derived organoids as a model system, Applicants successfully generated a structurally and physiologically representative in vitro PC population, enabling studies of host-microbe interactions, cellular development, and disease. The generation of rationally-improved cellular models will facilitate mechanistic exploration of specific disease-associated genes in their respective cell types.

In one aspect, the present invention provides for a method of generating an ex vivo cell-based system that faithfully recapitulates an in vivo phenotype of interest comprising: determining, using single cell RNA sequencing, one or more cell types or one or more cell states in an initial cell-based system; identifying differences in one or more cell types and/or cell states between the initial cell-based system and a target in vivo system having the phenotype of interest; and modulating the initial cell-based system to induce a shift in cell type and/or cell states that reduces the distance in gene expression space between the initial cell-based system and the in vivo system.

In certain embodiments, the gene expression space comprises 10 or more genes, 20 or more genes, 30 or more genes, 40 or more genes, 50 or more genes, 100 or more genes, 500 or more genes, or 1000 or more genes. In certain embodiments, the expression space defines one or more cell pathways. In certain embodiments, the expression space is a transcriptome of the target in vivo system.

In certain embodiments, identifying differences in cell type and/or cell states between the initial cell-based system and the target in vivo system comprises comparing a gene expression distribution as determined by single cell RNA sequencing of the initial cell-based system and a gene expression distribution as determined by single cell RNA sequencing of the ex vivo system.

In certain embodiments, the distance is measured by a Euclidean distance, Pearson coefficient, Spearman coefficient, or combination thereof.

In certain embodiments, the shift in cell type and/or cell states that reduces the distance in gene expression space in the initial cell-based system is a statistically significant shift in the gene expression distribution of the initial cell-based system toward that of the in vivo system. The statistically significant shift may be at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%. The statistical shift may include the overall transcriptional identity or the transcriptional identity of one or more genes, gene expression cassettes, or gene expression signatures of the ex vivo system compared to the in vivo system (i.e., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% of the genes, gene expression cassettes, or gene expression signatures are statistically shifted in a gene expression distribution). A shift of 0% means that there is no difference to the in vivo system. A gene distribution may be the average or range of expression of particular genes, gene expression cassettes, or gene expression signatures in the ex vivo or in vivo system (e.g., a plurality of a cell of interest from an in vivo subject may be sequenced and a distribution is determined for the expression of genes, gene expression cassettes, or gene expression signatures). In certain embodiments, the distribution is a count-based metric for the number of transcripts of each gene present in a cell. A statistical difference between the distributions indicates a shift. The one or more genes, gene expression cassettes, or gene expression signatures may be selected to compare transcriptional identity based on the one or more genes, gene expression cassettes, or gene expression signatures having the most variance as determined by methods of dimension reduction (e.g., tSNE analysis). In certain embodiments, comparing a gene expression distribution comprises comparing the initial cells with the lowest statistically significant shift as compared to the in vivo system (e.g., determining shifts when comparing only the ex vivo cells with a shift of less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10% to the in vivo system).

In certain embodiments, the method may further comprise modulating the initial cell-based system to induce a gain of function in addition to the in vivo phenotype of interest comprising modulating expression of one or more genes, gene expression cassettes, or gene expression signatures associated with the gain of function. In certain embodiments, the method may further comprise modulating the initial cell-based system to induce a loss of function in addition to the in vivo phenotype of interest comprising modulating expression of one or more genes, gene expression cassettes, or gene expression signatures associated with the loss of function.

In certain embodiments, modulating comprises increasing or decreasing expression of one or more genes, gene expression cassettes, or gene expression signatures. In certain embodiments, modulating comprises activating or inhibiting one or more genes, gene expression cassettes, or gene expression signatures (e.g., with an agonist or antagonist).

In certain embodiments, the initial cell-based system comprises a single cell type or sub-type, a combination of cell types and/or subtypes, cell-based therapeutic, an explant, or an organoid.

In certain embodiments, the single cell type or subtype or combination of cell types and/or subtypes comprises an immune cell, intestinal cell, liver cell, kidney cell, lung cell, brain cell, epithelial cell, endoderm cell, neuron, ectoderm cell, islet cell, acinar cell, oocyte, sperm, hematopoietic cell, hepatocyte, skin/keratinocyte, melanocyte, bone/osteocyte, hair/dermal papilla cell, cartilage/chondrocyte, fat cell/adipocyte, skeletal muscular cell, endothelium cell, cardiac muscle/cardiamyocyte, trophobtast, tumor cell, or tumor microenvironment (IME) cell.

In certain embodiments, the single cell type or sub-type is pluripotent, or the combination of cell types and/or subtypes comprises one or more stem cells. The one or more stem cells may be selected from the group consisting of lymphoid stem cells, myeloid stem cells, neural stem cells, skeletal muscle satellite cells, epithelial stem cells, endodermal and neuroectodermal stem cells, germ cells, extraembryonic and embryonic stem cells, mesenchymal stem cells, intestinal stem cells, embryonic stem cells, and induced pluripotent stem cells (iPSCs).

In certain embodiments, the cell-base therapy comprises iPSCs, autologous T cells, CAR T cells, suppressive T cells or tissue transplants. The cell based therapy may comprise adoptive cell transfer (ACT) of T cells. The T cells may be activated or effector T cells specific for a tumor antigen. The cell based therapy may provide cells for regeneration of tissue types or replacement or supplementation of diseased cell types. The cells may be ex vivo cells of the tissue type or stem cell types capable of differentiation into the target tissue.

In certain embodiments, the initial cell-based system is derived from a subject with a disease (e.g., to study the disease ex vivo). The disease may be selected from the group consisting of cancer, autoimmune disease, bone marrow failure, hematological conditions, aplastic anemia, beta-thalassemia, diabetes, motor neuron disease, Parkinson's disease, spinal cord injury, muscular dystrophy, kidney disease, liver disease, multiple sclerosis, congestive heart failure, head trauma, lung disease, psoriasis, liver cirrhosis, vision loss, cystic fibrosis, hepatitis C virus, human immunodeficiency virus, inflammatory bowel disease (IBD), and any disorder associated with tissue degeneration.

In certain embodiments, modulating the initial cell-based system comprises delivering one or more modulating agents that modify expression of one or more cell types or states in the initial cell-based system, delivering an additional cell type or sub-type to the initial cell-based system, or depleting an existing cell type or sub-type from the initial cell-based system. The one or more modulating agents may comprise one or more cytokines, growth factors, hormones, transcription factors, metabolites or small molecules. The one or more modulating agents may be a genetic modifying agent or an epigenetic modifying agent. The genetic modifying agent may comprise a CRISPR system, a zinc finger nuclease system, a TALEN, or a meganuclease. The epigenetic modifying agent may comprise a DNA methylation inhibitor, HDAC inhibitor, histone acetylation inhibitor, histone methylation inhibitor or histone demethylase inhibitor.

In certain embodiments, the one or more modulating agents modulate one or more cell-signaling pathways. The one or more pathways may comprise Notch signaling. The one or pathways may comprise Wnt signaling.

In certain embodiments, the ex vivo cell-based system comprises Paneth cells and the one or more agents comprise a Wnt signaling activator and Notch signaling inhibitor. The Wnt signaling activator may comprise CHIR99021. The Notch signaling inhibitor may comprise DAPT.

In certain embodiments, the method may further comprise: transplanting the initial cell-based system into an animal model; recovering cells from the transplanted cell-based system; performing single cell RNA sequencing on the recovered cells; and measuring statistically significant shifts in gene expression distribution compared to the in vivo system. Thus, the transplanted cells can be revaluated for fidelity compared to an in vivo system.

In another aspect, the present invention provides for an ex vivo cell-based system derived from the method according to any embodiment herein.

In another aspect, the present invention provides for use of the cell based system of any embodiment herein to identify a therapeutic agent or determine the efficacy of a therapeutic agent.

In another aspect, the present invention provides for use of the cell based system of any embodiment herein to select one or more therapeutic agents for treatment of a subject in need thereof.

In another aspect, the present invention provides for use of the cell based system of any embodiment herein to screen for one or more on-target or off-target genetic modifications.

In another aspect, the present invention provides for an ex vivo cell-based system derived from any embodiment herein, wherein the single cell type or subtype or combination of cell types and/or subtypes comprises a tumor cell. In another aspect, the present invention provides for an ex vivo cell-based system derived from any embodiment herein, wherein the single cell type or subtype or combination of cell types and/or subtypes comprises a tumor microenvironment cell. The tumor microenvironment cell may be a tumor infiltrating lymphocyte (TIL). The single cell type or subtype or combination of cell types and/or subtypes may faithfully recapitulate a phenotype from a subject responsive to cancer treatment. The single cell type or subtype or combination of cell types and/or subtypes may faithfully recapitulate a phenotype from a subject non-responsive to cancer treatment. The treatment may be an immunotherapy. The immunotherapy may be checkpoint blockade therapy (CBT). The single cell type or subtype or combination of cell types and/or subtypes may faithfully recapitulate a phenotype from a subject with a cancer recurrence.

In another aspect, the present invention provides for an ex vivo cell-based system derived from any embodiment herein, wherein the single cell type or subtype or combination of cell types and/or subtypes comprises an in vitro fertilized egg that faithfully recapitulates the phenotype of an in vivo fertilized egg. Not being bound by a theory, prior to the present invention it was unknown whether an in vitro fertilized egg faithfully recapitulates the phenotype of an in vivo fertilized egg.

In another aspect, the present invention provides for an ex vivo cell-based system derived from any embodiment herein, wherein the system is an organoid model selected from the group consisting of an intestinal, liver, kidney, lung, or brain organoid model.

In another aspect, the present invention provides for use of the system of any embodiment herein in a method for adoptive cell transfer (ACT), wherein a single cell type or subtype or combination of cell types and/or subtypes from the ex vivo cell-based system are transferred to a subject in need thereof. The subject may have a disease selected from the group consisting of cancer, autoimmune disease, bone marrow failure, hematological conditions, aplastic anemia, beta-thalassemia, diabetes, motor neuron disease, Parkinson's disease, spinal cord injury, muscular dystrophy, kidney disease, liver disease, multiple sclerosis, congestive heart failure, head trauma, lung disease, psoriasis, liver cirrhosis, vision loss, cystic fibrosis, hepatitis C virus, human immunodeficiency virus, inflammatory bowel disease (IBD), and any disorder associated with tissue degeneration.

In certain embodiments, T cells that faithfully recapitulate an in vivo phenotype of interest are transferred to a subject suffering from cancer or an autoimmune disease (e.g., activated, effector, or suppressive T cells). In certain embodiments, cells for regenerating a tissue are transferred (e.g., tissue cells or stem cells).

In another aspect, the present invention provides for use of the system of any cancer ex vivo system herein in a method for screening modulating agents. In another aspect, the present invention provides for use of the system of any cancer ex vivo system herein in a method for screening agents having antitumor activity. The cancer cells may be screened for agents capable of modulating an immune evasion phenotype (e.g., the tumor cells can evade the immune system). In certain embodiments, immune cells may be screened for antitumor cell activity. The immune cells may be screened for antitumor activity against an ex vivo tumor cell system.

In another aspect, the present invention provides for a method of screening for agents capable of modulating Paneth cell activity comprising: treating EGF, Noggin, R-spondin 1, CHIR99021 and DAPT (ENR+CD) cells with a stimulant capable of inducing Paneth cell secretion and an agent; and measuring Paneth cell antimicrobial secretion.

In another aspect, the present invention provides for a method of screening for agents capable of modulating Paneth cell antibacterial activity comprising: suspending EGF, Noggin, R-spondin 1, CHIR99021 and DAPT (ENR+CD) cells with bacteria and an agent; and measuring bacterial growth.

In another aspect, the present invention provides for a method of producing an in vitro Paneth cell enriched gut organoid system comprising: culturing an LGR5+ ISC-enriched population of cells in a hydrogel matrix in the presence of EGF, Noggin, R-spondin 1, CHIR99021 and valproic acid (ENR+CV); culturing the ENR+CV cells in the presence of EGF, Noggin, R-spondin 1, CHIR99021 and DAPT (ENR+CD); and modulating the activity of one or more nuclear receptors selected from the group consisting of progesterone receptor (PR), aldosterone receptor (AR) and glucocorticoid receptor (GR). In another aspect, the present invention provides for a cell obtained from by the method of above.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIGS. 1A-1I—Transcriptional benchmarking of in vitro Paneth cells to in vivo FIG. 1A) Schematic of intestinal epithelial cell isolation from terminal ileum for unbiased identification of in vivo Paneth cell (PC) signature genes, and system for intestinal stem cell (ISC) enrichment to characterize in vitro PCs, via high-throughput scRNA-seq. FIG. 1B) Marker gene overlay for binned count-based expression level (log(scaled UMI+1)) of Lyz1, a canonical PC marker gene, on a tSNE (t-stochastic neighbor embedding_FIG. 1G) plot of 7,667 small intestinal epithelial cells isolated from the terminal ileum; receiver operating characteristic (ROC)-test area under the curve (AUC)=0.995, n=2 mice, independent experiments (Table S1). FIG. 1C) Violin plot for the count-based expression level (log(scaled UMI+1)) of Lyz1 across clusters identified through shared nearest neighbor (SNN) analysis (see Methods) over small intestinal epithelial cells; n=196 cells in cluster 11, 7,667 cells total. FIG. 1D) A tSNE plot of 2,513 cells, with clusters identified through SNN (Table S1 for full gene lists with ROC>0.60) from conventional ENR organoids; n=6 wells of ENR organoids. FIG. 1E) Marker gene overlay for binned count-based expression level (log(scaled UMI+1)) of Lyz1 on a tSNE plot from (FIG. 1D); ROC-test AUC=0.856. FIG. 1F) Violin plot of expression contribution to a cell's transcriptome of PC genes across ENR organoid clusters from (FIG. 1D) (In vivo PC gene list AUC>0.65, Table S1); effect size 0.721, ENR-4 vs all ENR, *t-test $p<2.2\times10^{-16}$ FIG. 1G) Row-normalized heatmap of top differentially expressed genes using bimodal test over single-cells from the top 200 PC-like cells from ENR-4 and the 196 in vivo PCs (cluster 11, from (FIG. 1C)); *bimodal test, all displayed genes $p<1.89\times10^{-16}$ or less with Bonferroni correction. FIG. 1H) Violin plots for the count-based expression level (log(scaled UMI+1)) of Lyz1, Ang4, and Defa3 in ENR and in vivo PCs; *bimodal test, all $p<2.92\times10^{-37}$ or less with Bonferroni correction FIG. 1I) Violin plot of expression contribution to a cell's transcriptome of PC genes (effect size 1.25, InVivo vs. ENR, *t-test $p<2.2\times10^{-16}$), Wnt pathway (effect size 0.559, InVivo vs. ENR, *t-test $p<2.035\times10^{8}$) and Notch pathway (effect size –0.500, InVivo vs. ENR, *t-test $p<5.25\times10^{7}$) genes (see Table S2 for gene lists).

FIG. 2B) mRNA expression of PC (Lyz1, Defa1, Mmp7) and ISC (Lgr5) markers relative to ENR, for ENR+CV and ENR+CD at two (D2), four (D4), and six days (D6) (n=3 biological replicates; 2-way ANOVA with multiple comparison test versus ENR;  adj. p<0.01, * adj. p<0.001). FIG. 2C) Representative confocal imaging of whole cell clusters for PC antimicrobials following six days in ENR+CD versus ENR and ENR+CV: stained for anti-DEFA, anti-LYZ and counterstained with DAPI and for actin (phalloidin). FIG. 2D) High-resolution fluorescent imaging of in vivo and in vitro single cells from six-day culture in ENR+CD shows similar morphology and antimicrobial expression: stained for DEFA, LYZ and counterstained with DAPI and for actin (phalloidin). FIG. 2E) Viable cell populations from ENR, ENR+CD, and ENR+CV precursor culture have distinct populations based on CD24 and LYZ content, indicative of PC maturity (n=3 biological replicates).

FIG. 3B) Volcano plot of differentially regulated proteins between six day (6 D) ENR+CD and ENR cells shows clear enrichment in secreted and PC-associated proteins (labeled). Cut-offs are 2 standard deviations outside the mean expression level of the set and FDR<0.05. FIG. 3C) Rank-order log fold change of detected PC antimicrobial proteins (AMPs) and secretory proteins associated with enteroendocrine and goblet lineages demonstrates differential regulation of AMP classes between ENR+CD and ENR cultures, as well as enrichment in PC and enteroendocrine proteins. FIG. 3D) Protein variation by sample for ENR+CD- and ENR-enriched proteins demonstrated by coefficient of variation (CoV) vs. fold change relative to the median expression of the enriched proteins in ENR+CD and ENR samples for each replicate. FIG. 3E) PC normalized enrichment score (NES) for the full rank-ordered ENR+CD/ENR proteome by GSEA using the top 500 genes from de facto in vivo PC gene set (Sato et al. 2011). FIG. 3F) GSEA enrichment map of transcription factors linked to ENR+CD- and ENR-enriched proteins following a moderately conservative cutoff of p-value<0.005, FDR<0.075, and overlap coefficient of 0.2.

FIG. 4B) Marker gene overlays (on plot from (FIG. 4A)) for binned count-based expression level (log(scaled UMI+1)) of individual genes of interest. FIG. 4C) A tSNE plot, with clusters identified through SNN graph-based clustering (see Table 51 for marker gene lists), highlighting distinct cell states within each organoid; opacity of density clouds correspond to the Paneth cell score of ENR-4, ENR+CD-3, and ENR+CD-4 clusters (see FIG. 5B). FIG. 4D) Violin plot of expression contribution to a cell's transcriptome of ENR+CD proteome-enriched genes across organoid clusters from (FIG. 4C) (Table 51 for full gene list); effect size 2.40 ENR+CD-4 vs all cells, $p<2.2\times10^{-16}$ FIG. 4E) Frequency of each cluster observed within each organoid condition as a fraction of the total cells in each condition.

FIGS. 5A-5C—Transcriptional identity of Paneth cells within conditions and related to in vivo FIG. 5A) Violin plots for the count-based expression level (log(scaled UMI+1)) of selected genes across called clusters, colors correspond to clusters in FIG. 4C; *t-test, $p<6.80\times10^{74}$ or less with Bonferroni correction, for Lyz1, Defa24, Defa3, Mmp7 ENR+CD-4 relative to ENR-4 FIG. 5B) Violin plot of expression contribution to a cell's transcriptome of in vivo Paneth cell and enteroendocrine marker-cell genes (see Table S1 for full gene list, AUC>0.65); effect size 2.52 ENR+CD-4 vs. ENR-4, $p<2.2\times10^{-16}$ for Paneth cell score; effect size 0.0465, p=0.2339 ENR+CD-4 vs. ENR-4 for enteroendocrine cell score. FIG. 5C) Row-clustered heatmap of z-scores (−2.5 to 2.5; purple to yellow) for defining genes (n=69 with AUC>0.65) of in vivo Paneth cells, see Table S1 for full gene list) across top 200 cells for Paneth score (FIG. 5B) from ENR-4 and ENR+CD-4 conditions compared to two biological replicates of in vivo PCs from the terminal ileum (n=196 cells).

FIG. 6B) Supernatant LYZ from six day ENR+CD collected basally and following 10 μm CCh-stimulation for 0.5, 2, 4, 6, and 24 hours (top). DNA content from matched samples basally and following 10 μm CCh-stimulation (bottom) (n=8 well replicates). FIG. 6C) 24-hour basal (non-stimulated) and 10 μm CCh-stimulated LYZ secretion in six-day ENR+CD versus ENR and ENR+CV (n=8 well replicates; 2-way ANOVA with multiple comparison test; ns non-significant, * adj. p<0.05, **** adj. p<0.0001). FIG. 6D) 4-hour co-culture of freshly passaged six-day ENR and ENR+CD cells and select gram-negative and gram-positive aerobic bacteria (n=13 well replicates; 2-way ANOVA with multiple comparison test, * adj. p<0.05, * adj. p<0.001, ** adj. p<0.0001). FIG. 6E) Normalized cellular viability, caspase activity per viable cell, and cytotoxicity per viable cell from 24-hour and 48-hour ENR & ENR+CD co-cultures at specified mixing ratios (n=3 biological replicates; one sample t-test,* p<0.05,  p<0.01, * p<0.001, **** p<0.0001).

FIG. 7B) Violin plots for the count-based expression level (log(scaled UMI+1)) of Nupr1 across in vivo and in vitro called clusters. FIG. 7C) Trifluoperazine (TFP) treatment concurrent with 6-day ENR+CD differentiation reveals dose-dependent toxicity, with preference to PCs (CD24+& LYZ+) and PC-like (CD24+, LYZ+) populations as assessed by flow cytometry. FIG. 7D) Two-day Trifluoperazine (TFP) treatment following 6-day ENR+CD differentiation reveals dose-dependent toxicity, with preference to PCs (CD24+& LYZ+) and PC-like (CD24+, LYZ+) populations as assessed by flow cytometry.

FIG. 8B) Percentage of total cells that are LYZ+ and DEFA+ following six days of ENR, ENR+CV, and ENR+CD culture (from cell counting of whole clusters) (n=3 minimum biological replicates, 1-way ANOVA with multiple comparison test versus ENR, **** adj. p<0.0001). FIG. 8C) Collapsed z-stack of whole cluster with individual cells highlighted (1-3) following six days of ENR+CD, stained for LYZ and DEFA and counterstained with DAPI and for actin (phalloidin). 1-3) Normalized mean-area intensity versus z-axis depth profiles of representative individual LYZ+/DEFA+ co-staining cells. FIG. 8D) Representative flow cytometry of ENR and ENR+CD at six days with distinct populations of CD24+ and LYZ+ cells indicative of phenotypic PCs. FIG. 8E) Representative gating for flow cytometry, including removal of doublets and non-viable cells in final gating. FIG. 8F) Percentage of viable cells (membrane impermeable) over time of ENR versus ENR+CD culture.

FIGS. 9A-9E—Proteomic pipeline and sample-to-sample comparison FIG. 9A) Schematic of proteomic analysis for samples: culture, collection, lysis, reduction and alkylation, proteolytic digestion, labeling of peptides with isobaric mass tag reagents (Tandem Mass Tags, TMT10-plex; Thermo), off-line fractionation by basic reverse phase chromatography, analysis of fractions by LC-MS/MS, identification of peptides and proteins using Spectrum Mill software (Agilent), and statistical analysis of the resulting data (moderated T-test) to identify confidently differential proteins. FIG. 9B) Gross distribution of fold change for individual protein replicate pairs (ENR+CD/ENR). Dashed lines identify two standard deviations (±2σ). FIG. 9C) Proteome sample correlation between all biological (n=2) and technical (n=2/biological) replicates. FIG. 9D) Sample overlap comparison of ENR+CD-enriched (+2σ) proteins. FIG. 9E) Sample overlap comparison of ENR-enriched (−2σ) proteins.

FIG. 10B) ENR-enriched proteins are well annotated in the gene ontology database (GO) and show enrichment for functions and compartments of transcriptionally and translationally active cells determined by fold enrichment vs. FDR using DAVID.

FIG. 11B) Violin plot of expression contribution to a cell's transcriptome of mitochondrial and ribosomal genes across identified sub sets.

FIG. 12B) Violin plot of expression contribution to a cell's transcriptome of Notch pathways genes (inhibited by DAPT) across clusters as percent of transcriptome. FIG. 12C) Violin plot of expression contribution to a cell's transcriptome of respiratory electron transport gene set across clusters as percent of transcriptome.

Figure 1A:
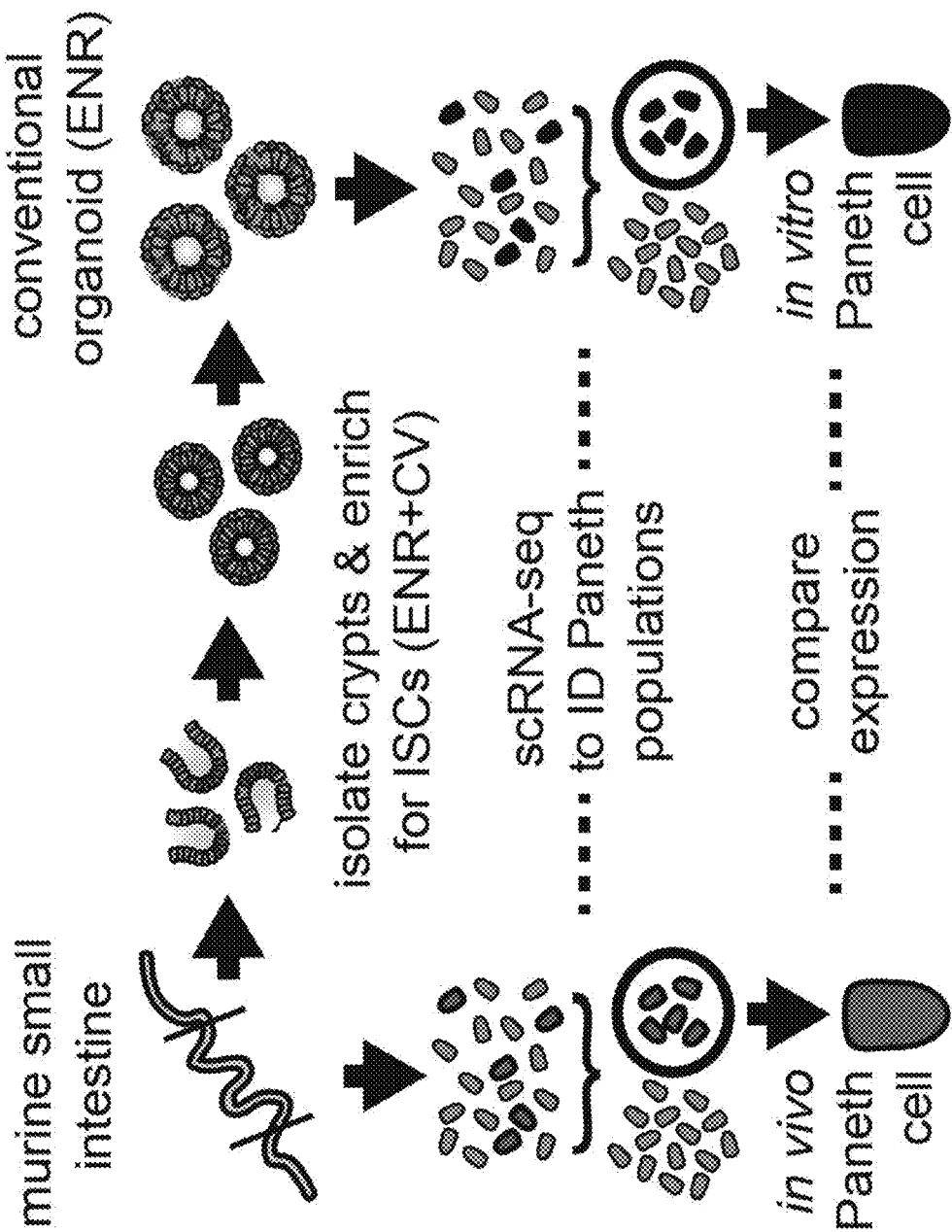

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, 2$^{nd}$ edition (1989) (Sambrook, Fritsch, and Maniatis); Molecular Cloning: A Laboratory Manual, 4$^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies, A Laboratory Manual, 2$^{nd}$ edition 2013 (E. A. Greenfield ed.); Animal Cell Culture (1987) (R. I. Freshney, ed.); Benjamin Lewin, Genes IX, published by Jones and Bartlett, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2$^{nd}$ ed., J. Wiley & Sons (New York, N.Y. 1994), March, Advanced Organic Chemistry Reactions, Mechanisms and Structure 4$^{th}$ ed., John Wiley & Sons (New York, N.Y. 1992); and Marten H. Hofker and Jan van Deursen, Transgenic Mouse Methods and Protocols, 2$^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +1-10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide for ex vivo cell-based systems that faithfully recapitulate an in vivo phenotype of interest and methods of generating and using the cell-based systems. As used herein, to "recapitulate an in vivo phenotype" may include increasing the biological fidelity of an ex vivo cell-based system to more closely mimic the physiology and/or structure of a target in vivo system. Mimicking the physiology and/or structure of target in vivo system may comprise mimicking expression signatures or modules found in the target in vivo system, mimicking a cell state or states found in the target in vivo system, and/or mimicking the composition of cell types or sub-types found in the in vivo target system. Applicants provide for the first time a genome wide method of comparing ex vivo and in vitro systems to in vivo systems to identify specific pathways and genes for modulation to obtain cells that more faithfully recapitulate the in vivo system's phenotype of interest. Thus, the method provides for an unbiased global comparison of whole transcriptomes that does not prioritize previously identified markers. Previous studies compared specific cell type markers and concluded that in vitro cells recapitulated the in vivo cells based only on these on expression of these cell-specific markers (See e.g., International Patent Publication WO 2014/159356A1). An "ex vivo cell-based system" may comprise single cells of a particular type, sub-type or state, or a combination of cells of the same or differing type, sub-type, or state. The ex vivo cell-based system may be a model for screening perturbations to better understand the underlying biology or to identify putative targets for treating a disease, or for screening putative therapeutics, and also include models derived ex vivo but further implanted into a living organism, such as a mouse or pig, prior to perturbation of the model. An ex vivo cell-based system may also be a cell-based therapeutic for delivery to an organism to treat disease, or an implant meant to restore or regenerate damaged tissue. An "in vivo system" may likewise comprise a single cell or a combination of cells of the same or differing type, sub-type, or state. As used herein ex vivo may include, but not be limited to, in vitro systems, unless otherwise specifically indicated. The "in vivo system" may comprise healthy tissue or cells, or tissues or cells in a homeostatic state, or diseased tissue or cells, or diseased tissue or cells in a non-homeostatic state, or tissues or cells within a viable organism, or diseased tissue or cells within a viable organism. A homeostatic state may include cells or tissues demonstrating a physiology and/or structure typically observed in an healthy living organism. In other embodiments, a homeostatic state may be considered the state that a cell or tissue naturally adopts under a given set of growth conditions and absent further defined genetic, chemical, or environmental perturbations.

Current in vitro models used to look at biology are not well characterized with reference to in vivo models. The embodiments disclosed herein provide a means for identifying differences in expression at a single cell level and use this information to prioritize how to improve the ex vivo system to more faithfully recapitulate the biological characteristics of the target in vivo system. Particular advantageous uses for ex vivo cell-based systems that faithfully recapitulate an in vivo phenotype of interest include methods for identifying agents capable of inducing or suppressing certain gene signatures or gene expression modules and/or inducing or suppressing certain cell states in the ex vivo cell-based systems. In the context of cell-based therapeutics, the methods disclosed herein may also be used to design ex vivo cell-based systems that based on their programmed gene expression profile or configured cell state can either induce or suppress particular in vivo cell (sub)populations at the site of delivery. In another aspect, the methods disclosed herein provide a method for preparing cell-based therapeutics.

In certain example embodiments, a method for generating an ex vivo cell-based system that faithfully recapitulates an in vivo phenotype or target system of interest comprises first determining, using single cell RNA sequencing (scRNA-seq) one or more cell (sub)types or one or more cell states in an initial or starting ex vivo cell-based system. It should be noted that the methods disclosed herein may be used to develop an ex vivo cell-based system de novo from a source starting material, or to improve an existing ex vivo cell-based system. Source starting materials may include cultured cell lines or cells or tissues isolated directly from an in vivo source, including explants and biopsies. The source materials may be pluripotent cells including stem cells. Next, differences are identified in the cell (sub)type(s) and/or cell state(s) between the ex vivo cell-based systems a target in vivo system. The cell (sub)type(s) and cell state(s) of the in vivo system may likewise be determined using scRNA-seq. The scRNA-seq analysis may be obtained at the time of running the methods described herein are based on previously archived scRNA-seq analysis. Based on the identified differences, steps to modulate the source material to induce a shift in cell (sub)type(s) and/or cell state(s) that may more closely mimics the target in vivo system may then selected and applied.

In certain embodiments, different methods of single sequencing are better suited for sequencing certain samples (e.g., neurons, rare samples may be more optimally sequenced with a plate based method or single nuclei sequencing). In certain embodiments, the invention involves plate based single cell RNA sequencing (see, e.g., Picelli, S. et al., 2014, "Full-length RNA-seq from single cells using Smart-seq2" Nature protocols 9, 171-181, doi:10.1038/nprot.2014.006).

In certain embodiments, the invention involves high-throughput single-cell RNA-seq and/or targeted nucleic acid profiling (for example, sequencing, quantitative reverse transcription polymerase chain reaction, and the like) where the RNAs from different cells are tagged individually, allowing a single library to be created while retaining the cell identity of each read. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO 2014210353 A2; Zilionis, et al., 2017, "Single-cell barcoding and sequencing using droplet microfluidics" Nat Protoc. January; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Vitak, et al., "Sequencing thousands of single-cell genomes with combinatorial indexing" Nature Methods, 14(3): 302-308, 2017; Cao, et al., Comprehensive single-cell transcriptional profiling of a multicellular organism. Science, 357(6352):661-667, 2017; and Gierahn et al., "Seq-Well: portable, low-cost RNA sequencing of single cells at high throughput" Nature Methods 14, 395-398 (2017), all the contents and disclosure of each of which are herein incorporated by reference in their entirety.

In certain embodiments, the invention involves single nucleus RNA sequencing. In this regard reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October; 14(10):955-958; and International patent application number PCT/US2016/059239, published as WO2017164936 on Sep. 28, 2017, which are herein incorporated by reference in their entirety.

In certain example embodiments, assessing the cell (sub) types and states present in the in vivo system may comprise analysis of expression matrices from the scRNA-seq data, performing dimensionality reduction, graph-based clustering and deriving list of cluster-specific genes in order to identify cell types and/or states present in the in vivo system. These marker genes may then be used throughout to relate the ex vivo system cell (sub)types and states to the in vivo system. The same analysis may then be applied to the source material for the ex vivo cell-based system. From both sets of sc-RNAseq analysis an initial distribution of gene expression data is obtained. In certain embodiments, the distribution may be a count-based metric for the number of transcripts of each gene present in a cell. Further the clustering and gene expression matrix analysis allow for the identification of key genes in the initial ex vivo system and the target in vivo system, such as differences in the expression of key transcription factors. In certain example embodiments, this may be done conducting differential expression analysis. For example, in the Working Examples below, differential gene expression analysis identified that in vivo PCs were enriched in defensins and antimicrobials including Defa22, Defa21, Zg16, Ang4, Defa3, and Lyz1. At the same time the analysis revealed that the in vitro organoid-derived PC cells had a global reduction in the total number of organoid derived cells producing the identified PC marker set. Thus, the methods disclosed herein can both identify key markers of the target in vivo system and potential targets for modulation to shift the expression distribution of the ex vivo system towards that of the target in vivo system. Again turning to the PC example provided herein, the single-cell transcriptomic steps of the methods disclosed herein were used to identify that the in vivo PC cells were enriched in Wnt-targeted genes relative to in vitro PCs, accordingly modulation of Wnt and inhibition of Notch were selected to shift the expression profile of the in vitro PCs to that of the in vivo PCs.

Other methods for assessing differences in the ex vivo and in vivo systems may be employed. In certain example embodiments, an assessment of differences in the in vivo and ex vivo proteome may be used to further identify key differences in cell type and sub-types or cells. states. For example isobaric mass tag labeling and liquid chromatography mass spectroscopy may used to determine relative protein abundances in the ex vivo and in vivo systems. The working examples below provide further disclosure on leveraging proteome analysis within the context of the methods disclosed herein.

In certain example embodiments, a statistically significant shift in the initial ex vivo gene expression distribution toward the gene expression distribution of the in vivo systems is sought post-modulation. A statistically significant shift in gene expression distribution can be at least 10%, at least 11%, at least 12%, at least 13%, at least 14%, at least 15%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

In certain example embodiments, statistical shifts may be determined by defining an in vivo score. For example, a gene list of key genes enriched in the in vivo model may be defined. To determine the fractional contribution to a cell's transcriptome to that gene list, the total log (scaled UMI+1) expression values for gene with the list of interest are summed and then divided by the total amount of scaled UMI detected in that cell giving a proportion of a cell's transcriptome dedicated to producing those genes. Thus, statistical significant shifts may be shifts in an initial score for the ex vivo system after modulation towards the in vivo score or after modulation with an aim of moving in a statistically significant fashion towards the in vivo score.

Modulation may be monitored in a number of ways. For example, expression of one or more key marker genes identified as described above may be measured at regular levels to assess increases in expression levels. Shifting of the ex vivo system to that of the in vivo system may also be measured phenotypically. For example, imaging an immunocytochemistry for key in vivo markers may be assessed at regular intervals to detect increased expression of the key in vivo markers. Likewise, flow cytometry may be used in a similar manner. In addition, to detecting key in vivo markers, imaging modalities such as those described above may be used to further detect changes in cell morphology of the ex vivo system to more closely resemble the target in vivo system.

In certain example embodiments, the ex vivo system may be further modulated to not only more faithfully recapitulate a target in vivo system, but the ex vivo system may be further modulated to induce a gain of function. For example, one or more genes, gene expression cassettes (modules), or gene expression signature associated with the gain of function may be induced. Example gain of functions include, but are not limited to, increased anti-apoptotic activity or improved anti-microbial secretion.

In certain embodiments, gene signatures are modulated to shift an ex vivo system to more faithfully recapitulate an in vivo system. As used herein a "signature" may encompass any gene or genes, protein or proteins, or epigenetic element(s) whose expression profile or whose occurrence is associated with a specific cell type, subtype, or cell state of a specific cell type or subtype within a population of cells. For ease of discussion, when discussing gene expression, any of gene or genes, protein or proteins, or epigenetic element(s) may be substituted. As used herein, the terms "signature", "expression profile", or "expression program" may be used interchangeably. It is to be understood that also when referring to proteins (e.g. differentially expressed proteins), such may fall within the definition of "gene" signature. Levels of expression or activity or prevalence may be compared between different cells in order to characterize or identify for instance signatures specific for cell (sub) populations. Increased or decreased expression or activity or prevalence of signature genes may be compared between different cells in order to characterize or identify for instance specific cell (sub)populations. The detection of a signature in single cells may be used to identify and quantitate for instance specific cell (sub)populations. A signature may include a gene or genes, protein or proteins, or epigenetic element(s) whose expression or occurrence is specific to a cell (sub)population, such that expression or occurrence is exclusive to the cell (sub)population. A gene signature as used herein, may thus refer to any set of up- and down-regulated genes that are representative of a cell type or subtype. A gene signature as used herein, may also refer to any set of up- and down-regulated genes between different cells or cell (sub)populations derived from a gene-expression profile. For example, a gene signature may comprise a list of genes differentially expressed in a distinction of interest.

The signature as defined herein (being it a gene signature, protein signature or other genetic or epigenetic signature) can be used to indicate the presence of a cell type, a subtype of the cell type, the state of the microenvironment of a population of cells, a particular cell type population or subpopulation, and/or the overall status of the entire cell (sub)population. Furthermore, the signature may be indicative of cells within a population of cells in vivo. The signature may also be used to suggest for instance particular therapies, or to follow up treatment, or to suggest ways to modulate immune systems. The signatures of the present invention may be discovered by analysis of expression profiles of single-cells within a population of cells from isolated samples (e.g. tumor samples), thus allowing the discovery of novel cell subtypes or cell states that were previously invisible or unrecognized. The presence of subtypes or cell states may be determined by subtype specific or cell state specific signatures. The presence of these specific cell (sub)types or cell states may be determined by applying the signature genes to bulk sequencing data in a sample. Not being bound by a theory the signatures of the present invention may be microenvironment specific, such as their expression in a particular spatio-temporal context. Not being bound by a theory, signatures as discussed herein are specific to a particular pathological context. Not being bound by a theory, a combination of cell subtypes having a particular signature may indicate an outcome. Not being bound by a theory, the signatures can be used to deconvolute the network of cells present in a particular pathological condition. Not being bound by a theory the presence of specific cells and cell subtypes are indicative of a particular response to treatment, such as including increased or decreased susceptibility to treatment. The signature may indicate the presence of one particular cell type. In one embodiment, the novel signatures are used to detect multiple cell states or hierarchies that occur in subpopulations of cancer cells that are linked to particular pathological condition (e.g. cancer grade), or linked to a particular outcome or progression of the disease (e.g. metastasis), or linked to a particular response to treatment of the disease.

The signature according to certain embodiments of the present invention may comprise or consist of one or more genes, proteins and/or epigenetic elements, such as for instance 1, 2, 3, 4, 5, 6, 7, 8, 9, 10 or more. In certain embodiments, the signature may comprise or consist of two or more genes, proteins and/or epigenetic elements, such as for instance 2, 3, 4, 5, 6, 7, 8, 9, 10 or more. In certain embodiments, the signature may comprise or consist of three or more genes, proteins and/or epigenetic elements, such as for instance 3, 4, 5, 6, 7, 8, 9, 10 or more. In certain embodiments, the signature may comprise or consist of four or more genes, proteins and/or epigenetic elements, such as for instance 4, 5, 6, 7, 8, 9, 10 or more. In certain embodiments, the signature may comprise or consist of five or more genes, proteins and/or epigenetic elements, such as for instance 5, 6, 7, 8, 9, 10 or more. In certain embodiments, the signature may comprise or consist of six or more genes, proteins and/or epigenetic elements, such as for instance 6, 7, 8, 9, 10 or more. In certain embodiments, the signature may comprise or consist of seven or more genes, proteins and/or epigenetic elements, such as for instance 7, 8, 9, 10 or more. In certain embodiments, the signature may comprise or consist of eight or more genes, proteins and/or epigenetic elements, such as for instance 8, 9, 10 or more. In certain embodiments, the signature may comprise or consist of nine or more genes, proteins and/or epigenetic elements, such as for instance 9, 10 or more. In certain embodiments, the signature may comprise or consist of ten or more genes, proteins and/or epigenetic elements, such as for instance 10, 11, 12, 13, 14, 15, or more. It is to be understood that a signature according to the invention may for instance also include genes or proteins as well as epigenetic elements combined.

In certain embodiments, a signature is characterized as being specific for a particular cell or cell (sub)population if it is upregulated or only present, detected or detectable in that particular cell or cell (sub)population, or alternatively is downregulated or only absent, or undetectable in that particular cell or cell (sub)population. In this context, a signature consists of one or more differentially expressed genes/proteins or differential epigenetic elements when comparing different cells or cell (sub)populations, including comparing different tumor cells or tumor cell (sub)populations, as well as comparing tumor cells or tumor cell (sub)populations with non-tumor cells or non-tumor cell (sub)populations. It is to be understood that "differentially expressed" genes/proteins include genes/proteins which are up- or down-regulated as well as genes/proteins which are turned on or off. When referring to up- or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art.

As discussed herein, differentially expressed genes/proteins, or differential epigenetic elements may be differentially expressed on a single cell level, or may be differentially expressed on a cell population level. Preferably, the differentially expressed genes/proteins or epigenetic elements as discussed herein, such as constituting the gene signatures as discussed herein, when as to the cell population level, refer to genes that are differentially expressed in all or substantially all cells of the population (such as at least 80%, preferably at least 90%, such as at least 95% of the individual cells). This allows one to define a particular subpopulation of cells. As referred to herein, a "subpopulation" of cells preferably refers to a particular subset of cells of a particular cell type which can be distinguished or are uniquely identifiable and set apart from other cells of this cell type. The cell subpopulation may be phenotypically characterized, and is preferably characterized by the signature as discussed herein. A cell (sub)population as referred to herein may constitute of a (sub)population of cells of a particular cell type characterized by a specific cell state.

When referring to induction, or alternatively suppression of a particular signature, preferable is meant induction or alternatively suppression (or upregulation or downregulation) of at least one gene/protein and/or epigenetic element of the signature, such as for instance at least to, at least three, at least four, at least five, at least six, or all genes/proteins and/or epigenetic elements of the signature.

In further aspects, the invention relates to gene signatures, protein signature, and/or other genetic or epigenetic signature of particular tumor cell subpopulations, as defined herein elsewhere. The invention hereto also further relates to particular tumor cell subpopulations, which may be identified based on the methods according to the invention as discussed herein; as well as methods to obtain such cell (sub)populations and screening methods to identify agents capable of inducing or suppressing particular tumor cell (sub)populations.

Modulating Agents

Selection of modulating agents will depend on key targets identified by the analysis describe above, and which aspects of gene expression need to be modified to shift expression towards that of the in vivo model. Modulating agents may comprise cytokines, growth factors, hormones, transcription factors, metabolites or small molecules. The modulating agent may also be a genetic modifying agent or an epigenetic modifying agent. The genetic modulating agent may be a CRISPR system, a zinc finger nuclease system, a TALEN, or a meganuclease. The epigenetic modifying agent may be a DNA methylation inhibitor, HDAC inhibitor, histone acetylation inhibitor, histone methylation inhibitor, or histone demethylase inhibitor.

Ex Vivo Cell Culture

In certain embodiments, the ex vivo cell-based system comprises a single cell type or sub-type, a combination of cell types and/or subtypes, cell-based therapeutic, an explant, or an organoid derived using the methods disclosed herein.

In certain embodiments, the single cell type or subtype or combination of cell types and/or subtypes comprises an immune cell, intestinal cell, liver cell, kidney cell, lung cell, brain cell, epithelial cell, endoderm cell, neuron, ectoderm cell, islet cell, acinar cell, oocyte, sperm, hem atopoieti c cell, hepaiocyie, ski nikerati nocyte, melanocyte, bonelosteocyte, hair/dermal papilla cell, cartilage/chondrocyte, fat cell/adipocyte, skeletal muscular cell, endothelium cell, cardiac muscle/cardiomyocyte, trophoblast, tumor cell, or tumor microenvironment (TME) cell.

In certain embodiments, the single cell type or sub-type is pluripotent, or the combination of cell types and/or subtypes comprises one or more stem cells. The one or more stem cells may be selected from the group consisting of lymphoid stem cells, myeloid stem cells, neural stem cells, skeletal muscle satellite cells, epithelial stem cells, endodermal and neuroectodermal stem cells, germ cells, extraembryonic and embryonic stem cells, mesenchymal stem cells, intestinal stem cells, embryonic stem cells, and induced pluripotent stem cells (iPSCs).

As used herein, the term "stem cell" refers to a multipotent cell having the capacity to self-renew and to differentiate into multiple cell lineages.

As used herein, the term "epithelial stem cell" refers to a multipotent cell which has the potential to become committed to multiple cell lineages, including cell lineages resulting in epithelial cells.

The tumor microenvironment (TME) is the cellular environment in which the tumor exists, including surrounding blood vessels, immune cells, cancer associated fibroblasts (CAFs), bone marrow-derived inflammatory cells, lymphocytes, signaling molecules and the extracellular matrix (ECM).

Tumor infiltrating lymphocytes (TILs) are lymphocytes that penetrate a tumor.

In certain embodiments, a cell-based therapeutic includes engraftment of the cells of the present invention. As used herein, the term "engraft" or "engraftment" refers to the process of cell incorporation into a tissue of interest in vivo through contact with existing cells of the tissue.

As used herein, a "population" of cells is any number of cells greater than 1, but is preferably at least $1\times10^3$ cells, at least $1\times10^4$ cells, at least at least $1\times10^5$ cells, at least $1\times10^6$ cells, at least $1\times10^7$ cells, at least $1\times10^8$ cells, at least $1\times10^9$ cells, or at least $1\times10^{19}$ cells.

As used herein, the term "organoid" or "epithelial organoid" refers to a cell cluster or aggregate that resembles an organ, or part of an organ, and possesses cell types relevant to that particular organ.

As used herein, a "subject" is a vertebrate, including any member of the class mammalia.

As used herein, a "mammal" refers to any mammal including but not limited to human, mouse, rat, sheep, monkey, goat, rabbit, hamster, horse, cow or pig.

A "non-human mammal", as used herein, refers to any mammal that is not a human.

General techniques useful in the practice of this invention in cell culture and media uses are known in the art (e.g., Large Scale Mammalian Cell Culture (Hu et al. 1997. Curr Opin Biotechnol 8: 148); Serum-free Media (K. Kitano. 1991. Biotechnology 17: 73); or Large Scale Mammalian Cell Culture (Curr Opin Biotechnol 2: 375, 1991). The terms "culturing" or "cell culture" are common in the art and broadly refer to maintenance of cells and potentially expansion (proliferation, propagation) of cells in vitro. Typically, animal cells, such as mammalian cells, such as human cells, are cultured by exposing them to (i.e., contacting them with) a suitable cell culture medium in a vessel or container adequate for the purpose (e.g., a 96-, 24-, or 6-well plate, a T-25, T-75, T-150 or T-225 flask, or a cell factory), at art-known conditions conducive to in vitro cell culture, such as temperature of 37° C., 5% v/v $CO_2$ and >95% humidity.

Methods related to stem cells and differentiating stem cells are known in the art (see, e.g., "Teratocarcinomas and embryonic stem cells: A practical approach" (E. J. Robertson, ed., IRL Press Ltd. 1987); "Guide to Techniques in Mouse Development" (P. M. Wasserman et al. eds., Academic Press 1993); "Embryonic Stem Cells: Methods and Protocols" (Kursad Turksen, ed., Humana Press, Totowa N.J., 2001); "Embryonic Stem Cell Differentiation in Vitro" (M. V. Wiles, Meth. Enzymol. 225: 900, 1993); "Properties and uses of Embryonic Stem Cells: Prospects for Application to Human Biology and Gene Therapy" (P. D. Rathjen et al., al., 1993). Differentiation of stem cells is reviewed, e.g., in Robertson. 1997. Meth Cell Biol 75: 173; Roach and McNeish. 2002. Methods Mol Biol 185: 1-16; and Pedersen. 1998. Reprod Fertil Dev 10: 31). For further elaboration of general techniques useful in the practice of this invention, the practitioner can refer to standard textbooks and reviews in cell biology, tissue culture, and embryology (see, e.g., Culture of Human Stem Cells (R. Ian Freshney, Glyn N. Stacey, Jonathan M. Auerbach—2007); Protocols for Neural Cell Culture (Laurie C. Doering—2009); Neural Stem Cell Assays (Navjot Kaur, Mohan C. Vemuri—2015); Working with Stem Cells (Henning Ulrich, Priscilla Davidson Negraes—2016); and Biomaterials as Stem Cell Niche (Krishnendu Roy—2010)).

Organoid technology has been previously described for example, for brain, retinal, stomach, lung, thyroid, small intestine, colon, liver, kidney, pancreas, prostate, mammary gland, fallopian tube, taste buds, salivary glands, and esophagus (see, e.g., Clevers, Modeling Development and Disease with Organoids, Cell. 2016 Jun. 16; 165(7):1586-1597).

For further methods of cell culture solutions and systems, see International Patent publication WO2014159356A1.

In certain embodiments, modulating the ex vivo cell-based system comprises delivering one or more modulating agents that modify expression of one or more cell types or states in the ex vivo cell-based system, delivering an additional cell type or sub-type to the ex vivo cell-based system, or depleting an existing cell type or sub-type from the ex vivo cell-based system. The one or more modulating agents may comprise one or more cytokines, growth factors, hormones, transcription factors, metabolites or small molecules.

The term "modulate" broadly denotes a qualitative and/or quantitative alteration, change or variation in that which is being modulated. Where modulation can be assessed quantitatively—for example, where modulation comprises or consists of a change in a quantifiable variable such as a quantifiable property of a cell or where a quantifiable variable provides a suitable surrogate for the modulation—modulation specifically encompasses both increase (e.g., activation) or decrease (e.g., inhibition) in the measured variable. The term encompasses any extent of such modulation, e.g., any extent of such increase or decrease, and may more particularly refer to statistically significant increase or decrease in the measured variable. By means of example, modulation may encompass an increase in the value of the measured variable by at least about 10%, e.g., by at least about 20%, preferably by at least about 30%, e.g., by at least about 40%, more preferably by at least about 50%, e.g., by at least about 75%, even more preferably by at least about 100%, e.g., by at least about 150%, 200%, 250%, 300%, 400% or by at least about 500%, compared to a reference situation without said modulation; or modulation may encompass a decrease or reduction in the value of the measured variable by at least about 10%, e.g., by at least about 20%, by at least about 30%, e.g., by at least about 40%, by at least about 50%, e.g., by at least about 60%, by at least about 70%, e.g., by at least about 80%, by at least about 90%, e.g., by at least about 95%, such as by at least about 96%, 97%, 98%, 99% or even by 100%, compared to a reference situation without said modulation. Preferably, modulation may be specific or selective, hence, one or more desired phenotypic aspects of a cell or cell population may be modulated without substantially altering other (unintended, undesired) phenotypic aspect(s).

Non-limiting examples of hormones include growth hormone (GH), adrenocorticotropic hormone (ACTH), dehydroepiandrosterone (DHEA), cortisol, epinephrine, thyroid hormone, estrogen, progesterone, testosterone, or combinations thereof.

Non-limiting examples of cytokines include lymphokines (e.g., interferon-γ, IL-2, IL-3, IL-4, IL-6, granulocyte-macrophage colony-stimulating factor (GM-CSF), interferon-γ, leukocyte migration inhibitory factors (T-LIF, B-LIF), lymphotoxin-alpha, macrophage-activating factor (MAF), macrophage migration-inhibitory factor (MIF), neuroleukin, immunologic suppressor factors, transfer factors, or combinations thereof), monokines (e.g., IL-1, TNF-alpha, interferon-α, interferon-β, colony stimulating factors, e.g., CSF2, CSF3, macrophage CSF or GM-CSF, or combinations thereof), chemokines (e.g., beta-thromboglobulin, C chemokines, CC chemokines, CXC chemokines, CX3C chemokines, macrophage inflammatory protein (MIP), or combinations thereof), interleukins (e.g., IL-1, IL-2, IL-3, IL-4, IL-5, IL-6, IL-7, IL-8, IL-9, IL-10, IL-11, IL-12, IL-13, IL-14, IL-15, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, or combinations thereof), and several related signalling molecules, such as tumour necrosis factor (TNF) and interferons (e.g., interferon-α, interferon-β, interferon-γ, interferon-k, or combinations thereof).

Non-limiting examples of growth factors include those of fibroblast growth factor (FGF) family, bone morphogenic protein (BMP) family, platelet derived growth factor (PDGF) family, transforming growth factor beta (TGFbeta) family, nerve growth factor (NGF) family, epidermal growth factor (EGF) family, insulin related growth factor (IGF) family, hepatocyte growth factor (HGF) family, hematopoietic growth factors (HeGFs), platelet-derived endothelial cell growth factor (PD-ECGF), angiopoietin, vascular endothelial growth factor (VEGF) family, glucocorticoids, or combinations thereof.

Non-limiting examples of mitogens include phytohaemagglutinin (PHA), concanavalin A (conA), lipopolysaccharide (LPS), pokeweed mitogen (PWM), phorbol ester such as phorbol myristate acetate (PMA) with or without ionomycin, or combinations thereof.

Non-limiting examples of cell surface receptors the ligands of which may act as immunomodulants include Toll-like receptors (TLRs) (e.g., TLR1, TLR2, TLR3, TLR4, TLR5, TLR6, TLR7, TLR8, TLR9, TLR10, TLR11, TLR12 or TLR13), CD80, CD86, CD40, CCR7, or C-type lectin receptors.

In certain embodiments, differentiation promoting agents may be used to obtain particular types of target cells. Differentiation promoting agents include anticoagulants, chelating agents, and antibiotics. Examples of such agents may be one or more of the following: vitamins and minerals or derivatives thereof, such as A (retinol), $B_3$, C (ascorbate), ascorbate 2-phosphate, D such as $D_2$ or $D_3$, K, retinoic acid, nicotinamide, zinc or zinc compound, and calcium or calcium compounds; natural or synthetic hormones such as hydrocortisone, and dexamethasone; amino acids or derivatives thereof, such as L-glutamine (L-glu), ethylene glycol tetraacetic acid (EGTA), proline, and non-essential amino acids (NEAA); compounds or derivatives thereof, such as β-mercaptoethal, dibutyl cyclic adenosine monophosphate (db-cAMP), monothioglycerol (MTG), putrescine, dimethyl sulfoxide (DMSO), hypoxanthine, adenine, forskolin, cilostamide, and 3-isobutyl-1-methylxanthine; nucleosides and analogues thereof, such as 5-azacytidine; acids or salts thereof, such as ascorbic acid, pyruvate, okadaic acid, linoleic acid, ethylenediaminetetraacetic acid (EDTA), anticoagulant citrate dextrose formula A (ACDA), disodium EDTA, sodium butyrate, and glycerophosphate; antibiotics or drugs, such as G418, gentamicin, Pentoxifylline (1-(5-oxohexyl)-3,7-dimethylxanthine), and indomethacin; and proteins such as tissue plasminogen activator (TPA).

Adoptive Cell Transfer

In certain embodiments, the cell based therapy may comprise adoptive cell transfer (ACT). The ex vivo cell-based system that is modulated to faithfully recapitulate an in vivo system may be transferred to a subject in need thereof. The cell based therapy may comprise adoptive cell transfer (ACT) of T cells. The T cells may be activated or effector T cells specific; for a tumor antigen. The T cells may be further modified as described herein.

In certain embodiments, cells as described herein and below may be used for adoptive cell transfer (ACT). ACT as used herein also refers to adoptive cell transfer. As used herein adoptive cell transfer and adoptive cell therapy are used interchangeably. In certain embodiments, the interaction of immune cells is advantageously used, such as modulating and/or transferring one immune cell subtype to cause an effect in another immune cell subtype. The transferred cells may include and be modulated by immune cells or immune cell populations as taught herein. In certain embodiments, the suppressive T cells of the present invention are depleted from cells used in ACT and may be transferred to a subject suffering from a disease (e.g., cancer). In certain embodiments, the cells of the present invention may be transferred to a subject suffering from a disease characteristic of an over reactive immune response (e.g., autoimmune disease). In certain embodiments, adoptive cell transfer may comprise: isolating from a biological sample of the subject a CD4$^+$ and/or C8$^+$ T cell or CD4$^+$ and/or C8$^+$ T cell population as described herein; in vitro expanding the T cell or T cell population; and administering the in vitro expanded T cell or T cell population to the subject. The method may further comprise enriching the expanded T cells for one subtype. In certain embodiments, the method may further comprise formulating the in vitro expanded immune cell or immune cell population into a pharmaceutical composition.

In certain embodiments, the present invention comprises adoptive cell therapy. Adoptive cell therapy can refer to the transfer of cells, most commonly immune-derived cells, back into the same patient or into a new recipient host with the goal of transferring the immunologic functionality and characteristics into the new host. If possible, use of autologous cells helps the recipient by minimizing GVHD issues. The adoptive transfer of autologous tumor infiltrating lymphocytes (TIL) (Besser et al., (2010) Clin. Cancer Res 16 (9) 2646-55; Dudley et al., (2002) Science 298 (5594): 850-4; and Dudley et al., (2005) Journal of Clinical Oncology 23 (10): 2346-57.) or genetically re-directed peripheral blood mononuclear cells (Johnson et al., (2009) Blood 114 (3): 535-46; and Morgan et al., (2006) Science 314(5796) 126-9) has been used to successfully treat patients with advanced solid tumors, including melanoma and colorectal carcinoma, as well as patients with CD19-expressing hematologic malignancies (Kalos et al., (2011) Science Translational Medicine 3 (95): 95ra73).

Aspects of the invention involve the adoptive transfer of immune system cells, such as T cells, specific for selected antigens, such as tumor associated antigens or tumor specific neoantigens (see Maus et al., 2014, Adoptive Immunotherapy for Cancer or Viruses, Annual Review of Immunology, Vol. 32: 189-225; Rosenberg and Restifo, 2015, Adoptive cell transfer as personalized immunotherapy for human cancer, Science Vol. 348 no. 6230 pp. 62-68; Restifo et al., 2015, Adoptive immunotherapy for cancer: harnessing the T cell response. Nat. Rev. Immunol. 12(4): 269-281; and Jenson and Riddell, 2014, Design and implementation of adoptive therapy with chimeric antigen receptor-modified T cells. Immunol Rev. 257(1): 127-144; and Rajasagi et al., 2014, Systematic identification of personal tumor-specific neoantigens in chronic lymphocytic leukemia. Blood. 2014 Jul. 17; 124(3):453-62).

In certain embodiments, an antigen (such as a tumor antigen) to be targeted in adoptive cell therapy (such as particularly CAR or TCR T-cell therapy) of a disease (such as particularly of tumor or cancer) may be selected from a group consisting of: B cell maturation antigen (BCMA); PSA (prostate-specific antigen); prostate-specific membrane antigen (PSMA); PSCA (Prostate stem cell antigen); Tyrosine-protein kinase transmembrane receptor ROR1; fibroblast activation protein (FAP); Tumor-associated glycoprotein 72 (TAG72); Carcinoembryonic antigen (CEA); Epithelial cell adhesion molecule (EPCAM); Mesothelin; Human Epidermal growth factor Receptor 2 (ERBB2 (Her2/neu)); Prostate; Prostatic acid phosphatase (PAP); elongation factor 2 mutant (ELF2M); Insulin-like growth factor 1 receptor (IGF-1R); gp100; BCR-ABL (breakpoint cluster region-Abelson); tyrosinase; New York esophageal squamous cell carcinoma 1 (NY-ESO-1); κ-light chain, LAGE (L antigen); MAGE (melanoma antigen); Melanoma-associated antigen 1 (MAGE-A1); MAGE A3; MAGE A6; legumain; Human papillomavirus (HPV) E6; HPV E7; prostein; survivin; PCTA1 (Galectin 8); Melan-A/MART-1; Ras mutant; TRP-1 (tyrosinase related protein 1, or gp75); Tyrosinase-related Protein 2 (TRP2); TRP-2/INT2 (TRP-2/intron 2); RAGE (renal antigen); receptor for advanced glycation end products 1 (RAGE1); Renal ubiquitous 1, 2 (RU1, RU2); intestinal carboxyl esterase (iCE); Heat shock protein 70-2 (HSP70-2) mutant; thyroid stimulating hormone receptor (TSHR); CD123; CD171; CD19; CD20; CD22; CD26; CD30; CD33; CD44v7/8 (cluster of differentiation 44, exons 7/8); CD53; CD92; CD100; CD148; CD150; CD200; CD261; CD262; CD362; CS-1 (CD2 subset 1, CRACC, SLAMF7, CD319, and 19A24); C-type lectin-like molecule-1 (CLL-1); ganglioside GD3 (aNeu5Ac (2-8)aNeu5Ac(2-3)bDGalp(1-4)bDG1cp(1-1)Cer); Tn antigen (Tn Ag); Fms-Like Tyrosine Kinase 3 (FLT3); CD38; CD138; CD44v6; B7H3 (CD276); KIT (CD117); Interleukin-13 receptor subunit alpha-2 (IL-13Ra2); Interleukin 11 receptor alpha (IL-11Ra); prostate stem cell antigen (PSCA); Protease Serine 21 (PRSS21); vascular endothelial growth factor receptor 2 (VEGFR2); Lewis(Y) antigen; CD24; Platelet-derived growth factor receptor beta (PDGFR-beta); stage-specific embryonic antigen-4 (SSEA-4); Mucin 1, cell surface associated (MUC1); mucin 16 (MUC16); epidermal growth factor receptor (EGFR); epidermal growth factor receptor variant III (EGFRvIII); neural cell adhesion molecule (NCAM); carbonic anhydrase IX (CAIX); Proteasome (Prosome, Macropain) Subunit, Beta Type, 9 (LMP2); ephrin type-A receptor 2 (EphA2); Ephrin B2; Fucosyl GM1; sialyl Lewis adhesion molecule (sLe); ganglioside GM3 (aNeu5Ac(2-3)bDGalp(1-4)bDG1cp(1-1)Cer); TGS5; high molecular weight-melanoma-associated antigen (HMWMAA); o-acetyl-GD2 ganglioside (OAcGD2); Folate receptor alpha; Folate receptor beta; tumor endothelial marker 1 (TEM1/CD248); tumor endothelial marker 7-related (TEM7R); claudin 6 (CLDN6); G protein-coupled receptor class C group 5, member D (GPRC5D); chromosome X open reading frame 61 (CX-ORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); CT (cancer/testis (antigen)); melanoma cancer testis antigen-1 (MAD-CT-1); melanoma cancer testis antigen-2 (MAD-CT-2); Fos-related antigen 1; p53; p53 mutant; human Telomerase reverse transcriptase (hTERT); sarcoma translocation breakpoints; melanoma inhibitor of apoptosis (ML-IAP); ERG (transmembrane protease, serine 2 (T1VIPRSS2) ETS fusion gene); N-Acetyl glucosaminyl-transferase V (NA17); paired box protein Pax-3 (PAX3); Androgen receptor; Cyclin B1; Cyclin D1; v-myc avian myelocytomatosis viral oncogene neuroblastoma derived homolog (MYCN); Ras Homolog Family Member C (RhoC); Cytochrome P450 1B1 (CYP1B1); CCCTC-Binding Factor (Zinc Finger Protein)-Like (BORIS); Squamous Cell Carcinoma Antigen Recognized By T Cells-1 or 3 (SART1, SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint-1, -2, -3 or -4 (SSX1, SSX2, SSX3, SSX4); CD79a; CD79b; CD72; Leukocyte-associated immunoglobulin-like receptor 1 (LAIR1); Fc fragment of IgA receptor (FCAR); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); mouse double minute 2 homolog (MDM2); livin; alphafetoprotein (AFP); transmembrane activator and CAML Interactor (TACI); B-cell activating factor receptor (BAFF-R); V-Ki-ras2 Kirsten rat sarcoma viral oncogene homolog (KRAS); immunoglobulin lambda-like polypeptide 1 (IGLL1); 707-AP (707 alanine proline); ART-4 (adenocarcinoma antigen recognized by T4 cells); BAGE (B antigen; b-catenin/m, b-catenin/mutated); CAMEL (CTL-recognized antigen on melanoma); CAP1 (carcinoembryonic antigen peptide 1); CASP-8 (caspase-8); CDC27m (cell-division cycle 27 mutated); CDK4/m (cycline-dependent kinase 4 mutated); Cyp-B (cyclophilin B); DAM (differentiation antigen melanoma); EGP-2 (epithelial glycoprotein 2); EGP-40 (epithelial glycoprotein 40); Erbb2, 3, 4 (erythroblastic leukemia viral oncogene homolog-2, -3, 4); FBP (folate binding protein); fAchR (Fetal acetylcholine receptor); G250 (glycoprotein 250); GAGE (G antigen); GnT-V (N-acetylglucosaminyltransferase V); HAGE (helicase antigen); ULA-A (human leukocyte antigen-A); HST2 (human signet ring tumor 2); KIAA0205; KDR (kinase insert domain receptor); LDLR/FUT (low density lipid receptor/GDP L-fucose: b-D-galactosidase 2-a-L fucosyl-transferase); L1CAM (L1 cell adhesion molecule); MC1R (melanocortin 1 receptor); Myosin/m (myosin mutated); MUM-1, -2, -3 (melanoma ubiquitous mutated 1, 2, 3); NA88-A (NA cDNA clone of patient M88); KG2D (Natural killer group 2, member D) ligands; oncofetal antigen (h5T4); p190 minor bcr-abl (protein of 190KD bcr-abl); Pml/RARa (promyelocytic leukaemia/retinoic acid receptor a); PRAME (preferentially expressed antigen of melanoma); SAGE (sarcoma antigen); TEL/AML1 (translocation Ets-family leukemia/acute myeloid leukemia 1); TPI/m (triose-phosphate isomerase mutated); and any combination thereof.

In certain embodiments, an antigen to be targeted in adoptive cell therapy (such as particularly CAR or TCR T-cell therapy) of a disease (such as particularly of tumor or cancer) is a tumor-specific antigen (TSA).

In certain embodiments, an antigen to be targeted in adoptive cell therapy (such as particularly CAR or TCR T-cell therapy) of a disease (such as particularly of tumor or cancer) is a neoantigen.

In certain embodiments, an antigen to be targeted in adoptive cell therapy (such as particularly CAR or TCR T-cell therapy) of a disease (such as particularly of tumor or cancer) is a tumor-associated antigen (TAA).

In certain embodiments, an antigen to be targeted in adoptive cell therapy (such as particularly CAR or TCR T-cell therapy) of a disease (such as particularly of tumor or cancer) is a universal tumor antigen. In certain preferred embodiments, the universal tumor antigen is selected from the group consisting of: a human telomerase reverse transcriptase (hTERT), survivin, mouse double minute 2 homolog (MDM2), cytochrome P450 1B 1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53, cyclin (D1), and any combinations thereof.

In certain embodiments, an antigen (such as a tumor antigen) to be targeted in adoptive cell therapy (such as particularly CAR or TCR T-cell therapy) of a disease (such as particularly of tumor or cancer) may be selected from a group consisting of: CD19, BCMA, CLL-1, MAGE A3, MAGE A6, HPV E6, HPV E7, WT1, CD22, CD171, ROR1, MUC16, and SSX2. In certain preferred embodiments, the antigen may be CD19. For example, CD19 may be targeted in hematologic malignancies, such as in lymphomas, more particularly in B-cell lymphomas, such as without limitation in diffuse large B-cell lymphoma, primary mediastinal b-cell lymphoma, transformed follicular lymphoma, marginal zone lymphoma, mantle cell lymphoma, acute lymphoblastic leukemia including adult and pediatric ALL, non-Hodgkin lymphoma, indolent non-Hodgkin lymphoma, or chronic lymphocytic leukemia. For example, BCMA may be targeted in multiple myeloma or plasma cell leukemia. For example, CLL1 may be targeted in acute myeloid leukemia. For example, MAGE A3, MAGE A6, SSX2, and/or KRAS may be targeted in solid tumors. For example, HPV E6 and/or HPV E7 may be targeted in cervical cancer or head and neck cancer. For example, WT1 may be targeted in acute myeloid leukemia (AML), myelodysplastic syndromes (MDS), chronic myeloid leukemia (CML), non-small cell lung cancer, breast, pancreatic, ovarian or colorectal cancers, or mesothelioma. For example, CD22 may be targeted in B cell malignancies, including non-Hodgkin lymphoma, diffuse large B-cell lymphoma, or acute lymphoblastic leukemia. For example, CD171 may be targeted in neuroblastoma, glioblastoma, or lung, pancreatic, or ovarian cancers. For example, ROR1 may be targeted in ROR1+ malignancies, including non-small cell lung cancer, triple negative breast cancer, pancreatic cancer, prostate cancer, ALL, chronic lymphocytic leukemia, or mantle cell lymphoma. For example, MUC16 may be targeted in MUC16ecto+ epithelial ovarian, fallopian tube or primary peritoneal cancer.

Various strategies may for example be employed to genetically modify T cells by altering the specificity of the T cell receptor (TCR) for example by introducing new TCR α and β chains with selected peptide specificity (see U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088,379).

As an alternative to, or addition to, TCR modifications, chimeric antigen receptors (CARs) may be used in order to generate immunoresponsive cells, such as T cells, specific for selected targets, such as malignant cells, with a wide variety of receptor chimera constructs having been described (see U.S. Pat. Nos. 5,843,728; 5,851,828; 5,912,170; 6,004,811; 6,284,240; 6,392,013; 6,410,014; 6,753,162; 8,211,422; and, PCT Publication WO9215322).

In general, CARs are comprised of an extracellular domain, a transmembrane domain, and an intracellular domain, wherein the extracellular domain comprises an antigen-binding domain that is specific for a predetermined target. While the antigen-binding domain of a CAR is often an antibody or antibody fragment (e.g., a single chain variable fragment, scFv), the binding domain is not particularly limited so long as it results in specific recognition of a target. For example, in some embodiments, the antigen-binding domain may comprise a receptor, such that the CAR is capable of binding to the ligand of the receptor. Alternatively, the antigen-binding domain may comprise a ligand, such that the CAR is capable of binding the endogenous receptor of that ligand.

The antigen-binding domain of a CAR is generally separated from the transmembrane domain by a hinge or spacer. The spacer is also not particularly limited, and it is designed to provide the CAR with flexibility. For example, a spacer domain may comprise a portion of a human Fc domain, including a portion of the CH3 domain, or the hinge region of any immunoglobulin, such as IgA, IgD, IgE, IgG, or IgM, or variants thereof. Furthermore, the hinge region may be modified so as to prevent off-target binding by FcRs or other potential interfering objects. For example, the hinge may comprise an IgG4 Fc domain with or without a S228P, L235E, and/or N297Q mutation (according to Kabat numbering) in order to decrease binding to FcRs. Additional spacers/hinges include, but are not limited to, CD4, CD8, and CD28 hinge regions.

The transmembrane domain of a CAR may be derived either from a natural or from a synthetic source. Where the source is natural, the domain may be derived from any membrane bound or transmembrane protein. Transmembrane regions of particular use in this disclosure may be derived from CD8, CD28, CD3, CD45, CD4, CD5, CDS, CD9, CD 16, CD22, CD33, CD37, CD64, CD80, CD86, CD 134, CD137, CD 154, TCR. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Alternative CAR constructs may be characterized as belonging to successive generations. First-generation CARs typically consist of a single-chain variable fragment of an antibody specific for an antigen, for example comprising a $V_L$ linked to a $V_H$ of a specific antibody, linked by a flexible linker, for example by a CD8α hinge domain and a CD8α transmembrane domain, to the transmembrane and intracellular signaling domains of either CD3 or FcRγ (scFv-CD3ζ or scFv-FcRγ; see U.S. Pat. Nos. 7,741,465; 5,912,172; 5,906,936). Second-generation CARs incorporate the intracellular domains of one or more costimulatory molecules, such as CD28, OX40 (CD134), or 4-1BB (CD137) within the endodomain (for example scFv-CD28/OX40/4-1BB-CD3ζ; see U.S. Pat. Nos. 8,911,993; 8,916,381; 8,975,071; 9,101,584; 9,102,760; 9,102,761). Third-generation CARs include a combination of costimulatory endodomains, such a CD3-chain, CD97, GDI 1a-CD18, CD2, ICOS, CD27, CD154, CDS, OX40, 4-1BB, CD2, CD7, LIGHT, LFA-1, NKG2C, B7-H3, CD30, CD40, or CD28 signaling domains (for example scFv-CD28-4-1BB-CD3ζ or scFv-CD28-OX40-CD3ζ; see U.S. Pat. Nos. 8,906,682; 8,399,645; 5,686,281; PCT Publication No. WO2014134165; PCT Publication No. WO2012079000). In certain embodiments, the primary signaling domain comprises a functional signaling domain of a protein selected from the group consisting of CD3 zeta, CD3 gamma, CD3 delta, CD3 epsilon, common FcR gamma (FCERIG), FcR beta (Fc Epsilon Rib), CD79a, CD79b, Fc gamma RIIa, DAP10, and DAP12. In certain preferred embodiments, the primary signaling domain comprises a functional signaling domain of CD3ζ or FcRγ. In certain embodiments, the one or more costimulatory signaling domains comprise a functional signaling domain of a protein selected, each independently, from the group consisting of: CD27, CD28, 4-1BB (CD137), OX40, CD30, CD40, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8 alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D. In certain embodiments, the one or more costimulatory signaling domains comprise a functional signaling domain of a protein selected, each independently, from the group consisting of: 4-1BB, CD27, and CD28. In certain embodiments, a chimeric antigen receptor may have the design as described in U.S. Pat. No. 7,446,190, comprising an intracellular domain of CD3ζ chain (such as amino acid residues 52-163 of the human CD3 zeta chain, as shown in SEQ ID NO: 14 of U.S. Pat. No. 7,446,190), a signaling region from CD28 and an antigen-binding element (or portion or domain; such as scFv). The CD28 portion, when between the zeta chain portion and the antigen-binding element, may suitably include the transmembrane and signaling domains of CD28 (such as amino acid residues 114-220 of SEQ ID NO: 10, full sequence shown in SEQ ID NO: 6 of U.S. Pat. No. 7,446,190; these can include the following portion of CD28 as set forth in Genbank identifier NM_006139 (sequence version 1, 2 or 3): IEVMYPPPYLD-NEK SNGTIIHVKGKHL CP SPLFP GP SKPFWVLVVVGGVLACYSLLVTVA FIIFWVR-SKRSRLLHSDYMNMTPRRPGPTRKHYQPYAPPRD-FAAYRS) (SEQ ID NO: 1). Alternatively, when the zeta sequence lies between the CD28 sequence and the antigen-binding element, intracellular domain of CD28 can be used alone (such as amino sequence set forth in SEQ ID NO: 9 of U.S. Pat. No. 7,446,190). Hence, certain embodiments employ a CAR comprising (a) a zeta chain portion comprising the intracellular domain of human CD3ζ chain, (b) a costimulatory signaling region, and (c) an antigen-binding element (or portion or domain), wherein the costimulatory signaling region comprises the amino acid sequence encoded by SEQ ID NO: 6 of U.S. Pat. No. 7,446,190.

Alternatively, costimulation may be orchestrated by expressing CARs in antigen-specific T cells, chosen so as to be activated and expanded following engagement of their native αβTCR, for example by antigen on professional antigen-presenting cells, with attendant costimulation. In addition, additional engineered receptors may be provided on the immunoresponsive cells, for example to improve targeting of a T-cell attack and/or minimize side effects.

By means of an example and without limitation, Kochenderfer et al., (2009) J Immunother. 32 (7): 689-702 described anti-CD19 chimeric antigen receptors (CAR). FMC63-28Z CAR contained a single chain variable region moiety (scFv) recognizing CD19 derived from the FMC63 mouse hybridoma (described in Nicholson et al., (1997) Molecular Immunology 34: 1157-1165), a portion of the human CD28 molecule, and the intracellular component of the human TCR-ζ molecule. FMC63-CD828BBZ CAR contained the FMC63 scFv, the hinge and transmembrane regions of the CD8 molecule, the cytoplasmic portions of CD28 and 4-1BB, and the cytoplasmic component of the TCR-ζ molecule. The exact sequence of the CD28 molecule included in the FMC63-28Z CAR corresponded to Genbank identifier NM_006139; the sequence included all amino acids starting with the amino acid sequence IEVMYPPPY and continuing all the way to the carboxy-terminus of the protein. To encode the anti-CD19 scFv component of the vector, the authors designed a DNA sequence which was based on a portion of a previously published CAR (Cooper et al., (2003) Blood 101: 1637-1644). This sequence encoded the following components in frame from the 5' end to the 3' end: an XhoI site, the human granulocyte-macrophage colony-stimulating factor (GM-CSF) receptor α-chain signal sequence, the FMC63 light chain variable region (as in Nicholson et al., supra), a linker peptide (as in Cooper et al., supra), the FMC63 heavy chain variable region (as in Nicholson et al., supra), and a NotI site. A plasmid encoding this sequence was digested with XhoI and NotI. To form the MSGV-FMC63-28Z retroviral vector, the XhoI and NotIdigested fragment encoding the FMC63 scFv was ligated into a second XhoI and NotIdigested fragment that encoded the MSGV retroviral backbone (as in Hughes et al., (2005) Human Gene Therapy 16: 457-472) as well as part of the extracellular portion of human CD28, the entire transmembrane and cytoplasmic portion of human CD28, and the cytoplasmic portion of the human TCR-t molecule (as in Maher et al., 2002) Nature Biotechnology 20: 70-75). The FMC63-28Z CAR is included in the KTE-C19 (axicabtagene ciloleucel) anti-CD19 CAR-T therapy product in development by Kite Pharma, Inc. for the treatment of inter alia patients with relapsed/refractory aggressive B-cell non-Hodgkin lymphoma (NHL). Accordingly, in certain embodiments, cells intended for adoptive cell therapies, more particularly immunoresponsive cells such as T cells, may express the FMC63-28Z CAR as described by Kochenderfer et al. (supra). Hence, in certain embodiments, cells intended for adoptive cell therapies, more particularly immunoresponsive cells such as T cells, may comprise a CAR comprising an extracellular antigen-binding element (or portion or domain; such as scFv) that specifically binds to an antigen, an intracellular signaling domain comprising an intracellular domain of a CD3ζ chain, and a costimulatory signaling region comprising a signaling domain of CD28. Preferably, the CD28 amino acid sequence is as set forth in Genbank identifier NM_006139 (sequence version 1, 2 or 3) starting with the amino acid sequence IEVMYPPPY (SEQ ID NO: 2) and continuing all the way to the carboxy-terminus of the protein. The sequence is reproduced herein: IEVMYPPPYLDNEK SNGTIIHVKGKHL CP SPLFP GP SKPFWVLVVVGGVLACYSLLVTVA FIIFWVR-SKRSRLLHSDYMNMTPRRPGPTRKHYQPYAPPRD-FAAYRS. Preferably, the antigen is CD19, more preferably the antigen-binding element is an anti-CD19 scFv, even more preferably the anti-CD19 scFv as described by Kochenderfer et al. (supra).

Additional anti-CD19 CARs are further described in WO2015187528. More particularly Example 1 and Table 1 of WO2015187528, incorporated by reference herein, demonstrate the generation of anti-CD19 CARs based on a fully human anti-CD19 monoclonal antibody (47G4, as described in US20100104509) and murine anti-CD19 monoclonal antibody (as described in Nicholson et al. and explained above). Various combinations of a signal sequence (human CD8-alpha or GM-CSF receptor), extracellular and transmembrane regions (human CD8-alpha) and intracellular T-cell signalling domains (CD28-CD3ζ; 4-1BB-CD3ζ; CD27-CD3; CD28-CD27-CD3ζ, 4-1BB-CD27-CD3ζ; CD27-4-1BB-CD3ζ; CD28-CD27-FcεRI gamma chain; or CD28-FcεRI gamma chain) were disclosed. Hence, in certain embodiments, cells intended for adoptive cell therapies, more particularly immunoresponsive cells such as T cells, may comprise a CAR comprising an extracellular antigen-binding element that specifically binds to an antigen, an extracellular and transmembrane region as set forth in Table 1 of WO2015187528 and an intracellular T-cell signalling domain as set forth in Table 1 of WO2015187528. Preferably, the antigen is CD19, more preferably the antigen-binding element is an anti-CD19 scFv, even more preferably the mouse or human anti-CD19 scFv as described in Example 1 of WO2015187528. In certain embodiments, the CAR comprises, consists essentially of or consists of an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13 as set forth in Table 1 of WO2015187528.

In certain embodiments, the immune cell may, in addition to a CAR or exogenous TCR as described herein, further comprise a chimeric inhibitory receptor (inhibitory CAR) that specifically binds to a second target antigen and is capable of inducing an inhibitory or immunosuppressive or repressive signal to the cell upon recognition of the second target antigen. In certain embodiments, the chimeric inhibitory receptor comprises an extracellular antigen-binding element (or portion or domain) configured to specifically bind to a target antigen, a transmembrane domain, and an intracellular immunosuppressive or repressive signaling domain. In certain embodiments, the second target antigen is an antigen that is not expressed on the surface of a cancer cell or infected cell or the expression of which is downregulated on a cancer cell or an infected cell. In certain embodiments, the second target antigen is an MHC-class I molecule. In certain embodiments, the intracellular signaling domain comprises a functional signaling portion of an immune checkpoint molecule, such as for example PD-1 or CTLA4. Advantageously, the inclusion of such inhibitory CAR reduces the chance of the engineered immune cells attacking non-target (e.g., non-cancer) tissues.

Alternatively, T-cells expressing CARs may be further modified to reduce or eliminate expression of endogenous TCRs in order to reduce off-target effects. Reduction or elimination of endogenous TCRs can reduce off-target effects and increase the effectiveness of the T cells (U.S. Pat. No. 9,181,527). T cells stably lacking expression of a functional TCR may be produced using a variety of approaches. T cells internalize, sort, and degrade the entire T cell receptor as a complex, with a half-life of about 10 hours in resting T cells and 3 hours in stimulated T cells (von Essen, M. et al. 2004. J. Immunol. 173:384-393). Proper functioning of the TCR complex requires the proper stoichiometric ratio of the proteins that compose the TCR complex. TCR function also requires two functioning TCR zeta proteins with ITAM motifs. The activation of the TCR upon engagement of its MHC-peptide ligand requires the engagement of several TCRs on the same T cell, which all must signal properly. Thus, if a TCR complex is destabilized with proteins that do not associate properly or cannot signal optimally, the T cell will not become activated sufficiently to begin a cellular response.

Accordingly, in some embodiments, TCR expression may eliminated using RNA interference (e.g., shRNA, siRNA, miRNA, etc.), CRISPR, or other methods that target the nucleic acids encoding specific TCRs (e.g., TCR-α and TCR-β) and/or CD3 chains in primary T cells. By blocking expression of one or more of these proteins, the T cell will no longer produce one or more of the key components of the TCR complex, thereby destabilizing the TCR complex and preventing cell surface expression of a functional TCR.

In some instances, CAR may also comprise a switch mechanism for controlling expression and/or activation of the CAR. For example, a CAR may comprise an extracellular, transmembrane, and intracellular domain, in which the extracellular domain comprises a target-specific binding element that comprises a label, binding domain, or tag that is specific for a molecule other than the target antigen that is expressed on or by a target cell. In such embodiments, the specificity of the CAR is provided by a second construct that comprises a target antigen binding domain (e.g., an scFv or a bispecific antibody that is specific for both the target antigen and the label or tag on the CAR) and a domain that is recognized by or binds to the label, binding domain, or tag on the CAR. See, e.g., WO 2013/044225, WO 2016/000304, WO 2015/057834, WO 2015/057852, WO 2016/070061, U.S. Pat. No. 9,233,125, US 2016/0129109. In this way, a T-cell that expresses the CAR can be administered to a subject, but the CAR cannot bind its target antigen until the second composition comprising an antigen-specific binding domain is administered.

Alternative switch mechanisms include CARs that require multimerization in order to activate their signaling function (see, e.g., US 2015/0368342, US 2016/0175359, US 2015/0368360) and/or an exogenous signal, such as a small molecule drug (US 2016/0166613, Yung et al., Science, 2015), in order to elicit a T-cell response. Some CARs may also comprise a "suicide switch" to induce cell death of the CAR T-cells following treatment (Buddee et al., PLoS One, 2013) or to downregulate expression of the CAR following binding to the target antigen (WO 2016/011210).

Alternative techniques may be used to transform target immunoresponsive cells, such as protoplast fusion, lipofection, transfection or electroporation. A wide variety of vectors may be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), may be used to introduce CARs, for example using 2nd generation antigen-specific CARs signaling through CD3ζ and either CD28 or CD137. Viral vectors may for example include vectors based on HIV, SV40, EBV, HSV or BPV.

Cells that are targeted for transformation may for example include T cells, Natural Killer (NK) cells, cytotoxic T lymphocytes (CTL), regulatory T cells, human embryonic stem cells, tumor-infiltrating lymphocytes (TIL) or a pluripotent stem cell from which lymphoid cells may be differentiated. T cells expressing a desired CAR may for example be selected through co-culture with γ-irradiated activating and propagating cells (AaPC), which co-express the cancer antigen and co-stimulatory molecules. The engineered CAR T-cells may be expanded, for example by co-culture on AaPC in presence of soluble factors, such as IL-2 and IL-21. This expansion may for example be carried out so as to provide memory CAR+ T cells (which may for example be assayed by non-enzymatic digital array and/or multi-panel flow cytometry). In this way, CAR T cells may be provided that have specific cytotoxic activity against antigen-bearing tumors (optionally in conjunction with production of desired chemokines such as interferon-γ). CART cells of this kind may for example be used in animal models, for example to treat tumor xenografts.

Unlike T-cell receptors (TCRs) that are MHC restricted, CARs can potentially bind any cell surface-expressed antigen and can thus be more universally used to treat patients (see Irving et al., Engineering Chimeric Antigen Receptor T-Cells for Racing in Solid Tumors: Don't Forget the Fuel, Front. Immunol., 3 Apr. 2017, doi.org/10.3389/fimmu.2017.00267). In certain embodiments, in the absence of endogenous T-cell infiltrate (e.g., due to aberrant antigen processing and presentation), which precludes the use of TIL therapy and immune checkpoint blockade, the transfer of CAR T-cells may be used to treat patients (see, e.g., Hinrichs C S, Rosenberg S A. Exploiting the curative potential of adoptive T-cell therapy for cancer. Immunol Rev (2014) 257(1):56-71. doi:10.1111/imr. 12132).

Approaches such as the foregoing may be adapted to provide methods of treating and/or increasing survival of a subject having a disease, such as a neoplasia, for example by administering an effective amount of an immunoresponsive cell comprising an antigen recognizing receptor that binds a selected antigen, wherein the binding activates the immunoresponsive cell, thereby treating or preventing the disease (such as a neoplasia, a pathogen infection, an autoimmune disorder, or an allogeneic transplant reaction).

In certain embodiments, the treatment can be administered after lymphodepleting pretreatment in the form of chemotherapy (typically a combination of cyclophosphamide and fludarabine) or radiation therapy. Initial studies in ACT had short lived responses and the transferred cells did not persist in vivo for very long (Houot et al., T-cell-based immunotherapy: adoptive cell transfer and checkpoint inhibition. Cancer Immunol Res (2015) 3(10):1115-22; and Kamta et al., Advancing Cancer Therapy with Present and Emerging Immuno-Oncology Approaches. Front. Oncol. (2017) 7:64). Immune suppressor cells like Tregs and MDSCs may attenuate the activity of transferred cells by outcompeting them for the necessary cytokines. Not being bound by a theory lymphodepleting pretreatment may eliminate the suppressor cells allowing the TILs to persist. In certain embodiments, transferred cells can be depleted for the suppressive T cells of the present invention. Not being bound by a theory, only effector cells are transferred and the transferred cells may persist longer.

In one embodiment, the treatment can be administrated into patients undergoing an immunosuppressive treatment. The cells or population of cells, may be made resistant to at least one immunosuppressive agent due to the inactivation of a gene encoding a receptor for such immunosuppressive agent. Not being bound by a theory, the immunosuppressive treatment should help the selection and expansion of the immunoresponsive or T cells according to the invention within the patient.

In certain embodiments, the treatment can be administered before primary treatment (e.g., surgery or radiation therapy) to shrink a tumor before the primary treatment. In another embodiment, the treatment can be administered after primary treatment to remove any remaining cancer cells.

In certain embodiments, immunometabolic barriers can be targeted therapeutically prior to and/or during ACT to enhance responses to ACT or CAR T-cell therapy and to support endogenous immunity (see, e.g., Irving et al., Engineering Chimeric Antigen Receptor T-Cells for Racing in Solid Tumors: Don't Forget the Fuel, Front. Immunol., Apr. 3, 2017, doi.org/10.3389/fimmu.2017.00267).

The administration of cells or population of cells, such as immune system cells or cell populations, such as more particularly immunoresponsive cells or cell populations, as disclosed herein may be carried out in any convenient manner, including by aerosol inhalation, injection, ingestion, transfusion, implantation or transplantation. The cells or population of cells may be administered to a patient subcutaneously, intradermally, intratumorally, intranodally, intramedullary, intramuscularly, intrathecally, by intravenous or intralymphatic injection, or intraperitoneally. In some embodiments, the disclosed CARs may be delivered or administered into a cavity formed by the resection of tumor tissue (i.e. intracavity delivery) or directly into a tumor prior to resection (i.e. intratumoral delivery). In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. Dosing in CAR T cell therapies may for example involve administration of from $10^6$ to $10^9$ cells/kg, with or without a course of lymphodepletion, for example with cyclophosphamide. The cells or population of cells can be administrated in one or more doses. In another embodiment, the effective amount of cells are administrated as a single dose. In another embodiment, the effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, the effective amount of cells or composition comprising those cells are administrated parenterally. The administration can be an intravenous administration. The administration can be directly done by injection within a tumor.

To guard against possible adverse reactions, engineered immunoresponsive cells may be equipped with a transgenic safety switch, in the form of a transgene that renders the cells vulnerable to exposure to a specific signal. For example, the herpes simplex viral thymidine kinase (TK) gene may be used in this way, for example by introduction into allogeneic T lymphocytes used as donor lymphocyte infusions following stem cell transplantation (Greco, et al., Improving the safety of cell therapy with the TK-suicide gene. Front. Pharmacol. 2015; 6: 95). In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication WO2011146862; PCT Patent Publication WO2014011987; PCT Patent Publication WO2013040371; Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28(6):1107-15 (2010)).

In a further refinement of adoptive therapies, genome editing may be used to tailor immunoresponsive cells to alternative implementations, for example providing edited CAR T cells (see Poirot et al., 2015, Multiplex genome edited T-cell manufacturing platform for "off-the-shelf" adoptive T-cell immunotherapies, Cancer Res 75 (18): 3853; Ren et al., 2016, Multiplex genome editing to generate universal CAR T cells resistant to PD1 inhibition, Clin Cancer Res. 2016 Nov. 4; and Qasim et al., 2017, Molecular remission of infant B-ALL after infusion of universal TALEN gene-edited CAR T cells, Sci Transl Med. 2017 Jan. 25; 9(374)). Cells may be edited using any CRISPR system and method of use thereof as described herein. CRISPR systems may be delivered to an immune cell by any method described herein. In preferred embodiments, cells are edited ex vivo and transferred to a subject in need thereof. Immunoresponsive cells, CART cells or any cells used for adoptive cell transfer may be edited. Editing may be performed for example to insert or knock-in an exogenous gene, such as an exogenous gene encoding a CAR or a TCR, at a preselected locus in a cell; to eliminate potential alloreactive T-cell receptors (TCR) or to prevent inappropriate pairing between endogenous and exogenous TCR chains, such as to knock-out or knock-down expression of an endogenous TCR in a cell; to disrupt the target of a chemotherapeutic agent in a cell; to block an immune checkpoint, such as to knock-out or knock-down expression of an immune checkpoint protein or receptor in a cell; to knock-out or knock-down expression of other gene or genes in a cell, the reduced expression or lack of expression of which can enhance the efficacy of adoptive therapies using the cell; to knock-out or knock-down expression of an endogenous gene in a cell, said endogenous gene encoding an antigen targeted by an exogenous CAR or TCR; to knock-out or knock-down expression of one or more WIC constituent proteins in a cell; to activate a T cell; to modulate cells such that the cells are resistant to exhaustion or dysfunction; and/or increase the differentiation and/or proliferation of functionally exhausted or dysfunctional CD8+ T-cells (see PCT Patent Publications: WO2013176915, WO2014059173, WO2014172606, WO2014184744, and WO2014191128). Editing may result in inactivation of a gene.

By inactivating a gene it is intended that the gene of interest is not expressed in a functional protein form. In a particular embodiment, the CRISPR system specifically catalyzes cleavage in one targeted gene thereby inactivating said targeted gene. The nucleic acid strand breaks caused are commonly repaired through the distinct mechanisms of homologous recombination or non-homologous end joining (NHEJ). However, NHEJ is an imperfect repair process that often results in changes to the DNA sequence at the site of the cleavage. Repair via non-homologous end joining (NHEJ) often results in small insertions or deletions (Indel) and can be used for the creation of specific gene knockouts. Cells in which a cleavage induced mutagenesis event has occurred can be identified and/or selected by well-known methods in the art.

Hence, in certain embodiments, editing of cells (such as by CRISPR/Cas), particularly cells intended for adoptive cell therapies, more particularly immunoresponsive cells such as T cells, may be performed to insert or knock-in an exogenous gene, such as an exogenous gene encoding a CAR or a TCR, at a preselected locus in a cell. Conventionally, nucleic acid molecules encoding CARs or TCRs are transfected or transduced to cells using randomly integrating vectors, which, depending on the site of integration, may lead to clonal expansion, oncogenic transformation, variegated transgene expression and/or transcriptional silencing of the transgene. Directing of transgene(s) to a specific locus in a cell can minimize or avoid such risks and advantageously provide for uniform expression of the transgene(s) by the cells. Without limitation, suitable 'safe harbor' loci for directed transgene integration include CCR5 or AAVS1. Homology-directed repair (HDR) strategies are known and described elsewhere in this specification allowing to insert transgenes into desired loci.

Further suitable loci for insertion of transgenes, in particular CAR or exogenous TCR transgenes, include without limitation loci comprising genes coding for constituents of endogenous T-cell receptor, such as T-cell receptor alpha locus (TRA) or T-cell receptor beta locus (TRB), for example T-cell receptor alpha constant (TRAC) locus, T-cell receptor beta constant 1 (TRBC1) locus or T-cell receptor beta constant 2 (TRBC1) locus. Advantageously, insertion of a transgene into such locus can simultaneously achieve expression of the transgene, potentially controlled by the endogenous promoter, and knock-out expression of the endogenous TCR. This approach has been exemplified in Eyquem et al., (2017) Nature 543: 113-117, wherein the authors used CRISPR/Cas9 gene editing to knock-in a DNA molecule encoding a CD19-specific CAR into the TRAC locus downstream of the endogenous promoter; the CAR-T cells obtained by CRISPR were significantly superior in terms of reduced tonic CAR signaling and exhaustion.

T cell receptors (TCR) are cell surface receptors that participate in the activation of T cells in response to the presentation of antigen. The TCR is generally made from two chains, α and β, which assemble to form a heterodimer and associates with the CD3-transducing subunits to form the T cell receptor complex present on the cell surface. Each α and β chain of the TCR consists of an immunoglobulin-like N-terminal variable (V) and constant (C) region, a hydrophobic transmembrane domain, and a short cytoplasmic region. As for immunoglobulin molecules, the variable region of the α and β chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of graft versus host disease (GVHD). The inactivation of TCRα or TCRβ can result in the elimination of the TCR from the surface of T cells preventing recognition of alloantigen and thus GVHD. However, TCR disruption generally results in the elimination of the CD3 signaling component and alters the means of further T cell expansion.

Hence, in certain embodiments, editing of cells (such as by CRISPR/Cas), particularly cells intended for adoptive cell therapies, more particularly immunoresponsive cells such as T cells, may be performed to knock-out or knock-down expression of an endogenous TCR in a cell. For example, NHEJ-based or HDR-based gene editing approaches can be employed to disrupt the endogenous TCR alpha and/or beta chain genes. For example, gene editing system or systems, such as CRISPR/Cas system or systems, can be designed to target a sequence found within the TCR beta chain conserved between the beta 1 and beta 2 constant region genes (TRBC1 and TRBC2) and/or to target the constant region of the TCR alpha chain (TRAC) gene.

Allogeneic cells are rapidly rejected by the host immune system. It has been demonstrated that, allogeneic leukocytes present in non-irradiated blood products will persist for no more than 5 to 6 days (Boni, Muranski et al. 2008 Blood 1; 112(12):4746-54). Thus, to prevent rejection of allogeneic cells, the host's immune system usually has to be suppressed to some extent. However, in the case of adoptive cell transfer the use of immunosuppressive drugs also have a detrimental effect on the introduced therapeutic T cells. Therefore, to effectively use an adoptive immunotherapy approach in these conditions, the introduced cells would need to be resistant to the immunosuppressive treatment. Thus, in a particular embodiment, the present invention further comprises a step of modifying T cells to make them resistant to an immunosuppressive agent, preferably by inactivating at least one gene encoding a target for an immunosuppressive agent. An immunosuppressive agent is an agent that suppresses immune function by one of several mechanisms of action. An immunosuppressive agent can be, but is not limited to a calcineurin inhibitor, a target of rapamycin, an interleukin-2 receptor α-chain blocker, an inhibitor of inosine monophosphate dehydrogenase, an inhibitor of dihydrofolic acid reductase, a corticosteroid or an immunosuppressive antimetabolite. The present invention allows conferring immunosuppressive resistance to T cells for immunotherapy by inactivating the target of the immunosuppressive agent in T cells. As non-limiting examples, targets for an immunosuppressive agent can be a receptor for an immunosuppressive agent such as: CD52, glucocorticoid receptor (GR), a FKBP family gene member and a cyclophilin family gene member.

In certain embodiments, editing of cells (such as by CRISPR/Cas), particularly cells intended for adoptive cell therapies, more particularly immunoresponsive cells such as T cells, may be performed to block an immune checkpoint, such as to knock-out or knock-down expression of an immune checkpoint protein or receptor in a cell. Immune checkpoints are inhibitory pathways that slow down or stop immune reactions and prevent excessive tissue damage from uncontrolled activity of immune cells. In certain embodiments, the immune checkpoint targeted is the programmed death-1 (PD-1 or CD279) gene (PDCD1). In other embodiments, the immune checkpoint targeted is cytotoxic T-lymphocyte-associated antigen (CTLA-4). In additional embodiments, the immune checkpoint targeted is another member of the CD28 and CTLA4 Ig superfamily such as TIM-3, BTLA, LAG3, ICOS, PDL1 or KIR.

Additional immune checkpoints include Src homology 2 domain-containing protein tyrosine phosphatase 1 (SHP-1) (Watson H A, et al., SHP-1: the next checkpoint target for cancer immunotherapy? Biochem Soc Trans. 2016 Apr. 15; 44(2):356-62). SHP-1 is a widely expressed inhibitory protein tyrosine phosphatase (PTP). In T-cells, it is a negative regulator of antigen-dependent activation and proliferation. It is a cytosolic protein, and therefore not amenable to antibody-mediated therapies, but its role in activation and proliferation makes it an attractive target for genetic manipulation in adoptive transfer strategies, such as chimeric antigen receptor (CAR) T cells. Immune checkpoints may also include T cell immunoreceptor with Ig and ITIM domains (TIGIT/Vstm3/WUCAM/VSIG9) and VISTA (Le Mercier I, et al., (2015) Beyond CTLA-4 and PD-1, the generation Z of negative checkpoint regulators. Front. Immunol. 6:418).

WO2014172606 relates to the use of MT1 and/or MT2 inhibitors to increase proliferation and/or activity of exhausted CD8+ T-cells and to decrease CD8+ T-cell0 exhaustion (e.g., decrease functionally exhausted or unresponsive CD8+ immune cells). In certain embodiments, metallothioneins are targeted by gene editing in adoptively transferred T cells.

In certain embodiments, editing of cells (such as by CRISPR/Cas), particularly cells intended for adoptive cell therapies, more particularly immunoresponsive cells such as T cells, may be performed to enhance or maintain expression of co-stimulatory receptors (co-stimulatory immune checkpoint molecule), such as a member of the TNFR superfamily including, but not limited to CD40, OX40, CD137 (4-1BB), GITR or CD27.

In certain embodiments, targets of gene editing may be at least one targeted locus involved in the expression of an immune checkpoint protein. Such targets may include, but are not limited to CTLA4, PPP2CA, PPP2CB, PTPN6, PTPN22, PDCD1, ICOS (CD278), PDL1, KIR, LAG3, HAVCR2, BTLA, CD160, TIGIT, CD96, CRTAM, LAIR1, SIGLEC7, SIGLEC9, CD244 (2B4), TNFRSF10B, TNFRSF10A, CASP8, CASP10, CASP3, CASP6, CASP7, FADD, FAS, TGFBRII, TGFRBRI, SMAD2, SMAD3, SMAD4, SMAD10, SKI, SKIL, TGIF1, IL 10RA, IL10RB, HMOX2, IL6R, IL6ST, EIF2AK4, CSK, PAG1, SITZ, FOXP3, PRDM1, BATF, VISTA, GUCY1A2, GUCY1A3, GUCY1B2, GUCY1B3, MT1, MT2, CD40, OX40, CD137, GITR, CD27, SHP-1, TIM-3, CEACAM-1, CEACAM-3, or CEACAM-5. In preferred embodiments, the gene locus involved in the expression of PD-1 or CTLA-4 genes is targeted. In other preferred embodiments, combinations of genes are targeted, such as but not limited to PD-1 and TIGIT.

By means of an example and without limitation, WO2016196388 concerns an engineered T cell comprising (a) a genetically engineered antigen receptor that specifically binds to an antigen, which receptor may be a CAR; and (b) a disrupted gene encoding a PD-L1, an agent for disruption of a gene encoding a PD-L1, and/or disruption of a gene encoding PD-L1, wherein the disruption of the gene may be mediated by a gene editing nuclease, a zinc finger nuclease (ZFN), CRISPR/Cas9 and/or TALEN. WO2015142675 relates to immune effector cells comprising a CAR in combination with an agent (such as CRISPR, TALEN or ZFN) that increases the efficacy of the immune effector cells in the treatment of cancer, wherein the agent may inhibit an immune inhibitory molecule, such as PD1, PD-L1, CTLA-4, TIM-3, LAG-3, VISTA, BTLA, TIGIT, LAIR1, CD160, 2B4, TGFR beta, CEACAM-1, CEACAM-3, or CEACAM-5. Ren et al., (2017) Clin Cancer Res 23 (9) 2255-2266 performed lentiviral delivery of CAR and electro-transfer of Cas9 mRNA and gRNAs targeting endogenous TCR, (3-2 microglobulin (B2M) and PD1 simultaneously, to generate gene-disrupted allogeneic CAR T cells deficient of TCR, HLA class I molecule and PD1.

In certain embodiments, cells may be engineered to express a CAR, wherein expression and/or function of methylcytosine dioxygenase genes (TET1, TET2 and/or TET3) in the cells has been reduced or eliminated, such as by CRISPR, ZNF or TALEN (for example, as described in WO201704916).

In certain embodiments, editing of cells (such as by CRISPR/Cas), particularly cells intended for adoptive cell therapies, more particularly immunoresponsive cells such as T cells, may be performed to knock-out or knock-down expression of an endogenous gene in a cell, said endogenous gene encoding an antigen targeted by an exogenous CAR or TCR, thereby reducing the likelihood of targeting of the engineered cells. In certain embodiments, the targeted antigen may be one or more antigen selected from the group consisting of CD38, CD138, CS-1, CD33, CD26, CD30, CD53, CD92, CD100, CD148, CD150, CD200, CD261, CD262, CD362, human telomerase reverse transcriptase (hTERT), survivin, mouse double minute 2 homolog (MDM2), cytochrome P450 1B1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53, cyclin (D1), B cell maturation antigen (BCMA), transmembrane activator and CAML Interactor (TACI), and B-cell activating factor receptor (BAFF-R) (for example, as described in WO2016011210 and WO2017011804).

In certain embodiments, editing of cells (such as by CRISPR/Cas), particularly cells intended for adoptive cell therapies, more particularly immunoresponsive cells such as T cells, may be performed to knock-out or knock-down expression of one or more MHC constituent proteins, such as one or more HLA proteins and/or beta-2 microglobulin (B2M), in a cell, whereby rejection of non-autologous (e.g., allogeneic) cells by the recipient's immune system can be reduced or avoided. In preferred embodiments, one or more HLA class I proteins, such as HLA-A, B and/or C, and/or B2M may be knocked-out or knocked-down. Preferably, B2M may be knocked-out or knocked-down. By means of an example, Ren et al., (2017) Clin Cancer Res 23 (9)

2255-2266 performed lentiviral delivery of CAR and electro-transfer of Cas9 mRNA and gRNAs targeting endogenous TCR, (3-2 microglobulin (B2M) and PD1 simultaneously, to generate gene-disrupted allogeneic CAR T cells deficient of TCR, HLA class I molecule and PD1.

In other embodiments, at least two genes are edited. Pairs of genes may include, but are not limited to PD1 and TCRa, PD1 and TCR(3, CTLA-4 and TCRa, CTLA-4 and TCR(3, LAG3 and TCRa, LAG3 and TCR(3, Tim3 and TCRa, Tim3 and TCR(3, BTLA and TCRa, BTLA and TCR(3, BY55 and TCRa, BY55 and TCR(3, TIGIT and TCRa, TIGIT and TCR(3, B7H5 and TCRa, B7H5 and TCR(3, LAIR1 and TCRa, LAIR1 and TCR(3, SIGLEC10 and TCRa, SIGLEC10 and TCR(3, 2B4 and TCRa, 2B4 and TCR(3.

In certain embodiments, a cell may be multiply edited (multiplex genome editing) as taught herein to (1) knock-out or knock-down expression of an endogenous TCR (for example, TRBC1, TRBC2 and/or TRAC), (2) knock-out or knock-down expression of an immune checkpoint protein or receptor (for example PD1, PD-L 1 and/or CTLA4); and β) knock-out or knock-down expression of one or more MHC constituent proteins (for example, HLA-A, B and/or C, and/or B2M, preferably B2M).

Whether prior to or after genetic modification of the T cells, the T cells can be activated and expanded generally using methods as described, for example, in U.S. Pat. Nos. 6,352,694; 6,534,055; 6,905,680; 5,858,358; 6,887,466; 6,905,681; 7,144,575; 7,232,566; 7,175,843; 5,883,223; 6,905,874; 6,797,514; 6,867,041; and 7,572,631. T cells can be expanded in vitro or in vivo.

Immune cells may be obtained using any method known in the art. In one embodiment T cells that have infiltrated a tumor are isolated. T cells may be removed during surgery. T cells may be isolated after removal of tumor tissue by biopsy. T cells may be isolated by any means known in the art. In one embodiment, the method may comprise obtaining a bulk population of T cells from a tumor sample by any suitable method known in the art. For example, a bulk population of T cells can be obtained from a tumor sample by dissociating the tumor sample into a cell suspension from which specific cell populations can be selected. Suitable methods of obtaining a bulk population of T cells may include, but are not limited to, any one or more of mechanically dissociating (e.g., mincing) the tumor, enzymatically dissociating (e.g., digesting) the tumor, and aspiration (e.g., as with a needle).

The bulk population of T cells obtained from a tumor sample may comprise any suitable type of T cell. Preferably, the bulk population of T cells obtained from a tumor sample comprises tumor infiltrating lymphocytes (TILs).

The tumor sample may be obtained from any mammal. Unless stated otherwise, as used herein, the term "mammal" refers to any mammal including, but not limited to, mammals of the order Lagomorpha, such as rabbits; the order Carnivora, including Felines (cats) and Canines (dogs); the order Artiodactyla, including Bovines (cows) and Swines (pigs); or of the order Perissodactyla, including Equines (horses). The mammals may be non-human primates, e.g., of the order Primates, Ceboids, or Sigmoids (monkeys) or of the order Anthropoids (humans and apes). In some embodiments, the mammal may be a mammal of the order Rodentia, such as mice and hamsters. Preferably, the mammal is a non-human primate or a human. An especially preferred mammal is the human.

T cells can be obtained from a number of sources, including peripheral blood mononuclear cells, bone marrow, lymph node tissue, spleen tissue, and tumors. In certain embodiments of the present invention, T cells can be obtained from a unit of blood collected from a subject using any number of techniques known to the skilled artisan, such as Ficoll separation. In one preferred embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor) according to the manufacturer's instructions. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient.

A specific subpopulation of T cells can be further isolated by positive or negative selection techniques. For example, in one preferred embodiment, T cells are isolated by incubation with antibody-conjugated beads (e.g., specific for any marker described herein), such as DYNABEADS® for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells.

Enrichment of a T cell population by negative selection can be accomplished with a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected.

Further, monocyte populations (i.e., CD14+ cells) may be depleted from blood preparations by a variety of methodologies, including anti-CD14 coated beads or columns, or utilization of the phagocytotic activity of these cells to facilitate removal. Accordingly, in one embodiment, the invention uses paramagnetic particles of a size sufficient to be engulfed by phagocytotic monocytes. In certain embodiments, the paramagnetic particles are commercially available beads, for example, those produced by Life Technologies under the trade name Dynabeads™. In one embodiment, other non-specific cells are removed by coating the paramagnetic particles with "irrelevant" proteins (e.g., serum proteins or antibodies). Irrelevant proteins and antibodies include those proteins and antibodies or fragments thereof that do not specifically target the T cells to be isolated. In certain embodiments the irrelevant beads include beads coated with sheep anti-mouse antibodies, goat anti-mouse antibodies, and human serum albumin.

In brief, such depletion of monocytes is performed by preincubating T cells isolated from whole blood, apheresed peripheral blood, or tumors with one or more varieties of irrelevant or non-antibody coupled paramagnetic particles at any amount that allows for removal of monocytes (approximately a 20:1 bead:cell ratio) for about 30 minutes to 2 hours at 22 to 37 degrees C., followed by magnetic removal of cells which have attached to or engulfed the paramagnetic particles. Such separation can be performed using standard methods available in the art. For example, any magnetic separation methodology may be used including a variety of which are commercially available, (e.g., DYNAL® Magnetic Particle Concentrator (DYNAL MPC®)). Assurance of requisite depletion can be monitored by a variety of methodologies known to those of ordinary skill in the art, including flow cytometric analysis of CD14 positive cells, before and after depletion.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest or from samples where there are many tumor cells present (i.e., leukemic blood, tumor tissue, etc). Such populations of cells may have therapeutic value and would be desirable to obtain.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. In one embodiment, the concentration of cells used is $5 \times 10^6$/ml. In other embodiments, the concentration used can be from about $1 \times 10^5$/ml to $1 \times 10^6$/ml, and any integer value in between.

In certain embodiments, T cells can also be frozen. Wishing not to be bound by theory, the freeze and subsequent thaw step provides a more uniform product by removing granulocytes and to some extent monocytes in the cell population. After a washing step to remove plasma and platelets, the cells may be suspended in a freezing solution. While many freezing solutions and parameters are known in the art and will be useful in this context, one method involves using PBS containing 20% DMSO and 8% human serum albumin, or other suitable cell freezing media, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

T cells for use in the present invention may also be antigen-specific T cells. For example, tumor-specific T cells can be used. In certain embodiments, antigen-specific T cells can be isolated from a patient of interest, such as a patient afflicted with a cancer or an infectious disease. In one embodiment neoepitopes are determined for a subject and T cells specific to these antigens are isolated. Antigen-specific cells for use in expansion may also be generated in vitro using any number of methods known in the art, for example, as described in U.S. Patent Publication No. US 20040224402 entitled, Generation and Isolation of Antigen-Specific T Cells, or in U.S. Pat. No. 6,040,177. Antigen-specific cells for use in the present invention may also be generated using any number of methods known in the art, for example, as described in Current Protocols in Immunology, or Current Protocols in Cell Biology, both published by John Wiley & Sons, Inc., Boston, Mass.

In a related embodiment, it may be desirable to sort or otherwise positively select (e.g. via magnetic selection) the antigen specific cells prior to or following one or two rounds of expansion. Sorting or positively selecting antigen-specific cells can be carried out using peptide-MHC tetramers (Altman, et al., Science. 1996 Oct. 4; 274(5284):94-6). In another embodiment the adaptable tetramer technology approach is used (Andersen et al., 2012 Nat Protoc. 7:891-902). Tetramers are limited by the need to utilize predicted binding peptides based on prior hypotheses, and the restriction to specific HLAs. Peptide-MHC tetramers can be generated using techniques known in the art and can be made with any MHC molecule of interest and any antigen of interest as described herein. Specific epitopes to be used in this context can be identified using numerous assays known in the art. For example, the ability of a polypeptide to bind to MHC class I may be evaluated indirectly by monitoring the ability to promote incorporation of $^{125}$I labeled β2-microglobulin (β2m) into MHC class I/02m/peptide heterotrimeric complexes (see Parker et al., J. Immunol. 152:163, 1994).

In one embodiment cells are directly labeled with an epitope-specific reagent for isolation by flow cytometry followed by characterization of phenotype and TCRs. In one T cells are isolated by contacting the T cell specific antibodies. Sorting of antigen-specific T cells, or generally any cells of the present invention, can be carried out using any of a variety of commercially available cell sorters, including, but not limited to, MoFlo sorter (DakoCytomation, Fort Collins, Colo.), FACSAria™, FACSArray™, FACSVantage™, BD™ LSR II, and FACSCalibur™ (BD Biosciences, San Jose, Calif.).

In a preferred embodiment, the method comprises selecting cells that also express CD3. The method may comprise specifically selecting the cells in any suitable manner. Preferably, the selecting is carried out using flow cytometry. The flow cytometry may be carried out using any suitable method known in the art. The flow cytometry may employ any suitable antibodies and stains. Preferably, the antibody is chosen such that it specifically recognizes and binds to the particular biomarker being selected. For example, the specific selection of CD3, CD8, TIM-3, LAG-3, 4-1BB, or PD-1 may be carried out using anti-CD3, anti-CD8, anti-TIM-3, anti-LAG-3, anti-4-1BB, or anti-PD-1 antibodies, respectively. The antibody or antibodies may be conjugated to a bead (e.g., a magnetic bead) or to a fluorochrome. Preferably, the flow cytometry is fluorescence-activated cell sorting (FACS). TCRs expressed on T cells can be selected based on reactivity to autologous tumors. Additionally, T cells that are reactive to tumors can be selected for based on markers using the methods described in patent publication Nos. WO2014133567 and WO2014133568, herein incorporated by reference in their entirety. Additionally, activated T cells can be selected for based on surface expression of CD107a.

In one embodiment of the invention, the method further comprises expanding the numbers of T cells in the enriched cell population. Such methods are described in U.S. Pat. No. 8,637,307 and is herein incorporated by reference in its entirety. The numbers of T cells may be increased at least about 3-fold (or 4-, 5-, 6-, 7-, 8-, or 9-fold), more preferably at least about 10-fold (or 20-, 30-, 40-, 50-, 60-, 70-, 80-, or 90-fold), more preferably at least about 100-fold, more preferably at least about 1,000 fold, or most preferably at least about 100,000-fold. The numbers of T cells may be expanded using any suitable method known in the art. Exemplary methods of expanding the numbers of cells are described in patent publication No. WO 2003057171, U.S. Pat. No. 8,034,334, and U.S. Patent Application Publication No. 2012/0244133, each of which is incorporated herein by reference.

In one embodiment, ex vivo T cell expansion can be performed by isolation of T cells and subsequent stimulation or activation followed by further expansion. In one embodiment of the invention, the T cells may be stimulated or activated by a single agent. In another embodiment, T cells are stimulated or activated with two agents, one that induces a primary signal and a second that is a co-stimulatory signal. Ligands useful for stimulating a single signal or stimulating a primary signal and an accessory molecule that stimulates a second signal may be used in soluble form. Ligands may be attached to the surface of a cell, to an Engineered Multivalent Signaling Platform (EMSP), or immobilized on a surface. In a preferred embodiment both primary and secondary agents are co-immobilized on a surface, for example a bead or a cell. In one embodiment, the molecule providing the primary activation signal may be a CD3 ligand, and the co-stimulatory molecule may be a CD28 ligand or 4-1BB ligand.

In certain embodiments, T cells comprising a CAR or an exogenous TCR, may be manufactured as described in WO2015120096, by a method comprising: enriching a population of lymphocytes obtained from a donor subject; stimulating the population of lymphocytes with one or more T-cell stimulating agents to produce a population of activated T cells, wherein the stimulation is performed in a closed system using serum-free culture medium; transducing the population of activated T cells with a viral vector comprising a nucleic acid molecule which encodes the CAR or TCR, using a single cycle transduction to produce a population of transduced T cells, wherein the transduction is performed in a closed system using serum-free culture medium; and expanding the population of transduced T cells for a predetermined time to produce a population of engineered T cells, wherein the expansion is performed in a closed system using serum-free culture medium. In certain embodiments, T cells comprising a CAR or an exogenous TCR, may be manufactured as described in WO2015120096, by a method comprising: obtaining a population of lymphocytes; stimulating the population of lymphocytes with one or more stimulating agents to produce a population of activated T cells, wherein the stimulation is performed in a closed system using serum-free culture medium; transducing the population of activated T cells with a viral vector comprising a nucleic acid molecule which encodes the CAR or TCR, using at least one cycle transduction to produce a population of transduced T cells, wherein the transduction is performed in a closed system using serum-free culture medium; and expanding the population of transduced T cells to produce a population of engineered T cells, wherein the expansion is performed in a closed system using serum-free culture medium. The predetermined time for expanding the population of transduced T cells may be 3 days. The time from enriching the population of lymphocytes to producing the engineered T cells may be 6 days. The closed system may be a closed bag system. Further provided is population of T cells comprising a CAR or an exogenous TCR obtainable or obtained by said method, and a pharmaceutical composition comprising such cells.

In certain embodiments, T cell maturation or differentiation in vitro may be delayed or inhibited by the method as described in WO2017070395, comprising contacting one or more T cells from a subject in need of a T cell therapy with an AKT inhibitor (such as, e.g., one or a combination of two or more AKT inhibitors disclosed in claim 8 of WO2017070395) and at least one of exogenous Interleukin-7 (IL-7) and exogenous Interleukin-15 (IL-15), wherein the resulting T cells exhibit delayed maturation or differentiation, and/or wherein the resulting T cells exhibit improved T cell function (such as, e.g., increased T cell proliferation; increased cytokine production; and/or increased cytolytic activity) relative to a T cell function of a T cell cultured in the absence of an AKT inhibitor.

In certain embodiments, a patient in need of a T cell therapy may be conditioned by a method as described in WO2016191756 comprising administering to the patient a dose of cyclophosphamide between 200 mg/m$^2$/day and 2000 mg/m$^2$/day and a dose of fludarabine between 20 mg/m$^2$/day and 900 mg/m$^2$/day.

In one embodiment, adoptive cell transfer may comprise: depleting T cells as defined herein from a population of T cells obtained from the subject; in vitro expanding the T cell population; and administering the in vitro expanded T cell population to the subject. In certain embodiments, the method may further comprise formulating the in vitro expanded immune cell or immune cell population into a pharmaceutical composition.

In certain embodiments, suppressive CD8+ T cells are administered in combination with an autoimmune drug. Non-limiting examples of such drugs include methotrexate, cyclophosphamide, Imuran (azathioprine), cyclosporin, and steroid compounds such as prednisone and methylprednisolone.

Genetic Modifying Agents

In certain embodiments, the one or more modulating agents may be a genetic modifying agent or an epigenetic modifying agent. The genetic modifying agent may comprise a CRISPR system, a zinc finger nuclease system, a TALEN, or a meganuclease. The epigenetic modifying agent may comprise a DNA methylation inhibitor, HDAC inhibitor, histone acetylation inhibitor, histone methylation inhibitor or histone demethylase inhibitor.

In general, a CRISPR-Cas or CRISPR system as used in herein and in documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g, Shmakov et al. (2015) "Discovery and Functional Characterization of Diverse Class 2 CRISPR-Cas Systems", Molecular Cell, DOI: dx.doi.org/10.1016/j.molcel.2015.10.008.

In certain embodiments, a protospacer adjacent motif (PAM) or PAM-like motif directs binding of the effector protein complex as disclosed herein to the target locus of interest. In some embodiments, the PAM may be a 5' PAM (i.e., located upstream of the 5' end of the protospacer). In other embodiments, the PAM may be a 3' PAM (i.e., located downstream of the 5' end of the protospacer). The term "PAM" may be used interchangeably with the term "PFS" or "protospacer flanking site" or "protospacer flanking sequence".

In a preferred embodiment, the CRISPR effector protein may recognize a 3' PAM. In certain embodiments, the CRISPR effector protein may recognize a 3' PAM which is 5'H, wherein H is A, C or U.

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to a RNA polynucleotide being or comprising the target sequence. In other words, the target RNA may be a RNA polynucleotide or a part of a RNA polynucleotide to which a part of the gRNA, i.e. the guide sequence, is designed to have complementarity and to which the effector function mediated by the complex comprising CRISPR effector protein and a gRNA is to be directed. In some embodiments, a target sequence is located in the nucleus or cytoplasm of a cell.

In certain example embodiments, the CRISPR effector protein may be delivered using a nucleic acid molecule encoding the CRISPR effector protein. The nucleic acid molecule encoding a CRISPR effector protein, may advantageously be a codon optimized CRISPR effector protein. An example of a codon optimized sequence, is in this instance a sequence optimized for expression in eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a CRISPR effector protein is a codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at kazusa.orjp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

In certain embodiments, the methods as described herein may comprise providing a Cas transgenic cell in which one or more nucleic acids encoding one or more guide RNAs are provided or introduced operably connected in the cell with a regulatory element comprising a promoter of one or more gene of interest. As used herein, the term "Cas transgenic cell" refers to a cell, such as a eukaryotic cell, in which a Cas gene has been genomically integrated. The nature, type, or origin of the cell are not particularly limiting according to the present invention. Also the way the Cas transgene is introduced in the cell may vary and can be any method as is known in the art. In certain embodiments, the Cas transgenic cell is obtained by introducing the Cas transgene in an isolated cell. In certain other embodiments, the Cas transgenic cell is obtained by isolating cells from a Cas transgenic organism. By means of example, and without limitation, the Cas transgenic cell as referred to herein may be derived from a Cas transgenic eukaryote, such as a Cas knock-in eukaryote. Reference is made to WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR Cas system of the present invention. Methods of US Patent Publication No. 20130236946 assigned to Cellectis directed to targeting the Rosa locus may also be modified to utilize the CRISPR Cas system of the present invention. By means of further example reference is made to Platt et. al. (Cell; 159(2):440-455 (2014)), describing a Cas9 knock-in mouse, which is incorporated herein by reference. The Cas transgene can further comprise a Lox-Stop-polyA-Lox(LSL) cassette thereby rendering Cas expression inducible by Cre recombinase. Alternatively, the Cas transgenic cell may be obtained by introducing the Cas transgene in an isolated cell. Delivery systems for transgenes are well known in the art. By means of example, the Cas transgene may be delivered in for instance eukaryotic cell by means of vector (e.g., AAV, adenovirus, lentivirus) and/or particle and/or nanoparticle delivery, as also described herein elsewhere.

It will be understood by the skilled person that the cell, such as the Cas transgenic cell, as referred to herein may comprise further genomic alterations besides having an integrated Cas gene or the mutations arising from the sequence specific action of Cas when complexed with RNA capable of guiding Cas to a target locus.

In certain aspects the invention involves vectors, e.g. for delivering or introducing in a cell Cas and/or RNA capable of guiding Cas to a target locus (i.e. guide RNA), but also for propagating these components (e.g. in prokaryotic cells). A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety. Thus, the embodiments disclosed herein may also comprise transgenic cells comprising the CRISPR effector system. In certain example embodiments, the transgenic cell may function as an individual discrete volume. In other words samples comprising a masking construct may be delivered to a cell, for example in a suitable delivery vesicle and if the target is present in the delivery vesicle the CRISPR effector is activated and a detectable signal generated.

The vector(s) can include the regulatory element(s), e.g., promoter(s). The vector(s) can comprise Cas encoding sequences, and/or a single, but possibly also can comprise at least 3 or 8 or 16 or 32 or 48 or 50 guide RNA(s) (e.g., sgRNAs) encoding sequences, such as 1-2, 1-3, 1-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s); and, when a single vector provides for more than 16 RNA(s), one or more promoter(s) can drive expression of more than one of the RNA(s), e.g., when there are 32 RNA(s), each promoter can drive expression of two RNA(s), and when there are 48 RNA(s), each promoter can drive expression of three RNA(s). By simple arithmetic and well established cloning protocols and the teachings in this disclosure one skilled in the art can readily practice the invention as to the RNA(s) for a suitable exemplary vector such as AAV, and a suitable promoter such as the U6 promoter. For example, the packaging limit of AAV is ~4.7 kb. The length of a single U6-gRNA (plus restriction sites for cloning) is 361 bp. Therefore, the skilled person can readily fit about 12-16, e.g., 13 U6-gRNA cassettes in a single vector. This can be assembled by any suitable means, such as a golden gate strategy used for TALE assembly (genome-engineering.org/taleffectors/). The skilled person can also use a tandem guide strategy to increase the number of U6-gRNAs by approximately 1.5 times, e.g., to increase from 12-16, e.g., 13 to approximately 18-24, e.g., about 19 U6-gRNAs. Therefore, one skilled in the art can readily reach approximately 18-24, e.g., about 19 promoter-RNAs, e.g., U6-gRNAs in a single vector, e.g., an AAV vector. A further means for increasing the number of promoters and RNAs in a vector is to use a single promoter (e.g., U6) to express an array of RNAs separated by cleavable sequences. And an even further means for increasing the number of promoter-RNAs in a vector, is to express an array of promoter-RNAs separated by cleavable sequences in the intron of a coding sequence or gene; and, in this instance it is advantageous to use a polymerase II promoter, which can have increased expression and enable the transcription of long RNA in a tissue specific manner. (see, e.g., nar.oxfordjournals.org/content/34/7/e53.short and nature.com/mt/journal/v16/n9/abs/mt2008144a.html). In an advantageous embodiment, AAV may package U6 tandem gRNA targeting up to about 50 genes. Accordingly, from the knowledge in the art and the teachings in this disclosure the skilled person can readily make and use vector(s), e.g., a single vector, expressing multiple RNAs or guides under the control or operatively or functionally linked to one or more promoters-especially as to the numbers of RNAs or guides discussed herein, without any undue experimentation.

The guide RNA(s) encoding sequences and/or Cas encoding sequences, can be functionally or operatively linked to regulatory element(s) and hence the regulatory element(s) drive expression. The promoter(s) can be constitutive promoter(s) and/or conditional promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the (3-actin promoter, the phosphoglycerol kinase (PGK) promoter, and the EFla promoter. An advantageous promoter is the promoter is U6.

Additional effectors for use according to the invention can be identified by their proximity to casl genes, for example, though not limited to, within the region 20 kb from the start of the cast gene and 20 kb from the end of the cast gene. In certain embodiments, the effector protein comprises at least one HEPN domain and at least 500 amino acids, and wherein the C2c2 effector protein is naturally present in a prokaryotic genome within 20 kb upstream or downstream of a Cas gene or a CRISPR array. Non-limiting examples of Cas proteins include Cas1, Cas1B, Cas2, Cas3, Cas4, Cas5, Cash, Cas7, Cas8, Cas9 (also known as Csn1 and Csx12), Cas10, Csy 1, Csy2, Csy3, Cse1, Cse2, Csc1, Csc2, Csa5, Csn2, Csm2, Csm3, Csm4, Csm5, Csm6, Cmrl, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In certain example embodiments, the C2c2 effector protein is naturally present in a prokaryotic genome within 20 kb upstream or downstream of a Cas 1 gene. The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related, or are only partially structurally related. An "orthologue" of a protein as used herein is a protein of a different species which performs the same or a similar function as the protein it is an orthologue of. Orthologous proteins may but need not be structurally related, or are only partially structurally related.

Guide Molecules

The methods described herein may be used to screen inhibition of CRISPR systems employing different types of guide molecules. As used herein, the term "guide sequence" and "guide molecule" in the context of a CRISPR-Cas system, comprises any polynucleotide sequence having sufficient complementarity with a target nucleic acid sequence to hybridize with the target nucleic acid sequence and direct sequence-specific binding of a nucleic acid-targeting complex to the target nucleic acid sequence. The guide sequences made using the methods disclosed herein may be a full-length guide sequence, a truncated guide sequence, a full-length sgRNA sequence, a truncated sgRNA sequence, or an E+F sgRNA sequence. In some embodiments, the degree of complementarity of the guide sequence to a given target sequence, when optimally aligned using a suitable alignment algorithm, is about or more than about 50%, 60%, 75%, 80%, 85%, 90%, 95%, 97.5%, 99%, or more. In certain example embodiments, the guide molecule comprises a guide sequence that may be designed to have at least one mismatch with the target sequence, such that a RNA duplex formed between the guide sequence and the target sequence. Accordingly, the degree of complementarity is preferably less than 99%. For instance, where the guide sequence consists of 24 nucleotides, the degree of complementarity is more particularly about 96% or less. In particular embodiments, the guide sequence is designed to have a stretch of two or more adjacent mismatching nucleotides, such that the degree of complementarity over the entire guide sequence is further reduced. For instance, where the guide sequence consists of 24 nucleotides, the degree of complementarity is more particularly about 96% or less, more particularly, about 92% or less, more particularly about 88% or less, more particularly about 84% or less, more particularly about 80% or less, more particularly about 76% or less, more particularly about 72% or less, depending on whether the stretch of two or more mismatching nucleotides encompasses 2, 3, 4, 5, 6 or 7 nucleotides, etc. In some embodiments, aside from the stretch of one or more mismatching nucleotides, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence (or a sequence in the vicinity thereof) may be evaluated in a test tube by providing the target nucleic acid sequence, components of a nucleic acid-targeting complex, including the guide sequence to be tested and a control guide sequence different from the test guide sequence, and comparing binding or rate of cleavage at or in the vicinity of the target sequence between the test and control guide sequence reactions. Other assays are possible, and will occur to those skilled in the art. A guide sequence, and hence a nucleic acid-targeting guide RNA may be selected to target any target nucleic acid sequence.

In certain embodiments, the guide sequence or spacer length of the guide molecules is from 15 to 50 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer. In certain example embodiment, the guide sequence is 15, 16, 17,18, 19, 20, 21, 22, 23, 24, 25, 26, 27, 28, 29, 30, 31, 32, 33, 34, 35, 36, 37, 38, 39 40, 41, 42, 43, 44, 45, 46, 47 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nt.

In some embodiments, the guide sequence is an RNA sequence of between 10 to 50 nt in length, but more particularly of about 20-30 nt advantageously about 20 nt, 23-25 nt or 24 nt. The guide sequence is selected so as to ensure that it hybridizes to the target sequence. This is described more in detail below. Selection can encompass further steps which increase efficacy and specificity.

In some embodiments, the guide sequence has a canonical length (e.g., about 15-30 nt) is used to hybridize with the target RNA or DNA. In some embodiments, a guide molecule is longer than the canonical length (e.g., >30 nt) is used to hybridize with the target RNA or DNA, such that a region of the guide sequence hybridizes with a region of the RNA or DNA strand outside of the Cas-guide target complex. This can be of interest where additional modifications, such deamination of nucleotides is of interest. In alternative embodiments, it is of interest to maintain the limitation of the canonical guide sequence length.

In some embodiments, the sequence of the guide molecule (direct repeat and/or spacer) is selected to reduce the degree secondary structure within the guide molecule. In some embodiments, about or less than about 75%, 50%, 40%, 30%, 25%, 20%, 15%, 10%, 5%, 1%, or fewer of the nucleotides of the nucleic acid-targeting guide RNA participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and PA Carr and GM Church, 2009, Nature Biotechnology 27(12): 1151-62).

In some embodiments, it is of interest to reduce the susceptibility of the guide molecule to RNA cleavage, such as to cleavage by Cas13. Accordingly, in particular embodiments, the guide molecule is adjusted to avoid cleavage by Cas13 or other RNA-cleaving enzymes.

In certain embodiments, the guide molecule comprises non-naturally occurring nucleic acids and/or non-naturally occurring nucleotides and/or nucleotide analogs, and/or chemically modifications. Preferably, these non-naturally occurring nucleic acids and non-naturally occurring nucleotides are located outside the guide sequence. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, a locked nucleic acid (LNA) nucleotides comprising a methylene bridge between the 2' and 4' carbons of the ribose ring, or bridged nucleic acids (BNA). Other examples of modified nucleotides include 2'-O-methyl analogs, 2'-deoxy analogs, or 2'-fluoro analogs. Further examples of modified bases include, but are not limited to, 2-aminopurine, 5-bromo-uridine, pseudouridine, inosine, 7-methylguanosine.

Examples of guide RNA chemical modifications include, without limitation, incorporation of 2'-O-methyl (M), 2'-O-methyl 3' phosphorothioate (MS), S-constrained ethyl(cEt), or 2'-O-methyl 3' thioPACE (MSP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33(9):985-9, doi: 10.1038/nbt.3290, published online 29 Jun. 2015 Ragdarm et al., 0215, PNAS, E7110-E7111; Allerson et al., *J. Med. Chem.* 2005, 48:901-904; Bramsen et al., *Front. Genet.*, 2012, 3:154; Deng et al., *PNAS*, 2015, 112:11870-11875; Sharma et al., *MedChemComm.*, 2014, 5:1454-1471; Hendel et al., *Nat. Biotechnol.* (2015) 33(9): 985-989; Li et al., *Nature Biomedical Engineering*, 2017, 1, 0066 DOI:10.1038/s41551-017-0066). In some embodiments, the 5' and/or 3' end of a guide RNA is modified by a variety of functional moieties including fluorescent dyes, polyethylene glycol, cholesterol, proteins, or detection tags. (See Kelly et al., 2016, *J. Biotech.* 233:74-83). In certain embodiments, a guide comprises ribonucleotides in a region that binds to a target RNA and one or more deoxyribonucleotides and/or nucleotide analogs in a region that binds to Cas13. In an embodiment of the invention, deoxyribonucleotides and/or nucleotide analogs are incorporated in engineered guide structures, such as, without limitation, stem-loop regions, and the seed region. For Cas13 guide, in certain embodiments, the modification is not in the 5'-handle of the stem-loop regions. Chemical modification in the 5'-handle of the stem-loop region of a guide may abolish its function (see Li, et al., Nature Biomedical Engineering, 2017, 1:0066). In certain embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or 75 nucleotides of a guide is chemically modified. In some embodiments, 3-5 nucleotides at either the 3' or the 5' end of a guide is chemically modified. In some embodiments, only minor modifications are introduced in the seed region, such as 2'-F modifications. In some embodiments, 2'-F modification is introduced at the 3' end of a guide. In certain embodiments, three to five nucleotides at the 5' and/or the 3' end of the guide are chemically modified with 2'-O-methyl (M), 2'-O-methyl 3' phosphorothioate (MS), S-constrained ethyl(cEt), or 2'-O-methyl 3' thioPACE (MSP). Such modification can enhance genome editing efficiency (see Hendel et al., *Nat. Biotechnol.* (2015) 33(9): 985-989). In certain embodiments, all of the phosphodiester bonds of a guide are substituted with phosphorothioates (PS) for enhancing levels of gene disruption. In certain embodiments, more than five nucleotides at the 5' and/or the 3' end of the guide are chemicially modified with 2'-O-Me, 2'-F or S-constrained ethyl(cEt). Such chemically modified guide can mediate enhanced levels of gene disruption (see Ragdarm et al., 0215, PNAS, E7110-E7111). In an embodiment of the invention, a guide is modified to comprise a chemical moiety at its 3' and/or 5' end. Such moieties include, but are not limited to amine, azide, alkyne, thio, dibenzocyclooctyne (DBCO), or Rhodamine. In certain embodiment, the chemical moiety is conjugated to the guide by a linker, such as an alkyl chain. In certain embodiments, the chemical moiety of the modified guide can be used to attach the guide to another molecule, such as DNA, RNA, protein, or nanoparticles. Such chemically modified guide can be used to identify or enrich cells generically edited by a CRISPR system (see Lee et al., *eLife*, 2017, 6:e25312, DOI:10.7554).

In some embodiments, the modification to the guide is a chemical modification, an insertion, a deletion or a split. In some embodiments, the chemical modification includes, but is not limited to, incorporation of 2'-O-methyl (M) analogs, 2'-deoxy analogs, 2-thiouridine analogs, N6-methyladenosine analogs, 2'-fluoro analogs, 2-aminopurine, 5-bromo-uridine, pseudouridine (Ψ), N1-methylpseudouridine (melΨ), 5-methoxyuridine(5moU), inosine, 7-methylguanosine, 2'-O-methyl 3'phosphorothioate (MS), S-constrained ethyl(cEt), phosphorothioate (PS), or 2'-O-methyl 3'thioPACE (MSP). In some embodiments, the guide comprises one or more of phosphorothioate modifications. In certain embodiments, at least 1, 2, 3, 4, 5, 6, 7, 8, 9, 10, 11, 12, 13, 14, 15, 16, 17, 18, 19, 20, or 25 nucleotides of the guide are chemically modified. In certain embodiments, one or more nucleotides in the seed region are chemically modified. In certain embodiments, one or more nucleotides in the 3'-terminus are chemically modified. In certain embodiments, none of the nucleotides in the 5'-handle is chemically modified. In some embodiments, the chemical modification in the seed region is a minor modification, such as incorporation of a 2'-fluoro analog. In a specific embodiment, one nucleotide of the seed region is replaced with a 2'-fluoro analog. In some embodiments, 5 to 10 nucleotides in the 3'-terminus are chemically modified. Such chemical modifications at the 3'-terminus of the Cas13 CrRNA may improve Cas13 activity. In a specific embodiment, 1, 2, 3, 4, 5, 6, 7, 8, 9 or 10 nucleotides in the 3'-terminus are replaced with 2'-fluoro analogues. In a specific embodiment, 1, 2, 3, 4, 5, 6, 7, 8, 9 or 10 nucleotides in the 3'-terminus are replaced with 2'-O-methyl (M) analogs.

In some embodiments, the loop of the 5'-handle of the guide is modified. In some embodiments, the loop of the 5'-handle of the guide is modified to have a deletion, an insertion, a split, or chemical modifications. In certain embodiments, the modified loop comprises 3, 4, or 5 nucleotides. In certain embodiments, the loop comprises the sequence of UCUU, UUUU, UAUU, or UGUU (SEQ ID NOs: 3-6).

In some embodiments, the guide molecule forms a stem-loop with a separate non-covalently linked sequence, which can be DNA or RNA. In particular embodiments, the sequences forming the guide are first synthesized using the standard phosphoramidite synthetic protocol (Herdewijn, P., ed., Methods in Molecular Biology Col 288, Oligonucleotide Synthesis: Methods and Applications, Humana Press, New Jersey (2012)). In some embodiments, these sequences can be functionalized to contain an appropriate functional group for ligation using the standard protocol known in the art (Hermanson, G. T., Bioconjugate Techniques, Academic Press (2013)). Examples of functional groups include, but are not limited to, hydroxyl, amine, carboxylic acid, carboxylic acid halide, carboxylic acid active ester, aldehyde, carbonyl, chlorocarbonyl, imidazolylcarbonyl, hydrozide, semicarbazide, thio semicarbazide, thiol, maleimide, haloalkyl, sulfonyl, ally, propargyl, diene, alkyne, and azide. Once this sequence is functionalized, a covalent chemical bond or linkage can be formed between this sequence and the direct repeat sequence. Examples of chemical bonds include, but are not limited to, those based on carbamates, ethers, esters, amides, imines, amidines, aminotriazines, hydrozone, disulfides, thioethers, thioesters, phosphorothioates, phosphorodithioates, sulfonamides, sulfonates, sulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, these stem-loop forming sequences can be chemically synthesized. In some embodiments, the chemical synthesis uses automated, solid-phase oligonucleotide synthesis machines with 2'-acetoxyethyl orthoester (2'-ACE) (Scaringe et al., J. Am. Chem. Soc. (1998) 120: 11820-11821; Scaringe, Methods Enzymol. (2000) 317: 3-18) or 2'-thionocarbamate (2'-TC) chemistry (Dellinger et al., J. Am. Chem. Soc. (2011) 133: 11540-11546; Hendel et al., Nat. Biotechnol. (2015) 33:985-989).

In certain embodiments, the guide molecule comprises (1) a guide sequence capable of hybridizing to a target locus and (2) a tracr mate or direct repeat sequence whereby the direct repeat sequence is located upstream (i.e., 5') from the guide sequence. In a particular embodiment the seed sequence (i.e. the sequence essential critical for recognition and/or hybridization to the sequence at the target locus) of the guide sequence is approximately within the first 10 nucleotides of the guide sequence.

In a particular embodiment the guide molecule comprises a guide sequence linked to a direct repeat sequence, wherein the direct repeat sequence comprises one or more stem loops or optimized secondary structures. In particular embodiments, the direct repeat has a minimum length of 16 nts and a single stem loop. In further embodiments the direct repeat has a length longer than 16 nts, preferably more than 17 nts, and has more than one stem loops or optimized secondary structures. In particular embodiments the guide molecule comprises or consists of the guide sequence linked to all or part of the natural direct repeat sequence. A typical Type V or Type VI CRISPR-cas guide molecule comprises (in 3' to 5' direction or in 5' to 3' direction): a guide sequence a first complimentary stretch (the "repeat"), a loop (which is typically 4 or 5 nucleotides long), a second complimentary stretch (the "anti-repeat" being complimentary to the repeat), and a poly A (often poly U in RNA) tail (terminator). In certain embodiments, the direct repeat sequence retains its natural architecture and forms a single stem loop. In particular embodiments, certain aspects of the guide architecture can be modified, for example by addition, subtraction, or substitution of features, whereas certain other aspects of guide architecture are maintained. Preferred locations for engineered guide molecule modifications, including but not limited to insertions, deletions, and substitutions include guide termini and regions of the guide molecule that are exposed when complexed with the CRISPR-Cas protein and/or target, for example the stemloop of the direct repeat sequence.

In particular embodiments, the stem comprises at least about 4 bp comprising complementary X and Y sequences, although stems of more, e.g., 5, 6, 7, 8, 9, 10, 11 or 12 or fewer, e.g., 3, 2, base pairs are also contemplated. Thus, for example X2-10 and Y2-10 (wherein X and Y represent any complementary set of nucleotides) may be contemplated. In one aspect, the stem made of the X and Y nucleotides, together with the loop will form a complete hairpin in the overall secondary structure; and, this may be advantageous and the amount of base pairs can be any amount that forms a complete hairpin. In one aspect, any complementary X:Y basepairing sequence (e.g., as to length) is tolerated, so long as the secondary structure of the entire guide molecule is preserved. In one aspect, the loop that connects the stem made of X:Y basepairs can be any sequence of the same length (e.g., 4 or 5 nucleotides) or longer that does not interrupt the overall secondary structure of the guide molecule. In one aspect, the stemloop can further comprise, e.g. an MS2 aptamer. In one aspect, the stem comprises about 5-7 bp comprising complementary X and Y sequences, although stems of more or fewer basepairs are also contemplated. In one aspect, non-Watson Crick basepairing is contemplated, where such pairing otherwise generally preserves the architecture of the stemloop at that position.

In particular embodiments the natural hairpin or stemloop structure of the guide molecule is extended or replaced by an extended stemloop. It has been demonstrated that extension of the stem can enhance the assembly of the guide molecule with the CRISPR-Cas protein (Chen et al. Cell. (2013); 155(7): 1479-1491). In particular embodiments the stem of the stemloop is extended by at least 1, 2, 3, 4, 5 or more complementary basepairs (i.e. corresponding to the addition of 2,4, 6, 8, 10 or more nucleotides in the guide molecule). In particular embodiments these are located at the end of the stem, adjacent to the loop of the stemloop.

In particular embodiments, the susceptibility of the guide molecule to RNAses or to decreased expression can be reduced by slight modifications of the sequence of the guide molecule which do not affect its function. For instance, in particular embodiments, premature termination of transcription, such as premature transcription of U6 Pol-III, can be removed by modifying a putative Pol-III terminator (4 consecutive U's) in the guide molecules sequence. Where such sequence modification is required in the stemloop of the guide molecule, it is preferably ensured by a basepair flip.

In a particular embodiment the direct repeat may be modified to comprise one or more protein-binding RNA aptamers. In a particular embodiment, one or more aptamers may be included such as part of optimized secondary structure. Such aptamers may be capable of binding a bacteriophage coat protein as detailed further herein.

In some embodiments, the guide molecule forms a duplex with a target RNA comprising at least one target cytosine residue to be edited. Upon hybridization of the guide RNA molecule to the target RNA, the cytidine deaminase binds to the single strand RNA in the duplex made accessible by the mismatch in the guide sequence and catalyzes deamination of one or more target cytosine residues comprised within the stretch of mismatching nucleotides.

A guide sequence, and hence a nucleic acid-targeting guide RNA may be selected to target any target nucleic acid sequence. The target sequence may be mRNA.

In certain embodiments, the target sequence should be associated with a PAM (protospacer adjacent motif) or PFS (protospacer flanking sequence or site); that is, a short sequence recognized by the CRISPR complex. Depending on the nature of the CRISPR-Cas protein, the target sequence should be selected such that its complementary sequence in the DNA duplex (also referred to herein as the non-target sequence) is upstream or downstream of the PAM. In the embodiments of the present invention where the CRISPR-Cas protein is a Cas13 protein, the complementary sequence of the target sequence is downstream or 3' of the PAM or upstream or 5' of the PAM. The precise sequence and length requirements for the PAM differ depending on the Cas13 protein used, but PAMs are typically 2-5 base pair sequences adjacent the protospacer (that is, the target sequence). Examples of the natural PAM sequences for different Cas13 orthologues are provided herein below and the skilled person will be able to identify further PAM sequences for use with a given Cas13 protein.

Further, engineering of the PAM Interacting (PI) domain may allow programing of PAM specificity, improve target site recognition fidelity, and increase the versatility of the CRISPR-Cas protein, for example as described for Cas9 in Kleinstiver B P et al. Engineered CRISPR-Cas9 nucleases with altered PAM specificities. Nature. 2015 Jul. 23; 523 (7561):481-5. doi: 10.1038/nature14592. As further detailed herein, the skilled person will understand that Cas13 proteins may be modified analogously.

In particular embodiment, the guide is an escorted guide. By "escorted" is meant that the CRISPR-Cas system or complex or guide is delivered to a selected time or place within a cell, so that activity of the CRISPR-Cas system or complex or guide is spatially or temporally controlled. For example, the activity and destination of the 3 CRISPR-Cas system or complex or guide may be controlled by an escort RNA aptamer sequence that has binding affinity for an aptamer ligand, such as a cell surface protein or other localized cellular component. Alternatively, the escort aptamer may for example be responsive to an aptamer effector on or in the cell, such as a transient effector, such as an external energy source that is applied to the cell at a particular time.

The escorted CRISPR-Cas systems or complexes have a guide molecule with a functional structure designed to improve guide molecule structure, architecture, stability, genetic expression, or any combination thereof. Such a structure can include an aptamer.

Aptamers are biomolecules that can be designed or selected to bind tightly to other ligands, for example using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can for example be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in biotechnology 26.8 (2008): 442-449; and, Hicke B J, Stephens A W. "Escort aptamers: a delivery service for diagnosis and therapy." J Clin Invest 2000, 106:923-928.). Aptamers may also be constructed that function as molecular switches, responding to a que by changing properties, such as RNA aptamers that bind fluorophores to mimic the activity of green fluorescent protein (Paige, Jeremy S., Karen Y. Wu, and Samie R. Jaffrey. "RNA mimics of green fluorescent protein." Science 333.6042 (2011): 642-646). It has also been suggested that aptamers may be used as components of targeted siRNA therapeutic delivery systems, for example targeting cell surface proteins (Zhou, Jiehua, and John J. Rossi. "Aptamer-targeted cell-specific RNA interference." Silence 1.1 (2010): 4).

Accordingly, in particular embodiments, the guide molecule is modified, e.g., by one or more aptamer(s) designed to improve guide molecule delivery, including delivery across the cellular membrane, to intracellular compartments, or into the nucleus. Such a structure can include, either in addition to the one or more aptamer(s) or without such one or more aptamer(s), moiety(ies) so as to render the guide molecule deliverable, inducible or responsive to a selected effector. The invention accordingly comprehends an guide molecule that responds to normal or pathological physiological conditions, including without limitation pH, hypoxia, $O_2$ concentration, temperature, protein concentration, enzymatic concentration, lipid structure, light exposure, mechanical disruption (e.g. ultrasound waves), magnetic fields, electric fields, or electromagnetic radiation.

Light responsiveness of an inducible system may be achieved via the activation and binding of cryptochrome-2 and CIB1. Blue light stimulation induces an activating conformational change in cryptochrome-2, resulting in recruitment of its binding partner CIB1. This binding is fast and reversible, achieving saturation in <15 sec following pulsed stimulation and returning to baseline <15 min after the end of stimulation. These rapid binding kinetics result in a system temporally bound only by the speed of transcription/translation and transcript/protein degradation, rather than uptake and clearance of inducing agents. Crytochrome-2 activation is also highly sensitive, allowing for the use of low light intensity stimulation and mitigating the risks of phototoxicity. Further, in a context such as the intact mammalian brain, variable light intensity may be used to control the size of a stimulated region, allowing for greater precision than vector delivery alone may offer.

The invention contemplates energy sources such as electromagnetic radiation, sound energy or thermal energy to induce the guide. Advantageously, the electromagnetic radiation is a component of visible light. In a preferred embodiment, the light is a blue light with a wavelength of about 450 to about 495 nm. In an especially preferred embodiment, the wavelength is about 488 nm. In another preferred embodiment, the light stimulation is via pulses. The light power may range from about 0-9 $mW/cm^2$. In a preferred embodiment, a stimulation paradigm of as low as 0.25 sec every 15 sec should result in maximal activation.

The chemical or energy sensitive guide may undergo a conformational change upon induction by the binding of a chemical source or by the energy allowing it act as a guide and have the Cas13 CRISPR-Cas system or complex function. The invention can involve applying the chemical source or energy so as to have the guide function and the Cas13 CRISPR-Cas system or complex function; and optionally further determining that the expression of the genomic locus is altered.

There are several different designs of this chemical inducible system: 1. ABI-PYL based system inducible by Abscisic Acid (ABA) (see, e.g., stke.sciencemag.org/cgi/content/abstract/sigtrans; 4/164/r52), 2. FKBP-FRB based system inducible by rapamycin (or related chemicals based on rapamycin) (see, e.g., www.nature.com/nmeth/journal/v2/n6/full/nmeth763.html), 3. GID1-GAI based system inducible by Gibberellin (GA) (see, e.g., www.nature.com/nchembio/journal/v8/n5/full/nchembio.922.html).

A chemical inducible system can be an estrogen receptor (ER) based system inducible by 4-hydroxytamoxifen (4OHT) (see, e.g., www.pnas.org/content/104/3/1027.abstract). A mutated ligand-binding domain of the estrogen receptor called ERT2 translocates into the nucleus of cells upon binding of 4-hydroxytamoxifen. In further embodiments of the invention any naturally occurring or engineered derivative of any nuclear receptor, thyroid hormone receptor, retinoic acid receptor, estrogen receptor, estrogen-related receptor, glucocorticoid receptor, progesterone receptor, androgen receptor may be used in inducible systems analogous to the ER based inducible system.

Another inducible system is based on the design using Transient receptor potential (TRP) ion channel based system inducible by energy, heat or radio-wave (see, e.g., www.sciencemag.org/content/336/6081/604). These TRP family proteins respond to different stimuli, including light and heat. When this protein is activated by light or heat, the ion channel will open and allow the entering of ions such as calcium into the plasma membrane. This influx of ions will bind to intracellular ion interacting partners linked to a polypeptide including the guide and the other components of the Cas13 CRISPR-Cas complex or system, and the binding will induce the change of sub-cellular localization of the polypeptide, leading to the entire polypeptide entering the nucleus of cells. Once inside the nucleus, the guide protein and the other components of the Cas13 CRISPR-Cas complex will be active and modulating target gene expression in cells.

While light activation may be an advantageous embodiment, sometimes it may be disadvantageous especially for in vivo applications in which the light may not penetrate the skin or other organs. In this instance, other methods of energy activation are contemplated, in particular, electric field energy and/or ultrasound which have a similar effect.

Electric field energy is preferably administered substantially as described in the art, using one or more electric pulses of from about 1 Volt/cm to about 10 kVolts/cm under in vivo conditions. Instead of or in addition to the pulses, the electric field may be delivered in a continuous manner. The electric pulse may be applied for between 1 μs and 500 milliseconds, preferably between 1 μs and 100 milliseconds. The electric field may be applied continuously or in a pulsed manner for 5 about minutes.

As used herein, 'electric field energy' is the electrical energy to which a cell is exposed. Preferably the electric field has a strength of from about 1 Volt/cm to about 10 kVolts/cm or more under in vivo conditions (see WO97/49450).

As used herein, the term "electric field" includes one or more pulses at variable capacitance and voltage and including exponential and/or square wave and/or modulated wave and/or modulated square wave forms. References to electric fields and electricity should be taken to include reference the presence of an electric potential difference in the environment of a cell. Such an environment may be set up by way of static electricity, alternating current (AC), direct current (DC), etc, as known in the art. The electric field may be uniform, non-uniform or otherwise, and may vary in strength and/or direction in a time dependent manner.

Single or multiple applications of electric field, as well as single or multiple applications of ultrasound are also possible, in any order and in any combination. The ultrasound and/or the electric field may be delivered as single or multiple continuous applications, or as pulses (pulsatile delivery).

Electroporation has been used in both in vitro and in vivo procedures to introduce foreign material into living cells. With in vitro applications, a sample of live cells is first mixed with the agent of interest and placed between electrodes such as parallel plates. Then, the electrodes apply an electrical field to the cell/implant mixture. Examples of systems that perform in vitro electroporation include the Electro Cell Manipulator ECM600 product, and the Electro Square Porator T820, both made by the BTX Division of Genetronics, Inc (see U.S. Pat. No. 5,869,326).

The known electroporation techniques (both in vitro and in vivo) function by applying a brief high voltage pulse to electrodes positioned around the treatment region. The electric field generated between the electrodes causes the cell membranes to temporarily become porous, whereupon molecules of the agent of interest enter the cells. In known electroporation applications, this electric field comprises a single square wave pulse on the order of 1000 V/cm, of about 100 .mu.s duration. Such a pulse may be generated, for example, in known applications of the Electro Square Porator T820.

Preferably, the electric field has a strength of from about 1 V/cm to about 10 kV/cm under in vitro conditions. Thus, the electric field may have a strength of 1 V/cm, 2 V/cm, 3 V/cm, 4 V/cm, 5 V/cm, 6 V/cm, 7 V/cm, 8 V/cm, 9 V/cm, 10 V/cm, 20 V/cm, 50 V/cm, 100 V/cm, 200 V/cm, 300 V/cm, 400 V/cm, 500 V/cm, 600 V/cm, 700 V/cm, 800 V/cm, 900 V/cm, 1 kV/cm, 2 kV/cm, 5 kV/cm, 10 kV/cm, 20 kV/cm, 50 kV/cm or more. More preferably from about 0.5 kV/cm to about 4.0 kV/cm under in vitro conditions. Preferably the electric field has a strength of from about 1 V/cm to about 10 kV/cm under in vivo conditions. However, the electric field strengths may be lowered where the number of pulses delivered to the target site are increased. Thus, pulsatile delivery of electric fields at lower field strengths is envisaged.

Preferably the application of the electric field is in the form of multiple pulses such as double pulses of the same strength and capacitance or sequential pulses of varying strength and/or capacitance. As used herein, the term "pulse" includes one or more electric pulses at variable capacitance and voltage and including exponential and/or square wave and/or modulated wave/square wave forms.

Preferably the electric pulse is delivered as a waveform selected from an exponential wave form, a square wave form, a modulated wave form and a modulated square wave form.

A preferred embodiment employs direct current at low voltage. Thus, Applicants disclose the use of an electric field which is applied to the cell, tissue or tissue mass at a field strength of between 1V/cm and 20V/cm, for a period of 100 milliseconds or more, preferably 15 minutes or more.

Ultrasound is advantageously administered at a power level of from about 0.05 W/cm2 to about 100 W/cm2. Diagnostic or therapeutic ultrasound may be used, or combinations thereof.

As used herein, the term "ultrasound" refers to a form of energy which consists of mechanical vibrations the frequencies of which are so high they are above the range of human hearing. Lower frequency limit of the ultrasonic spectrum may generally be taken as about 20 kHz. Most diagnostic applications of ultrasound employ frequencies in the range 1 and 15 MHz' (From Ultrasonics in Clinical Diagnosis, P. N. T. Wells, ed., 2nd. Edition, Publ. Churchill Livingstone [Edinburgh, London & NY, 1977]).

Ultrasound has been used in both diagnostic and therapeutic applications. When used as a diagnostic tool ("diagnostic ultrasound"), ultrasound is typically used in an energy density range of up to about 100 mW/cm2 (FDA recommendation), although energy densities of up to 750 mW/cm2 have been used. In physiotherapy, ultrasound is typically used as an energy source in a range up to about 3 to 4 W/cm2 (WHO recommendation). In other therapeutic applications, higher intensities of ultrasound may be employed, for example, HIFU at 100 W/cm up to 1 kW/cm2 (or even higher) for short periods of time. The term "ultrasound" as used in this specification is intended to encompass diagnostic, therapeutic and focused ultrasound.

Focused ultrasound (FUS) allows thermal energy to be delivered without an invasive probe (see Morocz et al 1998 Journal of Magnetic Resonance Imaging Vol. 8, No. 1, pp. 136-142. Another form of focused ultrasound is high intensity focused ultrasound (HIFU) which is reviewed by Moussatov et al in Ultrasonics (1998) Vol. 36, No. 8, pp. 893-900 and TranHuuHue et al in Acustica (1997) Vol. 83, No. 6, pp. 1103-1106.

Preferably, a combination of diagnostic ultrasound and a therapeutic ultrasound is employed. This combination is not intended to be limiting, however, and the skilled reader will appreciate that any variety of combinations of ultrasound may be used. Additionally, the energy density, frequency of ultrasound, and period of exposure may be varied.

Preferably the exposure to an ultrasound energy source is at a power density of from about 0.05 to about 100 Wcm-2. Even more preferably, the exposure to an ultrasound energy source is at a power density of from about 1 to about 15 Wcm-2.

Preferably the exposure to an ultrasound energy source is at a frequency of from about 0.015 to about 10.0 MHz. More preferably the exposure to an ultrasound energy source is at a frequency of from about 0.02 to about 5.0 MHz or about 6.0 MHz. Most preferably, the ultrasound is applied at a frequency of 3 MHz.

Preferably the exposure is for periods of from about 10 milliseconds to about 60 minutes. Preferably the exposure is for periods of from about 1 second to about 5 minutes. More preferably, the ultrasound is applied for about 2 minutes. Depending on the particular target cell to be disrupted, however, the exposure may be for a longer duration, for example, for 15 minutes.

Advantageously, the target tissue is exposed to an ultrasound energy source at an acoustic power density of from about 0.05 Wcm-2 to about 10 Wcm-2 with a frequency ranging from about 0.015 to about 10 MHz (see WO 98/52609). However, alternatives are also possible, for example, exposure to an ultrasound energy source at an acoustic power density of above 100 Wcm-2, but for reduced periods of time, for example, 1000 Wcm-2 for periods in the millisecond range or less.

Preferably the application of the ultrasound is in the form of multiple pulses; thus, both continuous wave and pulsed wave (pulsatile delivery of ultrasound) may be employed in any combination. For example, continuous wave ultrasound may be applied, followed by pulsed wave ultrasound, or vice versa. This may be repeated any number of times, in any order and combination. The pulsed wave ultrasound may be applied against a background of continuous wave ultrasound, and any number of pulses may be used in any number of groups.

Preferably, the ultrasound may comprise pulsed wave ultrasound. In a highly preferred embodiment, the ultrasound is applied at a power density of 0.7 Wcm-2 or 1.25 Wcm-2 as a continuous wave. Higher power densities may be employed if pulsed wave ultrasound is used.

Use of ultrasound is advantageous as, like light, it may be focused accurately on a target. Moreover, ultrasound is advantageous as it may be focused more deeply into tissues unlike light. It is therefore better suited to whole-tissue penetration (such as but not limited to a lobe of the liver) or whole organ (such as but not limited to the entire liver or an entire muscle, such as the heart) therapy. Another important advantage is that ultrasound is a non-invasive stimulus which is used in a wide variety of diagnostic and therapeutic applications. By way of example, ultrasound is well known in medical imaging techniques and, additionally, in orthopedic therapy. Furthermore, instruments suitable for the application of ultrasound to a subject vertebrate are widely available and their use is well known in the art.

In particular embodiments, the guide molecule is modified by a secondary structure to increase the specificity of the CRISPR-Cas system and the secondary structure can protect against exonuclease activity and allow for 5' additions to the guide sequence also referred to herein as a protected guide molecule.

In one aspect, the invention provides for hybridizing a "protector RNA" to a sequence of the guide molecule, wherein the "protector RNA" is an RNA strand complementary to the 3' end of the guide molecule to thereby generate a partially double-stranded guide RNA. In an embodiment of the invention, protecting mismatched bases (i.e. the bases of the guide molecule which do not form part of the guide sequence) with a perfectly complementary protector sequence decreases the likelihood of target RNA binding to the mismatched basepairs at the 3' end. In particular embodiments of the invention, additional sequences comprising an extended length may also be present within the guide molecule such that the guide comprises a protector sequence within the guide molecule. This "protector sequence" ensures that the guide molecule comprises a "protected sequence" in addition to an "exposed sequence" (comprising the part of the guide sequence hybridizing to the target sequence). In particular embodiments, the guide molecule is modified by the presence of the protector guide to comprise a secondary structure such as a hairpin. Advantageously there are three or four to thirty or more, e.g., about 10 or more, contiguous base pairs having complementarity to the protected sequence, the guide sequence or both. It is advantageous that the protected portion does not impede thermodynamics of the CRISPR-Cas system interacting with its target. By providing such an extension including a partially double stranded guide molecule, the guide molecule is considered protected and results in improved specific binding of the CRISPR-Cas complex, while maintaining specific activity.

In particular embodiments, use is made of a truncated guide (tru-guide), i.e. a guide molecule which comprises a guide sequence which is truncated in length with respect to the canonical guide sequence length. As described by Nowak et al. (Nucleic Acids Res (2016) 44 (20): 9555-9564), such guides may allow catalytically active CRISPR-Cas enzyme to bind its target without cleaving the target RNA. In particular embodiments, a truncated guide is used which allows the binding of the target but retains only nickase activity of the CRISPR-Cas enzyme.

The present invention may be further illustrated and extended based on aspects of CRISPR-Cas development and use as set forth in the following articles and particularly as relates to delivery of a CRISPR protein complex and uses of an RNA guided endonuclease in cells and organisms:

Multiplex genome engineering using CRISPR-Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121): 819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR-Cas-Mediated Genome Engineering. Wang H., Yang H., Shivalila C S., Dawlaty M M., Cheng A W., Zhang F., Jaenisch R. Cell May 9; 153(4):910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463):472-6. doi: 10.1038/Nature12466. Epub 2013 August 23 (2013);

Double Nicking by RNA-Guided CRISPR Cas9 for Enhanced Genome Editing Specificity. Ran, FA., Hsu, PD., Lin, CY., Gootenberg, J S., Konermann, S., Trevino, AE., Scott, DA., Inoue, A., Matoba, S., Zhang, Y., & Zhang, F. Cell August 28. pii: S0092-8674(13) 01015-5 (2013-A);

DNA targeting specificity of RNA-guided Cas9 nucleases. Hsu, P., Scott, D., Weinstein, J., Ran, FA., Konermann, S., Agarwala, V., Li, Y., Fine, E., Wu, X., Shalem, O., Cradick, TJ., Marraffini, LA., Bao, G., & Zhang, F. Nat Biotechnol doi:10.1038/nbt.2647 (2013);

Genome engineering using the CRISPR-Cas9 system. Ran, FA., Hsu, PD., Wright, J., Agarwala, V., Scott, DA., Zhang, F. Nature Protocols November; 8(11): 2281-308 (2013-B);

Genome-Scale CRISPR-Cas9 Knockout Screening in Human Cells. Shalem, O., Sanjana, NE., Hartenian, E., Shi, X., Scott, DA., Mikkelson, T., Heckl, D., Ebert, BL., Root, DE., Doench, JG., Zhang, F. Science December 12. (2013);

Crystal structure of cas9 in complex with guide RNA and target DNA. Nishimasu, H., Ran, FA., Hsu, PD., Konermann, S., Shehata, SI., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure $T_M$, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014);

Development and Applications of CRISPR-Cas9 for Genome Engineering, Hsu P D, Lander E S, Zhang F., Cell. June 5; 157(6):1262-78 (2014).

Genetic screens in human cells using the CRISPR-Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh 00, Barcena C, Hsu P D, Habib N, Gootenberg J S, Nishimasu H, Nureki O, Zhang F., Nature. January 29; 517(7536):583-8 (2015).

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520 (7546): 186-91 (2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., CRISPR-Cas9 cleavage of viral DNA efficiently suppresses hepatitis B virus," Scientific Reports 5:10833. doi: 10.1038/srep10833 (Jun. 2, 2015)

Nishimasu et al., Crystal Structure of *Staphylococcus aureus* Cas9," Cell 162, 1113-1126 (Aug. 27, 2015)

BCL11A enhancer dissection by Cas9-mediated in situ saturating mutagenesis, Canver et al., Nature 527 (7577):192-7 (Nov. 12, 2015) doi: 10.1038/nature15521. Epub 2015 September 16.

*Cpf1 Is a Single RNA-Guided Endonuclease of a Class 2 CRISPR-Cas System*, Zetsche et al., Cell 163, 759-71 (Sep. 25, 2015).

*Discovery and Functional Characterization of Diverse Class 2 CRISPR-Cas Systems*, Shmakov et al., Molecular Cell, 60(3), 385-397 doi: 10.1016/j.molce1.2015.10.008 Epub Oct. 22, 2015.

*Rationally engineered Cas9 nucleases with improved specificity*, Slaymaker et al., Science 2016 January 1 351(6268): 84-88 doi: 10.1126/science.aad5227. Epub 2015 December 1.

Gao et al, "Engineered Cpf1 Enzymes with Altered PAM Specificities," bioRxiv 091611; doi: http://dx.doi.org/10.1101/091611 (Dec. 4, 2016).

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)— associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR-Cas system for the one-step generation of mice carrying mutations in multiple genes which were traditionally generated in multiple steps by sequential recombination in embryonic stem cells and/or time-consuming intercrossing of mice with a single mutation. The CRISPR-Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and guide RNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR-Cas9 knockout and nucleotide preference at the cleavage site. The authors also found that the sequence preference for CRISPRi/a is substantially different from that for CRISPR-Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Canver et al. (2015) demonstrated a CRISPR-Cas9-based functional investigation of non-coding genomic elements. The authors we developed pooled CRISPR-Cas9 guide RNA libraries to perform in situ saturating mutagenesis of the human and mouse BCL11A enhancers which revealed critical features of the enhancers.

Zetsche et al. (2015) reported characterization of Cpf1, a class 2 CRISPR nuclease from *Francisella novicida* U112 having features distinct from Cas9. Cpf1 is a single RNA-guided endonuclease lacking tracrRNA, utilizes a T-rich protospacer-adjacent motif, and cleaves DNA via a staggered DNA double-stranded break.

Shmakov et al. (2015) reported three distinct Class 2 CRISPR-Cas systems. Two system CRISPR enzymes (C2c1 and C2c3) contain RuvC-like endonuclease domains distantly related to Cpf1. Unlike Cpf1, C2c1 depends on both crRNA and tracrRNA for DNA cleavage. The third enzyme (C2c2) contains two predicted HEPN RNase domains and is tracrRNA independent.

Slaymaker et al (2016) reported the use of structure-guided protein engineering to improve the specificity of *Streptococcus pyogenes* Cas9 (SpCas9). The authors developed "enhanced specificity" SpCas9 (eSpCas9) variants which maintained robust on-target cleavage with reduced off-target effects.

The methods and tools provided herein may be designed for use with or Cas13, a type II nuclease that does not make use of tracrRNA. Orthologs of Cas13 have been identified in different bacterial species as described herein. Further type II nucleases with similar properties can be identified using methods described in the art (Shmakov et al. 2015, 60:385-397; Abudayeh et al. 2016, Science, 5; 353(6299)). In particular embodiments, such methods for identifying novel CRISPR effector proteins may comprise the steps of selecting sequences from the database encoding a seed which identifies the presence of a CRISPR Cas locus, identifying loci located within 10 kb of the seed comprising Open Reading Frames (ORFs) in the selected sequences, selecting therefrom loci comprising ORFs of which only a single ORF encodes a novel CRISPR effector having greater than 700 amino acids and no more than 90% homology to a known CRISPR effector. In particular embodiments, the seed is a protein that is common to the CRISPR-Cas system, such as Cas1. In further embodiments, the CRISPR array is used as a seed to identify new effector proteins.

Also, "Dimeric CRISPR RNA-guided Fold nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided Fold Nucleases that recognize extended sequences and can edit endogenous genes with high efficiencies in human cells.

With respect to general information on CRISPR/Cas Systems, components thereof, and delivery of such components, including methods, materials, delivery vehicles, vectors, particles, and making and using thereof, including as to amounts and formulations, as well as CRISPR-Cas-expressing eukaryotic cells, CRISPR-Cas expressing eukaryotes, such as a mouse, reference is made to: U.S. Pat. Nos. 8,999,641, 8,993,233, 8,697,359, 8,771,945, 8,795,965, 8,865,406, 8,871,445, 8,889,356, 8,889,418, 8,895,308, 8,906,616, 8,932,814, and 8,945,839; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US 2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); US 2015-0184139 (U.S. application Ser. No. 14/324,960); Ser. No. 14/054,414 European Patent Applications EP 2 771 468 (EP13818570.7), EP 2 764 103 (EP13824232.6), and EP 2 784 162 (EP14170383.5); and PCT Patent Publications WO2014/093661 (PCT/US2013/074743), WO2014/093694 (PCT/US2013/074790), WO2014/093595 (PCT/US2013/074611), WO2014/093718 (PCT/US2013/074825), WO2014/093709 (PCT/US2013/074812), WO2014/093622 (PCT/US2013/074667), WO2014/093635 (PC T/US2013/074691), WO2014/093655 (PCT/US2013/074736), WO2014/093712 (PC T/US2013/074819), WO2014/093701 (PCT/US2013/074800), WO2014/018423 (PC T/US2013/051418), WO2014/204723 (PCT/US2014/041790), WO2014/204724 (PC T/US2014/041800), WO2014/204725 (PCT/US2014/041803), WO2014/204726 (PC T/US2014/041804), WO2014/204727 (PCT/US2014/041806), WO2014/204728 (PCT/US2014/041808), WO2014/204729 (PCT/US2014/041809), WO2015/089351 (PC T/US2014/069897), WO2015/089354 (PCT/US2014/069902), WO2015/089364 (PC T/US2014/069925), WO2015/089427 (PCT/US2014/070068), WO2015/089462 (PC T/US2014/070127), WO2015/089419 (PCT/US2014/070057), WO2015/089465 (PC T/US2014/070135), WO2015/089486 (PCT/US2014/070175), WO2015/058052 (PC T/US2014/061077), WO2015/070083 (PCT/US2014/064663), WO2015/089354 (PC T/US2014/069902), WO2015/089351 (PCT/US2014/069897), WO2015/089364 (PC T/US2014/069925), WO2015/089427 (PCT/US2014/070068), WO2015/089473 (PCT/US2014/070152), WO2015/089486 (PCT/US2014/070175), WO2016/049258 (PC T/US2015/051830), WO2016/094867 (PCT/US2015/

065385), WO2016/094872 (PC T/US2015/065393), WO2016/094874 (PCT/US2015/065396), WO2016/106244 (PCT/US2015/067177).

Mention is also made of U.S. application 62/180,709, Jun. 17, 2015, PROTECTED GUIDE RNAS (PGRNAS); U.S. application 62/091,455, filed, Dec. 12, 2014, PROTECTED GUIDE RNAS (PGRNAS); U.S. application 62/096,708, Dec. 24, 2014, PROTECTED GUIDE RNAS (PGRNAS); U.S. applications 62/091,462, Dec. 12, 2014, 62/096,324, Dec. 23, 2014, 62/180,681, Jun. 17, 2015, and 62/237,496, Oct. 5, 2015, DEAD GUIDES FOR CRISPR TRANSCRIPTION FACTORS; U.S. application 62/091,456, Dec. 12, 2014 and 62/180,692, Jun. 17, 2015, ESCORTED AND FUNCTIONALIZED GUIDES FOR CRISPR-CAS SYSTEMS; U.S. application 62/091,461, Dec. 12, 2014, DELIVERY, USE AND THERAPEUTIC APPLICATIONS OF THE CRISPR-CAS SYSTEMS AND COMPOSITIONS FOR GENOME EDITING AS TO HEMATOPOETIC STEM CELLS (HSCs); U.S. application 62/094,903, Dec. 19, 2014, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, Dec. 24, 2014, ENGINEERING OF SYSTEMS, METHODS AND OPTIMIZED ENZYME AND GUIDE SCAFFOLDS FOR SEQUENCE MANIPULATION; U.S. application 62/098, 059, Dec. 30, 2014, 62/181,641, Jun. 18, 2015, and 62/181, 667, Jun. 18, 2015, RNA-TARGETING SYSTEM; U.S. application 62/096,656, Dec. 24, 2014 and 62/181,151, Jun. 17, 2015, CRISPR HAVING OR ASSOCIATED WITH DESTABILIZATION DOMAINS; U.S. application 62/096, 697, Dec. 24, 2014, CRISPR HAVING OR ASSOCIATED WITH AAV; U.S. application 62/098,158, Dec. 30, 2014, ENGINEERED CRISPR COMPLEX INSERTIONAL TARGETING SYSTEMS; U.S. application 62/151,052, Apr. 22, 2015, CELLULAR TARGETING FOR EXTRACELLULAR EXOSOMAL REPORTING; U.S. application 62/054,490, Sep. 24, 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 61/939,154, Feb. 12, 2014, SYSTEMS, METHODS AND COMPOSITIONS FOR SEQUENCE MANIPULATION WITH OPTIMIZED FUNCTIONAL CRISPR-CAS SYSTEMS; U.S. application 62/055,484, Sep. 25, 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, Dec. 4, 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, Sep. 24, 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, Oct. 23, 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. applications 62/054, 675, Sep. 24, 2014 and 62/181,002, Jun. 17, 2015, DELIVERY, USE AND THERAPEUTIC APPLICATIONS OF THE CRISPR-CAS SYSTEMS AND COMPOSITIONS IN NEURONAL CELLS/TISSUES; U.S. application 62/054, 528, Sep. 24, 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, Sep. 25, 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, Sep. 25, 2014, MULTIFUNCTIONAL-CRISPR COMPLEXES AND/OR OPTIMIZED ENZYME LINKED FUNCTIONAL-CRISPR COMPLEXES; U.S. application 62/087,475, Dec. 4, 2014 and 62/181,690, Jun. 18, 2015, FUNCTIONAL SCREENING WITH OPTIMIZED FUNCTIONAL CRISPR-CAS SYSTEMS; U.S. application 62/055,487, Sep. 25, 2014, FUNCTIONAL SCREENING WITH OPTIMIZED FUNCTIONAL CRISPR-CAS SYSTEMS; U.S. application 62/087,546, Dec. 4, 2014 and 62/181,687, Jun. 18, 2015, MULTIFUNCTIONAL CRISPR COMPLEXES AND/OR OPTIMIZED ENZYME LINKED FUNCTIONAL-CRISPR COMPLEXES; and U.S. application 62/098,285, Dec. 30, 2014, CRISPR MEDIATED IN VIVO MODELING AND GENETIC SCREENING OF TUMOR GROWTH AND METASTASIS.

Mention is made of U.S. applications 62/181,659, Jun. 18, 2015 and 62/207,318, Aug. 19, 2015, ENGINEERING AND OPTIMIZATION OF SYSTEMS, METHODS, ENZYME AND GUIDE SCAFFOLDS OF CAS9 ORTHOLOGS AND VARIANTS FOR SEQUENCE MANIPULATION. Mention is made of U.S. applications 62/181,663, Jun. 18, 2015 and 62/245,264, Oct. 22, 2015, NOVEL CRISPR ENZYMES AND SYSTEMS, U.S. applications 62/181,675, Jun. 18, 2015, 62/285,349, Oct. 22, 2015, 62/296,522, Feb. 17, 2016, and 62/320,231, Apr. 8, 2016, NOVEL CRISPR ENZYMES AND SYSTEMS, U.S. application 62/232,067, Sep. 24, 2015, U.S. application Ser. No. 14/975,085, Dec. 18, 2015, European application No. 16150428.7, U.S. application 62/205,733, Aug. 16, 2015, U.S. application 62/201, 542, Aug. 5, 2015, U.S. application 62/193,507, Jul. 16, 2015, and U.S. application 62/181,739, Jun. 18, 2015, each entitled NOVEL CRISPR ENZYMES AND SYSTEMS and of U.S. application 62/245,270, Oct. 22, 2015, NOVEL CRISPR ENZYMES AND SYSTEMS. Mention is also made of U.S. application 61/939,256, Feb. 12, 2014, and WO 2015/089473 (PCT/US2014/070152), Dec. 12, 2014, each entitled ENGINEERING OF SYSTEMS, METHODS AND OPTIMIZED GUIDE COMPOSITIONS WITH NEW ARCHITECTURES FOR SEQUENCE MANIPULATION. Mention is also made of PCT/US2015/045504, Aug. 15, 2015, U.S. application 62/180,699, Jun. 17, 2015, and U.S. application 62/038,358, Aug. 17, 2014, each entitled GENOME EDITING USING CAS9 NICKASES.

Each of these patents, patent publications, and applications, and all documents cited therein or during their prosecution ("appin cited documents") and all documents cited or referenced in the appin cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appin cited documents) are incorporated herein by reference to the same extent as if each individual document was specifically and individually indicated to be incorporated by reference.

Tale Systems

As disclosed herein editing can be made by way of the transcription activator-like effector nucleases (TALENs)

system. Transcription activator-like effectors (TALEs) can be engineered to bind practically any desired DNA sequence. Exemplary methods of genome editing using the TALEN system can be found for example in Cermak T. Doyle E L. Christian M. Wang L. Zhang Y. Schmidt C, et al. Efficient design and assembly of custom TALEN and other TAL effector-based constructs for DNA targeting. Nucleic Acids Res. 2011; 39:e82; Zhang F. Cong L. Lodato S. Kosuri S. Church G M. Arlotta P Efficient construction of sequence-specific TAL effectors for modulating mammalian transcription. Nat Biotechnol. 2011; 29:149-153 and U.S. Pat. Nos. 8,450,471, 8,440,431 and 8,440,432, all of which are specifically incorporated by reference.

In advantageous embodiments of the invention, the methods provided herein use isolated, non-naturally occurring, recombinant or engineered DNA binding proteins that comprise TALE monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", or "TALE monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is X1-11-(X12X13)-X14-33 or 34 or 35, where the subscript indicates the amino acid position and X represents any amino acid. X12X13 indicate the RVDs. In some polypeptide monomers, the variable amino acid at position 13 is missing or absent and in such polypeptide monomers, the RVD consists of a single amino acid. In such cases the RVD may be alternatively represented as X*, where X represents X12 and (*) indicates that X13 is absent. The DNA binding domain comprises several repeats of TALE monomers and this may be represented as (X1-11-(X12X13)-X14-33 or 34 or 35)z, where in an advantageous embodiment, z is at least 5 to 40. In a further advantageous embodiment, z is at least 10 to 26.

The TALE monomers have a nucleotide binding affinity that is determined by the identity of the amino acids in its RVD. For example, polypeptide monomers with an RVD of NI preferentially bind to adenine (A), polypeptide monomers with an RVD of NG preferentially bind to thymine (T), polypeptide monomers with an RVD of HD preferentially bind to cytosine (C) and polypeptide monomers with an RVD of NN preferentially bind to both adenine (A) and guanine (G). In yet another embodiment of the invention, polypeptide monomers with an RVD of IG preferentially bind to T. Thus, the number and order of the polypeptide monomer repeats in the nucleic acid binding domain of a TALE determines its nucleic acid target specificity. In still further embodiments of the invention, polypeptide monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated by reference in its entirety.

The TALE polypeptides used in methods of the invention are isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In a preferred embodiment of the invention, polypeptide monomers having RVDs RN, NN, NK, SN, NH, KN, HN, NQ, HH, RG, KH, RH and SS preferentially bind to guanine. In a much more advantageous embodiment of the invention, polypeptide monomers having RVDs RN, NK, NQ, HH, KH, RH, SS and SN preferentially bind to guanine and thereby allow the generation of TALE polypeptides with high binding specificity for guanine containing target nucleic acid sequences. In an even more advantageous embodiment of the invention, polypeptide monomers having RVDs HH, KH, NH, NK, NQ, RH, RN and SS preferentially bind to guanine and thereby allow the generation of TALE polypeptides with high binding specificity for guanine containing target nucleic acid sequences. In a further advantageous embodiment, the RVDs that have high binding specificity for guanine are RN, NH RH and KH. Furthermore, polypeptide monomers having an RVD of NV preferentially bind to adenine and guanine. In more preferred embodiments of the invention, polypeptide monomers having RVDs of H*, HA, KA, N*, NA, NC, NS, RA, and S* bind to adenine, guanine, cytosine and thymine with comparable affinity.

The predetermined N-terminal to C-terminal order of the one or more polypeptide monomers of the nucleic acid or DNA binding domain determines the corresponding predetermined target nucleic acid sequence to which the TALE polypeptides will bind. As used herein the polypeptide monomers and at least one or more half polypeptide monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases this region may be referred to as repeat 0. In animal genomes, TALE binding sites do not necessarily have to begin with a thymine (T) and TALE polypeptides may target DNA sequences that begin with T, A, G or C. The tandem repeat of TALE monomers always ends with a half-length repeat or a stretch of sequence that may share identity with only the first 20 amino acids of a repetitive full length TALE monomer and this half repeat may be referred to as a half-monomer (FIG. 8), which is included in the term "TALE monomer". Therefore, it follows that the length of the nucleic acid or DNA being targeted is equal to the number of full polypeptide monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region.

An exemplary amino acid sequence of a N-terminal capping region is:

(SEQ ID NO: 7)
MDPIRSRTPSPARELLSGPQPDGVQPTADRGVSP

PAGGPLDGLPARRTMSRTRLPSPPAPSPAFSADS

FSDLLRQFDPSLFNTSLFDSLPPFGAHHTEAATG

EWDEVQSGLRAADAPPPTMRVAVTAARPPRAKPA

PRRRAAQPSDASPAAQVDLRTLGYSQQQQEKIKP

KVRSTVAQHHEALVGHGFTHAHIVALSQHPAALG

TVAVKYQDMIAALPEATHEAIVGVGKQWSGARAL

EALLTVAGELRGPPLQLDTGQLLKIAKRGGVTAV

EAVHAWRNALTGAPLN

An exemplary amino acid sequence of a C-terminal capping region is:

(SEQ ID NO: 8)
RPALESIVAQLSRPDPALAALTNDHLVALACLG

GRPALDAVKKGLPHAPALIKRTNRRIPERTSHR

VADHAQVVRVLGFFQCHSHPAQAFDDAMTQFGM

SRHGLLQLFRRVGVTELEARSGTLPPASQRWDR

ILQASGMKRAKPSPTSTQTPDQASLHAFADSLE

RDLDAPSPMHEGDQTRAS

As used herein the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full length capping region, while fragments that include the C-terminal 20 amino acids retain greater than 50% of the efficacy of the full length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies may be generated by any of a number of computer programs known in the art, which include but are not limited to BLAST or FASTA. Suitable computer program for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In advantageous embodiments described herein, the TALE polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the TALE polypeptides described herein, the activity mediated by the effector domain is a biological activity. For example, in some embodiments the effector domain is a transcriptional inhibitor (i.e., a repressor domain), such as an mSin interaction domain (SID). SID4X domain or a Krüppel-associated box (KRAB) or fragments of the KRAB domain. In some embodiments the effector domain is an enhancer of transcription (i.e. an activation domain), such as the VP16, VP64 or p65 activation domain. In some embodiments, the nucleic acid binding is linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination the activities described herein.

ZN-Finger Nucleases

Other preferred tools for genome editing for use in the context of this invention include zinc finger systems and TALE systems. One type of programmable DNA-binding domain is provided by artificial zinc-finger (ZF) technology, which involves arrays of ZF modules to target new DNA-binding sites in the genome. Each finger module in a ZF array targets three DNA bases. A customized array of individual zinc finger domains is assembled into a ZF protein (ZFP).

ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to FokI cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms.Exemplary methods of genome editing using ZFNs can be found for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference.

Meganucleases

As disclosed herein editing can be made by way of meganucleases, which are endodeoxyribonucleases characterized by a large recognition site (double-stranded DNA sequences of 12 to 40 base pairs). Exemplary method for using meganucleases can be found in U.S. Pat. Nos. 8,163,514; 8,133,697; 8,021,867; 8,119,361; 8,119,381; 8,124,369; and 8,129,134, which are specifically incorporated by reference.

Delivery

The programmable nucleic acid modifying agents and other modulating agents, or components thereof, or nucleic acid molecules thereof (including, for instance HDR template), or nucleic acid molecules encoding or providing components thereof, may be delivered by a delivery system herein described.

Vector delivery, e.g., plasmid, viral delivery: the modulating agents, can be delivered using any suitable vector, e.g., plasmid or viral vectors, such as adeno associated virus (AAV), lentivirus, adenovirus or other viral vector types, or combinations thereof. In some embodiments, the vector, e.g., plasmid or viral vector is delivered to the tissue of interest by, for example, an intramuscular injection, while other times the delivery is via intravenous, transdermal, intranasal, oral, mucosal, or other delivery methods. Such delivery may be either via a single dose, or multiple doses. One skilled in the art understands that the actual dosage to be delivered herein may vary greatly depending upon a variety of factors, such as the vector choice, the target cell, organism, or tissue, the general condition of the subject to be treated, the degree of transformation/modification sought, the administration route, the administration mode, the type of transformation/modification sought, etc.

Diseases

In certain embodiments, the ex vivo system is derived from a subject with a disease (e.g., to study the disease ex vivo). In certain embodiments, the ex vivo system is used as a cell-based therapy to treat a subject suffering from a disease. The disease may be selected from the group consisting of cancer, autoimmune disease, bone marrow failure, hematological conditions, aplastic anemia, beta-thalassemia, diabetes, motor neuron disease, Parkinson's disease, spinal cord injury, muscular dystrophy, kidney disease, liver disease, multiple sclerosis, congestive heart failure, head trauma, lung disease, psoriasis, liver cirrhosis, vision loss, cystic fibrosis, hepatitis C virus, human immunodeficiency virus, inflammatory bowel disease (IBD), and any disorder associated with tissue degeneration.

Cancer

In certain example embodiments, the pharmaceutical compositions and adoptive cell transfer strategies may be used to treat various forms of cancer. Examples of cancer include but are not limited to carcinoma, lymphoma, blastoma, sarcoma, and leukemia or lymphoid malignancies.

More particular examples of such cancers include without limitation: squamous cell cancer (e.g., epithelial squamous cell cancer), lung cancer including small-cell lung cancer, non-small cell lung cancer, adenocarcinoma of the lung, squamous carcinoma of the lung and large cell carcinoma of the lung, cancer of the peritoneum, hepatocellular cancer, gastric or stomach cancer including gastrointestinal cancer, pancreatic cancer, glioma, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, as well as CNS cancer, melanoma, head and neck cancer, bone cancer, bone marrow cancer, duodenum cancer, oesophageal cancer, thyroid cancer, or hematological cancer.

Other non-limiting examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumours, Breast Cancer, Cancer of the Renal Pelvis and Urethra, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Glioblastoma, Childhood Cerebellar Astrocytoma, Childhood Cerebral Astrocytoma, Childhood Extracranial Germ Cell Tumours, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumours, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumours, Exocrine Pancreatic Cancer, Extracranial Germ Cell Tumour, Extragonadal Germ Cell Tumour, Extrahepatic Bile Duct Cancer, Eye Cancer, Female Breast Cancer, Gaucher's Disease, Gallbladder Cancer, Gastric Cancer, Gastrointestinal Carcinoid Tumour, Gastrointestinal Tumours, Germ Cell Tumours, Gestational Trophoblastic Tumour, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumour, Ovarian Low Malignant Potential Tumour, Pancreatic Cancer, Paraproteinemias, Purpura, Parathyroid Cancer, Penile Cancer, Pheochromocytoma, Pituitary Tumour, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Urethra Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumours, T-Cell Lymphoma, Testicular Cancer, Thymoma, Thyroid Cancer, Transitional Cell Cancer of the Renal Pelvis and Urethra, Transitional Renal Pelvis and Urethra Cancer, Trophoblastic Tumours, Urethra and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, or Wilms' Tumour.

Autoimmune Diseases

In certain example embodiments, the pharmaceutical compositions and adoptive cell transfer strategies may be used to treat various autoimmune diseases. As used throughout the present specification, the terms "autoimmune disease" or "autoimmune disorder" used interchangeably refer to a diseases or disorders caused by an immune response against a self-tissue or tissue component (self-antigen) and include a self-antibody response and/or cell-mediated response. The terms encompass organ-specific autoimmune diseases, in which an autoimmune response is directed against a single tissue, as well as non-organ specific autoimmune diseases, in which an autoimmune response is directed against a component present in two or more, several or many organs throughout the body.

Non-limiting examples of autoimmune diseases include but are not limited to acute disseminated encephalomyelitis (ADEM); Addison's disease; ankylosing spondylitis; antiphospholipid antibody syndrome (APS); aplastic anemia; autoimmune gastritis; autoimmune hepatitis; autoimmune thrombocytopenia; Behcet's disease; coeliac disease; dermatomyositis; diabetes mellitus type I; Goodpasture's syndrome; Graves' disease; Guillain-Barré syndrome (GBS); Hashimoto's disease; idiopathic thrombocytopenic purpura; inflammatory bowel disease (IBD) including Crohn's disease and ulcerative colitis; mixed connective tissue disease; multiple sclerosis (MS); myasthenia gravis; opsoclonus myoclonus syndrome (OMS); optic neuritis; Ord's thyroiditis; pemphigus; pernicious anaemia; polyarteritis nodosa; polymyositis; primary biliary cirrhosis; primary myxoedema; psoriasis; rheumatic fever; rheumatoid arthritis; Reiter's syndrome; scleroderma; Sjögren's syndrome; systemic lupus erythematosus; Takayasu's arteritis;

temporal arteritis; vitiligo; warm autoimmune hemolytic anemia; or Wegener's granulomatosis.

Other Diseases

In certain embodiments, disease may be treated by infusion of target cell types (see, e.g., US20110091433A1 and Table 2 of application). In certain embodiments, target cell types can be modulated according to the present invention to more faithfully recapitulate the in vivo cells.

Aplastic anemia is a rare but fatal bone marrow disorder, marked by pancytopenia and hypocellular bone marrow (Young et al. Blood 2006, 108: 2509-2519). The disorder may be caused by an immune-mediated pathophysiology with activated type I cytotoxic T cells expressing Th1 cytokine, especially γ-interferon targeted towards the haematopoietic stem cell compartment, leading to bone marrow failure and hence hematopoiesis (Bacigalupo et al. Hematology 2007, 23-28). The majority of aplastic anaemia patients can be treated with stem cell transplantation obtained from HLA-matched siblings (Locasciulli et al. Haematologica. 2007; 92:11-18.).

Thalassaemia is an inherited autosomal recessive blood disease marked by a reduced synthesis rate of one of the globin chains that make up hemoglobin. Thus, there is an underproduction of normal globin proteins, often due to mutations in regulatory genes, which results in formation of abnormal hemoglobin molecules, causing anemia. Different types of thalassemia include alpha thalassemia, beta thalassemia, and delta thalassemia, which affect production of the alpha globin, beta globin, and delta globin, respectively.

Diabetes is a syndrome resulting in abnormally high blood sugar levels (hyperglycemia). Diabetes refers to a group of diseases that lead to high blood glucose levels due to defects in either insulin secretion or insulin action in the body. Diabetes is typically separated into two types: type 1 diabetes, marked by a diminished production of insulin, or type 2 diabetes, marked by a resistance to the effects of insulin. Both types lead to hyperglycemia, which largely causes the symptoms generally associated with diabetes, e.g., excessive urine production, resulting compensatory thirst and increased fluid intake, blurred vision, unexplained weight loss, lethargy, and changes in energy metabolism.

Motor neuron diseases refer to a group of neurological disorders that affect motor neurons. Such diseases include amyotrophic lateral sclerosis (ALS), primary lateral sclerosis (PLS), and progressive muscular atrophy (PMA). ALS is marked by degeneration of both the upper and lower motor neurons, which ceases messages to the muscles and results in their weakening and eventual atrophy. PLS is a rare motor neuron disease affecting upper motor neurons only, which causes difficulties with balance, weakness and stiffness in legs, spasticity, and speech problems. PMA is a subtype of ALS that affects only the lower motor neurons, which can cause muscular atrophy, fasciculations, and weakness.

Parkinson's disease (PD) is a neurodegenerative disorder marked by the loss of the nigrostriatal pathway, resulting from degeneration of dopaminergic neurons within the substantia nigra. The cause of PD is not known, but is associated with the progressive death of dopaminergic (tyrosine hydroxylase (TH) positive) mesencephalic neurons, inducing motor impairment. Hence, PD is characterized by muscle rigidity, tremor, bradykinesia, and potentially akinesia.

Spinal cord injury is characterized by damage to the spinal cord and, in particular, the nerve fibers, resulting in impairment of part or all muscles or nerves below the injury site. Such damage may occur through trauma to the spine that fractures, dislocates, crushes, or compresses one or more of the vertebrae, or through nontraumatic injuries caused by arthritis, cancer, inflammation, or disk degeneration.

Muscular dystrophy (MD) refers to a set of hereditary muscle diseases that weaken skeletal muscles. MD may be characterized by progressive muscle weakness, defects in muscle proteins, muscle cell apoptosis, and tissue atrophy. There are over 100 diseases which exhibit MD characteristics, although nine diseases in particular—Duchenne, Becker, limb girdle, congenital, facioscapulohumeral, myotonic, oculopharyngeal, distal, and Emery-Dreifuss—are classified as MD.

Kidney disease refers to conditions that damage the kidneys and decrease their ability to function, which includes removal of wastes and excess water from the blood, regulation of electrolytes, blood pressure, acid-base balance, and reabsorption of glucose and amino acids. The two main causes of kidney disease are diabetes and high blood pressure, although other causes include glomerulonephritis, lupus, and malformations and obstructions in the kidney.

Multiple sclerosis is an autoimmune condition in which the immune system attacks the central nervous system, leading to demyelination. MS affects the ability of nerve cells in the brain and spinal cord to communicate with each other, as the body's own immune system attacks and damages the myelin which enwraps the neuron axons. When myelin is lost, the axons can no longer effectively conduct signals. This can lead to various neurological symptoms which usually progresses into physical and cognitive disability.

Congestive heart failure refers to a condition in which the heart cannot pump enough blood to the body's other organs. This condition can result from coronary artery disease, scar tissue on the heart cause by myocardial infarction, high blood pressure, heart valve disease, heart defects, and heart valve infection. Treatment programs typically consist of rest, proper diet, modified daily activities, and drugs such as angiotensin-converting enzyme (ACE) inhibitors, beta blockers, digitalis, diuretics, vasodilators. However, the treatment program will not reverse the damage or condition of the heart.

Hepatitis C is an infectious disease in the liver, caused by hepatitis C virus. Hepatitis C can progress to scarring (fibrosis) and advanced scarring (cirrhosis). Cirrhosis can lead to liver failure and other complications such as liver cancer.

Head trauma refers to an injury of the head that may or may not cause injury to the brain. Common causes of head trauma include traffic accidents, home and occupational accidents, falls, and assaults. Various types of problems may result from head trauma, including skull fracture, lacerations of the scalp, subdural hematoma (bleeding below the dura mater), epidural hematoma (bleeding between the dura mater and the skull), cerebral contusion (brain bruise), concussion (temporary loss of function due to trauma), coma, or even death.

Lung disease is a broad term for diseases of the respiratory system, which includes the lung, pleural cavity, bronchial tubes, trachea, upper respiratory tract, and nerves and muscles for breathing. Examples of lung diseases include obstructive lung diseases, in which the bronchial tubes become narrowed; restrictive or fibrotic lung diseases, in which the lung loses compliance and causes incomplete lung expansion and increased lung stiffness; respiratory tract infections, which can be caused by the common cold or pneumonia; respiratory tumors, such as those caused by cancer; pleural cavity diseases; and pulmonary vascular diseases, which affect pulmonary circulation.

Pharmaceutical Compositions

Target cells of the present invention may be combined with various components to produce compositions of the invention. The compositions may be combined with one or more pharmaceutically acceptable carriers or diluents to produce a pharmaceutical composition (which may be for human or animal use). Suitable carriers and diluents include, but are not limited to, isotonic saline solutions, for example phosphate-buffered saline. The composition of the invention may be administered by direct injection. The composition may be formulated for parenteral, intramuscular, intravenous, subcutaneous, intraocular, oral, transdermal administration, or injection into the spinal fluid.

Compositions comprising target cells may be delivered by injection or implantation. Cells may be delivered in suspension or embedded in a support matrix such as natural and/or synthetic biodegradable matrices. Natural matrices include, but are not limited to, collagen matrices. Synthetic biodegradable matrices include, but are not limited to, polyanhydrides and polylactic acid. These matrices may provide support for fragile cells in vivo.

The compositions may also comprise the target cells of the present invention, and at least one pharmaceutically acceptable excipient, carrier, or vehicle.

Delivery may also be by controlled delivery, i.e., delivered over a period of time which may be from several minutes to several hours or days. Delivery may be systemic (for example by intravenous injection) or directed to a particular site of interest. Cells may be introduced in vivo using liposomal transfer.

Target cells may be administered in doses of from $1 \times 10^5$ to $1 \times 10^7$ cells per kg. For example a 70 kg patient may be administered $1.4 \times 10^6$ cells for reconstitution of tissues. The dosages may be any combination of the target cells listed in this application.

The invention is further described in the following examples, which do not limit the scope of the invention described in the claims.

EXAMPLES

Example 1—Benchmarking Paneth Cells of Conventional Organoids with their In Vivo Counterparts Conventional intestinal organoids produced from the spontaneous differentiation of ISCs have been used to study PCs in vitro in multiple contexts [28,29]. These in vitro PCs exist as part of a heterogeneous system, yet to be rigorously benchmarked against their in vivo counterparts. To better understand the composition of PCs within conventional organoids and how well those PCs approximate their in vivo counterparts, Applicants sought to globally compare the conventional organoid-derived PCs and their in vivo counterpart (FIG. 1A).

To relate the organoid-derived PC state to in vivo PCs, Applicants first generated an unbiased reference in vivo scRNA-seq data set. Applicants performed massively-parallel scRNA-seq using the recently developed Seq-Well platform on epithelial cells from the ileal region of the small intestine acquired as two biological replicates (Methods). Applicants assessed quality metrics for number of genes, unique molecular identifies (UMIs), mitochondrial genes, and ribosomal genes, all of which fell within expectations (all cells average: 1,043 genes, 2,168 UMI, 5.4% ribosomal genes, 10.4% mitochondrial genes). UMI-collapsed cells-by-genes (7,667 cells×17,505 genes). Expression matrices were analyzed using Seurat (Methods), performing dimensionality reduction, graph-based clustering and deriving lists of cluster-specific genes in order to identify PCs. Within the spectrum of cell types, Applicants identified two clusters (2 and 11) enriched for Lyz1 expression (FIG. 1B,C), of which Applicants determined cluster 11 to be fully mature PCs (n=189 cells) based on uniform expression of a set of associated antimicrobial peptide marker genes such as Defa22, Defa21, and Ang4 (receiver operating characteristic (ROC) test, area under the curve (AUC)>0.99 for markers listed (cluster 11 average: 866 genes, 3,357 UMI, 3.5% ribosomal genes, 4.8% mitochondrial genes) (Table 1). Applicants further utilize these genes (genes with AUC>0.65 for in vivo PC) throughout the study to relate organoid-derived cell states to in vivo PCs. They are fully inclusive of the 14 high confidence markers described for Paneth cells from the terminal ileum in the recently published mouse small intestinal atlas [3]. (NB: Applicants extend the gene list beyond truly specific marker genes that are not expressed in other cell types as Applicants are interested in a more comprehensive set of Paneth-enriched genes for further comparison).

Here, Applicants establish a systematic workflow for characterizing and improving the physiological-representation of to enable the creation of better in vitro models for advancing research and therapeutic development. Taking the PC as a test case, Applicants utilize single-cell transcriptomics to benchmark the current state-of-the-art organoid model against its in vivo counterpart, and identify differences in developmental pathway signaling between in vitro and in vivo cell states. This profiling guides the rational augmentation of pathway activity during stem cell differentiation with a small molecule chemical induction method previously validated to enhance in vitro LYZ1 gene expression in organoids [30]. Applicants validate the pipeline by generating an enhanced in vitro physiological mimic of the in vivo PC, and provide a detailed characterization of the derived cell state through morphologic, proteomic, transcriptomic, and functional assays based on known signatures of in vivo PCs. Furthermore, Applicants use the enhanced model and findings from its transcriptomic and proteomic characterization to identify Nupr1 as a potential stress-response factor that facilitates the survival of PCs, demonstrating the improved ability to examine gene function in vitro within a more representative cell type.

Figure 1D:
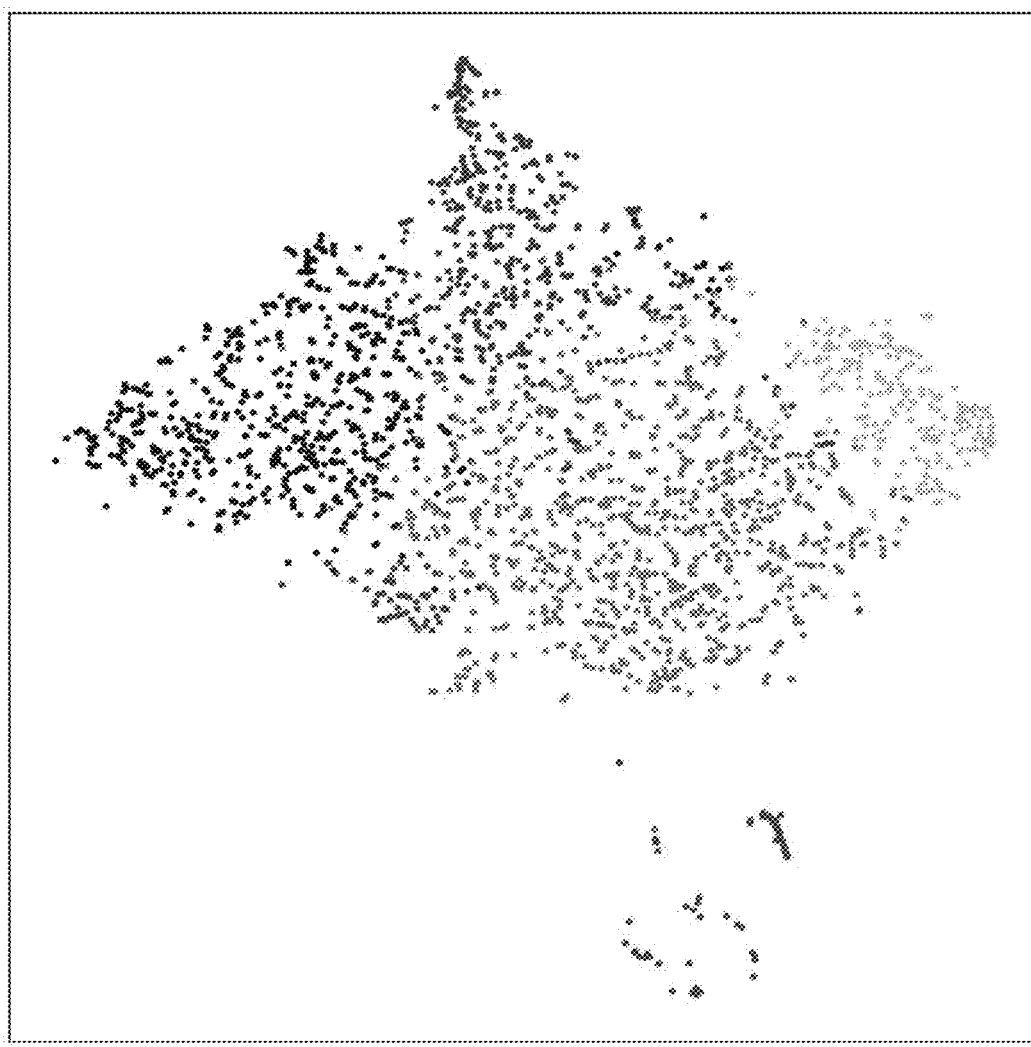
Figures 1E, 1F:
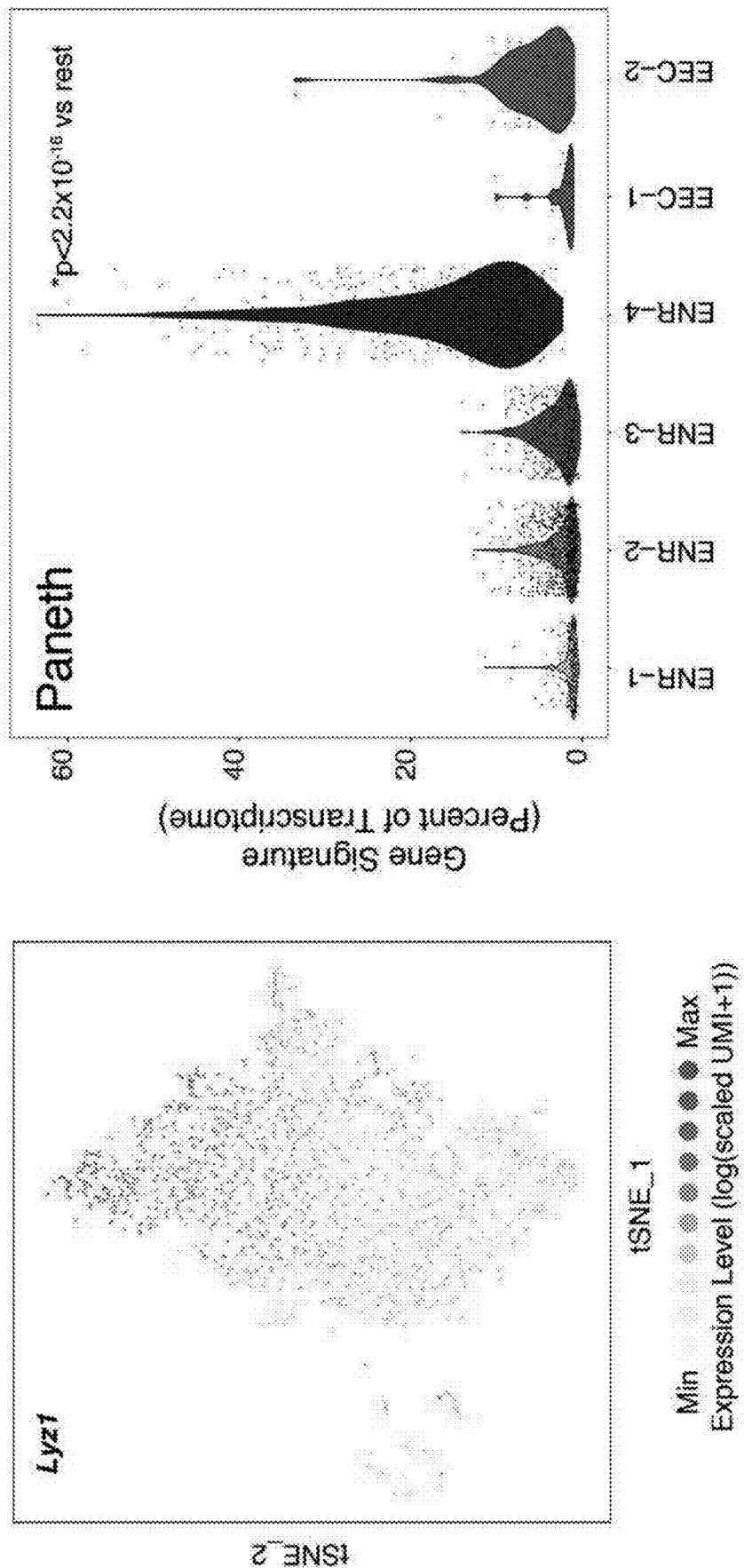
Figure 1G:
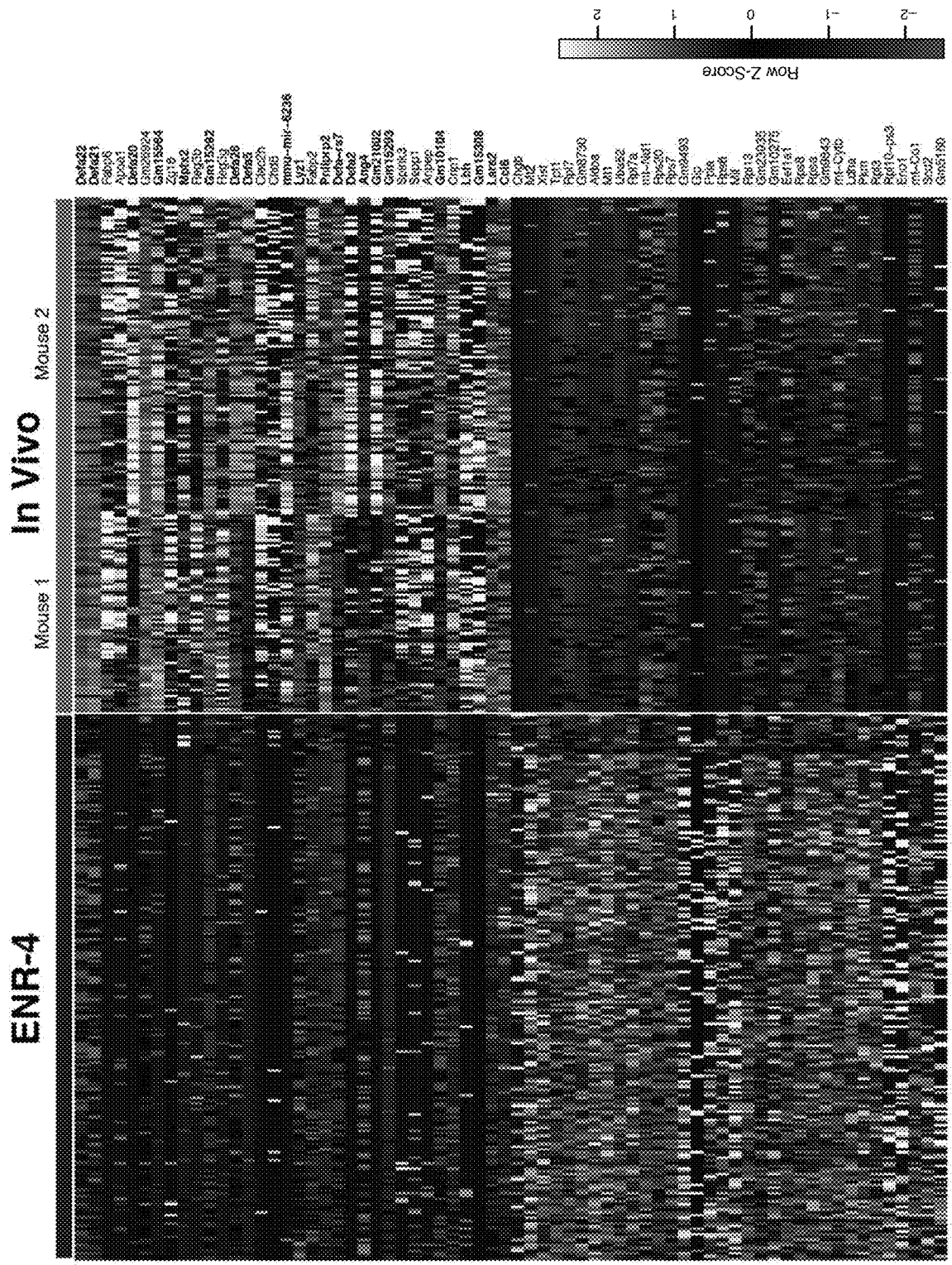
Figure 1H:
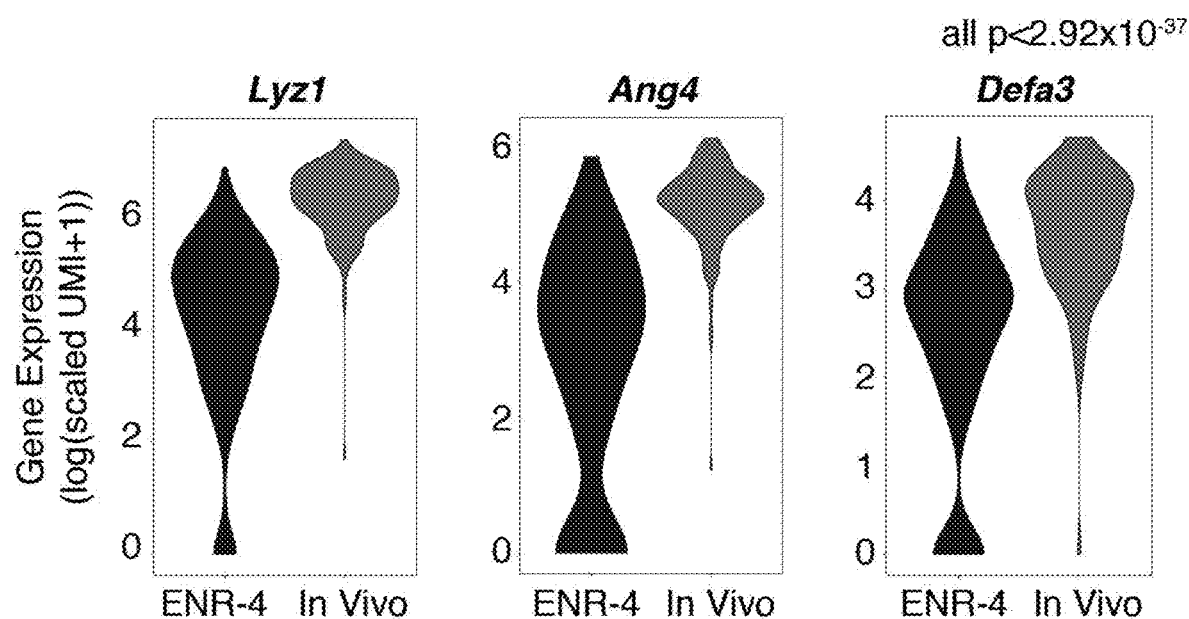
Figure 1I:
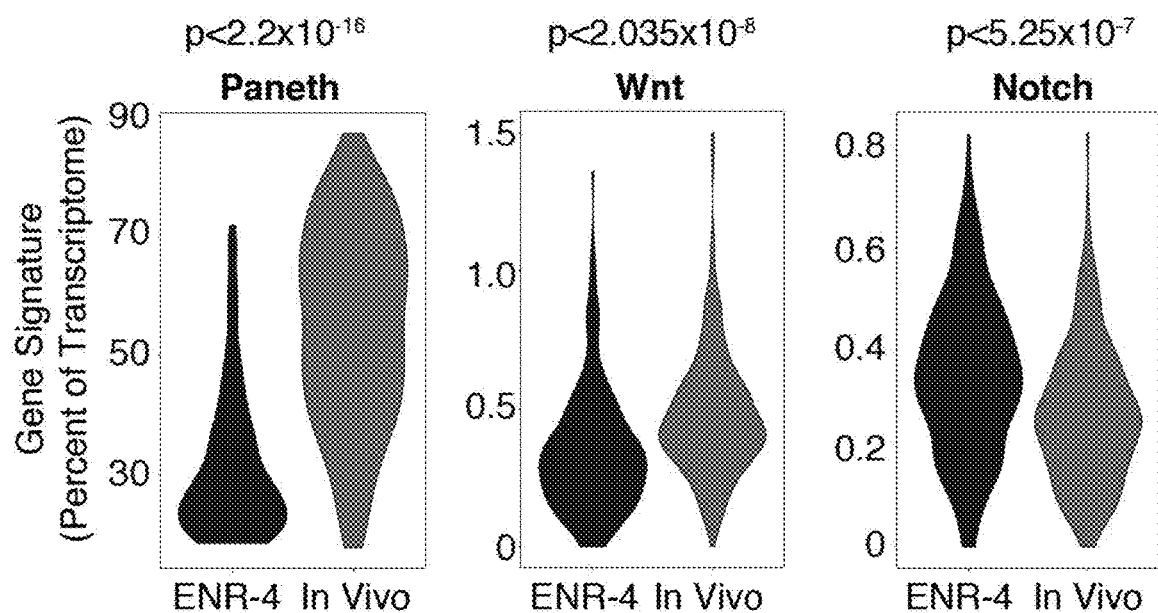

Applicants next performed scRNA-seq using Seq-Well on conventional organoids derived from an ISC-enriched state (FIG. 1A). Beginning with murine small intestinal crypts, Applicants directly enriched for LGR5+ ISCs over six days following isolation within a Matrigel scaffold and medium containing recombinant growth factors EGF (E), Noggin (N), and R-spondin 1 (R), small molecules CHIR99021 (C) and valproic acid (V), as well as Y-27632 for the first two days to inhibit rho kinase and mitigate anoikis, as previously described (ENR+CV) [30]. Cells were passaged into conventional ENR culture for an additional six days to allow multi-lineage differentiation and produce stem cell-derived in vitro PCs. Following scRNA-seq, Applicants computationally identified six clusters (amongst 2,513 cells×16,198 genes meeting quality standards, see Methods) in ENR organoids, which Applicants label as ENR1-4, and EEC-1 and -2, for two enteroendocrine cell types (FIG. 1D). Applicants identified ENR-4 as the cluster most enriched for Lyz1 and the PC reference gene set (effect size 0.721, ENR-4 vs all ENR, *t-test p<$2.2 \times 10^{-16}$) (FIG. 1E,F). Having identified ENR-4 as the cell state of interest in organoids, Applicants directly compared the top 200 most Paneth-like cells in ENR-4 to in vivo PCs by performing differential expression analysis (FIG. 1G). In comparing the two cell types, it became evident that the majority of genes enriched by in vivo PCs were defensins and antimicrobials, including Defa22, Defa21, Zg16, Ang4, Defa3, and Lyz1 (all $p<2.92 \times 10^{-37}$, bimodal test, Bonferroni corrected for multiple comparisons) (FIG. 1G,H). ENR-4 cells were enriched for Chgb, an enteroendocrine marker, and translational biosynthetic genes likely indicative of the high rates of proliferation present in ENR organoids (FIG. 1G). Beyond these selected genes, Applicants note a global reduction in the fraction of the transcriptome of ENR-4 cells producing the total cadre of in vivo PC marker genes (effect size 1.25, InVivo vs. ENR, *t-test $p<2.2 \times 10^{-16}$), suggesting that the current in vitro organoid-derived PCs are suboptimal for physiological studies (FIG. 1I).

Modulating key developmental pathways of stem cell-derived systems has emerged as a paradigm in bioengineering to rationally generate cell types for basic research and therapeutic aims [32,33]. Specifically, modulating Wnt and Notch signaling has been suggested in the literature to increase the frequency and magnitude of Lyz1 expression and protein in ISC-derived cells [30,34-36]. Leveraging the single-cell transcriptomes of the in vitro and in vivo-derived PCs, Applicants confirmed that Wnt-target genes are enriched in vivo relative to in vitro PCs (effect size 0.559, InVivo vs. ENR, *t-test $p<2.035 \times 10^{-8}$) and Notch-target genes were decreased (effect size −0.500, InVivo vs. ENR, *t-test $p<5.25 \times 10^{-7}$) (FIG. 1I, Table 2). As a result, Applicants sought to comprehensively test if driving Wnt and inhibiting Notch truly results in a more physiologically representative PC versus the organoid-derived PC, beyond increased expression of Lyz1.

Figure 2A:
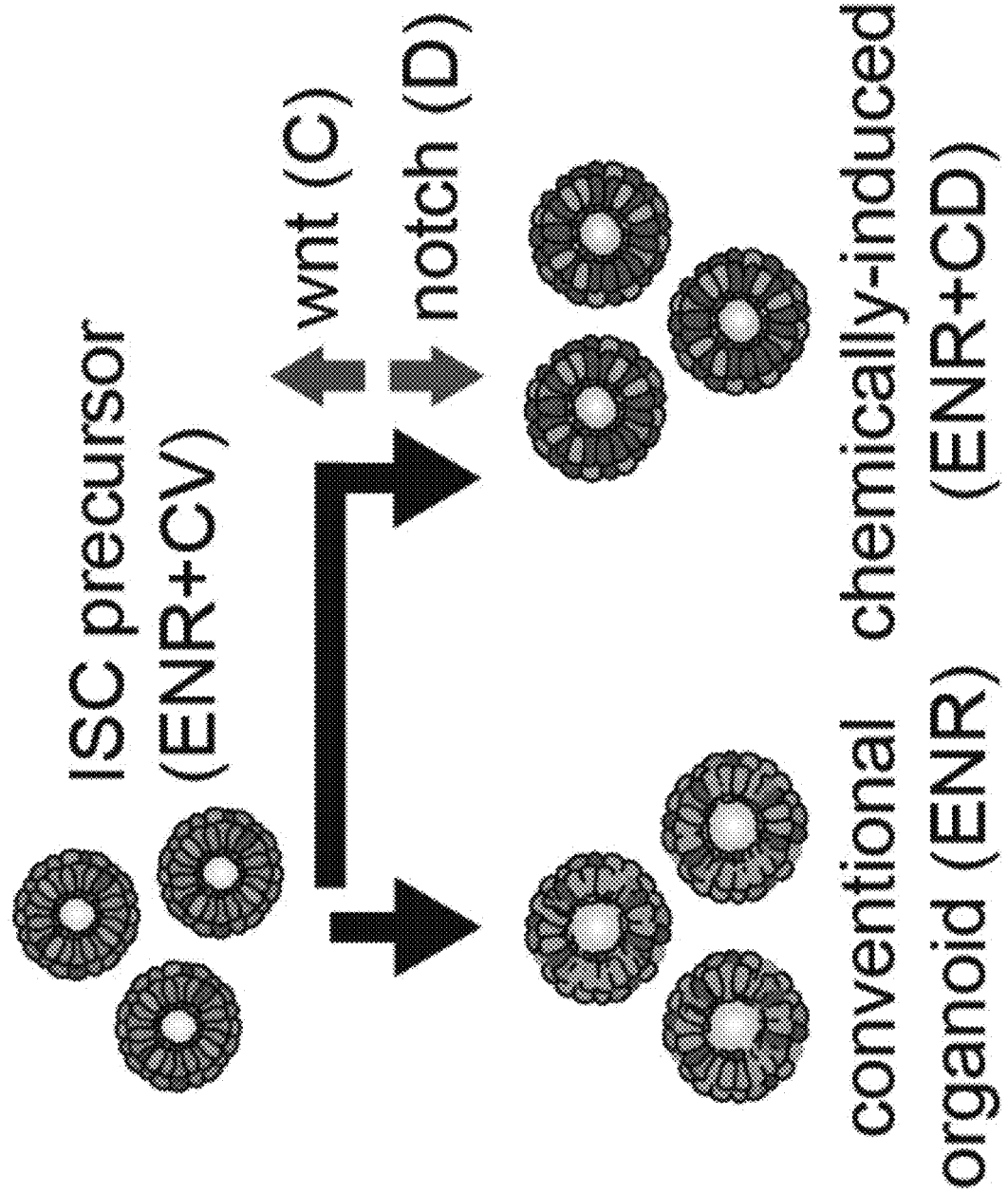
FIGS. 2A-2E—Establishing chemically-induced PC-enriched cultures FIG. 2A) Schematic of small molecule-driven differentiation of LGR5+ ISCs (C—CHIR99021, D—DAPT) and non-specific differentiation.
Figure 2B:
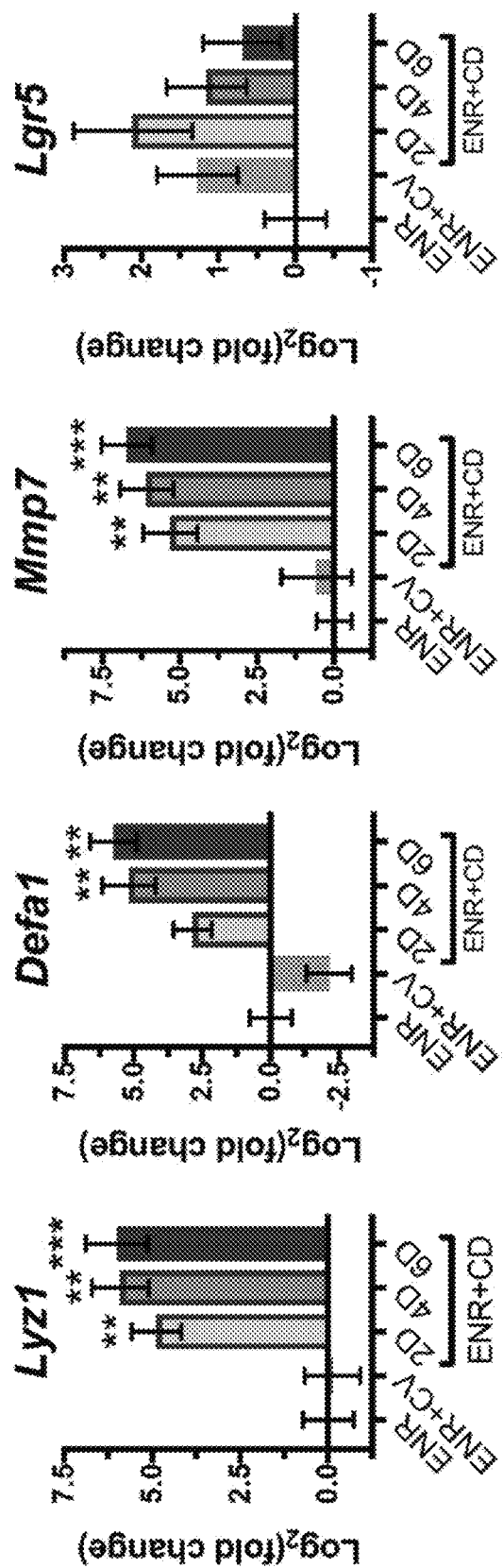

Example 2—Chemical Induction of Wnt and Inhibition of Notch Drives Paneth-Cell Marker Enrichment Beginning with an LGR5+ ISC-enriched population (ENR+CV), Applicants sought to profile how the modulation of Wnt and Notch signaling through small molecule inhibitors would alter the in vitro PC state, as suggested by the transcriptional profiling. Applicants performed chemical induction (CI) using the previously identified compounds C to drive Wnt signaling and DAPT (D), a gamma-secretase inhibitor, to inhibit Notch (ENR+CD) (FIG. 2A) and measured gene expression of ISC (Lgr5) and PC (Lyz1, DefA1, Mmp7) markers every two days for six days total (FIG. 2B). ENR+CD-treated cells had statistically significant increases in Lyz1 (adj. p=0.005, see Methods) and Mmp7 (adj. p=0.005) within two days compared to ENR, with differences plateauing around four days. DefA1(adj. p=0.004) expression was significantly increased by day four and plateaued by day six in ENR+CD versus ENR populations. Lgr5 expression in ENR+CD at two days versus ENR showed an insignificant plateau of expression, which trended down by six days. This may be indicative of an expansion in 'label-retaining' secretory precursors [37]. Precursor population ENR+CV had no significant difference in PC or ISC markers relative to ENR. The significant increase in PC gene expression in ENR+CD relative to ENR and ENR+CV over the six-day treatment suggests rapid enrichment following CI, supporting the hypothesis that alterations in Wnt and Notch result in superior PC enrichment in vitro.

Figure 2C:
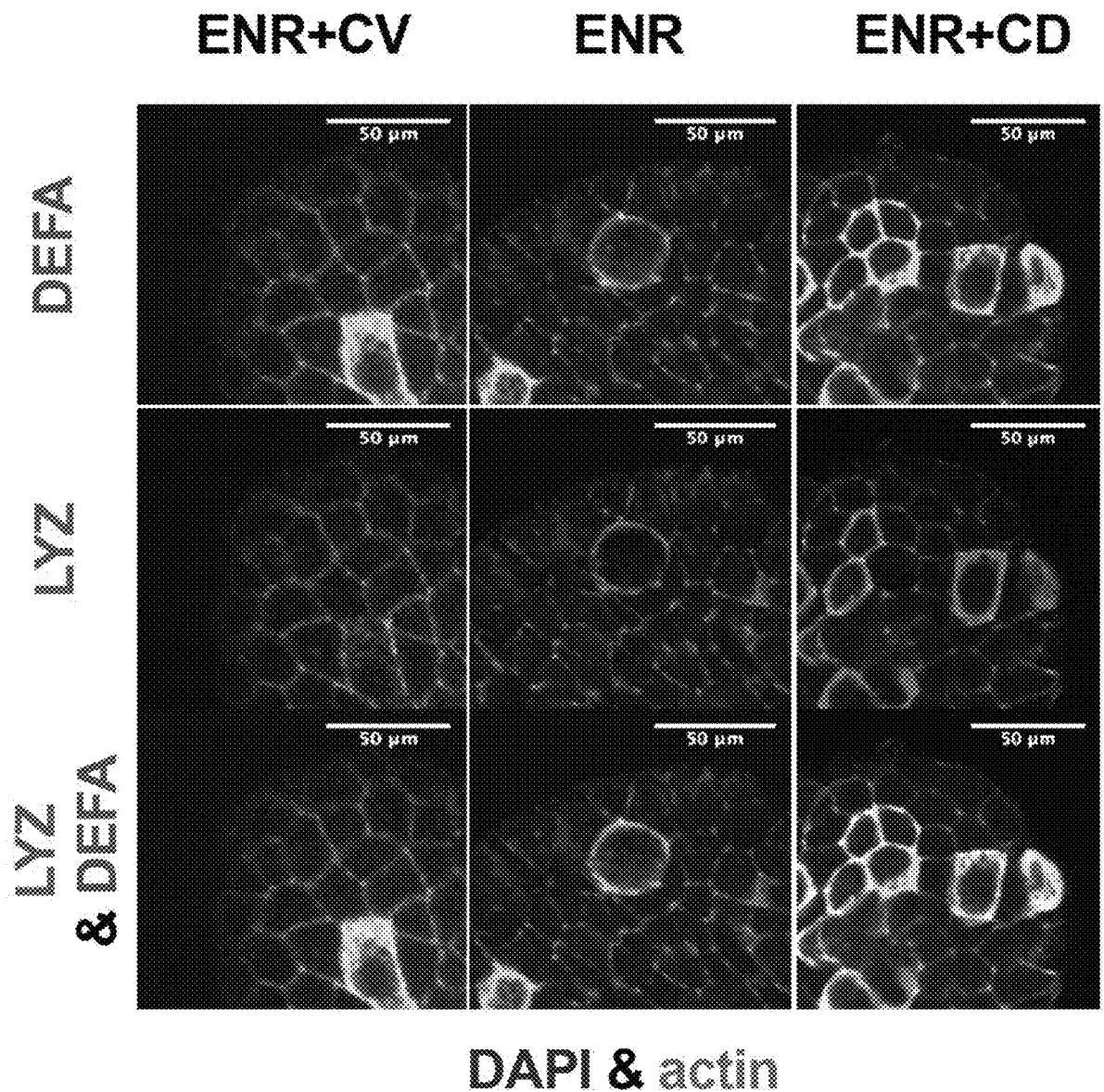
Figure 2D:
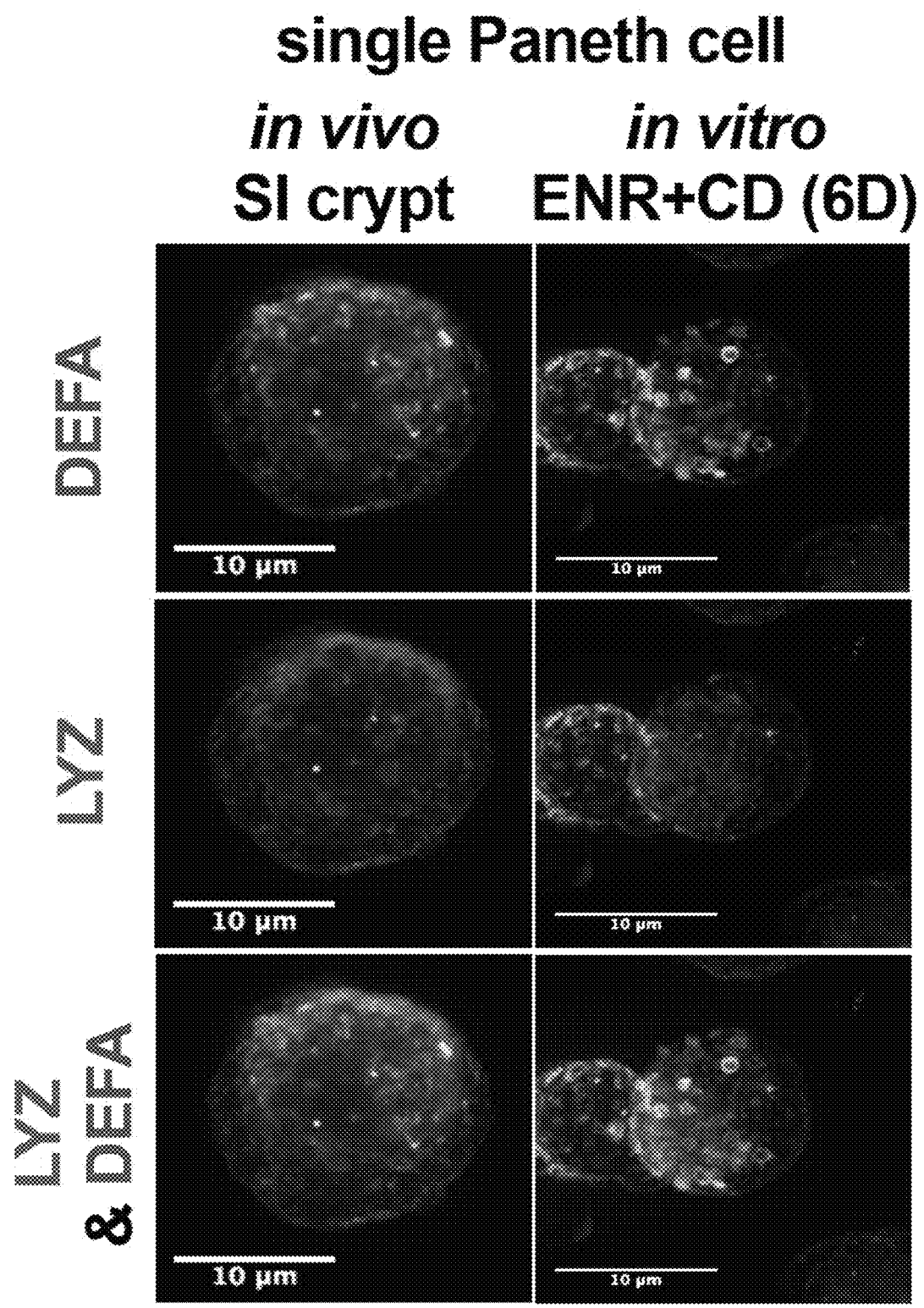
Figure 8B:
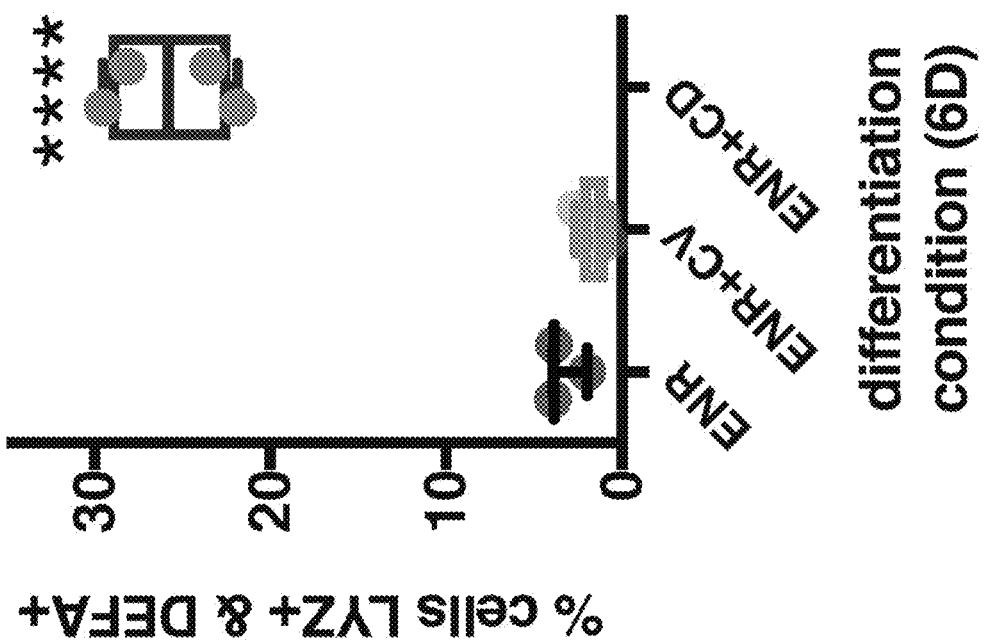
FIGS. 8A-8F—Image analysis of cell clusters and flow cytometry FIG. 8A) Bright-field microscopy after six days of ENR+CD culture shows annular morphology and darkened lumen of cell clusters consistent with presence of granule-rich cells.
Figure 8A:
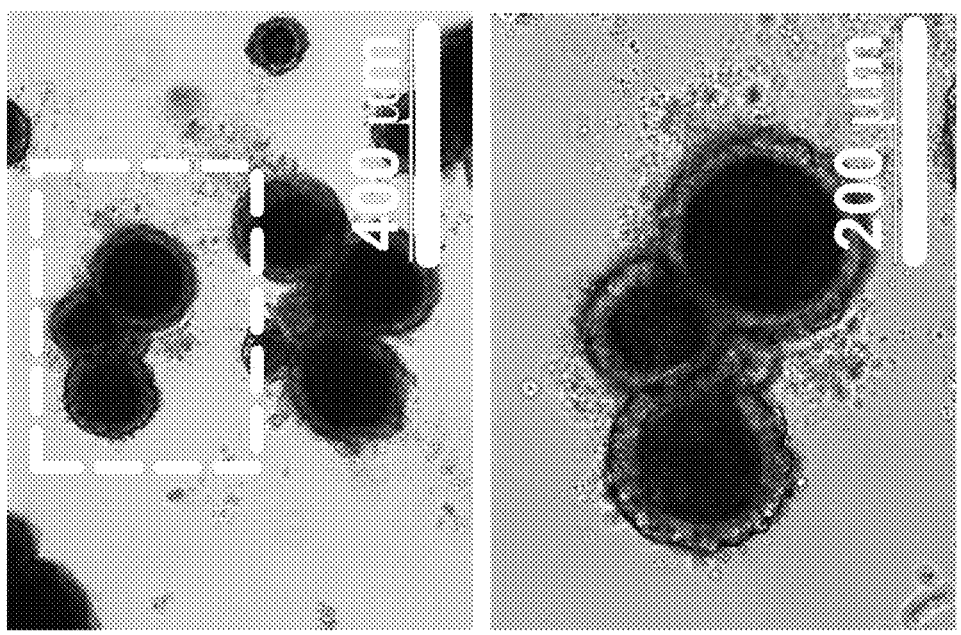
Figure 8C:
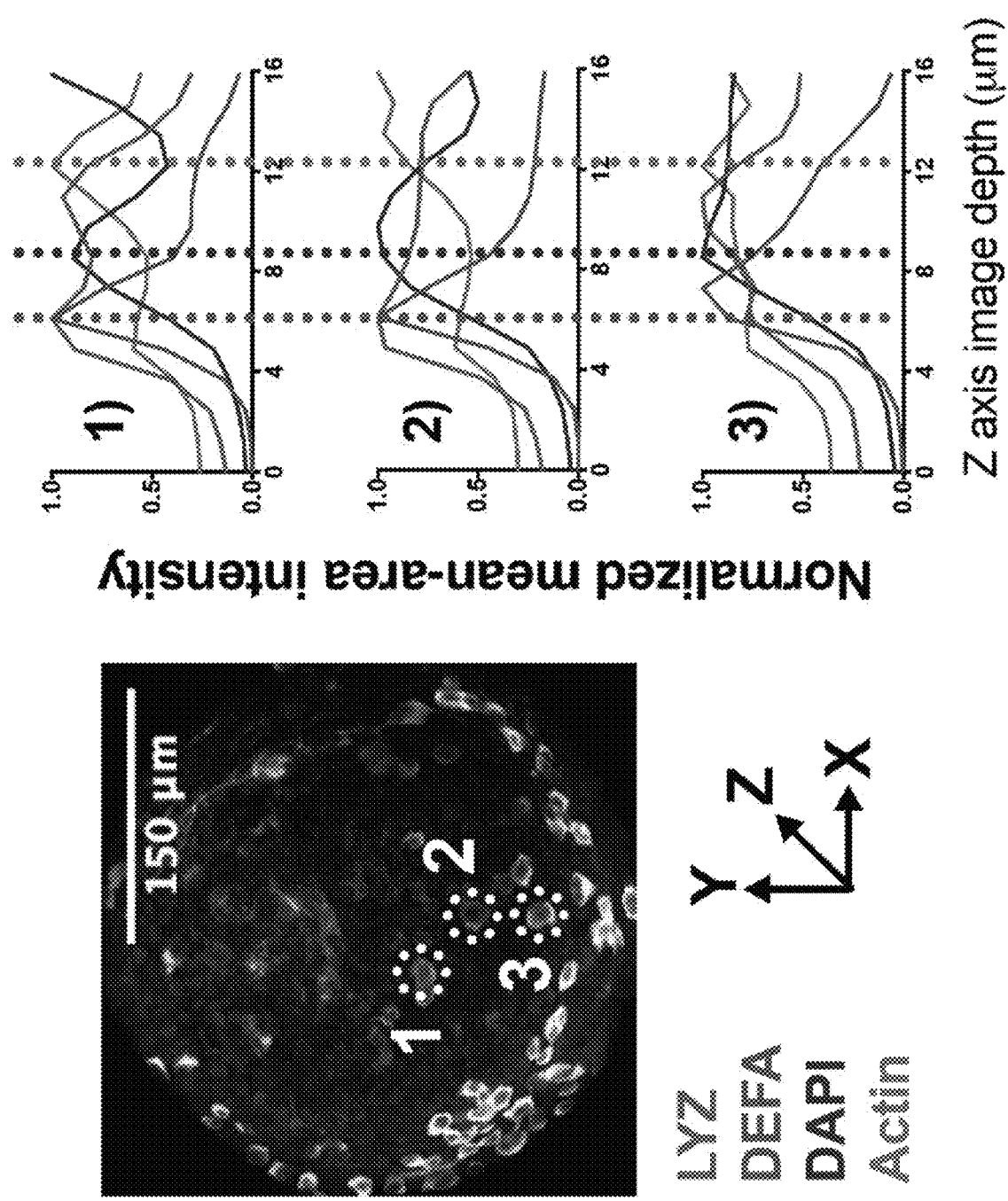

To phenotypically describe PC enrichment following CI, Applicants performed imaging and immunocytochemistry for PC-associated features. After six days of ENR+CD, cell populations exhibited darkened annular morphology consistent with increased numbers of granule-rich cells (FIG. 8A). Confocal microscopy of whole cell clusters stained for anti-DEFA and anti-LYZ showed an increase in LYZ+ and DEFA+ cells in ENR+CD compared to both ENR and ENR+CV (FIG. 2C). Single-cell counting of confocal imaging showed a significant increase of DEFA and LYZ co-staining cells in ENR+CD (20-30% of cells) versus either ENR or ENR+CV (both <5%) (adj. p=0.0001) (FIG. 8B). Additionally, normalized z-axis profiles of individual co-staining cells within cell clusters revealed a consistent distribution of DEFA (luminally-polarized) and LYZ (diffuse) (FIG. 8C 1-3). High-resolution fluorescent imaging of individual co-staining cells from freshly-isolated small intestinal crypts (in vivo equivalent) and six day-ENR+CD-treated cells showed similar polarized distribution of LYZ and DEFA-staining granules, although freshly-isolated cells appeared to be more granular than CI-PCs (FIG. 2D).

Figure 8D:
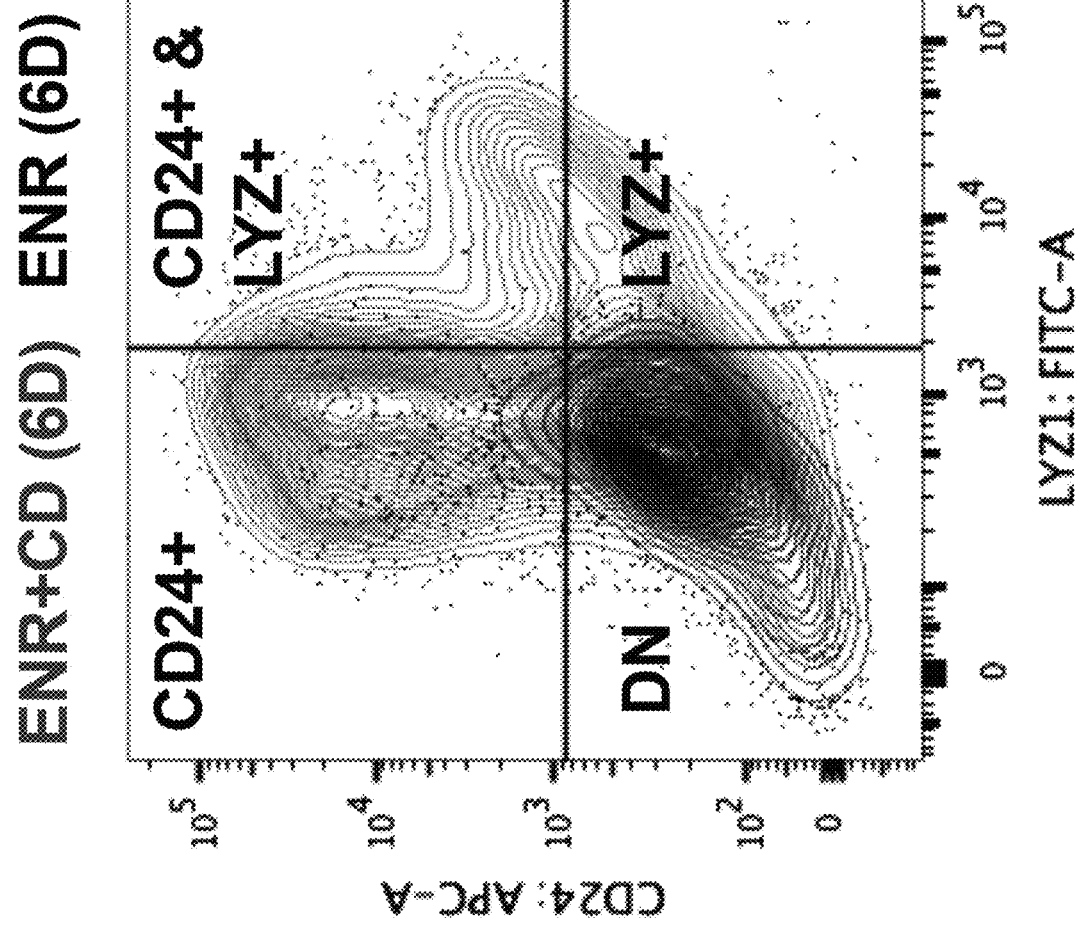
Figure 8E:
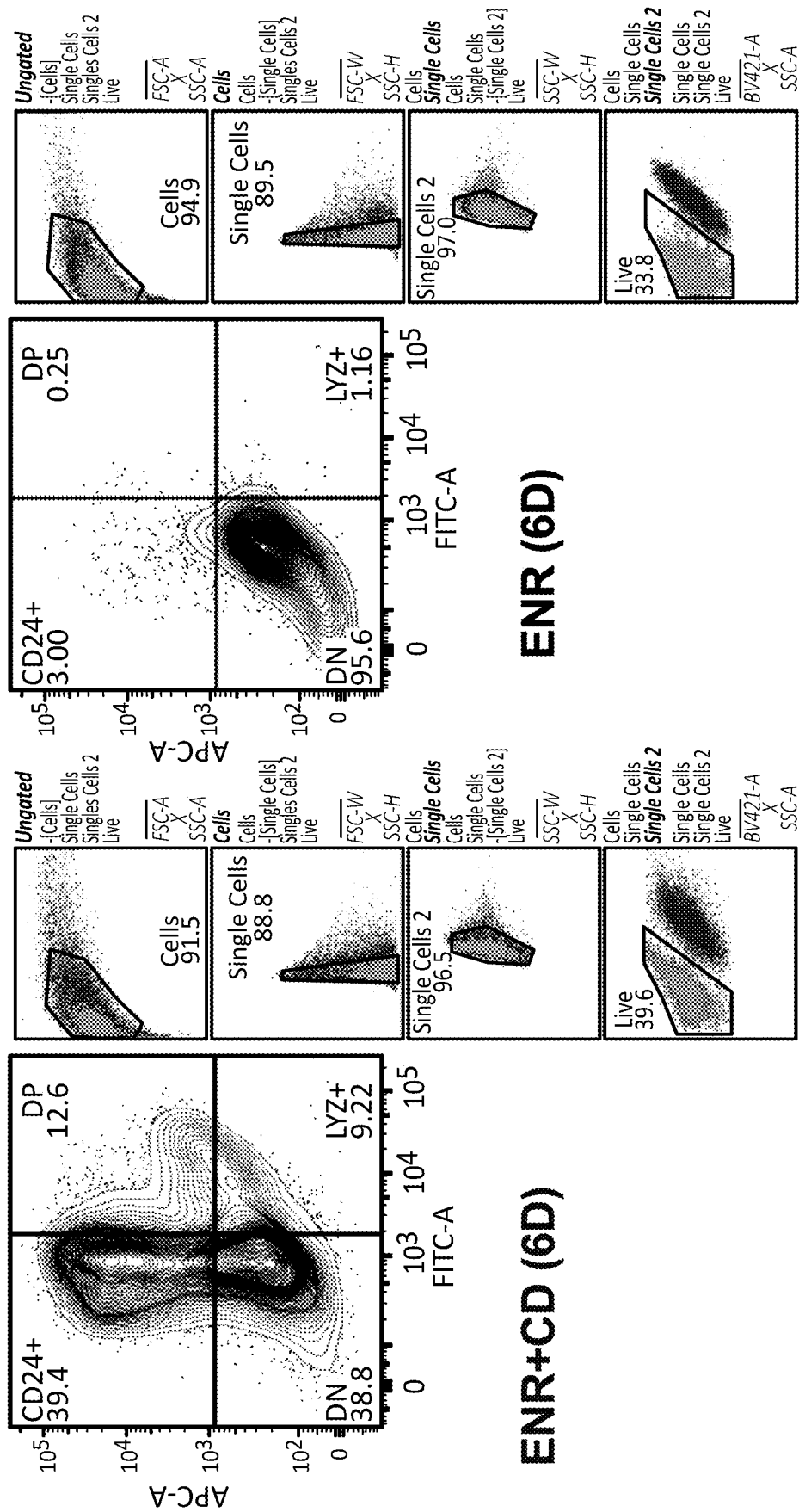
Figure 8F:
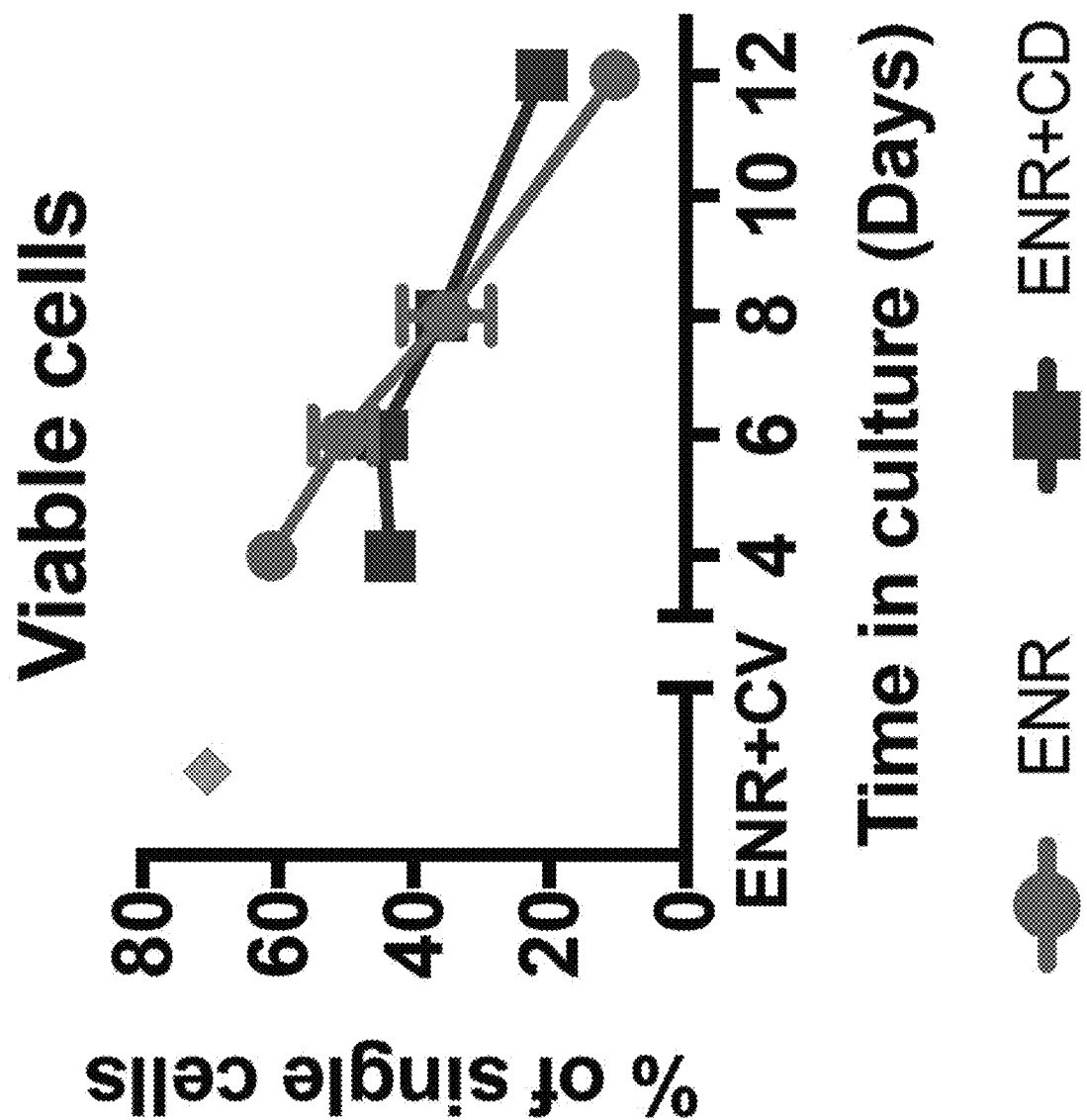

To confirm the extent of enrichment seen in whole population imaging, the prevalence of PCs in ENR+CD relative to ENR was assessed by flow cytometry over the course of 12 days. Applicants identified an in vivo PC phenotype as CD24 and LYZ co-positive cells, per previous reports [38], and noted the presence of single-positive LYZ+ or single-positive CD24+ populations, indicative of alternative cell differentiation, immature, or non-physiological PCs. ENR+CD had substantial enrichment at all time points for double-positive, and single-positive LYZ+ or CD24+ populations relative to ENR, as well as a consistent decrease in double negative population consistent with the PC phenotype (FIG. 2E) (representative populations FIG. 8D, representative gating FIG. 8E). Notably, both ENR and ENR+CD experience declines in total cell viability, with ENR+CD having greater survival at longer times, suggesting both a reduction in anoikis, a potentially physiological 'long-lived' PC phenotype in ENR+CD versus ENR, or an enhancement in niche-supporting functionality (FIG. 8F). Overall, imaging and flow cytometry demonstrate a significant increase in cells morphologically resembling in vivo PCs with respect to granularity, polarity, and antimicrobial co-expression in ENR+CD compared to conventional ENR organoids (FIGS. 2C-E & 8A-F).

Figure 3A:
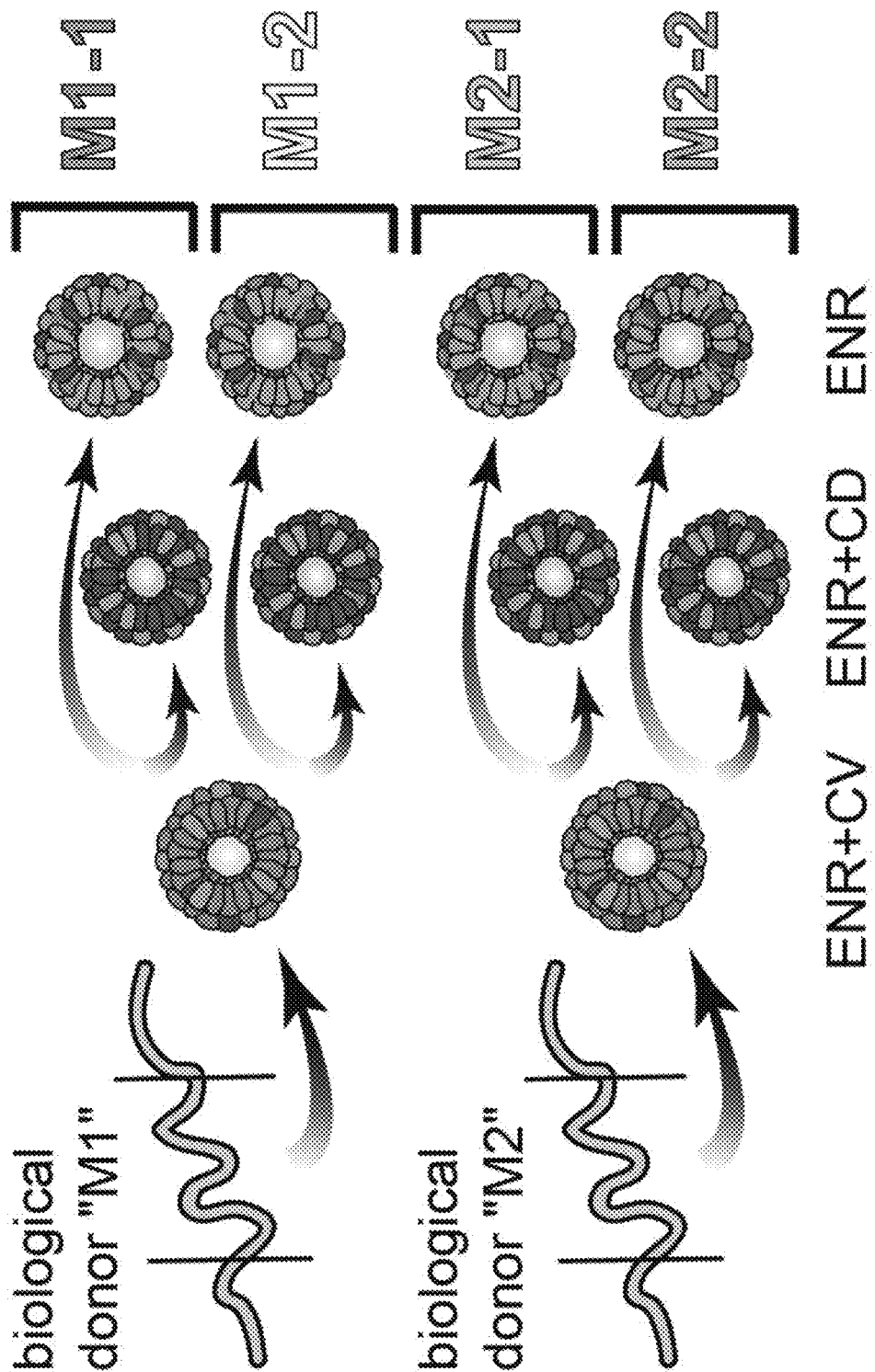
FIGS. 3A-3F—Characterizing the in vitro PC proteome FIG. 3A) Samples used to interrogate the PC-enriched proteomes of ENR+CD- and ENR-treated cells by high resolution, accurate mass LC-MS/MS-based proteomics, including sample nomenclature.
Figure 9A:
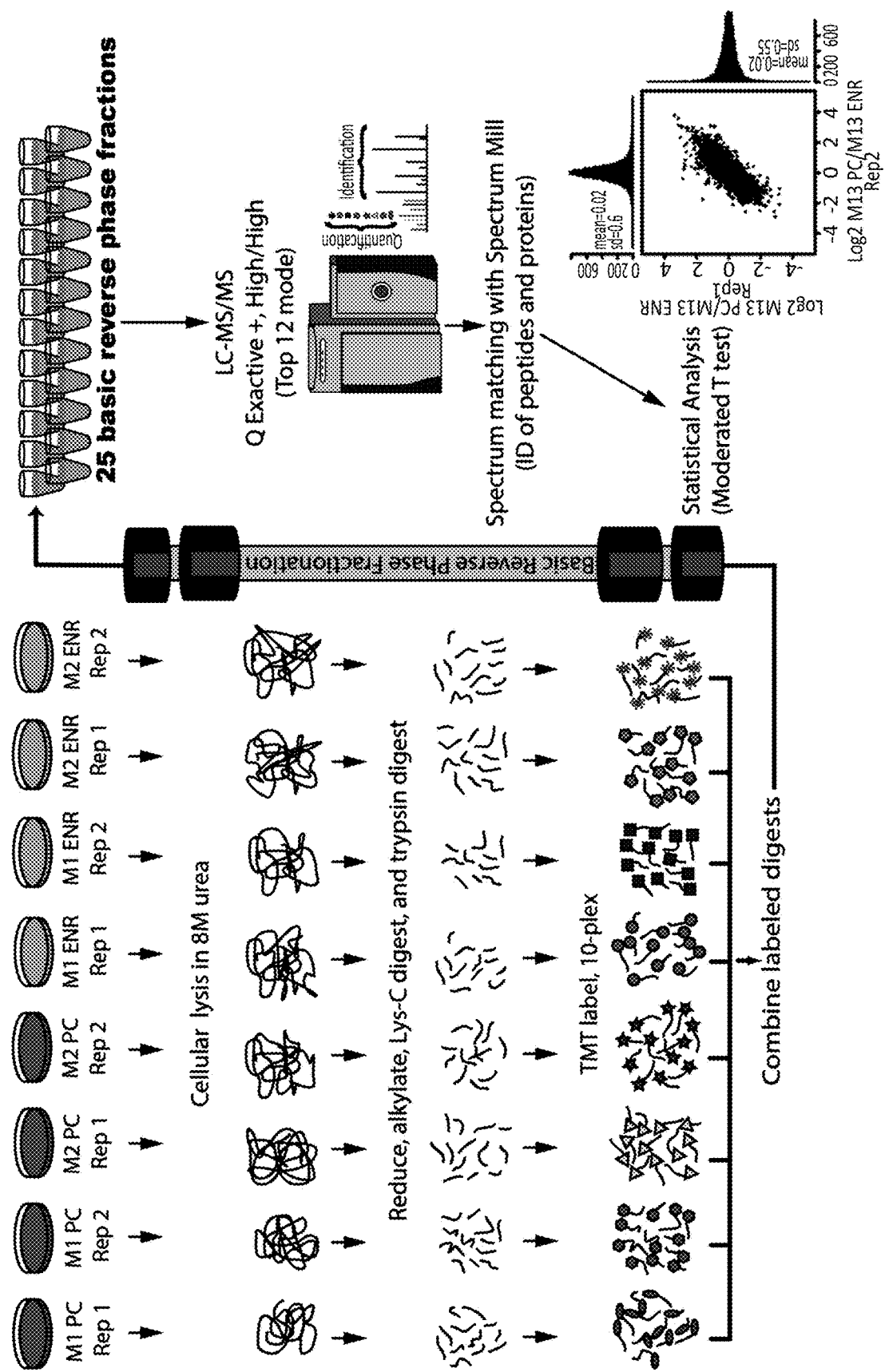

Example 3—Chemically-Induced Paneth Cell Proteome is Enriched for Components of Secretory Lineages With ENR+CD apparently providing a more prevalent and physiological PC population, Applicants sought to more globally characterize the differences between in vitro PCs (ENR vs. ENR+CD at six days). Because PCs are highly secretory, protein-rich cells, Applicants sought to assess the total intracellular proteome between conditions through liquid chromatography mass spectrometry (LC-MS/MS)-based proteomics. Applicants quantified relative protein abundance across eight samples using isobaric mass tag labeling from four ENR and four ENR+CD samples (M1-1 through M2-2, first digit denotes biological donor, second digit denotes technical replicate) (FIG. 3A). Samples were processed and analyzed in a single 10-plex by LC-MS/MS (FIG. 9A). Applicants identified 8,015 unique proteins within all samples; each replicate pair (ENR+CD/ENR) was normally distributed (FIG. 9B) and correlated with all others, indicating consistent proteome enrichment (FIG. 9C).

Approximately 21% of the ENR+CD-enriched proteins (+2σ fold change) were present in all four samples, while 38% were unique to specific samples (FIG. 9D). In contrast, only 7% of the ENR-enriched proteins (−2σ fold change) were present in all four samples, while 51% of the proteins were unique, suggestive of greater heterogeneity in conventional organoids (ENR) as compared to ENR+CD (FIG. 9E). In total, the intracellular proteome of ENR+CD shows relatively consistent protein set enrichment across samples.

Figure 3B:
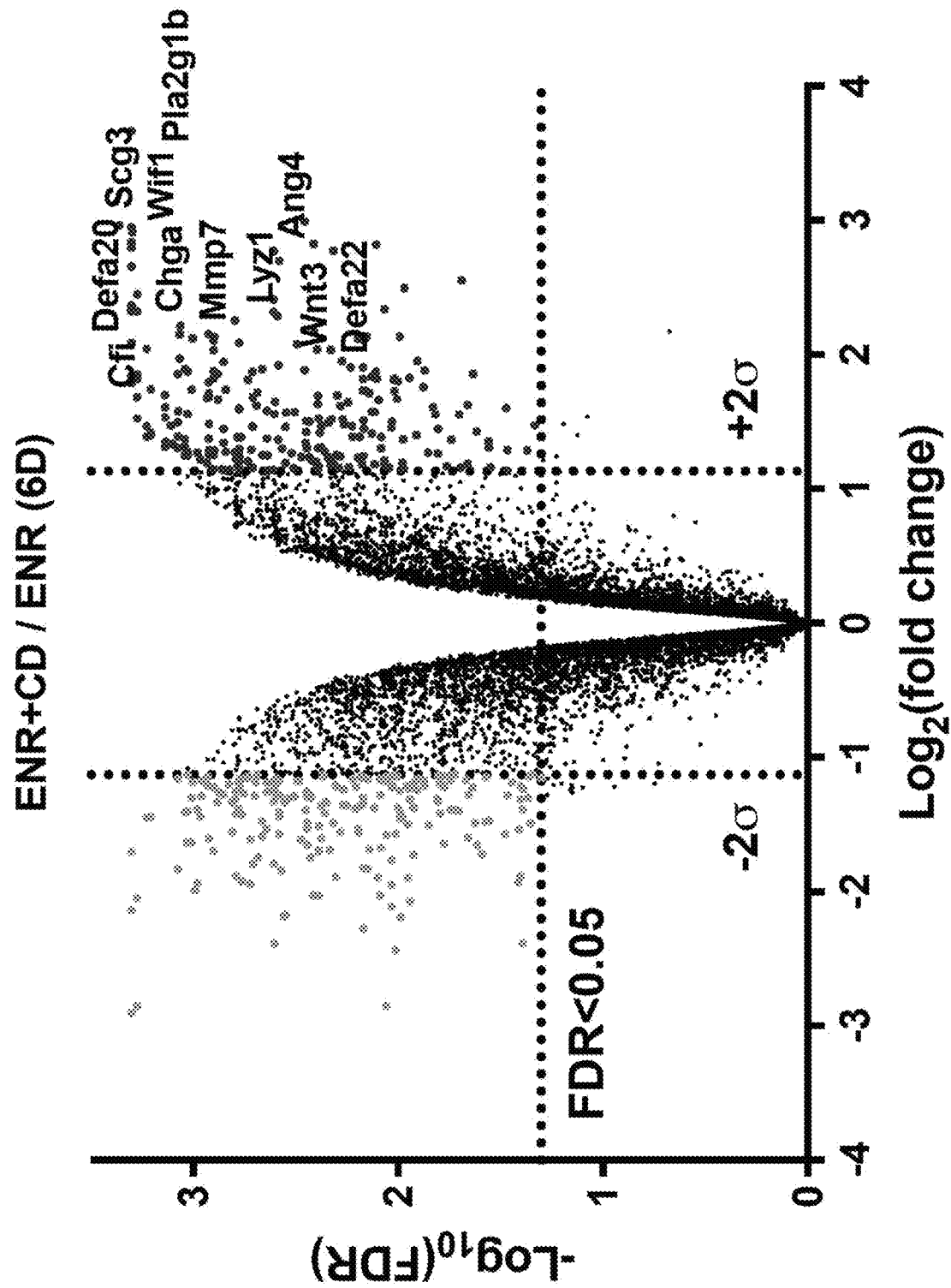
Figure 3C:
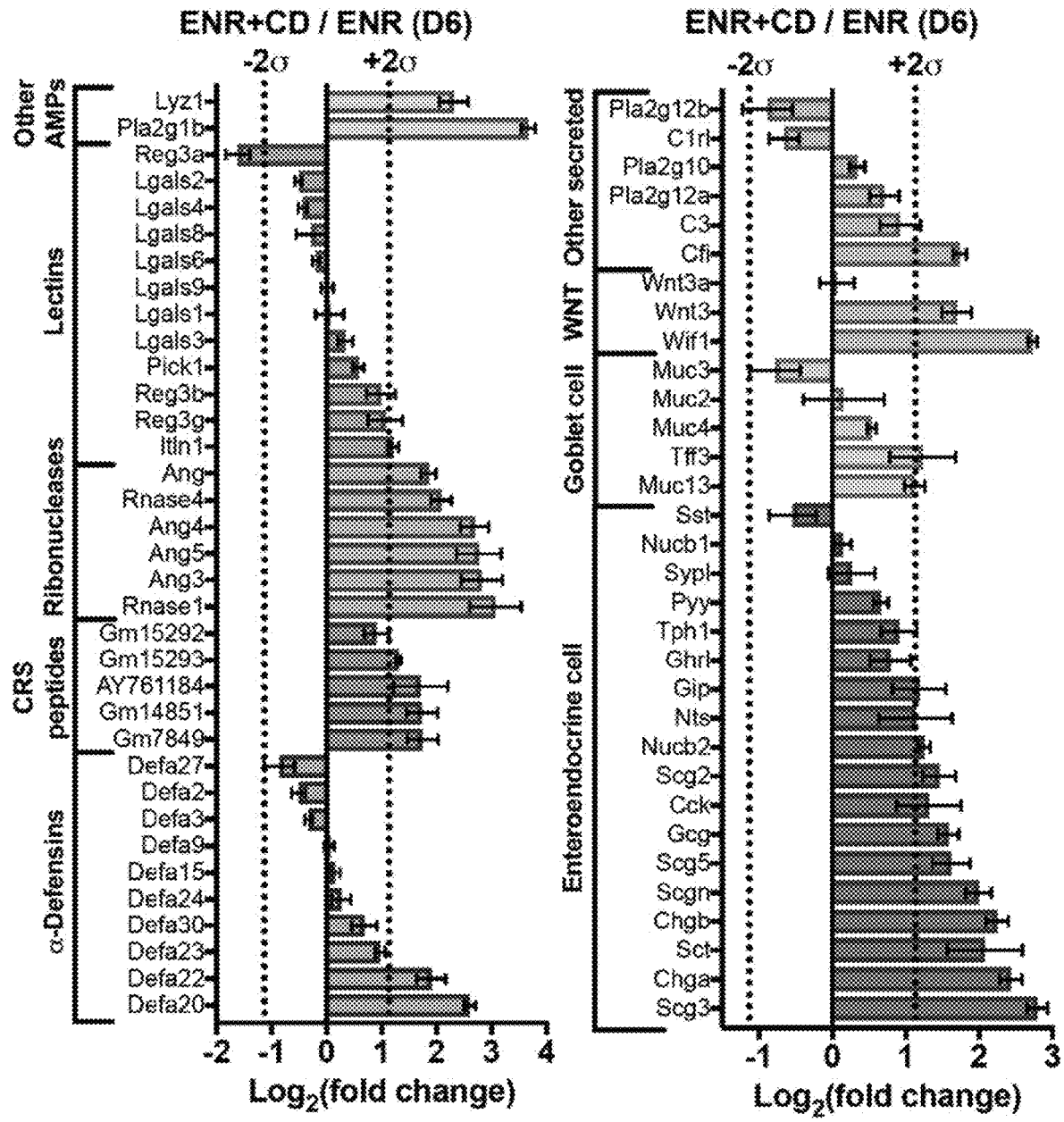
Figure 3D:
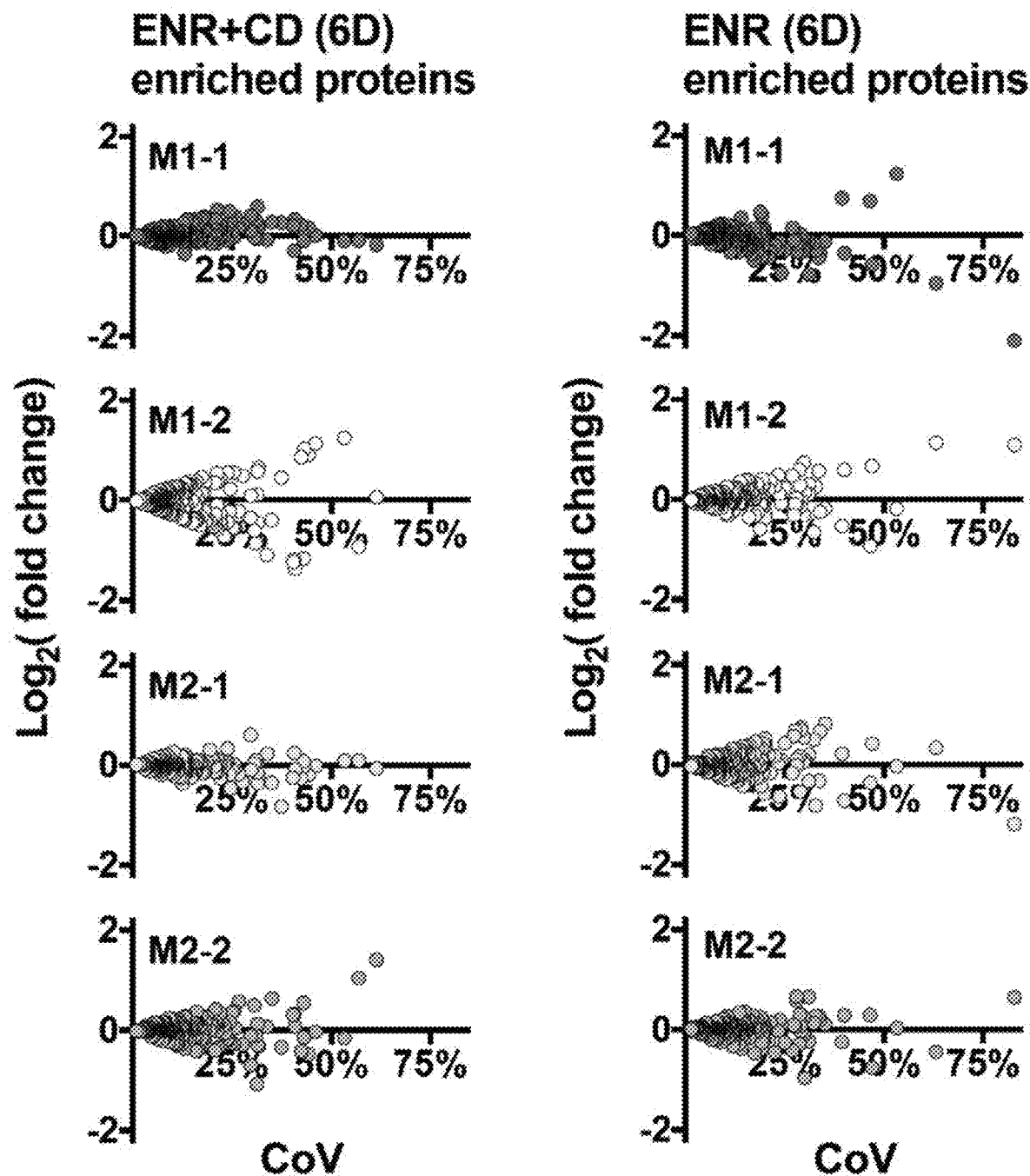

Applicants next looked at the sample pairs in aggregate and classified proteins significantly enriched in ENR+CD and ENR by a false discovery rate (FDR)<0.05 and log fold change (±2a) (FIG. 3B and Table 3). There were 249 ENR+CD-enriched proteins, 212 ENR-enriched proteins, and 7,553 shared proteins. Known PC markers, including LYZ, DEFAs, and other secretory pathway components, were identified as significantly enriched in ENR+CD versus ENR alone. Of known antimicrobial proteins produced by PCs, Applicants detected 10 DEFAs, 5 CRS peptides, 6 ribonucleases, 12 lectins, LYZ1, and PLA2G1B with differential abundance between ENR+CD and ENR (FIG. 3C). Each class of antimicrobials had at least one ENR+CD enriched protein (+2σ), with the ribonucleases significantly enriched and a majority of the lectins and DEFAs unregulated between the two conditions. Proteins associated with the EEC lineage (secretogranins, chromogranins, and neuropeptides) were also enriched in ENR+CD, in addition to multiple other secreted components, including Wnt ligands, and the complement pathway components C3 and CFI. To affirm the reproducibility of the associated proteins in the ENR+CD-enriched proteome, Applicants performed relative quantification within differentiation sets. The coefficient of variation (CoV) of the 249 ENR+CD-enriched proteins within the four ENR+CD samples lies within the expected variation of the detection method, as does the CoV for the 212 ENR-enriched proteins observed across the four ENR samples (FIG. 3D). Low variation across samples in both condition-enriched sets suggests the PC and EEC enrichment occur together, as opposed to distinct samples preferring a lineage during CI. In sum, Applicants see a broad diversity of PC-associated antimicrobials with some enrichment of EEC-associated proteins in ENR+CD relative to ENR.

Figure 3E:
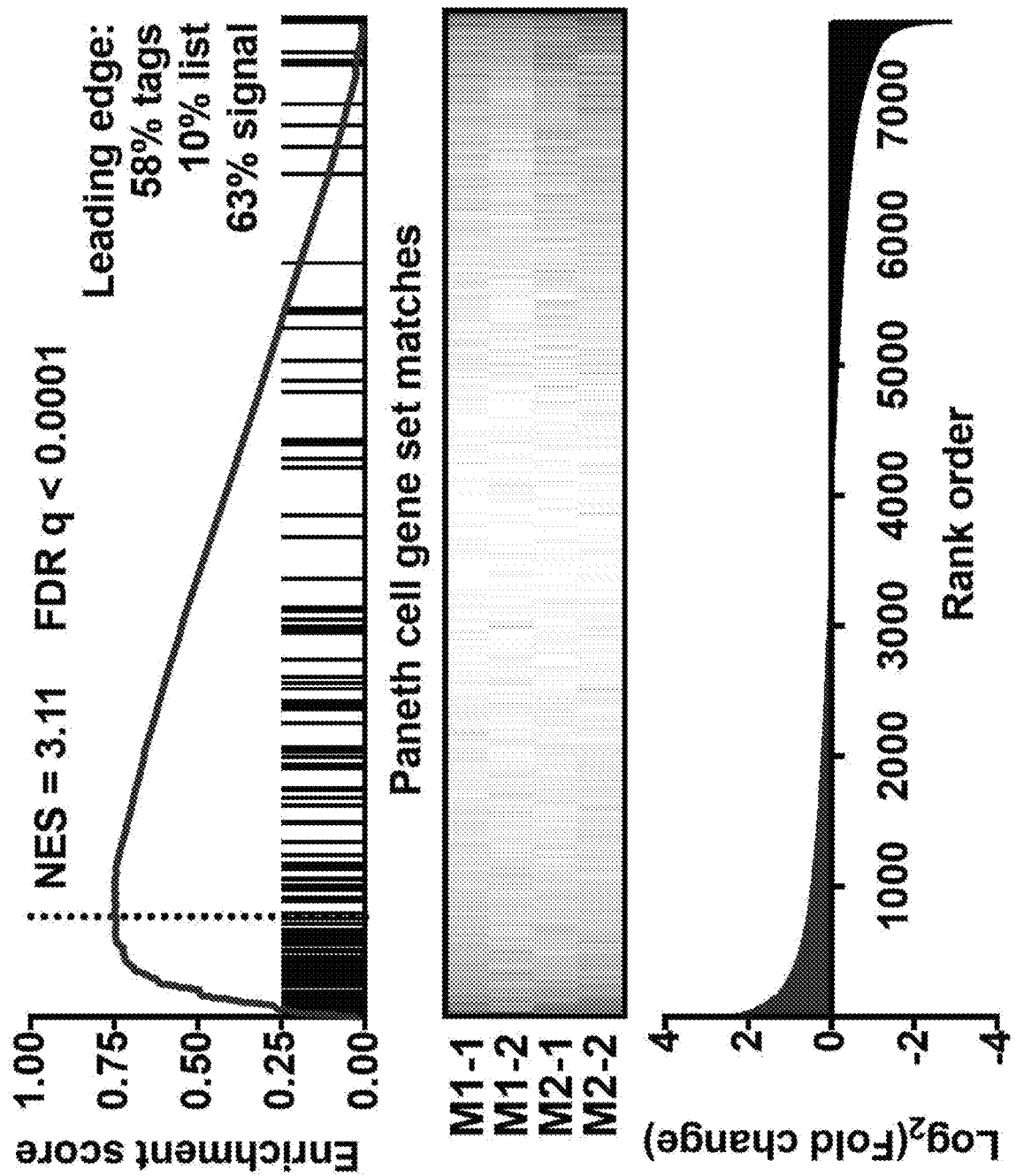
Figure 3F:
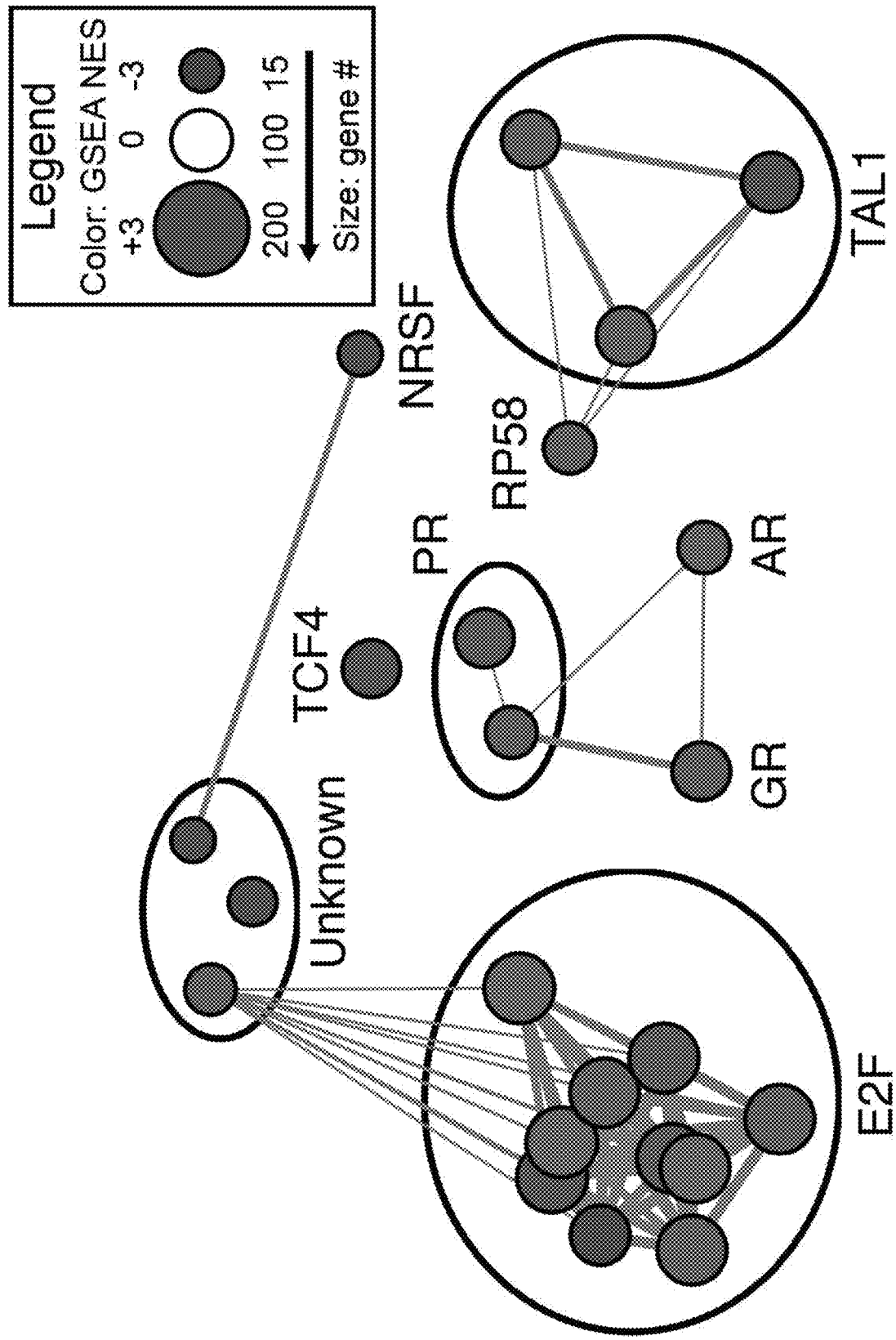
Figure 10A:
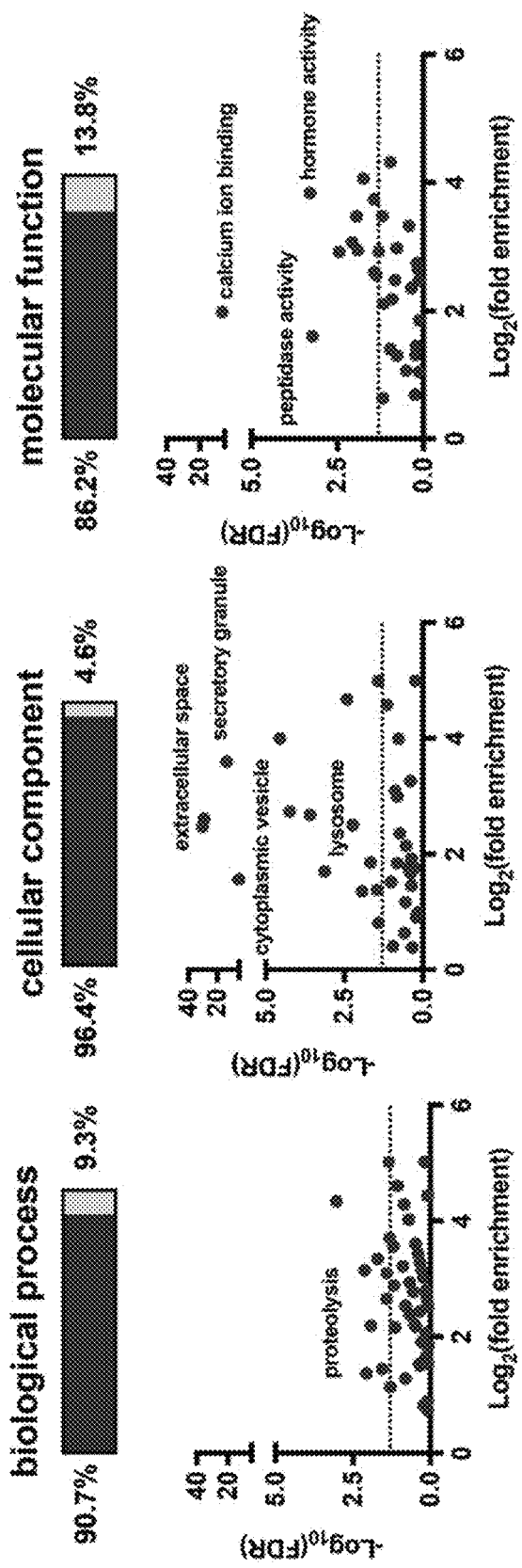
FIGS. 10A-10B—Structural and functional insights from the in vitro PC proteome FIG. 10A) ENR+CD-enriched proteins are well-annotated in the gene ontology (GO) database and show robust enrichment for functions and compartments of secretory cells determined by fold enrichment vs. FDR using DAVID.
Figure 10B:
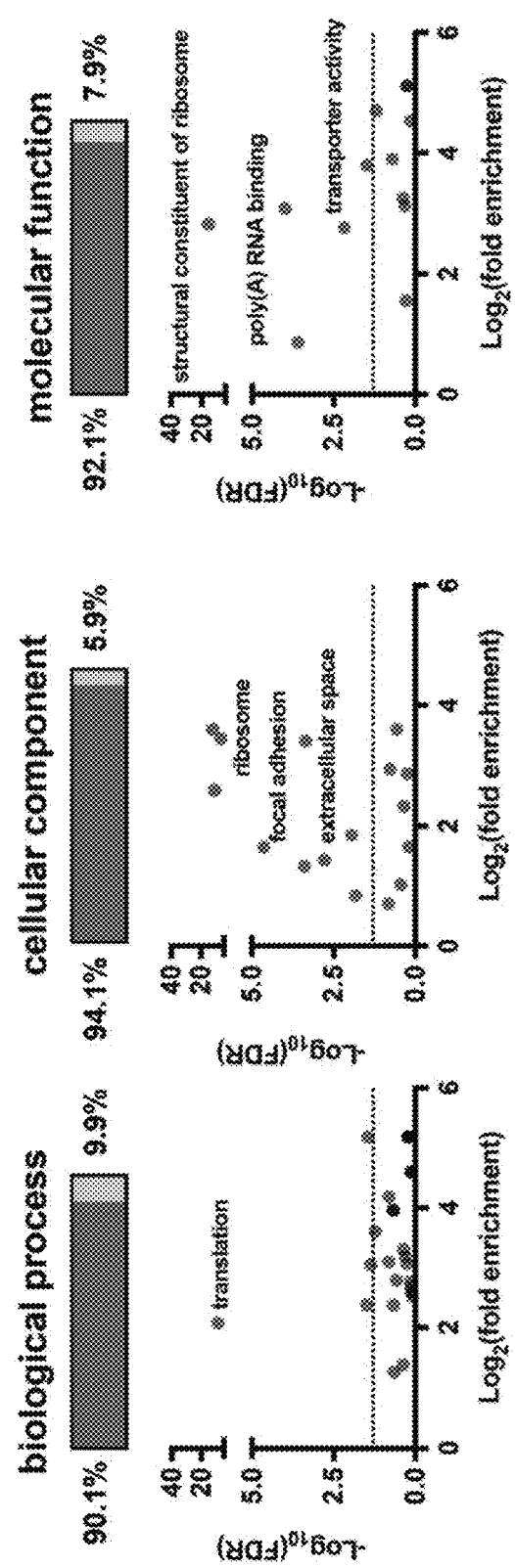

Example 4—Proteome Enrichment Analysis Reveals Expected Components of Paneth and Secretory Cells and Potential Nuclear Receptor Regulation of Differentiation To further describe cell lineage of the CI-PC proteome, Gene Set Enrichment Analysis (GSEA) [39,40] was performed. Using an alternative de facto in vivo PC gene set (top 500 genes PC vs. ISC microarray) on the full rank-ordered proteome (ENR+CD/ENR), GSEA provided a normalized enrichment score (NES) of 3.11, FDR q-value<0.0001, and 58% of tags coming before the leading edge, indicating that the CI-PC culture was enriched for the proteins of previously identified PC genes identified in bulk transcriptomic measurements (FIG. 3E). Applicants also identified transcription factors (TFs) that may mediate PC-specific differentiation using GSEA with the MSigDB transcription factor target (v5.2) gene set database with a moderately conservative cutoff (see Methods). Applicants generated an enrichment map [42,43] of several TF targets significantly enriched in both the ENR+CD and ENR proteomes. In ENR+CD, the nuclear receptors for progesterone (PR), aldosterone (AR), and glucocorticoid (GR), as well as the cellular differentiation-implicated TALI, RP58, and NRSF, are significantly enriched. In ENR, the primary known enrichment was for the cell cycle and proliferation-related E2F TF family (FIG. 3F). These potential TFs are consistent with CI-PC treatment driving expected terminal differentiation of specialized cells, as opposed to conventional organoid culture, which supports a broad mix of intestinal epithelial cells, including proliferating populations. Furthermore, this analysis suggests potential targets, such as PR, AR, and GR, to modulate the differentiation programs of this secretory cell population in future studies. Finally, Applicants characterized enriched biological functions (BP), cellular compartments (CC), and molecular functions (MF) using DAVID v6.8 and the gene ontology database (GO). All sets had high database coverage (greater than 85%) of queried proteins. The ENR+CD proteome is significantly enriched for extracellular and protein processing compartments and secretory-associated functions (FIG. 10A), while the ENR proteome favors translation, intracellular compartments, and translational activities (FIG. 10B). Of note are the extracellular exosome and calcium ion-binding associated proteins in the ENR+CD proteome that are indicative of the intestinal epithelial secretory phenotype (for complete list of DAVID enrichments, refer to Table 4). These functional enrichments further support that the ENR+CD-cultured organoids are enriched in secretory cells, including PCs, although it does not rule out potential co-enrichment for the EEC lineage.

Figure 4A:
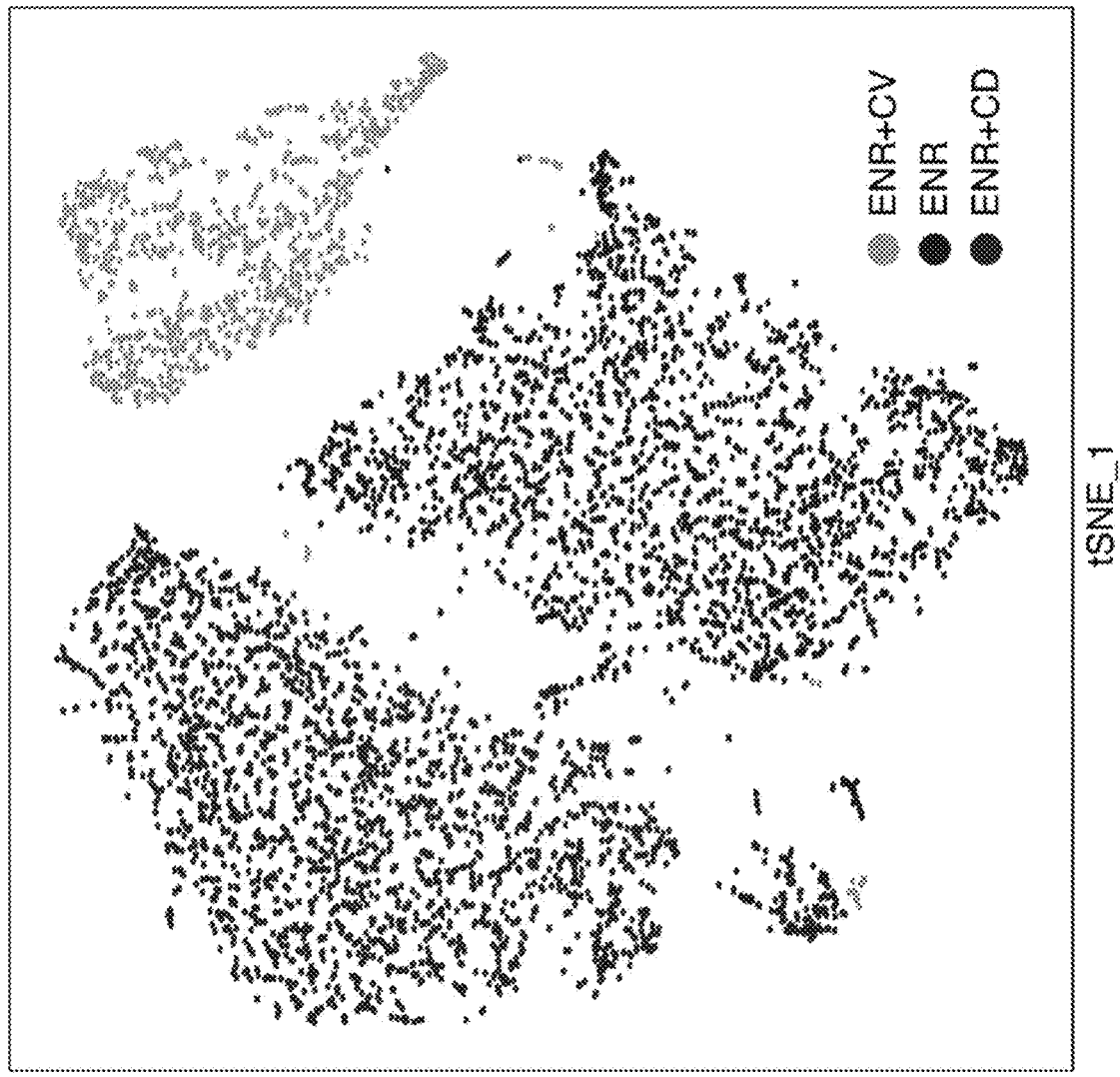
FIGS. 4A-4E—Single-cell RNA-sequencing reveals cellular composition across treatments and origins of proteomic data FIG. 4A) A tSNE plot of single cells derived from ENR+CV (n=985 cells), ENR (n=2544 cells), and ENR+CD (n=2382 cells) harvested at day 6 of differentiation, colored by treatment; n=6 wells for each condition.
Figure 4B:
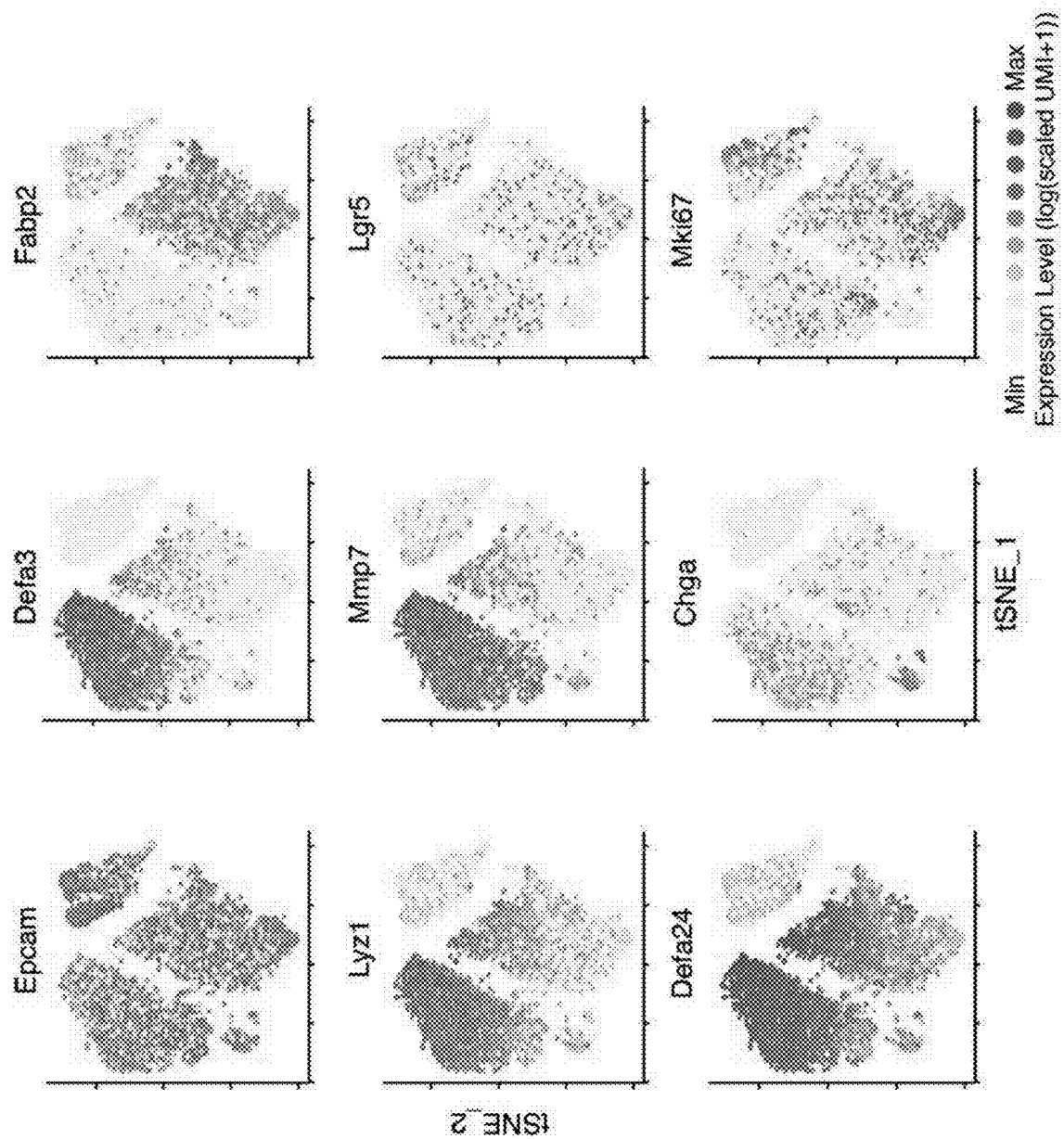
Figure 11A:
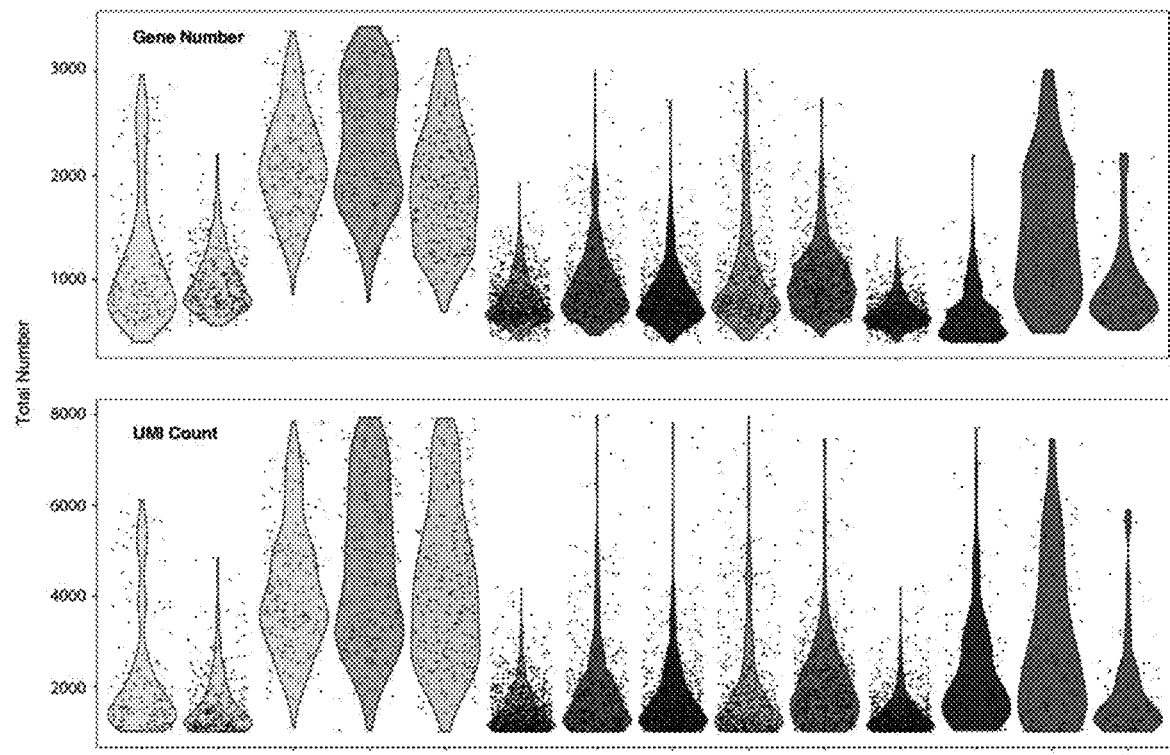
FIGS. 11A-11B—Quality metrics for single-cell RNA sequencing FIG. 11A) Total gene number of cells maintained in analyses with a lower cutoff of n=400 unique genes per cell. Total unique molecular identifiers (UMIs) used as the basis for cell-by-gene tables collapsed to UMI as input into Seurat with lower bound representing n=400 unique genes and upper bound 8000 UMIs. Note: Clusters ENR+CV-3, ENR+CV-4, and ENR-1 had significantly higher levels of genes and UMIs and, intriguingly, were also the three clusters with highest levels of Lgr5 (see FIG. 5A), indicating that stem cells may contain larger contents of RNA, as they are in a biosynthetic state before differentiation and maturation.
Figure 11B:
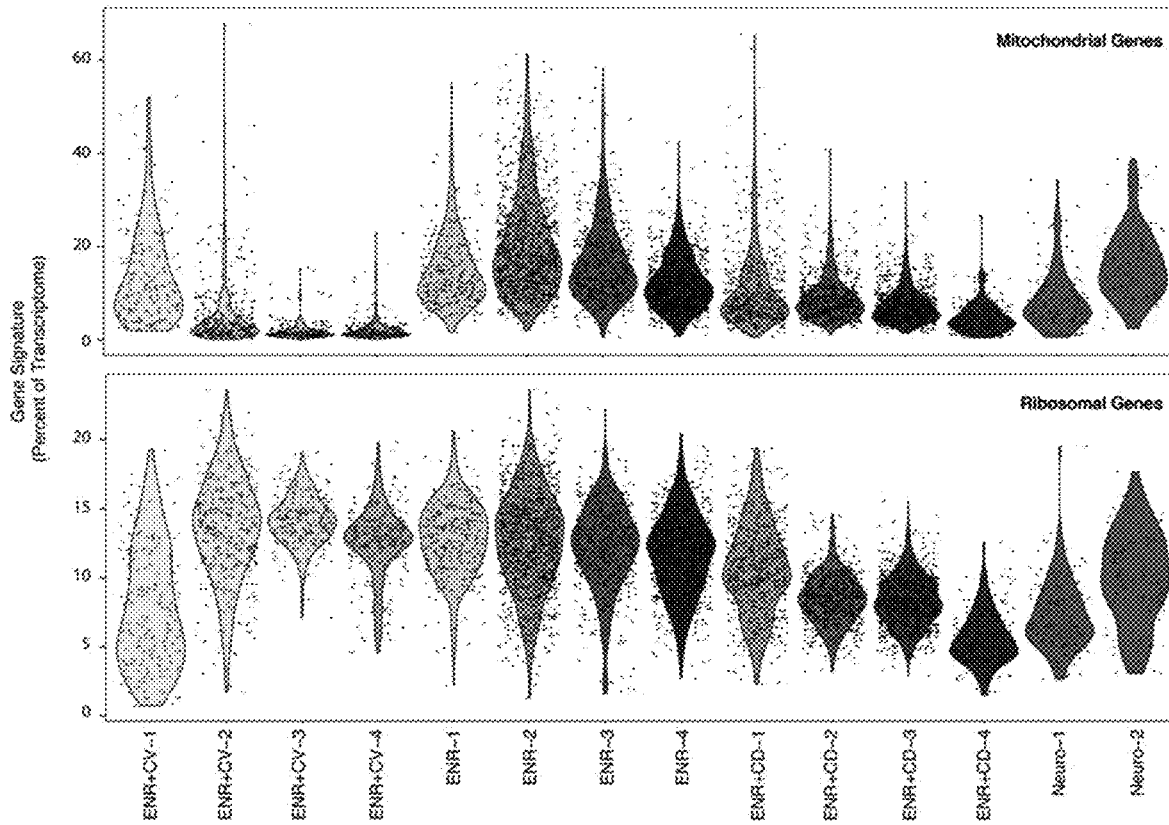

Example 5—Single-Cell RNA Sequencing Reveals Subsets in Chemically-Induced Paneth Cells that Show Improved Transcriptional Similarity with In Vivo Paneth Cells With the apparent co-enrichment of canonical PC and EEC proteins in the ENR+CD proteome, Applicants sought to identify whether Applicants produce a homogenous population of mixed-lineage secretory cells or a spectrum of unique cell states between EEC and PC. Applicants performed scRNA-seq using the Seq-Well platform on cells from ENR+CD and the precursor ENR+CV conditions to analyze alongside conventional ENR organoids. To ensure experimental robustness, Applicants assessed quality metrics for number of genes, unique molecular identifiers (UMIs), mitochondrial genes, and ribosomal genes by cluster, all of which fell within expectation (FIG. 11). UMI-collapsed digital gene expression matrices were analyzed using Seurat (Methods); and displaying all three treatments (ENR+CV, ENR, ENR+CD) in tSNE space demonstrated clear separation between each condition (FIG. 4A). This illustrates unique transcriptional differences induced by each treatment conserved across all cells. Plotting key genes demonstrated that, as expected, all cells expressed high levels of Epcam; ENR+CV cells had enhanced Mki67, a marker of proliferation; the ENR+CD condition enriched for cells expressing antimicrobial Lyz1, Defa24, Defa3, Mmp7, and EEC marker Chga; and ENR enriched for absorptive marker Fabp2-expressing cells (FIG. 4B).

Figures 4C, 4D:
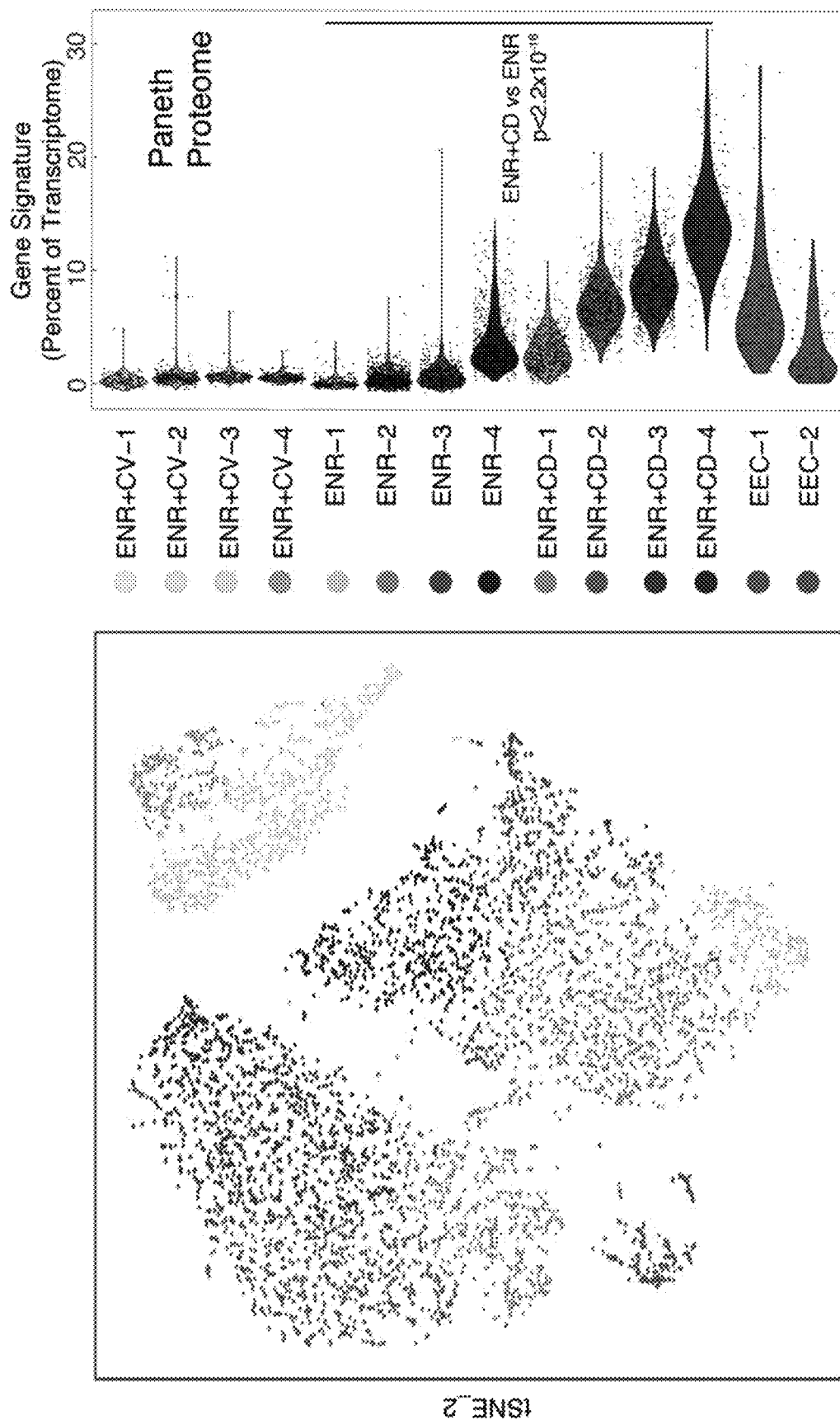
Figure 4E:
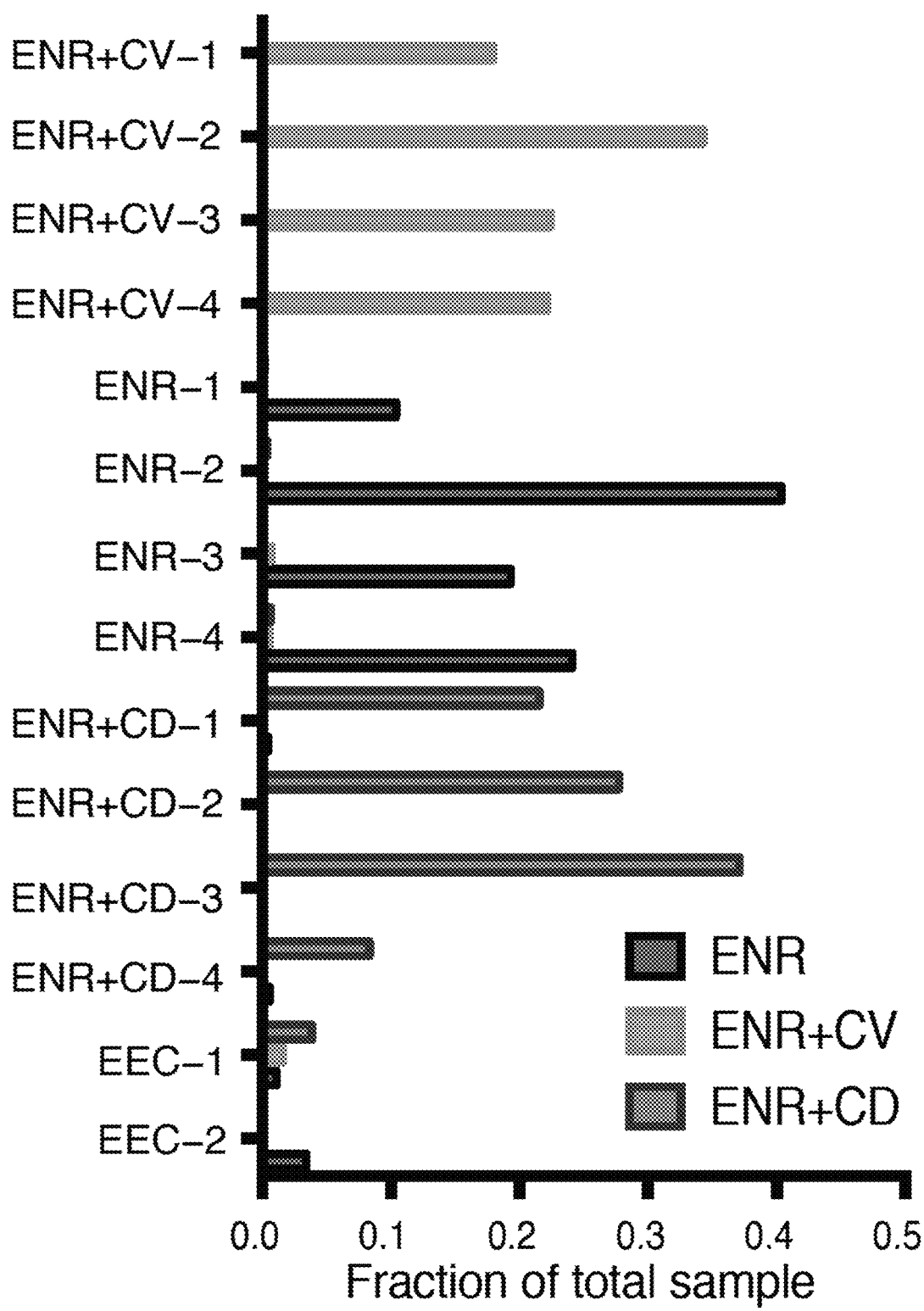

To assess sub-population structure and provide a more robust measure of composition beyond canonical marker genes, Applicants performed unsupervised KNN graph-based clustering on the captured cells (FIG. 4C,D and Table 1 for full gene lists), distinguishing four clusters in each treatment condition. Applicants then scored individual clusters according to the amount of the transcriptome within each cell dedicated to synthesizing the respective enriched proteins from the bulk proteome data. Applicants observed that ENR+CD clusters yield a significant enrichment for those proteins detected in the up-regulated proteome (effect size 1.38 ENR+CD vs ENR clusters, $p<2.2\times10^{-16}$) and that the down-regulated proteins were enriched in the ENR and ENR+CV conditions (FIG. 4D,E and data not shown). Intriguingly, at the level of clusters, the upregulated proteome was not evenly distributed across all cells in ENR+CD, but rather most enriched in cluster ENR+CD-4 (effect size 2.40 ENR+CD-4 vs all cells, $p<2.2\times10^{-16}$) (FIG. 4D,E).

To address ENR+CD composition and how it relates to conventional organoids, Applicants interrogated the expression of Lyz1, Chga, and other select genes across each cluster (FIG. 5A). Applicants noted that clusters ENR-4 and ENR+CD-4 shared expression of Lyz1, Defa24, Defa3, and Mmp7, yet ENR+CD-4 cells produced significantly more of each canonical PC gene (bimodal test, $p<6.80\times10^{74}$ for genes listed, Bonferroni corrected for multiple comparisons). Furthermore, both ENR-4 and ENR+CD-4 cells lacked expression of EEC genes like Chga, which was observed in the EEC-1 and EEC-2 clusters arising from mixed-grouping of the sample, as well as in ENR+CD-2 and ENR+CD-3 (FIG. 5A). Altogether, this suggests that ENR+CD drives PC differentiation while also inducing a secretory transition state (ENR+CD-2 and 3) expressing a mix of PC and EEC marker genes (Table S1 for full gene lists).

Applicants next sought to compare the states generated in vitro to those observed in vivo with the refined system. Using the gene list of in vivo PC markers and further defining a list for in vivo EECs (see Methods) captured on the Seq-Well platform (Table 1), Applicants observed that the percentage of a cell's transcriptome dedicated to synthesizing defining Paneth genes was significantly enriched relative to ENR-4 in clusters ENR+CD-2, 3 and 4 (effect size 0.15, $p<3.43\times10^5$; effect size 0.829, $p<2.2\times10^{-16}$; effect size 2.52, $p<2.2\times10^{-16}$, respectively) with an increase in expression of EEC genes across ENR+CD-1, 2 and 3 but not ENR+CD-4 (effect size 1.30, $p<2.2\times10$-16; effect size 1.82, $p<2.2\times10$-16; effect size 1.118, $p<2.2\times10^{-16}$; effect size 0.0465, $p=0.2339$, respectively) (FIG. 5B). Notably, ENR+CD4 cells (~10%) had a three-fold increase in the transcriptional resemblance to in vivo PCs relative to ENR-4 (53.4% of transcriptome ENR+CD-4 vs. 16.5% of transcriptome ENR-4) (quantification of FIG. 5B). Furthermore, 45% of ENR+CD cells express a secretory Paneth-like transcriptional phenotype that is at least two-fold enhanced relative to conventional organoids (33.9% of transcriptome ENR+CD-3 and 4 vs. 16.5% ENR-4). Comparing the ENR+CD4 cells relative to in vivo PCs demonstrated striking similarity relative to the difference observed between in vivo and ENR-4 cells (Paneth cell fraction of in vivo transcriptome: effect size 0.237 InVivo vs. ENR+CD-4, $p<0.0055$; effect size 1.25 InVivo vs ENR-4, $p<2.2\times10^{-16}$, Table 1).

Figure 5C:
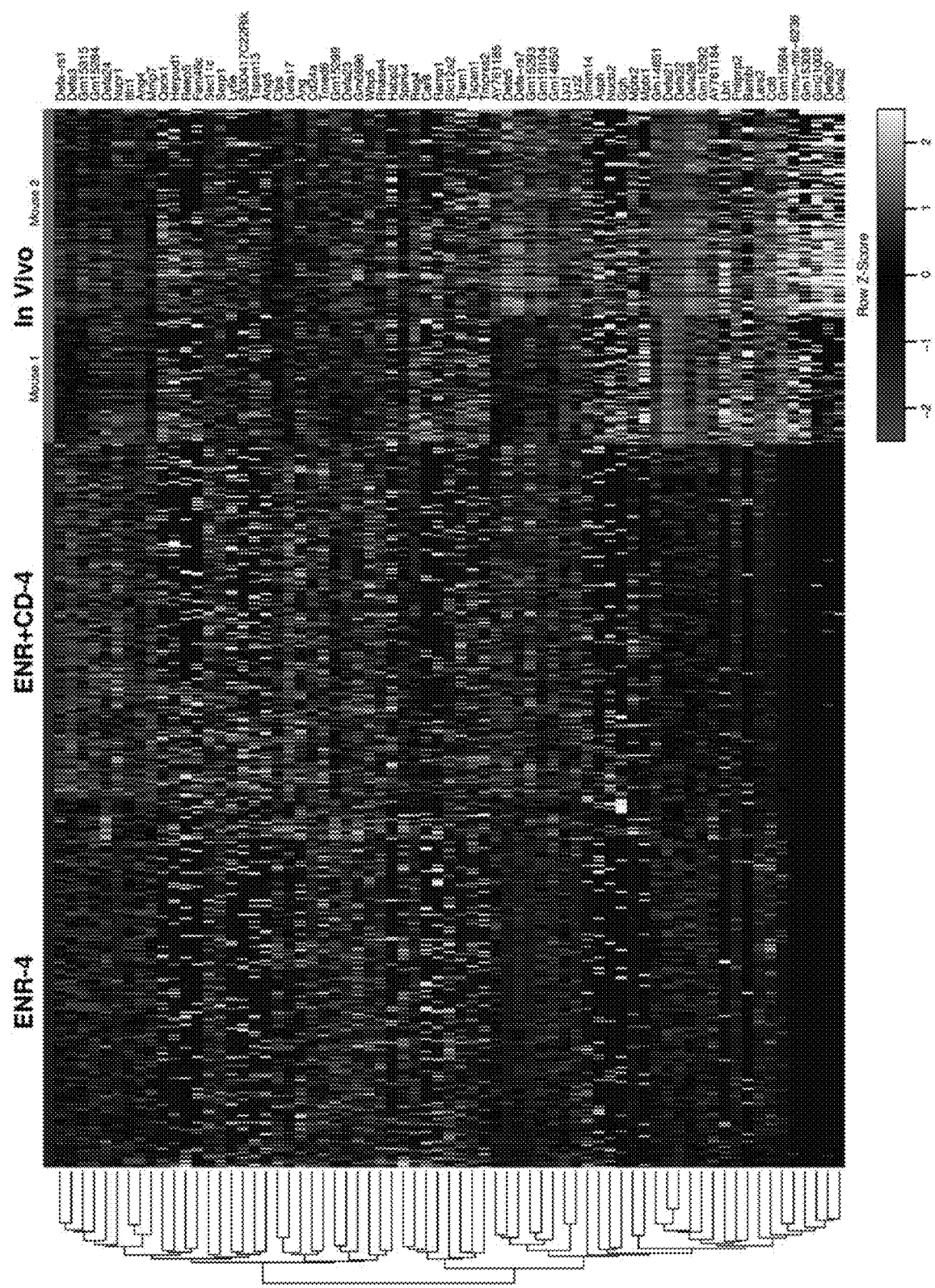

In FIG. 5C, Applicants present a heatmap of scaled expression values for the top genes (AUC>0.65) used for the in vivo Paneth score across ENR-4, ENR+CD-4, and the in vivo cluster used to define PCs. Applicants observe that the enhanced PC phenotype in ENR+CD-4 (effect size 1.144 ENR+CD4 vs ENR-4, $p<2.2\times10^{-16}$) correlates with greater expression of signature genes, such as Lyz1, Lyz2, and Defa5, and greater diversity of antimicrobial peptides genes, such as Ang4, Defa3, and the metalloprotease Mmp7.

Figure 12A:
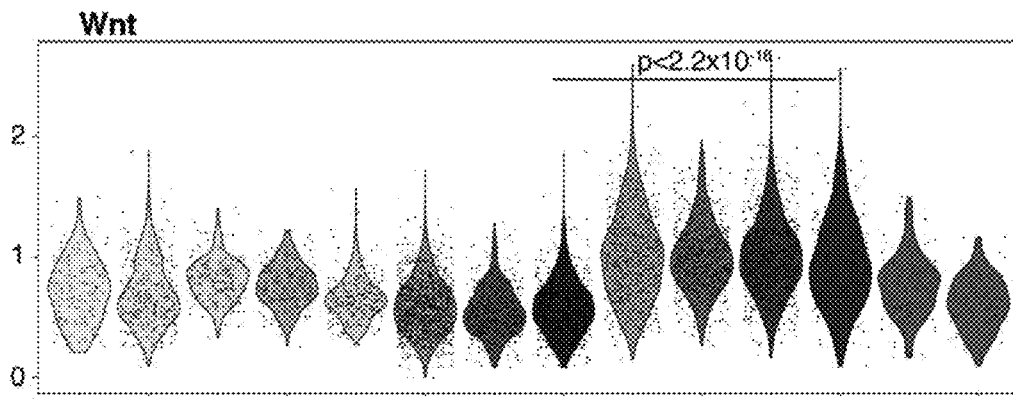
FIGS. 12A-12C—Signaling pathways and processes associated with in vitro PC enrichment FIG. 12A) Violin plot of expression contribution to a cell's transcriptome of Wnt pathway genes (activated by CHIR) across clusters as percent of transcriptome.
Figure 12B:
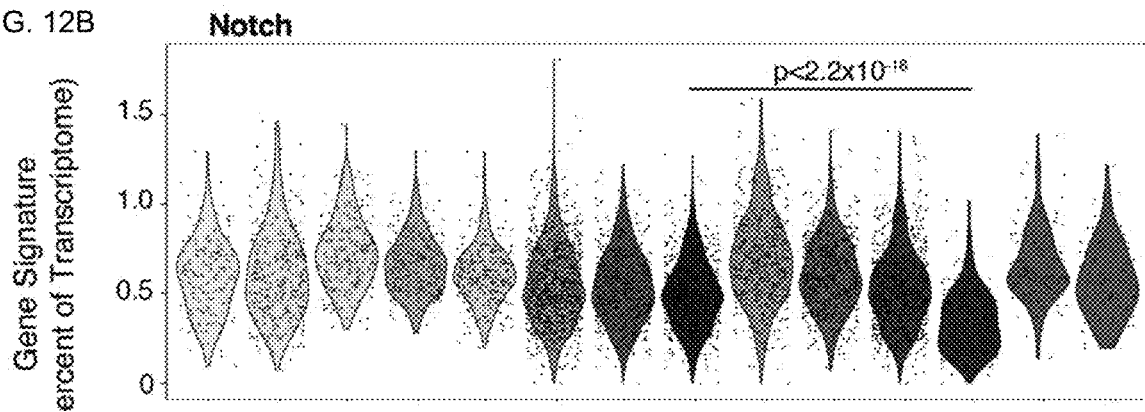
Figure 12C:
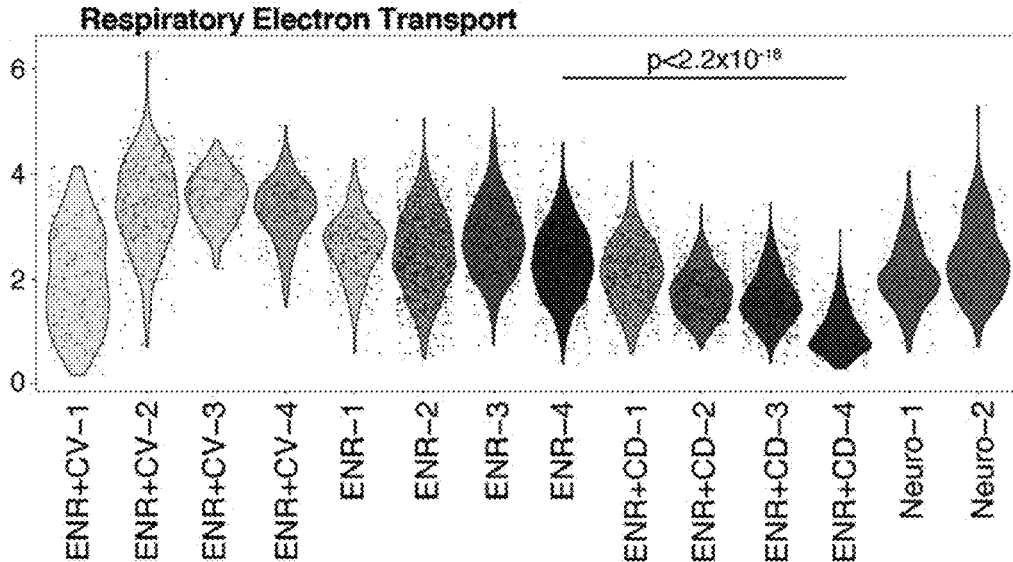

To confirm and extend the findings of pathway-based modulation, Applicants scored clusters for enrichment or depletion of canonical growth factor-induced pathways. CHIR activates the Wnt pathway, and Applicants observed a significant enrichment for Wnt target genes in all CI-PC clusters (effect size>0.999, $p<2.2\times10^{-16}$ for all ENR+CD clusters vs ENR-4) (FIG. 12A). While DAPT is a Notch pathway inhibitor, levels of Notch target genes were largely greater than or equivalent to ENR-4 cells across CI-PC clusters, except for significant depletion in ENR+CD-4 (effect size −0.658, $p<2.2\times10^{-16}$ ENR+CD-4 vs ENR-4) (FIG. 12B). This suggests that complete Notch suppression is key for PC differentiation distinct from an EEC fate. As well, given the recognized role for distinct respiratory potential in enterocytes, ISCs, and PCs, Applicants scored cells across respiratory electron transport genes [44,45]. ENR+CD-4 had the lowest cluster score relative to all cell subsets (effect size −1.4649, $p<2.2\times10$-16) (FIG. 12C). Together, this suggests that Wnt signaling is necessary but not sufficient to specify the mature PC phenotype and that Notch and metabolic conditions play a larger role in the decision between PC and EEC fates.

Figure 6A:
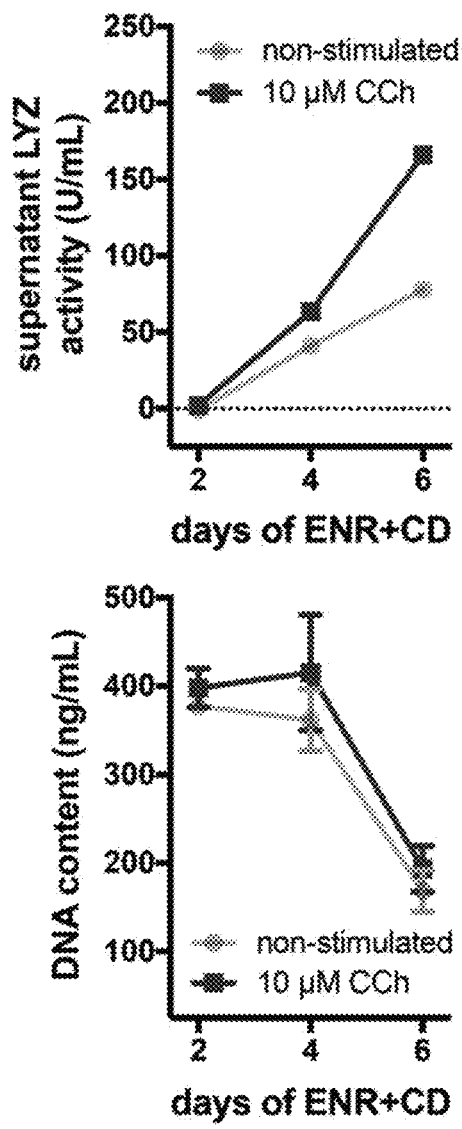
FIGS. 6A-6E—CI-PCs are functional in response to host and microbial stimuli FIG. 6A) Supernatant LYZ from 24-hr basal and 10 μm CCh-stimulated LYZ cells at varying number of days in ENR+CD culture (top). DNA content from matched samples (bottom) (n=8 well replicates; error bars too small to visualize).
Figure 6B:
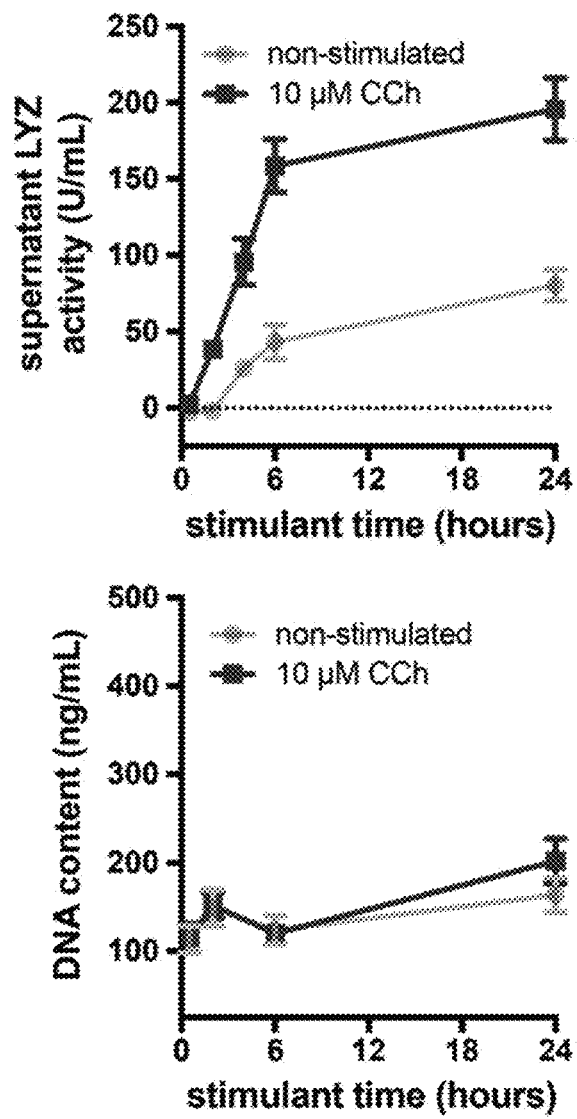
Figure 6C:
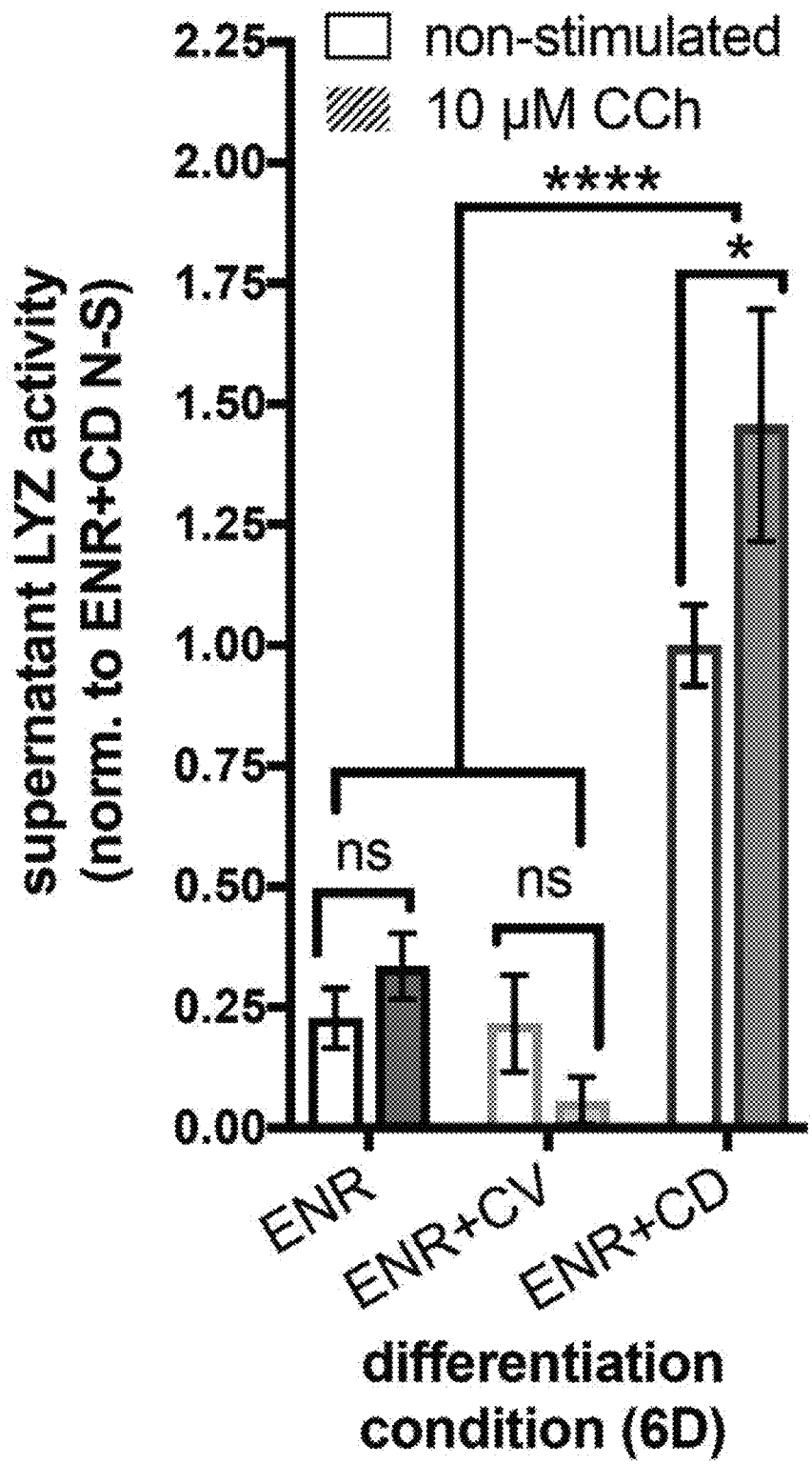

Example 6—Chemically-Induced Paneth Cells Mimic In Vivo Stimulant-Induced Secretion and Demonstrate Selective Modulation of Bacteria in Co-Culture In addition to the morphological, proteomic, and transcriptional characterization of PC phenotype in ENR+CD and ENR, Applicants sought to measure physiological function by assessing stimulant-induced secretion of antimicrobials. Applicants assessed the dynamics of LYZ accumulation in media supernatant of cultures following media wash, basally and after stimulation with carbachol (CCh), a cholinergic agonist known to induce PC secretion [46]. 10 μM CCh induced a rapid accumulation of LYZ within two hours that plateaued around six hours post-wash (2-way ANOVA, stimulant $p<0.0001$, time-point $p<0.0001$) (FIG. 6B). The observed PC secretion in response to CCh is consistent with observations made in ex vivo crypts, though over appreciably longer time scales, likely due to the added diffusion barrier of the organoid structure and matrigel [46]. Applicants next identified how LYZ secretion changes over the course of differentiation. Beginning with an ISC-enriched population, Applicants assayed for secreted LYZ in cell culture supernatants every two days for six days of ENR+CD culture, following a 24-hour stimulation with CCh or without (basal collection/non-stimulated). Notable increases in functional secretion (stimulated relative to basal) occurred at days four and six (2-way ANOVA, stimulant $p<0.0001$, time-point $p<0.0001$) (FIG. 6A). Compared to conventional organoids and ISC-enriched precursors, ENR+CD secreted significantly more basal LYZ ($p<0.0001$) and was the only population that showed grossly measurable CCh-induced secretion (adj. $p=0.03$) (FIG. 6C). This result is consistent with the observed enrichment, and demonstrates a system to easily measure physiologic PC antimicrobial secretion.

Figure 6D:
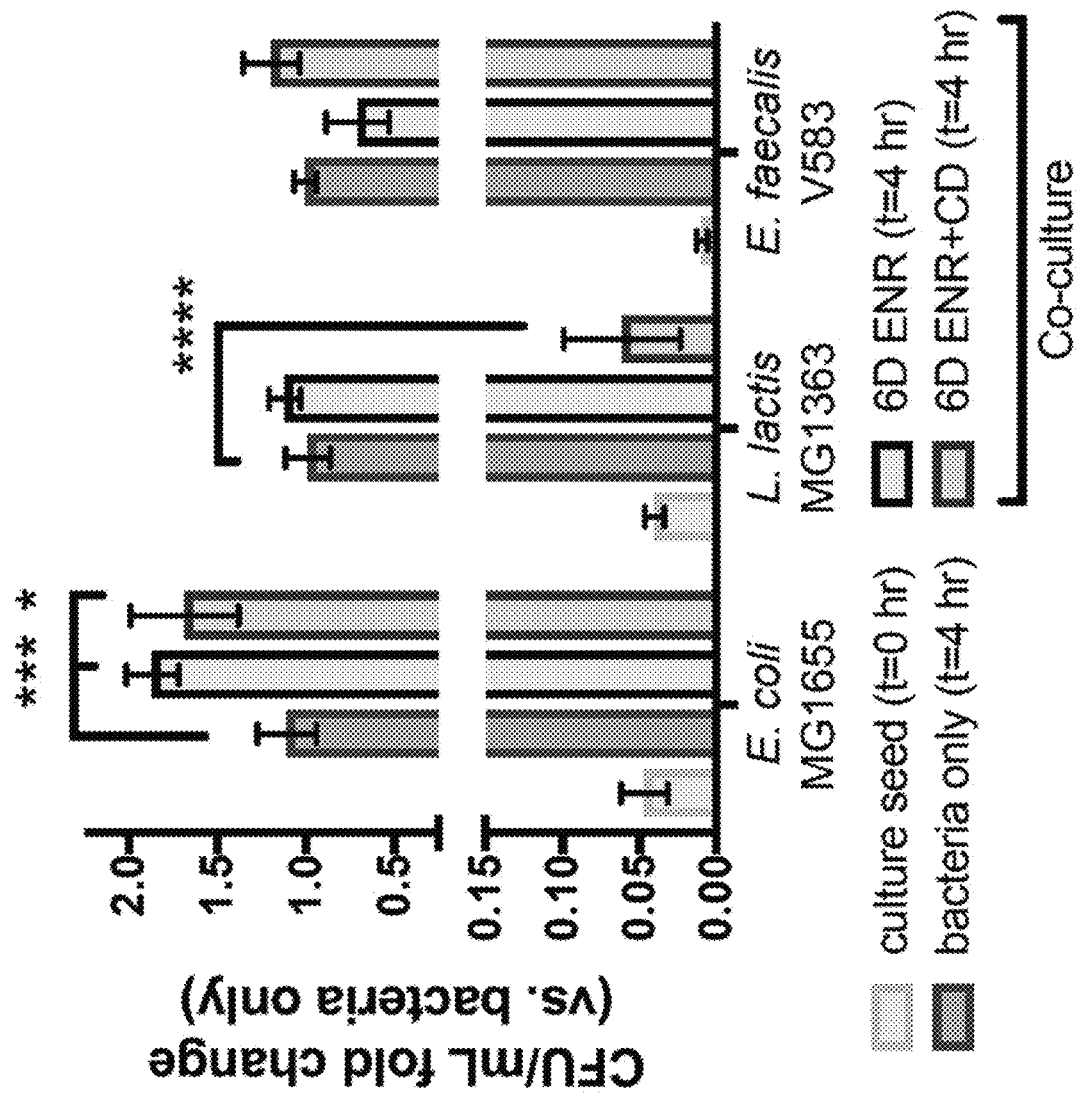

Based on the broad spectrum of antimicrobials detected proteomically, transcriptionally, and functionally, Applicants hypothesized that ENR+CD possess greater bactericidal effects than conventional organoids. Applicants assayed for bacterial growth modulation by suspending cell clusters with common laboratory strains of gram-negative and gram-positive bacteria in exponential growth. CI-PCs significantly suppressed growth of gram-positive L. lactis MG1363 (adj. $p=0.0001$), which did not occur with conventional organoids, indicative of increased PC-associated antimicrobial activity. Both ENR (adj. $p=0.0005$) and ENR+CD (adj. $p=0.01$) co-culture showed significant increase in gram-negative E. coli MG1655 growth but no appreciable effect on the growth of gram-positive E. faecalis V583 versus bacteria alone (FIG. 6D). While this assay simplifies the PCs' physiological environment and may not be a direct proxy for strain-specific growth modulation, it does demonstrate that the PC-enrichment of ENR+CD versus conventional organoids enables detectable in vitro bacteria species-specific PC antimicrobial response, opening avenues for future experimentation.

Figure 6E:
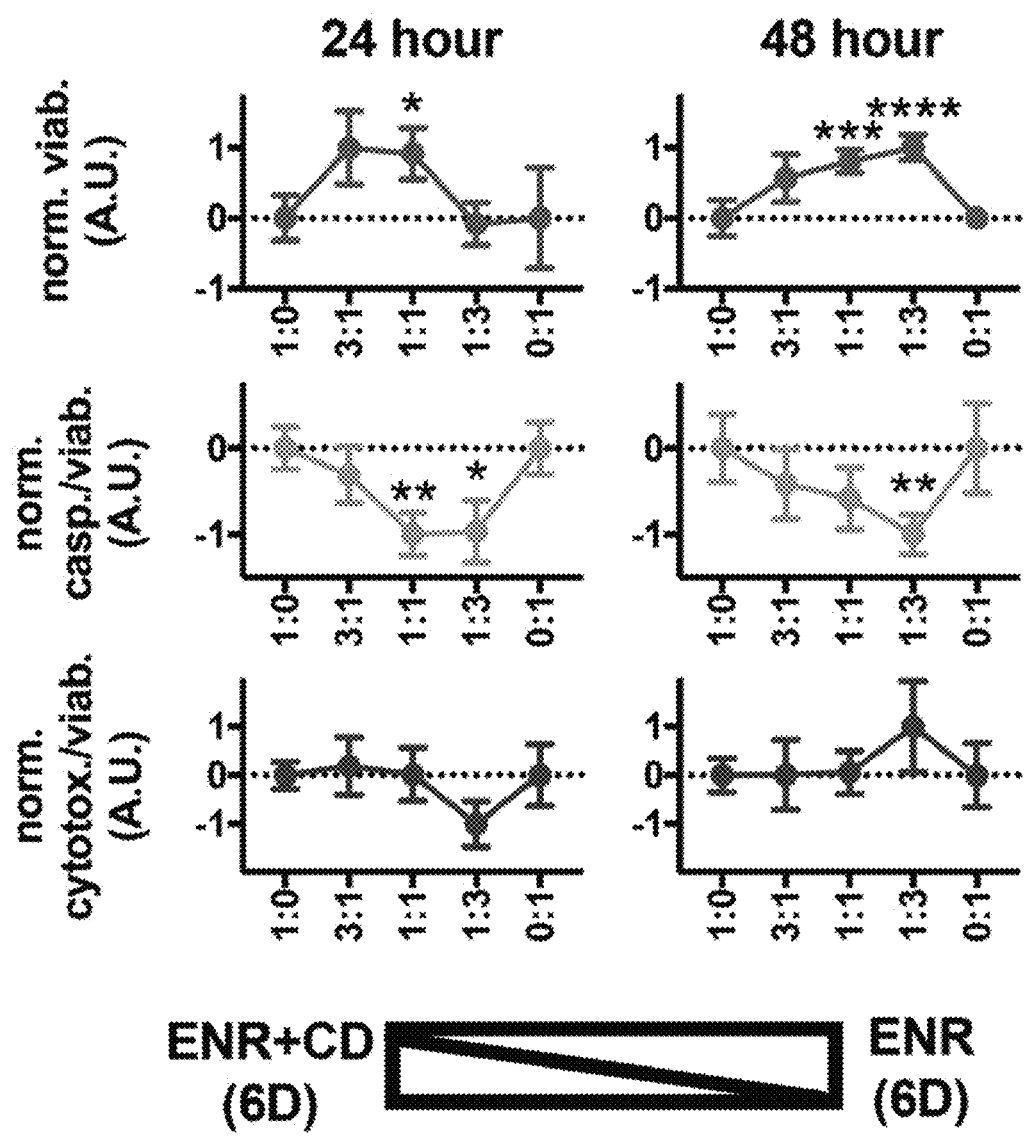

Example 7—Chemically-Induced Paneth Cells Provide Niche Support and Enhance Conventional Organoid Survival Beyond the generation of antimicrobial peptides, PCs provide niche support for ISCs. Applicants sought to test if CI-PCs provided niche factors known to drive epithelial regenerative turnover. Applicants performed co-culture experiments, mixing and re-plating cell populations derived from six-days of ENR or ENR+CD culture and assayed co-culture viability, caspase activity, and cytotoxicity 24 and 48 hours following re-plating in ENR-media. If there were no appreciable interaction, positive or negative, between the two populations Applicants would expect to see a linear trend of every measured variable throughout mixing ratios. However, Applicants observe a significant positive interaction where the presence of both populations drives an overall increase in cellular viability, beginning at 24 hours (one sample t-test 1:1 p=0.037) and increasing at 48 hours (one sample t-test 1:1 p=0.001 and 1:3 p<0.001) (FIG. 6E). This is likely due to a significant decrease in overall apoptosis relative to the total cell population (one sample t-test 24-hour 1:1 p=0.004 and 1:3 p=0.032, 48-hour 1:3 p=0.003), and unrelated to changes in cellular cytotoxicity. Applicants believe that the presence of a PC-enriched population (from ENR+CD) is driving this effect by providing increased soluble regenerative factors to the ISC population in ENR organoids, increasing the generation of new cells, and resulting in a lower overall rate of apoptosis.

Figure 7A:
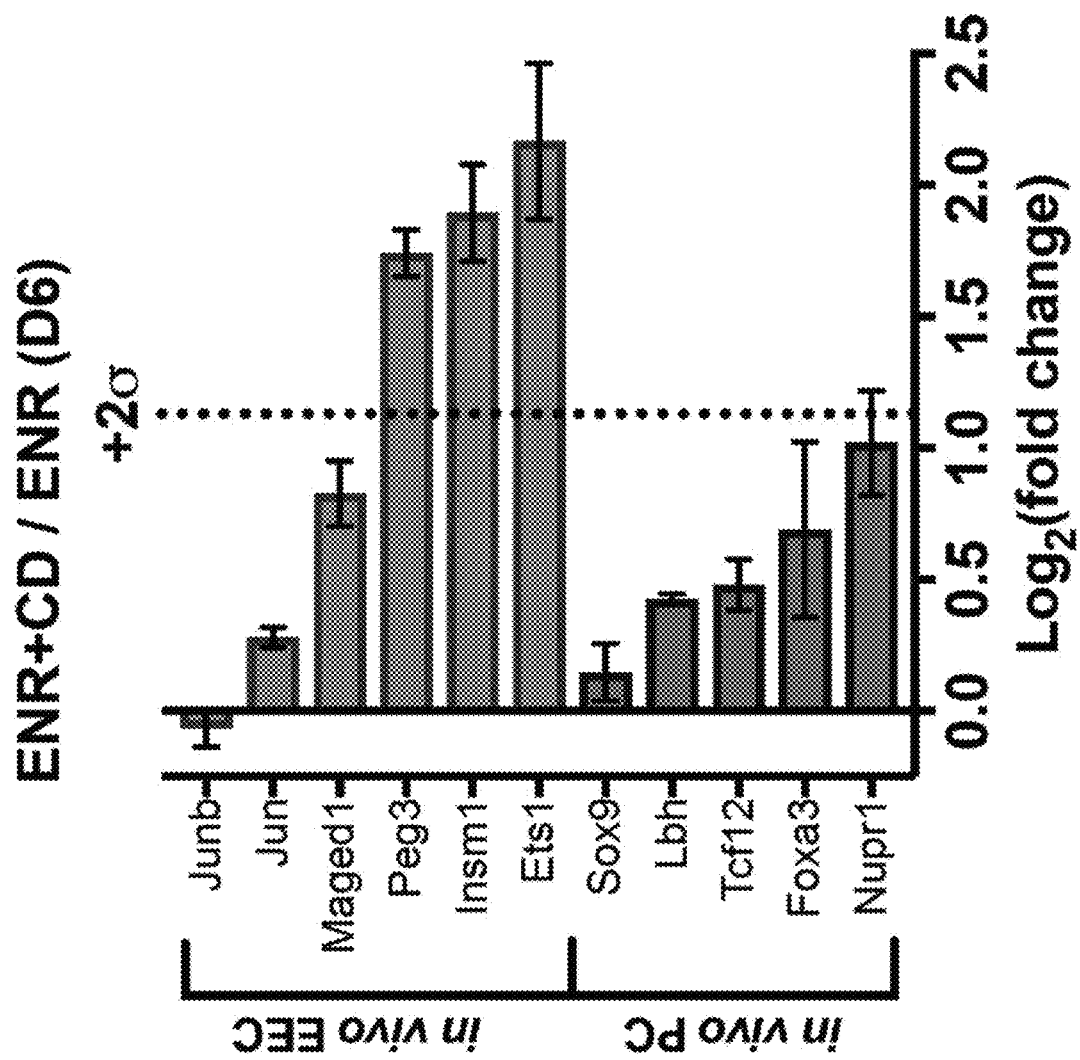
FIGS. 7A-7D—CI-PCs reveal putative function of Nupr1 transcription factor in PC survival FIG. 7A) ENR+CD is enriched for in vivo PC and EEC transcription factors, including Nupr1.
Figure 7B:
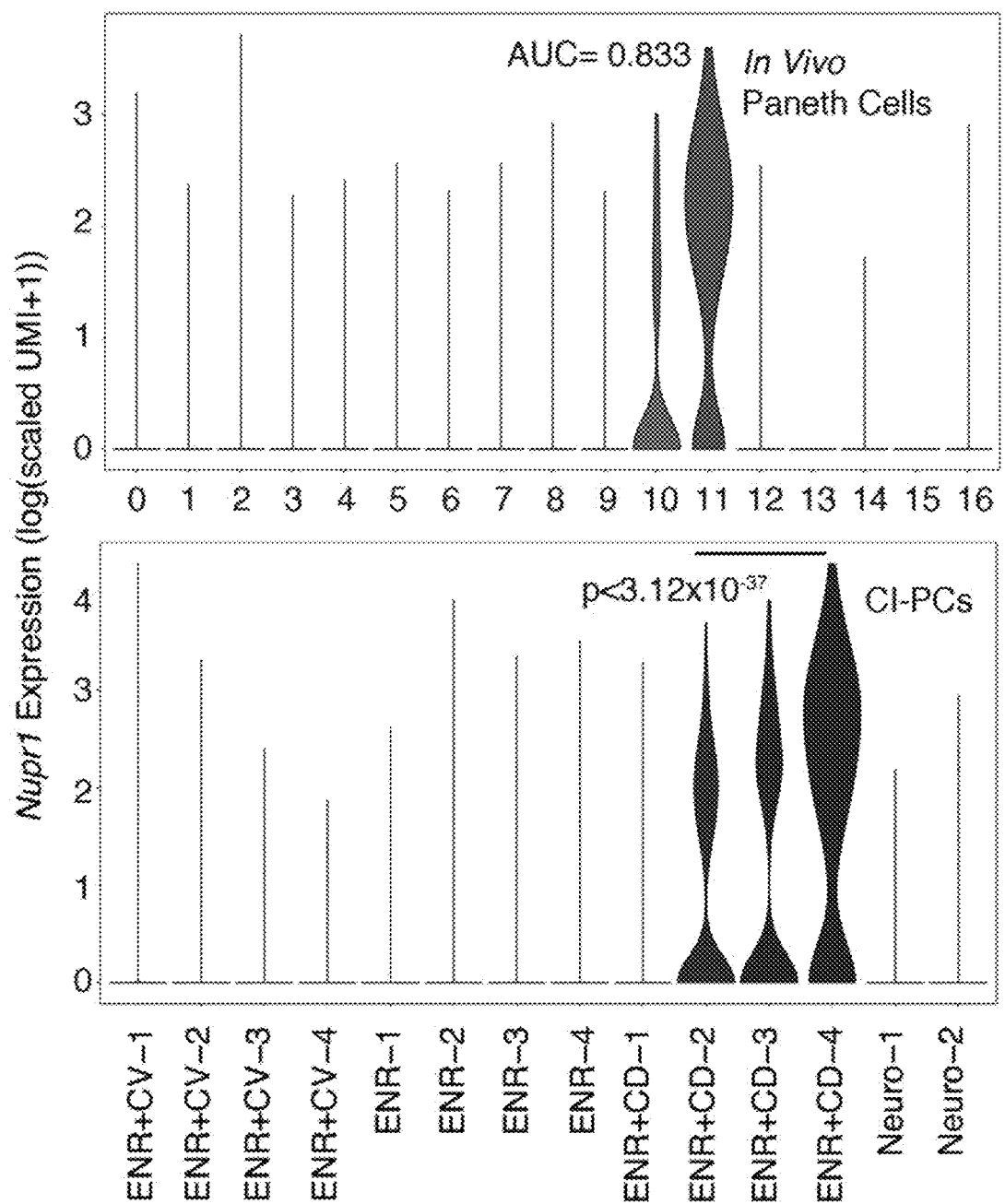
Figure 7C:
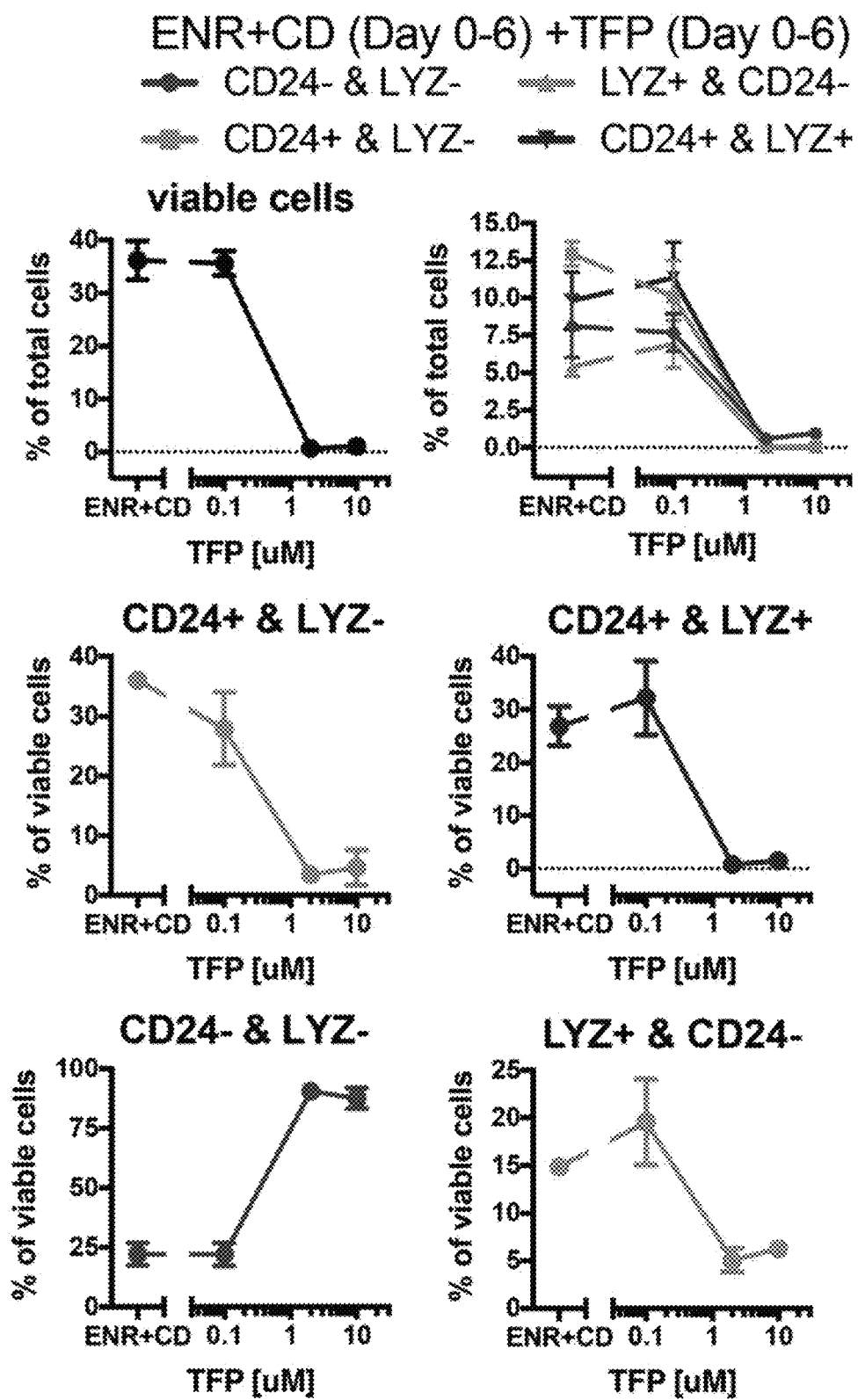
Figure 7D:
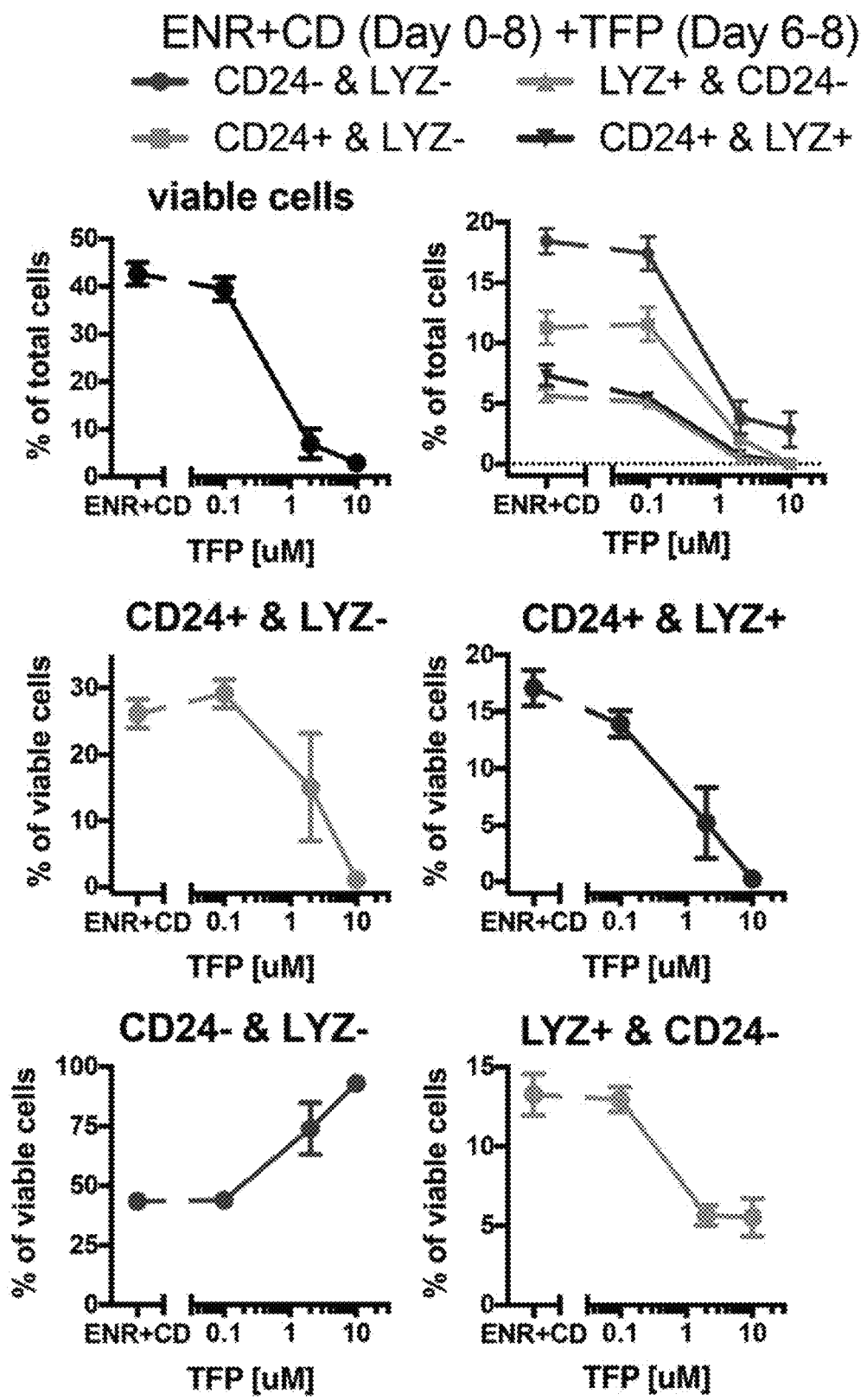

Example 8—Mapping of In Vivo Paneth Cell-Associated Transcription Factors to In Vitro Proteome and Transcriptome Reveals Nupr1 as Important in Epithelial Survival Lastly, Applicants sought to use this physiologically-improved in vitro PC system (ENR+CD) to identify novel factors potentially supportive of PC survival or differentiation. Using the in vivo PC and EEC gene lists, and filtering for only transcription factors (TFs) (using TFdb, downloaded September 2017) [47], Applicants identified a set of PC- or EEC-specific TFs. Applicants mapped these TFs to the in vitro proteome (FIG. 7A & Table 3), which revealed the previously-unreported NUPR1 as the most enriched PC-specific TF in ENR+CD. This finding was supported by differential expression between ENR+CD2 (most enteroendocrine-like cells) and ENR+CD4 (p<$3.12 \times 10^{-37}$, bimodal test, Bonferroni corrected for multiple comparisons) (FIG. 7B). Applicants further identified Nupr1 in the in vivo PC populations which showed specific and enriched expression of Nupr1 by in vivo PCs (ROC test, AUC=0.833) (FIG. 7B). Intriguingly, Nupr1 is a stress-response gene, known to promote cellular survival and senescence through mediation of autophagy, and has primarily been studied in the context of cancer [48-50]. Autophagy and stress response have repeatedly been implicated through GWAS study in PCs in IBD, however Nupr1 has only ever been reported in a single IBD GWAS study, and its role in PC biology has not been formally investigated [51]. With the model, Applicants sought to test the role of NUPR1 on in vitro PC survival, through the small molecule inhibition of NUPR1 with trifluoperazine (TFP) [52,53]. Applicants first tested how different dosages impact PC differentiation in combination with ENR+CD for six days, where doses above 1uM lead to near total cell death, and where the few surviving cells are primarily non-Paneth (FIG. 7C). This suggests that Nupr1 is likely critical to cellular survival during the CI-differentiation process. Applicants also tested the addition of TFP for two days following a six-day course of ENR+CD, where again Applicants see a profound, but not total, decline in cellular viability. Further, it appears that TFP treatment is selectively more toxic to PC and PC-progenitor populations relative to non-PC populations (FIG. 7D). In total, this initial investigation suggests that NUPR1 may be a critical TF in PC development and survival, which carries therapeutic implications and Applicants will seek to validate in vivo in future work.

Example 9—Discussion

Applicants sought to directly compare a specific cell type present in vivo to that derived in vitro, with the main goal of understanding the nature and extent of divergence between the in vivo and in vitro conditions. Empowered by recent advances in massively-parallel scRNA-seq, Applicants define the current cell types and propose a potentially improved cell state derived through rational modulation of developmental pathways. Applicants identified that the PC-state of conventional intestinal organoid shows a poor representation of antimicrobials, and that modulation of Wnt and Notch during differentiation may improve physiological representation. To this end, Applicants enriched and expanded primary murine adult LGR5$^+$ ISCs, which are stable over many divisions [54], to provide a near-unlimited pool from which to differentiate starting from minimal adult tissue. This "ground state" expansion prior to differentiation is an emerging theme within models to characterize epithelial biology in vitro [9,10,55,56].

Figure 2E:
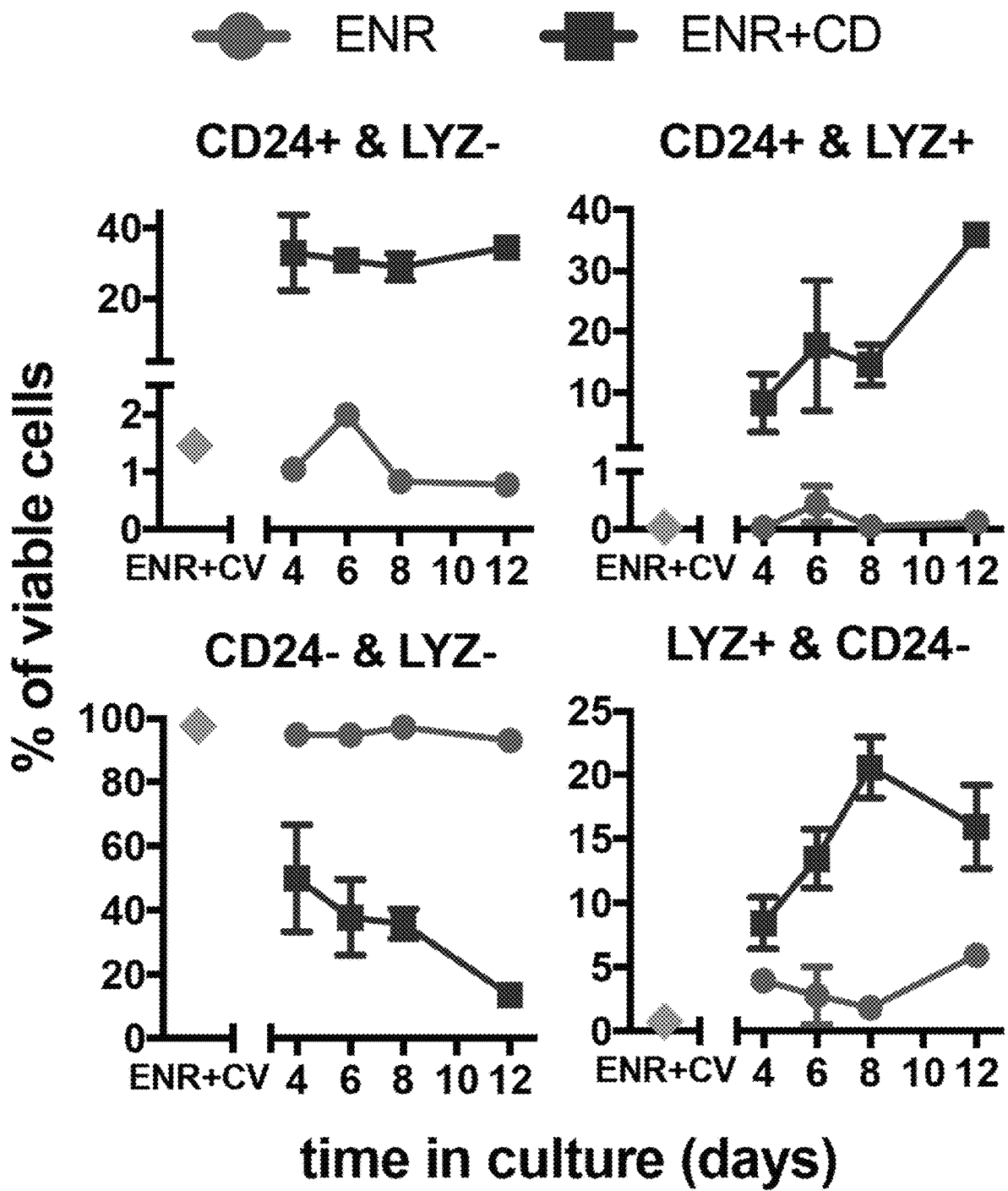

Using targeted small molecule promotion of Wnt and inhibition of Notch signaling, Applicants drove a secretory differentiation program and enriched for mature PCs with greater diversity and expression of antimicrobial peptides relative to existing in vitro PC models and, thus, are more representative of in vivo PCs. Imaging of this population revealed that they are positive for the antimicrobials LYZ and DEFA, clearly polarized, and granule-rich, suggestive of a mature PC. This population is approximately six-fold more abundant in ENR+CD than an ENR organoid, as confirmed through image quantification, flow cytometry and scRNA-seq. Applicants further characterized the subpopulation enrichments of the ENR+CD culture and directly compared it to conventional organoids. Applicants identified two subpopulations in scRNA-seq (ENR+CD-3 and ENR+CD-4) that account for approximately half of the ENR+CD-treated cells with a high-degree of transcriptional similarity to in vivo PCs, a greater percentage/matching than the ENR-subpopulation that most resembles an in vivo PC (ENR-4). From this analysis, Applicants believe that in vitro PCs characterized in the past [28,29] likely represent secretory precursor populations lacking the full phenotypic repertoire of the in vivo PC, which Applicants identify as the approximately 5% of single-staining LYZ+ cells present in ENR organoids as assessed by flow cytometry (FIG. 2E). The in vitro PCs, however, are morphologically, transcriptionally, and functionally representative of their in vivo counterparts, easily generated from primary tissue samples, and can provide near unlimited numbers of PCs for further studies.

While this approach moves us much closer to generating the in vivo cell type (Paneth cell fraction of in vivo transcriptome: effect size 0.237 InVivo vs. ENR+CD-4, p<0.0055; effect size 1.25 InVivo vs ENR, $p<2.2\times10^{-16}$), Applicants still do not capture the total amount of antimicrobial peptides present in vivo, and propose pathways to modulate in future studies.

Evidence suggests that PC antimicrobial expression and function are influenced by genetic background and implicated in intestinal disease, including IBD [58]. The identical genetic background of the population Applicants studied likely influenced the observed low variation in protein abundance within the ENR+CD-enriched proteome. How genetic background may influence differentiation through this protocol is yet to be studied but especially prudent, as Applicants demonstrated the ability to detect a broad spectrum of antimicrobial proteins and peptides and their differential abundance within a PC-enriched population. Interestingly, Applicants identified that the same sub-population (ENR+CD-4) with the most transcriptional overlap to the bulk ENR+CD-enriched proteome also most closely resembles the in vivo PC. While this sub-population does not account for the majority of ENR+CD-cultured cells, it appears that ENR+CD-4 consistently drives the PC phenotype in vitro. In addition to assessing the role of genetic background or disease state on antimicrobial content, the platform also affords the ability to interrogate how alterations in protein processing and storage in PCs affects the proteome, which has been shown to drive shifts in the microbiome and may be implicated in disease [59,60]. Finally, while Applicants demonstrate an enriched phenotypic spectrum of antimicrobials and Wnt ligands, Applicants also identified several neuropeptides and hormone products associated with the EEC lineage within the system. Given that multiple studies have linked the differentiation of PCs and EECs through a common progenitor population [61], it is reasonable to expect enrichment in one population would also allow for some overlap with the other, as Applicants see in the scRNA-seq.

To understand how the chemical induction led to distinct secretory sub-populations within the CI-PCs, Applicants mapped Wnt, Notch, and metabolic gene sets onto each subpopulation. In the system, Notch-signature is highest in the stem cells and EECs, lower in enterocytes, and lower in PCs. The system's Wnt signature is relatively decreased in enterocytes (ENR largely) and increased in PCs and EECs, which both occur predominantly in the Wnt-driven condition ENR+CD (CI-PCs). In total, this suggests that Wnt is necessary for ISCs to commit to PC and EEC lineages and that future experimentation with specific synthetic Wnt ligands may prove fruitful in distinguishing Wnt target genes that discriminatorily yield PCs or EECs. Also clear is that strong Notch inhibition is important for mature PC development, possibly as a balance between differentiation and cell survival. Future studies should incorporate temporal aspects to growth factor delivery akin to what has been shown for degradable matrices to enhance purity and yield. Finally, Applicants see a notable gradient in cellular respiration across subpopulations, lowest in the PC and highest in the stem cell and EEC lineages, in agreement with recent work on the metabolic differences within the stem cell niche [45], as another potential cue to further specify PC differentiation. In all, the analysis of single cell heterogeneity shows that the system is well-positioned to further investigate the effects of both known and unknown physiological cues on PC differentiation and function.

One of the most important features Applicants established with the CI-PCs was the ability to measure PC functional enrichment through simple soluble assays. Applicants demonstrated sufficient functional enrichment in PCs such that enzymatic activity assays can detect stimulant-induced secretion of antimicrobials as well as the promotion of the ISC niche. Moreover, microbe co-culture assays with the enriched cells produce measurable and selective microbial growth modulation not observed using conventional organoids. Co-culture strains were chosen to demonstrate proof of concept of selective antimicrobial action and assess functionality compared to conventional organoids. Given the results showing selective modulation of bacterial growth, Applicants believe that the system could serve as a tool to further probe host-microbe interaction in vitro. Furthermore, it would allow for investigations of both microbial mechanisms that elicit PC response (e.g. TLRs) and the properties of complex mixtures of secreted components, including multiple antimicrobial proteins.

The generation of comprehensive cellular atlases from humans and model organisms will certainly yield a revolution in the understanding of complex tissues [3]. Intestinal organoids have already proven their value in studying human and murine epithelial biology. However, to rigorously test hypotheses of basic biological or disease mechanism, it will be essential to have reliable protocols for the generation of specialized subsets of cells which cannot be readily isolated from tissue. The representativeness of cell states present in organoids and the specialized cell types present in vivo [3] is an outstanding question with implications in mucosal immunology, developmental biology, and translational medicine. The single-cell genomics approach provides compelling evidence that organoid-derived cell populations must be validated to ensure physiological relevance, and additionally provides a rational framework for identifying cell states and their potential upstream drivers to modulate cellular composition. This approach could enable advances beyond conventional organoid systems to provide an enriched highly-specialized cell population that recapitulates important physiological functions of the intestinal epithelium, and could represent an improvement in in vitro PC culture for the purposes of high-throughput screening, the study of host-microbe interactions, bioengineering (e.g. precision gene editing), and the identification of novel genetic candidates in PC function (e.g. Nupr1). With this framework, Applicants illustrate the power and importance of rigorously characterizing the specialized cell types derived in organoids to those defined in "atlas-level" surveys of the intestinal epithelium.

Example 10—Methods

Mice for tissue isolation. Proximal small intestine was isolated from C57BL/6 mice of both sexes, aged between three to six months in all experiments.

Bacteria strains. Cells were stored at −80 C and grown as follows. *E. coli* strain MG1655 was grown overnight in LB. For experiments, overnight cultures of MG1655 were resuspended in M9 supplemented with 0.4% glucose and 0.2% cas amino acids. *L. lactis* strain MG1363 was grown in M17 media supplemented with 0.5% glucose, and *E. faecalis* strain V583 was grown in Brain Heart Infusion (BHI) media.

Crypt culture, enrichment, and differentiation. Small intestinal crypts were cultured as previously described [64]. Briefly, crypts were resuspended in basal culture medium (Advanced DMEM/F12 with 2 mM GlutaMAX and 10 mM HEPES; Thermo Fisher Scientific) at a 1:1 ratio with Corning™ Matrigel™ Membrane Matrix—GFR (Fisher Scientific) and plated at the center of each well of 24-well plates. Following Matrigel polymerization, 500 µL of small intestinal crypt culture medium (basal media plus 100×N2 supplement, 50×B27 supplement; Life Technologies, 500× N-acetyl-L-cysteine; Sigma-Aldrich) supplemented with growth factors EGF—E (50 ng/mL, Life Technologies), Noggin—N (100 ng/mL, PeproTech) and R-spondin 1—R (500 ng/mL, PeproTech) and small molecules CHIR99021—C (3 µM, LC Laboratories) and valproic acid—V (1 mM, Sigma-Aldrich) was added to each well. ROCK inhibitor Y-27632—Y (10 µM, R&D Systems) was added for the first 2 days of culture. Cells were cultured at 37° C. with 5% $CO_2$, and cell culture medium was changed every other day. After 6 days of culture, crypt organoids were isolated from Matrigel by mechanical dissociation. Isolated organoids were resuspended in TrypLE Express (Life Tech) to dissociate into single cells, then replated in Matrigel with ENR+CV+Y media for 2 days. Cells were once again passaged, either into freezing media (Life Tech) for cryopreservation or replated at approximately 200 organoids per well (24-well plate) for ISC-enriched organoid expansion. ISC-enriched organoids were passaged or differentiated every 6 days in the ENR+CV condition. To differentiate, cells were passaged as previously described, and crypt culture medium containing growth factors ENR only or ENR+CD (D—DAPT, 10 µM; Sigma-Aldrich) was added to each well.

RNA extraction & qRT-PCR. Organoids were isolated from Matrigel in 24-well plates following culture as previously described, and pellets were lysed in TRI reagent with RNA extracted according to the manufacturer's protocol (T9424, Sigma). Resulting RNA pellets were dissolved in UltraPure water and cDNA synthesis was performed using QuantiTect Reverse Transcription Kit (Qiagen). qPCR reactions were performed using TaqMan Universal Master Mix II (no UNG), pre-designed TaqMan probes (Table S5), and 500 ng of sample cDNA (LifeTech). Reactions were carried out using an Applied Biosystems 7900HT system. qPCR results were analyzed using RQ manager 1.2 software to obtain CT values used for relative quantification to the housekeeping gene Hprt.

Confocal imaging of whole cell clusters. ISC-enriched cell clusters (ENR+CV) suspended in 40 µL of Matrigel were seeded onto round coverslips inside a 24-well plate. Cells were treated with ENR+CD, ENR+CV, or ENR as previously described. At day 6, organoids were rinsed (PBS0 3X) and fixed to the coverslips by incubating with 4% paraformaldehyde (PFA) for 30 minutes at room temperature (RT). Gels were blocked and permeabilized by incubating at RT for one hour with 0.1% Triton X-100 and 5% Powerblock in PBS0. Organoids were stained for DEFA and LYZ by incubating with rat anti-mouse Crp1 (Ayabe Lab clone 77-R63, 5 µg/mL, 50X) and rabbit anti-human Lyz (Dako, 200X) primary antibodies diluted to 10 µg/mL in staining solution (0.1% Triton X-100 and 10× Powerblock in PBS0) overnight at 4° C., followed by secondary antibodies Alexa Fluor 647 anti-Rabbit IgG (400X) and Alexa Fluor 488 anti-Rat IgG (400X) diluted in staining solution for 1 hour at RT. Actin was stained with Alexa Fluor 555 Phalloidin (40X) for 20 minutes, followed by staining of the nucleus with 3 µM DAPI for 5 minutes. Coverslips were mounted onto slides with Vectashield and imaged within 5 days using an Olympus FV2000 confocal microscope. Whole organoid confocal microscopy images were processed and analyzed using ImageJ. To determine the PC purity percentage, the ImageJ Point Picker plugin was used to count the number of nuclei to determine total number of cells and to count the number of DEFA- and LYZ-containing PCs across all z-slices. To investigate cell polarity in whole organoids, individual cells were selected using ImageJ and mean area intensity within selected cell areas was computed in each z-slice throughout the depth of the image across every channel imaged.

High-resolution single-cell imaging. Cell clusters were harvested and rinsed (basal culture media 3X) to remove Matrigel as previously described. Isolated clusters were resuspended in TrypLE Express and incubated at 37° C. for 20 minutes to dissociate into single cells, then rinsed (basal culture media 2X) and resuspended in PBS containing magnesium and calcium. Pre-coated poly-L-lysine coverslips (Fisher Scientific) were placed into wells of a 24-well plate, a cell suspension containing approximately 50,000 cells per well was added to each well, and the plate was centrifuged at 700 rcf for 5 minutes. PBS supernatant was removed from the wells, and the cells attached to the coverslips were fixed by incubating with 4% PFA for 30 minutes at RT. After each step, cells were rinsed (PBS 2-5 min 3X). Cells were blocked and permeabilized by incubating at RT for 30 minutes with permeabilization solution and stained with for DEFA and LYZ by incubating with rat anti-mouse Crp1 and rabbit anti-human Lyz primary antibodies diluted in staining solution overnight at 4° C. Secondary antibodies Alexa Fluor 647 anti-Rabbit IgG and Alexa Fluor 488 anti-Rat IgG diluted in staining solution were incubated with the coverslips for 1 hour at RT. Actin was stained with Alexa Fluor 555 Phalloidin incubated for 20 minutes at RT, and the nucleus was stained with DAPI by incubating at RT for 5 mins. Coverslips were mounted on to slides with Vectashield and imaged within 48 hours using an Applied Precision DeltaVision Microscope.

Flow cytometry. Cell clusters were isolated from Matrigel as previously described and resuspended in TrypLE Express at 37° C. for 20 mins to dissociate into single cells. Dissociated cells were centrifuged at 300 g for 3 mins at 4° C. The pellet was resuspended in FACS buffer (1% FBS in PBS, Thermo Fisher Scientific) and strained into a 5-mL filter cap tube using a 40 µm filter. The cell suspension was transferred to a flow prep microcentrifuge tube and centrifuged at 300 rcf for 3 min. Cell pellets were resuspended in a Zombie violet dye (BioLegend 100X) in FACS buffer for viability staining followed with 1% PFA fixation for 20 minutes at RT. Pellets were permeabilized for 20 minutes at RT with staining buffer (0.5% Tween-20 in FACS buffer, Sigma), and co-stained with rabbit anti-human FITC-Lyz (100X) and rat anti-mouse APC-CD24 (100X) antibodies diluted in staining buffer for 45 min at RT. Flow cytometry was performed using a BD LSR II HTS (BD; Koch Institute Flow Cytometry Core at MIT). Initial settings and laser voltages were determined with unstained, single channel stains or secondary-only controls (data not shown). Flow cytometry data was analyzed using FlowJo v10.7 software. Briefly, gating was performed as seen in FIG. 8F by removing doubles and debris, then selecting the BV421-(viable) cell population; within this population, gating was based on LYZ- and CD24-populations.

Lysozyme functional secretion assay. Lysozyme secretion was measured using a Lysozyme Assay Kit (EnzChek; Thermo Fisher). Briefly, cells suspended in Matrigel in 24-well plates were washed (basal culture media 3X) and either supplemented with 500 µL of basal culture media or basal culture media plus 10 µM Carbachol (CCh, Sigma Aldrich) for 24 hours at 37° C. Following stimulation, culture plates were spun at high speed (>2000 g) for 5 min at RT to pellet cell debris and loose Matrigel. 25 µL of conditioned supernatant was removed from the top of each well and quantified per manufacturer's protocol.

Quantification of cell viability, apoptosis, cytotoxicity. To track proliferation and cell viability, DNA content was quantified over the course of differentiation and CCh-stimulation using a CyQUANT Cell Proliferation Assay Kit (Thermo Fisher) per manufacturer's protocol. Briefly, culture media was aspirated from each well, and the wells washed (PBS 3X). Gels were then mechanically dissociated into PBS, contents transferred into a Falcon tube, centrifuged at 300 rcf for 3 min at 4° C., and the pellet resuspended in PBS to wash. Tubes were centrifuged at 300 rcf for 5 min at 4° C., and the pellet resuspended in 1 mL assay working solution (20× cell-lysis buffer, 400× GR dye in DI water). 200 µL of samples and DNA standards were plated in triplicate in a black 96-well plate, shaken for 5 min, then fluorescence was measured on a plate reader (480 nm/520 nm).

For ENR/ENR+CD co-culture, ISC-enriched organoids (ENR+CV) were differentiated in ENR and ENR+CD and isolated as previously described. The cell pellets were counted and resuspended in basal culture medium, mixed at 0:100, 25:75, 50:50, 75:25, and 100:0% ENR:ENR+CD ratios (number of clusters), and plated as previously described in Matrigel in a 96-well plate at approximately 50 clusters/well in ENR media. After 24 and 48 hours of co-culture, viability versus cytotoxicity and caspase activation were assessed using ApoTox-Glo Triplex Assay (Promega) according to the manufacturer's protocol. Briefly, 20 µL of "V/C reagent" (10 µL each of GF-AFC and bis-AAF-R110 substrates in 2.0 mL of assay buffer) were added to all wells and mixed by orbital shaking at 500 rpm for 30 sec. After 30 minutes of incubation at 37° C., fluorescence was measured on a plate reader (400 nm/505 nm for viability and 485 nm/520 nm for cytotoxicity). 100 µL of Caspase-Glo 3/7 reagent was then added to all wells and mixed by orbital shaking at 500 rpm for 30 sec. After 30 minutes of incubation at RT, luminescence was measured on a plate reader.

Bacteria co-culture. For bacteria co-culture, ISC-enriched cells (ENR+CV) were differentiated in ENR and ENR+CD as previously described. After six days of differentiation, cell clusters were isolated as previously described. The cell pellet was resuspended in basal culture medium and plated in suspension in a 96-well plate at approximately 150 clusters/well. A 1:1 volume of bacteria in respective media (see "Bacterial strains," above; in exponential growth, as confirmed by plate reader OD) was added, and bacterial growth was measured by serial plating (CFU) after a 4-hour incubation. Results for bacteria co-culture were normalized to no cell (bacteria only) controls.

Mass spectrometry proteomics sample preparation, sequencing, and quantification. Organoid cell pellets were isolated from Matrigel with mechanical dissociation and washed (cold PBS 5X) to remove residual extracellular protein. Proteins were extracted from cell pellets with 8 M urea (Sigma), reduced with 5 mM DTT (Thermo Fisher Pierce) for 45 minutes, alkylated with 10 mM IAA (Sigma) for 45 minutes in the dark, and double digested with both Lysyl Endopeptidase "LysC" (Wako) and trypsin (Promega) overnight at RT. A small aliquot of cellular lysate was removed from each sample for protein quantification via the Pierce™ BCA Protein Assay Kit (Pierce). After proteolytic digestion, the samples were quenched using formic acid to a final concentration of 1.0% and subsequently desalted on 10 mg OASIS HLB solid phase columns (Waters).

From each condition (n=8), 50 µg aliquots of the Ng KD dried tryptic peptides were reconstituted in 100 mM HEPES pH 8.0 to a final concentration of 1.0 mg/mL. The peptides were labeled with TMT-10 isobaric mass tag reagent according to manufacturer's instructions (ThermoFisher Scientific). The peptides were labeled at a 1:8 ratio of peptide to TMT reagent, followed by 1-hour incubation at RT with bench top shaking at 850 rpm. After incubation, a 1.0 aliquot of labeled tryptic peptide was removed from each labeled condition, desalted with C18 stage tips, and analyzed via LC-MS/MS using a Thermo Fisher Q Exactive Plus Hybrid Mass Spectrometer (QE-Plus) coupled to a Thermo Fisher EASY-nLC 1000 liquid chromatograph to ensure isobaric label incorporation >95%. An additional 1.0 µg of labeled tryptic peptide was removed from each channel, mixed together, desalted on a C18 stage tip, and analyzed via LC-MS to ensure equal relative protein loads. During these quality control steps, the labeled peptides were stored, unquenched at −80° C. After validation, each channel was quenched with a 5% hydroxylamine solution to a final sample concentration of 0.3% to quench any unbound isobaric tags. The corresponding 8 channels were mixed together for a total amount of 400 µg of labeled tryptic peptides. The labeled peptide mixture was dried down in a speedvac and subsequently desalted on 30 mg OASIS HLB solid phase column (Waters).

The dried, labeled peptides were fractionated into 24 fractions by basic reversed-phase (bRP) using an Agilent Zorbax 300 A 4.6 mm×250 mm Extend-C18 column on an Agilent 1100 Series HPLC instrument (Agilent Technologies) to decrease sample complexity and increase the dynamic range of detection. Solvent A (2% acetonitrile, 5 mM ammonium formate, pH 10), and a nonlinear increasing concentration of solvent B (90% acetonitrile, 5 mM ammonium formate, pH 10) was used as the mobile phase with a flow rate of 1 mL/min through the column. A nonlinear gradient with increasing percentages of solvent B with 4 different slopes was used (0% for 7 min; 0% to 16% in 6 min; 16% to 40% in 60 min; 40% to 44% in 4 min; 44% to 60% in 5 min; 60% for 14 min), and the eluted peptides were collected in a Whatman polypropylene 2 mL 96-well plate (Whatman). The 96 fractions were concatenated down to 25 fractions.

The global proteome (25 fractions) was analyzed by LC-MS/MS using the same system described above. Peptides were separated at a flow rate of 200 nL/min on a capillary column (Picofrit with a 10-µm tip opening and 75 µm diameter, New Objective, PF360-75-10-N-5) packed at the Broad Institute with 20 cm of C18 1.9 µm silica beads (1.9-µm ReproSil-Pur C18-AQ medium, Dr. Maisch GmbH, r119.aq). Injected peptides were separated at a flow rate of 200 nL/min with a linear 84-min gradient from 100% solvent A (3% acetonitrile, 0.1% formic acid) to 30% solvent B (90% acetonitrile, 0.1% formic acid), followed by a linear 9-min gradient from 30% solvent A to 90% solvent B for a total of 110 minutes. The QE-Plus instrument was operated in the data-dependent mode acquiring higher-energy collisional dissociation tandem mass spectrometry (HCD MS/MS) scans (Resolution=35,000) for TMT-10 on the 12 most abundant ions using an MS1 ion target of $3\times10^6$ ions and an MS2 target of $5\times10^4$ ions. The maximum ion time used for the MS/MS scans was 120 ms; the HCD-normalized collision energy was set to 31; the dynamic exclusion time was set to 20 secs, and the peptide-match preferred setting was enabled.

Quality Control of Mass Spectrometry Performance and Data Generated. Before running batches of samples, the liquid chromatography (LC) and mass spectrometer (MS) performance (retention time, chromatographic peak width, sensitivity, signal-to-noise, and mass accuracy) were verified by analyzing a reference material (a mixture of 5-7 standard peptides). Applicants have implemented calculation of the primary NIST LC-MS/MS metrics into Spectrum Mill (SM) to monitor ongoing system performance quality when analyzing samples. Specific metrics measure: enzyme cleavage fidelity, deamidation, carbamylation, chromatographic peak width, relative dynamic sampling of MS/MS near the chromatographic apex, the portion of the LC gradient over which peptides are identified, distribution of precursor charges, mass accuracy, portion of collected MS/MS that are identifiable, distribution of peptide pI (for IEF based separations) and/or solution charge (for SCX based separations), certainty in localization of phosphorylation sites, variability in peptide/protein quantification, and FDR for peptide/protein identification.

Protein and peptide identification and quantification. Peptide spectrum matching and protein identification was performed using Agilent Technologies SM software package (developed at the Broad Institute). In SM, false discovery rates (FDRs) are calculated at three different levels: spectrum, distinct peptide, and distinct protein. Peptide FDRs are calculated in SM using essentially the same pseudo-reversal strategy evaluated by Elias and Gygi and shown to perform the same as library concatenation. A false distinct protein ID occurs when all the distinct peptides that group together to constitute a distinct protein have a deltaForwardReverseScore ≤0. Applicants adjust settings to provide peptide FDR of 1-2% and protein FDR of 0-1%. SM also carries out sophisticated protein grouping using the methods previously described [67]. Only proteins with >2 peptides and at least 2 TMT ratios in each replicate are counted as being identified and quantified. Additionally, Applicants added the capability to flag potentially unreliable TMT quantification results based on detection of more than one precursor in the selection window for MS/MS. The precursor ion flagging is similar to that recently reported but is carried out post-data acquisition. As an output, SM generates protein and peptide reports for downstream differential regulation, pathway, and network analysis. Prior to comprehensive differential marker, pathway, and network analysis with the SM generated protein reports, Applicants ensure that the data is of high quality and has been properly normalized. The first level of normalization is accomplished by guaranteeing that equivalent amount of peptide (50 µg per) is labeled for each of the 10 TMT channels. Once the SM reports are generated, Applicants calculate the median ratios for each of the channels where the denominator of the ratio is a predetermined TMT channel signifying the control condition. The underlying assumption is that the null distribution is centered at zero in log 2 space. Therefore, in this step of normalization, Applicants normalize the median log 2 ratio for each ratio column so that the median log 2 ratio is zero. To robustly and confidently detect real differential peptides and proteins in the TMT-labeled experiment, Applicants performed a moderated t-test [69,70]. Unlike the standard t-test, which is not robust for small numbers of samples, the moderated t-test uses an empirical Bayes approach that "moderates" variance estimates for peptides (i.e., shrunk towards a common value), thereby significantly improving the stability of variance estimates for individual peptides. The p-values reported by the moderated t-test are adjusted for multiple testing using the Benjamini-Hochberg FDR method [70]. Additionally, Venn diagrams showing sample overlap were produced with Venny 2.0 software [71].

Proteome pathway and network analysis. Using the identified and quantified proteins from the TMT-10 labeling experiment, multiple pathway and network analyses were performed. Sample correlations were represented as r-values and determined using GraphPad Prism version 7.0a. To assess sample variability, Applicants computed the median-normalized relative abundance of each protein identified as significantly enriched (from the median-normalized ratio of ENR+CD/ENR paired samples) within the four ENR+CD samples and four ENR samples, and calculated the coefficient of variation (CoV) (sample standard deviation over mean) for each protein across the four samples. To assess proteome enrichment for a standard Paneth cell gene set, Applicants rank-ordered all 8,015 detected proteins, and used GSEA v3.0b2 [39,40] "Preranked" to compute set enrichment against a gene set of the top 500 genes differentially regulated in a microarray comparison of in vivo Paneth cells versus LRG5$^+$ ISCs performed by [16]. To elucidate potential transcriptional drivers of proteome structure, Applicants performed GSEA using the full rank-ordered proteome against the transcription factor target gene set database (v5.2 MSigDB) [41], then performed enrichment map visualization using GSEA-P-based implementation and Cytoscape v3.4.0 [42,43] with a moderately conservative cutoff (p-value<0.005 and FDR<0.075) and an overlap coefficient of 0.2. To assess the functional and compartmental functions associated with the ENR+CD-enriched proteome and ENR-enriched proteome, Applicants used DAVID v6.8 [72,73] and the gene ontology (GO) database, looking only at experimentally verified associations within biological processes (BP), cellular compartments (CC), and molecular function (MF) against a background set of all 8,015 quantified proteins.

Single-cell RNA-sequencing. A single-cell suspension was obtained from organoids cultured under ENR+CV, ENR, and ENR+CD conditions for six days as described above. Applicants utilized the Seq-Well platform for massively parallel scRNA-seq to capture transcriptomes of single cells on barcoded mRNA capture beads. Full methods on implementation of this platform are available in [31]. In brief, 20,000 cells from one organoid condition were loaded onto one array containing 100,000 barcoded mRNA capture beads. The loaded arrays containing cells and beads were then sealed using a polycarbonate membrane with a pore size of 0.01 µm, which allows for exchange of buffers but retains biological molecules confined within each microwell. Subsequent exchange of buffers allows for cell lysis, transcript hybridization, and bead recovery before performing reverse transcription en masse. Following reverse transcription and exonuclease treatment to remove excess primers, PCR amplification was carried out using KAPA HiFi PCR Mastermix with 2,000 beads per 50 µL reaction volume. Six libraries (totaling 12,000 beads) were then pooled and purified using Agencourt AMPure XP beads (Beckman Coulter, A63881) by a 0.6× SPRI followed by a 0.7× SPRI and quantified using Qubit hsDNA Assay (Thermo Fisher). Libraries were constructed using the Nextera Tagmentation method on a total of 800 pg of pooled cDNA library from 12,000 recovered beads. Tagmented and amplified sequences were purified at a 0.6× SPRI ratio yielding library sizes with an average distribution of 650-750 base pairs in length as determined using the Agilent hsD1000 Screen Tape System (Agilent Genomics). Arrays were sequenced with an Illumina 75 Cycle NextSeq500/550v2 kit at a final concentration of 2.8 µM. The read structure was paired end with Read 1 starting from a custom read 1 primer containing 20 bases with a 12 bp cell barcode and 8 bp unique molecular identifier (UMI) and Read 2 being 50 bases containing transcript information.

Single-cell RNA-sequencing computational pipelines and analysis. Read alignment was performed as in [74]. Briefly, for each NextSeq sequencing run, raw sequencing data was converted to demultiplexed FASTQ files using bc12fastq2 based on Nextera N700 indices corresponding to individual samples/arrays. Reads were then aligned to mm10 genome using the Galaxy portal maintained by the Broad Institute for Drop-Seq alignment using standard settings. Individual reads were tagged according to the 12-bp barcode sequencing and the 8-bp UMI contained in Read 1 of each fragment. Following alignment, reads were binned onto 12-bp cell barcodes and collapsed by their 8-bp UMI. Digital gene expression matrices (e.g. cell by gene tables) for each sample were obtained from quality filtered and mapped reads and UMI-collapsed data, are deposited in GSE100274, and were utilized as input into Seurat and github.com/satijalab/seurat] for further analysis.

To analyze ENR+CV, ENR, and ENR+CD organoids together, Applicants merged UMI matrices across all genes detected in any condition and generated a matrix retaining all cells with at least 1000 UMI detected. This table was then utilized to setup the Seurat object in which any cell with at least 400 unique genes was retained and any gene expressed in at least 5 cells was retained. The object was initiated with log-normalization, scaling, and centering set to True. Before performing dimensionality reduction, data was subset to include cells with less than 8,000 UMI, and a list of 1,676 most variable genes was generated by including genes with an average normalized and scaled expression value greater than 0.14 and with a dispersion (variance/mean) greater than 0.4. The total number of ENR+CV, ENR, and ENR+CD cells included in the analysis was 985, 2,544, and 2,382, respectively with quality metrics for nGene, nUMI, and percentage of ribosomal and mitochondrial genes reported in FIG. 11. Applicants then performed principal component analysis over the list of variable genes. For both clustering and t-stochastic neighbor embedding (tSNE), Applicants utilized the first 12 principal components based on the elbow method, as upon visual inspection of genes contained within, each contributed to important biological processes of intestinal cells. Applicants used FindClusters with a resolution of 1.35 and 1000 iterations of tSNE to identify 14 clusters across the 3 input samples. To identify genes which defined each cluster, Applicants performed a ROC test implemented in Seurat with a threshold set to an AUC of 0.60.

Transcriptional Scoring. To determine the fractional contribution to a cell's transcriptome of a gene list, Applicants summed the total log(scaled UMI+1) expression values for genes within a list of interest and divided by the total amount of scaled UMI detected in that cell giving a proportion of a cell's transcriptome dedicated to producing those genes. From the proteomic screen, Applicants took a list of upregulated proteins (249) or downregulated proteins (212) that were detected within the single-cell RNA-sequencing data. To determine the relationship to in vivo Paneth cells and EECs, Applicants took reference data from two Seq-Well experiments run on epithelial cells dissociated from the ileal region of the small intestine of two C57BL/6J mice run in separate experiments. Ileum was first rinsed in 30 mL of ice cold PBS and allowed to settle. The segment was then sliced with scissors and transferred to 10 mL epithelial cell solution (HBSS Ca/Mg-Free 10 mM EDTA, 100 U/mL penicillin, 100 µg/mL streptomycin, 10 mM HEPES, 2% FCS (ThermoFisher)) freshly supplemented with 200 µL of 0.5 M EDTA. The epithelial separation from the underlying lamina propria was performed for 15 minutes at 37° C. in a rotisserie rack with end-over-end rotation. The tube was then removed and placed on ice immediately for 10 minutes before shaking vigorously 15 times. Visual macroscopic inspection of the tube at this point should yield visible epithelial sheets, and microscopic examination confirms the presence of single-layer sheets and crypt-villus structures. The epithelial fraction was spun down at 400 g for 7 minutes and resuspended in 1 mL of epithelial cell solution before transferring to a 1.5 mL Eppendorf tube to minimize time spent centrifuging. Cells were spun down at 800 g for 2 minutes and resuspended in TrypLE Express for 5 minutes in a 37° C. bath followed by gentle trituration with a P1000 pipette. Cells were spun down at 800 g for 2 minutes and resuspended in ACK lysis buffer (ThermoFisher) for 3 minutes on ice to remove red blood cells and dying cells. Cells were spun down at 800 g for 2 minutes and resuspended in 1 mL of epithelial cell solution and placed on ice for 3 minutes before triturating with a P1000 pipette and filtering into a new Eppendorf through a 40 µm cell strainer (Falcon/VWR). Cells were spun down at 800 g for 2 minutes and then resuspended in 200 µL of epithelial cell solution and placed on ice for counting. Single-cell RNA-seq data was then generated as described in (Single-cell RNA-sequencing and Single-cell RNA-sequencing computational pipelines and analysis) sections of methods. To generate Paneth and EEC signatures, Applicants ran unbiased SNN-graph based clustering, performed a ROC test, identified the two mature Paneth and EEC clusters, and report all genes with an AUC above 0.60, and use all genes with an AUC above 0.65 for scoring, within each cluster (gene lists in Table S1) representing any gene with enrichment in Paneth and EE cells. These lists capture genes which are enriched in Paneth (Lyz-high) and EE (Chga-high) cells, and separate them from the rest of the cells present in intestinal epithelium. For pathway analysis, Applicants inspected curated gene lists deposited in the GSEA platform and used KEGG-derived Wnt and Reactome-derived Notch and Respiratory Electron Transport Chain signatures (Table 2).

Quantification and statistical analysis. Statistical analyses were performed using GraphPad Prism v7.0a, Seurat implemented in RStudio, and Agilent Technologies Spectrum Mill software package. All graphs show mean±SEM, unless otherwise noted. Unpaired 2-tail t-test and 2-way ANOVA with Dunnett's multiple comparison test (reported as adj. p value) were used to assess statistical significance as appropriate and unless otherwise noted (* indicates $p<0.05$,  $p<0.01$ * $p<0.001$, ** $p<0.0001$, and ns non-significant). In each experiment, tissues were isolated from multiple mice housed in the same facility with each mouse providing tissue designated as a distinct biological donor: n=3 donor-averaged values of four technical replicates for data reported in FIG. 2B; n=3 donor of two technical replicates for data reported in FIG. 2E and FIG. 8F; n=4 (2 technical replicates from two biological donors each) for data reported in FIGS. 3, 9, and 10; n=1 biological donor for in vitro data reported in FIGS. 4-5 and 11-12; n=8 single-well replicates from one and five biological donors for data reported in FIGS. 6A-B and 6C, respectively; n=13 co-culture well replicates randomly selected without replacement from 4 donors for data reported in FIG. 6D; n=6 well replicates (2 per 3 biological donors) in FIG. 6E; n=3 biological donors in FIGS. 7C-D**.

TABLE 1

Derived gene list of the top defining genes from in vivo ileal
small intestine PCs and EECs captured on the Seq-Well platform Table 1A. Results of ROC-test for Paneth-enriched marker genes
from all in vivo isolated small intestinal epithelial cells
(FIG. 1C Paneth InVivo)

|  | myAUC | avg_diff | power | pct.1 | pct.2 | cluster | gene |
|---|---|---|---|---|---|---|---|
| Gm1485110 | 0.998 | 3.54974509 | 0.996 | 1 | 0.248 | 11 | Gm14851 |
| Defa248 | 0.998 | 3.310135059 | 0.996 | 1 | 0.749 | 11 | Defa24 |
| Gm1528411 | 0.997 | 3.376627144 | 0.994 | 1 | 0.522 | 11 | Gm15284 |
| Defa1710 | 0.996 | 3.272012679 | 0.992 | 1 | 0.242 | 11 | Defa17 |
| Itln110 | 0.996 | 3.205344786 | 0.992 | 1 | 0.492 | 11 | Itln1 |
| Defa2210 | 0.995 | 3.488570378 | 0.99 | 1 | 0.276 | 11 | Defa22 |
| Lyz110 | 0.995 | 3.449655842 | 0.99 | 1 | 0.487 | 11 | Lyz1 |
| Defa2110 | 0.993 | 3.476885473 | 0.986 | 1 | 0.295 | 11 | Defa21 |
| Defa265 | 0.992 | 3.330019381 | 0.984 | 0.994 | 0.129 | 11 | Defa26 |
| Defa-rs12 | 0.992 | 3.295903275 | 0.984 | 0.997 | 0.092 | 11 | Defa-rs1 |
| Ang410 | 0.99 | 3.013942122 | 0.98 | 1 | 0.381 | 11 | Ang4 |
| AY76118410 | 0.989 | 3.35421008 | 0.978 | 0.997 | 0.213 | 11 | AY761184 |
| Defa38 | 0.989 | 3.064599256 | 0.978 | 0.994 | 0.117 | 11 | Defa3 |
| Gm153151 | 0.977 | 2.986060661 | 0.954 | 0.974 | 0.067 | 11 | Gm15315 |
| Clps3 | 0.977 | 2.850671309 | 0.954 | 0.974 | 0.091 | 11 | Clps |
| Gm101041 | 0.976 | 2.924572319 | 0.952 | 0.971 | 0.057 | 11 | Gm10104 |
| Gm152921 | 0.97 | 2.78093711 | 0.94 | 0.966 | 0.078 | 11 | Gm15292 |
| Mmp72 | 0.969 | 2.732627523 | 0.938 | 0.966 | 0.095 | 11 | Mmp7 |
| AY7611851 | 0.953 | 2.902034038 | 0.906 | 0.925 | 0.046 | 11 | AY761185 |
| Reg41 | 0.951 | 2.7690051 | 0.902 | 0.934 | 0.086 | 11 | Reg4 |
| Pnliprp22 | 0.936 | 2.515088835 | 0.872 | 0.911 | 0.092 | 11 | Pnliprp2 |
| Gm152991 | 0.936 | 2.478413248 | 0.872 | 0.897 | 0.045 | 11 | Gm15299 |
| Spink410 | 0.93 | 1.510850666 | 0.86 | 1 | 0.567 | 11 | Spink4 |
| Defa-rs71 | 0.921 | 2.634772041 | 0.842 | 0.862 | 0.033 | 11 | Defa-rs7 |
| Ccl69 | 0.899 | 1.857462818 | 0.798 | 0.885 | 0.125 | 11 | Ccl6 |
| Gm148501 | 0.897 | 2.286355764 | 0.794 | 0.816 | 0.028 | 11 | Gm14850 |
| Gm152931 | 0.891 | 2.193886938 | 0.782 | 0.802 | 0.025 | 11 | Gm15293 |
| Mptx21 | 0.883 | 3.092439953 | 0.766 | 0.816 | 0.083 | 11 | Mptx2 |
| Lyz21 | 0.837 | 1.794805054 | 0.674 | 0.701 | 0.028 | 11 | Lyz2 |
| Nupr11 | 0.833 | 1.766838324 | 0.666 | 0.704 | 0.043 | 11 | Nupr1 |
| Cd24a5 | 0.832 | 1.202885956 | 0.664 | 0.799 | 0.174 | 11 | Cd24a |
| Defa5 | 0.817 | 1.993723258 | 0.634 | 0.644 | 0.01 | 11 | Defa5 |
| Lars2 | 0.804 | 1.01036761 | 0.608 | 0.899 | 0.551 | 11 | Lars2 |
| Defa23 | 0.792 | 2.141723321 | 0.584 | 0.598 | 0.013 | 11 | Defa23 |
| Gm155641 | 0.791 | 1.070350926 | 0.582 | 0.83 | 0.385 | 11 | Gm15564 |
| Gm7861 | 0.76 | 1.463726478 | 0.52 | 0.529 | 0.007 | 11 | Gm7861 |
| Defa20 | 0.739 | 1.746076506 | 0.478 | 0.483 | 0.005 | 11 | Defa20 |
| Gm21498 | 0.73 | 1.275479302 | 0.46 | 0.466 | 0.006 | 11 | Gm21498 |
| Lbh | 0.728 | 1.236030548 | 0.456 | 0.489 | 0.03 | 11 | Lbh |
| Gm6696 | 0.714 | 1.151645801 | 0.428 | 0.437 | 0.007 | 11 | Gm6696 |
| Gm21002 | 0.709 | 1.303327251 | 0.418 | 0.422 | 0.004 | 11 | Gm21002 |
| Defa2 | 0.703 | 1.220649508 | 0.406 | 0.411 | 0.004 | 11 | Defa2 |
| Gm15308 | 0.703 | 1.079396917 | 0.406 | 0.414 | 0.006 | 11 | Gm15308 |
| Mptx12 | 0.696 | 1.376763812 | 0.392 | 0.457 | 0.064 | 11 | Mptx1 |
| Rnase44 | 0.689 | 0.671704918 | 0.378 | 0.592 | 0.22 | 11 | Rnase4 |
| Tmed6 | 0.688 | 0.934851402 | 0.376 | 0.394 | 0.018 | 11 | Tmed6 |
| Habp2 | 0.687 | 1.004624823 | 0.374 | 0.379 | 0.006 | 11 | Habp2 |
| Gm7849 | 0.675 | 1.028781992 | 0.35 | 0.353 | 0.002 | 11 | Gm7849 |
| Nucb21 | 0.675 | 0.886781076 | 0.35 | 0.371 | 0.02 | 11 | Nucb2 |
| Ggh | 0.667 | 0.823103237 | 0.334 | 0.356 | 0.021 | 11 | Ggh |
| Qsox12 | 0.666 | 0.693239013 | 0.332 | 0.434 | 0.095 | 11 | Qsox1 |
| Tspan16 | 0.665 | 0.515819615 | 0.33 | 0.572 | 0.227 | 11 | Tspan1 |
| Tmprss22 | 0.659 | 0.676826722 | 0.318 | 0.422 | 0.101 | 11 | Tmprss2 |
| mmu-mir-6236 | 0.658 | 0.522921887 | 0.316 | 0.552 | 0.216 | 11 | mmu-mir-6236 |
| Ramp12 | 0.655 | 0.689299748 | 0.31 | 0.376 | 0.059 | 11 | Ramp1 |
| Bambi | 0.648 | 0.861536976 | 0.296 | 0.305 | 0.008 | 11 | Bambi |
| Gm97651 | 0.643 | 1.066347908 | 0.286 | 0.313 | 0.025 | 11 | Gm9765 |
| Ang5 | 0.641 | 0.722917045 | 0.282 | 0.293 | 0.01 | 11 | Ang5 |
| Smim142 | 0.639 | 0.37355984 | 0.278 | 0.46 | 0.161 | 11 | Smim14 |
| Wbp57 | 0.636 | 0.356539074 | 0.272 | 0.48 | 0.181 | 11 | Wbp5 |
| Car81 | 0.635 | 0.597328844 | 0.27 | 0.319 | 0.046 | 11 | Car8 |
| Asph2 | 0.635 | 0.562816272 | 0.27 | 0.356 | 0.081 | 11 | Asph |
| Tram12 | 0.633 | 0.479273876 | 0.266 | 0.517 | 0.248 | 11 | Tram1 |
| Fam46c | 0.626 | 0.620047992 | 0.252 | 0.261 | 0.008 | 11 | Fam46c |
| Ly6e1 | 0.622 | 0.500854668 | 0.244 | 0.316 | 0.067 | 11 | Ly6e |
| Olfm47 | 0.622 | 0.328982619 | 0.244 | 0.425 | 0.162 | 11 | Olfm4 |
| 5330417C22Rik2 | 0.62 | 0.500934933 | 0.24 | 0.305 | 0.059 | 11 | 5330417C22Rik |
| Slc12a28 | 0.618 | 0.321997521 | 0.236 | 0.457 | 0.195 | 11 | Slc12a2 |
| Dnajc32 | 0.615 | 0.360035595 | 0.23 | 0.497 | 0.256 | 11 | Dnajc3 |
| Sox92 | 0.611 | 0.523456428 | 0.222 | 0.282 | 0.056 | 11 | Sox9 |
| Hpd1 | 0.609 | 0.555541502 | 0.218 | 0.239 | 0.019 | 11 | Hpd |

TABLE 1-continued

Derived gene list of the top defining genes from in vivo ileal
small intestine PCs and EECs captured on the Seq-Well platform

| | | | | | | |
|---|---|---|---|---|---|---|
| Gadd45g | 0.608 | 0.504412695 | 0.216 | 0.287 | 0.067 | 11 | Gadd45g |
| Ang1 | 0.608 | 0.496801656 | 0.216 | 0.282 | 0.063 | 11 | Ang |
| Reep51 | 0.607 | 0.360389211 | 0.214 | 0.259 | 0.04 | 11 | Reep5 |
| Sypl5 | 0.604 | 0.27513369 | 0.208 | 0.5 | 0.274 | 11 | Sypl |
| Ang6 | 0.603 | 0.528311205 | 0.206 | 0.213 | 0.006 | 11 | Ang6 |
| Trp53inp1 | 0.601 | 0.527522118 | 0.202 | 0.218 | 0.016 | 11 | Trp53inp1 |

Table 1B. ROC-test on conventional ENR organoids to determine
cluster-enriched marker genes (FIG. 1E Paneth ENR-4)

| | myAUC | avg_diff | power | pct.1 | pct.2 | cluster | gene |
|---|---|---|---|---|---|---|---|
| Defa24 | 0.954 | 2.171101878 | 0.908 | 0.998 | 0.912 | ENR-4 | Defa24 |
| Defa17 | 0.947 | 2.17783303 | 0.894 | 0.992 | 0.669 | ENR-4 | Defa17 |
| Gm15284 | 0.916 | 2.280079164 | 0.832 | 0.982 | 0.633 | ENR-4 | Gm15284 |
| Spink4 | 0.914 | 1.711003544 | 0.828 | 0.997 | 0.747 | ENR-4 | Spink4 |
| Clps | 0.885 | 1.862014447 | 0.77 | 0.9 | 0.305 | ENR-4 | Clps |
| Itln1 | 0.882 | 2.101891237 | 0.764 | 0.946 | 0.552 | ENR-4 | Itln1 |
| Tff3 | 0.864 | 1.457124813 | 0.728 | 0.969 | 0.602 | ENR-4 | Tff3 |
| Lyz1 | 0.856 | 1.976178002 | 0.712 | 0.91 | 0.457 | ENR-4 | Lyz1 |
| Gm14851 | 0.854 | 2.07922191 | 0.708 | 0.834 | 0.236 | ENR-4 | Gm14851 |
| Defa-rs1 | 0.838 | 1.979555244 | 0.676 | 0.783 | 0.184 | ENR-4 | Defa-rs1 |
| AY761184 | 0.837 | 2.028401106 | 0.674 | 0.819 | 0.245 | ENR-4 | AY761184 |
| Gm15299 | 0.804 | 1.722132795 | 0.608 | 0.706 | 0.149 | ENR-4 | Gm15299 |
| Guca2a | 0.77 | 1.343910845 | 0.54 | 0.723 | 0.254 | ENR-4 | Guca2a |
| Ang4 | 0.765 | 1.902429314 | 0.53 | 0.656 | 0.188 | ENR-4 | Ang4 |
| Defa3 | 0.762 | 1.625202786 | 0.524 | 0.608 | 0.119 | ENR-4 | Defa3 |
| Defa26 | 0.761 | 1.501994758 | 0.522 | 0.62 | 0.128 | ENR-4 | Defa26 |
| AY761185 | 0.76 | 1.546633485 | 0.52 | 0.607 | 0.122 | ENR-4 | AY761185 |
| Mmp7 | 0.76 | 1.517042969 | 0.52 | 0.643 | 0.173 | ENR-4 | Mmp7 |
| Agr2 | 0.753 | 1.172849401 | 0.506 | 0.76 | 0.392 | ENR-4 | Agr2 |
| Defa21 | 0.726 | 1.61303835 | 0.452 | 0.517 | 0.078 | ENR-4 | Defa21 |
| Gm15315 | 0.682 | 1.46990469 | 0.364 | 0.418 | 0.063 | ENR-4 | Gm15315 |
| Fcgbp | 0.672 | 1.160467398 | 0.344 | 0.488 | 0.167 | ENR-4 | Fcgbp |
| Gm10104 | 0.67 | 1.334688224 | 0.34 | 0.38 | 0.046 | ENR-4 | Gm10104 |
| Defa22 | 0.668 | 1.525928795 | 0.336 | 0.398 | 0.071 | ENR-4 | Defa22 |
| Defa23 | 0.665 | 1.184665633 | 0.33 | 0.369 | 0.043 | ENR-4 | Defa23 |
| Gm14850 | 0.623 | 1.082882852 | 0.246 | 0.271 | 0.028 | ENR-4 | Gm14850 |
| Klk1 | 0.618 | 0.865184481 | 0.236 | 0.305 | 0.074 | ENR-4 | Klk1 |
| Rnase4 | 0.618 | 0.71009465 | 0.236 | 0.4 | 0.177 | ENR-4 | Rnase4 |
| Cd24a | 0.609 | 0.395125457 | 0.218 | 0.639 | 0.472 | ENR-4 | Cd24a |
| Guca2b | 0.605 | 0.522266578 | 0.21 | 0.346 | 0.135 | ENR-4 | Guca2b |
| Ccl6 | 0.603 | 0.992561968 | 0.206 | 0.253 | 0.05 | ENR-4 | Ccl6 |
| Ccl9 | 0.601 | 0.95781627 | 0.202 | 0.248 | 0.051 | ENR-4 | Ccl9 |
| Fabp1 | 0.811 | 1.96298575 | 0.622 | 0.789 | 0.28 | ENR-3 | Fabp1 |
| Aldob | 0.785 | 1.2268382 | 0.57 | 0.892 | 0.572 | ENR-3 | Aldob |
| Sis | 0.756 | 1.48058628 | 0.512 | 0.689 | 0.237 | ENR-3 | Sis |
| Prap1 | 0.737 | 1.104136722 | 0.474 | 0.768 | 0.435 | ENR-3 | Prap1 |
| Mt1 | 0.699 | 0.5895937 | 0.398 | 0.963 | 0.885 | ENR-3 | Mt1 |
| Adh1 | 0.693 | 1.158484368 | 0.386 | 0.533 | 0.178 | ENR-3 | Adh1 |
| Reg1 | 0.681 | 1.91335161 | 0.362 | 0.449 | 0.104 | ENR-3 | Reg1 |
| Fabp2 | 0.676 | 0.671558173 | 0.352 | 0.862 | 0.688 | ENR-3 | Fabp2 |
| 2210404O07Rik | 0.669 | 0.792083339 | 0.338 | 0.675 | 0.406 | ENR-3 | 2210404O07Rik |
| Gsta1 | 0.655 | 1.27693185 | 0.31 | 0.384 | 0.082 | ENR-3 | Gsta1 |
| Apoa1 | 0.653 | 1.312903918 | 0.306 | 0.382 | 0.085 | ENR-3 | Apoa1 |
| Mt2 | 0.649 | 0.412988151 | 0.298 | 0.892 | 0.782 | ENR-3 | Mt2 |
| Spink3 | 0.639 | 1.032180742 | 0.278 | 0.329 | 0.051 | ENR-3 | Spink3 |
| Dbi | 0.638 | 0.408183411 | 0.276 | 0.913 | 0.829 | ENR-3 | Dbi |
| Khk | 0.637 | 0.786298444 | 0.274 | 0.453 | 0.201 | ENR-3 | Khk |
| Apoa4 | 0.627 | 1.202209448 | 0.254 | 0.313 | 0.063 | ENR-3 | Apoa4 |
| Fth1 | 0.624 | 0.369737625 | 0.248 | 0.888 | 0.789 | ENR-3 | Fth1 |
| Apoc3 | 0.622 | 1.099829904 | 0.244 | 0.285 | 0.044 | ENR-3 | Apoc3 |
| Slc5a1 | 0.621 | 0.812338448 | 0.242 | 0.388 | 0.165 | ENR-3 | Slc5a1 |
| Phgr1 | 0.62 | 0.33204232 | 0.24 | 0.833 | 0.698 | ENR-3 | Phgr1 |
| Dak | 0.619 | 0.739659127 | 0.238 | 0.425 | 0.209 | ENR-3 | Dak |
| 2200002D01Rik | 0.614 | 0.553046643 | 0.228 | 0.492 | 0.287 | ENR-3 | 2200002D01Rik |
| Leap2 | 0.607 | 0.945169933 | 0.214 | 0.258 | 0.046 | ENR-3 | Leap2 |
| Mttp | 0.606 | 0.676001129 | 0.212 | 0.319 | 0.115 | ENR-3 | Mttp |
| Rbp2 | 0.601 | 0.77439673 | 0.202 | 0.24 | 0.04 | ENR-3 | Rbp2 |
| Hsp90ab1 | 0.698 | 0.334241713 | 0.396 | 0.996 | 0.937 | ENR-1 | Hsp90ab1 |
| Myh9 | 0.675 | 0.409130665 | 0.35 | 0.762 | 0.332 | ENR-1 | Myh9 |
| Hook1 | 0.67 | 0.364663341 | 0.34 | 0.891 | 0.473 | ENR-1 | Hook1 |
| Cdca7 | 0.659 | 0.334855426 | 0.318 | 0.638 | 0.234 | ENR-1 | Cdca7 |
| Hspa8 | 0.659 | 0.290871832 | 0.318 | 0.985 | 0.771 | ENR-1 | Hspa8 |
| Myb | 0.658 | 0.360067147 | 0.316 | 0.491 | 0.133 | ENR-1 | Myb |
| Smc3 | 0.658 | 0.340833172 | 0.316 | 0.57 | 0.193 | ENR-1 | Smc3 |
| Npm1 | 0.658 | 0.276110838 | 0.316 | 0.985 | 0.794 | ENR-1 | Npm1 |

TABLE 1-continued

Derived gene list of the top defining genes from in vivo ileal
small intestine PCs and EECs captured on the Seq-Well platform

| Gene | | | | | | | |
|---|---|---|---|---|---|---|---|
| Rbbp4 | 0.658 | 0.269846162 | 0.316 | 0.675 | 0.254 | ENR-1 | Rbbp4 |
| Olfm4 | 0.657 | 0.545651489 | 0.314 | 0.872 | 0.6 | ENR-1 | Olfm4 |
| Gmnn | 0.657 | 0.380979899 | 0.314 | 0.558 | 0.19 | ENR-1 | Gmnn |
| Tpr | 0.657 | 0.329120992 | 0.314 | 0.691 | 0.29 | ENR-1 | Tpr |
| Sfpq | 0.657 | 0.282887682 | 0.314 | 0.725 | 0.3 | ENR-1 | Sfpq |
| Clca4 | 0.656 | 0.454481479 | 0.312 | 0.853 | 0.551 | ENR-1 | Clca4 |
| Cps1 | 0.656 | 0.33978679 | 0.312 | 0.932 | 0.569 | ENR-1 | Cps1 |
| Ehf | 0.656 | 0.325039493 | 0.312 | 0.691 | 0.283 | ENR-1 | Ehf |
| Fus | 0.656 | 0.300083245 | 0.312 | 0.725 | 0.304 | ENR-1 | Fus |
| Bzw1 | 0.655 | 0.347160369 | 0.31 | 0.709 | 0.311 | ENR-1 | Bzw1 |
| Dhx9 | 0.655 | 0.280910067 | 0.31 | 0.619 | 0.224 | ENR-1 | Dhx9 |
| Hspd1 | 0.653 | 0.30016784 | 0.306 | 0.928 | 0.566 | ENR-1 | Hspd1 |
| Lbr | 0.65 | 0.326705408 | 0.3 | 0.596 | 0.225 | ENR-1 | Lbr |
| Sdc4 | 0.649 | 0.269766391 | 0.298 | 0.664 | 0.265 | ENR-1 | Sdc4 |
| Smoc2 | 0.648 | 0.3369791 | 0.296 | 0.747 | 0.352 | ENR-1 | Smoc2 |
| Baz1b | 0.648 | 0.283798796 | 0.296 | 0.543 | 0.186 | ENR-1 | Baz1b |
| G3bp1 | 0.648 | 0.25867788 | 0.296 | 0.649 | 0.255 | ENR-1 | G3bp1 |
| Otc | 0.648 | 0.25350988 | 0.296 | 0.638 | 0.255 | ENR-1 | Otc |
| Nedd4 | 0.647 | 0.322402778 | 0.294 | 0.823 | 0.426 | ENR-1 | Nedd4 |
| Fkbp3 | 0.647 | 0.289611023 | 0.294 | 0.83 | 0.456 | ENR-1 | Fkbp3 |
| Naa50 | 0.647 | 0.285354396 | 0.294 | 0.543 | 0.186 | ENR-1 | Naa50 |
| Caprin1 | 0.647 | 0.266494852 | 0.294 | 0.664 | 0.278 | ENR-1 | Caprin1 |
| Mki67 | 0.646 | 0.393499983 | 0.292 | 0.687 | 0.359 | ENR-1 | Mki67 |
| Sae1 | 0.646 | 0.330549185 | 0.292 | 0.558 | 0.205 | ENR-1 | Sae1 |
| Hnrnpu | 0.646 | 0.299131548 | 0.292 | 0.906 | 0.528 | ENR-1 | Hnrnpu |
| Hnrnpa2b1 | 0.646 | 0.277900834 | 0.292 | 0.958 | 0.716 | ENR-1 | Hnrnpa2b1 |
| Bzw2 | 0.645 | 0.316393214 | 0.29 | 0.626 | 0.258 | ENR-1 | Bzw2 |
| Srrm1 | 0.645 | 0.292826665 | 0.29 | 0.623 | 0.261 | ENR-1 | Srrm1 |
| Naa15 | 0.645 | 0.280446006 | 0.29 | 0.506 | 0.162 | ENR-1 | Naa15 |
| Nop58 | 0.645 | 0.270458021 | 0.29 | 0.77 | 0.376 | ENR-1 | Nop58 |
| Ncl | 0.644 | 0.268323897 | 0.288 | 0.992 | 0.834 | ENR-1 | Ncl |
| Hjurp | 0.643 | 0.282338669 | 0.286 | 0.521 | 0.177 | ENR-1 | Hjurp |
| Ywhab | 0.643 | 0.266608555 | 0.286 | 0.642 | 0.27 | ENR-1 | Ywhab |
| Ewsr1 | 0.642 | 0.31223685 | 0.284 | 0.54 | 0.198 | ENR-1 | Ewsr1 |
| Bclaf1 | 0.642 | 0.268926732 | 0.284 | 0.611 | 0.245 | ENR-1 | Bclaf1 |
| Tra2b | 0.642 | 0.268817853 | 0.284 | 0.558 | 0.2 | ENR-1 | Tra2b |
| Prdx4 | 0.642 | 0.264527859 | 0.284 | 0.562 | 0.21 | ENR-1 | Prdx4 |
| Sypl | 0.641 | 0.271683218 | 0.282 | 0.713 | 0.325 | ENR-1 | Sypl |
| Slc12a2 | 0.64 | 0.293751642 | 0.28 | 0.879 | 0.5 | ENR-1 | Slc12a2 |
| Cct2 | 0.64 | 0.263489435 | 0.28 | 0.785 | 0.38 | ENR-1 | Cct2 |
| Ptma | 0.639 | 0.283084487 | 0.278 | 0.97 | 0.712 | ENR-1 | Ptma |
| Nap1l1 | 0.639 | 0.267612422 | 0.278 | 0.592 | 0.233 | ENR-1 | Nap1l1 |
| Ifitm3 | 0.639 | 0.260879559 | 0.278 | 0.615 | 0.255 | ENR-1 | Ifitm3 |
| Ccnd1 | 0.638 | 0.290978798 | 0.276 | 0.521 | 0.188 | ENR-1 | Ccnd1 |
| Hmgn1 | 0.638 | 0.284595319 | 0.276 | 0.819 | 0.452 | ENR-1 | Hmgn1 |
| Sf3b2 | 0.638 | 0.271204506 | 0.276 | 0.574 | 0.23 | ENR-1 | Sf3b2 |
| Usp1 | 0.636 | 0.272893787 | 0.272 | 0.498 | 0.174 | ENR-1 | Usp1 |
| Khdrbs1 | 0.635 | 0.270282197 | 0.27 | 0.438 | 0.13 | ENR-1 | Khdrbs1 |
| Lsm5 | 0.635 | 0.264283642 | 0.27 | 0.442 | 0.13 | ENR-1 | Lsm5 |
| Pa2g4 | 0.634 | 0.293891929 | 0.268 | 0.853 | 0.509 | ENR-1 | Pa2g4 |
| Zfp292 | 0.634 | 0.276209814 | 0.268 | 0.547 | 0.218 | ENR-1 | Zfp292 |
| Set | 0.634 | 0.268891816 | 0.268 | 0.694 | 0.325 | ENR-1 | Set |
| Serbp1 | 0.634 | 0.26379132 | 0.268 | 0.955 | 0.723 | ENR-1 | Serbp1 |
| Plcb3 | 0.633 | 0.263428885 | 0.266 | 0.638 | 0.274 | ENR-1 | Plcb3 |
| Top2a | 0.631 | 0.386782218 | 0.262 | 0.664 | 0.364 | ENR-1 | Top2a |
| Uchl5 | 0.631 | 0.273390369 | 0.262 | 0.411 | 0.117 | ENR-1 | Uchl5 |
| Shmt2 | 0.631 | 0.25849999 | 0.262 | 0.46 | 0.149 | ENR-1 | Shmt2 |
| Zfp326 | 0.63 | 0.391592517 | 0.26 | 0.351 | 0.075 | ENR-1 | Zfp326 |
| Smchd1 | 0.63 | 0.349892312 | 0.26 | 0.396 | 0.109 | ENR-1 | Smchd1 |
| Smc4 | 0.63 | 0.300538359 | 0.26 | 0.615 | 0.293 | ENR-1 | Smc4 |
| Nudc | 0.63 | 0.286242444 | 0.26 | 0.419 | 0.124 | ENR-1 | Nudc |
| Mcm7 | 0.627 | 0.261145303 | 0.254 | 0.442 | 0.146 | ENR-1 | Mcm7 |
| Lgr5 | 0.626 | 0.281390771 | 0.252 | 0.445 | 0.153 | ENR-1 | Lgr5 |
| Rrm1 | 0.625 | 0.283364925 | 0.25 | 0.475 | 0.18 | ENR-1 | Rrm1 |
| Aqp4 | 0.625 | 0.267685021 | 0.25 | 0.438 | 0.145 | ENR-1 | Aqp4 |
| Tsix | 0.624 | 0.311631552 | 0.248 | 0.374 | 0.1 | ENR-1 | Tsix |
| Smarca5 | 0.624 | 0.263274671 | 0.248 | 0.468 | 0.174 | ENR-1 | Smarca5 |
| 2810417H13Rik | 0.623 | 0.322764824 | 0.246 | 0.57 | 0.268 | ENR-1 | 2810417H13Rik |
| Smarca4 | 0.623 | 0.318678776 | 0.246 | 0.46 | 0.169 | ENR-1 | Smarca4 |
| Hat1 | 0.621 | 0.289215145 | 0.242 | 0.396 | 0.123 | ENR-1 | Hat1 |
| Dnajc9 | 0.619 | 0.263494313 | 0.238 | 0.411 | 0.138 | ENR-1 | Dnajc9 |
| Xist | 0.619 | 0.260299383 | 0.238 | 0.921 | 0.705 | ENR-1 | Xist |
| Zfp36l2 | 0.619 | 0.253757487 | 0.238 | 0.423 | 0.146 | ENR-1 | Zfp36l2 |
| Mrps5 | 0.618 | 0.267493357 | 0.236 | 0.374 | 0.111 | ENR-1 | Mrps5 |
| Fnbp1l | 0.618 | 0.257135033 | 0.236 | 0.404 | 0.134 | ENR-1 | Fnbp1l |
| Cenpe | 0.617 | 0.316507736 | 0.234 | 0.411 | 0.148 | ENR-1 | Cenpe |
| Mrpl19 | 0.617 | 0.262521642 | 0.234 | 0.355 | 0.097 | ENR-1 | Mrpl19 |

TABLE 1-continued

Derived gene list of the top defining genes from in vivo ileal
small intestine PCs and EECs captured on the Seq-Well platform

| Gene | | | | | | | |
|---|---|---|---|---|---|---|---|
| Prim1 | 0.617 | 0.255494095 | 0.234 | 0.396 | 0.132 | ENR-1 | Prim1 |
| Zbtb38 | 0.615 | 0.290816135 | 0.23 | 0.351 | 0.099 | ENR-1 | Zbtb38 |
| Atic | 0.615 | 0.265040334 | 0.23 | 0.381 | 0.119 | ENR-1 | Atic |
| Tpx2 | 0.614 | 0.379022789 | 0.228 | 0.332 | 0.087 | ENR-1 | Tpx2 |
| Wwp1 | 0.61 | 0.283271291 | 0.22 | 0.336 | 0.096 | ENR-1 | Wwp1 |
| Pold3 | 0.61 | 0.272431026 | 0.22 | 0.302 | 0.067 | ENR-1 | Pold3 |
| Cdca3 | 0.609 | 0.280047233 | 0.218 | 0.423 | 0.169 | ENR-1 | Cdca3 |
| AI747448 | 0.608 | 0.266683788 | 0.216 | 0.457 | 0.198 | ENR-1 | AI747448 |
| Wasf2 | 0.608 | 0.251327648 | 0.216 | 0.351 | 0.109 | ENR-1 | Wasf2 |
| Smc2 | 0.607 | 0.289369633 | 0.214 | 0.442 | 0.189 | ENR-1 | Smc2 |
| Suclg2 | 0.604 | 0.252788739 | 0.208 | 0.347 | 0.111 | ENR-1 | Suclg2 |
| Fam98b | 0.602 | 0.294037917 | 0.204 | 0.279 | 0.062 | ENR-1 | Fam98b |
| Topbp1 | 0.601 | 0.279548647 | 0.202 | 0.317 | 0.096 | ENR-1 | Topbp1 |
| Chgb | 0.964 | 3.091633248 | 0.928 | 0.989 | 0.328 | Neuro-2 | Chgb |
| Chga | 0.88 | 2.943854249 | 0.76 | 0.818 | 0.114 | Neuro-2 | Chga |
| Tac1 | 0.843 | 2.431672411 | 0.686 | 0.761 | 0.136 | Neuro-2 | Tac1 |
| Reg41 | 0.841 | 3.285182681 | 0.682 | 0.818 | 0.369 | Neuro-2 | Reg4 |
| Afp | 0.788 | 3.531645662 | 0.576 | 0.602 | 0.048 | Neuro-2 | Afp |
| Tph1 | 0.771 | 2.073030929 | 0.542 | 0.557 | 0.02 | Neuro-2 | Tph1 |
| Sepp1 | 0.765 | 1.704289699 | 0.53 | 0.636 | 0.155 | Neuro-2 | Sepp1 |
| Gstt1 | 0.706 | 1.591833899 | 0.412 | 0.466 | 0.073 | Neuro-2 | Gstt1 |
| S100a1 | 0.698 | 1.623168802 | 0.396 | 0.455 | 0.078 | Neuro-2 | S100a1 |
| Cystm1 | 0.681 | 0.693905241 | 0.362 | 0.807 | 0.629 | Neuro-2 | Cystm1 |
| Me2 | 0.679 | 1.346412804 | 0.358 | 0.466 | 0.162 | Neuro-2 | Me2 |
| Rab3c | 0.676 | 1.608459983 | 0.352 | 0.364 | 0.014 | Neuro-2 | Rab3c |
| Resp18 | 0.668 | 1.368961996 | 0.336 | 0.364 | 0.03 | Neuro-2 | Resp18 |
| Pcsk1 | 0.665 | 1.533187939 | 0.33 | 0.364 | 0.041 | Neuro-2 | Pcsk1 |
| Ctsl | 0.65 | 0.966768573 | 0.3 | 0.364 | 0.071 | Neuro-2 | Ctsl |
| Tpbg | 0.648 | 1.266163184 | 0.296 | 0.307 | 0.012 | Neuro-2 | Tpbg |
| Ddc | 0.648 | 1.073792267 | 0.296 | 0.386 | 0.104 | Neuro-2 | Ddc |
| Cd63 | 0.646 | 0.600552027 | 0.292 | 0.625 | 0.4 | Neuro-2 | Cd63 |
| Vim | 0.641 | 1.253503003 | 0.282 | 0.307 | 0.026 | Neuro-2 | Vim |
| Rgs2 | 0.639 | 1.346366867 | 0.278 | 0.295 | 0.02 | Neuro-2 | Rgs2 |
| Ucn3 | 0.638 | 1.506643227 | 0.276 | 0.284 | 0.01 | Neuro-2 | Ucn3 |
| Wbp5 | 0.638 | 0.785474921 | 0.276 | 0.534 | 0.3 | Neuro-2 | Wbp5 |
| Fam183b | 0.631 | 0.942389731 | 0.262 | 0.307 | 0.044 | Neuro-2 | Fam183b |
| Trpa1 | 0.628 | 1.153317961 | 0.256 | 0.261 | 0.005 | Neuro-2 | Trpa1 |
| Gng12 | 0.625 | 0.910179636 | 0.25 | 0.386 | 0.158 | Neuro-2 | Gng12 |
| Bex1 | 0.624 | 1.026203151 | 0.248 | 0.295 | 0.054 | Neuro-2 | Bex1 |
| Akr1c14 | 0.618 | 1.189632011 | 0.236 | 0.273 | 0.042 | Neuro-2 | Akr1c14 |
| Prnp | 0.618 | 0.808232752 | 0.236 | 0.25 | 0.014 | Neuro-2 | Prnp |
| Rasd1 | 0.615 | 1.017995093 | 0.23 | 0.261 | 0.035 | Neuro-2 | Rasd1 |
| Ngfrap1 | 0.615 | 0.906830195 | 0.23 | 0.33 | 0.112 | Neuro-2 | Ngfrap1 |
| Cpe | 0.614 | 0.710599258 | 0.228 | 0.284 | 0.056 | Neuro-2 | Cpe |
| 2810025M15Rik | 0.613 | 0.968217482 | 0.226 | 0.307 | 0.086 | Neuro-2 | 2810025M15Rik |
| Glud1 | 0.613 | 0.799107704 | 0.226 | 0.409 | 0.217 | Neuro-2 | Glud1 |
| S100a13 | 0.61 | 1.051760465 | 0.22 | 0.25 | 0.034 | Neuro-2 | S100a13 |
| Pam | 0.609 | 0.859083644 | 0.218 | 0.25 | 0.033 | Neuro-2 | Pam |
| Qdpr | 0.609 | 0.763429752 | 0.218 | 0.352 | 0.151 | Neuro-2 | Qdpr |
| Cd81 | 0.609 | 0.481210094 | 0.218 | 0.602 | 0.456 | Neuro-2 | Cd81 |
| Lmx1a | 0.606 | 0.750313071 | 0.212 | 0.216 | 0.004 | Neuro-2 | Lmx1a |
| Scn3a | 0.604 | 0.937871535 | 0.208 | 0.216 | 0.009 | Neuro-2 | Scn3a |
| Atf6 | 0.602 | 1.111947141 | 0.204 | 0.25 | 0.055 | Neuro-2 | Atf6 |
| Atp6v0b | 0.602 | 0.59668372 | 0.204 | 0.341 | 0.149 | Neuro-2 | Atp6v0b |
| Neurod1 | 0.884 | 2.128413385 | 0.768 | 0.786 | 0.026 | Neuro-1 | Neurod1 |
| Sct | 0.847 | 2.612646934 | 0.694 | 0.75 | 0.075 | Neuro-1 | Sct |
| Tuba1a | 0.842 | 1.822329461 | 0.684 | 0.714 | 0.041 | Neuro-1 | Tuba1a |
| Tm4sf4 | 0.825 | 1.651242079 | 0.65 | 0.75 | 0.125 | Neuro-1 | Tm4sf4 |
| Chgb1 | 0.819 | 2.376568039 | 0.638 | 0.786 | 0.346 | Neuro-1 | Chgb |
| Cpe1 | 0.806 | 2.243591797 | 0.612 | 0.643 | 0.057 | Neuro-1 | Cpe |
| 5330417C22Rik | 0.805 | 1.340264649 | 0.61 | 0.679 | 0.07 | Neuro-1 | 5330417C22Rik |
| Cystm11 | 0.793 | 0.885206025 | 0.586 | 0.929 | 0.632 | Neuro-1 | Cystm1 |
| Cdkn1c | 0.791 | 1.841786919 | 0.582 | 0.607 | 0.027 | Neuro-1 | Cdkn1c |
| Plac8 | 0.788 | 1.189142517 | 0.576 | 0.893 | 0.568 | Neuro-1 | Plac8 |
| Pcsk11 | 0.783 | 1.764650166 | 0.566 | 0.607 | 0.046 | Neuro-1 | Pcsk1 |
| Scgn | 0.78 | 2.035384076 | 0.56 | 0.571 | 0.018 | Neuro-1 | Scgn |
| Sepp11 | 0.775 | 1.452403134 | 0.55 | 0.679 | 0.166 | Neuro-1 | Sepp1 |
| Chga1 | 0.771 | 1.525323817 | 0.542 | 0.643 | 0.133 | Neuro-1 | Chga |
| Fxyd3 | 0.771 | 1.366721839 | 0.542 | 0.714 | 0.244 | Neuro-1 | Fxyd3 |
| Ptprn2 | 0.768 | 1.390558352 | 0.536 | 0.571 | 0.037 | Neuro-1 | Ptprn2 |
| Fam183b1 | 0.766 | 1.652620862 | 0.532 | 0.571 | 0.047 | Neuro-1 | Fam183b |
| Maged1 | 0.759 | 1.07059618 | 0.518 | 0.643 | 0.122 | Neuro-1 | Maged1 |
| Oaz1 | 0.759 | 0.664384063 | 0.518 | 0.964 | 0.59 | Neuro-1 | Oaz1 |
| Btg2 | 0.749 | 1.171651845 | 0.498 | 0.607 | 0.127 | Neuro-1 | Btg2 |
| Eid1 | 0.743 | 1.191332762 | 0.486 | 0.536 | 0.053 | Neuro-1 | Eid1 |
| Rfx6 | 0.74 | 1.593703157 | 0.48 | 0.5 | 0.02 | Neuro-1 | Rfx6 |
| Gm609 | 0.734 | 1.188549643 | 0.468 | 0.5 | 0.031 | Neuro-1 | Gm609 |

TABLE 1-continued

Derived gene list of the top defining genes from in vivo ileal
small intestine PCs and EECs captured on the Seq-Well platform

| | | | | | | | |
|---|---|---|---|---|---|---|---|
| Hmgcr | 0.731 | 0.872682879 | 0.462 | 0.643 | 0.184 | Neuro-1 | Hmgcr |
| Hist1h2bc | 0.73 | 0.889355047 | 0.46 | 0.679 | 0.219 | Neuro-1 | Hist1h2bc |
| Gfra3 | 0.727 | 1.473620087 | 0.454 | 0.464 | 0.01 | Neuro-1 | Gfra3 |
| Olfm1 | 0.727 | 1.206923684 | 0.454 | 0.464 | 0.01 | Neuro-1 | Olfm1 |
| Mien1 | 0.727 | 0.876810583 | 0.454 | 0.607 | 0.159 | Neuro-1 | Mien1 |
| Cacna2d1 | 0.726 | 1.322721371 | 0.452 | 0.464 | 0.013 | Neuro-1 | Cacna2d1 |
| Serpinb1a | 0.725 | 1.255358649 | 0.45 | 0.643 | 0.224 | Neuro-1 | Serpinb1a |
| Hepacam2 | 0.724 | 1.208501264 | 0.448 | 0.5 | 0.052 | Neuro-1 | Hepacam2 |
| Cck | 0.723 | 3.72352546 | 0.446 | 0.571 | 0.192 | Neuro-1 | Cck |
| Krt7 | 0.723 | 0.983664388 | 0.446 | 0.643 | 0.224 | Neuro-1 | Krt7 |
| Scg2 | 0.721 | 2.509476892 | 0.442 | 0.464 | 0.034 | Neuro-1 | Scg2 |
| Ddc1 | 0.719 | 1.106062259 | 0.438 | 0.536 | 0.109 | Neuro-1 | Ddc |
| Bnip3 | 0.718 | 1.06453224 | 0.436 | 0.607 | 0.194 | Neuro-1 | Bnip3 |
| Hopx | 0.718 | 0.73792621 | 0.436 | 0.679 | 0.235 | Neuro-1 | Hopx |
| Pam1 | 0.717 | 1.443220648 | 0.434 | 0.464 | 0.035 | Neuro-1 | Pam |
| Rab11a | 0.714 | 0.727237716 | 0.428 | 0.607 | 0.169 | Neuro-1 | Rab11a |
| St18 | 0.709 | 1.319288478 | 0.418 | 0.429 | 0.01 | Neuro-1 | St18 |
| Syt13 | 0.709 | 1.136751386 | 0.418 | 0.429 | 0.011 | Neuro-1 | Syt13 |
| Scg5 | 0.707 | 1.410374245 | 0.414 | 0.429 | 0.017 | Neuro-1 | Scg5 |
| Insm1 | 0.706 | 1.20268774 | 0.412 | 0.429 | 0.014 | Neuro-1 | Insm1 |
| Itm2c | 0.706 | 1.091365278 | 0.412 | 0.5 | 0.089 | Neuro-1 | Itm2c |
| Egr1 | 0.705 | 0.885933557 | 0.41 | 0.643 | 0.294 | Neuro-1 | Egr1 |
| Slc25a4 | 0.703 | 0.931164692 | 0.406 | 0.571 | 0.174 | Neuro-1 | Slc25a4 |
| Hmgn3 | 0.702 | 1.403371696 | 0.404 | 0.429 | 0.024 | Neuro-1 | Hmgn3 |
| Sult1d1 | 0.702 | 0.923394046 | 0.404 | 0.571 | 0.193 | Neuro-1 | Sult1d1 |
| Selm | 0.701 | 1.058416696 | 0.402 | 0.536 | 0.144 | Neuro-1 | Selm |
| Scp2 | 0.699 | 0.933147579 | 0.398 | 0.571 | 0.178 | Neuro-1 | Scp2 |
| Prkar1a | 0.699 | 0.754455307 | 0.398 | 0.607 | 0.202 | Neuro-1 | Prkar1a |
| Junb | 0.697 | 0.946778551 | 0.394 | 0.643 | 0.289 | Neuro-1 | Junb |
| Lgals3bp | 0.695 | 1.120877589 | 0.39 | 0.536 | 0.166 | Neuro-1 | Lgals3bp |
| Ctsl1 | 0.694 | 0.932099684 | 0.388 | 0.464 | 0.077 | Neuro-1 | Ctsl |
| Rev3l | 0.693 | 0.843542085 | 0.386 | 0.464 | 0.077 | Neuro-1 | Rev3l |
| Atp6v1b2 | 0.693 | 0.824876135 | 0.386 | 0.464 | 0.074 | Neuro-1 | Atp6v1b2 |
| Cdkn1a | 0.688 | 1.334292329 | 0.376 | 0.536 | 0.186 | Neuro-1 | Cdkn1a |
| Cplx2 | 0.688 | 0.891165625 | 0.376 | 0.393 | 0.014 | Neuro-1 | Cplx2 |
| Nae1 | 0.688 | 0.768573833 | 0.376 | 0.5 | 0.113 | Neuro-1 | Nae1 |
| Peg3 | 0.686 | 1.681191988 | 0.372 | 0.393 | 0.021 | Neuro-1 | Peg3 |
| Sis3 | 0.683 | 0.903960317 | 0.366 | 0.607 | 0.322 | Neuro-1 | Sis |
| Ttr | 0.682 | 0.97496334 | 0.364 | 0.464 | 0.108 | Neuro-1 | Ttr |
| Plscr1 | 0.681 | 0.921872169 | 0.362 | 0.464 | 0.113 | Neuro-1 | Plscr1 |
| Rap1a | 0.68 | 0.65415806 | 0.36 | 0.5 | 0.126 | Neuro-1 | Rap1a |
| Nefm | 0.674 | 1.397081922 | 0.348 | 0.357 | 0.01 | Neuro-1 | Nefm |
| Atp6v0d1 | 0.674 | 0.891032138 | 0.348 | 0.393 | 0.042 | Neuro-1 | Atp6v0d1 |
| Ldlr | 0.674 | 0.843862593 | 0.348 | 0.5 | 0.161 | Neuro-1 | Ldlr |
| Gcc2 | 0.673 | 0.565358566 | 0.346 | 0.571 | 0.218 | Neuro-1 | Gcc2 |
| Aplp1 | 0.671 | 1.274724387 | 0.342 | 0.357 | 0.015 | Neuro-1 | Aplp1 |
| Myo6 | 0.671 | 0.862340558 | 0.342 | 0.571 | 0.247 | Neuro-1 | Myo6 |
| Neurog3 | 0.669 | 1.358073317 | 0.338 | 0.357 | 0.021 | Neuro-1 | Neurog3 |
| Ceacam10 | 0.669 | 1.0046749 | 0.338 | 0.357 | 0.017 | Neuro-1 | Ceacam10 |
| Cdkn1b | 0.668 | 0.788704545 | 0.336 | 0.464 | 0.13 | Neuro-1 | Cdkn1b |
| Cst3 | 0.668 | 0.770195781 | 0.336 | 0.607 | 0.353 | Neuro-1 | Cst3 |
| Dpp4 | 0.667 | 0.984749188 | 0.334 | 0.429 | 0.111 | Neuro-1 | Dpp4 |
| Sdcbp | 0.667 | 0.569776053 | 0.334 | 0.571 | 0.235 | Neuro-1 | Sdcbp |
| Selk | 0.666 | 0.736753309 | 0.332 | 0.5 | 0.168 | Neuro-1 | Selk |
| Bsg | 0.665 | 0.352410847 | 0.33 | 0.964 | 0.748 | Neuro-1 | Bsg |
| Rbx1 | 0.664 | 0.649248485 | 0.328 | 0.607 | 0.288 | Neuro-1 | Rbx1 |
| Nenf | 0.663 | 1.011947665 | 0.326 | 0.393 | 0.076 | Neuro-1 | Nenf |
| Fryl | 0.663 | 0.852112737 | 0.326 | 0.393 | 0.068 | Neuro-1 | Fryl |
| Cyp4b1 | 0.661 | 1.021061373 | 0.322 | 0.357 | 0.039 | Neuro-1 | Cyp4b1 |
| Ube2b | 0.66 | 0.646500382 | 0.32 | 0.536 | 0.233 | Neuro-1 | Ube2b |
| Lamp2 | 0.659 | 0.728091995 | 0.318 | 0.464 | 0.142 | Neuro-1 | Lamp2 |
| Dctn2 | 0.659 | 0.625768165 | 0.318 | 0.464 | 0.136 | Neuro-1 | Dctn2 |
| Jun | 0.659 | 0.498081031 | 0.318 | 0.786 | 0.456 | Neuro-1 | Jun |
| Sh3bgrl | 0.658 | 0.651226106 | 0.316 | 0.429 | 0.101 | Neuro-1 | Sh3bgrl |
| H2-D1 | 0.658 | 0.468992101 | 0.316 | 0.643 | 0.29 | Neuro-1 | H2-D1 |
| Reg42 | 0.342 | 0.627414828 | 0.316 | 0.071 | 0.388 | Neuro-1 | Reg4 |
| Gadd45g | 0.656 | 0.930147109 | 0.312 | 0.357 | 0.044 | Neuro-1 | Gadd45g |
| Scg3 | 0.656 | 0.922207851 | 0.312 | 0.321 | 0.009 | Neuro-1 | Scg3 |
| Smim6 | 0.656 | 0.755273791 | 0.312 | 0.393 | 0.074 | Neuro-1 | Smim6 |
| Tecpr1 | 0.656 | 0.737106574 | 0.312 | 0.357 | 0.043 | Neuro-1 | Tecpr1 |
| Marcks | 0.656 | 0.562172873 | 0.312 | 0.536 | 0.218 | Neuro-1 | Marcks |
| Aldoa | 0.656 | 0.434817231 | 0.312 | 0.929 | 0.816 | Neuro-1 | Aldoa |
| Isl1 | 0.655 | 1.111153862 | 0.31 | 0.321 | 0.012 | Neuro-1 | Isl1 |
| Fev | 0.655 | 1.046624972 | 0.31 | 0.321 | 0.011 | Neuro-1 | Fev |
| Anxa6 | 0.655 | 1.024208104 | 0.31 | 0.321 | 0.01 | Neuro-1 | Anxa6 |
| Acly | 0.655 | 0.571220039 | 0.31 | 0.5 | 0.186 | Neuro-1 | Acly |
| Ddx5 | 0.655 | 0.395316282 | 0.31 | 0.821 | 0.607 | Neuro-1 | Ddx5 |

TABLE 1-continued

Derived gene list of the top defining genes from in vivo ileal
small intestine PCs and EECs captured on the Seq-Well platform

| Gene | | | | | | Gene |
|---|---|---|---|---|---|---|
| Jak1 | 0.654 | 0.708996101 | 0.308 | 0.429 | 0.117 | Neuro-1 Jak1 |
| Map1b | 0.653 | 0.999915565 | 0.306 | 0.321 | 0.014 | Neuro-1 Map1b |
| Hspa4l | 0.653 | 0.91811242 | 0.306 | 0.357 | 0.053 | Neuro-1 Hspa4l |
| Prnp1 | 0.652 | 0.989747816 | 0.304 | 0.321 | 0.019 | Neuro-1 Prnp |
| Tspan1 | 0.652 | 0.590275966 | 0.304 | 0.5 | 0.198 | Neuro-1 Tspan1 |
| Os9 | 0.652 | 0.534705563 | 0.304 | 0.464 | 0.14 | Neuro-1 Os9 |
| Cyp51 | 0.651 | 0.483046862 | 0.302 | 0.607 | 0.28 | Neuro-1 Cyp51 |
| Upp1 | 0.65 | 1.068866358 | 0.3 | 0.321 | 0.021 | Neuro-1 Upp1 |
| Ids | 0.65 | 0.826515129 | 0.3 | 0.321 | 0.02 | Neuro-1 Ids |
| Ndufa1 | 0.65 | 0.3916149 | 0.3 | 0.607 | 0.274 | Neuro-1 Ndufa1 |
| Qdpr1 | 0.649 | 0.626748098 | 0.298 | 0.464 | 0.155 | Neuro-1 Qdpr |
| Tspo | 0.649 | 0.525363652 | 0.298 | 0.464 | 0.152 | Neuro-1 Tspo |
| Morf4l2 | 0.649 | 0.483584301 | 0.298 | 0.464 | 0.149 | Neuro-1 Morf4l2 |
| Mrfap1 | 0.649 | 0.398472237 | 0.298 | 0.607 | 0.293 | Neuro-1 Mrfap1 |
| Tac11 | 0.648 | 2.510656534 | 0.296 | 0.429 | 0.155 | Neuro-1 Tac1 |
| Ghrl | 0.648 | 1.993849009 | 0.296 | 0.393 | 0.103 | Neuro-1 Ghrl |
| Fyttd1 | 0.647 | 0.611171171 | 0.294 | 0.429 | 0.128 | Neuro-1 Fyttd1 |
| Ubl3 | 0.647 | 0.557099795 | 0.294 | 0.429 | 0.124 | Neuro-1 Ubl3 |
| Eps8l2 | 0.647 | 0.528100525 | 0.294 | 0.429 | 0.12 | Neuro-1 Eps8l2 |
| Ginm1 | 0.646 | 1.043963068 | 0.292 | 0.357 | 0.069 | Neuro-1 Ginm1 |
| Gm15200 | 0.646 | 0.920483537 | 0.292 | 0.321 | 0.029 | Neuro-1 Gm15200 |
| Kif5b | 0.646 | 0.661685371 | 0.292 | 0.643 | 0.349 | Neuro-1 Kif5b |
| Baiap2l2 | 0.646 | 0.594645445 | 0.292 | 0.464 | 0.16 | Neuro-1 Baiap2l2 |
| Copb1 | 0.645 | 0.60961529 | 0.29 | 0.464 | 0.173 | Neuro-1 Copb1 |
| Tusc3 | 0.645 | 0.609314836 | 0.29 | 0.357 | 0.061 | Neuro-1 Tusc3 |
| Tax1bp1 | 0.645 | 0.402266006 | 0.29 | 0.714 | 0.428 | Neuro-1 Tax1bp1 |
| Dst | 0.644 | 0.905724655 | 0.288 | 0.321 | 0.032 | Neuro-1 Dst |
| Gadd45a | 0.644 | 0.850106118 | 0.288 | 0.357 | 0.067 | Neuro-1 Gadd45a |
| Arrdc4 | 0.644 | 0.620840624 | 0.288 | 0.357 | 0.064 | Neuro-1 Arrdc4 |
| Arf1 | 0.644 | 0.482495611 | 0.288 | 0.571 | 0.301 | Neuro-1 Arf1 |
| Cd631 | 0.644 | 0.428425151 | 0.288 | 0.643 | 0.405 | Neuro-1 Cd63 |
| Hk2 | 0.643 | 0.879733309 | 0.286 | 0.393 | 0.109 | Neuro-1 Hk2 |
| Cldn4 | 0.643 | 0.809875647 | 0.286 | 0.393 | 0.113 | Neuro-1 Cldn4 |
| Dynlt3 | 0.643 | 0.480059235 | 0.286 | 0.429 | 0.128 | Neuro-1 Dynlt3 |
| Etv1 | 0.642 | 1.064894846 | 0.284 | 0.286 | 0.002 | Neuro-1 Etv1 |
| Gch1 | 0.642 | 1.0450736 | 0.284 | 0.321 | 0.04 | Neuro-1 Gch1 |
| Resp18l | 0.641 | 1.091625187 | 0.282 | 0.321 | 0.039 | Neuro-1 Resp18 |
| Emb | 0.641 | 1.00297377 | 0.282 | 0.286 | 0.003 | Neuro-1 Emb |
| Ngfrap1l | 0.641 | 0.735608982 | 0.282 | 0.393 | 0.117 | Neuro-1 Ngfrap1 |
| Gucy2c | 0.641 | 0.495671294 | 0.282 | 0.429 | 0.131 | Neuro-1 Gucy2c |
| Psmb4 | 0.641 | 0.451439702 | 0.282 | 0.643 | 0.346 | Neuro-1 Psmb4 |
| Insig1 | 0.641 | 0.363268224 | 0.282 | 0.464 | 0.151 | Neuro-1 Insig1 |
| Serinc1 | 0.64 | 0.710023389 | 0.28 | 0.357 | 0.076 | Neuro-1 Serinc1 |
| Actr3 | 0.64 | 0.483016253 | 0.28 | 0.607 | 0.313 | Neuro-1 Actr3 |
| Arl3 | 0.639 | 0.695992244 | 0.278 | 0.321 | 0.04 | Neuro-1 Arl3 |
| Txnip | 0.639 | 0.626351931 | 0.278 | 0.571 | 0.317 | Neuro-1 Txnip |
| Ddx6 | 0.639 | 0.497496576 | 0.278 | 0.5 | 0.209 | Neuro-1 Ddx6 |
| Cdhr5 | 0.638 | 0.767618087 | 0.276 | 0.357 | 0.082 | Neuro-1 Cdhr5 |
| Dynlrb1 | 0.638 | 0.545490132 | 0.276 | 0.571 | 0.271 | Neuro-1 Dynlrb1 |
| Krt20 | 0.637 | 1.415109505 | 0.274 | 0.321 | 0.056 | Neuro-1 Krt20 |
| Pla2g2f | 0.637 | 0.769734401 | 0.274 | 0.286 | 0.01 | Neuro-1 Pla2g2f |
| Brk1 | 0.637 | 0.637311984 | 0.274 | 0.5 | 0.225 | Neuro-1 Brk1 |
| Pkm | 0.637 | 0.386573977 | 0.274 | 0.857 | 0.693 | Neuro-1 Pkm |
| H2-K1 | 0.637 | 0.386500238 | 0.274 | 0.714 | 0.458 | Neuro-1 H2-K1 |
| Ypel3 | 0.636 | 0.854256751 | 0.272 | 0.286 | 0.014 | Neuro-1 Ypel3 |
| Phip | 0.634 | 0.678502118 | 0.268 | 0.393 | 0.124 | Neuro-1 Phip |
| Surf1 | 0.634 | 0.605793937 | 0.268 | 0.357 | 0.084 | Neuro-1 Surf1 |
| Tpm4 | 0.634 | 0.51443206 | 0.268 | 0.464 | 0.176 | Neuro-1 Tpm4 |
| Dnm2 | 0.634 | 0.419419665 | 0.268 | 0.393 | 0.109 | Neuro-1 Dnm2 |
| Rhob | 0.633 | 0.721306707 | 0.266 | 0.321 | 0.052 | Neuro-1 Rhob |
| Ece1 | 0.633 | 0.615307723 | 0.266 | 0.321 | 0.052 | Neuro-1 Ece1 |
| Myl7 | 0.632 | 1.69538567 | 0.264 | 0.286 | 0.026 | Neuro-1 Myl7 |
| Idh3b | 0.632 | 0.583175021 | 0.264 | 0.536 | 0.269 | Neuro-1 Idh3b |
| Slc35g1 | 0.631 | 0.670626441 | 0.262 | 0.357 | 0.089 | Neuro-1 Slc35g1 |
| Slc30a9 | 0.631 | 0.662004597 | 0.262 | 0.357 | 0.088 | Neuro-1 Slc30a9 |
| Mast2 | 0.631 | 0.538466203 | 0.262 | 0.321 | 0.052 | Neuro-1 Mast2 |
| Bex2 | 0.63 | 0.735198114 | 0.26 | 0.286 | 0.024 | Neuro-1 Bex2 |
| Itpr1 | 0.63 | 0.664400404 | 0.26 | 0.286 | 0.025 | Neuro-1 Itpr1 |
| Rab3c1 | 0.63 | 0.660261674 | 0.26 | 0.286 | 0.023 | Neuro-1 Rab3c |
| Selt | 0.63 | 0.486789684 | 0.26 | 0.429 | 0.155 | Neuro-1 Selt |
| H3f3a | 0.63 | 0.468318912 | 0.26 | 0.679 | 0.451 | Neuro-1 H3f3a |
| Tpst2 | 0.629 | 0.855541142 | 0.258 | 0.286 | 0.031 | Neuro-1 Tpst2 |
| Rab3d | 0.629 | 0.834085966 | 0.258 | 0.321 | 0.062 | Neuro-1 Rab3d |
| Gipc2 | 0.629 | 0.418737057 | 0.258 | 0.5 | 0.212 | Neuro-1 Gipc2 |
| Prdx5 | 0.628 | 0.72018067 | 0.256 | 0.429 | 0.173 | Neuro-1 Prdx5 |
| Tmem126a | 0.628 | 0.426597956 | 0.256 | 0.393 | 0.122 | Neuro-1 Tmem126a |
| Ugp2 | 0.628 | 0.417434372 | 0.256 | 0.429 | 0.158 | Neuro-1 Ugp2 |

TABLE 1-continued

Derived gene list of the top defining genes from in vivo ileal
small intestine PCs and EECs captured on the Seq-Well platform

| | | | | | | | |
|---|---|---|---|---|---|---|---|
| Vim1 | 0.627 | 1.339906798 | 0.254 | 0.286 | 0.033 | Neuro-1 | Vim |
| Sec24d | 0.627 | 0.755106003 | 0.254 | 0.286 | 0.03 | Neuro-1 | Sec24d |
| Sqstm1 | 0.627 | 0.485067042 | 0.254 | 0.357 | 0.091 | Neuro-1 | Sqstm1 |
| Arf5 | 0.626 | 0.592232353 | 0.252 | 0.464 | 0.216 | Neuro-1 | Arf5 |
| Cyb5r3 | 0.625 | 0.606738759 | 0.25 | 0.393 | 0.149 | Neuro-1 | Cyb5r3 |
| Vegfa | 0.625 | 0.535171115 | 0.25 | 0.393 | 0.133 | Neuro-1 | Vegfa |
| Sar1b | 0.625 | 0.490212683 | 0.25 | 0.429 | 0.167 | Neuro-1 | Sar1b |
| Cap1 | 0.625 | 0.383025912 | 0.25 | 0.393 | 0.125 | Neuro-1 | Cap1 |
| Ubb | 0.625 | 0.334489342 | 0.25 | 0.786 | 0.712 | Neuro-1 | Ubb |
| Nefl | 0.624 | 1.20990632 | 0.248 | 0.25 | 0.002 | Neuro-1 | Nefl |
| Etnk1 | 0.624 | 0.649458229 | 0.248 | 0.321 | 0.071 | Neuro-1 | Etnk1 |
| Eif4a2 | 0.624 | 0.523563686 | 0.248 | 0.5 | 0.252 | Neuro-1 | Eif4a2 |
| Hsbp1 | 0.624 | 0.461879545 | 0.248 | 0.5 | 0.252 | Neuro-1 | Hsbp1 |
| Laptm4a | 0.624 | 0.441442055 | 0.248 | 0.536 | 0.281 | Neuro-1 | Laptm4a |
| Mtch1 | 0.623 | 0.640341828 | 0.246 | 0.357 | 0.112 | Neuro-1 | Mtch1 |
| Gng4 | 0.622 | 0.723471733 | 0.244 | 0.25 | 0.006 | Neuro-1 | Gng4 |
| Rundc3a | 0.622 | 0.713732891 | 0.244 | 0.25 | 0.006 | Neuro-1 | Rundc3a |
| Dpysl2 | 0.622 | 0.704441597 | 0.244 | 0.321 | 0.075 | Neuro-1 | Dpysl2 |
| Tm4sf5 | 0.622 | 0.61049843 | 0.244 | 0.536 | 0.335 | Neuro-1 | Tm4sf5 |
| Efcab1 | 0.622 | 0.562908231 | 0.244 | 0.25 | 0.005 | Neuro-1 | Efcab1 |
| Aamp | 0.622 | 0.486727018 | 0.244 | 0.393 | 0.144 | Neuro-1 | Aamp |
| Ier2 | 0.622 | 0.483283425 | 0.244 | 0.643 | 0.505 | Neuro-1 | Ier2 |
| Smarce1 | 0.622 | 0.476584743 | 0.244 | 0.321 | 0.07 | Neuro-1 | Smarce1 |
| Psma2 | 0.622 | 0.36892654 | 0.244 | 0.714 | 0.496 | Neuro-1 | Psma2 |
| Rgs17 | 0.621 | 0.826822635 | 0.242 | 0.25 | 0.008 | Neuro-1 | Rgs17 |
| Rab4a | 0.621 | 0.628796173 | 0.242 | 0.286 | 0.041 | Neuro-1 | Rab4a |
| Rnf214 | 0.621 | 0.533108865 | 0.242 | 0.286 | 0.041 | Neuro-1 | Rnf214 |
| Ap3d1 | 0.621 | 0.509905514 | 0.242 | 0.357 | 0.109 | Neuro-1 | Ap3d1 |
| Gcg | 0.62 | 3.616153547 | 0.24 | 0.321 | 0.107 | Neuro-1 | Gcg |
| Rprml | 0.62 | 0.767657089 | 0.24 | 0.25 | 0.01 | Neuro-1 | Rprml |
| Pim2 | 0.62 | 0.746028585 | 0.24 | 0.25 | 0.01 | Neuro-1 | Pim2 |
| Oxr1 | 0.62 | 0.732104036 | 0.24 | 0.286 | 0.043 | Neuro-1 | Oxr1 |
| Kif12 | 0.62 | 0.721616828 | 0.24 | 0.286 | 0.046 | Neuro-1 | Kif12 |
| Celf3 | 0.62 | 0.511439169 | 0.24 | 0.25 | 0.008 | Neuro-1 | Celf3 |
| Psap | 0.619 | 0.578210901 | 0.238 | 0.393 | 0.152 | Neuro-1 | Psap |
| Nktr | 0.619 | 0.466699725 | 0.238 | 0.393 | 0.146 | Neuro-1 | Nktr |
| Gnai2 | 0.619 | 0.453226523 | 0.238 | 0.393 | 0.145 | Neuro-1 | Gnai2 |
| Rab2a | 0.619 | 0.370444818 | 0.238 | 0.464 | 0.21 | Neuro-1 | Rab2a |
| Tbrg1 | 0.619 | 0.335365008 | 0.238 | 0.429 | 0.161 | Neuro-1 | Tbrg1 |
| 4833439L19Rik | 0.618 | 0.712557481 | 0.236 | 0.321 | 0.087 | Neuro-1 | 4833439L19Rik |
| Vps28 | 0.618 | 0.554298496 | 0.236 | 0.429 | 0.181 | Neuro-1 | Vps28 |
| Hnrnph1 | 0.618 | 0.430451631 | 0.236 | 0.464 | 0.228 | Neuro-1 | Hnrnph1 |
| Ostc | 0.618 | 0.408836402 | 0.236 | 0.571 | 0.334 | Neuro-1 | Ostc |
| Eif3a | 0.618 | 0.287279795 | 0.236 | 0.679 | 0.435 | Neuro-1 | Eif3a |
| Cacna1a | 0.617 | 0.889867318 | 0.234 | 0.25 | 0.019 | Neuro-1 | Cacna1a |
| Pdzd8 | 0.617 | 0.829682861 | 0.234 | 0.321 | 0.09 | Neuro-1 | Pdzd8 |
| Gtf2a1 | 0.617 | 0.544648382 | 0.234 | 0.286 | 0.048 | Neuro-1 | Gtf2a1 |
| Gnas | 0.617 | 0.427487767 | 0.234 | 0.643 | 0.398 | Neuro-1 | Gnas |
| Vasp | 0.617 | 0.319618042 | 0.234 | 0.464 | 0.203 | Neuro-1 | Vasp |
| Camk2n1 | 0.616 | 0.733682344 | 0.232 | 0.286 | 0.055 | Neuro-1 | Camk2n1 |
| Slc25a11 | 0.616 | 0.63834965 | 0.232 | 0.357 | 0.127 | Neuro-1 | Slc25a11 |
| Golim4 | 0.616 | 0.550686611 | 0.232 | 0.321 | 0.086 | Neuro-1 | Golim4 |
| Gng12l | 0.616 | 0.495169993 | 0.232 | 0.393 | 0.163 | Neuro-1 | Gng12 |
| Glud1l | 0.616 | 0.400650613 | 0.232 | 0.464 | 0.221 | Neuro-1 | Glud1 |
| Sp3 | 0.616 | 0.320202491 | 0.232 | 0.321 | 0.078 | Neuro-1 | Sp3 |
| Srrm2 | 0.616 | 0.294104548 | 0.232 | 0.714 | 0.457 | Neuro-1 | Srrm2 |
| Ppp1r15a | 0.615 | 0.763700584 | 0.23 | 0.286 | 0.058 | Neuro-1 | Ppp1r15a |
| Sirt2 | 0.615 | 0.664318184 | 0.23 | 0.286 | 0.056 | Neuro-1 | Sirt2 |
| Ppil4 | 0.615 | 0.552357747 | 0.23 | 0.321 | 0.085 | Neuro-1 | Ppil4 |
| Minos1 | 0.615 | 0.413443932 | 0.23 | 0.714 | 0.519 | Neuro-1 | Minos1 |
| Xiap | 0.615 | 0.376258722 | 0.23 | 0.321 | 0.08 | Neuro-1 | Xiap |
| Gabarap | 0.615 | 0.352401663 | 0.23 | 0.607 | 0.354 | Neuro-1 | Gabarap |
| Cnot4 | 0.614 | 0.752997617 | 0.228 | 0.321 | 0.09 | Neuro-1 | Cnot4 |
| Wbp5l | 0.614 | 0.517147324 | 0.228 | 0.5 | 0.306 | Neuro-1 | Wbp5 |
| Sfr1 | 0.614 | 0.458355534 | 0.228 | 0.393 | 0.161 | Neuro-1 | Sfr1 |
| Azin1 | 0.614 | 0.431231125 | 0.228 | 0.393 | 0.153 | Neuro-1 | Azin1 |
| Srp14 | 0.614 | 0.423130446 | 0.228 | 0.464 | 0.217 | Neuro-1 | Srp14 |
| Tmem234 | 0.614 | 0.371723178 | 0.228 | 0.464 | 0.224 | Neuro-1 | Tmem234 |
| Leprotl1 | 0.613 | 0.824622431 | 0.226 | 0.286 | 0.058 | Neuro-1 | Leprotl1 |
| Atp6ap1 | 0.613 | 0.660330681 | 0.226 | 0.286 | 0.06 | Neuro-1 | Atp6ap1 |
| Slc18a1 | 0.613 | 0.632640516 | 0.226 | 0.25 | 0.022 | Neuro-1 | Slc18a1 |
| Tbc1d9 | 0.613 | 0.523268838 | 0.226 | 0.25 | 0.023 | Neuro-1 | Tbc1d9 |
| Chmp5 | 0.613 | 0.422534415 | 0.226 | 0.393 | 0.157 | Neuro-1 | Chmp5 |
| Canx | 0.613 | 0.353930878 | 0.226 | 0.714 | 0.468 | Neuro-1 | Canx |
| Cldn25 | 0.612 | 0.68249012 | 0.224 | 0.321 | 0.091 | Neuro-1 | Cldn25 |
| Top1 | 0.612 | 0.511068369 | 0.224 | 0.5 | 0.266 | Neuro-1 | Top1 |
| Ubn2 | 0.611 | 0.576308843 | 0.222 | 0.286 | 0.062 | Neuro-1 | Ubn2 |

TABLE 1-continued

Derived gene list of the top defining genes from in vivo ileal
small intestine PCs and EECs captured on the Seq-Well platform

| | | | | | | | |
|---|---|---|---|---|---|---|---|
| Vamp3 | 0.611 | 0.505427761 | 0.222 | 0.321 | 0.094 | Neuro-1 | Vamp3 |
| Fam216a | 0.611 | 0.490493248 | 0.222 | 0.25 | 0.024 | Neuro-1 | Fam216a |
| Cd24a2 | 0.61 | 0.746128857 | 0.22 | 0.607 | 0.512 | Neuro-1 | Cd24a |
| Atf2 | 0.61 | 0.736043031 | 0.22 | 0.286 | 0.068 | Neuro-1 | Atf2 |
| Tmem176b | 0.61 | 0.595835674 | 0.22 | 0.393 | 0.162 | Neuro-1 | Tmem176b |
| Adh11 | 0.61 | 0.498501311 | 0.22 | 0.464 | 0.245 | Neuro-1 | Adh1 |
| Cxxc5 | 0.61 | 0.463738294 | 0.22 | 0.25 | 0.026 | Neuro-1 | Cxxc5 |
| Atp1b3 | 0.61 | 0.40646453 | 0.22 | 0.321 | 0.093 | Neuro-1 | Atp1b3 |
| Arpc5l | 0.61 | 0.367536358 | 0.22 | 0.393 | 0.157 | Neuro-1 | Arpc5l |
| Atp8b1 | 0.61 | 0.363695805 | 0.22 | 0.5 | 0.271 | Neuro-1 | Atp8b1 |
| Uqcc2 | 0.61 | 0.252681284 | 0.22 | 0.607 | 0.378 | Neuro-1 | Uqcc2 |
| Dusp4 | 0.609 | 0.836244373 | 0.218 | 0.25 | 0.034 | Neuro-1 | Dusp4 |
| Anxa5 | 0.609 | 0.705362716 | 0.218 | 0.25 | 0.032 | Neuro-1 | Anxa5 |
| Jhdm1d | 0.609 | 0.645347078 | 0.218 | 0.25 | 0.032 | Neuro-1 | Jhdm1d |
| Snap47 | 0.609 | 0.551184309 | 0.218 | 0.25 | 0.031 | Neuro-1 | Snap47 |
| Clk1 | 0.609 | 0.510283388 | 0.218 | 0.429 | 0.209 | Neuro-1 | Clk1 |
| Map1lc3b | 0.609 | 0.45690213 | 0.218 | 0.357 | 0.133 | Neuro-1 | Map1lc3b |
| Churc1 | 0.609 | 0.444224524 | 0.218 | 0.393 | 0.174 | Neuro-1 | Churc1 |
| Ndufc1 | 0.609 | 0.408347599 | 0.218 | 0.714 | 0.486 | Neuro-1 | Ndufc1 |
| Luc7l3 | 0.609 | 0.374051946 | 0.218 | 0.571 | 0.339 | Neuro-1 | Luc7l3 |
| Tspan13 | 0.608 | 0.891546219 | 0.216 | 0.357 | 0.145 | Neuro-1 | Tspan13 |
| Lcorl | 0.608 | 0.841990473 | 0.216 | 0.286 | 0.074 | Neuro-1 | Lcorl |
| Sema4a | 0.608 | 0.747362665 | 0.216 | 0.286 | 0.072 | Neuro-1 | Sema4a |
| Phldb2 | 0.608 | 0.739667636 | 0.216 | 0.25 | 0.035 | Neuro-1 | Phldb2 |
| Rab15 | 0.608 | 0.647713069 | 0.216 | 0.25 | 0.033 | Neuro-1 | Rab15 |
| Gpbp1l1 | 0.608 | 0.566865246 | 0.216 | 0.357 | 0.135 | Neuro-1 | Gpbp1l1 |
| Acbd5 | 0.608 | 0.491092398 | 0.216 | 0.286 | 0.065 | Neuro-1 | Acbd5 |
| Lcor | 0.608 | 0.367222093 | 0.216 | 0.286 | 0.061 | Neuro-1 | Lcor |
| Fabp5 | 0.607 | 1.225503564 | 0.214 | 0.286 | 0.082 | Neuro-1 | Fabp5 |
| P4ha1 | 0.607 | 0.612242959 | 0.214 | 0.286 | 0.067 | Neuro-1 | P4ha1 |
| H1f0 | 0.607 | 0.487676267 | 0.214 | 0.536 | 0.308 | Neuro-1 | H1f0 |
| Nucb1 | 0.607 | 0.483110445 | 0.214 | 0.357 | 0.14 | Neuro-1 | Nucb1 |
| Glyr1 | 0.607 | 0.476943139 | 0.214 | 0.357 | 0.142 | Neuro-1 | Glyr1 |
| Azi2 | 0.607 | 0.427652555 | 0.214 | 0.357 | 0.136 | Neuro-1 | Azi2 |
| Pycr2 | 0.607 | 0.384289142 | 0.214 | 0.286 | 0.063 | Neuro-1 | Pycr2 |
| Sacm1l | 0.607 | 0.326862348 | 0.214 | 0.286 | 0.061 | Neuro-1 | Sacm1l |
| Fam105a | 0.606 | 0.743129233 | 0.212 | 0.214 | 0.002 | Neuro-1 | Fam105a |
| Mical2 | 0.606 | 0.689768591 | 0.212 | 0.25 | 0.039 | Neuro-1 | Mical2 |
| Acadsb | 0.606 | 0.669507803 | 0.212 | 0.25 | 0.037 | Neuro-1 | Acadsb |
| Cnot6l | 0.606 | 0.616579048 | 0.212 | 0.286 | 0.074 | Neuro-1 | Cnot6l |
| Sh3glb1 | 0.606 | 0.594927841 | 0.212 | 0.357 | 0.157 | Neuro-1 | Sh3glb1 |
| Smarcc2 | 0.606 | 0.502202951 | 0.212 | 0.321 | 0.108 | Neuro-1 | Smarcc2 |
| Irf2bp2 | 0.606 | 0.373199108 | 0.212 | 0.429 | 0.206 | Neuro-1 | Irf2bp2 |
| Pax6 | 0.605 | 0.827820437 | 0.21 | 0.214 | 0.004 | Neuro-1 | Pax6 |
| Rasd1l | 0.605 | 0.793247153 | 0.21 | 0.25 | 0.041 | Neuro-1 | Rasd1 |
| Rnf32 | 0.605 | 0.740146072 | 0.21 | 0.286 | 0.079 | Neuro-1 | Rnf32 |
| Gnao1 | 0.605 | 0.71472288 | 0.21 | 0.214 | 0.004 | Neuro-1 | Gnao1 |
| Man2a1 | 0.605 | 0.574074471 | 0.21 | 0.321 | 0.108 | Neuro-1 | Man2a1 |
| Echdc2 | 0.605 | 0.509785118 | 0.21 | 0.286 | 0.069 | Neuro-1 | Echdc2 |
| Znrf2 | 0.605 | 0.498279831 | 0.21 | 0.286 | 0.072 | Neuro-1 | Znrf2 |
| D17Wsu104e | 0.605 | 0.268534857 | 0.21 | 0.429 | 0.19 | Neuro-1 | D17Wsu104e |
| Lect2 | 0.604 | 0.798940842 | 0.208 | 0.214 | 0.006 | Neuro-1 | Lect2 |
| Disp2 | 0.604 | 0.723720707 | 0.208 | 0.214 | 0.006 | Neuro-1 | Disp2 |
| Nudt4 | 0.604 | 0.616102524 | 0.208 | 0.286 | 0.08 | Neuro-1 | Nudt4 |
| Clcn3 | 0.604 | 0.569540015 | 0.208 | 0.357 | 0.145 | Neuro-1 | Clcn3 |
| Akr1c12 | 0.604 | 0.56406058 | 0.208 | 0.393 | 0.198 | Neuro-1 | Akr1c12 |
| Kdelr2 | 0.604 | 0.529169196 | 0.208 | 0.464 | 0.288 | Neuro-1 | Kdelr2 |
| Slc35b1 | 0.604 | 0.463153386 | 0.208 | 0.321 | 0.108 | Neuro-1 | Slc35b1 |
| Rnf20 | 0.604 | 0.413882774 | 0.208 | 0.321 | 0.105 | Neuro-1 | Rnf20 |
| 0610011F06Rik | 0.604 | 0.388542866 | 0.208 | 0.393 | 0.179 | Neuro-1 | 0610011F06Rik |
| Psmb5 | 0.604 | 0.273148038 | 0.208 | 0.464 | 0.23 | Neuro-1 | Psmb5 |
| Cryba2 | 0.603 | 0.793991136 | 0.206 | 0.214 | 0.009 | Neuro-1 | Cryba2 |
| Dgkd | 0.603 | 0.736177799 | 0.206 | 0.286 | 0.084 | Neuro-1 | Dgkd |
| Hmox2 | 0.603 | 0.685828848 | 0.206 | 0.286 | 0.082 | Neuro-1 | Hmox2 |
| A1cf | 0.603 | 0.636558699 | 0.206 | 0.25 | 0.045 | Neuro-1 | A1cf |
| Tmem66 | 0.603 | 0.610368198 | 0.206 | 0.286 | 0.075 | Neuro-1 | Tmem66 |
| Rap1b | 0.603 | 0.604009718 | 0.206 | 0.286 | 0.082 | Neuro-1 | Rap1b |
| Gnptg | 0.603 | 0.51977512 | 0.206 | 0.25 | 0.042 | Neuro-1 | Gnptg |
| Tuba4a | 0.603 | 0.393541007 | 0.206 | 0.393 | 0.181 | Neuro-1 | Tuba4a |
| Rpn1 | 0.603 | 0.35873066 | 0.206 | 0.536 | 0.303 | Neuro-1 | Rpn1 |
| Vwa5b2 | 0.602 | 0.837552302 | 0.204 | 0.214 | 0.01 | Neuro-1 | Vwa5b2 |
| Fgd2 | 0.602 | 0.692969634 | 0.204 | 0.214 | 0.01 | Neuro-1 | Fgd2 |
| Glul | 0.602 | 0.597853242 | 0.204 | 0.286 | 0.085 | Neuro-1 | Glul |
| Ppap2a | 0.602 | 0.542704762 | 0.204 | 0.25 | 0.044 | Neuro-1 | Ppap2a |
| Impa1 | 0.602 | 0.526924865 | 0.204 | 0.321 | 0.121 | Neuro-1 | Impa1 |
| Rhoa | 0.602 | 0.452337591 | 0.204 | 0.464 | 0.258 | Neuro-1 | Rhoa |
| Emc7 | 0.602 | 0.374283991 | 0.204 | 0.321 | 0.107 | Neuro-1 | Emc7 |

TABLE 1-continued

Derived gene list of the top defining genes from in vivo ileal
small intestine PCs and EECs captured on the Seq-Well platform

| | | | | | | | |
|---|---|---|---|---|---|---|---|
| Fos | 0.602 | 0.366765775 | 0.204 | 0.607 | 0.409 | Neuro-1 | Fos |
| Ppp4c | 0.602 | 0.344513394 | 0.204 | 0.429 | 0.21 | Neuro-1 | Ppp4c |
| Ssu72 | 0.602 | 0.280576353 | 0.204 | 0.464 | 0.225 | Neuro-1 | Ssu72 |
| 2810025M15Rik1 | 0.601 | 0.806213089 | 0.202 | 0.286 | 0.092 | Neuro-1 | 2810025M15Rik |
| Tle6 | 0.601 | 0.612081752 | 0.202 | 0.214 | 0.011 | Neuro-1 | Tle6 |
| Nrp1 | 0.601 | 0.583612063 | 0.202 | 0.214 | 0.011 | Neuro-1 | Nrp1 |
| Pdhb | 0.601 | 0.545941142 | 0.202 | 0.357 | 0.136 | Neuro-1 | Pdhb |
| Slu7 | 0.601 | 0.445622881 | 0.202 | 0.286 | 0.078 | Neuro-1 | Slu7 |
| Rrp1 | 0.601 | 0.437041314 | 0.202 | 0.429 | 0.228 | Neuro-1 | Rrp1 |
| Sdf4 | 0.601 | 0.363891924 | 0.202 | 0.357 | 0.145 | Neuro-1 | Sdf4 |
| Papss1 | 0.601 | 0.352345333 | 0.202 | 0.286 | 0.074 | Neuro-1 | Papss1 |
| Papola | 0.601 | 0.334457209 | 0.202 | 0.464 | 0.232 | Neuro-1 | Papola |
| Bdp1 | 0.601 | 0.306372422 | 0.202 | 0.321 | 0.106 | Neuro-1 | Bdp1 |
| Arpc5 | 0.601 | 0.297752962 | 0.202 | 0.464 | 0.249 | Neuro-1 | Arpc5 |

Table 1C. InVivo Cluster 11 (Paneth Cells) vs Top 200 ENR-4
cells (FIG. 1G InVivo vs ENR)

| Gene | p_val | avg_diff | pct.1 | pct.2 |
|---|---|---|---|---|
| Defa22 | 4.37E−141 | 2.971300119 | 1 | 0.625 |
| Defa21 | 4.13E−135 | 2.928723434 | 1 | 0.765 |
| Fabp6 | 3.29E−71 | 2.794414465 | 0.799 | 0 |
| Apoa1 | 5.19E−41 | 2.167526278 | 0.735 | 0.125 |
| Defa20 | 3.41E−48 | 2.136944081 | 0.635 | 0.005 |
| Gm26924 | 9.46E−139 | 2.121543914 | 1 | 0.915 |
| Gm15564 | 2.05E−61 | 2.024788068 | 0.878 | 0.135 |
| Zg16 | 6.80E−23 | 1.974431612 | 0.471 | 0.045 |
| Mptx2 | 1.38E−45 | 1.946653592 | 0.788 | 0.095 |
| Reg3b | 1.46E−29 | 1.895225306 | 0.561 | 0.055 |
| Gm15292 | 4.85E−66 | 1.843395367 | 0.952 | 0.37 |
| Reg3g | 7.87E−34 | 1.734499905 | 0.608 | 0.07 |
| Defa26 | 1.30E−81 | 1.67834991 | 0.995 | 0.855 |
| Defa5 | 6.75E−34 | 1.665483508 | 0.698 | 0.13 |
| Clec2h | 5.66E−38 | 1.665239259 | 0.545 | 0.01 |
| Chd8 | 6.88E−16 | 1.658113819 | 0.36 | 0.04 |
| mmu-mir-6236 | 1.22E−42 | 1.641473397 | 0.587 | 0.005 |
| Lyz1 | 4.54E−77 | 1.581447916 | 1 | 0.93 |
| Fabp2 | 8.63E−37 | 1.546973338 | 0.942 | 0.625 |
| Pnliprp2 | 5.32E−41 | 1.520921921 | 0.878 | 0.32 |
| Defa-rs7 | 3.06E−38 | 1.513071859 | 0.841 | 0.43 |
| Defa2 | 3.22E−37 | 1.503489671 | 0.508 | 0 |
| Ang4 | 3.92E−75 | 1.496055114 | 1 | 0.765 |
| Gm21002 | 2.36E−33 | 1.443051807 | 0.466 | 0 |
| Gm15293 | 2.15E−38 | 1.41558284 | 0.852 | 0.23 |
| Spink3 | 3.43E−25 | 1.412229842 | 0.481 | 0.04 |
| Sepp1 | 5.17E−20 | 1.367808281 | 0.524 | 0.12 |
| Anpep | 2.20E−26 | 1.322268451 | 0.524 | 0.05 |
| Gm10104 | 1.62E−42 | 1.264917901 | 0.979 | 0.63 |
| Crip1 | 1.59E−31 | 1.157051096 | 0.894 | 0.45 |
| Lbh | 2.73E−22 | 1.145440013 | 0.487 | 0.06 |
| Gm15308 | 2.36E−33 | 1.12386933 | 0.466 | 0 |
| Lars2 | 8.64E−33 | 1.09806747 | 0.91 | 0.56 |
| Ccl6 | 6.02E−31 | 1.024182325 | 0.905 | 0.385 |
| Mptx1 | 4.76E−12 | 0.992620758 | 0.413 | 0.095 |
| Slc51a | 2.21E−16 | 0.984051209 | 0.28 | 0.005 |
| Bambi | 7.58E−17 | 0.977064848 | 0.37 | 0.04 |
| Krt20 | 1.39E−16 | 0.972788693 | 0.36 | 0.04 |
| Clca3 | 2.99E−10 | 0.967743346 | 0.19 | 0.015 |
| Defa3 | 2.92E−37 | 0.952791523 | 0.989 | 0.835 |
| Gm15315 | 2.21E−26 | 0.943824914 | 0.974 | 0.65 |
| Hpgd | 7.14E−18 | 0.879485606 | 0.439 | 0.065 |
| Lyz2 | 1.21E−19 | 0.849112831 | 0.804 | 0.345 |
| Plb1 | 3.74E−13 | 0.787790121 | 0.206 | 0 |
| Atf3 | 7.30E−10 | 0.767720706 | 0.444 | 0.155 |
| Fos | 3.10E−14 | 0.760694898 | 0.788 | 0.42 |
| Nupr1 | 9.01E−14 | 0.75178466 | 0.741 | 0.365 |
| Apoa4 | 1.54E−07 | 0.744899359 | 0.286 | 0.075 |
| St3gal4 | 2.78E−11 | 0.744187874 | 0.317 | 0.07 |
| Gm7849 | 2.39E−11 | 0.737872833 | 0.386 | 0.095 |
| Slc6a19 | 6.56E−12 | 0.73638031 | 0.169 | 0.01 |
| Naaladl1 | 1.42E−11 | 0.727332221 | 0.212 | 0.005 |
| Guca2b | 1.29E−16 | 0.708643403 | 0.804 | 0.385 |
| Pepd | 4.24E−08 | 0.701308814 | 0.228 | 0.04 |
| Muc3 | 1.02E−11 | 0.689025992 | 0.185 | 0 |
| Ace2 | 2.99E−10 | 0.6808095 | 0.233 | 0.03 |
| Dpep1 | 1.28E−09 | 0.666476273 | 0.153 | 0 |

TABLE 1-continued

Derived gene list of the top defining genes from in vivo ileal
small intestine PCs and EECs captured on the Seq-Well platform

| | | | | |
|---|---|---|---|---|
| Sgk1 | 2.33E−15 | 0.654045271 | 0.238 | 0 |
| Tram1 | 5.74E−13 | 0.651849688 | 0.54 | 0.2 |
| Enpep | 5.00E−10 | 0.65108564 | 0.19 | 0.01 |
| Nucb2 | 4.31E−12 | 0.650267512 | 0.386 | 0.08 |
| Slc15a1 | 6.19E−09 | 0.643708175 | 0.143 | 0 |
| Reg4 | 6.58E−13 | 0.638836262 | 0.899 | 0.695 |
| Cndp2 | 2.65E−08 | 0.629322791 | 0.238 | 0.035 |
| Trp53inp1 | 1.08E−13 | 0.620023867 | 0.249 | 0.015 |
| Habp2 | 6.60E−11 | 0.612716764 | 0.402 | 0.105 |
| AY761185 | 7.79E−13 | 0.605913705 | 0.974 | 0.91 |
| 2010106E10Rik | 2.82E−09 | 0.604128191 | 0.148 | 0 |
| Mep1b | 4.15E−07 | 0.602377603 | 0.206 | 0.03 |
| Ggh | 6.28E−14 | 0.595102485 | 0.392 | 0.08 |
| Maf | 6.42E−08 | 0.592753887 | 0.127 | 0 |
| 2200002D01Rik | 1.12E−05 | 0.591231351 | 0.481 | 0.27 |
| Qsox1 | 5.34E−10 | 0.588808803 | 0.455 | 0.15 |
| Lct | 1.26E−05 | 0.57120206 | 0.138 | 0.015 |
| Fosb | 6.76E−11 | 0.560028909 | 0.323 | 0.065 |
| Ace | 6.42E−08 | 0.554965613 | 0.127 | 0 |
| Tmigd1 | 6.19E−09 | 0.55155353 | 0.143 | 0 |
| Ccl5 | 1.39E−07 | 0.544612494 | 0.122 | 0 |
| Cyp4f14 | 3.06E−07 | 0.526821249 | 0.233 | 0.045 |
| Slc27a4 | 9.26E−05 | 0.517682324 | 0.169 | 0.035 |
| Agpat2 | 3.38E−07 | 0.516384527 | 0.175 | 0.02 |
| Slc9a3r1 | 5.69E−07 | 0.513423379 | 0.27 | 0.075 |
| Snord13 | 8.67E−08 | 0.510552511 | 0.402 | 0.15 |
| Muc2 | 1.39E−11 | 0.509630225 | 0.661 | 0.305 |
| Gm10936 | 1.97E−12 | 0.509271194 | 0.196 | 0 |
| Slc5a1 | 6.57E−08 | 0.50910138 | 0.36 | 0.115 |
| Sult1d1 | 2.87E−12 | 0.50864725 | 0.36 | 0.1 |
| Aoc1 | 4.26E−05 | 0.506515765 | 0.222 | 0.06 |
| Ggt1 | 5.66E−08 | 0.50249154 | 0.159 | 0.02 |
| Maoa | 7.11E−06 | 0.502189218 | 0.302 | 0.105 |
| Mpp1 | 2.26E−06 | 0.499008165 | 0.148 | 0.015 |
| Specc1l | 3.33E−06 | 0.489499836 | 0.196 | 0.035 |
| Acox1 | 2.64E−09 | 0.487666729 | 0.201 | 0.04 |
| P4hb | 2.80E−10 | 0.486750375 | 0.889 | 0.71 |
| Apob | 0.002443035 | 0.485889273 | 0.206 | 0.08 |
| Serpinb1a | 2.36E−05 | 0.485316763 | 0.37 | 0.155 |
| Herpud1 | 1.64E−11 | 0.482518432 | 0.487 | 0.175 |
| Smim22 | 0.000134645 | 0.480130631 | 0.27 | 0.1 |
| n-R5-8s1 | 5.18E−11 | 0.477213392 | 0.175 | 0 |
| Tmem59 | 1.72E−10 | 0.474309308 | 0.54 | 0.225 |
| Smim14 | 4.75E−12 | 0.471404187 | 0.508 | 0.185 |
| Sel1l | 9.55E−10 | 0.46843993 | 0.339 | 0.09 |
| Cd74 | 2.91E−06 | 0.467581391 | 0.101 | 0 |
| Mmp7 | 8.54E−12 | 0.462845043 | 0.958 | 0.78 |
| Dnajc3 | 3.31E−08 | 0.459761476 | 0.529 | 0.24 |
| Agt | 1.53E−07 | 0.453836347 | 0.185 | 0.025 |
| Gm14850 | 2.84E−06 | 0.453763771 | 0.794 | 0.565 |
| Slc51b | 1.91E−06 | 0.453513929 | 0.127 | 0.005 |
| Tmem120a | 3.51E−07 | 0.45153161 | 0.127 | 0.01 |
| Rpl41 | 4.20E−10 | 0.450732693 | 0.825 | 0.71 |
| Gm1123 | 2.93E−09 | 0.448735633 | 0.73 | 0.415 |
| Cdh17 | 2.98E−08 | 0.447834443 | 0.471 | 0.21 |
| Dgat1 | 7.71E−09 | 0.447274671 | 0.259 | 0.065 |
| Apoc3 | 0.000902415 | 0.441130264 | 0.18 | 0.055 |
| Xpnpep2 | 0.001543925 | 0.439544921 | 0.106 | 0.02 |
| Egr1 | 4.63E−06 | 0.428981363 | 0.524 | 0.3 |
| Dnajb1 | 5.76E−05 | 0.423553841 | 0.132 | 0.015 |
| Prr15 | 3.91E−10 | 0.422498409 | 0.392 | 0.125 |
| Tob1 | 2.30E−08 | 0.421001312 | 0.328 | 0.1 |
| Rfk | 4.62E−06 | 0.419983828 | 0.36 | 0.15 |
| Cap1 | 7.01E−05 | 0.414248403 | 0.19 | 0.055 |
| Gdpd1 | 1.85E−06 | 0.406359879 | 0.302 | 0.1 |
| Mep1a | 3.50E−07 | 0.405859626 | 0.138 | 0.005 |
| Klf6 | 3.56E−07 | 0.405271351 | 0.349 | 0.135 |
| H2-Q2 | 0.000259328 | 0.404634689 | 0.175 | 0.045 |
| Amn | 3.35E−05 | 0.404149314 | 0.138 | 0.025 |
| Galnt3 | 0.000191936 | 0.403926453 | 0.185 | 0.05 |
| Ell2 | 1.30E−08 | 0.40366623 | 0.254 | 0.05 |
| Car4 | 2.91E−06 | 0.403314629 | 0.101 | 0 |
| Hsd17b11 | 0.002400711 | 0.402198995 | 0.153 | 0.055 |
| Muc13 | 1.30E−07 | 0.401509767 | 0.651 | 0.38 |
| Lamp1 | 1.96E−09 | 0.401141149 | 0.46 | 0.195 |
| Tspan1 | 1.41E−07 | 0.400356554 | 0.582 | 0.295 |
| Pim3 | 2.72E−09 | 0.39587135 | 0.286 | 0.065 |

TABLE 1-continued

Derived gene list of the top defining genes from in vivo ileal
small intestine PCs and EECs captured on the Seq-Well platform

| | | | | |
|---|---|---|---|---|
| Mcfd2 | 9.13E-07 | 0.392218274 | 0.27 | 0.075 |
| Gfpt1 | 3.45E-07 | 0.387017679 | 0.434 | 0.195 |
| Uba5 | 2.36E-12 | 0.385892816 | 0.265 | 0.04 |
| Mgat4c | 2.91E-06 | 0.381944744 | 0.101 | 0 |
| Dap | 1.11E-09 | 0.375080268 | 0.312 | 0.085 |
| Ahnak | 0.000128755 | 0.374612673 | 0.106 | 0.025 |
| Xpnpep1 | 7.27E-06 | 0.374399986 | 0.206 | 0.05 |
| Slc30a2 | 9.59E-11 | 0.373579233 | 0.201 | 0.015 |
| Tapbp | 0.011259039 | 0.367549589 | 0.138 | 0.045 |
| Vil1 | 1.34E-05 | 0.366379599 | 0.45 | 0.235 |
| Arf6 | 6.40E-06 | 0.363901601 | 0.265 | 0.085 |
| Ano6 | 2.26E-06 | 0.362532519 | 0.19 | 0.04 |
| Ifngr2 | 8.01E-06 | 0.358845113 | 0.201 | 0.045 |
| Cobl | 5.71E-05 | 0.356541596 | 0.18 | 0.04 |
| Galnt5 | 1.93E-06 | 0.351590655 | 0.169 | 0.025 |
| Creb3l3 | 0.000415311 | 0.350252677 | 0.111 | 0.02 |
| Dio1 | 2.65E-10 | 0.350121362 | 0.175 | 0.005 |
| Naip5 | 0.000142433 | 0.348866348 | 0.106 | 0.01 |
| Sult2b1 | 0.000270839 | 0.348098073 | 0.101 | 0.015 |
| Sox9 | 7.43E-06 | 0.344985408 | 0.333 | 0.13 |
| Mlx | 4.37E-05 | 0.344789164 | 0.18 | 0.04 |
| Tmem54 | 0.000506993 | 0.344438204 | 0.18 | 0.05 |
| Mgam | 0.000123288 | 0.343745106 | 0.402 | 0.215 |
| Btg2 | 0.000121852 | 0.341475665 | 0.312 | 0.135 |
| Smpdl3a | 4.57E-08 | 0.341385732 | 0.175 | 0.03 |
| Lman1 | 5.05E-09 | 0.33990403 | 0.397 | 0.175 |
| Jun | 0.000267656 | 0.338610563 | 0.672 | 0.49 |
| Mia3 | 1.69E-06 | 0.335872209 | 0.302 | 0.11 |
| Surf4 | 3.77E-08 | 0.333373357 | 0.402 | 0.16 |
| Cdhr2 | 0.000143206 | 0.333323199 | 0.217 | 0.07 |
| Chka | 0.038995206 | 0.333035923 | 0.127 | 0.05 |
| Itm2c | 3.77E-06 | 0.326377206 | 0.196 | 0.04 |
| Abhd2 | 3.70E-05 | 0.326335546 | 0.201 | 0.06 |
| Gorasp2 | 2.51E-05 | 0.325246575 | 0.201 | 0.065 |
| Pdxdc1 | 2.12E-06 | 0.325063024 | 0.275 | 0.11 |
| Psmb10 | 2.49E-05 | 0.324199131 | 0.243 | 0.09 |
| Gm24601 | 2.82E-09 | 0.323704332 | 0.148 | 0 |
| Uggt1 | 0.000114071 | 0.32358108 | 0.196 | 0.055 |
| Iqgap2 | 0.000868689 | 0.322731261 | 0.116 | 0.02 |
| Mogat2 | 0.003938893 | 0.322648461 | 0.106 | 0.02 |
| Fahd1 | 0.000260504 | 0.322487688 | 0.148 | 0.035 |
| Slc43a2 | 8.66E-08 | 0.322337795 | 0.143 | 0.01 |
| Rnf128 | 4.69E-09 | 0.321252309 | 0.503 | 0.235 |
| Slc35b1 | 0.000272326 | 0.319967392 | 0.302 | 0.14 |
| Ube2q1 | 7.73E-05 | 0.319246074 | 0.111 | 0.02 |
| Id3 | 0.001645875 | 0.318742649 | 0.169 | 0.07 |
| Gna11 | 0.003336519 | 0.317578908 | 0.201 | 0.08 |
| Ms4a8a | 0.006912337 | 0.316318026 | 0.143 | 0.05 |
| Cdx1 | 2.57E-06 | 0.312896649 | 0.354 | 0.155 |
| Asph | 5.44E-08 | 0.311566443 | 0.386 | 0.155 |
| Sis | 0.001703562 | 0.310173334 | 0.439 | 0.265 |
| Atg7 | 0.00413282 | 0.308839601 | 0.132 | 0.04 |
| Prpsap1 | 0.043738471 | 0.307741514 | 0.148 | 0.07 |
| Gucy2c | 4.20E-06 | 0.307721748 | 0.212 | 0.06 |
| Klf4 | 0.000604214 | 0.30710746 | 0.233 | 0.095 |
| Ilvbl | 0.000887904 | 0.304942158 | 0.111 | 0.02 |
| Ubl3 | 9.61E-07 | 0.303993675 | 0.302 | 0.11 |
| Aqp1 | 9.45E-05 | 0.30070659 | 0.291 | 0.13 |
| Sppl2a | 1.40E-09 | 0.300006334 | 0.36 | 0.125 |
| Il17rc | 0.001566829 | 0.298723577 | 0.106 | 0.02 |
| Itm2b | 3.19E-08 | 0.295962793 | 0.571 | 0.33 |
| Faah | 0.012089429 | 0.295046927 | 0.111 | 0.03 |
| Creld2 | 0.001229486 | 0.294560522 | 0.169 | 0.06 |
| Ndfip1 | 7.03E-07 | 0.291913484 | 0.175 | 0.03 |
| Osbpl2 | 5.11E-05 | 0.291474585 | 0.143 | 0.025 |
| Krt19 | 0.000106004 | 0.288785016 | 0.63 | 0.475 |
| Ces2e | 0.000691047 | 0.288567477 | 0.27 | 0.15 |
| Edem1 | 5.75E-08 | 0.288168169 | 0.243 | 0.06 |
| Slc13a1 | 0.000142059 | 0.286560678 | 0.101 | 0.005 |
| Nucb1 | 5.67E-08 | 0.286046342 | 0.323 | 0.14 |
| Alpi | 0.000522112 | 0.285914771 | 0.101 | 0.02 |
| Arfgap3 | 2.29E-07 | 0.284604745 | 0.328 | 0.135 |
| Ghr | 7.96E-07 | 0.282348463 | 0.111 | 0.015 |
| Ckmt1 | 0.003470725 | 0.282030097 | 0.296 | 0.15 |
| Galnt4 | 1.13E-05 | 0.279673278 | 0.185 | 0.04 |
| Erlin2 | 7.55E-07 | 0.279047894 | 0.127 | 0.015 |
| Erp44 | 5.53E-06 | 0.278446677 | 0.265 | 0.1 |

TABLE 1-continued

Derived gene list of the top defining genes from in vivo ileal
small intestine PCs and EECs captured on the Seq-Well platform

| | | | | |
|---|---|---|---|---|
| Tulp4 | 3.17E−08 | 0.277590145 | 0.243 | 0.07 |
| Nlrc4 | 8.78E−05 | 0.277361037 | 0.159 | 0.04 |
| Defa25 | 0.000529513 | 0.276550267 | 0.185 | 0.06 |
| Samd5 | 1.46E−07 | 0.276534496 | 0.143 | 0.005 |
| Mttp | 0.002099111 | 0.276373894 | 0.18 | 0.09 |
| Tm9sf3 | 1.69E−05 | 0.276308422 | 0.614 | 0.41 |
| Pllp | 2.46E−06 | 0.276273409 | 0.159 | 0.02 |
| Tmprss2 | 9.22E−11 | 0.274430929 | 0.439 | 0.185 |
| Cox7a1 | 0.000591463 | 0.272661291 | 0.106 | 0.025 |
| Me2 | 0.001469951 | 0.272428052 | 0.254 | 0.12 |
| Slc41a1 | 1.32E−05 | 0.272322566 | 0.116 | 0.005 |
| Sult1b1 | 0.052418679 | 0.272261175 | 0.153 | 0.07 |
| Zzef1 | 0.04064896 | 0.271587691 | 0.101 | 0.03 |
| Zcchc6 | 0.005104942 | 0.27126706 | 0.143 | 0.045 |
| Pls1 | 1.18E−05 | 0.271040751 | 0.312 | 0.165 |
| Wnt3 | 1.91E−06 | 0.270361588 | 0.217 | 0.065 |
| Dpp4 | 0.013324936 | 0.269524372 | 0.175 | 0.08 |
| Spop | 6.48E−05 | 0.268255044 | 0.243 | 0.09 |
| Mtus1 | 5.54E−05 | 0.268190034 | 0.159 | 0.035 |
| Rsrc2 | 3.03E−05 | 0.26619444 | 0.212 | 0.065 |
| Lsm2 | 0.011241648 | 0.266112529 | 0.111 | 0.045 |
| Tm9sf2 | 2.80E−06 | 0.26578344 | 0.333 | 0.15 |
| Cast | 1.67E−06 | 0.265356048 | 0.19 | 0.045 |
| Serpinb6a | 2.25E−05 | 0.265321679 | 0.349 | 0.17 |
| B2m | 1.22E−07 | 0.265294692 | 0.624 | 0.37 |
| Usp4 | 0.047805332 | 0.264431871 | 0.122 | 0.055 |
| Chpt1 | 0.00051801 | 0.263791385 | 0.122 | 0.03 |
| Lasp1 | 0.002783276 | 0.261137016 | 0.175 | 0.065 |
| 0610007N19Rik | 4.63E−05 | 0.260238033 | 0.254 | 0.095 |
| Bex1 | 0.000128886 | 0.258681196 | 0.217 | 0.075 |
| Tsc22d3 | 0.000742124 | 0.258389596 | 0.106 | 0.015 |
| Becn1 | 0.019633687 | 0.258366841 | 0.138 | 0.075 |
| Rab11fip1 | 0.000104016 | 0.257750496 | 0.175 | 0.05 |
| Coro2a | 0.069057442 | 0.257080355 | 0.138 | 0.06 |
| Epb4.1l3 | 0.102862223 | 0.256648972 | 0.138 | 0.065 |
| Sord | 1.84E−05 | 0.256495779 | 0.365 | 0.175 |
| Mgat4a | 1.70E−07 | 0.256129885 | 0.175 | 0.05 |
| Jup | 0.000332364 | 0.255734102 | 0.159 | 0.06 |
| Itch | 0.000553636 | 0.255632 | 0.159 | 0.045 |
| Adipor2 | 0.000133973 | 0.255453283 | 0.249 | 0.1 |
| Aftph | 0.000228287 | 0.254680924 | 0.143 | 0.03 |
| Pdcd4 | 0.000306405 | 0.254674262 | 0.312 | 0.16 |
| Golph3 | 0.000415686 | 0.253598707 | 0.148 | 0.04 |
| Chdh | 0.00055323 | 0.25303635 | 0.111 | 0.02 |
| Erbb2ip | 2.04E−05 | 0.253005599 | 0.212 | 0.065 |
| Hspa5 | 1.23E−06 | 0.252047696 | 0.841 | 0.595 |
| Fam174b | 3.11E−07 | 0.251850066 | 0.222 | 0.06 |
| Azin1 | 5.36E−08 | 0.25153542 | 0.228 | 0.07 |
| Ufl1 | 0.002157661 | 0.251488874 | 0.164 | 0.06 |
| Ndufa3 | 9.12E−05 | 0.251323466 | 0.392 | 0.225 |
| Cdhr5 | 8.38E−06 | 0.251201316 | 0.307 | 0.145 |
| Rpl27 | 0.127703322 | −0.255954126 | 0.058 | 0.12 |
| Trappc1 | 0.0057506 | −0.25942388 | 0.053 | 0.105 |
| Coro1b | 0.048898712 | −0.260140134 | 0.111 | 0.165 |
| Rtn3 | 1.62E−09 | −0.263284381 | 0.249 | 0.18 |
| Xpot | 0.08381105 | −0.263596897 | 0.053 | 0.105 |
| Ptp4a2 | 1.67E−08 | −0.264228486 | 0.349 | 0.265 |
| Kcnq1 | 0.161443028 | −0.272560147 | 0.085 | 0.14 |
| Rpl34 | 3.84E−07 | −0.2732009 | 0.667 | 0.73 |
| Psmb7 | 0.063524749 | −0.280529908 | 0.037 | 0.105 |
| Kif5b | 6.88E−09 | −0.281414188 | 0.386 | 0.295 |
| Smarcb1 | 0.014359485 | −0.289993549 | 0.042 | 0.12 |
| Marcks | 0.037513635 | −0.293336842 | 0.079 | 0.13 |
| Fau | 0.041224122 | −0.293696089 | 0.159 | 0.22 |
| Mlf2 | 0.012682846 | −0.297165151 | 0.132 | 0.185 |
| Gm7589 | 0.010202787 | −0.297802749 | 0.053 | 0.115 |
| Ppp1r14d | 0.002510985 | −0.301894835 | 0.138 | 0.19 |
| Srebf2 | 0.008271236 | −0.310036738 | 0.048 | 0.11 |
| Mpdu1 | 0.000543468 | −0.313369273 | 0.058 | 0.115 |
| Dpy30 | 0.006589504 | −0.313641409 | 0.122 | 0.185 |
| Slc29a1 | 0.000912654 | −0.318739334 | 0.048 | 0.11 |
| Nono | 0.012584766 | −0.319001563 | 0.079 | 0.16 |
| Dbnl | 0.014534277 | −0.3229847 | 0.053 | 0.12 |
| Tagln2 | 0.000294237 | −0.325409509 | 0.238 | 0.295 |
| Esrp1 | 0.016142497 | −0.331057179 | 0.074 | 0.125 |
| Car9 | 0.004265633 | −0.331187058 | 0.063 | 0.125 |
| Drg1 | 0.023481733 | −0.332309493 | 0.074 | 0.14 |

TABLE 1-continued

Derived gene list of the top defining genes from in vivo ileal
small intestine PCs and EECs captured on the Seq-Well platform

| | | | | |
|---|---|---|---|---|
| Spr | 0.012739204 | −0.333206136 | 0.074 | 0.135 |
| Rsbn1l | 0.036794841 | −0.339510977 | 0.058 | 0.11 |
| Dars | 0.002015536 | −0.339945586 | 0.095 | 0.16 |
| Sin3b | 0.010991341 | −0.340271235 | 0.069 | 0.135 |
| Gm15299 | 0.000939182 | −0.341600428 | 0.873 | 0.93 |
| Ndufa12 | 0.006525634 | −0.342054107 | 0.222 | 0.29 |
| Huwe1 | 0.001734803 | −0.342766858 | 0.122 | 0.175 |
| Ldlr | 0.001764872 | −0.343292498 | 0.101 | 0.155 |
| 1500011K16Rik | 0.082359853 | −0.347961666 | 0.095 | 0.175 |
| Reep6 | 0.037455675 | −0.348190857 | 0.069 | 0.135 |
| Sdc1 | 0.018810094 | −0.350542057 | 0.042 | 0.115 |
| Adh5 | 0.003478901 | −0.351308036 | 0.127 | 0.185 |
| Krcc1 | 0.00084717 | −0.355527421 | 0.148 | 0.21 |
| Ndufab1 | 0.000336451 | −0.355935419 | 0.212 | 0.275 |
| Myl12a | 0.003503618 | −0.356203714 | 0.233 | 0.285 |
| Mtx2 | 0.002650821 | −0.357088917 | 0.079 | 0.13 |
| Ddx39 | 0.004509039 | −0.359706067 | 0.048 | 0.125 |
| Siva1 | 0.001396691 | −0.360067427 | 0.074 | 0.125 |
| Cnih1 | 0.002652698 | −0.361640512 | 0.069 | 0.135 |
| Ptpla | 0.003697567 | −0.361645865 | 0.069 | 0.155 |
| Csrp2 | 0.001939061 | −0.362818073 | 0.169 | 0.22 |
| Phf5a | 0.000298916 | −0.365855881 | 0.095 | 0.15 |
| Rnaset2b | 0.000421673 | −0.366072338 | 0.053 | 0.11 |
| Cmc1 | 0.009540242 | −0.367479096 | 0.058 | 0.135 |
| Bzw2 | 0.006296271 | −0.368043119 | 0.085 | 0.145 |
| Cct8 | 0.013411026 | −0.368975722 | 0.169 | 0.225 |
| Hspd1 | 5.60E−06 | −0.36940695 | 0.349 | 0.435 |
| Sec61g | 0.001204529 | −0.369587077 | 0.058 | 0.12 |
| Mlxipl | 0.003207373 | −0.369662267 | 0.074 | 0.135 |
| Smc2 | 0.011280986 | −0.370477194 | 0.069 | 0.12 |
| Rps18-ps3 | 0.010664087 | −0.370689313 | 0.079 | 0.16 |
| Hk2 | 0.001735551 | −0.371079347 | 0.042 | 0.115 |
| Rrs1 | 0.012692596 | −0.371114753 | 0.048 | 0.11 |
| Lsm3 | 0.003177197 | −0.372083598 | 0.069 | 0.14 |
| Slc25a4 | 0.019197025 | −0.373137077 | 0.037 | 0.12 |
| Ndufs7 | 1.17E−06 | −0.37455708 | 0.238 | 0.3 |
| Atad2 | 0.021168596 | −0.374980489 | 0.037 | 0.105 |
| Sqle | 0.021315342 | −0.37548791 | 0.085 | 0.155 |
| Nfib | 0.000862975 | −0.376946487 | 0.048 | 0.115 |
| Hist1h1e | 0.012839513 | −0.377323631 | 0.122 | 0.22 |
| Trappc6a | 0.001874064 | −0.377461527 | 0.095 | 0.18 |
| Gm4204 | 0.002031844 | −0.37823936 | 0.026 | 0.115 |
| Cct3 | 0.000292286 | −0.37919542 | 0.18 | 0.24 |
| Cyr61 | 0.000709331 | −0.379718957 | 0.063 | 0.12 |
| Bbip1 | 0.024183248 | −0.380138122 | 0.101 | 0.16 |
| Smim11 | 0.00081875 | −0.380275098 | 0.063 | 0.125 |
| Rbm3 | 0.003354399 | −0.380533039 | 0.063 | 0.12 |
| Pnn | 0.001375366 | −0.380929729 | 0.101 | 0.175 |
| Cyc1 | 1.76E−06 | −0.381028444 | 0.259 | 0.355 |
| Lsm5 | 0.014353946 | −0.381788077 | 0.026 | 0.105 |
| Dtymk | 0.003462617 | −0.382914926 | 0.159 | 0.23 |
| Gpx4 | 0.001236908 | −0.385447789 | 0.085 | 0.17 |
| Prmt1 | 0.005873983 | −0.38737595 | 0.106 | 0.18 |
| Akr1c13 | 0.000615651 | −0.388385966 | 0.143 | 0.21 |
| Phpt1 | 0.001175685 | −0.38875707 | 0.058 | 0.135 |
| Zfp292 | 0.006069326 | −0.389741258 | 0.153 | 0.21 |
| Gm3940 | 0.003149773 | −0.390000209 | 0.021 | 0.105 |
| Ugdh | 0.00203156 | −0.390862375 | 0.111 | 0.17 |
| Cox8a | 6.81E−07 | −0.392352404 | 0.587 | 0.645 |
| Sdhb | 0.003482545 | −0.394556643 | 0.233 | 0.335 |
| S100a6 | 0.000126973 | −0.394972675 | 0.101 | 0.155 |
| Cct4 | 0.000124021 | −0.396040082 | 0.222 | 0.295 |
| Rpl31 | 0.009329667 | −0.396617136 | 0.106 | 0.195 |
| Hint1 | 1.28E−05 | −0.396735031 | 0.635 | 0.71 |
| Ccdc59 | 0.000483844 | −0.398492584 | 0.053 | 0.12 |
| Lss | 0.000507684 | −0.399008959 | 0.021 | 0.105 |
| Rps26-ps1 | 0.000324404 | −0.399038177 | 0.132 | 0.185 |
| Snrpd2 | 0.000284499 | −0.399355159 | 0.201 | 0.29 |
| Eef1e1 | 6.43E−05 | −0.399521435 | 0.069 | 0.125 |
| Gcat | 0.010409293 | −0.400031144 | 0.058 | 0.12 |
| Rbbp7 | 0.000173531 | −0.400052877 | 0.138 | 0.205 |
| Esf1 | 0.001968666 | −0.400652886 | 0.074 | 0.13 |
| Dnajc15 | 0.001562907 | −0.401490758 | 0.079 | 0.15 |
| U2surp | 0.001546117 | −0.402009386 | 0.111 | 0.175 |
| Aqp4 | 0.000123984 | −0.402019345 | 0.053 | 0.125 |
| Cyb5b | 0.000128385 | −0.402989636 | 0.18 | 0.235 |
| Cpox | 0.000314131 | −0.403859864 | 0.037 | 0.105 |

TABLE 1-continued

Derived gene list of the top defining genes from in vivo ileal
small intestine PCs and EECs captured on the Seq-Well platform

| | | | | |
|---|---|---|---|---|
| Tmem97 | 0.000129303 | −0.403971676 | 0.069 | 0.205 |
| Polr2e | 0.000723205 | −0.404438373 | 0.116 | 0.195 |
| Lyar | 0.000849363 | −0.405128888 | 0.085 | 0.145 |
| Gsta1 | 0.008488495 | −0.406214333 | 0.058 | 0.115 |
| Hist1h1b | 0.015463707 | −0.409282642 | 0.053 | 0.14 |
| Ppp1r11 | 0.00076078 | −0.409341331 | 0.074 | 0.15 |
| Mrpl20 | 0.000222405 | −0.4097286 | 0.169 | 0.225 |
| Prap1 | 0.000322123 | −0.410147265 | 0.317 | 0.39 |
| Fus | 0.001200168 | −0.410755506 | 0.153 | 0.225 |
| Galk1 | 0.000966106 | −0.411001986 | 0.042 | 0.14 |
| Actr3 | 0.000472547 | −0.411992211 | 0.243 | 0.325 |
| Shfm1 | 1.16E−06 | −0.412270568 | 0.429 | 0.5 |
| Anp32b | 5.33E−05 | −0.412314848 | 0.249 | 0.32 |
| Dnajc2 | 0.006981482 | −0.413764325 | 0.122 | 0.2 |
| Ddx39b | 2.31E−05 | −0.414727855 | 0.169 | 0.23 |
| Ktn1 | 0.000858275 | −0.414734759 | 0.132 | 0.195 |
| Gm1840 | 6.64E−05 | −0.414910439 | 0.016 | 0.115 |
| Dynlt1a | 0.00069428 | −0.415288469 | 0.021 | 0.12 |
| Mrps26 | 0.000178848 | −0.416003885 | 0.063 | 0.145 |
| Fubp1 | 0.001359574 | −0.416020211 | 0.138 | 0.205 |
| Chchd1 | 0.010693856 | −0.416079298 | 0.122 | 0.19 |
| H2afx | 0.008029842 | −0.417628727 | 0.058 | 0.135 |
| Mrpl40 | 0.007616431 | −0.418501576 | 0.101 | 0.155 |
| Oard1 | 0.000339221 | −0.418575087 | 0.063 | 0.13 |
| Tbca | 0.000688725 | −0.419134115 | 0.159 | 0.21 |
| Taf9 | 7.14E−06 | −0.420752889 | 0.111 | 0.17 |
| Gsto1 | 0.001802233 | −0.420965768 | 0.296 | 0.37 |
| Gsta4 | 0.003632296 | −0.421782008 | 0.048 | 0.12 |
| Park7 | 0.001832937 | −0.422425482 | 0.254 | 0.33 |
| Sssca1 | 0.000453976 | −0.424845578 | 0.032 | 0.105 |
| Esco2 | 0.003298742 | −0.42524584 | 0.026 | 0.11 |
| Cdca8 | 0.015823827 | −0.425969757 | 0.058 | 0.145 |
| Pak1ip1 | 0.001678301 | −0.426570744 | 0.069 | 0.14 |
| Nop56 | 4.45E−05 | −0.427123551 | 0.143 | 0.195 |
| Eif3e | 7.20E−05 | −0.427342463 | 0.212 | 0.265 |
| Tmem261 | 0.002187429 | −0.428519281 | 0.095 | 0.17 |
| Slc1a5 | 2.46E−06 | −0.4287541 | 0.153 | 0.205 |
| 2410006H16Rik | 9.53E−06 | −0.429497157 | 0.471 | 0.55 |
| Lgals2 | 3.38E−16 | −0.43136214 | 0.862 | 0.935 |
| Tpm4 | 0.000105125 | −0.431476714 | 0.111 | 0.19 |
| Pa2g4 | 1.84E−06 | −0.432182506 | 0.344 | 0.395 |
| Pafah1b3 | 0.001454846 | −0.433493801 | 0.138 | 0.21 |
| Tnfrsf12a | 0.00128252 | −0.433556527 | 0.026 | 0.105 |
| Ndufa4 | 1.30E−06 | −0.433746388 | 0.64 | 0.71 |
| Nudcd2 | 0.00058607 | −0.436797764 | 0.085 | 0.145 |
| Glrx3 | 0.000274264 | −0.436973196 | 0.153 | 0.22 |
| Alad | 0.002003834 | −0.437174302 | 0.063 | 0.14 |
| Hsd17b13 | 0.001039365 | −0.437323307 | 0.026 | 0.13 |
| Cnn3 | 8.87E−05 | −0.437469591 | 0.085 | 0.15 |
| Mrps28 | 0.000527309 | −0.437536599 | 0.074 | 0.15 |
| Hspa4 | 0.000168537 | −0.437692081 | 0.196 | 0.265 |
| Gm10073 | 0.004118379 | −0.437808073 | 0.063 | 0.165 |
| Iah1 | 0.001130548 | −0.438405123 | 0.058 | 0.135 |
| Psmb1 | 1.61E−05 | −0.43864532 | 0.402 | 0.46 |
| Gnl3 | 1.56E−05 | −0.438657513 | 0.148 | 0.205 |
| Rpl36-ps3 | 0.000953701 | −0.439253378 | 0.058 | 0.16 |
| Josd2 | 0.001224583 | −0.439700566 | 0.037 | 0.105 |
| Esd | 4.64E−05 | −0.440843374 | 0.243 | 0.33 |
| 0610009B22Rik | 2.00E−06 | −0.443812702 | 0.042 | 0.115 |
| Gm17430 | 6.18E−05 | −0.443838706 | 0.063 | 0.125 |
| Trim27 | 0.00016397 | −0.44496242 | 0.048 | 0.125 |
| Smoc2 | 0.001514418 | −0.4451081 | 0.238 | 0.32 |
| Sepw1 | 0.000502909 | −0.445526261 | 0.132 | 0.195 |
| Mrpl12 | 1.09E−07 | −0.445549068 | 0.254 | 0.325 |
| Pfkp | 0.000561123 | −0.446513952 | 0.058 | 0.14 |
| Nasp | 0.012646494 | −0.446850026 | 0.063 | 0.145 |
| Ndufa2 | 1.42E−09 | −0.447289951 | 0.36 | 0.435 |
| Set | 3.66E−06 | −0.448964645 | 0.169 | 0.29 |
| Polr3k | 0.005121693 | −0.449065307 | 0.079 | 0.16 |
| Eif3i | 6.32E−08 | −0.449706207 | 0.291 | 0.395 |
| Mrpl28 | 0.000553959 | −0.450265998 | 0.143 | 0.215 |
| Polr2g | 2.63E−05 | −0.452332415 | 0.063 | 0.135 |
| Atf5 | 1.08E−06 | −0.452393729 | 0 | 0.11 |
| Slc25a39 | 0.00010006 | −0.453722911 | 0.138 | 0.205 |
| Rpl39 | 2.49E−13 | −0.453761377 | 0.741 | 0.8 |
| Commd3 | 0.000307934 | −0.454288259 | 0.101 | 0.165 |
| Mrps10 | 0.002572342 | −0.455359878 | 0.021 | 0.11 |

TABLE 1-continued

Derived gene list of the top defining genes from in vivo ileal
small intestine PCs and EECs captured on the Seq-Well platform

| | | | | |
|---|---|---|---|---|
| Dazap1 | 3.16E−05 | −0.455370577 | 0.074 | 0.16 |
| Tstd1 | 0.001212988 | −0.455430685 | 0.106 | 0.175 |
| Ahcy | 3.72E−05 | −0.45666475 | 0.122 | 0.205 |
| Cox7a2l | 1.48E−05 | −0.456700532 | 0.27 | 0.38 |
| 1190007I07Rik | 0.000250159 | −0.456781329 | 0.058 | 0.145 |
| Hspa8 | 1.80E−09 | −0.458268807 | 0.651 | 0.725 |
| Atp5j2 | 1.95E−09 | −0.459501596 | 0.54 | 0.655 |
| Uqcrh | 9.19E−10 | −0.460044483 | 0.54 | 0.64 |
| Atp6v1f | 6.68E−07 | −0.460322844 | 0.169 | 0.255 |
| Tyms | 0.003364971 | −0.461312009 | 0.079 | 0.16 |
| Birc5 | 0.002080218 | −0.461323711 | 0.037 | 0.135 |
| 1810009A15Rik | 0.000873289 | −0.462298376 | 0.085 | 0.145 |
| Nhp2l1 | 0.000111665 | −0.462353491 | 0.021 | 0.135 |
| Acss2 | 0.001170604 | −0.462378608 | 0.042 | 0.135 |
| Cth | 0.000374245 | −0.463058297 | 0.069 | 0.155 |
| mt-Co3 | 1.81E−05 | −0.464537778 | 0.365 | 0.465 |
| Gm2000 | 0.000231137 | −0.465125929 | 0.228 | 0.34 |
| Cotl1 | 4.82E−05 | −0.465958007 | 0.116 | 0.195 |
| Acp1 | 0.000155081 | −0.467085333 | 0.058 | 0.135 |
| Gm15013 | 7.05E−06 | −0.468197025 | 0.011 | 0.105 |
| Slc35b2 | 2.61E−06 | −0.46848618 | 0.074 | 0.125 |
| Rps3a3 | 0.000817177 | −0.468723482 | 0.069 | 0.2 |
| Sltm | 0.000349106 | −0.46911727 | 0.111 | 0.18 |
| Hn1 | 1.86E−05 | −0.469390434 | 0.196 | 0.27 |
| Eef1g | 1.00E−08 | −0.469750373 | 0.444 | 0.53 |
| Asns | 9.62E−05 | −0.471303481 | 0.19 | 0.275 |
| Tpsg1 | 0.000363266 | −0.471901739 | 0.048 | 0.13 |
| Dak | 0.007874916 | −0.472124737 | 0.09 | 0.18 |
| Gm16477 | 1.08E−06 | −0.472565431 | 0 | 0.11 |
| Ndufv2 | 7.09E−07 | −0.473290774 | 0.243 | 0.365 |
| 1110004F10Rik | 9.58E−05 | −0.474609204 | 0.095 | 0.155 |
| Gng5 | 3.09E−06 | −0.479960246 | 0.164 | 0.245 |
| Ndufaf2 | 0.004110958 | −0.479975335 | 0.069 | 0.135 |
| Ndufa13 | 1.66E−07 | −0.48083147 | 0.402 | 0.49 |
| Gm23061 | 7.14E−06 | −0.482775907 | 0.016 | 0.125 |
| Shmt2 | 8.01E−05 | −0.483080489 | 0.074 | 0.16 |
| Gm10076 | 1.72E−10 | −0.484503743 | 0.45 | 0.56 |
| Cdca3 | 6.36E−05 | −0.484624632 | 0.042 | 0.125 |
| Cbx5 | 4.00E−05 | −0.485128427 | 0.111 | 0.215 |
| Eif3f | 1.43E−06 | −0.485424802 | 0.296 | 0.385 |
| Pck2 | 0.000208141 | −0.485540607 | 0.053 | 0.145 |
| Eprs | 6.89E−08 | −0.485931753 | 0.228 | 0.29 |
| Gm10020 | 0.000108183 | −0.487004123 | 0.016 | 0.105 |
| Tecr | 3.14E−05 | −0.487182978 | 0.138 | 0.2 |
| Rangap1 | 0.000162202 | −0.487612162 | 0.095 | 0.155 |
| Tmem205 | 0.000121965 | −0.487850162 | 0.101 | 0.185 |
| Nop58 | 0.000225767 | −0.489454013 | 0.206 | 0.29 |
| Pcna-ps2 | 8.85E−06 | −0.489873887 | 0.005 | 0.11 |
| Pklr | 0.002367444 | −0.491970544 | 0.058 | 0.15 |
| Lsm4 | 9.53E−05 | −0.492705301 | 0.233 | 0.315 |
| Atp5l | 0.000539431 | −0.49273644 | 0.101 | 0.205 |
| Gstm1 | 0.000272395 | −0.493816218 | 0.026 | 0.145 |
| Psmd7 | 1.48E−06 | −0.493969285 | 0.164 | 0.22 |
| Fh1 | 0.000202604 | −0.49442165 | 0.095 | 0.17 |
| Tmsb4x | 4.43E−11 | −0.49479822 | 0.651 | 0.79 |
| Fgfbp1 | 0.000750633 | −0.495437365 | 0.085 | 0.18 |
| Atf4 | 2.88E−07 | −0.496445223 | 0.36 | 0.46 |
| Areg | 0.000275857 | −0.49685122 | 0.053 | 0.17 |
| Fcf1 | 0.000162147 | −0.497021273 | 0.058 | 0.12 |
| Mrpl51 | 7.33E−06 | −0.497538972 | 0.095 | 0.165 |
| Smchd1 | 0.002305186 | −0.498378269 | 0.053 | 0.12 |
| Polr2j | 0.000684831 | −0.498673938 | 0.111 | 0.185 |
| Pfkl | 6.73E−05 | −0.499634165 | 0.042 | 0.135 |
| Prdx6 | 4.07E−06 | −0.500505721 | 0.249 | 0.33 |
| Cyb5 | 3.57E−05 | −0.500808599 | 0.228 | 0.305 |
| Ankrd11 | 0.002369846 | −0.501490943 | 0.085 | 0.185 |
| Eif4a1 | 2.86E−06 | −0.501859788 | 0.28 | 0.37 |
| Naa38 | 3.74E−05 | −0.502212809 | 0.069 | 0.195 |
| Magoh | 0.000587613 | −0.502865808 | 0.159 | 0.26 |
| Wdr18 | 0.001085917 | −0.503215799 | 0.032 | 0.12 |
| Srsf7 | 2.81E−05 | −0.50490254 | 0.18 | 0.28 |
| Smc4 | 8.64E−06 | −0.505173492 | 0.132 | 0.185 |
| Gstt2 | 0.000561655 | −0.506462769 | 0.063 | 0.175 |
| Cdk1 | 0.000146053 | −0.508137557 | 0.021 | 0.14 |
| Rps21 | 5.63E−12 | −0.509661685 | 0.725 | 0.84 |
| Psma2 | 7.00E−07 | −0.509671402 | 0.354 | 0.425 |
| Cetn3 | 0.000326123 | −0.50981447 | 0.164 | 0.245 |

TABLE 1-continued

Derived gene list of the top defining genes from in vivo ileal
small intestine PCs and EECs captured on the Seq-Well platform

| | | | | |
|---|---|---|---|---|
| Rps18 | 4.49E−15 | −0.51110149 | 0.788 | 0.91 |
| Gm11808 | 5.65E−05 | −0.511808741 | 0.069 | 0.18 |
| Cldn4 | 1.30E−07 | −0.51370029 | 0.153 | 0.22 |
| Pdk1 | 3.35E−05 | −0.513914438 | 0.032 | 0.15 |
| Rpl21 | 7.70E−06 | −0.513972335 | 0.058 | 0.175 |
| Snrpe | 1.74E−05 | −0.516593931 | 0.238 | 0.34 |
| Gm8444 | 1.08E−06 | −0.51667756 | 0.085 | 0.19 |
| Mrps21 | 1.48E−06 | −0.521055466 | 0.127 | 0.19 |
| Sc4mol | 0.000468775 | −0.521179845 | 0.111 | 0.21 |
| Mki67 | 0.000338076 | −0.522404477 | 0.116 | 0.22 |
| Psma6 | 8.62E−09 | −0.522605652 | 0.228 | 0.305 |
| Gm11273 | 0.00020713 | −0.523567879 | 0.026 | 0.14 |
| Clca4 | 1.14E−05 | −0.523666086 | 0.291 | 0.405 |
| Nars | 6.49E−09 | −0.524789582 | 0.397 | 0.49 |
| Tcp1 | 5.32E−05 | −0.525377019 | 0.19 | 0.3 |
| Polr2f | 1.53E−07 | −0.525945365 | 0.228 | 0.315 |
| Eif3k | 4.38E−07 | −0.526346694 | 0.254 | 0.325 |
| Nap1l1 | 2.19E−05 | −0.527538598 | 0.09 | 0.185 |
| Tomm70a | 9.27E−06 | −0.527579374 | 0.132 | 0.22 |
| Yeats4 | 2.31E−06 | −0.527655223 | 0.058 | 0.12 |
| Stoml2 | 4.16E−05 | −0.527839292 | 0.042 | 0.165 |
| 2810417H13Rik | 0.001607571 | −0.52804929 | 0.101 | 0.185 |
| Hells | 0.000243783 | −0.529360928 | 0.058 | 0.165 |
| Ndufa6 | 1.40E−12 | −0.533999242 | 0.545 | 0.65 |
| AC102758.1 | 2.63E−07 | −0.534923967 | 0 | 0.12 |
| 2700094K13Rik | 0.000512807 | −0.535013337 | 0.09 | 0.205 |
| Pdgfa | 1.19E−05 | −0.536558959 | 0.063 | 0.175 |
| Ndrg1 | 6.05E−08 | −0.537273895 | 0.159 | 0.25 |
| Sf3b5 | 9.20E−05 | −0.537490233 | 0.148 | 0.265 |
| Nucks1 | 1.24E−06 | −0.538891601 | 0.148 | 0.22 |
| Swi5 | 4.77E−08 | −0.541198142 | 0.212 | 0.28 |
| Uqcrb | 7.34E−08 | −0.541280369 | 0.265 | 0.33 |
| Gm10288 | 8.91E−05 | −0.542500756 | 0.058 | 0.17 |
| Hnrnpab | 1.31E−07 | −0.54318878 | 0.302 | 0.375 |
| Slc20a1 | 4.53E−06 | −0.543898499 | 0.021 | 0.165 |
| Cox7b | 2.27E−08 | −0.545343393 | 0.561 | 0.675 |
| Ndufa7 | 2.99E−09 | −0.545820272 | 0.418 | 0.49 |
| Tuba1c | 1.04E−08 | −0.549013752 | 0.265 | 0.325 |
| Rsl1d1 | 6.88E−06 | −0.549358007 | 0.233 | 0.33 |
| mt-Nd6 | 1.16E−05 | −0.549641911 | 0.095 | 0.235 |
| Fcgbp | 5.95E−09 | −0.549750762 | 0.291 | 0.52 |
| Tm4sf20 | 2.84E−05 | −0.549763824 | 0.228 | 0.305 |
| Rbx1 | 3.12E−06 | −0.551654044 | 0.169 | 0.28 |
| Ccnd2 | 4.94E−05 | −0.551933365 | 0.19 | 0.325 |
| Nhp2 | 1.70E−06 | −0.55337121 | 0.196 | 0.29 |
| Eif3m | 5.72E−08 | −0.55339479 | 0.159 | 0.26 |
| Cyp51 | 1.22E−05 | −0.554103319 | 0.138 | 0.23 |
| Ddit4 | 2.46E−06 | −0.555502258 | 0.143 | 0.25 |
| Top2a | 0.001567232 | −0.555561891 | 0.143 | 0.255 |
| BC003965 | 0.000266797 | −0.559685008 | 0.053 | 0.155 |
| Smarcc1 | 2.83E−07 | −0.560608277 | 0.079 | 0.18 |
| Rpl9 | 0.000271667 | −0.561257384 | 0.074 | 0.19 |
| Hspa9 | 1.67E−07 | −0.56195966 | 0.307 | 0.37 |
| Ccdc34 | 9.27E−07 | −0.564514804 | 0.148 | 0.24 |
| Gm12728 | 5.87E−07 | −0.565583001 | 0.021 | 0.155 |
| Mrp63 | 4.92E−07 | −0.565784445 | 0.18 | 0.255 |
| Hook1 | 9.72E−09 | −0.565962572 | 0.354 | 0.43 |
| Ran | 1.51E−05 | −0.567446092 | 0.201 | 0.295 |
| Eif4ebp1 | 2.02E−06 | −0.567805133 | 0.132 | 0.245 |
| Ankrd37 | 1.81E−06 | −0.568385883 | 0.016 | 0.115 |
| Rplp2 | 3.67E−13 | −0.568701153 | 0.772 | 0.83 |
| Prdx4 | 4.04E−05 | −0.568737278 | 0.069 | 0.195 |
| Ppdpf | 3.75E−06 | −0.569191101 | 0.074 | 0.205 |
| Vaultrc5 | 2.37E−07 | −0.569267163 | 0.185 | 0.335 |
| Fasn | 4.42E−05 | −0.569471635 | 0.026 | 0.155 |
| Mrpl36 | 5.05E−05 | −0.57001908 | 0.101 | 0.19 |
| Krtcap2 | 6.02E−08 | −0.571380129 | 0.254 | 0.365 |
| Cct5 | 8.16E−08 | −0.572992216 | 0.312 | 0.445 |
| Pgls | 1.99E−08 | −0.573511636 | 0.228 | 0.31 |
| Rpa3 | 1.19E−05 | −0.574575445 | 0.127 | 0.235 |
| Eif3c | 1.32E−09 | −0.574719054 | 0.312 | 0.38 |
| Mrpl17 | 4.29E−06 | −0.575838065 | 0.148 | 0.23 |
| Mki67ip | 1.12E−05 | −0.576197418 | 0.058 | 0.165 |
| Pgk1 | 3.33E−08 | −0.585357423 | 0.011 | 0.175 |
| S100a11 | 8.20E−06 | −0.586880309 | 0.053 | 0.205 |
| Ssr2 | 1.56E−09 | −0.587438682 | 0.354 | 0.415 |
| Gm8420 | 3.83E−08 | −0.587473026 | 0.048 | 0.18 |

TABLE 1-continued

Derived gene list of the top defining genes from in vivo ileal
small intestine PCs and EECs captured on the Seq-Well platform

| | | | | |
|---|---|---|---|---|
| Gm16519 | 4.26E−07 | −0.587507744 | 0.005 | 0.14 |
| Prdx1 | 1.85E−13 | −0.587905501 | 0.709 | 0.82 |
| Tmem14c | 1.00E−05 | −0.588165576 | 0.111 | 0.21 |
| Ftl1 | 1.88E−07 | −0.589908505 | 0.201 | 0.33 |
| Rpl15 | 7.25E−07 | −0.59009606 | 0.079 | 0.21 |
| Nme1 | 6.20E−08 | −0.591521443 | 0.323 | 0.455 |
| Rpl23a-ps3 | 3.00E−07 | −0.592301497 | 0.005 | 0.15 |
| Gstp1 | 3.83E−06 | −0.592934613 | 0.132 | 0.28 |
| Eml4 | 2.92E−06 | −0.593265524 | 0.18 | 0.3 |
| Gm17541 | 1.70E−05 | −0.594037036 | 0.042 | 0.195 |
| Ndufb11 | 4.13E−07 | −0.594473406 | 0.307 | 0.435 |
| Rps23 | 6.24E−06 | −0.595046667 | 0.069 | 0.195 |
| Avpi1 | 1.76E−08 | −0.596459688 | 0.048 | 0.175 |
| Pcsk9 | 3.38E−07 | −0.59674704 | 0.005 | 0.135 |
| Psmb6 | 1.17E−06 | −0.596971787 | 0.254 | 0.35 |
| Psma4 | 8.41E−10 | −0.597387553 | 0.259 | 0.405 |
| Ifitm2 | 1.03E−09 | −0.598786595 | 0.228 | 0.35 |
| Cfl1 | 3.22E−07 | −0.600313526 | 0.233 | 0.365 |
| Mrpl13 | 0.000371267 | −0.601725408 | 0.095 | 0.2 |
| Sox4 | 5.16E−06 | −0.603429861 | 0.069 | 0.165 |
| Mcm6 | 1.72E−06 | −0.603547383 | 0.042 | 0.145 |
| Srsf3 | 1.95E−07 | −0.6039602 | 0.312 | 0.42 |
| H3f3a | 6.49E−09 | −0.604007875 | 0.18 | 0.345 |
| Rbm39 | 1.17E−09 | −0.606043989 | 0.37 | 0.425 |
| Eif2s2 | 5.24E−10 | −0.607068949 | 0.265 | 0.325 |
| Rpl22l1 | 2.45E−09 | −0.609051327 | 0.471 | 0.6 |
| Rpl37 | 1.17E−08 | −0.610075998 | 0.365 | 0.57 |
| Rpl35 | 1.95E−10 | −0.610353294 | 0.508 | 0.67 |
| Rpl36al | 7.33E−11 | −0.610486021 | 0.434 | 0.565 |
| Dut | 7.95E−05 | −0.612192819 | 0.085 | 0.205 |
| Cdk4 | 2.45E−07 | −0.614018654 | 0.196 | 0.31 |
| Atp5h | 2.86E−08 | −0.614183227 | 0.381 | 0.55 |
| Psat1 | 1.39E−05 | −0.615721908 | 0.021 | 0.135 |
| Rpl23a | 6.00E−06 | −0.617198542 | 0.069 | 0.205 |
| Cct6a | 5.86E−09 | −0.617549769 | 0.19 | 0.32 |
| Rps15a | 3.21E−17 | −0.617950261 | 0.725 | 0.885 |
| Utp11l | 2.21E−06 | −0.620348167 | 0.053 | 0.155 |
| H2afz | 1.59E−05 | −0.622245697 | 0.074 | 0.22 |
| Malat1 | 8.65E−18 | −0.622877884 | 0.825 | 0.95 |
| Tceb1 | 7.01E−08 | −0.62356922 | 0.127 | 0.22 |
| Rps19 | 2.21E−22 | −0.626883398 | 0.778 | 0.935 |
| Cystm1 | 8.21E−07 | −0.629720696 | 0.27 | 0.48 |
| Snrpd1 | 5.61E−06 | −0.630109732 | 0.175 | 0.31 |
| Taf1d | 2.26E−06 | −0.635069863 | 0.116 | 0.28 |
| Rpl22 | 4.49E−11 | −0.635175288 | 0.571 | 0.71 |
| Gm8226 | 1.68E−09 | −0.636342072 | 0 | 0.155 |
| Atpif1 | 3.12E−16 | −0.636535803 | 0.614 | 0.715 |
| Rps26 | 1.20E−13 | −0.636580958 | 0.64 | 0.85 |
| Romo1 | 6.98E−07 | −0.636823826 | 0.164 | 0.29 |
| Mrps14 | 1.65E−07 | −0.640726979 | 0.217 | 0.33 |
| H2afj | 1.71E−10 | −0.646903336 | 0.386 | 0.525 |
| Calml4 | 3.18E−07 | −0.647748686 | 0.328 | 0.435 |
| 1110038B12Rik | 2.16E−05 | −0.648324894 | 0.19 | 0.33 |
| Gm10269 | 9.46E−08 | −0.648683508 | 0.185 | 0.335 |
| Gm7808 | 1.55E−07 | −0.655072973 | 0.153 | 0.3 |
| Grcc10 | 1.10E−06 | −0.656610053 | 0.042 | 0.195 |
| 0610009D07Rik | 1.48E−07 | −0.657728458 | 0.122 | 0.26 |
| Dynll1 | 6.27E−11 | −0.662579856 | 0.27 | 0.37 |
| Ddx21 | 1.31E−05 | −0.662956383 | 0.127 | 0.22 |
| Rpph1 | 1.55E−06 | −0.66500112 | 0.206 | 0.35 |
| Gm9396 | 1.83E−10 | −0.667349981 | 0 | 0.17 |
| Gm10260 | 4.78E−08 | −0.66852283 | 0.19 | 0.32 |
| Snhg3 | 2.14E−05 | −0.668806581 | 0.053 | 0.165 |
| Gm10704 | 1.24E−08 | −0.669633097 | 0.048 | 0.205 |
| Actg1 | 3.64E−08 | −0.670416972 | 0.063 | 0.195 |
| Tmbim4 | 5.61E−11 | −0.671558907 | 0.164 | 0.3 |
| Rpl8 | 2.27E−19 | −0.673589579 | 0.841 | 0.93 |
| Pglyrp1 | 1.08E−12 | −0.674095426 | 0.286 | 0.38 |
| Tmpo | 4.88E−08 | −0.674296706 | 0.106 | 0.26 |
| Ndufb5 | 1.69E−07 | −0.675956675 | 0.238 | 0.375 |
| Hmgcs1 | 3.71E−08 | −0.681395435 | 0.18 | 0.31 |
| Fkbp3 | 9.67E−08 | −0.683013521 | 0.217 | 0.365 |
| Tubb4b | 6.55E−07 | −0.6830716 | 0.238 | 0.36 |
| Tceb2 | 4.28E−08 | −0.683897902 | 0.254 | 0.36 |
| Rps14 | 3.75E−35 | −0.685397949 | 0.942 | 1 |
| Pebp1 | 1.09E−06 | −0.686785465 | 0.085 | 0.26 |
| Ranbp1 | 2.17E−07 | −0.689278828 | 0.238 | 0.4 |

TABLE 1-continued

Derived gene list of the top defining genes from in vivo ileal small intestine PCs and EECs captured on the Seq-Well platform

| | | | | |
|---|---|---|---|---|
| Aldob | 2.10E−07 | −0.689756337 | 0.423 | 0.51 |
| Fundc2 | 7.28E−06 | −0.692795472 | 0.09 | 0.235 |
| Rps13 | 2.33E−07 | −0.6933494 | 0.053 | 0.235 |
| Nop10 | 8.07E−09 | −0.698210368 | 0.302 | 0.435 |
| Ubb | 9.78E−14 | −0.699686199 | 0.534 | 0.72 |
| Rpl11 | 2.25E−08 | −0.700723709 | 0.079 | 0.245 |
| Rpl36a | 1.95E−08 | −0.701466664 | 0.063 | 0.235 |
| Ssb | 3.17E−09 | −0.70170735 | 0.275 | 0.365 |
| Rplp0 | 1.31E−24 | −0.702831276 | 0.889 | 0.98 |
| Fdft1 | 2.85E−09 | −0.705422138 | 0.026 | 0.18 |
| Sod1 | 4.95E−09 | −0.706167279 | 0.339 | 0.5 |
| Chchd2 | 3.49E−14 | −0.7100971 | 0.556 | 0.66 |
| Gm8186 | 1.37E−11 | −0.714755531 | 0.058 | 0.265 |
| Oaz1 | 1.71E−11 | −0.716097575 | 0.339 | 0.515 |
| Rpl9-ps6 | 9.23E−11 | −0.718652704 | 0.228 | 0.41 |
| Adh1 | 7.58E−07 | −0.718939375 | 0.021 | 0.175 |
| Dbi | 1.76E−12 | −0.721709502 | 0.54 | 0.7 |
| Bsg | 3.13E−17 | −0.725739341 | 0.561 | 0.7 |
| Pcna | 3.16E−08 | −0.727067188 | 0.032 | 0.22 |
| Cd81 | 4.29E−07 | −0.727642531 | 0.143 | 0.305 |
| Rps3 | 1.18E−35 | −0.728040462 | 0.868 | 0.955 |
| Ndufc2 | 3.90E−11 | −0.732825784 | 0.286 | 0.435 |
| Rpl4 | 2.16E−29 | −0.732837039 | 0.862 | 0.96 |
| Mrpl18 | 3.39E−06 | −0.735394926 | 0.101 | 0.23 |
| Lrrc58 | 8.20E−10 | −0.735447558 | 0.222 | 0.44 |
| Orc5 | 1.54E−07 | −0.736124896 | 0.116 | 0.31 |
| Eef1d | 8.14E−12 | −0.73613252 | 0.222 | 0.375 |
| Gm17087 | 1.56E−10 | −0.736677957 | 0.074 | 0.26 |
| Tomm5 | 8.27E−09 | −0.737516923 | 0.153 | 0.28 |
| Rps27l | 6.13E−19 | −0.737787094 | 0.63 | 0.755 |
| Rpl19 | 6.63E−10 | −0.740440475 | 0.143 | 0.38 |
| Rpl9-ps1 | 5.47E−10 | −0.740929464 | 0.058 | 0.23 |
| Tubb5 | 3.16E−07 | −0.741863963 | 0.275 | 0.47 |
| Tomm20 | 4.91E−08 | −0.743078547 | 0.063 | 0.23 |
| Gm10132 | 1.51E−09 | −0.744416506 | 0.016 | 0.195 |
| Hsp90aa1 | 2.17E−08 | −0.750639113 | 0.217 | 0.395 |
| Gpx2 | 8.61E−15 | −0.753317799 | 0.534 | 0.73 |
| Ifitm3 | 1.90E−07 | −0.754046651 | 0.048 | 0.215 |
| Nme2 | 3.36E−09 | −0.762130663 | 0.037 | 0.24 |
| Txn1 | 1.13E−16 | −0.763435316 | 0.582 | 0.74 |
| Gm21957 | 6.44E−12 | −0.763632491 | 0.021 | 0.24 |
| Hspe1 | 2.73E−10 | −0.763729014 | 0.307 | 0.505 |
| Gm10036 | 8.61E−10 | −0.775609028 | 0.079 | 0.3 |
| BX465866.1 | 5.39E−11 | −0.778403388 | 0.005 | 0.21 |
| Rpl5 | 5.26E−10 | −0.782091406 | 0.032 | 0.25 |
| Reg1 | 3.08E−08 | −0.787506491 | 0 | 0.135 |
| Banf1 | 1.48E−11 | −0.789476706 | 0.243 | 0.4 |
| Ccl9 | 3.27E−07 | −0.792780324 | 0.159 | 0.29 |
| Chga | 3.96E−06 | −0.793861188 | 0.021 | 0.14 |
| Atp5g1 | 1.38E−09 | −0.793991628 | 0.116 | 0.305 |
| Rpl21-ps4 | 8.54E−11 | −0.796368647 | 0.042 | 0.23 |
| Mrpl42 | 6.44E−07 | −0.796407767 | 0.095 | 0.285 |
| Gm8225 | 1.36E−08 | −0.796678298 | 0.032 | 0.21 |
| Gm10250 | 2.26E−09 | −0.799321997 | 0.111 | 0.325 |
| Bnip3 | 3.54E−11 | −0.802498019 | 0.011 | 0.205 |
| mt-Atp6 | 3.27E−09 | −0.803188824 | 0.101 | 0.36 |
| Gm24245 | 2.52E−08 | −0.804754086 | 0.095 | 0.29 |
| Ero1l | 8.42E−11 | −0.808827653 | 0.058 | 0.205 |
| 2700060E02Rik | 6.36E−12 | −0.809707393 | 0.185 | 0.375 |
| Hmgn1 | 1.17E−08 | −0.818283446 | 0.164 | 0.37 |
| Ptma | 2.14E−16 | −0.819418803 | 0.413 | 0.6 |
| Rpl23 | 3.11E−14 | −0.820359999 | 0.429 | 0.7 |
| 1810022K09Rik | 2.80E−09 | −0.824323285 | 0.138 | 0.325 |
| Amica1 | 4.48E−08 | −0.825072785 | 0.053 | 0.245 |
| Gm24146 | 1.51E−10 | −0.82659799 | 0.005 | 0.2 |
| Prelid1 | 2.69E−12 | −0.828185548 | 0.18 | 0.355 |
| Ube2c | 4.07E−08 | −0.841087055 | 0.063 | 0.26 |
| Rpl29 | 5.87E−12 | −0.845848483 | 0.243 | 0.495 |
| Myl6 | 2.92E−13 | −0.846731289 | 0.106 | 0.32 |
| Snrpg | 5.91E−10 | −0.853050582 | 0.143 | 0.365 |
| Rps2-ps10 | 2.46E−13 | −0.855611608 | 0.005 | 0.245 |
| Rpl12 | 9.24E−11 | −0.860202503 | 0.079 | 0.31 |
| Rpl10a | 1.83E−09 | −0.865535687 | 0.106 | 0.33 |
| Gapdh | 9.03E−12 | −0.867175893 | 0.005 | 0.21 |
| Rpl13a | 1.87E−30 | −0.867533003 | 0.825 | 0.98 |
| Uqcc2 | 5.42E−10 | −0.871542218 | 0.18 | 0.355 |
| Fxyd3 | 1.05E−13 | −0.874025559 | 0.265 | 0.4 |

TABLE 1-continued

Derived gene list of the top defining genes from in vivo ileal
small intestine PCs and EECs captured on the Seq-Well platform

| | | | | |
|---|---|---|---|---|
| Rps25 | 4.73E−12 | −0.875372311 | 0.228 | 0.51 |
| Wdr89 | 5.09E−13 | −0.8772842 | 0.233 | 0.5 |
| Gpi1 | 1.02E−13 | −0.88042701 | 0.148 | 0.385 |
| Ncl | 4.93E−19 | −0.888155805 | 0.577 | 0.765 |
| Rpl14 | 4.89E−26 | −0.88889146 | 0.667 | 0.93 |
| Rps27a | 1.86E−13 | −0.891977047 | 0.143 | 0.385 |
| Gas5 | 2.89E−16 | −0.893410101 | 0.455 | 0.705 |
| mt-Nd4 | 5.56E−22 | −0.895096253 | 0.714 | 0.905 |
| Btf3 | 2.34E−12 | −0.895141698 | 0.185 | 0.38 |
| mt-Nd2 | 1.69E−21 | −0.898574406 | 0.683 | 0.9 |
| Rpl13-ps3 | 5.10E−11 | −0.900883199 | 0.111 | 0.34 |
| Rpl26 | 2.06E−28 | −0.905611362 | 0.735 | 0.96 |
| Npm1 | 1.52E−16 | −0.906073879 | 0.418 | 0.68 |
| Gm5786 | 4.79E−11 | −0.907534399 | 0.032 | 0.26 |
| Rpsa-ps10 | 2.74E−13 | −0.907911938 | 0.011 | 0.25 |
| Gm5619 | 1.70E−15 | −0.909743635 | 0 | 0.245 |
| Rpl30 | 2.32E−14 | −0.910450661 | 0.254 | 0.46 |
| Rpl38 | 5.24E−21 | −0.911300739 | 0.54 | 0.785 |
| Rps10-ps1 | 6.46E−15 | −0.912387807 | 0.233 | 0.51 |
| Tpi1 | 3.85E−18 | −0.912837229 | 0.354 | 0.63 |
| Rpl32 | 4.10E−48 | −0.915624328 | 0.91 | 0.99 |
| Gm20594 | 1.19E−12 | −0.915936193 | 0.016 | 0.24 |
| Tuba1b | 1.77E−09 | −0.919547117 | 0.101 | 0.345 |
| Rnase1 | 3.84E−09 | −0.920553754 | 0.164 | 0.325 |
| Fdps | 5.76E−11 | −0.92143491 | 0.048 | 0.3 |
| Rps17 | 3.99E−12 | −0.927361901 | 0.058 | 0.315 |
| Rps24 | 3.23E−44 | −0.92858835 | 0.852 | 0.985 |
| Gm9765 | 2.15E−15 | −0.935465649 | 0.206 | 0.405 |
| Rn7sk | 1.83E−10 | −0.935482095 | 0.413 | 0.67 |
| Fabp1 | 2.90E−08 | −0.962647304 | 0.138 | 0.295 |
| Rps2 | 2.28E−32 | −0.969513628 | 0.725 | 0.95 |
| Gm26917 | 8.57E−11 | −0.975909586 | 0.048 | 0.265 |
| Naca | 5.88E−18 | −0.976691391 | 0.365 | 0.655 |
| Rpl27a | 4.20E−16 | −0.98731053 | 0.196 | 0.5 |
| Rps9 | 1.03E−35 | −0.991425345 | 0.778 | 0.98 |
| Rgcc | 1.82E−12 | −0.998185133 | 0.101 | 0.35 |
| Rpl13a-ps1 | 9.79E−14 | −1.004455068 | 0.085 | 0.385 |
| Ckb | 1.08E−14 | −1.009532596 | 0.048 | 0.29 |
| Fam162a | 1.13E−12 | −1.012037257 | 0.111 | 0.37 |
| Rpl10 | 1.07E−13 | −1.022990312 | 0.063 | 0.335 |
| Hmgb2 | 6.56E−13 | −1.025038207 | 0.159 | 0.41 |
| Tac1 | 1.29E−07 | −1.030418687 | 0 | 0.125 |
| Gm4968 | 4.37E−18 | −1.032143247 | 0.021 | 0.345 |
| Rps3a1 | 5.74E−30 | −1.044284182 | 0.603 | 0.865 |
| Eef1b2 | 4.34E−32 | −1.04512757 | 0.635 | 0.9 |
| Gm6472 | 3.88E−14 | −1.048488978 | 0.037 | 0.3 |
| Rpl6 | 5.47E−18 | −1.0518541 | 0.196 | 0.515 |
| Rpl18 | 4.56E−23 | −1.060753594 | 0.291 | 0.625 |
| Gnb2l1 | 1.02E−38 | −1.072659987 | 0.725 | 0.93 |
| Klk1 | 5.35E−11 | −1.075285863 | 0.122 | 0.385 |
| Rps15 | 7.56E−32 | −1.079539296 | 0.571 | 0.85 |
| Tmsb10 | 6.52E−25 | −1.08589897 | 0.333 | 0.61 |
| Rplp1 | 2.63E−51 | −1.092634805 | 0.878 | 0.985 |
| mt-Nd5 | 5.47E−27 | −1.09416199 | 0.598 | 0.875 |
| Rps11 | 1.31E−31 | −1.124264453 | 0.593 | 0.895 |
| Rps10 | 2.72E−38 | −1.147671836 | 0.614 | 0.9 |
| Rps4x | 7.61E−23 | −1.147709224 | 0.228 | 0.6 |
| Rps16 | 6.32E−19 | −1.147777751 | 0.175 | 0.525 |
| Rps5 | 5.05E−52 | −1.165218291 | 0.862 | 0.995 |
| Gm6576 | 2.63E−20 | −1.168707414 | 0.085 | 0.455 |
| Rpl18a | 1.01E−27 | −1.179638123 | 0.376 | 0.79 |
| Gm5160 | 1.89E−16 | −1.182020528 | 0.048 | 0.385 |
| Scd2 | 1.79E−19 | −1.186244206 | 0.079 | 0.445 |
| mt-Co1 | 2.35E−40 | −1.190862701 | 0.72 | 0.95 |
| Eno1 | 2.35E−21 | −1.209794757 | 0.032 | 0.36 |
| Rpl10-ps3 | 1.38E−21 | −1.2108781 | 0.032 | 0.41 |
| Rpl3 | 1.77E−26 | −1.215044536 | 0.333 | 0.755 |
| Pkm | 4.44E−20 | −1.222324635 | 0.19 | 0.56 |
| Ldha | 6.40E−39 | −1.237276982 | 0.508 | 0.84 |
| mt-Cytb | 3.39E−53 | −1.237635959 | 0.878 | 0.99 |
| Gm9843 | 2.41E−33 | −1.248833345 | 0.481 | 0.815 |
| Rpsa | 2.79E−25 | −1.260253035 | 0.228 | 0.655 |
| Rps8 | 4.91E−35 | −1.26046721 | 0.503 | 0.835 |
| Eef1a1 | 4.73E−63 | −1.262523757 | 0.772 | 0.995 |
| Gm10275 | 4.82E−24 | −1.263892591 | 0.095 | 0.475 |
| Gm23935 | 1.82E−41 | −1.30516138 | 0.762 | 0.94 |
| Rpl13 | 5.82E−43 | −1.306098605 | 0.561 | 0.915 |

TABLE 1-continued

Derived gene list of the top defining genes from in vivo ileal small intestine PCs and EECs captured on the Seq-Well platform

| | | | | |
|---|---|---|---|---|
| Mif | 9.40E−23 | −1.370920115 | 0.106 | 0.485 |
| Rps6 | 2.16E−24 | −1.378898393 | 0.063 | 0.52 |
| Ppia | 1.87E−20 | −1.387574713 | 0.058 | 0.44 |
| Gip | 2.45E−06 | −1.444689624 | 0.021 | 0.12 |
| Gm9493 | 7.55E−26 | −1.461422006 | 0.048 | 0.485 |
| Rps7 | 8.10E−43 | −1.467472606 | 0.365 | 0.795 |
| Rps20 | 5.68E−65 | −1.472318469 | 0.656 | 0.975 |
| mt-Nd1 | 1.10E−62 | −1.493267245 | 0.852 | 0.995 |
| Rpl7a | 3.66E−31 | −1.493650494 | 0.116 | 0.635 |
| Uba52 | 1.20E−36 | −1.495718174 | 0.259 | 0.76 |
| Mt1 | 8.51E−39 | −1.566984123 | 0.365 | 0.82 |
| Aldoa | 6.68E−41 | −1.581290123 | 0.265 | 0.745 |
| Gm8730 | 1.14E−42 | −1.651230838 | 0.206 | 0.8 |
| Rpl7 | 9.55E−52 | −1.695523228 | 0.349 | 0.865 |
| Tpt1 | 4.70E−51 | −1.766089197 | 0.286 | 0.79 |
| Xist | 1.61E−43 | −1.856025581 | 0 | 0.58 |
| Mt2 | 1.87E−44 | −2.004274188 | 0.079 | 0.7 |
| Chgb | 1.68E−16 | −2.00780355 | 0.011 | 0.28 |

Table 1D. ROC-test on ENR+CV, ENR, and ENR+CD organoids to determine cluster-enriched marker genes (FIG. 4D ENR+CV, ENR, ENR+CD)

| | myAUC | avg_diff | power | pct.1 | pct.2 | cluster | gene |
|---|---|---|---|---|---|---|---|
| Rpph1 | 0.986 | 3.319373077 | 0.972 | 1 | 0.382 | ENR+CV-1 | Rpph1 |
| Gm26924 | 0.956 | 1.658756335 | 0.912 | 1 | 0.936 | ENR+CV-1 | Gm26924 |
| Rn7sk | 0.949 | 3.047657851 | 0.898 | 0.989 | 0.546 | ENR+CV-1 | Rn7sk |
| Snord13 | 0.919 | 2.638557932 | 0.838 | 0.899 | 0.168 | ENR+CV-1 | Snord13 |
| Gm15564 | 0.914 | 2.398421613 | 0.828 | 0.911 | 0.205 | ENR+CV-1 | Gm15564 |
| Lars2 | 0.91 | 1.723005835 | 0.82 | 0.989 | 0.604 | ENR+CV-1 | Lars2 |
| Gm24616 | 0.899 | 2.923018252 | 0.798 | 0.81 | 0.028 | ENR+CV-1 | Gm24616 |
| Vaultrc5 | 0.879 | 2.060246989 | 0.758 | 0.872 | 0.285 | ENR+CV-1 | Vaultrc5 |
| Snord118 | 0.867 | 2.548026049 | 0.734 | 0.788 | 0.107 | ENR+CV-1 | Snord118 |
| Rny1 | 0.864 | 2.437116646 | 0.728 | 0.765 | 0.08 | ENR+CV-1 | Rny1 |
| Gm24146 | 0.856 | 2.241813583 | 0.712 | 0.788 | 0.154 | ENR+CV-1 | Gm24146 |
| n-R5-8s1 | 0.853 | 2.496592253 | 0.706 | 0.726 | 0.032 | ENR+CV-1 | n-R5-8s1 |
| Gm26917 | 0.852 | 1.955131302 | 0.704 | 0.855 | 0.317 | ENR+CV-1 | Gm26917 |
| Gm24601 | 0.82 | 2.13893558 | 0.64 | 0.659 | 0.028 | ENR+CV-1 | Gm24601 |
| Gm23037 | 0.817 | 2.378194081 | 0.634 | 0.665 | 0.055 | ENR+CV-1 | Gm23037 |
| Pabpc1 | 0.812 | 0.838615671 | 0.624 | 0.966 | 0.8 | ENR+CV-1 | Pabpc1 |
| Gm26205 | 0.805 | 2.694605811 | 0.61 | 0.631 | 0.039 | ENR+CV-1 | Gm26205 |
| Gm23924 | 0.758 | 2.278844246 | 0.516 | 0.52 | 0.006 | ENR+CV-1 | Gm23924 |
| mmu-mir-6236 | 0.746 | 1.51273369 | 0.492 | 0.531 | 0.052 | ENR+CV-1 | mmu-mir-6236 |
| Gm23973 | 0.741 | 1.661730228 | 0.482 | 0.497 | 0.02 | ENR+CV-1 | Gm23973 |
| Tpi1 | 0.741 | 0.890232989 | 0.482 | 0.866 | 0.588 | ENR+CV-1 | Tpi1 |
| Gm23935 | 0.74 | 0.938297465 | 0.48 | 1 | 0.932 | ENR+CV-1 | Gm23935 |
| Rny3 | 0.739 | 1.501659109 | 0.478 | 0.553 | 0.1 | ENR+CV-1 | Rny3 |
| Rpl41 | 0.725 | 0.720514673 | 0.45 | 0.944 | 0.825 | ENR+CV-1 | Rpl41 |
| Bsg | 0.722 | 0.900022309 | 0.444 | 0.849 | 0.733 | ENR+CV-1 | Bsg |
| Gpi1 | 0.719 | 0.943848591 | 0.438 | 0.721 | 0.385 | ENR+CV-1 | Gpi1 |
| Neat1 | 0.718 | 1.153263742 | 0.436 | 0.575 | 0.16 | ENR+CV-1 | Neat1 |
| Rrbp1 | 0.711 | 0.791087255 | 0.422 | 0.749 | 0.436 | ENR+CV-1 | Rrbp1 |
| Gm23731 | 0.707 | 1.685390231 | 0.414 | 0.419 | 0.007 | ENR+CV-1 | Gm23731 |
| Ero1l | 0.707 | 1.269058774 | 0.414 | 0.559 | 0.182 | ENR+CV-1 | Ero1l |
| mt-Tc | 0.701 | 1.173516039 | 0.402 | 0.458 | 0.062 | ENR+CV-1 | mt-Tc |
| Egr1 | 0.695 | 0.88360283 | 0.39 | 0.676 | 0.401 | ENR+CV-1 | Egr1 |
| Gm2000 | 0.692 | 0.775271431 | 0.384 | 0.726 | 0.447 | ENR+CV-1 | Gm2000 |
| Pabpc4 | 0.69 | 1.055382571 | 0.38 | 0.525 | 0.179 | ENR+CV-1 | Pabpc4 |
| Gm24289 | 0.686 | 1.507727803 | 0.372 | 0.385 | 0.018 | ENR+CV-1 | Gm24289 |
| Gm22620 | 0.684 | 1.544347591 | 0.368 | 0.374 | 0.008 | ENR+CV-1 | Gm22620 |
| Rpl37a | 0.682 | 0.634110211 | 0.364 | 0.788 | 0.593 | ENR+CV-1 | Rpl37a |
| Gm26339 | 0.681 | 1.286835564 | 0.362 | 0.391 | 0.032 | ENR+CV-1 | Gm26339 |
| Gm22982 | 0.68 | 1.358383995 | 0.36 | 0.385 | 0.029 | ENR+CV-1 | Gm22982 |
| Atp5d | 0.678 | 0.612211468 | 0.356 | 0.704 | 0.425 | ENR+CV-1 | Atp5d |
| H2-Q10 | 0.677 | 0.998914091 | 0.354 | 0.464 | 0.125 | ENR+CV-1 | H2-Q10 |
| Ndufv3 | 0.677 | 0.734944941 | 0.354 | 0.626 | 0.327 | ENR+CV-1 | Ndufv3 |
| H1f0 | 0.677 | 0.719102822 | 0.354 | 0.67 | 0.381 | ENR+CV-1 | H1f0 |
| Gm25538 | 0.676 | 1.398247413 | 0.352 | 0.363 | 0.014 | ENR+CV-1 | Gm25538 |
| Hes1 | 0.671 | 0.868351272 | 0.342 | 0.542 | 0.227 | ENR+CV-1 | Hes1 |
| Ubc | 0.671 | 0.631162449 | 0.342 | 0.754 | 0.567 | ENR+CV-1 | Ubc |
| Scd2 | 0.671 | 0.63057596 | 0.342 | 0.76 | 0.531 | ENR+CV-1 | Scd2 |
| Pkm | 0.67 | 0.596380704 | 0.34 | 0.782 | 0.641 | ENR+CV-1 | Pkm |
| Scd1 | 0.668 | 1.090989415 | 0.336 | 0.425 | 0.102 | ENR+CV-1 | Scd1 |
| n-R5s2 | 0.665 | 1.323674266 | 0.33 | 0.341 | 0.013 | ENR+CV-1 | n-R5s2 |
| Gm25541 | 0.661 | 1.231078118 | 0.322 | 0.33 | 0.01 | ENR+CV-1 | Gm25541 |
| Aes | 0.66 | 0.818117808 | 0.32 | 0.531 | 0.255 | ENR+CV-1 | Aes |

TABLE 1-continued

Derived gene list of the top defining genes from in vivo ileal
small intestine PCs and EECs captured on the Seq-Well platform

| | | | | | | |
|---|---|---|---|---|---|---|
| Junb | 0.66 | 0.71068372 | 0.32 | 0.648 | 0.385 | ENR+CV-1 | Junb |
| Gm22063 | 0.658 | 1.272082171 | 0.316 | 0.33 | 0.015 | ENR+CV-1 | Gm22063 |
| Gm26035 | 0.657 | 1.321304052 | 0.314 | 0.318 | 0.006 | ENR+CV-1 | Gm26035 |
| Gm22307 | 0.657 | 1.238608875 | 0.314 | 0.324 | 0.011 | ENR+CV-1 | Gm22307 |
| Jun | 0.656 | 0.613726056 | 0.312 | 0.743 | 0.542 | ENR+CV-1 | Jun |
| Galk1 | 0.655 | 0.78447389 | 0.31 | 0.48 | 0.196 | ENR+CV-1 | Galk1 |
| n-R5s193 | 0.654 | 1.138720844 | 0.308 | 0.318 | 0.011 | ENR+CV-1 | n-R5s193 |
| Gm24336 | 0.653 | 1.206891752 | 0.306 | 0.318 | 0.016 | ENR+CV-1 | Gm24336 |
| Gm22633 | 0.651 | 1.239750758 | 0.302 | 0.307 | 0.005 | ENR+CV-1 | Gm22633 |
| mt-Tp | 0.649 | 1.140133173 | 0.298 | 0.341 | 0.047 | ENR+CV-1 | mt-Tp |
| Atf4 | 0.649 | 0.609094522 | 0.298 | 0.654 | 0.442 | ENR+CV-1 | Atf4 |
| H2afj | 0.648 | 0.561595967 | 0.296 | 0.721 | 0.503 | ENR+CV-1 | H2afj |
| Gm25588 | 0.647 | 1.145184011 | 0.294 | 0.296 | 0.002 | ENR+CV-1 | Gm25588 |
| Pdap1 | 0.647 | 0.59265881 | 0.294 | 0.648 | 0.409 | ENR+CV-1 | Pdap1 |
| Gm25822 | 0.646 | 1.020422353 | 0.292 | 0.335 | 0.047 | ENR+CV-1 | Gm25822 |
| Eef2 | 0.646 | 0.369209213 | 0.292 | 0.916 | 0.849 | ENR+CV-1 | Eef2 |
| Snord35a | 0.645 | 1.136681512 | 0.29 | 0.302 | 0.014 | ENR+CV-1 | Snord35a |
| Snora68 | 0.643 | 1.091810479 | 0.286 | 0.313 | 0.031 | ENR+CV-1 | Snora68 |
| Bola2 | 0.643 | 0.675089957 | 0.286 | 0.553 | 0.304 | ENR+CV-1 | Bola2 |
| mt-Tq | 0.641 | 1.089303891 | 0.282 | 0.318 | 0.042 | ENR+CV-1 | mt-Tq |
| Snord49b | 0.641 | 1.000738074 | 0.282 | 0.324 | 0.047 | ENR+CV-1 | Snord49b |
| Ppp2r3a | 0.641 | 0.826612201 | 0.282 | 0.374 | 0.102 | ENR+CV-1 | Ppp2r3a |
| Por | 0.64 | 0.781992824 | 0.28 | 0.43 | 0.167 | ENR+CV-1 | Por |
| Tkt | 0.639 | 0.561209409 | 0.278 | 0.642 | 0.466 | ENR+CV-1 | Tkt |
| Rnu3a | 0.637 | 1.076134966 | 0.274 | 0.296 | 0.024 | ENR+CV-1 | Rnu3a |
| mt-Tm | 0.635 | 1.007755682 | 0.27 | 0.296 | 0.031 | ENR+CV-1 | mt-Tm |
| Gm26335 | 0.634 | 1.175296399 | 0.268 | 0.274 | 0.006 | ENR+CV-1 | Gm26335 |
| Gm24044 | 0.634 | 1.138065841 | 0.268 | 0.274 | 0.006 | ENR+CV-1 | Gm24044 |
| Slc25a1 | 0.634 | 0.705016848 | 0.268 | 0.453 | 0.202 | ENR+CV-1 | Slc25a1 |
| Elf3 | 0.634 | 0.647172014 | 0.268 | 0.531 | 0.299 | ENR+CV-1 | Elf3 |
| Mir5136 | 0.632 | 0.774248421 | 0.264 | 0.38 | 0.125 | ENR+CV-1 | Mir5136 |
| Pcsk9 | 0.632 | 0.761198774 | 0.264 | 0.419 | 0.169 | ENR+CV-1 | Pcsk9 |
| Slc16a3 | 0.631 | 0.79340192 | 0.262 | 0.363 | 0.108 | ENR+CV-1 | Slc16a3 |
| Gm23248 | 0.63 | 1.151415243 | 0.26 | 0.263 | 0.002 | ENR+CV-1 | Gm23248 |
| Gm22748 | 0.63 | 1.074148554 | 0.26 | 0.268 | 0.008 | ENR+CV-1 | Gm22748 |
| Insig1 | 0.63 | 0.767669394 | 0.26 | 0.408 | 0.166 | ENR+CV-1 | Insig1 |
| Ier2 | 0.63 | 0.505662744 | 0.26 | 0.698 | 0.536 | ENR+CV-1 | Ier2 |
| Rmrp | 0.629 | 1.126647888 | 0.258 | 0.268 | 0.011 | ENR+CV-1 | Rmrp |
| Fasn | 0.629 | 0.739065288 | 0.258 | 0.385 | 0.141 | ENR+CV-1 | Fasn |
| Gcat | 0.628 | 0.692805606 | 0.256 | 0.413 | 0.176 | ENR+CV-1 | Gcat |
| Kcnq1 | 0.627 | 0.6410026 | 0.254 | 0.402 | 0.159 | ENR+CV-1 | Kcnq1 |
| Ptms | 0.627 | 0.609672251 | 0.254 | 0.458 | 0.217 | ENR+CV-1 | Ptms |
| Arpp19 | 0.627 | 0.493294604 | 0.254 | 0.581 | 0.351 | ENR+CV-1 | Arpp19 |
| Hmgcs2 | 0.626 | 0.759089952 | 0.252 | 0.358 | 0.111 | ENR+CV-1 | Hmgcs2 |
| Dhcr24 | 0.626 | 0.631557553 | 0.252 | 0.453 | 0.222 | ENR+CV-1 | Dhcr24 |
| Atf3 | 0.625 | 0.643973891 | 0.25 | 0.486 | 0.258 | ENR+CV-1 | Atf3 |
| Acot1 | 0.622 | 0.710419081 | 0.244 | 0.335 | 0.099 | ENR+CV-1 | Acot1 |
| Mpnd | 0.621 | 0.708997116 | 0.242 | 0.335 | 0.099 | ENR+CV-1 | Mpnd |
| 2410015M20Rik | 0.621 | 0.536752663 | 0.242 | 0.475 | 0.254 | ENR+CV-1 | 2410015M20Rik |
| Cs | 0.62 | 0.568703916 | 0.24 | 0.469 | 0.243 | ENR+CV-1 | Cs |
| Atp1a1 | 0.62 | 0.473515788 | 0.24 | 0.603 | 0.411 | ENR+CV-1 | Atp1a1 |
| Mt1 | 0.62 | 0.445838672 | 0.24 | 0.816 | 0.662 | ENR+CV-1 | Mt1 |
| mt-Tv | 0.619 | 0.81271412 | 0.238 | 0.279 | 0.043 | ENR+CV-1 | mt-Tv |
| P4hb | 0.619 | 0.586657125 | 0.238 | 0.715 | 0.594 | ENR+CV-1 | P4hb |
| Egln3 | 0.618 | 0.799738642 | 0.236 | 0.302 | 0.069 | ENR+CV-1 | Egln3 |
| Gm24018 | 0.617 | 0.993377346 | 0.234 | 0.24 | 0.006 | ENR+CV-1 | Gm24018 |
| Rpn1 | 0.617 | 0.428805504 | 0.234 | 0.592 | 0.379 | ENR+CV-1 | Rpn1 |
| Lonp1 | 0.616 | 0.589583395 | 0.232 | 0.408 | 0.186 | ENR+CV-1 | Lonp1 |
| Btg2 | 0.615 | 0.633739142 | 0.23 | 0.441 | 0.234 | ENR+CV-1 | Btg2 |
| Gm23624 | 0.614 | 1.000409547 | 0.228 | 0.235 | 0.006 | ENR+CV-1 | Gm23624 |
| Tmem245 | 0.614 | 0.808401751 | 0.228 | 0.285 | 0.06 | ENR+CV-1 | Tmem245 |
| Slc1a5 | 0.614 | 0.66247978 | 0.228 | 0.425 | 0.224 | ENR+CV-1 | Slc1a5 |
| Hist1h1d | 0.613 | 0.912426636 | 0.226 | 0.318 | 0.102 | ENR+CV-1 | Hist1h1d |
| Ccnd2 | 0.613 | 0.472375902 | 0.226 | 0.57 | 0.392 | ENR+CV-1 | Ccnd2 |
| Ddx21 | 0.613 | 0.463809532 | 0.226 | 0.536 | 0.328 | ENR+CV-1 | Ddx21 |
| Mir3068 | 0.612 | 1.512462215 | 0.224 | 0.229 | 0.007 | ENR+CV-1 | Mir3068 |
| Xist | 0.612 | 0.358497733 | 0.224 | 0.838 | 0.675 | ENR+CV-1 | Xist |
| Gm23792 | 0.611 | 1.204540163 | 0.222 | 0.223 | 0.002 | ENR+CV-1 | Gm23792 |
| Aldh9a1 | 0.611 | 0.545665229 | 0.222 | 0.397 | 0.183 | ENR+CV-1 | Aldh9a1 |
| Jund | 0.611 | 0.500197084 | 0.222 | 0.441 | 0.226 | ENR+CV-1 | Jund |
| Dbi | 0.61 | 0.275424139 | 0.22 | 0.905 | 0.822 | ENR+CV-1 | Dbi |
| Aqp1 | 0.609 | 0.695003335 | 0.218 | 0.363 | 0.157 | ENR+CV-1 | Aqp1 |
| Hist1h1c | 0.609 | 0.627009124 | 0.218 | 0.38 | 0.169 | ENR+CV-1 | Hist1h1c |
| Snd1 | 0.609 | 0.551192281 | 0.218 | 0.408 | 0.204 | ENR+CV-1 | Snd1 |
| Gm25080 | 0.608 | 1.067209442 | 0.216 | 0.218 | 0.002 | ENR+CV-1 | Gm25080 |
| Gm22308 | 0.608 | 1.053725297 | 0.216 | 0.218 | 0.003 | ENR+CV-1 | Gm22308 |
| Snhg9 | 0.607 | 0.585546114 | 0.214 | 0.413 | 0.221 | ENR+CV-1 | Snhg9 |

TABLE 1-continued

Derived gene list of the top defining genes from in vivo ileal
small intestine PCs and EECs captured on the Seq-Well platform

| | | | | | | |
|---|---|---|---|---|---|---|
| Gm24494 | 0.606 | 0.925369526 | 0.212 | 0.218 | 0.007 ENR+CV-1 | Gm24494 |
| Snord104 | 0.606 | 0.794148166 | 0.212 | 0.274 | 0.065 ENR+CV-1 | Snord104 |
| Pcyt2 | 0.606 | 0.561190093 | 0.212 | 0.38 | 0.176 ENR+CV-1 | Pcyt2 |
| Itpr3 | 0.606 | 0.549014385 | 0.212 | 0.324 | 0.113 ENR+CV-1 | Itpr3 |
| Mapk13 | 0.606 | 0.537793429 | 0.212 | 0.419 | 0.232 ENR+CV-1 | Mapk13 |
| Psmc1 | 0.606 | 0.496157383 | 0.212 | 0.447 | 0.248 ENR+CV-1 | Psmc1 |
| Pfkp | 0.603 | 0.642014619 | 0.206 | 0.33 | 0.132 ENR+CV-1 | Pfkp |
| Gm24968 | 0.602 | 0.942841931 | 0.204 | 0.212 | 0.008 ENR+CV-1 | Gm24968 |
| Gm25835 | 0.601 | 0.981819841 | 0.202 | 0.207 | 0.004 ENR+CV-1 | Gm25835 |
| Snora47 | 0.601 | 0.956714744 | 0.202 | 0.207 | 0.004 ENR+CV-1 | Snora47 |
| Gm22003 | 0.601 | 0.925185229 | 0.202 | 0.207 | 0.005 ENR+CV-1 | Gm22003 |
| Slc39a14 | 0.601 | 0.790768526 | 0.202 | 0.268 | 0.072 ENR+CV-1 | Slc39a14 |
| Huwe1 | 0.601 | 0.51920054 | 0.202 | 0.419 | 0.232 ENR+CV-1 | Huwe1 |
| Sox4 | 0.601 | 0.447952131 | 0.202 | 0.553 | 0.376 ENR+CV-1 | Sox4 |
| Rpl41l | 0.923 | 1.449606719 | 0.846 | 0.985 | 0.819 ENR+CV-2 | Rpl41 |
| Pabpc1l | 0.886 | 1.104712088 | 0.772 | 0.982 | 0.794 ENR+CV-2 | Pabpc1 |
| Gm269241 | 0.885 | 1.229874544 | 0.77 | 1 | 0.934 ENR+CV-2 | Gm26924 |
| Gm20001 | 0.833 | 1.234565899 | 0.666 | 0.864 | 0.431 ENR+CV-2 | Gm2000 |
| Rpl37a1 | 0.811 | 1.085909223 | 0.622 | 0.867 | 0.583 ENR+CV-2 | Rpl37a |
| Rpl35a | 0.797 | 0.820000153 | 0.594 | 0.938 | 0.781 ENR+CV-2 | Rpl35a |
| Rpph1l | 0.796 | 0.893345021 | 0.592 | 0.817 | 0.375 ENR+CV-2 | Rpph1 |
| Dbi1 | 0.77 | 0.665563321 | 0.54 | 0.959 | 0.816 ENR+CV-2 | Dbi |
| Uqcr10 | 0.763 | 0.754156685 | 0.526 | 0.914 | 0.666 ENR+CV-2 | Uqcr10 |
| Rpl37 | 0.76 | 0.827663322 | 0.52 | 0.853 | 0.651 ENR+CV-2 | Rpl37 |
| Gm155641 | 0.754 | 1.215487686 | 0.508 | 0.649 | 0.201 ENR+CV-2 | Gm15564 |
| Uqcr1l | 0.74 | 0.71183618 | 0.48 | 0.87 | 0.624 ENR+CV-2 | Uqcr11 |
| Rpl34 | 0.73 | 0.605848951 | 0.46 | 0.917 | 0.814 ENR+CV-2 | Rpl34 |
| Gm10076 | 0.727 | 0.7719867 | 0.454 | 0.808 | 0.609 ENR+CV-2 | Gm10076 |
| Taldo1 | 0.725 | 0.897515362 | 0.45 | 0.723 | 0.429 ENR+CV-2 | Taldo1 |
| Ifitm2 | 0.714 | 0.760262269 | 0.428 | 0.785 | 0.548 ENR+CV-2 | Ifitm2 |
| Cox4i1 | 0.714 | 0.511170832 | 0.428 | 0.953 | 0.851 ENR+CV-2 | Cox4i1 |
| Smoc2 | 0.708 | 0.82571651 | 0.416 | 0.729 | 0.438 ENR+CV-2 | Smoc2 |
| Cox6a1 | 0.703 | 0.555318243 | 0.406 | 0.888 | 0.7 ENR+CV-2 | Cox6a1 |
| Bex1 | 0.697 | 0.938299508 | 0.394 | 0.608 | 0.275 ENR+CV-2 | Bex1 |
| Uqcrq | 0.696 | 0.535634296 | 0.392 | 0.897 | 0.756 ENR+CV-2 | Uqcrq |
| Tubb5 | 0.693 | 0.648505913 | 0.386 | 0.794 | 0.587 ENR+CV-2 | Tubb5 |
| Snord131 | 0.69 | 1.0744826 | 0.38 | 0.516 | 0.17 ENR+CV-2 | Snord13 |
| Tpi1l | 0.689 | 0.580926605 | 0.378 | 0.811 | 0.584 ENR+CV-2 | Tpi1 |
| H1f01 | 0.683 | 0.830904784 | 0.366 | 0.646 | 0.375 ENR+CV-2 | H1f0 |
| Atp5k | 0.683 | 0.717227227 | 0.366 | 0.708 | 0.471 ENR+CV-2 | Atp5k |
| Rpl13 | 0.682 | 0.409862915 | 0.364 | 0.965 | 0.904 ENR+CV-2 | Rpl13 |
| Atp5e | 0.676 | 0.519168361 | 0.352 | 0.82 | 0.667 ENR+CV-2 | Atp5e |
| Bola21 | 0.675 | 0.86455296 | 0.35 | 0.572 | 0.296 ENR+CV-2 | Bola2 |
| Aldoa | 0.675 | 0.587357363 | 0.35 | 0.838 | 0.649 ENR+CV-2 | Aldoa |
| Eef21 | 0.67 | 0.409268422 | 0.34 | 0.917 | 0.847 ENR+CV-2 | Eef2 |
| 2010107E04Rik | 0.668 | 0.470785165 | 0.336 | 0.838 | 0.669 ENR+CV-2 | 2010107E04Rik |
| Rpl18 | 0.665 | 0.497225913 | 0.33 | 0.817 | 0.665 ENR+CV-2 | Rpl18 |
| Fth1 | 0.664 | 0.513255274 | 0.328 | 0.879 | 0.824 ENR+CV-2 | Fth1 |
| Rpl35 | 0.664 | 0.49714052 | 0.328 | 0.805 | 0.715 ENR+CV-2 | Rpl35 |
| Vaultrc51 | 0.662 | 0.878420544 | 0.324 | 0.54 | 0.289 ENR+CV-2 | Vaultrc5 |
| Mif | 0.66 | 0.577530321 | 0.32 | 0.717 | 0.502 ENR+CV-2 | Mif |
| Mlec | 0.658 | 0.688143109 | 0.316 | 0.596 | 0.362 ENR+CV-2 | Mlec |
| Hmgcs21 | 0.656 | 1.05211155 | 0.312 | 0.395 | 0.102 ENR+CV-2 | Hmgcs2 |
| Pkm1 | 0.656 | 0.549587475 | 0.312 | 0.77 | 0.637 ENR+CV-2 | Pkm |
| Atp5b | 0.647 | 0.391221588 | 0.294 | 0.844 | 0.727 ENR+CV-2 | Atp5b |
| Ndufb8 | 0.646 | 0.554698006 | 0.292 | 0.673 | 0.509 ENR+CV-2 | Ndufb8 |
| Ybx1l | 0.646 | 0.43841017 | 0.292 | 0.826 | 0.73 ENR+CV-2 | Ybx1 |
| Psma7 | 0.643 | 0.484191486 | 0.286 | 0.752 | 0.577 ENR+CV-2 | Psma7 |
| Wbp5 | 0.642 | 0.488756426 | 0.284 | 0.699 | 0.497 ENR+CV-2 | Wbp5 |
| Eef1g | 0.641 | 0.470537797 | 0.282 | 0.717 | 0.592 ENR+CV-2 | Eef1g |
| Atp5j | 0.641 | 0.446003672 | 0.282 | 0.805 | 0.692 ENR+CV-2 | Atp5j |
| Mdh2 | 0.639 | 0.620470079 | 0.278 | 0.599 | 0.402 ENR+CV-2 | Mdh2 |
| Myeov2 | 0.639 | 0.58079712 | 0.278 | 0.575 | 0.38 ENR+CV-2 | Myeov2 |
| Lars21 | 0.638 | 0.528667832 | 0.276 | 0.74 | 0.608 ENR+CV-2 | Lars2 |
| Mt1l | 0.638 | 0.422568466 | 0.276 | 0.835 | 0.656 ENR+CV-2 | Mt1 |
| Snrpg1 | 0.636 | 0.534102284 | 0.272 | 0.634 | 0.47 ENR+CV-2 | Snrpg |
| Cox6c1 | 0.636 | 0.365763656 | 0.272 | 0.885 | 0.781 ENR+CV-2 | Cox6c |
| Ldha | 0.636 | 0.346603618 | 0.272 | 0.858 | 0.684 ENR+CV-2 | Ldha |
| Atp1a1l | 0.635 | 0.625292307 | 0.27 | 0.596 | 0.406 ENR+CV-2 | Atp1a1 |
| Trappc6a | 0.632 | 0.713824666 | 0.264 | 0.481 | 0.267 ENR+CV-2 | Trappc6a |
| Tmem256 | 0.63 | 0.630557964 | 0.26 | 0.563 | 0.389 ENR+CV-2 | Tmem256 |
| Bsg1 | 0.629 | 0.369608482 | 0.258 | 0.823 | 0.731 ENR+CV-2 | Bsg |
| Crip1 | 0.628 | 0.517095126 | 0.256 | 0.605 | 0.4 ENR+CV-2 | Crip1 |
| Ctsb | 0.627 | 0.575366147 | 0.254 | 0.549 | 0.357 ENR+CV-2 | Ctsb |
| Atp5o | 0.627 | 0.487221882 | 0.254 | 0.67 | 0.534 ENR+CV-2 | Atp5o |
| Eif3h | 0.627 | 0.453915099 | 0.254 | 0.658 | 0.514 ENR+CV-2 | Eif3h |
| mmu-mir-62361 | 0.626 | 1.379712556 | 0.252 | 0.295 | 0.053 ENR+CV-2 | mmu-mir-6236 |

TABLE 1-continued

Derived gene list of the top defining genes from in vivo ileal small intestine PCs and EECs captured on the Seq-Well platform

| Gene | V1 | V2 | V3 | V4 | V5 | Label | Gene |
|---|---|---|---|---|---|---|---|
| Egr11 | 0.626 | 0.580474249 | 0.252 | 0.575 | 0.399 | ENR+CV-2 | Egr1 |
| Park7 | 0.626 | 0.537910241 | 0.252 | 0.599 | 0.432 | ENR+CV-2 | Park7 |
| Atp5d1 | 0.626 | 0.537560089 | 0.252 | 0.593 | 0.424 | ENR+CV-2 | Atp5d |
| Ier21 | 0.625 | 0.50775205 | 0.25 | 0.667 | 0.533 | ENR+CV-2 | Ier2 |
| Uqcrh | 0.625 | 0.38223009 | 0.25 | 0.752 | 0.644 | ENR+CV-2 | Uqcrh |
| Rpl22 | 0.625 | 0.354788499 | 0.25 | 0.873 | 0.788 | ENR+CV-2 | Rpl22 |
| Rpl3 | 0.625 | 0.321398044 | 0.25 | 0.841 | 0.763 | ENR+CV-2 | Rpl3 |
| Hmgb1 | 0.624 | 0.668332042 | 0.248 | 0.457 | 0.252 | ENR+CV-2 | Hmgb1 |
| Hes11 | 0.622 | 0.849232716 | 0.244 | 0.428 | 0.225 | ENR+CV-2 | Hes1 |
| Gm9846 | 0.621 | 0.839305743 | 0.242 | 0.342 | 0.121 | ENR+CV-2 | Gm9846 |
| Rps28 | 0.621 | 0.610513108 | 0.242 | 0.513 | 0.341 | ENR+CV-2 | Rps28 |
| Calm11 | 0.621 | 0.291073464 | 0.242 | 0.935 | 0.873 | ENR+CV-2 | Calm1 |
| Rps25 | 0.62 | 0.459056364 | 0.24 | 0.67 | 0.552 | ENR+CV-2 | Rps25 |
| Uqcrc1 | 0.619 | 0.502558199 | 0.238 | 0.575 | 0.423 | ENR+CV-2 | Uqcrc1 |
| Rny31 | 0.618 | 0.782424076 | 0.236 | 0.324 | 0.101 | ENR+CV-2 | Rny3 |
| Ndufb4 | 0.618 | 0.665537805 | 0.236 | 0.454 | 0.271 | ENR+CV-2 | Ndufb4 |
| Ndufc1 | 0.618 | 0.515273264 | 0.236 | 0.617 | 0.482 | ENR+CV-2 | Ndufc1 |
| Snrpf | 0.616 | 0.577507749 | 0.232 | 0.516 | 0.35 | ENR+CV-2 | Snrpf |
| Snrpd3 | 0.616 | 0.517596058 | 0.232 | 0.549 | 0.383 | ENR+CV-2 | Snrpd3 |
| Tax1bp1 | 0.616 | 0.46207462 | 0.232 | 0.617 | 0.465 | ENR+CV-2 | Tax1bp1 |
| Serbp1 | 0.616 | 0.340116471 | 0.232 | 0.799 | 0.717 | ENR+CV-2 | Serbp1 |
| Galk11 | 0.614 | 0.735817485 | 0.228 | 0.386 | 0.193 | ENR+CV-2 | Galk1 |
| Ak2 | 0.614 | 0.672868468 | 0.228 | 0.463 | 0.288 | ENR+CV-2 | Ak2 |
| Tomm7 | 0.614 | 0.440422459 | 0.228 | 0.649 | 0.542 | ENR+CV-2 | Tomm7 |
| Rpn11 | 0.613 | 0.520693113 | 0.226 | 0.531 | 0.376 | ENR+CV-2 | Rpn1 |
| Ndufa3 | 0.613 | 0.49423351 | 0.226 | 0.56 | 0.399 | ENR+CV-2 | Ndufa3 |
| Cox6b1 | 0.612 | 0.306843599 | 0.224 | 0.814 | 0.721 | ENR+CV-2 | Cox6b1 |
| Ndufs6 | 0.611 | 0.503816087 | 0.222 | 0.56 | 0.419 | ENR+CV-2 | Ndufs6 |
| Ccdc34 | 0.611 | 0.467047338 | 0.222 | 0.59 | 0.428 | ENR+CV-2 | Ccdc34 |
| Vim | 0.609 | 0.744614865 | 0.218 | 0.313 | 0.105 | ENR+CV-2 | Vim |
| Sub1 | 0.608 | 0.566390645 | 0.216 | 0.501 | 0.342 | ENR+CV-2 | Sub1 |
| Arpp191 | 0.606 | 0.530395782 | 0.212 | 0.499 | 0.35 | ENR+CV-2 | Arpp19 |
| Ndufv31 | 0.606 | 0.522576188 | 0.212 | 0.484 | 0.327 | ENR+CV-2 | Ndufv3 |
| Psmc11 | 0.605 | 0.631261775 | 0.21 | 0.413 | 0.244 | ENR+CV-2 | Psmc1 |
| Fkbp4 | 0.605 | 0.450484271 | 0.21 | 0.543 | 0.41 | ENR+CV-2 | Fkbp4 |
| Gm10221 | 0.604 | 0.728960362 | 0.208 | 0.324 | 0.14 | ENR+CV-2 | Gm10221 |
| Phlda1 | 0.604 | 0.574851336 | 0.208 | 0.481 | 0.324 | ENR+CV-2 | Phlda1 |
| Rny11 | 0.602 | 0.686061504 | 0.204 | 0.286 | 0.09 | ENR+CV-2 | Rny1 |
| Mrpl52 | 0.602 | 0.426405403 | 0.204 | 0.558 | 0.438 | ENR+CV-2 | Mrpl52 |
| Serinc3 | 0.602 | 0.40813969 | 0.204 | 0.619 | 0.489 | ENR+CV-2 | Serinc3 |
| Atox1 | 0.601 | 0.494023687 | 0.202 | 0.501 | 0.358 | ENR+CV-2 | Atox1 |
| Ptma1 | 0.601 | 0.323415558 | 0.202 | 0.794 | 0.74 | ENR+CV-2 | Ptma |
| Rpl412 | 0.946 | 1.38951703 | 0.892 | 1 | 0.822 | ENR+CV-3 | Rpl41 |
| Pabpc12 | 0.932 | 1.115421045 | 0.864 | 1 | 0.797 | ENR+CV-3 | Pabpc1 |
| Gm20002 | 0.911 | 1.280969343 | 0.822 | 0.982 | 0.436 | ENR+CV-3 | Gm2000 |
| Rps18 | 0.901 | 0.82816016 | 0.802 | 1 | 0.918 | ENR+CV-3 | Rps18 |
| Rpl37a2 | 0.895 | 1.070848195 | 0.79 | 0.991 | 0.584 | ENR+CV-3 | Rpl37a |
| Rpl371 | 0.87 | 0.893121596 | 0.74 | 0.986 | 0.65 | ENR+CV-3 | Rpl37 |
| Rpl35a1 | 0.856 | 0.753731854 | 0.712 | 0.995 | 0.782 | ENR+CV-3 | Rpl35a |
| Smoc21 | 0.854 | 1.086694526 | 0.708 | 0.968 | 0.434 | ENR+CV-3 | Smoc2 |
| Gm269242 | 0.853 | 0.662581228 | 0.706 | 1 | 0.935 | ENR+CV-3 | Gm26924 |
| Taldo11 | 0.849 | 0.947738264 | 0.698 | 0.995 | 0.425 | ENR+CV-3 | Taldo1 |
| Gm100761 | 0.838 | 0.827562473 | 0.676 | 0.995 | 0.605 | ENR+CV-3 | Gm10076 |
| Bex11 | 0.819 | 1.038498168 | 0.638 | 0.882 | 0.271 | ENR+CV-3 | Bex1 |
| Dbi2 | 0.818 | 0.645084543 | 0.636 | 1 | 0.818 | ENR+CV-3 | Dbi |
| Uqcr101 | 0.816 | 0.743532524 | 0.632 | 0.995 | 0.668 | ENR+CV-3 | Uqcr10 |
| Hmgcs22 | 0.814 | 1.12069006 | 0.628 | 0.738 | 0.095 | ENR+CV-3 | Hmgcs2 |
| Ifitm21 | 0.811 | 0.801154702 | 0.622 | 0.973 | 0.546 | ENR+CV-3 | Ifitm2 |
| Uqcr111 | 0.807 | 0.712178189 | 0.614 | 0.991 | 0.625 | ENR+CV-3 | Uqcr11 |
| Rpl341 | 0.804 | 0.594945676 | 0.608 | 0.995 | 0.814 | ENR+CV-3 | Rpl34 |
| Fth11 | 0.8 | 0.708081491 | 0.6 | 0.995 | 0.821 | ENR+CV-3 | Fth1 |
| Ier22 | 0.796 | 0.856531438 | 0.592 | 0.959 | 0.525 | ENR+CV-3 | Ier2 |
| Ndufb41 | 0.788 | 0.852050568 | 0.576 | 0.842 | 0.26 | ENR+CV-3 | Ndufb4 |
| Cox4i11 | 0.784 | 0.511379831 | 0.568 | 1 | 0.852 | ENR+CV-3 | Cox4i1 |
| Hsp90ab1 | 0.784 | 0.478451763 | 0.568 | 1 | 0.932 | ENR+CV-3 | Hsp90ab1 |
| Gm155642 | 0.782 | 0.609088093 | 0.564 | 0.81 | 0.204 | ENR+CV-3 | Gm15564 |
| Hes12 | 0.781 | 1.218509871 | 0.562 | 0.756 | 0.216 | ENR+CV-3 | Hes1 |
| Bola22 | 0.778 | 0.799308292 | 0.556 | 0.855 | 0.291 | ENR+CV-3 | Bola2 |
| Egr12 | 0.777 | 0.849665913 | 0.554 | 0.896 | 0.39 | ENR+CV-3 | Egr1 |
| Atp5k1 | 0.772 | 0.661800658 | 0.544 | 0.968 | 0.466 | ENR+CV-3 | Atp5k |
| Gm98461 | 0.77 | 0.873334033 | 0.54 | 0.674 | 0.112 | ENR+CV-3 | Gm9846 |
| Atp5j1 | 0.77 | 0.584171958 | 0.54 | 0.991 | 0.687 | ENR+CV-3 | Atp5j |
| H1f02 | 0.768 | 0.74386176 | 0.536 | 0.896 | 0.37 | ENR+CV-3 | H1f0 |
| Cox6a11 | 0.768 | 0.54798628 | 0.536 | 0.995 | 0.7 | ENR+CV-3 | Cox6a1 |
| Wbp51 | 0.766 | 0.641666207 | 0.532 | 0.968 | 0.491 | ENR+CV-3 | Wbp5 |
| Rplp2 | 0.765 | 0.452349039 | 0.53 | 0.995 | 0.902 | ENR+CV-3 | Rplp2 |
| Sypl | 0.762 | 0.749466665 | 0.524 | 0.882 | 0.391 | ENR+CV-3 | Sypl |

TABLE 1-continued

Derived gene list of the top defining genes from in vivo ileal
small intestine PCs and EECs captured on the Seq-Well platform

| | | | | | | |
|---|---|---|---|---|---|---|
| Rpl141 | 0.759 | 0.430205949 | 0.518 | 1 | 0.922 ENR+CV-3 | Rpl14 |
| Ybx12 | 0.758 | 0.55934825 | 0.516 | 0.995 | 0.726 ENR+CV-3 | Ybx1 |
| Ctsb1 | 0.757 | 0.670810669 | 0.514 | 0.873 | 0.349 ENR+CV-3 | Ctsb |
| Aldoa1 | 0.754 | 0.666483028 | 0.508 | 0.986 | 0.647 ENR+CV-3 | Aldoa |
| Ak21 | 0.753 | 0.721421159 | 0.506 | 0.814 | 0.278 ENR+CV-3 | Ak2 |
| Myeov21 | 0.75 | 0.631872152 | 0.5 | 0.882 | 0.372 ENR+CV-3 | Myeov2 |
| Eif3h1 | 0.75 | 0.591732165 | 0.5 | 0.964 | 0.505 ENR+CV-3 | Eif3h |
| Ckb | 0.749 | 0.682869362 | 0.498 | 0.81 | 0.276 ENR+CV-3 | Ckb |
| Atp1a12 | 0.749 | 0.627419723 | 0.498 | 0.914 | 0.397 ENR+CV-3 | Atp1a1 |
| Rps15a1 | 0.749 | 0.449087169 | 0.498 | 0.991 | 0.887 ENR+CV-3 | Rps15a |
| Phlda11 | 0.748 | 0.777401118 | 0.496 | 0.796 | 0.315 ENR+CV-3 | Phlda1 |
| Rpl131 | 0.748 | 0.417357415 | 0.496 | 0.995 | 0.904 ENR+CV-3 | Rpl13 |
| Mgst1 | 0.745 | 0.619861192 | 0.49 | 0.928 | 0.425 ENR+CV-3 | Mgst1 |
| Tmem2561 | 0.744 | 0.636439891 | 0.488 | 0.887 | 0.38 ENR+CV-3 | Tmem256 |
| Gm102211 | 0.743 | 0.766666364 | 0.486 | 0.638 | 0.132 ENR+CV-3 | Gm10221 |
| Psma71 | 0.743 | 0.538305792 | 0.486 | 0.95 | 0.573 ENR+CV-3 | Psma7 |
| Sub11 | 0.741 | 0.624102379 | 0.482 | 0.842 | 0.332 ENR+CV-3 | Sub1 |
| Cdca7 | 0.74 | 0.697599918 | 0.48 | 0.756 | 0.246 ENR+CV-3 | Cdca7 |
| Rps281 | 0.74 | 0.624818021 | 0.48 | 0.851 | 0.331 ENR+CV-3 | Rps28 |
| Rps22 | 0.74 | 0.376684404 | 0.48 | 0.995 | 0.933 ENR+CV-3 | Rps2 |
| Uqcrq1 | 0.738 | 0.498622019 | 0.476 | 0.991 | 0.755 ENR+CV-3 | Uqcrq |
| Vim1 | 0.737 | 0.954678585 | 0.474 | 0.588 | 0.099 ENR+CV-3 | Vim |
| Ndufb81 | 0.736 | 0.562751922 | 0.472 | 0.941 | 0.502 ENR+CV-3 | Ndufb8 |
| Trappc6a1 | 0.734 | 0.621645462 | 0.468 | 0.774 | 0.26 ENR+CV-3 | Trappc6a |
| Mlec1 | 0.734 | 0.593030871 | 0.468 | 0.864 | 0.356 ENR+CV-3 | Mlec |
| Cox6c2 | 0.734 | 0.454695247 | 0.468 | 1 | 0.779 ENR+CV-3 | Cox6c |
| Galk12 | 0.733 | 0.645641873 | 0.466 | 0.692 | 0.185 ENR+CV-3 | Galk1 |
| Pfdn1 | 0.733 | 0.638528383 | 0.466 | 0.742 | 0.231 ENR+CV-3 | Pfdn1 |
| Park71 | 0.733 | 0.567813504 | 0.466 | 0.914 | 0.423 ENR+CV-3 | Park7 |
| Rpl32 | 0.733 | 0.46022263 | 0.466 | 0.968 | 0.759 ENR+CV-3 | Rpl3 |
| Slc25a4 | 0.732 | 0.584781706 | 0.464 | 0.819 | 0.306 ENR+CV-3 | Slc25a4 |
| Mif1 | 0.732 | 0.568883378 | 0.464 | 0.919 | 0.499 ENR+CV-3 | Mif |
| Atp5e1 | 0.732 | 0.486500813 | 0.464 | 0.982 | 0.664 ENR+CV-3 | Atp5e |
| Mtch2 | 0.73 | 0.601281 | 0.46 | 0.81 | 0.3 ENR+CV-3 | Mtch2 |
| Rpl181 | 0.73 | 0.474439384 | 0.46 | 0.991 | 0.662 ENR+CV-3 | Rpl18 |
| Atox11 | 0.727 | 0.580173269 | 0.454 | 0.846 | 0.347 ENR+CV-3 | Atox1 |
| Psmc12 | 0.727 | 0.573994153 | 0.454 | 0.747 | 0.234 ENR+CV-3 | Psmc1 |
| 2010107E04Rik1 | 0.727 | 0.487017903 | 0.454 | 0.977 | 0.667 ENR+CV-3 | 2010107E04Rik |
| Slc25a51 | 0.726 | 0.460599637 | 0.452 | 0.995 | 0.761 ENR+CV-3 | Slc25a5 |
| Epcam | 0.726 | 0.424475339 | 0.452 | 1 | 0.807 ENR+CV-3 | Epcam |
| Eef22 | 0.726 | 0.414431312 | 0.452 | 0.995 | 0.845 ENR+CV-3 | Eef2 |
| Rpl391 | 0.726 | 0.394109583 | 0.452 | 0.995 | 0.857 ENR+CV-3 | Rpl39 |
| Add3 | 0.725 | 0.628880588 | 0.45 | 0.701 | 0.211 ENR+CV-3 | Add3 |
| Eef1g1 | 0.725 | 0.512951349 | 0.45 | 0.964 | 0.585 ENR+CV-3 | Eef1g |
| Atp5b1 | 0.725 | 0.452478372 | 0.45 | 0.977 | 0.724 ENR+CV-3 | Atp5b |
| Rpl4 | 0.725 | 0.338087884 | 0.45 | 1 | 0.938 ENR+CV-3 | Rpl4 |
| Dynll2 | 0.724 | 0.618623907 | 0.448 | 0.751 | 0.267 ENR+CV-3 | Dynll2 |
| Gm4540 | 0.723 | 0.672610546 | 0.446 | 0.647 | 0.166 ENR+CV-3 | Gm4540 |
| Ccnd21 | 0.723 | 0.557995735 | 0.446 | 0.873 | 0.379 ENR+CV-3 | Ccnd2 |
| Ndufa12 | 0.723 | 0.543807321 | 0.446 | 0.842 | 0.347 ENR+CV-3 | Ndufa12 |
| Snord132 | 0.722 | 0.498183418 | 0.444 | 0.647 | 0.172 ENR+CV-3 | Snord13 |
| Cyba | 0.721 | 0.554165323 | 0.442 | 0.701 | 0.205 ENR+CV-3 | Cyba |
| Ndufab1 | 0.721 | 0.520188929 | 0.442 | 0.833 | 0.331 ENR+CV-3 | Ndufab1 |
| Eif5a | 0.721 | 0.500946988 | 0.442 | 0.928 | 0.515 ENR+CV-3 | Eif5a |
| Tomm71 | 0.721 | 0.500029484 | 0.442 | 0.946 | 0.533 ENR+CV-3 | Tomm7 |
| Arl3 | 0.719 | 0.69994313 | 0.438 | 0.57 | 0.113 ENR+CV-3 | Arl3 |
| Mdh21 | 0.719 | 0.522376731 | 0.438 | 0.855 | 0.396 ENR+CV-3 | Mdh2 |
| Crip11 | 0.719 | 0.506638097 | 0.438 | 0.878 | 0.394 ENR+CV-3 | Crip1 |
| Fuca1 | 0.718 | 0.581660075 | 0.436 | 0.697 | 0.22 ENR+CV-3 | Fuca1 |
| Lamp1 | 0.718 | 0.555105189 | 0.436 | 0.833 | 0.358 ENR+CV-3 | Lamp1 |
| Uqcrc11 | 0.718 | 0.544241079 | 0.436 | 0.882 | 0.414 ENR+CV-3 | Uqcrc1 |
| Snrpd31 | 0.718 | 0.538084323 | 0.436 | 0.864 | 0.374 ENR+CV-3 | Snrpd3 |
| Pkm2 | 0.718 | 0.509105355 | 0.436 | 0.964 | 0.633 ENR+CV-3 | Pkm |
| Oaz11 | 0.716 | 0.491148852 | 0.432 | 0.955 | 0.613 ENR+CV-3 | Oaz1 |
| Rpl351 | 0.716 | 0.442431829 | 0.432 | 0.955 | 0.711 ENR+CV-3 | Rpl35 |
| Hmgb11 | 0.715 | 0.644395771 | 0.43 | 0.71 | 0.246 ENR+CV-3 | Hmgb1 |
| Cdx1 | 0.715 | 0.551181651 | 0.43 | 0.67 | 0.192 ENR+CV-3 | Cdx1 |
| Snrpg2 | 0.715 | 0.542019009 | 0.43 | 0.9 | 0.463 ENR+CV-3 | Snrpg |
| Rny12 | 0.715 | 0.439986527 | 0.43 | 0.538 | 0.084 ENR+CV-3 | Rny1 |
| Csde1 | 0.714 | 0.552550741 | 0.428 | 0.801 | 0.309 ENR+CV-3 | Csde1 |
| Eno1 | 0.714 | 0.524899177 | 0.428 | 0.833 | 0.342 ENR+CV-3 | Eno1 |
| Pebp1 | 0.714 | 0.50495432 | 0.428 | 0.842 | 0.357 ENR+CV-3 | Pebp1 |
| Rps251 | 0.714 | 0.499252028 | 0.428 | 0.946 | 0.544 ENR+CV-3 | Rps25 |
| Uqcrh1 | 0.714 | 0.458430983 | 0.428 | 0.977 | 0.637 ENR+CV-3 | Uqcrh |
| Csnk2a1 | 0.713 | 0.642110189 | 0.426 | 0.606 | 0.155 ENR+CV-3 | Csnk2a1 |
| Mrpl521 | 0.713 | 0.501094602 | 0.426 | 0.91 | 0.427 ENR+CV-3 | Mrpl52 |
| Ndufs61 | 0.712 | 0.433312477 | 0.424 | 0.905 | 0.408 ENR+CV-3 | Ndufs6 |

TABLE 1-continued

Derived gene list of the top defining genes from in vivo ileal
small intestine PCs and EECs captured on the Seq-Well platform

| | | | | | | |
|---|---|---|---|---|---|---|
| Calm12 | 0.712 | 0.382793703 | 0.424 | 0.991 | 0.872 ENR+CV-3 | Calm1 |
| Ndufs2 | 0.71 | 0.45481868 | 0.42 | 0.819 | 0.309 ENR+CV-3 | Ndufs2 |
| Prmt1 | 0.709 | 0.531759271 | 0.418 | 0.724 | 0.258 ENR+CV-3 | Prmt1 |
| Cox17 | 0.709 | 0.51590104 | 0.418 | 0.747 | 0.272 ENR+CV-3 | Cox17 |
| Jun | 0.708 | 0.515651681 | 0.416 | 0.914 | 0.534 ENR+CV-3 | Jun |
| Arpc1b | 0.707 | 0.551180402 | 0.414 | 0.796 | 0.336 ENR+CV-3 | Arpc1b |
| Tmed9 | 0.707 | 0.546826427 | 0.414 | 0.647 | 0.194 ENR+CV-3 | Tmed9 |
| Arpp192 | 0.707 | 0.495929126 | 0.414 | 0.819 | 0.34 ENR+CV-3 | Arpp19 |
| Tead2 | 0.706 | 0.621919046 | 0.412 | 0.502 | 0.072 ENR+CV-3 | Tead2 |
| Dsg2 | 0.706 | 0.566764688 | 0.412 | 0.638 | 0.189 ENR+CV-3 | Dsg2 |
| Serf2 | 0.706 | 0.552876052 | 0.412 | 0.701 | 0.239 ENR+CV-3 | Serf2 |
| Tmem97 | 0.706 | 0.547784866 | 0.412 | 0.697 | 0.24 ENR+CV-3 | Tmem97 |
| Dnajc8 | 0.706 | 0.50563781 | 0.412 | 0.724 | 0.251 ENR+CV-3 | Dnajc8 |
| Tpi12 | 0.706 | 0.46461955 | 0.412 | 0.955 | 0.583 ENR+CV-3 | Tpi1 |
| Snrpd2 | 0.705 | 0.485441588 | 0.41 | 0.851 | 0.387 ENR+CV-3 | Snrpd2 |
| Ndufa31 | 0.705 | 0.478980309 | 0.41 | 0.864 | 0.391 ENR+CV-3 | Ndufa3 |
| Ndufa5 | 0.705 | 0.465778497 | 0.41 | 0.833 | 0.374 ENR+CV-3 | Ndufa5 |
| Gm10269 | 0.703 | 0.50077729 | 0.406 | 0.864 | 0.433 ENR+CV-3 | Gm10269 |
| Ndufa1 | 0.703 | 0.489976971 | 0.406 | 0.814 | 0.366 ENR+CV-3 | Ndufa1 |
| Serbp11 | 0.703 | 0.39044087 | 0.406 | 0.995 | 0.711 ENR+CV-3 | Serbp1 |
| Ndufa10 | 0.702 | 0.508640029 | 0.404 | 0.719 | 0.257 ENR+CV-3 | Ndufa10 |
| Psmb3 | 0.702 | 0.499568081 | 0.404 | 0.719 | 0.262 ENR+CV-3 | Psmb3 |
| Comt | 0.701 | 0.521829423 | 0.402 | 0.615 | 0.175 ENR+CV-3 | Comt |
| Rpn12 | 0.701 | 0.48864935 | 0.402 | 0.814 | 0.368 ENR+CV-3 | Rpn1 |
| Ndufc11 | 0.701 | 0.471415311 | 0.402 | 0.882 | 0.475 ENR+CV-3 | Ndufc1 |
| Metap2 | 0.7 | 0.457477292 | 0.4 | 0.765 | 0.295 ENR+CV-3 | Metap2 |
| Soat1 | 0.699 | 0.534161128 | 0.398 | 0.719 | 0.272 ENR+CV-3 | Soat1 |
| Atp5o1 | 0.699 | 0.465570085 | 0.398 | 0.937 | 0.526 ENR+CV-3 | Atp5o |
| Usmg51 | 0.699 | 0.416724209 | 0.398 | 0.955 | 0.595 ENR+CV-3 | Usmg5 |
| Rad23b | 0.698 | 0.550281074 | 0.396 | 0.611 | 0.182 ENR+CV-3 | Rad23b |
| Idh2 | 0.698 | 0.504268037 | 0.396 | 0.674 | 0.231 ENR+CV-3 | Idh2 |
| Laptm4b | 0.697 | 0.593510643 | 0.394 | 0.566 | 0.145 ENR+CV-3 | Laptm4b |
| Rpl17 | 0.697 | 0.501069685 | 0.394 | 0.647 | 0.202 ENR+CV-3 | Rpl17 |
| Cbx1 | 0.697 | 0.486674593 | 0.394 | 0.747 | 0.301 ENR+CV-3 | Cbx1 |
| Akr7a5 | 0.697 | 0.486341871 | 0.394 | 0.643 | 0.201 ENR+CV-3 | Akr7a5 |
| Ppp1r1b | 0.697 | 0.483458592 | 0.394 | 0.719 | 0.27 ENR+CV-3 | Ppp1r1b |
| Acin1 | 0.697 | 0.477968862 | 0.394 | 0.756 | 0.301 ENR+CV-3 | Acin1 |
| Pet100 | 0.697 | 0.470323212 | 0.394 | 0.611 | 0.175 ENR+CV-3 | Pet100 |
| Txnip | 0.697 | 0.452523054 | 0.394 | 0.814 | 0.346 ENR+CV-3 | Txnip |
| Gltscr2 | 0.696 | 0.493536009 | 0.392 | 0.729 | 0.289 ENR+CV-3 | Gltscr2 |
| Eml4 | 0.696 | 0.461386059 | 0.392 | 0.738 | 0.281 ENR+CV-3 | Eml4 |
| Ehf | 0.696 | 0.450087744 | 0.392 | 0.783 | 0.319 ENR+CV-3 | Ehf |
| Hnrnpu | 0.696 | 0.437482268 | 0.392 | 0.95 | 0.565 ENR+CV-3 | Hnrnpu |
| Thoc7 | 0.696 | 0.413274323 | 0.392 | 0.837 | 0.374 ENR+CV-3 | Thoc7 |
| Ap1s1 | 0.695 | 0.526769717 | 0.39 | 0.588 | 0.163 ENR+CV-3 | Ap1s1 |
| Snrpf1 | 0.695 | 0.458744027 | 0.39 | 0.801 | 0.342 ENR+CV-3 | Snrpf |
| Minos1 | 0.695 | 0.422558135 | 0.39 | 0.932 | 0.534 ENR+CV-3 | Minos1 |
| Pkig | 0.694 | 0.564847015 | 0.388 | 0.548 | 0.133 ENR+CV-3 | Pkig |
| Cyp2j6 | 0.694 | 0.542500854 | 0.388 | 0.548 | 0.13 ENR+CV-3 | Cyp2j6 |
| Tax1bp11 | 0.694 | 0.535992833 | 0.388 | 0.837 | 0.459 ENR+CV-3 | Tax1bp1 |
| Apex1 | 0.694 | 0.480283271 | 0.388 | 0.62 | 0.185 ENR+CV-3 | Apex1 |
| Hook1 | 0.694 | 0.449640984 | 0.388 | 0.864 | 0.446 ENR+CV-3 | Hook1 |
| Atp6v1e1 | 0.694 | 0.41904861 | 0.388 | 0.661 | 0.21 ENR+CV-3 | Atp6v1e1 |
| Ndufv32 | 0.694 | 0.41551974 | 0.388 | 0.796 | 0.318 ENR+CV-3 | Ndufv3 |
| Dnaja1 | 0.693 | 0.472692722 | 0.386 | 0.629 | 0.194 ENR+CV-3 | Dnaja1 |
| Aprt | 0.693 | 0.435115211 | 0.386 | 0.738 | 0.279 ENR+CV-3 | Aprt |
| Sord | 0.692 | 0.557387596 | 0.384 | 0.611 | 0.192 ENR+CV-3 | Sord |
| Acat1 | 0.692 | 0.553756071 | 0.384 | 0.566 | 0.151 ENR+CV-3 | Acat1 |
| Wdr43 | 0.692 | 0.530751722 | 0.384 | 0.624 | 0.201 ENR+CV-3 | Wdr43 |
| Tmed2 | 0.692 | 0.481892892 | 0.384 | 0.624 | 0.194 ENR+CV-3 | Tmed2 |
| Aldh9a11 | 0.692 | 0.481803816 | 0.384 | 0.602 | 0.173 ENR+CV-3 | Aldh9a1 |
| Arpc5 | 0.692 | 0.430571372 | 0.384 | 0.774 | 0.313 ENR+CV-3 | Arpc5 |
| 1110004F10Rik | 0.691 | 0.48303973 | 0.382 | 0.638 | 0.208 ENR+CV-3 | 1110004F10Rik |
| Spcs2 | 0.691 | 0.427443596 | 0.382 | 0.819 | 0.371 ENR+CV-3 | Spcs2 |
| Oat | 0.69 | 0.485645315 | 0.38 | 0.824 | 0.405 ENR+CV-3 | Oat |
| Snw1 | 0.69 | 0.478948898 | 0.38 | 0.665 | 0.237 ENR+CV-3 | Snw1 |
| 2410015M20Rik1 | 0.69 | 0.470502234 | 0.38 | 0.683 | 0.245 ENR+CV-3 | 2410015M20Rik |
| Mrpl33 | 0.69 | 0.433850397 | 0.38 | 0.828 | 0.379 ENR+CV-3 | Mrpl33 |
| Junb1 | 0.689 | 0.573703823 | 0.378 | 0.76 | 0.379 ENR+CV-3 | Junb |
| Axin2 | 0.689 | 0.524359624 | 0.378 | 0.643 | 0.228 ENR+CV-3 | Axin2 |
| Mfge8 | 0.689 | 0.49247588 | 0.378 | 0.597 | 0.173 ENR+CV-3 | Mfge8 |
| Lamtor2 | 0.689 | 0.475494943 | 0.378 | 0.615 | 0.193 ENR+CV-3 | Lamtor2 |
| Lima1 | 0.689 | 0.45266264 | 0.378 | 0.679 | 0.244 ENR+CV-3 | Lima1 |
| Ubqln1 | 0.688 | 0.534669301 | 0.376 | 0.584 | 0.178 ENR+CV-3 | Ubqln1 |
| Psmc3 | 0.688 | 0.524369149 | 0.376 | 0.643 | 0.225 ENR+CV-3 | Psmc3 |
| Lad1 | 0.688 | 0.514307509 | 0.376 | 0.629 | 0.213 ENR+CV-3 | Lad1 |
| Uchl3 | 0.688 | 0.500086828 | 0.376 | 0.557 | 0.144 ENR+CV-3 | Uchl3 |

TABLE 1-continued

Derived gene list of the top defining genes from in vivo ileal
small intestine PCs and EECs captured on the Seq-Well platform

| Gene | | | | | | |
|---|---|---|---|---|---|---|
| Mapk131 | 0.688 | 0.493697597 | 0.376 | 0.647 | 0.222 ENR+CV-3 | Mapk13 |
| 0610011F06Rik | 0.688 | 0.485923426 | 0.376 | 0.606 | 0.192 ENR+CV-3 | 0610011F06Rik |
| Tecr | 0.688 | 0.474383501 | 0.376 | 0.783 | 0.342 ENR+CV-3 | Tecr |
| Sars | 0.688 | 0.417812344 | 0.376 | 0.742 | 0.296 ENR+CV-3 | Sars |
| Fgfbp1 | 0.687 | 0.493895446 | 0.374 | 0.656 | 0.235 ENR+CV-3 | Fgfbp1 |
| Tmem160 | 0.687 | 0.47622251 | 0.374 | 0.624 | 0.203 ENR+CV-3 | Tmem160 |
| Tubb51 | 0.687 | 0.375347083 | 0.374 | 0.982 | 0.584 ENR+CV-3 | Tubb5 |
| Gsk3b | 0.686 | 0.500189713 | 0.372 | 0.566 | 0.159 ENR+CV-3 | Gsk3b |
| App | 0.686 | 0.471694593 | 0.372 | 0.783 | 0.348 ENR+CV-3 | App |
| Cd9 | 0.686 | 0.427843824 | 0.372 | 0.679 | 0.247 ENR+CV-3 | Cd9 |
| Dnase2a | 0.685 | 0.613718118 | 0.37 | 0.511 | 0.12 ENR+CV-3 | Dnase2a |
| Rpl36 | 0.685 | 0.481849544 | 0.37 | 0.561 | 0.156 ENR+CV-3 | Rpl36 |
| Cldn7 | 0.685 | 0.432196745 | 0.37 | 0.946 | 0.605 ENR+CV-3 | Cldn7 |
| Hsd17b10 | 0.685 | 0.42841952 | 0.37 | 0.62 | 0.199 ENR+CV-3 | Hsd17b10 |
| Cyb5b | 0.685 | 0.398828102 | 0.37 | 0.679 | 0.238 ENR+CV-3 | Cyb5b |
| Eif3e | 0.685 | 0.385606147 | 0.37 | 0.824 | 0.363 ENR+CV-3 | Eif3e |
| Idh3a | 0.684 | 0.456073175 | 0.368 | 0.633 | 0.214 ENR+CV-3 | Idh3a |
| Ndufb7 | 0.684 | 0.427776183 | 0.368 | 0.756 | 0.32 ENR+CV-3 | Ndufb7 |
| Bzw1 | 0.684 | 0.426022225 | 0.368 | 0.796 | 0.37 ENR+CV-3 | Bzw1 |
| Mrpl12 | 0.684 | 0.419145279 | 0.368 | 0.769 | 0.327 ENR+CV-3 | Mrpl12 |
| Glrx | 0.683 | 0.52357108 | 0.366 | 0.538 | 0.144 ENR+CV-3 | Glrx |
| Ctsa | 0.683 | 0.47825754 | 0.366 | 0.557 | 0.154 ENR+CV-3 | Ctsa |
| Pcsk91 | 0.683 | 0.469291573 | 0.366 | 0.566 | 0.161 ENR+CV-3 | Pcsk9 |
| Mvb12a | 0.683 | 0.454207468 | 0.366 | 0.548 | 0.145 ENR+CV-3 | Mvb12a |
| Arpc2 | 0.683 | 0.422174137 | 0.366 | 0.851 | 0.426 ENR+CV-3 | Arpc2 |
| Bzw2 | 0.683 | 0.421530304 | 0.366 | 0.719 | 0.289 ENR+CV-3 | Bzw2 |
| Atp5d2 | 0.683 | 0.414779573 | 0.366 | 0.873 | 0.417 ENR+CV-3 | Atp5d |
| Ndufa61 | 0.683 | 0.340849804 | 0.366 | 0.977 | 0.718 ENR+CV-3 | Ndufa6 |
| Rpl221 | 0.683 | 0.322613878 | 0.366 | 0.991 | 0.785 ENR+CV-3 | Rpl22 |
| Acot11 | 0.682 | 0.614570561 | 0.364 | 0.471 | 0.092 ENR+CV-3 | Acot1 |
| Pdcd10 | 0.682 | 0.438298087 | 0.364 | 0.548 | 0.145 ENR+CV-3 | Pdcd10 |
| Suclg1 | 0.682 | 0.416695547 | 0.364 | 0.76 | 0.334 ENR+CV-3 | Suclg1 |
| Cops6 | 0.682 | 0.409094336 | 0.364 | 0.674 | 0.238 ENR+CV-3 | Cops6 |
| Mdh1 | 0.682 | 0.387172038 | 0.364 | 0.819 | 0.367 ENR+CV-3 | Mdh1 |
| Znhit1 | 0.681 | 0.524642877 | 0.362 | 0.529 | 0.139 ENR+CV-3 | Znhit1 |
| Pabpc41 | 0.681 | 0.521062663 | 0.362 | 0.566 | 0.175 ENR+CV-3 | Pabpc4 |
| Lta4h | 0.681 | 0.50672711 | 0.362 | 0.57 | 0.176 ENR+CV-3 | Lta4h |
| Ywhab | 0.681 | 0.399289516 | 0.362 | 0.76 | 0.32 ENR+CV-3 | Ywhab |
| Gsta4 | 0.681 | 0.389742797 | 0.362 | 0.661 | 0.231 ENR+CV-3 | Gsta4 |
| Aqp11 | 0.68 | 0.557672201 | 0.36 | 0.534 | 0.149 ENR+CV-3 | Aqp1 |
| Arhgef26 | 0.68 | 0.548666846 | 0.36 | 0.529 | 0.144 ENR+CV-3 | Arhgef26 |
| H2-Q101 | 0.68 | 0.52104614 | 0.36 | 0.507 | 0.121 ENR+CV-3 | H2-Q10 |
| Twf1 | 0.68 | 0.439306173 | 0.36 | 0.67 | 0.252 ENR+CV-3 | Twf1 |
| Nme1 | 0.68 | 0.387850695 | 0.36 | 0.923 | 0.559 ENR+CV-3 | Nme1 |
| Cope | 0.68 | 0.374611929 | 0.36 | 0.747 | 0.306 ENR+CV-3 | Cope |
| Zfp36 | 0.679 | 0.543233338 | 0.358 | 0.593 | 0.204 ENR+CV-3 | Zfp36 |
| Hmg20b | 0.679 | 0.53467553 | 0.358 | 0.566 | 0.177 ENR+CV-3 | Hmg20b |
| Dcun1d5 | 0.679 | 0.486130114 | 0.358 | 0.548 | 0.158 ENR+CV-3 | Dcun1d5 |
| Psmb2 | 0.679 | 0.433742397 | 0.358 | 0.665 | 0.25 ENR+CV-3 | Psmb2 |
| Pls1 | 0.679 | 0.423596256 | 0.358 | 0.593 | 0.189 ENR+CV-3 | Pls1 |
| Hopx | 0.679 | 0.409355664 | 0.358 | 0.742 | 0.305 ENR+CV-3 | Hopx |
| Chchd10 | 0.679 | 0.408157904 | 0.358 | 0.742 | 0.309 ENR+CV-3 | Chchd10 |
| Dad1 | 0.679 | 0.381908568 | 0.358 | 0.769 | 0.331 ENR+CV-3 | Dad1 |
| Canx | 0.679 | 0.380533037 | 0.358 | 0.891 | 0.499 ENR+CV-3 | Canx |
| Aldh2 | 0.678 | 0.4639208 | 0.356 | 0.552 | 0.161 ENR+CV-3 | Aldh2 |
| Sox41 | 0.678 | 0.4392346 | 0.356 | 0.783 | 0.366 ENR+CV-3 | Sox4 |
| Ywhaz | 0.678 | 0.400032937 | 0.356 | 0.805 | 0.376 ENR+CV-3 | Ywhaz |
| H2afv | 0.678 | 0.37940599 | 0.356 | 0.828 | 0.387 ENR+CV-3 | H2afv |
| G3bp1 | 0.678 | 0.37671642 | 0.356 | 0.729 | 0.287 ENR+CV-3 | G3bp1 |
| Sfxn1 | 0.677 | 0.441768707 | 0.354 | 0.575 | 0.182 ENR+CV-3 | Sfxn1 |
| Ctsz | 0.677 | 0.430988794 | 0.354 | 0.611 | 0.208 ENR+CV-3 | Ctsz |
| Eif4a1 | 0.677 | 0.385100864 | 0.354 | 0.905 | 0.476 ENR+CV-3 | Eif4a1 |
| Ndufb2 | 0.677 | 0.364182611 | 0.354 | 0.828 | 0.388 ENR+CV-3 | Ndufb2 |
| Bex4 | 0.676 | 0.545701687 | 0.352 | 0.443 | 0.076 ENR+CV-3 | Bex4 |
| Bri3 | 0.676 | 0.452087739 | 0.352 | 0.557 | 0.168 ENR+CV-3 | Bri3 |
| Serinc31 | 0.676 | 0.420862488 | 0.352 | 0.864 | 0.483 ENR+CV-3 | Serinc3 |
| Cers6 | 0.676 | 0.395466968 | 0.352 | 0.638 | 0.227 ENR+CV-3 | Cers6 |
| Eif3f | 0.676 | 0.386926285 | 0.352 | 0.864 | 0.429 ENR+CV-3 | Eif3f |
| Srrm1 | 0.676 | 0.37766384 | 0.352 | 0.751 | 0.331 ENR+CV-3 | Srrm1 |
| 1110001J03Rik | 0.676 | 0.363553813 | 0.352 | 0.633 | 0.218 ENR+CV-3 | 1110001J03Rik |
| Rpl8 | 0.676 | 0.260214241 | 0.352 | 1 | 0.923 ENR+CV-3 | Rpl8 |
| mt-Tc1 | 0.675 | 0.639123219 | 0.35 | 0.421 | 0.061 ENR+CV-3 | mt-Tc |
| Cps1 | 0.675 | 0.426588497 | 0.35 | 0.765 | 0.354 ENR+CV-3 | Cps1 |
| 1500012F01Rik | 0.675 | 0.406799037 | 0.35 | 0.937 | 0.572 ENR+CV-3 | 1500012F01Rik |
| Cacybp | 0.675 | 0.366274181 | 0.35 | 0.719 | 0.295 ENR+CV-3 | Cacybp |
| Clybl | 0.674 | 0.611557978 | 0.348 | 0.434 | 0.073 ENR+CV-3 | Clybl |
| Rpl7l1 | 0.674 | 0.492337758 | 0.348 | 0.552 | 0.174 ENR+CV-3 | Rpl7l1 |

TABLE 1-continued

Derived gene list of the top defining genes from in vivo ileal
small intestine PCs and EECs captured on the Seq-Well platform

| Gene | | | | | | Gene |
|---|---|---|---|---|---|---|
| Rny32 | 0.674 | 0.470854807 | 0.348 | 0.471 | 0.1 ENR+CV-3 | Rny3 |
| Cbx3 | 0.674 | 0.469049363 | 0.348 | 0.529 | 0.15 ENR+CV-3 | Cbx3 |
| Aifm1 | 0.674 | 0.444019111 | 0.348 | 0.525 | 0.145 ENR+CV-3 | Aifm1 |
| Nsun2 | 0.674 | 0.436448825 | 0.348 | 0.602 | 0.211 ENR+CV-3 | Nsun2 |
| Ppp1ca | 0.674 | 0.382771358 | 0.348 | 0.824 | 0.399 ENR+CV-3 | Ppp1ca |
| Lamp2 | 0.674 | 0.368635373 | 0.348 | 0.719 | 0.288 ENR+CV-3 | Lamp2 |
| Tkt1 | 0.674 | 0.358386366 | 0.348 | 0.878 | 0.456 ENR+CV-3 | Tkt |
| Selm | 0.674 | 0.358159816 | 0.348 | 0.674 | 0.241 ENR+CV-3 | Selm |
| Mrpl15 | 0.674 | 0.347372791 | 0.348 | 0.692 | 0.268 ENR+CV-3 | Mrpl15 |
| Nrtn | 0.673 | 0.53091795 | 0.346 | 0.439 | 0.079 ENR+CV-3 | Nrtn |
| Clptm1 | 0.673 | 0.469160678 | 0.346 | 0.507 | 0.135 ENR+CV-3 | Clptm1 |
| Tspo | 0.673 | 0.46243975 | 0.346 | 0.534 | 0.156 ENR+CV-3 | Tspo |
| Cct7 | 0.673 | 0.409761799 | 0.346 | 0.729 | 0.319 ENR+CV-3 | Cct7 |
| Tbca | 0.673 | 0.380328447 | 0.346 | 0.719 | 0.311 ENR+CV-3 | Tbca |
| Sptssa | 0.673 | 0.37717076 | 0.346 | 0.715 | 0.298 ENR+CV-3 | Sptssa |
| Rbm8a | 0.673 | 0.376574226 | 0.346 | 0.62 | 0.216 ENR+CV-3 | Rbm8a |
| Ndufa41 | 0.673 | 0.32906803 | 0.346 | 0.977 | 0.748 ENR+CV-3 | Ndufa4 |
| Ndufs5 | 0.672 | 0.500986975 | 0.344 | 0.498 | 0.129 ENR+CV-3 | Ndufs5 |
| Sdhc | 0.672 | 0.426909918 | 0.344 | 0.611 | 0.219 ENR+CV-3 | Sdhc |
| Pdha1 | 0.672 | 0.416285807 | 0.344 | 0.674 | 0.27 ENR+CV-3 | Pdha1 |
| Anp32a | 0.672 | 0.404571369 | 0.344 | 0.787 | 0.372 ENR+CV-3 | Anp32a |
| Eif4e2 | 0.672 | 0.40339984 | 0.344 | 0.557 | 0.17 ENR+CV-3 | Eif4e2 |
| Etfb | 0.672 | 0.349009015 | 0.344 | 0.805 | 0.374 ENR+CV-3 | Etfb |
| Cox6b11 | 0.672 | 0.317394065 | 0.344 | 0.977 | 0.717 ENR+CV-3 | Cox6b1 |
| Phb | 0.671 | 0.507311685 | 0.342 | 0.502 | 0.136 ENR+CV-3 | Phb |
| Rgcc | 0.671 | 0.440443985 | 0.342 | 0.747 | 0.366 ENR+CV-3 | Rgcc |
| Ggh | 0.671 | 0.382163233 | 0.342 | 0.525 | 0.147 ENR+CV-3 | Ggh |
| Nol7 | 0.671 | 0.377761019 | 0.342 | 0.738 | 0.325 ENR+CV-3 | Nol7 |
| Psmb5 | 0.671 | 0.340881727 | 0.342 | 0.656 | 0.244 ENR+CV-3 | Psmb5 |
| Rab14 | 0.67 | 0.420691706 | 0.34 | 0.548 | 0.17 ENR+CV-3 | Rab14 |
| Cdc37 | 0.67 | 0.352091696 | 0.34 | 0.665 | 0.257 ENR+CV-3 | Cdc37 |
| Tmem234 | 0.67 | 0.338674832 | 0.34 | 0.679 | 0.265 ENR+CV-3 | Tmem234 |
| Ndufs4 | 0.67 | 0.279670847 | 0.34 | 0.751 | 0.311 ENR+CV-3 | Ndufs4 |
| Sec31a | 0.669 | 0.448918499 | 0.338 | 0.543 | 0.171 ENR+CV-3 | Sec31a |
| Ubc1 | 0.669 | 0.431980907 | 0.338 | 0.887 | 0.56 ENR+CV-3 | Ubc |
| Ugp2 | 0.669 | 0.411997002 | 0.338 | 0.538 | 0.165 ENR+CV-3 | Ugp2 |
| Psap | 0.669 | 0.382956096 | 0.338 | 0.579 | 0.193 ENR+CV-3 | Psap |
| Mtdh | 0.669 | 0.376522728 | 0.338 | 0.706 | 0.307 ENR+CV-3 | Mtdh |
| Cox7c | 0.669 | 0.363624068 | 0.338 | 0.774 | 0.36 ENR+CV-3 | Cox7c |
| Hbegf | 0.668 | 0.557694397 | 0.336 | 0.575 | 0.211 ENR+CV-3 | Hbegf |
| Rgmb | 0.668 | 0.551997456 | 0.336 | 0.471 | 0.117 ENR+CV-3 | Rgmb |
| Anapc13 | 0.668 | 0.385261924 | 0.336 | 0.674 | 0.285 ENR+CV-3 | Anapc13 |
| Eif1 | 0.668 | 0.381477039 | 0.336 | 0.837 | 0.429 ENR+CV-3 | Eif1 |
| Aldh1b1 | 0.668 | 0.377830257 | 0.336 | 0.756 | 0.341 ENR+CV-3 | Aldh1b1 |
| Cyc1 | 0.668 | 0.344214435 | 0.336 | 0.765 | 0.333 ENR+CV-3 | Cyc1 |
| Rpl11 | 0.668 | 0.329616289 | 0.336 | 0.692 | 0.274 ENR+CV-3 | Rpl11 |
| Agpat5 | 0.667 | 0.463994026 | 0.334 | 0.507 | 0.146 ENR+CV-3 | Agpat5 |
| Mrps9 | 0.667 | 0.421553246 | 0.334 | 0.475 | 0.115 ENR+CV-3 | Mrps9 |
| Dhcr241 | 0.667 | 0.419815518 | 0.334 | 0.593 | 0.215 ENR+CV-3 | Dhcr24 |
| M6pr | 0.667 | 0.418331301 | 0.334 | 0.538 | 0.169 ENR+CV-3 | M6pr |
| Lsmd1 | 0.667 | 0.417065804 | 0.334 | 0.606 | 0.227 ENR+CV-3 | Lsmd1 |
| Rnf43 | 0.667 | 0.402866103 | 0.334 | 0.557 | 0.179 ENR+CV-3 | Rnf43 |
| Romo1 | 0.667 | 0.384855022 | 0.334 | 0.787 | 0.388 ENR+CV-3 | Romo1 |
| G3bp2 | 0.667 | 0.381242612 | 0.334 | 0.624 | 0.235 ENR+CV-3 | G3bp2 |
| Cs1 | 0.667 | 0.375513523 | 0.334 | 0.629 | 0.235 ENR+CV-3 | Cs |
| Rpl31 | 0.667 | 0.36337708 | 0.334 | 0.747 | 0.336 ENR+CV-3 | Rpl31 |
| Tma7 | 0.667 | 0.356008977 | 0.334 | 0.62 | 0.228 ENR+CV-3 | Tma7 |
| Dhrs4 | 0.667 | 0.355896436 | 0.334 | 0.606 | 0.214 ENR+CV-3 | Dhrs4 |
| Rars | 0.667 | 0.34475371 | 0.334 | 0.688 | 0.283 ENR+CV-3 | Rars |
| Mrpl28 | 0.667 | 0.31968058 | 0.334 | 0.656 | 0.247 ENR+CV-3 | Mrpl28 |
| 2810004N23Rik | 0.666 | 0.444384453 | 0.332 | 0.516 | 0.154 ENR+CV-3 | 2810004N23Rik |
| Psmd12 | 0.666 | 0.402564136 | 0.332 | 0.561 | 0.189 ENR+CV-3 | Psmd12 |
| Gstm5 | 0.666 | 0.388455782 | 0.332 | 0.611 | 0.23 ENR+CV-3 | Gstm5 |
| Cox5a | 0.666 | 0.349363164 | 0.332 | 0.873 | 0.471 ENR+CV-3 | Cox5a |
| Tmem9 | 0.665 | 0.490674293 | 0.33 | 0.443 | 0.096 ENR+CV-3 | Tmem9 |
| Bax | 0.665 | 0.394924644 | 0.33 | 0.624 | 0.242 ENR+CV-3 | Bax |
| 1-Sep | 0.665 | 0.357230826 | 0.33 | 0.611 | 0.226 ENR+CV-3 | 1-Sep |
| H3f3b | 0.665 | 0.340444196 | 0.33 | 0.982 | 0.723 ENR+CV-3 | H3f3b |
| Dhx15 | 0.665 | 0.327910415 | 0.33 | 0.665 | 0.262 ENR+CV-3 | Dhx15 |
| Slc30a2 | 0.664 | 0.604270773 | 0.328 | 0.403 | 0.066 ENR+CV-3 | Slc30a2 |
| Tspan3 | 0.664 | 0.33623694 | 0.328 | 0.656 | 0.26 ENR+CV-3 | Tspan3 |
| Ube2d3 | 0.664 | 0.324640178 | 0.328 | 0.724 | 0.309 ENR+CV-3 | Ube2d3 |
| Hdac1 | 0.663 | 0.481607952 | 0.326 | 0.507 | 0.154 ENR+CV-3 | Hdac1 |
| Nipsnap1 | 0.663 | 0.457181968 | 0.326 | 0.48 | 0.129 ENR+CV-3 | Nipsnap1 |
| Zfp36l1 | 0.663 | 0.420553912 | 0.326 | 0.588 | 0.219 ENR+CV-3 | Zfp36l1 |
| Capzb | 0.663 | 0.363835893 | 0.326 | 0.67 | 0.278 ENR+CV-3 | Capzb |
| Wdr61 | 0.663 | 0.360212059 | 0.326 | 0.584 | 0.207 ENR+CV-3 | Wdr61 |

TABLE 1-continued

Derived gene list of the top defining genes from in vivo ileal
small intestine PCs and EECs captured on the Seq-Well platform

| | | | | | | |
|---|---|---|---|---|---|---|
| Pla2g12a | 0.662 | 0.424855263 | 0.324 | 0.475 | 0.125 | ENR+CV-3 | Pla2g12a |
| Cox19 | 0.662 | 0.405330027 | 0.324 | 0.466 | 0.116 | ENR+CV-3 | Cox19 |
| Itga6 | 0.662 | 0.395628914 | 0.324 | 0.525 | 0.162 | ENR+CV-3 | Itga6 |
| Map1lc3b | 0.662 | 0.372603853 | 0.324 | 0.561 | 0.194 | ENR+CV-3 | Map1lc3b |
| Snrnp27 | 0.662 | 0.36980055 | 0.324 | 0.529 | 0.164 | ENR+CV-3 | Snrnp27 |
| Pdap11 | 0.662 | 0.363650304 | 0.324 | 0.814 | 0.401 | ENR+CV-3 | Pdap1 |
| Pfdn5 | 0.662 | 0.337866101 | 0.324 | 0.851 | 0.434 | ENR+CV-3 | Pfdn5 |
| Nop56 | 0.662 | 0.332577331 | 0.324 | 0.715 | 0.308 | ENR+CV-3 | Nop56 |
| Ngfrap1 | 0.662 | 0.318460504 | 0.324 | 0.584 | 0.197 | ENR+CV-3 | Ngfrap1 |
| Rabac1 | 0.661 | 0.382964087 | 0.322 | 0.534 | 0.173 | ENR+CV-3 | Rabac1 |
| Psmd4 | 0.661 | 0.379567113 | 0.322 | 0.588 | 0.218 | ENR+CV-3 | Psmd4 |
| Hadh | 0.661 | 0.356440385 | 0.322 | 0.706 | 0.31 | ENR+CV-3 | Hadh |
| Atxn7l3b | 0.661 | 0.310746992 | 0.322 | 0.697 | 0.301 | ENR+CV-3 | Atxn7l3b |
| Eif3k | 0.661 | 0.281320925 | 0.322 | 0.828 | 0.393 | ENR+CV-3 | Eif3k |
| Sec61a1 | 0.661 | 0.271179249 | 0.322 | 0.643 | 0.239 | ENR+CV-3 | Sec61a1 |
| Ide | 0.66 | 0.488756057 | 0.32 | 0.439 | 0.102 | ENR+CV-3 | Ide |
| Mrpl19 | 0.66 | 0.413515979 | 0.32 | 0.452 | 0.11 | ENR+CV-3 | Mrpl19 |
| Ndufaf2 | 0.66 | 0.394393121 | 0.32 | 0.534 | 0.176 | ENR+CV-3 | Ndufaf2 |
| Eif4g1 | 0.66 | 0.367880563 | 0.32 | 0.778 | 0.389 | ENR+CV-3 | Eif4g1 |
| Ndufa11 | 0.66 | 0.326364143 | 0.32 | 0.688 | 0.299 | ENR+CV-3 | Ndufa11 |
| Hsbp1 | 0.66 | 0.323790398 | 0.32 | 0.692 | 0.303 | ENR+CV-3 | Hsbp1 |
| Mrps12 | 0.659 | 0.465508517 | 0.318 | 0.493 | 0.149 | ENR+CV-3 | Mrps12 |
| Vps29 | 0.659 | 0.430839301 | 0.318 | 0.552 | 0.199 | ENR+CV-3 | Vps29 |
| Psmd11 | 0.659 | 0.413800457 | 0.318 | 0.511 | 0.162 | ENR+CV-3 | Psmd11 |
| Mybbp1a | 0.659 | 0.378988338 | 0.318 | 0.593 | 0.224 | ENR+CV-3 | Mybbp1a |
| Rpn2 | 0.659 | 0.366068839 | 0.318 | 0.674 | 0.282 | ENR+CV-3 | Rpn2 |
| Naa50 | 0.659 | 0.355733005 | 0.318 | 0.588 | 0.215 | ENR+CV-3 | Naa50 |
| Mbnl1 | 0.659 | 0.324920647 | 0.318 | 0.566 | 0.194 | ENR+CV-3 | Mbnl1 |
| Hnrnpc | 0.659 | 0.297096126 | 0.318 | 0.778 | 0.364 | ENR+CV-3 | Hnrnpc |
| Rpl23 | 0.659 | 0.291269289 | 0.318 | 0.977 | 0.738 | ENR+CV-3 | Rpl23 |
| Fbln1 | 0.658 | 0.586105927 | 0.316 | 0.407 | 0.082 | ENR+CV-3 | Fbln1 |
| Tsc22d4 | 0.658 | 0.495217738 | 0.316 | 0.434 | 0.102 | ENR+CV-3 | Tsc22d4 |
| Mrps5 | 0.658 | 0.428060518 | 0.316 | 0.48 | 0.138 | ENR+CV-3 | Mrps5 |
| Acaa2 | 0.658 | 0.400591759 | 0.316 | 0.543 | 0.192 | ENR+CV-3 | Acaa2 |
| Set | 0.658 | 0.345662177 | 0.316 | 0.778 | 0.369 | ENR+CV-3 | Set |
| Fkbp41 | 0.658 | 0.333120081 | 0.316 | 0.805 | 0.403 | ENR+CV-3 | Fkbp4 |
| Atp1b1 | 0.658 | 0.329673354 | 0.316 | 0.946 | 0.603 | ENR+CV-3 | Atp1b1 |
| Echs1 | 0.658 | 0.321404678 | 0.316 | 0.647 | 0.262 | ENR+CV-3 | Echs1 |
| Sec61b1 | 0.658 | 0.319870671 | 0.316 | 0.941 | 0.586 | ENR+CV-3 | Sec61b |
| Ccdc341 | 0.658 | 0.309400549 | 0.316 | 0.824 | 0.422 | ENR+CV-3 | Ccdc34 |
| Rsl1d1 | 0.658 | 0.264753373 | 0.316 | 0.846 | 0.412 | ENR+CV-3 | Rsl1d1 |
| Blvrb | 0.657 | 0.52375726 | 0.314 | 0.412 | 0.083 | ENR+CV-3 | Blvrb |
| Utp14a | 0.657 | 0.43647759 | 0.314 | 0.471 | 0.132 | ENR+CV-3 | Utp14a |
| Sec61g | 0.657 | 0.368221777 | 0.314 | 0.52 | 0.166 | ENR+CV-3 | Sec61g |
| Vps36 | 0.657 | 0.355144395 | 0.314 | 0.529 | 0.175 | ENR+CV-3 | Vps36 |
| Timm8b | 0.657 | 0.330304073 | 0.314 | 0.747 | 0.36 | ENR+CV-3 | Timm8b |
| Eif1a | 0.657 | 0.318393238 | 0.314 | 0.606 | 0.23 | ENR+CV-3 | Eif1a |
| Ctsd | 0.657 | 0.28821548 | 0.314 | 0.624 | 0.241 | ENR+CV-3 | Ctsd |
| Hdac3 | 0.656 | 0.378849022 | 0.312 | 0.466 | 0.126 | ENR+CV-3 | Hdac3 |
| Slc25a11 | 0.656 | 0.368217853 | 0.312 | 0.552 | 0.196 | ENR+CV-3 | Slc25a1 |
| Psmd7 | 0.656 | 0.343184176 | 0.312 | 0.602 | 0.238 | ENR+CV-3 | Psmd7 |
| Ndufs8 | 0.656 | 0.338336758 | 0.312 | 0.706 | 0.337 | ENR+CV-3 | Ndufs8 |
| Rp9 | 0.656 | 0.312939772 | 0.312 | 0.584 | 0.216 | ENR+CV-3 | Rp9 |
| Psmb1 | 0.656 | 0.309764773 | 0.312 | 0.937 | 0.592 | ENR+CV-3 | Psmb1 |
| Cox7b1 | 0.656 | 0.262152249 | 0.312 | 0.982 | 0.718 | ENR+CV-3 | Cox7b |
| Got2 | 0.655 | 0.450646661 | 0.31 | 0.462 | 0.129 | ENR+CV-3 | Got2 |
| Cdx2 | 0.655 | 0.435416547 | 0.31 | 0.452 | 0.122 | ENR+CV-3 | Cdx2 |
| Hnrnpd | 0.655 | 0.432673927 | 0.31 | 0.507 | 0.17 | ENR+CV-3 | Hnrnpd |
| Rps6ka1 | 0.655 | 0.367238198 | 0.31 | 0.484 | 0.143 | ENR+CV-3 | Rps6ka1 |
| Tuba1a | 0.655 | 0.355001098 | 0.31 | 0.575 | 0.209 | ENR+CV-3 | Tuba1a |
| D8Ertd738e | 0.655 | 0.314709962 | 0.31 | 0.593 | 0.224 | ENR+CV-3 | D8Ertd738e |
| Tmed10 | 0.655 | 0.287977245 | 0.31 | 0.615 | 0.24 | ENR+CV-3 | Tmed10 |
| 1700021F05Rik | 0.654 | 0.43773033 | 0.308 | 0.412 | 0.086 | ENR+CV-3 | 1700021F05Rik |
| Glrx5 | 0.654 | 0.408510597 | 0.308 | 0.475 | 0.139 | ENR+CV-3 | Glrx5 |
| Tmco1 | 0.654 | 0.360663004 | 0.308 | 0.548 | 0.195 | ENR+CV-3 | Tmco1 |
| Calm3 | 0.654 | 0.333689293 | 0.308 | 0.683 | 0.302 | ENR+CV-3 | Calm3 |
| Hnf4a | 0.654 | 0.329935812 | 0.308 | 0.602 | 0.236 | ENR+CV-3 | Hnf4a |
| Ubb1 | 0.654 | 0.317064389 | 0.308 | 0.95 | 0.736 | ENR+CV-3 | Ubb |
| Nedd8 | 0.654 | 0.312957903 | 0.308 | 0.76 | 0.368 | ENR+CV-3 | Nedd8 |
| Eif5b | 0.654 | 0.310991506 | 0.308 | 0.724 | 0.332 | ENR+CV-3 | Eif5b |
| Cnn3 | 0.654 | 0.307853601 | 0.308 | 0.597 | 0.228 | ENR+CV-3 | Cnn3 |
| Eif3g | 0.654 | 0.295226771 | 0.308 | 0.67 | 0.283 | ENR+CV-3 | Eif3g |
| Ssx2ip | 0.653 | 0.521029014 | 0.306 | 0.407 | 0.091 | ENR+CV-3 | Ssx2ip |
| Nlrp6 | 0.653 | 0.416098058 | 0.306 | 0.493 | 0.154 | ENR+CV-3 | Nlrp6 |
| Serinc2 | 0.653 | 0.398049586 | 0.306 | 0.502 | 0.163 | ENR+CV-3 | Serinc2 |
| Ppa2 | 0.653 | 0.379126938 | 0.306 | 0.489 | 0.151 | ENR+CV-3 | Ppa2 |
| Mrpl46 | 0.653 | 0.359344953 | 0.306 | 0.48 | 0.142 | ENR+CV-3 | Mrpl46 |

TABLE 1-continued

Derived gene list of the top defining genes from in vivo ileal
small intestine PCs and EECs captured on the Seq-Well platform

| Gene | | | | | | Gene |
|---|---|---|---|---|---|---|
| Gstm1 | 0.653 | 0.355427205 | 0.306 | 0.543 | 0.196 ENR+CV-3 | Gstm1 |
| Hnrnpm | 0.653 | 0.351476052 | 0.306 | 0.665 | 0.307 ENR+CV-3 | Hnrnpm |
| Creg1 | 0.653 | 0.345693685 | 0.306 | 0.529 | 0.18 ENR+CV-3 | Creg1 |
| Cdc123 | 0.653 | 0.340527625 | 0.306 | 0.543 | 0.193 ENR+CV-3 | Cdc123 |
| Fam96a | 0.653 | 0.331605712 | 0.306 | 0.566 | 0.207 ENR+CV-3 | Fam96a |
| Grpel1 | 0.653 | 0.330019138 | 0.306 | 0.57 | 0.213 ENR+CV-3 | Grpel1 |
| Rrp1 | 0.653 | 0.32387393 | 0.306 | 0.606 | 0.244 ENR+CV-3 | Rrp1 |
| Arf1 | 0.653 | 0.319639847 | 0.306 | 0.715 | 0.333 ENR+CV-3 | Arf1 |
| Glrx3 | 0.653 | 0.31778968 | 0.306 | 0.643 | 0.271 ENR+CV-3 | Glrx3 |
| Txn2 | 0.653 | 0.30125191 | 0.306 | 0.624 | 0.25 ENR+CV-3 | Txn2 |
| Sdhb | 0.653 | 0.274872548 | 0.306 | 0.796 | 0.385 ENR+CV-3 | Sdhb |
| Slc16a31 | 0.652 | 0.552984854 | 0.304 | 0.421 | 0.104 ENR+CV-3 | Slc16a3 |
| Aqp4 | 0.652 | 0.430300806 | 0.304 | 0.439 | 0.114 ENR+CV-3 | Aqp4 |
| Mecr | 0.652 | 0.424678617 | 0.304 | 0.412 | 0.091 ENR+CV-3 | Mecr |
| Smarcd2 | 0.652 | 0.416444849 | 0.304 | 0.434 | 0.108 ENR+CV-3 | Smarcd2 |
| Rab3d | 0.652 | 0.411728795 | 0.304 | 0.457 | 0.128 ENR+CV-3 | Rab3d |
| Elf31 | 0.652 | 0.40681823 | 0.304 | 0.643 | 0.293 ENR+CV-3 | Elf3 |
| Lamtor5 | 0.652 | 0.341273367 | 0.304 | 0.475 | 0.139 ENR+CV-3 | Lamtor5 |
| Golm1 | 0.652 | 0.320971197 | 0.304 | 0.507 | 0.162 ENR+CV-3 | Golm1 |
| Copz1 | 0.652 | 0.313980132 | 0.304 | 0.543 | 0.189 ENR+CV-3 | Copz1 |
| Cox5b | 0.652 | 0.305534058 | 0.304 | 0.846 | 0.433 ENR+CV-3 | Cox5b |
| Eif3b | 0.652 | 0.300546197 | 0.304 | 0.548 | 0.191 ENR+CV-3 | Eif3b |
| Psmb4 | 0.652 | 0.300465821 | 0.304 | 0.719 | 0.325 ENR+CV-3 | Psmb4 |
| Pisd | 0.651 | 0.395463229 | 0.302 | 0.457 | 0.13 ENR+CV-3 | Pisd |
| Ubxn2a | 0.651 | 0.388763849 | 0.302 | 0.443 | 0.119 ENR+CV-3 | Ubxn2a |
| Smarcc1 | 0.651 | 0.324418825 | 0.302 | 0.579 | 0.224 ENR+CV-3 | Smarcc1 |
| Amica1 | 0.65 | 0.350100595 | 0.3 | 0.615 | 0.264 ENR+CV-3 | Amica1 |
| Slc38a2 | 0.65 | 0.346975256 | 0.3 | 0.548 | 0.204 ENR+CV-3 | Slc38a2 |
| Hsd17b12 | 0.65 | 0.29507241 | 0.3 | 0.624 | 0.254 ENR+CV-3 | Hsd17b12 |
| Ptma2 | 0.65 | 0.293587788 | 0.3 | 0.959 | 0.735 ENR+CV-3 | Ptma |
| Tomm70a | 0.65 | 0.280206151 | 0.3 | 0.615 | 0.249 ENR+CV-3 | Tomm70a |
| Xrn2 | 0.65 | 0.277571574 | 0.3 | 0.62 | 0.26 ENR+CV-3 | Xrn2 |
| Stip1 | 0.65 | 0.275127738 | 0.3 | 0.629 | 0.257 ENR+CV-3 | Stip1 |
| Cap1 | 0.649 | 0.392687434 | 0.298 | 0.475 | 0.15 ENR+CV-3 | Cap1 |
| Sumo3 | 0.649 | 0.386685597 | 0.298 | 0.48 | 0.152 ENR+CV-3 | Sumo3 |
| Sumo1 | 0.649 | 0.342421649 | 0.298 | 0.561 | 0.215 ENR+CV-3 | Sumo1 |
| Pomp | 0.649 | 0.336108489 | 0.298 | 0.706 | 0.338 ENR+CV-3 | Pomp |
| Zranb2 | 0.649 | 0.334525165 | 0.298 | 0.516 | 0.179 ENR+CV-3 | Zranb2 |
| Cpne3 | 0.649 | 0.328110325 | 0.298 | 0.52 | 0.183 ENR+CV-3 | Cpne3 |
| D17Wsu104e | 0.649 | 0.327585136 | 0.298 | 0.566 | 0.217 ENR+CV-3 | D17Wsu104e |
| Ppp1cb | 0.649 | 0.314287032 | 0.298 | 0.579 | 0.227 ENR+CV-3 | Ppp1cb |
| Glo1 | 0.649 | 0.313039606 | 0.298 | 0.502 | 0.164 ENR+CV-3 | Glo1 |
| Tomm22 | 0.649 | 0.312294276 | 0.298 | 0.633 | 0.278 ENR+CV-3 | Tomm22 |
| Ndufv1 | 0.649 | 0.304765319 | 0.298 | 0.593 | 0.234 ENR+CV-3 | Ndufv1 |
| Wdr891 | 0.649 | 0.295565578 | 0.298 | 0.882 | 0.527 ENR+CV-3 | Wdr89 |
| Eif3c | 0.649 | 0.271873036 | 0.298 | 0.842 | 0.445 ENR+CV-3 | Eif3c |
| Ass1 | 0.648 | 0.506817715 | 0.296 | 0.344 | 0.042 ENR+CV-3 | Ass1 |
| mmu-mir-62362 | 0.648 | 0.369307757 | 0.296 | 0.362 | 0.055 ENR+CV-3 | mmu-mir-6236 |
| Stt3b | 0.648 | 0.346988483 | 0.296 | 0.525 | 0.191 ENR+CV-3 | Stt3b |
| Ccdc107 | 0.648 | 0.316305859 | 0.296 | 0.48 | 0.146 ENR+CV-3 | Ccdc107 |
| Hnrnpk1 | 0.648 | 0.308928821 | 0.296 | 0.855 | 0.495 ENR+CV-3 | Hnrnpk |
| Ddost | 0.648 | 0.291953994 | 0.296 | 0.683 | 0.304 ENR+CV-3 | Ddost |
| Eif1ax | 0.648 | 0.267122284 | 0.296 | 0.606 | 0.243 ENR+CV-3 | Eif1ax |
| Cct2 | 0.648 | 0.256968702 | 0.296 | 0.824 | 0.409 ENR+CV-3 | Cct2 |
| Prelid2 | 0.647 | 0.411835492 | 0.294 | 0.439 | 0.121 ENR+CV-3 | Prelid2 |
| Rtcb | 0.647 | 0.388380605 | 0.294 | 0.484 | 0.159 ENR+CV-3 | Rtcb |
| U2af1 | 0.647 | 0.377912896 | 0.294 | 0.475 | 0.151 ENR+CV-3 | U2af1 |
| Snrpb2 | 0.647 | 0.375695413 | 0.294 | 0.484 | 0.158 ENR+CV-3 | Snrpb2 |
| Strbp | 0.647 | 0.357229211 | 0.294 | 0.511 | 0.182 ENR+CV-3 | Strbp |
| Cftr | 0.647 | 0.354386892 | 0.294 | 0.466 | 0.141 ENR+CV-3 | Cftr |
| Aldh18a1 | 0.647 | 0.344465858 | 0.294 | 0.48 | 0.152 ENR+CV-3 | Aldh18a1 |
| Dnm1l | 0.647 | 0.311371794 | 0.294 | 0.52 | 0.182 ENR+CV-3 | Dnm1l |
| Immt | 0.647 | 0.298640382 | 0.294 | 0.584 | 0.234 ENR+CV-3 | Immt |
| Myl12b | 0.647 | 0.275917313 | 0.294 | 0.837 | 0.452 ENR+CV-3 | Myl12b |
| Psmc4 | 0.646 | 0.364910255 | 0.292 | 0.516 | 0.185 ENR+CV-3 | Psmc4 |
| Dap3 | 0.646 | 0.326528683 | 0.292 | 0.52 | 0.188 ENR+CV-3 | Dap3 |
| Usp10 | 0.646 | 0.325921398 | 0.292 | 0.452 | 0.129 ENR+CV-3 | Usp10 |
| Gale | 0.646 | 0.313605258 | 0.292 | 0.502 | 0.167 ENR+CV-3 | Gale |
| Ier3ip1 | 0.646 | 0.305174497 | 0.292 | 0.548 | 0.207 ENR+CV-3 | Ier3ip1 |
| Nap1l4 | 0.646 | 0.303317978 | 0.292 | 0.552 | 0.21 ENR+CV-3 | Nap1l4 |
| Gnb2 | 0.646 | 0.295638501 | 0.292 | 0.719 | 0.343 ENR+CV-3 | Gnb2 |
| Fam162a | 0.646 | 0.295326161 | 0.292 | 0.715 | 0.347 ENR+CV-3 | Fam162a |
| Gm10036 | 0.646 | 0.279939182 | 0.292 | 0.665 | 0.292 ENR+CV-3 | Gm10036 |
| Bnip3 | 0.645 | 0.393338347 | 0.29 | 0.484 | 0.165 ENR+CV-3 | Bnip3 |
| Uri1 | 0.645 | 0.341193804 | 0.29 | 0.448 | 0.131 ENR+CV-3 | Uri1 |
| Dctpp1 | 0.645 | 0.334637826 | 0.29 | 0.529 | 0.194 ENR+CV-3 | Dctpp1 |
| Tmem50a | 0.645 | 0.334286511 | 0.29 | 0.489 | 0.165 ENR+CV-3 | Tmem50a |

TABLE 1-continued

Derived gene list of the top defining genes from in vivo ileal
small intestine PCs and EECs captured on the Seq-Well platform

| | | | | | | |
|---|---|---|---|---|---|---|
| Ccnd1 | 0.645 | 0.326635361 | 0.29 | 0.516 | 0.184 | ENR+CV-3 | Ccnd1 |
| 1110008F13Rik | 0.645 | 0.310849832 | 0.29 | 0.606 | 0.258 | ENR+CV-3 | 1110008F13Rik |
| Denr | 0.645 | 0.305628743 | 0.29 | 0.529 | 0.194 | ENR+CV-3 | Denr |
| Bsg2 | 0.645 | 0.305584942 | 0.29 | 0.977 | 0.727 | ENR+CV-3 | Bsg |
| Tceb1 | 0.645 | 0.292599058 | 0.29 | 0.652 | 0.293 | ENR+CV-3 | Tceb1 |
| Impa1 | 0.645 | 0.285801929 | 0.29 | 0.502 | 0.169 | ENR+CV-3 | Impa1 |
| Hnrnpl | 0.645 | 0.278111231 | 0.29 | 0.633 | 0.271 | ENR+CV-3 | Hnrnpl |
| Acot7 | 0.644 | 0.458173346 | 0.288 | 0.385 | 0.084 | ENR+CV-3 | Acot7 |
| Cdkn2aipnl | 0.644 | 0.395076573 | 0.288 | 0.421 | 0.112 | ENR+CV-3 | Cdkn2aipnl |
| Cggbp1 | 0.644 | 0.386049236 | 0.288 | 0.48 | 0.161 | ENR+CV-3 | Cggbp1 |
| Ipo7 | 0.644 | 0.380692032 | 0.288 | 0.448 | 0.135 | ENR+CV-3 | Ipo7 |
| Dctn3 | 0.644 | 0.368267225 | 0.288 | 0.462 | 0.145 | ENR+CV-3 | Dctn3 |
| Ptgr1 | 0.644 | 0.365445714 | 0.288 | 0.552 | 0.226 | ENR+CV-3 | Ptgr1 |
| Drap1 | 0.644 | 0.353677705 | 0.288 | 0.466 | 0.148 | ENR+CV-3 | Drap1 |
| Acadl | 0.644 | 0.348704738 | 0.288 | 0.434 | 0.121 | ENR+CV-3 | Acadl |
| Carhsp1 | 0.644 | 0.345915621 | 0.288 | 0.462 | 0.141 | ENR+CV-3 | Carhsp1 |
| Lpcat3 | 0.644 | 0.339806156 | 0.288 | 0.466 | 0.146 | ENR+CV-3 | Lpcat3 |
| Pcbp2 | 0.644 | 0.322415443 | 0.288 | 0.765 | 0.392 | ENR+CV-3 | Pcbp2 |
| H2-D1 | 0.644 | 0.316236466 | 0.288 | 0.729 | 0.365 | ENR+CV-3 | H2-D1 |
| Ghitm | 0.644 | 0.300525729 | 0.288 | 0.71 | 0.345 | ENR+CV-3 | Ghitm |
| Abcf1 | 0.644 | 0.292064404 | 0.288 | 0.588 | 0.24 | ENR+CV-3 | Abcf1 |
| Ldha1 | 0.644 | 0.272884837 | 0.288 | 0.955 | 0.684 | ENR+CV-3 | Ldha |
| Cct8 | 0.644 | 0.264337282 | 0.288 | 0.674 | 0.311 | ENR+CV-3 | Cct8 |
| Cd2ap | 0.644 | 0.262480761 | 0.288 | 0.643 | 0.281 | ENR+CV-3 | Cd2ap |
| Cox7a21 | 0.644 | 0.255700195 | 0.288 | 0.964 | 0.692 | ENR+CV-3 | Cox7a2 |
| Prmt5 | 0.643 | 0.407067306 | 0.286 | 0.434 | 0.126 | ENR+CV-3 | Prmt5 |
| Rabl6 | 0.643 | 0.348100347 | 0.286 | 0.475 | 0.157 | ENR+CV-3 | Rabl6 |
| Atad3a | 0.643 | 0.325756693 | 0.286 | 0.471 | 0.15 | ENR+CV-3 | Atad3a |
| Fyttd1 | 0.643 | 0.304003921 | 0.286 | 0.489 | 0.166 | ENR+CV-3 | Fyttd1 |
| Phb2 | 0.643 | 0.29687848 | 0.286 | 0.643 | 0.287 | ENR+CV-3 | Phb2 |
| Ppm1g | 0.643 | 0.28710945 | 0.286 | 0.48 | 0.154 | ENR+CV-3 | Ppm1g |
| Ndufb10 | 0.643 | 0.283373315 | 0.286 | 0.584 | 0.235 | ENR+CV-3 | Ndufb10 |
| Bola1 | 0.643 | 0.265556971 | 0.286 | 0.529 | 0.193 | ENR+CV-3 | Bola1 |
| Hadha | 0.643 | 0.253343852 | 0.286 | 0.611 | 0.259 | ENR+CV-3 | Hadha |
| Agmat | 0.642 | 0.533478721 | 0.284 | 0.353 | 0.062 | ENR+CV-3 | Agmat |
| Gm10263 | 0.642 | 0.407675419 | 0.284 | 0.394 | 0.094 | ENR+CV-3 | Gm10263 |
| Sephs2 | 0.642 | 0.382786254 | 0.284 | 0.448 | 0.138 | ENR+CV-3 | Sephs2 |
| Tbcb | 0.642 | 0.333854537 | 0.284 | 0.471 | 0.154 | ENR+CV-3 | Tbcb |
| 2410006H16Rik | 0.642 | 0.328988722 | 0.284 | 0.891 | 0.6 | ENR+CV-3 | 2410006H16Rik |
| Pdia4 | 0.642 | 0.328531061 | 0.284 | 0.575 | 0.242 | ENR+CV-3 | Pdia4 |
| Cotl1 | 0.642 | 0.304644693 | 0.284 | 0.588 | 0.243 | ENR+CV-3 | Cotl1 |
| Nucb1 | 0.642 | 0.295736178 | 0.284 | 0.498 | 0.172 | ENR+CV-3 | Nucb1 |
| Gpa33 | 0.642 | 0.294875661 | 0.284 | 0.502 | 0.177 | ENR+CV-3 | Gpa33 |
| Psmc5 | 0.642 | 0.292447264 | 0.284 | 0.552 | 0.214 | ENR+CV-3 | Psmc5 |
| Rnf32 | 0.642 | 0.290946411 | 0.284 | 0.511 | 0.185 | ENR+CV-3 | Rnf32 |
| Swi5 | 0.642 | 0.287036783 | 0.284 | 0.76 | 0.392 | ENR+CV-3 | Swi5 |
| Khdrbs1 | 0.642 | 0.283789529 | 0.284 | 0.516 | 0.186 | ENR+CV-3 | Khdrbs1 |
| Cd81 | 0.642 | 0.277677375 | 0.284 | 0.851 | 0.481 | ENR+CV-3 | Cd81 |
| 1810022K09Rik | 0.642 | 0.273662337 | 0.284 | 0.756 | 0.383 | ENR+CV-3 | 1810022K09Rik |
| Ptp4a2 | 0.642 | 0.272261866 | 0.284 | 0.701 | 0.34 | ENR+CV-3 | Ptp4a2 |
| Cct5 | 0.642 | 0.253198522 | 0.284 | 0.851 | 0.456 | ENR+CV-3 | Cct5 |
| Pfdn2 | 0.641 | 0.399190242 | 0.282 | 0.434 | 0.129 | ENR+CV-3 | Pfdn2 |
| Slc6a6 | 0.641 | 0.389936797 | 0.282 | 0.43 | 0.125 | ENR+CV-3 | Slc6a6 |
| Aamp | 0.641 | 0.316157004 | 0.282 | 0.489 | 0.172 | ENR+CV-3 | Aamp |
| Gpi1l | 0.641 | 0.30168727 | 0.282 | 0.742 | 0.382 | ENR+CV-3 | Gpi1 |
| Rps18-ps3 | 0.641 | 0.29936363 | 0.282 | 0.498 | 0.173 | ENR+CV-3 | Rps18-ps3 |
| Rpl36-ps3 | 0.641 | 0.286796945 | 0.282 | 0.52 | 0.194 | ENR+CV-3 | Rpl36-ps3 |
| Ymel1l | 0.641 | 0.276923568 | 0.282 | 0.516 | 0.188 | ENR+CV-3 | Ymel1l |
| Arf5 | 0.641 | 0.275587472 | 0.282 | 0.611 | 0.262 | ENR+CV-3 | Arf5 |
| Mrpl50 | 0.641 | 0.274480326 | 0.282 | 0.484 | 0.162 | ENR+CV-3 | Mrpl50 |
| Sgta | 0.64 | 0.376095148 | 0.28 | 0.43 | 0.127 | ENR+CV-3 | Sgta |
| Dera | 0.64 | 0.346430842 | 0.28 | 0.452 | 0.145 | ENR+CV-3 | Dera |
| Bri3bp | 0.64 | 0.308914611 | 0.28 | 0.439 | 0.128 | ENR+CV-3 | Bri3bp |
| Paics | 0.64 | 0.291080125 | 0.28 | 0.566 | 0.23 | ENR+CV-3 | Paics |
| Ddit4 | 0.64 | 0.271961657 | 0.28 | 0.584 | 0.239 | ENR+CV-3 | Ddit4 |
| Txnrd1 | 0.64 | 0.264857672 | 0.28 | 0.615 | 0.264 | ENR+CV-3 | Txnrd1 |
| Hspa4 | 0.64 | 0.260914695 | 0.28 | 0.71 | 0.344 | ENR+CV-3 | Hspa4 |
| Ywhae | 0.64 | 0.254152661 | 0.28 | 0.873 | 0.472 | ENR+CV-3 | Ywhae |
| Bdh1 | 0.639 | 0.408849677 | 0.278 | 0.416 | 0.119 | ENR+CV-3 | Bdh1 |
| Alg5 | 0.639 | 0.405440815 | 0.278 | 0.425 | 0.127 | ENR+CV-3 | Alg5 |
| Timm44 | 0.639 | 0.394476702 | 0.278 | 0.443 | 0.143 | ENR+CV-3 | Timm44 |
| Foxa3 | 0.639 | 0.358262364 | 0.278 | 0.412 | 0.111 | ENR+CV-3 | Foxa3 |
| Pik3r1 | 0.639 | 0.351660959 | 0.278 | 0.466 | 0.157 | ENR+CV-3 | Pik3r1 |
| Dnttip2 | 0.639 | 0.348354516 | 0.278 | 0.502 | 0.187 | ENR+CV-3 | Dnttip2 |
| Acsl3 | 0.639 | 0.34709397 | 0.278 | 0.425 | 0.122 | ENR+CV-3 | Acsl3 |
| Rab7 | 0.639 | 0.343699796 | 0.278 | 0.466 | 0.158 | ENR+CV-3 | Rab7 |
| Rpf2 | 0.639 | 0.335391152 | 0.278 | 0.457 | 0.151 | ENR+CV-3 | Rpf2 |

TABLE 1-continued

Derived gene list of the top defining genes from in vivo ileal
small intestine PCs and EECs captured on the Seq-Well platform

| | | | | | | |
|---|---|---|---|---|---|---|
| Pdcd5 | 0.639 | 0.312924478 | 0.278 | 0.493 | 0.175 | ENR+CV-3 | Pdcd5 |
| Ddx39 | 0.639 | 0.302882185 | 0.278 | 0.484 | 0.169 | ENR+CV-3 | Ddx39 |
| Rbm47 | 0.639 | 0.277911557 | 0.278 | 0.561 | 0.227 | ENR+CV-3 | Rbm47 |
| Ndufs3 | 0.639 | 0.275305977 | 0.278 | 0.489 | 0.169 | ENR+CV-3 | Ndufs3 |
| Commd6 | 0.639 | 0.266876047 | 0.278 | 0.516 | 0.191 | ENR+CV-3 | Commd6 |
| Npc2 | 0.639 | 0.260223325 | 0.278 | 0.774 | 0.399 | ENR+CV-3 | Npc2 |
| Hsp90b1 | 0.639 | 0.250429186 | 0.278 | 0.968 | 0.704 | ENR+CV-3 | Hsp90b1 |
| Rnd3 | 0.638 | 0.409572262 | 0.276 | 0.407 | 0.112 | ENR+CV-3 | Rnd3 |
| Fam32a | 0.638 | 0.368268944 | 0.276 | 0.466 | 0.16 | ENR+CV-3 | Fam32a |
| Slc31a1 | 0.638 | 0.354502771 | 0.276 | 0.416 | 0.117 | ENR+CV-3 | Slc31a1 |
| Ankrd10 | 0.638 | 0.344810576 | 0.276 | 0.371 | 0.08 | ENR+CV-3 | Ankrd10 |
| Eci2 | 0.638 | 0.335670906 | 0.276 | 0.425 | 0.124 | ENR+CV-3 | Eci2 |
| Galnt7 | 0.638 | 0.329784345 | 0.276 | 0.448 | 0.143 | ENR+CV-3 | Galnt7 |
| Rab5c | 0.638 | 0.328865173 | 0.276 | 0.425 | 0.124 | ENR+CV-3 | Rab5c |
| Ssrp1 | 0.638 | 0.286622219 | 0.276 | 0.588 | 0.25 | ENR+CV-3 | Ssrp1 |
| Phgdh | 0.638 | 0.272401728 | 0.276 | 0.48 | 0.162 | ENR+CV-3 | Phgdh |
| Etfa | 0.638 | 0.265488845 | 0.276 | 0.597 | 0.259 | ENR+CV-3 | Etfa |
| Prdx2 | 0.638 | 0.257569695 | 0.276 | 0.882 | 0.531 | ENR+CV-3 | Prdx2 |
| Tomm5 | 0.638 | 0.255195027 | 0.276 | 0.629 | 0.279 | ENR+CV-3 | Tomm5 |
| Gm2a | 0.637 | 0.442542039 | 0.274 | 0.33 | 0.049 | ENR+CV-3 | Gm2a |
| Atf31 | 0.637 | 0.437550899 | 0.274 | 0.561 | 0.253 | ENR+CV-3 | Atf3 |
| Smn1 | 0.637 | 0.426463376 | 0.274 | 0.389 | 0.102 | ENR+CV-3 | Smn1 |
| Fam13a | 0.637 | 0.404221351 | 0.274 | 0.367 | 0.079 | ENR+CV-3 | Fam13a |
| Wdr45b | 0.637 | 0.387586209 | 0.274 | 0.385 | 0.095 | ENR+CV-3 | Wdr45b |
| Dhrs7 | 0.637 | 0.364690226 | 0.274 | 0.403 | 0.108 | ENR+CV-3 | Dhrs7 |
| Glg1 | 0.637 | 0.33486882 | 0.274 | 0.43 | 0.13 | ENR+CV-3 | Glg1 |
| Eif2a | 0.637 | 0.309781091 | 0.274 | 0.48 | 0.171 | ENR+CV-3 | Eif2a |
| Sepw1 | 0.637 | 0.280746054 | 0.274 | 0.652 | 0.303 | ENR+CV-3 | Sepw1 |
| Fbp2 | 0.637 | 0.25504568 | 0.274 | 0.529 | 0.207 | ENR+CV-3 | Fbp2 |
| Cdh17 | 0.637 | 0.253382194 | 0.274 | 0.575 | 0.236 | ENR+CV-3 | Cdh17 |
| Nmt1 | 0.636 | 0.359317216 | 0.272 | 0.443 | 0.146 | ENR+CV-3 | Nmt1 |
| Scd21 | 0.636 | 0.345455069 | 0.272 | 0.869 | 0.525 | ENR+CV-3 | Scd2 |
| Rae1 | 0.636 | 0.329458425 | 0.272 | 0.403 | 0.109 | ENR+CV-3 | Rae1 |
| Sfr1 | 0.636 | 0.316313039 | 0.272 | 0.507 | 0.193 | ENR+CV-3 | Sfr1 |
| Mcm7 | 0.636 | 0.306503784 | 0.272 | 0.452 | 0.148 | ENR+CV-3 | Mcm7 |
| Mapre1 | 0.636 | 0.276078958 | 0.272 | 0.507 | 0.187 | ENR+CV-3 | Mapre1 |
| Sox9 | 0.636 | 0.275217565 | 0.272 | 0.606 | 0.267 | ENR+CV-3 | Sox9 |
| Tpd52 | 0.636 | 0.271598637 | 0.272 | 0.774 | 0.42 | ENR+CV-3 | Tpd52 |
| Adipor1 | 0.636 | 0.265255848 | 0.272 | 0.525 | 0.203 | ENR+CV-3 | Adipor1 |
| Aplp2 | 0.636 | 0.265198365 | 0.272 | 0.606 | 0.27 | ENR+CV-3 | Aplp2 |
| Marcksl1 | 0.636 | 0.263325643 | 0.272 | 0.502 | 0.181 | ENR+CV-3 | Marcksl1 |
| Psmd14 | 0.636 | 0.251104443 | 0.272 | 0.561 | 0.231 | ENR+CV-3 | Psmd14 |
| Mpnd1 | 0.635 | 0.460902238 | 0.27 | 0.38 | 0.096 | ENR+CV-3 | Mpnd |
| Prkar2a | 0.635 | 0.365478848 | 0.27 | 0.407 | 0.118 | ENR+CV-3 | Prkar2a |
| Pgrmc2 | 0.635 | 0.363070874 | 0.27 | 0.434 | 0.138 | ENR+CV-3 | Pgrmc2 |
| Ilf2 | 0.635 | 0.344787264 | 0.27 | 0.466 | 0.165 | ENR+CV-3 | Ilf2 |
| Brix1 | 0.635 | 0.329196212 | 0.27 | 0.434 | 0.138 | ENR+CV-3 | Brix1 |
| Utp11l | 0.635 | 0.327863946 | 0.27 | 0.443 | 0.146 | ENR+CV-3 | Utp11l |
| Arl1 | 0.635 | 0.293064664 | 0.27 | 0.466 | 0.161 | ENR+CV-3 | Arl1 |
| Gars | 0.635 | 0.28182193 | 0.27 | 0.579 | 0.252 | ENR+CV-3 | Gars |
| Arpc5l | 0.635 | 0.251685865 | 0.27 | 0.507 | 0.19 | ENR+CV-3 | Arpc5l |
| Mpzl1 | 0.634 | 0.393191521 | 0.268 | 0.398 | 0.115 | ENR+CV-3 | Mpzl1 |
| Sqle | 0.634 | 0.29708436 | 0.268 | 0.471 | 0.166 | ENR+CV-3 | Sqle |
| Anp32e | 0.634 | 0.277062793 | 0.268 | 0.511 | 0.197 | ENR+CV-3 | Anp32e |
| Actn1 | 0.634 | 0.266530162 | 0.268 | 0.484 | 0.174 | ENR+CV-3 | Actn1 |
| Dkc1 | 0.634 | 0.262720409 | 0.268 | 0.502 | 0.189 | ENR+CV-3 | Dkc1 |
| B4galnt2 | 0.633 | 0.349955278 | 0.266 | 0.403 | 0.115 | ENR+CV-3 | B4galnt2 |
| Psmd2 | 0.633 | 0.343364013 | 0.266 | 0.462 | 0.165 | ENR+CV-3 | Psmd2 |
| Hes6 | 0.633 | 0.336088371 | 0.266 | 0.507 | 0.208 | ENR+CV-3 | Hes6 |
| Pes1 | 0.633 | 0.333617268 | 0.266 | 0.421 | 0.13 | ENR+CV-3 | Pes1 |
| Fam104a | 0.633 | 0.313868511 | 0.266 | 0.439 | 0.144 | ENR+CV-3 | Fam104a |
| Pfkl | 0.633 | 0.310615413 | 0.266 | 0.475 | 0.174 | ENR+CV-3 | Pfkl |
| Hspa5 | 0.633 | 0.295436816 | 0.266 | 0.928 | 0.666 | ENR+CV-3 | Hspa5 |
| Atp6v1a | 0.633 | 0.293983742 | 0.266 | 0.407 | 0.118 | ENR+CV-3 | Atp6v1a |
| Aig1 | 0.633 | 0.288333287 | 0.266 | 0.434 | 0.139 | ENR+CV-3 | Aig1 |
| Ddx24 | 0.633 | 0.280144629 | 0.266 | 0.457 | 0.156 | ENR+CV-3 | Ddx24 |
| Hnrnpf | 0.633 | 0.272028352 | 0.266 | 0.548 | 0.226 | ENR+CV-3 | Hnrnpf |
| Sarnp | 0.633 | 0.271213172 | 0.266 | 0.475 | 0.169 | ENR+CV-3 | Sarnp |
| Vcp | 0.633 | 0.258540848 | 0.266 | 0.575 | 0.249 | ENR+CV-3 | Vcp |
| 2700060E02Rik | 0.633 | 0.256336656 | 0.266 | 0.765 | 0.415 | ENR+CV-3 | 2700060E02Rik |
| Sod2 | 0.633 | 0.252480444 | 0.266 | 0.493 | 0.185 | ENR+CV-3 | Sod2 |
| Amn | 0.632 | 0.422108076 | 0.264 | 0.339 | 0.065 | ENR+CV-3 | Amn |
| Clic6 | 0.632 | 0.413717007 | 0.264 | 0.371 | 0.096 | ENR+CV-3 | Clic6 |
| Nob1 | 0.632 | 0.350049824 | 0.264 | 0.376 | 0.094 | ENR+CV-3 | Nob1 |
| Nudc | 0.632 | 0.289837676 | 0.264 | 0.475 | 0.172 | ENR+CV-3 | Nudc |
| Nars | 0.632 | 0.275312013 | 0.264 | 0.814 | 0.477 | ENR+CV-3 | Nars |
| Psmd1 | 0.632 | 0.27330622 | 0.264 | 0.493 | 0.188 | ENR+CV-3 | Psmd1 |

TABLE 1-continued

Derived gene list of the top defining genes from in vivo ileal
small intestine PCs and EECs captured on the Seq-Well platform

| | | | | | | |
|---|---|---|---|---|---|---|
| Me2 | 0.632 | 0.273097535 | 0.264 | 0.448 | 0.153 | ENR+CV-3 Me2 |
| Ndufa9 | 0.632 | 0.272242558 | 0.264 | 0.452 | 0.155 | ENR+CV-3 Ndufa9 |
| Rab1 | 0.632 | 0.268337852 | 0.264 | 0.579 | 0.255 | ENR+CV-3 Rab1 |
| Lgr5 | 0.632 | 0.253999276 | 0.264 | 0.475 | 0.171 | ENR+CV-3 Lgr5 |
| B3galtl | 0.631 | 0.421534581 | 0.262 | 0.33 | 0.06 | ENR+CV-3 B3galtl |
| Ralgps2 | 0.631 | 0.382368518 | 0.262 | 0.371 | 0.093 | ENR+CV-3 Ralgps2 |
| Fads1 | 0.631 | 0.368838744 | 0.262 | 0.394 | 0.115 | ENR+CV-3 Fads1 |
| Rbm34 | 0.631 | 0.357864852 | 0.262 | 0.416 | 0.133 | ENR+CV-3 Rbm34 |
| Acp1 | 0.631 | 0.325332684 | 0.262 | 0.457 | 0.165 | ENR+CV-3 Acp1 |
| Trnt1 | 0.631 | 0.31780767 | 0.262 | 0.412 | 0.128 | ENR+CV-3 Trnt1 |
| Mrps18a | 0.631 | 0.306025225 | 0.262 | 0.421 | 0.132 | ENR+CV-3 Mrps18a |
| Kcnq1l | 0.631 | 0.305219535 | 0.262 | 0.448 | 0.156 | ENR+CV-3 Kcnq1 |
| Prkcsh | 0.631 | 0.304924765 | 0.262 | 0.466 | 0.17 | ENR+CV-3 Prkcsh |
| Zfp106 | 0.631 | 0.297963124 | 0.262 | 0.475 | 0.178 | ENR+CV-3 Zfp106 |
| Tsn | 0.631 | 0.293628677 | 0.262 | 0.48 | 0.184 | ENR+CV-3 Tsn |
| Pkn2 | 0.631 | 0.26132162 | 0.262 | 0.448 | 0.153 | ENR+CV-3 Pkn2 |
| Psma3 | 0.631 | 0.252628847 | 0.262 | 0.471 | 0.169 | ENR+CV-3 Psma3 |
| Ociad2 | 0.631 | 0.252431317 | 0.262 | 0.471 | 0.17 | ENR+CV-3 Ociad2 |
| Vapb | 0.63 | 0.330218733 | 0.26 | 0.398 | 0.117 | ENR+CV-3 Vapb |
| Mrps33 | 0.63 | 0.322138126 | 0.26 | 0.407 | 0.124 | ENR+CV-3 Mrps33 |
| Nfia | 0.629 | 0.372344905 | 0.258 | 0.403 | 0.126 | ENR+CV-3 Nfia |
| Dpysl2 | 0.629 | 0.357662173 | 0.258 | 0.394 | 0.116 | ENR+CV-3 Dpysl2 |
| Nsdhl | 0.629 | 0.335956565 | 0.258 | 0.367 | 0.093 | ENR+CV-3 Nsdhl |
| Ccdc59 | 0.629 | 0.317569242 | 0.258 | 0.416 | 0.134 | ENR+CV-3 Ccdc59 |
| Prpf19 | 0.629 | 0.28960532 | 0.258 | 0.48 | 0.186 | ENR+CV-3 Prpf19 |
| Ppil1 | 0.629 | 0.279161865 | 0.258 | 0.416 | 0.13 | ENR+CV-3 Ppil1 |
| Slc12a2 | 0.629 | 0.267494012 | 0.258 | 0.837 | 0.496 | ENR+CV-3 Slc12a2 |
| Zfp91 | 0.629 | 0.266726186 | 0.258 | 0.502 | 0.203 | ENR+CV-3 Zfp91 |
| Atp5l | 0.629 | 0.265186965 | 0.258 | 0.538 | 0.228 | ENR+CV-3 Atp5l |
| Polr1c | 0.628 | 0.32267448 | 0.256 | 0.38 | 0.104 | ENR+CV-3 Polr1c |
| Szrd1 | 0.628 | 0.314005056 | 0.256 | 0.398 | 0.119 | ENR+CV-3 Szrd1 |
| Tmod3 | 0.628 | 0.262672408 | 0.256 | 0.457 | 0.165 | ENR+CV-3 Tmod3 |
| Eif3l | 0.628 | 0.254619945 | 0.256 | 0.579 | 0.261 | ENR+CV-3 Eif3l |
| Rps4y2 | 0.627 | 0.369445785 | 0.254 | 0.389 | 0.116 | ENR+CV-3 Rps4y2 |
| Brd7 | 0.627 | 0.336291517 | 0.254 | 0.394 | 0.118 | ENR+CV-3 Brd7 |
| RP24-176F12.14 | 0.627 | 0.318702184 | 0.254 | 0.376 | 0.104 | ENR+CV-3 RP24-176F12.14 |
| Tra2b | 0.627 | 0.308633265 | 0.254 | 0.538 | 0.241 | ENR+CV-3 Tra2b |
| Polr2i | 0.627 | 0.305887341 | 0.254 | 0.43 | 0.148 | ENR+CV-3 Polr2i |
| Pnkd | 0.627 | 0.289044897 | 0.254 | 0.398 | 0.12 | ENR+CV-3 Pnkd |
| Gm11808 | 0.627 | 0.280317569 | 0.254 | 0.484 | 0.191 | ENR+CV-3 Gm11808 |
| Magohb | 0.627 | 0.274427447 | 0.254 | 0.385 | 0.109 | ENR+CV-3 Magohb |
| Npepps | 0.627 | 0.272387869 | 0.254 | 0.448 | 0.16 | ENR+CV-3 Npepps |
| Sae1 | 0.627 | 0.256222215 | 0.254 | 0.516 | 0.21 | ENR+CV-3 Sae1 |
| Desi2 | 0.626 | 0.414731718 | 0.252 | 0.339 | 0.077 | ENR+CV-3 Desi2 |
| Mpst | 0.626 | 0.364949377 | 0.252 | 0.321 | 0.059 | ENR+CV-3 Mpst |
| Cetn2 | 0.626 | 0.339756681 | 0.252 | 0.394 | 0.122 | ENR+CV-3 Cetn2 |
| Elp5 | 0.626 | 0.333591369 | 0.252 | 0.362 | 0.093 | ENR+CV-3 Elp5 |
| Gar1 | 0.626 | 0.328173435 | 0.252 | 0.376 | 0.106 | ENR+CV-3 Gar1 |
| Alkbh5 | 0.626 | 0.319023862 | 0.252 | 0.416 | 0.139 | ENR+CV-3 Alkbh5 |
| Snx2 | 0.626 | 0.26982392 | 0.252 | 0.398 | 0.122 | ENR+CV-3 Snx2 |
| Plod2 | 0.625 | 0.491981948 | 0.25 | 0.29 | 0.036 | ENR+CV-3 Plod2 |
| Gm22426 | 0.625 | 0.433954831 | 0.25 | 0.299 | 0.044 | ENR+CV-3 Gm22426 |
| Pld3 | 0.625 | 0.359197611 | 0.25 | 0.357 | 0.092 | ENR+CV-3 Pld3 |
| Yrdc | 0.625 | 0.358995577 | 0.25 | 0.357 | 0.093 | ENR+CV-3 Yrdc |
| Sbno1 | 0.625 | 0.290746042 | 0.25 | 0.475 | 0.187 | ENR+CV-3 Sbno1 |
| Plin3 | 0.625 | 0.28080554 | 0.25 | 0.416 | 0.138 | ENR+CV-3 Plin3 |
| Pdgfa | 0.625 | 0.278929754 | 0.25 | 0.597 | 0.289 | ENR+CV-3 Pdgfa |
| Galm | 0.624 | 0.319336332 | 0.248 | 0.371 | 0.105 | ENR+CV-3 Galm |
| Gcat1 | 0.624 | 0.292233697 | 0.248 | 0.452 | 0.172 | ENR+CV-3 Gcat |
| Por1 | 0.624 | 0.286876979 | 0.248 | 0.443 | 0.164 | ENR+CV-3 Por |
| Timm10b | 0.624 | 0.272168866 | 0.248 | 0.443 | 0.162 | ENR+CV-3 Timm10b |
| Stk38 | 0.623 | 0.37447416 | 0.246 | 0.348 | 0.089 | ENR+CV-3 Stk38 |
| Tnpo3 | 0.623 | 0.360966642 | 0.246 | 0.362 | 0.1 | ENR+CV-3 Tnpo3 |
| Pphln1 | 0.623 | 0.351582995 | 0.246 | 0.326 | 0.069 | ENR+CV-3 Pphln1 |
| Scd11 | 0.623 | 0.346466 | 0.246 | 0.367 | 0.102 | ENR+CV-3 Scd1 |
| Tcof1 | 0.623 | 0.306197939 | 0.246 | 0.398 | 0.128 | ENR+CV-3 Tcof1 |
| Ncln | 0.623 | 0.300110241 | 0.246 | 0.38 | 0.115 | ENR+CV-3 Ncln |
| Lrig1 | 0.623 | 0.296665618 | 0.246 | 0.412 | 0.138 | ENR+CV-3 Lrig1 |
| Uck2 | 0.623 | 0.294847078 | 0.246 | 0.407 | 0.137 | ENR+CV-3 Uck2 |
| Fxr1 | 0.623 | 0.283047586 | 0.246 | 0.416 | 0.142 | ENR+CV-3 Fxr1 |
| Qdpr | 0.623 | 0.26875615 | 0.246 | 0.439 | 0.162 | ENR+CV-3 Qdpr |
| Tmprss4 | 0.623 | 0.254359478 | 0.246 | 0.412 | 0.136 | ENR+CV-3 Tmprss4 |
| Zfand6 | 0.623 | 0.25170891 | 0.246 | 0.462 | 0.179 | ENR+CV-3 Zfand6 |
| Tmem261 | 0.623 | 0.251224785 | 0.246 | 0.443 | 0.164 | ENR+CV-3 Tmem261 |
| Prox1 | 0.622 | 0.416870183 | 0.244 | 0.38 | 0.117 | ENR+CV-3 Prox1 |
| Seh1l | 0.622 | 0.340132025 | 0.244 | 0.357 | 0.098 | ENR+CV-3 Seh1l |
| Klhdc2 | 0.622 | 0.30307816 | 0.244 | 0.394 | 0.126 | ENR+CV-3 Klhdc2 |

TABLE 1-continued

Derived gene list of the top defining genes from in vivo ileal
small intestine PCs and EECs captured on the Seq-Well platform

| Gene | | | | | | Gene |
|---|---|---|---|---|---|---|
| Ndufaf4 | 0.622 | 0.288337133 | 0.244 | 0.394 | 0.126 ENR+CV-3 | Ndufaf4 |
| Cryzl1 | 0.622 | 0.28002871 | 0.244 | 0.371 | 0.106 ENR+CV-3 | Cryzl1 |
| Ndfip2 | 0.622 | 0.278660582 | 0.244 | 0.385 | 0.119 ENR+CV-3 | Ndfip2 |
| Raly | 0.622 | 0.26685766 | 0.244 | 0.434 | 0.159 ENR+CV-3 | Raly |
| Prlr | 0.621 | 0.397356898 | 0.242 | 0.326 | 0.074 ENR+CV-3 | Prlr |
| Kdm5b | 0.621 | 0.361426418 | 0.242 | 0.367 | 0.108 ENR+CV-3 | Kdm5b |
| Asna1 | 0.621 | 0.335721761 | 0.242 | 0.362 | 0.104 ENR+CV-3 | Asna1 |
| Zfp703 | 0.621 | 0.318732988 | 0.242 | 0.367 | 0.107 ENR+CV-3 | Zfp703 |
| Dap | 0.621 | 0.312117704 | 0.242 | 0.348 | 0.091 ENR+CV-3 | Dap |
| Lrrc59 | 0.621 | 0.3107705 | 0.242 | 0.376 | 0.112 ENR+CV-3 | Lrrc59 |
| Hibadh | 0.621 | 0.308437617 | 0.242 | 0.398 | 0.135 ENR+CV-3 | Hibadh |
| Pdcd4 | 0.621 | 0.306418693 | 0.242 | 0.443 | 0.172 ENR+CV-3 | Pdcd4 |
| Efr3a | 0.621 | 0.297326411 | 0.242 | 0.367 | 0.105 ENR+CV-3 | Efr3a |
| Emc2 | 0.621 | 0.272014463 | 0.242 | 0.376 | 0.114 ENR+CV-3 | Emc2 |
| Snx1 | 0.621 | 0.26623895 | 0.242 | 0.394 | 0.128 ENR+CV-3 | Snx1 |
| Atp6ap2 | 0.621 | 0.265413821 | 0.242 | 0.462 | 0.181 ENR+CV-3 | Atp6ap2 |
| Rnf6 | 0.621 | 0.251243163 | 0.242 | 0.376 | 0.113 ENR+CV-3 | Rnf6 |
| Ntmt1 | 0.62 | 0.408945897 | 0.24 | 0.326 | 0.077 ENR+CV-3 | Ntmt1 |
| Lhpp | 0.62 | 0.399587024 | 0.24 | 0.312 | 0.065 ENR+CV-3 | Lhpp |
| Rassf4 | 0.62 | 0.364120801 | 0.24 | 0.312 | 0.063 ENR+CV-3 | Rassf4 |
| Elovl1 | 0.62 | 0.337464335 | 0.24 | 0.362 | 0.105 ENR+CV-3 | Elovl1 |
| Wbp11 | 0.62 | 0.277567753 | 0.24 | 0.412 | 0.143 ENR+CV-3 | Wbp11 |
| Mrpl22 | 0.62 | 0.251906734 | 0.24 | 0.362 | 0.102 ENR+CV-3 | Mrpl22 |
| Ikbkap | 0.619 | 0.411348721 | 0.238 | 0.303 | 0.059 ENR+CV-3 | Ikbkap |
| Naf1 | 0.619 | 0.390331237 | 0.238 | 0.303 | 0.056 ENR+CV-3 | Naf1 |
| Rrp15 | 0.619 | 0.35492878 | 0.238 | 0.321 | 0.072 ENR+CV-3 | Rrp15 |
| Cdk6 | 0.619 | 0.345788648 | 0.238 | 0.344 | 0.093 ENR+CV-3 | Cdk6 |
| Rfc3 | 0.619 | 0.342265028 | 0.238 | 0.389 | 0.131 ENR+CV-3 | Rfc3 |
| Ufsp2 | 0.619 | 0.32017561 | 0.238 | 0.367 | 0.11 ENR+CV-3 | Ufsp2 |
| Stx7 | 0.619 | 0.312131727 | 0.238 | 0.394 | 0.134 ENR+CV-3 | Stx7 |
| Nop16 | 0.619 | 0.294292884 | 0.238 | 0.389 | 0.129 ENR+CV-3 | Nop16 |
| Slc5a1 | 0.619 | 0.270388417 | 0.238 | 0.421 | 0.154 ENR+CV-3 | Slc5a1 |
| Aup1 | 0.619 | 0.268483214 | 0.238 | 0.439 | 0.168 ENR+CV-3 | Aup1 |
| Fkbp8 | 0.619 | 0.257443894 | 0.238 | 0.466 | 0.191 ENR+CV-3 | Fkbp8 |
| Cdk2ap2 | 0.619 | 0.256512074 | 0.238 | 0.425 | 0.155 ENR+CV-3 | Cdk2ap2 |
| Klf3 | 0.618 | 0.351367814 | 0.236 | 0.335 | 0.087 ENR+CV-3 | Klf3 |
| 0610031J06Rik | 0.618 | 0.346276069 | 0.236 | 0.344 | 0.094 ENR+CV-3 | 0610031J06Rik |
| Hmga1 | 0.618 | 0.339561037 | 0.236 | 0.344 | 0.095 ENR+CV-3 | Hmga1 |
| Exosc4 | 0.618 | 0.333259277 | 0.236 | 0.335 | 0.084 ENR+CV-3 | Exosc4 |
| Hexim1 | 0.618 | 0.331104877 | 0.236 | 0.371 | 0.117 ENR+CV-3 | Hexim1 |
| Tmem66 | 0.618 | 0.320639412 | 0.236 | 0.376 | 0.121 ENR+CV-3 | Tmem66 |
| Leprot | 0.618 | 0.320018935 | 0.236 | 0.344 | 0.094 ENR+CV-3 | Leprot |
| Mrpl2 | 0.618 | 0.293530504 | 0.236 | 0.362 | 0.108 ENR+CV-3 | Mrpl2 |
| Thop1 | 0.618 | 0.291395301 | 0.236 | 0.339 | 0.087 ENR+CV-3 | Thop1 |
| Acat2 | 0.618 | 0.282959794 | 0.236 | 0.376 | 0.118 ENR+CV-3 | Acat2 |
| Spop | 0.618 | 0.27614651 | 0.236 | 0.416 | 0.154 ENR+CV-3 | Spop |
| Elf1 | 0.618 | 0.270267669 | 0.236 | 0.394 | 0.133 ENR+CV-3 | Elf1 |
| Net1 | 0.618 | 0.26541165 | 0.236 | 0.425 | 0.161 ENR+CV-3 | Net1 |
| Gsr | 0.618 | 0.259679394 | 0.236 | 0.457 | 0.185 ENR+CV-3 | Gsr |
| U2af2 | 0.618 | 0.255860477 | 0.236 | 0.385 | 0.124 ENR+CV-3 | U2af2 |
| Msx1 | 0.617 | 0.468030677 | 0.234 | 0.285 | 0.045 ENR+CV-3 | Msx1 |
| Grn | 0.617 | 0.340436379 | 0.234 | 0.335 | 0.087 ENR+CV-3 | Grn |
| 4833439L19Rik | 0.617 | 0.337882454 | 0.234 | 0.357 | 0.109 ENR+CV-3 | 4833439L19Rik |
| Fam136a | 0.617 | 0.310596901 | 0.234 | 0.421 | 0.16 ENR+CV-3 | Fam136a |
| Btg1 | 0.617 | 0.300644016 | 0.234 | 0.416 | 0.156 ENR+CV-3 | Btg1 |
| Timm50 | 0.617 | 0.294942893 | 0.234 | 0.394 | 0.137 ENR+CV-3 | Timm50 |
| Dlat | 0.617 | 0.272947513 | 0.234 | 0.376 | 0.121 ENR+CV-3 | Dlat |
| Higd1a | 0.617 | 0.255700338 | 0.234 | 0.407 | 0.144 ENR+CV-3 | Higd1a |
| D10Wsu102e | 0.616 | 0.372360998 | 0.232 | 0.317 | 0.075 ENR+CV-3 | D10Wsu102e |
| Tst | 0.616 | 0.334046744 | 0.232 | 0.299 | 0.058 ENR+CV-3 | Tst |
| Elovl5 | 0.616 | 0.326040888 | 0.232 | 0.33 | 0.085 ENR+CV-3 | Elovl5 |
| Fam96b | 0.616 | 0.311746555 | 0.232 | 0.362 | 0.114 ENR+CV-3 | Fam96b |
| Suclg2 | 0.616 | 0.285130677 | 0.232 | 0.376 | 0.122 ENR+CV-3 | Suclg2 |
| Sigmar1 | 0.616 | 0.269596127 | 0.232 | 0.344 | 0.094 ENR+CV-3 | Sigmar1 |
| Ppie | 0.616 | 0.269023298 | 0.232 | 0.367 | 0.114 ENR+CV-3 | Ppie |
| Asnsd1 | 0.616 | 0.260858767 | 0.232 | 0.376 | 0.122 ENR+CV-3 | Asnsd1 |
| Igf2r | 0.616 | 0.25663532 | 0.232 | 0.389 | 0.134 ENR+CV-3 | Igf2r |
| Mex3a | 0.615 | 0.433430778 | 0.23 | 0.29 | 0.053 ENR+CV-3 | Mex3a |
| Ccz1 | 0.615 | 0.350533738 | 0.23 | 0.344 | 0.101 ENR+CV-3 | Ccz1 |
| Rapgef6 | 0.615 | 0.33230009 | 0.23 | 0.344 | 0.099 ENR+CV-3 | Rapgef6 |
| Dnajc22 | 0.615 | 0.296784797 | 0.23 | 0.385 | 0.134 ENR+CV-3 | Dnajc22 |
| Gna11 | 0.615 | 0.258355419 | 0.23 | 0.376 | 0.121 ENR+CV-3 | Gna11 |
| 1110001A16Rik | 0.615 | 0.25286696 | 0.23 | 0.394 | 0.139 ENR+CV-3 | 1110001A16Rik |
| Tmem171 | 0.614 | 0.352367097 | 0.228 | 0.299 | 0.061 ENR+CV-3 | Tmem171 |
| Id2 | 0.614 | 0.334716711 | 0.228 | 0.416 | 0.162 ENR+CV-3 | Id2 |
| Pmvk | 0.614 | 0.329991942 | 0.228 | 0.344 | 0.102 ENR+CV-3 | Pmvk |
| Blmh | 0.614 | 0.270990381 | 0.228 | 0.371 | 0.121 ENR+CV-3 | Blmh |

TABLE 1-continued

Derived gene list of the top defining genes from in vivo ileal
small intestine PCs and EECs captured on the Seq-Well platform

| Gene | | | | | | |
|---|---|---|---|---|---|---|
| Slc38a1 | 0.614 | 0.254568558 | 0.228 | 0.43 | 0.17 | ENR+CV-3 | Slc38a1 |
| Acads | 0.613 | 0.324186672 | 0.226 | 0.33 | 0.092 | ENR+CV-3 | Acads |
| Lsm7 | 0.613 | 0.302123591 | 0.226 | 0.335 | 0.096 | ENR+CV-3 | Lsm7 |
| Snx4 | 0.613 | 0.294212817 | 0.226 | 0.376 | 0.131 | ENR+CV-3 | Snx4 |
| Dnpep | 0.613 | 0.276265733 | 0.226 | 0.348 | 0.105 | ENR+CV-3 | Dnpep |
| Homer2 | 0.613 | 0.27548174 | 0.226 | 0.403 | 0.151 | ENR+CV-3 | Homer2 |
| Ssscal | 0.613 | 0.266419115 | 0.226 | 0.353 | 0.109 | ENR+CV-3 | Ssscal |
| Srm | 0.612 | 0.320701033 | 0.224 | 0.362 | 0.118 | ENR+CV-3 | Srm |
| Eif2b4 | 0.612 | 0.319058884 | 0.224 | 0.33 | 0.092 | ENR+CV-3 | Eif2b4 |
| Pold2 | 0.612 | 0.310170337 | 0.224 | 0.339 | 0.099 | ENR+CV-3 | Pold2 |
| Ltv1 | 0.612 | 0.2869893 | 0.224 | 0.335 | 0.096 | ENR+CV-3 | Ltv1 |
| Abi1 | 0.612 | 0.282020168 | 0.224 | 0.376 | 0.13 | ENR+CV-3 | Abi1 |
| Id3 | 0.612 | 0.278098076 | 0.224 | 0.489 | 0.22 | ENR+CV-3 | Id3 |
| Trib1 | 0.612 | 0.272703162 | 0.224 | 0.357 | 0.113 | ENR+CV-3 | Trib1 |
| Pgd | 0.612 | 0.263513383 | 0.224 | 0.439 | 0.183 | ENR+CV-3 | Pgd |
| Aimp2 | 0.612 | 0.250744234 | 0.224 | 0.394 | 0.145 | ENR+CV-3 | Aimp2 |
| Scpep1 | 0.611 | 0.321104092 | 0.222 | 0.321 | 0.087 | ENR+CV-3 | Scpep1 |
| Pcbd2 | 0.611 | 0.31640147 | 0.222 | 0.335 | 0.098 | ENR+CV-3 | Pcbd2 |
| Itpr31 | 0.611 | 0.285304682 | 0.222 | 0.353 | 0.111 | ENR+CV-3 | Itpr3 |
| Rfc2 | 0.611 | 0.266888028 | 0.222 | 0.367 | 0.124 | ENR+CV-3 | Rfc2 |
| Man1a | 0.611 | 0.262321764 | 0.222 | 0.344 | 0.105 | ENR+CV-3 | Man1a |
| Epb4.1l3 | 0.611 | 0.259302568 | 0.222 | 0.389 | 0.143 | ENR+CV-3 | Epb4.1l3 |
| mt-Tq1 | 0.61 | 0.40426559 | 0.22 | 0.267 | 0.042 | ENR+CV-3 | mt-Tq |
| Rbm38 | 0.61 | 0.362559847 | 0.22 | 0.299 | 0.07 | ENR+CV-3 | Rbm38 |
| Zfp36l2 | 0.61 | 0.341893789 | 0.22 | 0.367 | 0.127 | ENR+CV-3 | Zfp36l2 |
| Stk38l | 0.61 | 0.322543455 | 0.22 | 0.303 | 0.072 | ENR+CV-3 | Stk38l |
| Nufip2 | 0.61 | 0.322270517 | 0.22 | 0.348 | 0.113 | ENR+CV-3 | Nufip2 |
| Wwp1 | 0.61 | 0.292019818 | 0.22 | 0.353 | 0.117 | ENR+CV-3 | Wwp1 |
| Gtl3 | 0.61 | 0.273809159 | 0.22 | 0.371 | 0.129 | ENR+CV-3 | Gtl3 |
| Psmd13 | 0.61 | 0.268493546 | 0.22 | 0.385 | 0.141 | ENR+CV-3 | Psmd13 |
| Abcd3 | 0.61 | 0.250521568 | 0.22 | 0.394 | 0.147 | ENR+CV-3 | Abcd3 |
| Tubb2b | 0.609 | 0.404769251 | 0.218 | 0.285 | 0.061 | ENR+CV-3 | Tubb2b |
| Mfsd1 | 0.609 | 0.325334218 | 0.218 | 0.312 | 0.082 | ENR+CV-3 | Mfsd1 |
| Mtfp1 | 0.609 | 0.324482132 | 0.218 | 0.281 | 0.056 | ENR+CV-3 | Mtfp1 |
| Saysd1 | 0.609 | 0.306817574 | 0.218 | 0.308 | 0.078 | ENR+CV-3 | Saysd1 |
| Vat1 | 0.609 | 0.280575618 | 0.218 | 0.294 | 0.064 | ENR+CV-3 | Vat1 |
| Med10 | 0.609 | 0.277896986 | 0.218 | 0.33 | 0.097 | ENR+CV-3 | Med10 |
| Snrpc | 0.609 | 0.266562146 | 0.218 | 0.362 | 0.123 | ENR+CV-3 | Snrpc |
| Acadvl | 0.609 | 0.26563737 | 0.218 | 0.33 | 0.096 | ENR+CV-3 | Acadvl |
| Wdr12 | 0.608 | 0.292666818 | 0.216 | 0.344 | 0.113 | ENR+CV-3 | Wdr12 |
| Senp2 | 0.608 | 0.289581275 | 0.216 | 0.33 | 0.1 | ENR+CV-3 | Senp2 |
| Pum1 | 0.608 | 0.287760438 | 0.216 | 0.357 | 0.122 | ENR+CV-3 | Pum1 |
| Pigt | 0.608 | 0.286777318 | 0.216 | 0.317 | 0.089 | ENR+CV-3 | Pigt |
| Camta1 | 0.607 | 0.323001702 | 0.214 | 0.281 | 0.059 | ENR+CV-3 | Camta1 |
| Mvd | 0.607 | 0.312656662 | 0.214 | 0.299 | 0.073 | ENR+CV-3 | Mvd |
| Irf8 | 0.607 | 0.309223965 | 0.214 | 0.303 | 0.079 | ENR+CV-3 | Irf8 |
| Mpzl2 | 0.607 | 0.283260694 | 0.214 | 0.335 | 0.105 | ENR+CV-3 | Mpzl2 |
| Tmem242 | 0.607 | 0.261007344 | 0.214 | 0.353 | 0.121 | ENR+CV-3 | Tmem242 |
| Cpox | 0.606 | 0.317825012 | 0.212 | 0.326 | 0.1 | ENR+CV-3 | Cpox |
| Tmem57 | 0.606 | 0.290728898 | 0.212 | 0.308 | 0.084 | ENR+CV-3 | Tmem57 |
| Snrpa | 0.605 | 0.327393024 | 0.21 | 0.33 | 0.108 | ENR+CV-3 | Snrpa |
| Tns3 | 0.605 | 0.277191665 | 0.21 | 0.33 | 0.104 | ENR+CV-3 | Tns3 |
| Smek2 | 0.605 | 0.254570889 | 0.21 | 0.398 | 0.164 | ENR+CV-3 | Smek2 |
| Csnk2a2 | 0.604 | 0.407357302 | 0.208 | 0.262 | 0.049 | ENR+CV-3 | Csnk2a2 |
| Lgals1 | 0.604 | 0.394722012 | 0.208 | 0.267 | 0.053 | ENR+CV-3 | Lgals1 |
| Arl4a | 0.604 | 0.328339808 | 0.208 | 0.317 | 0.096 | ENR+CV-3 | Arl4a |
| Cited2 | 0.604 | 0.303362787 | 0.208 | 0.294 | 0.074 | ENR+CV-3 | Cited2 |
| Tceal8 | 0.604 | 0.298448901 | 0.208 | 0.33 | 0.108 | ENR+CV-3 | Tceal8 |
| Casp3 | 0.604 | 0.280017387 | 0.208 | 0.308 | 0.087 | ENR+CV-3 | Casp3 |
| Cisd1 | 0.604 | 0.275596402 | 0.208 | 0.357 | 0.129 | ENR+CV-3 | Cisd1 |
| Cyb561 | 0.604 | 0.261953768 | 0.208 | 0.29 | 0.071 | ENR+CV-3 | Cyb561 |
| Dag1 | 0.604 | 0.252119133 | 0.208 | 0.339 | 0.114 | ENR+CV-3 | Dag1 |
| Gramd3 | 0.603 | 0.333171151 | 0.206 | 0.281 | 0.067 | ENR+CV-3 | Gramd3 |
| Trim37 | 0.603 | 0.301015518 | 0.206 | 0.308 | 0.089 | ENR+CV-3 | Trim37 |
| Usp33 | 0.603 | 0.271767928 | 0.206 | 0.326 | 0.105 | ENR+CV-3 | Usp33 |
| Psenen | 0.603 | 0.269489223 | 0.206 | 0.29 | 0.073 | ENR+CV-3 | Psenen |
| Rbbp8 | 0.603 | 0.255932171 | 0.206 | 0.308 | 0.088 | ENR+CV-3 | Rbbp8 |
| Crlf1 | 0.602 | 0.425309976 | 0.204 | 0.24 | 0.034 | ENR+CV-3 | Crlf1 |
| Cd82 | 0.602 | 0.288228889 | 0.204 | 0.308 | 0.091 | ENR+CV-3 | Cd82 |
| Znrf2 | 0.602 | 0.260124534 | 0.204 | 0.312 | 0.094 | ENR+CV-3 | Znrf2 |
| Shmt1 | 0.602 | 0.251927386 | 0.204 | 0.344 | 0.121 | ENR+CV-3 | Shmt1 |
| Abhd17a | 0.601 | 0.259082574 | 0.202 | 0.33 | 0.111 | ENR+CV-3 | Abhd17a |
| Pdk1 | 0.601 | 0.253925716 | 0.202 | 0.348 | 0.127 | ENR+CV-3 | Pdk1 |
| Nubp1 | 0.601 | 0.250201216 | 0.202 | 0.33 | 0.113 | ENR+CV-3 | Nubp1 |
| Rpl413 | 0.914 | 1.27710129 | 0.828 | 0.991 | 0.822 | ENR+CV-4 | Rpl41 |
| Pabpc13 | 0.91 | 0.987057951 | 0.82 | 1 | 0.797 | ENR+CV-4 | Pabpc1 |
| Tubb52 | 0.879 | 1.079830906 | 0.758 | 0.991 | 0.584 | ENR+CV-4 | Tubb5 |

TABLE 1-continued

Derived gene list of the top defining genes from in vivo ileal
small intestine PCs and EECs captured on the Seq-Well platform

| | | | | | | | |
|---|---|---|---|---|---|---|---|
| Gm20003 | 0.873 | 1.138545443 | 0.746 | 0.963 | 0.437 | ENR+CV-4 | Gm2000 |
| Gm269243 | 0.873 | 0.917007836 | 0.746 | 1 | 0.935 | ENR+CV-4 | Gm26924 |
| Rpl37a3 | 0.864 | 0.923564177 | 0.728 | 0.986 | 0.584 | ENR+CV-4 | Rpl37a |
| Top2a | 0.833 | 1.063774035 | 0.666 | 0.936 | 0.311 | ENR+CV-4 | Top2a |
| H1f03 | 0.82 | 1.014029909 | 0.64 | 0.922 | 0.37 | ENR+CV-4 | H1f0 |
| Smoc22 | 0.819 | 0.912134984 | 0.638 | 0.95 | 0.435 | ENR+CV-4 | Smoc2 |
| Uqcr102 | 0.818 | 0.750489221 | 0.636 | 1 | 0.668 | ENR+CV-4 | Uqcr10 |
| 2810417H13Rik | 0.817 | 1.118599214 | 0.634 | 0.839 | 0.23 | ENR+CV-4 | 2810417H13Rik |
| Dbi3 | 0.817 | 0.635827462 | 0.634 | 1 | 0.818 | ENR+CV-4 | Dbi |
| Gm155643 | 0.816 | 0.862925758 | 0.632 | 0.867 | 0.202 | ENR+CV-4 | Gm15564 |
| Smc4 | 0.814 | 0.939051587 | 0.628 | 0.908 | 0.26 | ENR+CV-4 | Smc4 |
| Rpph12 | 0.808 | 0.46376516 | 0.616 | 0.963 | 0.379 | ENR+CV-4 | Rpph1 |
| Bola23 | 0.793 | 0.789188442 | 0.586 | 0.899 | 0.289 | ENR+CV-4 | Bola2 |
| Taldo12 | 0.791 | 0.7520657 | 0.582 | 0.945 | 0.427 | ENR+CV-4 | Taldo1 |
| Uqcr112 | 0.791 | 0.67996669 | 0.582 | 0.968 | 0.626 | ENR+CV-4 | Uqcr11 |
| Hmgb12 | 0.789 | 0.915811857 | 0.578 | 0.826 | 0.242 | ENR+CV-4 | Hmgb1 |
| Gm100762 | 0.788 | 0.722580202 | 0.576 | 0.963 | 0.607 | ENR+CV-4 | Gm10076 |
| Rpl35a2 | 0.788 | 0.629467239 | 0.576 | 0.977 | 0.783 | ENR+CV-4 | Rpl35a |
| Mlec2 | 0.785 | 0.753675464 | 0.57 | 0.936 | 0.354 | ENR+CV-4 | Mlec |
| Hes13 | 0.776 | 0.979220055 | 0.552 | 0.775 | 0.216 | ENR+CV-4 | Hes1 |
| Bex12 | 0.771 | 0.75160367 | 0.542 | 0.853 | 0.273 | ENR+CV-4 | Bex1 |
| Rpl372 | 0.769 | 0.623370319 | 0.538 | 0.959 | 0.651 | ENR+CV-4 | Rpl37 |
| Mki67 | 0.767 | 0.788146731 | 0.534 | 0.853 | 0.296 | ENR+CV-4 | Mki67 |
| Ifitm22 | 0.763 | 0.619884638 | 0.526 | 0.986 | 0.545 | ENR+CV-4 | Ifitm2 |
| Psmc31 | 0.76 | 0.7190257 | 0.52 | 0.78 | 0.22 | ENR+CV-4 | Psmc3 |
| Hist1h1b | 0.759 | 0.885790981 | 0.518 | 0.693 | 0.151 | ENR+CV-4 | Hist1h1b |
| Smc2 | 0.756 | 0.697876671 | 0.512 | 0.725 | 0.163 | ENR+CV-4 | Smc2 |
| Dynll21 | 0.756 | 0.689622449 | 0.512 | 0.817 | 0.265 | ENR+CV-4 | Dynll2 |
| Cox4i12 | 0.756 | 0.450685885 | 0.512 | 0.991 | 0.852 | ENR+CV-4 | Cox4i1 |
| Egr13 | 0.754 | 0.762185697 | 0.508 | 0.876 | 0.391 | ENR+CV-4 | Egr1 |
| Cox6a12 | 0.752 | 0.500037044 | 0.504 | 0.982 | 0.701 | ENR+CV-4 | Cox6a1 |
| Psmc13 | 0.751 | 0.706706977 | 0.502 | 0.775 | 0.234 | ENR+CV-4 | Psmc1 |
| Uqcrc12 | 0.751 | 0.603530854 | 0.502 | 0.931 | 0.413 | ENR+CV-4 | Uqcrc1 |
| Wbp52 | 0.751 | 0.598776284 | 0.502 | 0.963 | 0.491 | ENR+CV-4 | Wbp5 |
| Ptma3 | 0.749 | 0.52115301 | 0.498 | 0.963 | 0.735 | ENR+CV-4 | Ptma |
| Nusap1 | 0.748 | 0.875835989 | 0.496 | 0.615 | 0.097 | ENR+CV-4 | Nusap1 |
| Idh3a1 | 0.748 | 0.62531889 | 0.496 | 0.761 | 0.21 | ENR+CV-4 | Idh3a |
| Sypl1 | 0.748 | 0.624209872 | 0.496 | 0.917 | 0.39 | ENR+CV-4 | Sypl |
| Serinc32 | 0.747 | 0.666831341 | 0.494 | 0.927 | 0.48 | ENR+CV-4 | Serinc3 |
| Ak22 | 0.747 | 0.649696188 | 0.494 | 0.812 | 0.278 | ENR+CV-4 | Ak2 |
| Atp5k2 | 0.747 | 0.623960273 | 0.494 | 0.913 | 0.469 | ENR+CV-4 | Atp5k |
| Uqcrq2 | 0.745 | 0.48641841 | 0.49 | 0.995 | 0.755 | ENR+CV-4 | Uqcrq |
| Rpl132 | 0.745 | 0.413951895 | 0.49 | 0.991 | 0.905 | ENR+CV-4 | Rpl13 |
| Idh21 | 0.744 | 0.660825146 | 0.488 | 0.766 | 0.228 | ENR+CV-4 | Idh2 |
| Tmem971 | 0.744 | 0.614696525 | 0.488 | 0.78 | 0.237 | ENR+CV-4 | Tmem97 |
| Ndufb42 | 0.743 | 0.694175013 | 0.486 | 0.789 | 0.262 | ENR+CV-4 | Ndufb4 |
| Ndufb82 | 0.742 | 0.571997471 | 0.484 | 0.94 | 0.502 | ENR+CV-4 | Ndufb8 |
| Atp5o2 | 0.742 | 0.532588249 | 0.484 | 0.954 | 0.526 | ENR+CV-4 | Atp5o |
| Ybx13 | 0.741 | 0.563247665 | 0.482 | 0.954 | 0.727 | ENR+CV-4 | Ybx1 |
| Rny13 | 0.741 | 0.562935888 | 0.482 | 0.587 | 0.082 | ENR+CV-4 | Rny1 |
| Snord133 | 0.74 | 0.697563844 | 0.48 | 0.674 | 0.171 | ENR+CV-4 | Snord13 |
| Tpi13 | 0.74 | 0.578456184 | 0.48 | 0.968 | 0.582 | ENR+CV-4 | Tpi1 |
| Gm98462 | 0.739 | 0.743380999 | 0.478 | 0.619 | 0.115 | ENR+CV-4 | Gm9846 |
| Prc1 | 0.739 | 0.719942861 | 0.478 | 0.628 | 0.116 | ENR+CV-4 | Prc1 |
| Mdh22 | 0.739 | 0.589122035 | 0.478 | 0.904 | 0.395 | ENR+CV-4 | Mdh2 |
| Hmgb2 | 0.736 | 0.6253128 | 0.472 | 0.922 | 0.479 | ENR+CV-4 | Hmgb2 |
| Hmgcs23 | 0.735 | 0.806516034 | 0.47 | 0.592 | 0.101 | ENR+CV-4 | Hmgcs2 |
| Ccdc342 | 0.734 | 0.616465377 | 0.468 | 0.885 | 0.42 | ENR+CV-4 | Ccdc34 |
| Tmem2562 | 0.734 | 0.589648713 | 0.468 | 0.872 | 0.381 | ENR+CV-4 | Tmem256 |
| Cbx11 | 0.734 | 0.563672515 | 0.468 | 0.826 | 0.298 | ENR+CV-4 | Cbx1 |
| Pcsk92 | 0.733 | 0.60991063 | 0.466 | 0.665 | 0.158 | ENR+CV-4 | Pcsk9 |
| Csnk2a11 | 0.732 | 0.649642724 | 0.464 | 0.656 | 0.153 | ENR+CV-4 | Csnk2a1 |
| Tuba1c | 0.731 | 0.647405482 | 0.462 | 0.876 | 0.387 | ENR+CV-4 | Tuba1c |
| H2-Q102 | 0.73 | 0.665684835 | 0.46 | 0.606 | 0.117 | ENR+CV-4 | H2-Q10 |
| H2afv1 | 0.73 | 0.580617561 | 0.46 | 0.872 | 0.385 | ENR+CV-4 | H2afv |
| Arpp193 | 0.73 | 0.551691056 | 0.46 | 0.858 | 0.339 | ENR+CV-4 | Arpp19 |
| Rpl342 | 0.729 | 0.436853753 | 0.458 | 0.968 | 0.815 | ENR+CV-4 | Rpl34 |
| Gcat2 | 0.728 | 0.602060203 | 0.456 | 0.661 | 0.164 | ENR+CV-4 | Gcat |
| Nucks1 | 0.728 | 0.539838631 | 0.456 | 0.83 | 0.307 | ENR+CV-4 | Nucks1 |
| Cdca8 | 0.727 | 0.594264131 | 0.454 | 0.647 | 0.149 | ENR+CV-4 | Cdca8 |
| Hmg20b1 | 0.725 | 0.620419336 | 0.45 | 0.665 | 0.174 | ENR+CV-4 | Hmg20b |
| Pdap12 | 0.725 | 0.526391966 | 0.45 | 0.899 | 0.398 | ENR+CV-4 | Pdap1 |
| Sub12 | 0.723 | 0.560126338 | 0.446 | 0.83 | 0.333 | ENR+CV-4 | Sub1 |
| Atp5d3 | 0.723 | 0.548048727 | 0.446 | 0.908 | 0.415 | ENR+CV-4 | Atp5d |
| Galk13 | 0.723 | 0.53982809 | 0.446 | 0.688 | 0.186 | ENR+CV-4 | Galk1 |
| Fgfbp11 | 0.723 | 0.472748414 | 0.446 | 0.766 | 0.231 | ENR+CV-4 | Fgfbp1 |
| Arl6ip1 | 0.722 | 0.763163913 | 0.444 | 0.725 | 0.282 | ENR+CV-4 | Arl6ip1 |

TABLE 1-continued

Derived gene list of the top defining genes from in vivo ileal
small intestine PCs and EECs captured on the Seq-Well platform

| | | | | | | |
|---|---|---|---|---|---|---|
| 2410015M20Rik2 | 0.722 | 0.553079541 | 0.444 | 0.743 | 0.243 ENR+CV-4 | 2410015M20Rik |
| Prmt11 | 0.722 | 0.547636331 | 0.444 | 0.766 | 0.256 ENR+CV-4 | Prmt1 |
| Aldh1b11 | 0.722 | 0.535950813 | 0.444 | 0.835 | 0.338 ENR+CV-4 | Aldh1b1 |
| Srrm11 | 0.722 | 0.526477733 | 0.444 | 0.826 | 0.328 ENR+CV-4 | Srrm1 |
| Mif2 | 0.721 | 0.537589281 | 0.442 | 0.922 | 0.499 ENR+CV-4 | Mif |
| Eif5a1 | 0.721 | 0.536312264 | 0.442 | 0.917 | 0.516 ENR+CV-4 | Eif5a |
| Atp5e2 | 0.721 | 0.449399589 | 0.442 | 0.963 | 0.665 ENR+CV-4 | Atp5e |
| Cbx31 | 0.72 | 0.624650764 | 0.44 | 0.619 | 0.146 ENR+CV-4 | Cbx3 |
| Pfdn11 | 0.719 | 0.571105188 | 0.438 | 0.725 | 0.232 ENR+CV-4 | Pfdn1 |
| Mrpl281 | 0.719 | 0.523768186 | 0.438 | 0.748 | 0.244 ENR+CV-4 | Mrpl28 |
| Ndufa101 | 0.719 | 0.514497454 | 0.438 | 0.761 | 0.256 ENR+CV-4 | Ndufa10 |
| Psma72 | 0.719 | 0.474044792 | 0.438 | 0.959 | 0.573 ENR+CV-4 | Psma7 |
| Hsp90ab11 | 0.719 | 0.34768932 | 0.438 | 1 | 0.932 ENR+CV-4 | Hsp90ab1 |
| Dek | 0.718 | 0.522855438 | 0.436 | 0.826 | 0.317 ENR+CV-4 | Dek |
| Nol71 | 0.718 | 0.512547775 | 0.436 | 0.821 | 0.322 ENR+CV-4 | Nol7 |
| Trappc6a2 | 0.717 | 0.527000451 | 0.434 | 0.757 | 0.261 ENR+CV-4 | Trappc6a |
| Tacc3 | 0.716 | 0.764261261 | 0.432 | 0.528 | 0.08 ENR+CV-4 | Tacc3 |
| Pbk | 0.716 | 0.615892696 | 0.432 | 0.56 | 0.098 ENR+CV-4 | Pbk |
| Hnrnpd1 | 0.716 | 0.565255386 | 0.432 | 0.638 | 0.165 ENR+CV-4 | Hnrnpd |
| Snrpd32 | 0.716 | 0.513976258 | 0.432 | 0.867 | 0.374 ENR+CV-4 | Snrpd3 |
| mt-Tc2 | 0.715 | 0.778396502 | 0.43 | 0.5 | 0.058 ENR+CV-4 | mt-Tc |
| Rny33 | 0.715 | 0.642039771 | 0.43 | 0.55 | 0.097 ENR+CV-4 | Rny3 |
| Add31 | 0.715 | 0.570862767 | 0.43 | 0.688 | 0.211 ENR+CV-4 | Add3 |
| D8Ertd738e1 | 0.715 | 0.52518644 | 0.43 | 0.702 | 0.22 ENR+CV-4 | D8Ertd738e |
| Anp32e1 | 0.715 | 0.492639902 | 0.43 | 0.679 | 0.191 ENR+CV-4 | Anp32e |
| Atp5b2 | 0.715 | 0.425036017 | 0.43 | 0.982 | 0.724 ENR+CV-4 | Atp5b |
| 2010107E04Rik2 | 0.714 | 0.444015425 | 0.428 | 0.977 | 0.667 ENR+CV-4 | 2010107E04Rik |
| Hn1 | 0.713 | 0.524760229 | 0.426 | 0.867 | 0.395 ENR+CV-4 | Hn1 |
| Mtch21 | 0.713 | 0.503831272 | 0.426 | 0.789 | 0.301 ENR+CV-4 | Mtch2 |
| Cyc11 | 0.713 | 0.488752984 | 0.426 | 0.826 | 0.331 ENR+CV-4 | Cyc1 |
| Fuca11 | 0.713 | 0.481392149 | 0.426 | 0.711 | 0.22 ENR+CV-4 | Fuca1 |
| Cenpf | 0.712 | 0.759271744 | 0.424 | 0.573 | 0.128 ENR+CV-4 | Cenpf |
| Rangap1 | 0.712 | 0.561114219 | 0.424 | 0.619 | 0.156 ENR+CV-4 | Rangap1 |
| Anp32a1 | 0.712 | 0.500905675 | 0.424 | 0.849 | 0.37 ENR+CV-4 | Anp32a |
| Ndufa32 | 0.712 | 0.48789893 | 0.424 | 0.876 | 0.391 ENR+CV-4 | Ndufa3 |
| Chchd101 | 0.712 | 0.467163032 | 0.424 | 0.807 | 0.307 ENR+CV-4 | Chchd10 |
| Rad23b1 | 0.711 | 0.555656866 | 0.422 | 0.647 | 0.181 ENR+CV-4 | Rad23b |
| Ilf21 | 0.711 | 0.543297591 | 0.422 | 0.624 | 0.159 ENR+CV-4 | Ilf2 |
| Sae11 | 0.711 | 0.538853645 | 0.422 | 0.679 | 0.204 ENR+CV-4 | Sae1 |
| Mrps121 | 0.711 | 0.519282432 | 0.422 | 0.61 | 0.144 ENR+CV-4 | Mrps12 |
| Rps282 | 0.711 | 0.518618509 | 0.422 | 0.817 | 0.333 ENR+CV-4 | Rps28 |
| Ier23 | 0.711 | 0.510282677 | 0.422 | 0.922 | 0.526 ENR+CV-4 | Ier2 |
| Ndufc12 | 0.711 | 0.477345452 | 0.422 | 0.881 | 0.475 ENR+CV-4 | Ndufc1 |
| Atp1a13 | 0.71 | 0.515422791 | 0.42 | 0.876 | 0.399 ENR+CV-4 | Atp1a1 |
| Gm102212 | 0.709 | 0.64227589 | 0.418 | 0.578 | 0.134 ENR+CV-4 | Gm10221 |
| Aqp12 | 0.709 | 0.578468857 | 0.418 | 0.601 | 0.146 ENR+CV-4 | Aqp1 |
| Birc5 | 0.709 | 0.565936071 | 0.418 | 0.592 | 0.133 ENR+CV-4 | Birc5 |
| Lmnb1 | 0.709 | 0.562933198 | 0.418 | 0.601 | 0.146 ENR+CV-4 | Lmnb1 |
| Sord1 | 0.709 | 0.511292798 | 0.418 | 0.661 | 0.19 ENR+CV-4 | Sord |
| Nudc1 | 0.709 | 0.497272443 | 0.418 | 0.633 | 0.167 ENR+CV-4 | Nudc |
| Hnf4a1 | 0.709 | 0.478357727 | 0.418 | 0.716 | 0.232 ENR+CV-4 | Hnf4a |
| Myeov22 | 0.709 | 0.449730154 | 0.418 | 0.876 | 0.372 ENR+CV-4 | Myeov2 |
| Pkm3 | 0.709 | 0.445718729 | 0.418 | 0.963 | 0.633 ENR+CV-4 | Pkm |
| Kif20b | 0.708 | 0.718689213 | 0.416 | 0.55 | 0.111 ENR+CV-4 | Kif20b |
| Timm501 | 0.708 | 0.562724868 | 0.416 | 0.578 | 0.13 ENR+CV-4 | Timm50 |
| Mvb12a1 | 0.708 | 0.554731529 | 0.416 | 0.596 | 0.143 ENR+CV-4 | Mvb12a |
| Ckb1 | 0.708 | 0.510804146 | 0.416 | 0.766 | 0.278 ENR+CV-4 | Ckb |
| Ssrp11 | 0.708 | 0.506507721 | 0.416 | 0.72 | 0.245 ENR+CV-4 | Ssrp1 |
| Cs2 | 0.708 | 0.503298421 | 0.416 | 0.711 | 0.232 ENR+CV-4 | Cs |
| Crip12 | 0.708 | 0.471144199 | 0.416 | 0.862 | 0.395 ENR+CV-4 | Crip1 |
| Hmmr | 0.707 | 0.665841267 | 0.414 | 0.528 | 0.092 ENR+CV-4 | Hmmr |
| Aifm11 | 0.707 | 0.513757201 | 0.414 | 0.596 | 0.142 ENR+CV-4 | Aifm1 |
| Psmb21 | 0.707 | 0.497633741 | 0.414 | 0.72 | 0.248 ENR+CV-4 | Psmb2 |
| Tmed91 | 0.707 | 0.459736838 | 0.414 | 0.67 | 0.194 ENR+CV-4 | Tmed9 |
| Pabpc42 | 0.706 | 0.530275564 | 0.412 | 0.628 | 0.172 ENR+CV-4 | Pabpc4 |
| Ap1s11 | 0.706 | 0.491848799 | 0.412 | 0.619 | 0.162 ENR+CV-4 | Ap1s1 |
| Ndufv11 | 0.706 | 0.474565855 | 0.412 | 0.702 | 0.23 ENR+CV-4 | Ndufv1 |
| Cdc1231 | 0.706 | 0.454481634 | 0.412 | 0.656 | 0.189 ENR+CV-4 | Cdc123 |
| Znhit11 | 0.705 | 0.538647366 | 0.41 | 0.583 | 0.138 ENR+CV-4 | Znhit1 |
| Tecr1 | 0.705 | 0.465936723 | 0.41 | 0.826 | 0.34 ENR+CV-4 | Tecr |
| Tmem2341 | 0.705 | 0.440371247 | 0.41 | 0.748 | 0.263 ENR+CV-4 | Tmem234 |
| Ndufab11 | 0.705 | 0.439127805 | 0.41 | 0.821 | 0.332 ENR+CV-4 | Ndufab1 |
| Tpx2 | 0.704 | 0.689152583 | 0.408 | 0.514 | 0.086 ENR+CV-4 | Tpx2 |
| Pkig1 | 0.704 | 0.584896893 | 0.408 | 0.573 | 0.133 ENR+CV-4 | Pkig |
| Phb1 | 0.704 | 0.524200669 | 0.408 | 0.578 | 0.133 ENR+CV-4 | Phb |
| Cps11 | 0.704 | 0.520139545 | 0.408 | 0.812 | 0.353 ENR+CV-4 | Cps1 |
| Rbm8a1 | 0.704 | 0.505343033 | 0.408 | 0.674 | 0.214 ENR+CV-4 | Rbm8a |

TABLE 1-continued

Derived gene list of the top defining genes from in vivo ileal
small intestine PCs and EECs captured on the Seq-Well platform

| | | | | | | |
|---|---|---|---|---|---|---|
| Ndufv33 | 0.704 | 0.48806605 | 0.408 | 0.789 | 0.319 ENR+CV-4 | Ndufv3 |
| Slc25a12 | 0.704 | 0.448982999 | 0.408 | 0.661 | 0.192 ENR+CV-4 | Slc25a1 |
| Dhcr242 | 0.703 | 0.522901763 | 0.406 | 0.67 | 0.212 ENR+CV-4 | Dhcr24 |
| Cdca71 | 0.703 | 0.521715817 | 0.406 | 0.711 | 0.248 ENR+CV-4 | Cdca7 |
| Clptm11 | 0.703 | 0.51666567 | 0.406 | 0.573 | 0.132 ENR+CV-4 | Clptm1 |
| Abcf11 | 0.703 | 0.47080962 | 0.406 | 0.702 | 0.236 ENR+CV-4 | Abcf1 |
| Ugp21 | 0.703 | 0.429712242 | 0.406 | 0.619 | 0.162 ENR+CV-4 | Ugp2 |
| mmu-mir-62363 | 0.702 | 0.869674721 | 0.404 | 0.468 | 0.051 ENR+CV-4 | mmu-mir-6236 |
| Cyba1 | 0.702 | 0.524012317 | 0.404 | 0.661 | 0.207 ENR+CV-4 | Cyba |
| Ndufaf21 | 0.702 | 0.469278309 | 0.404 | 0.628 | 0.173 ENR+CV-4 | Ndufaf2 |
| Rpl33 | 0.702 | 0.366344853 | 0.404 | 0.982 | 0.759 ENR+CV-4 | Rpl3 |
| Immt1 | 0.701 | 0.442997866 | 0.402 | 0.697 | 0.23  ENR+CV-4 | Immt |
| Serf21 | 0.7 | 0.476718974 | 0.4 | 0.706 | 0.239 ENR+CV-4 | Serf2 |
| Eef23 | 0.7 | 0.36667656 | 0.4 | 0.991 | 0.845 ENR+CV-4 | Eef2 |
| Rabl61 | 0.699 | 0.490735115 | 0.398 | 0.592 | 0.153 ENR+CV-4 | Rabl6 |
| Grpel11 | 0.699 | 0.472747985 | 0.398 | 0.661 | 0.209 ENR+CV-4 | Grpel1 |
| Etfa1 | 0.699 | 0.438302028 | 0.398 | 0.725 | 0.254 ENR+CV-4 | Etfa |
| Ndufb71 | 0.699 | 0.436334912 | 0.398 | 0.798 | 0.319 ENR+CV-4 | Ndufb7 |
| Park72 | 0.699 | 0.431204796 | 0.398 | 0.885 | 0.425 ENR+CV-4 | Park7 |
| Serbp12 | 0.699 | 0.413645488 | 0.398 | 0.991 | 0.711 ENR+CV-4 | Serbp1 |
| Sars1 | 0.699 | 0.392541833 | 0.398 | 0.789 | 0.294 ENR+CV-4 | Sars |
| Ezh2 | 0.698 | 0.49179889 | 0.396 | 0.656 | 0.207 ENR+CV-4 | Ezh2 |
| Psmc41 | 0.698 | 0.488510197 | 0.396 | 0.624 | 0.181 ENR+CV-4 | Psmc4 |
| Mapk132 | 0.698 | 0.460229018 | 0.396 | 0.679 | 0.221 ENR+CV-4 | Mapk13 |
| Sfr11 | 0.698 | 0.428236196 | 0.396 | 0.642 | 0.188 ENR+CV-4 | Sfr1 |
| Cdc371 | 0.698 | 0.41794008 | 0.396 | 0.725 | 0.255 ENR+CV-4 | Cdc37 |
| Rrp11 | 0.698 | 0.370299279 | 0.396 | 0.72 | 0.24  ENR+CV-4 | Rrp1 |
| Cenpe | 0.697 | 0.5594754 | 0.394 | 0.564 | 0.135 ENR+CV-4 | Cenpe |
| Rfc21 | 0.697 | 0.521394755 | 0.394 | 0.541 | 0.118 ENR+CV-4 | Rfc2 |
| Agpat51 | 0.697 | 0.477156338 | 0.394 | 0.578 | 0.144 ENR+CV-4 | Agpat5 |
| Snrpg3 | 0.697 | 0.475227871 | 0.394 | 0.867 | 0.464 ENR+CV-4 | Snrpg |
| Lad11 | 0.697 | 0.470003525 | 0.394 | 0.665 | 0.212 ENR+CV-4 | Lad1 |
| Mrpl461 | 0.697 | 0.459740746 | 0.394 | 0.573 | 0.138 ENR+CV-4 | Mrpl46 |
| Tax1bp12 | 0.697 | 0.450349166 | 0.394 | 0.899 | 0.457 ENR+CV-4 | Tax1bp1 |
| Scaf11 | 0.697 | 0.43556153 | 0.394 | 0.702 | 0.241 ENR+CV-4 | Scaf11 |
| Ywhae1 | 0.697 | 0.422199685 | 0.394 | 0.931 | 0.47  ENR+CV-4 | Ywhae |
| Slc25a41 | 0.696 | 0.441960168 | 0.392 | 0.766 | 0.308 ENR+CV-4 | Slc25a4 |
| Snw11 | 0.696 | 0.409154776 | 0.392 | 0.697 | 0.236 ENR+CV-4 | Snw1 |
| Ndufa51 | 0.696 | 0.406236589 | 0.392 | 0.849 | 0.373 ENR+CV-4 | Ndufa5 |
| Psmd121 | 0.695 | 0.463600968 | 0.39 | 0.624 | 0.187 ENR+CV-4 | Psmd12 |
| Rpl171 | 0.695 | 0.461322885 | 0.39 | 0.647 | 0.202 ENR+CV-4 | Rpl17 |
| Mrpl121 | 0.695 | 0.458885892 | 0.39 | 0.789 | 0.327 ENR+CV-4 | Mrpl12 |
| H2-D11 | 0.695 | 0.449059067 | 0.39 | 0.826 | 0.362 ENR+CV-4 | H2-D1 |
| Mapre11 | 0.695 | 0.444681807 | 0.39 | 0.624 | 0.183 ENR+CV-4 | Mapre1 |
| Mtdh1 | 0.695 | 0.438023366 | 0.39 | 0.766 | 0.305 ENR+CV-4 | Mtdh |
| Bola11 | 0.695 | 0.434011732 | 0.39 | 0.633 | 0.189 ENR+CV-4 | Bola1 |
| Ect2 | 0.694 | 0.542026793 | 0.388 | 0.514 | 0.099 ENR+CV-4 | Ect2 |
| Glrx1 | 0.694 | 0.514942064 | 0.388 | 0.564 | 0.143 ENR+CV-4 | Glrx |
| Rpl182 | 0.694 | 0.389984399 | 0.388 | 0.972 | 0.663 ENR+CV-4 | Rpl18 |
| Scd12 | 0.693 | 0.603960684 | 0.386 | 0.505 | 0.096 ENR+CV-4 | Scd1 |
| Cdk1 | 0.693 | 0.451972309 | 0.386 | 0.587 | 0.152 ENR+CV-4 | Cdk1 |
| Ppp1r1b1 | 0.693 | 0.449015105 | 0.386 | 0.725 | 0.27  ENR+CV-4 | Ppp1r1b |
| Sfxn11 | 0.693 | 0.43744708 | 0.386 | 0.619 | 0.181 ENR+CV-4 | Sfxn1 |
| Eif3h2 | 0.693 | 0.427541746 | 0.386 | 0.894 | 0.508 ENR+CV-4 | Eif3h |
| Snrpd21 | 0.693 | 0.424549721 | 0.386 | 0.849 | 0.387 ENR+CV-4 | Snrpd2 |
| Pdia41 | 0.693 | 0.410532561 | 0.386 | 0.697 | 0.237 ENR+CV-4 | Pdia4 |
| Dnajc81 | 0.692 | 0.48879261 | 0.384 | 0.688 | 0.253 ENR+CV-4 | Dnajc8 |
| Soat11 | 0.692 | 0.466173003 | 0.384 | 0.716 | 0.272 ENR+CV-4 | Soat1 |
| Apex11 | 0.692 | 0.446467394 | 0.384 | 0.624 | 0.185 ENR+CV-4 | Apex1 |
| Eef1g2 | 0.692 | 0.405879357 | 0.384 | 0.959 | 0.585 ENR+CV-4 | Eef1g |
| Incenp | 0.691 | 0.601208119 | 0.382 | 0.491 | 0.087 ENR+CV-4 | Incenp |
| Uchl31 | 0.691 | 0.532112841 | 0.382 | 0.555 | 0.145 ENR+CV-4 | Uchl3 |
| Acat21 | 0.691 | 0.515288516 | 0.382 | 0.523 | 0.112 ENR+CV-4 | Acat2 |
| Tcof11 | 0.691 | 0.481950364 | 0.382 | 0.537 | 0.123 ENR+CV-4 | Tcof1 |
| Strbp1 | 0.691 | 0.450940884 | 0.382 | 0.61 | 0.179 ENR+CV-4 | Strbp |
| Acin11 | 0.691 | 0.447877303 | 0.382 | 0.743 | 0.302 ENR+CV-4 | Acin1 |
| Tyms | 0.691 | 0.436162759 | 0.382 | 0.619 | 0.185 ENR+CV-4 | Tyms |
| Ybx3 | 0.691 | 0.425015384 | 0.382 | 0.706 | 0.252 ENR+CV-4 | Ybx3 |
| Mrpl14 | 0.691 | 0.413521008 | 0.382 | 0.679 | 0.234 ENR+CV-4 | Mrpl14 |
| Metap21 | 0.691 | 0.379871297 | 0.382 | 0.766 | 0.295 ENR+CV-4 | Metap2 |
| Tmed21 | 0.69 | 0.45723172 | 0.38 | 0.624 | 0.194 ENR+CV-4 | Tmed2 |
| Ubb2 | 0.69 | 0.447771969 | 0.38 | 0.945 | 0.737 ENR+CV-4 | Ubb |
| Aldoa2 | 0.69 | 0.431681964 | 0.38 | 0.963 | 0.649 ENR+CV-4 | Aldoa |
| Hnrnpu1 | 0.69 | 0.423615054 | 0.38 | 0.936 | 0.566 ENR+CV-4 | Hnrnpu |
| Ubqln11 | 0.69 | 0.420017195 | 0.38 | 0.61 | 0.177 ENR+CV-4 | Ubqln1 |
| Fth12 | 0.69 | 0.407299381 | 0.38 | 0.977 | 0.822 ENR+CV-4 | Fth1 |
| Lamp11 | 0.69 | 0.394363071 | 0.38 | 0.83 | 0.358 ENR+CV-4 | Lamp1 |

TABLE 1-continued

Derived gene list of the top defining genes from in vivo ileal
small intestine PCs and EECs captured on the Seq-Well platform

| | | | | | | |
|---|---|---|---|---|---|---|
| Minos1l | 0.69 | 0.382478654 | 0.38 | 0.945 | 0.533 | ENR+CV-4 | Minos1 |
| Slc30a21 | 0.689 | 0.645432197 | 0.378 | 0.454 | 0.064 | ENR+CV-4 | Slc30a2 |
| Txnrd1l | 0.689 | 0.43755032 | 0.378 | 0.706 | 0.261 | ENR+CV-4 | Txnrd1 |
| Rpl36l | 0.689 | 0.437531772 | 0.378 | 0.583 | 0.156 | ENR+CV-4 | Rpl36 |
| Dnaja1l | 0.689 | 0.433718696 | 0.378 | 0.628 | 0.195 | ENR+CV-4 | Dnaja1 |
| Utp3 | 0.689 | 0.425254984 | 0.378 | 0.564 | 0.145 | ENR+CV-4 | Utp3 |
| Prim1 | 0.688 | 0.50038712 | 0.376 | 0.541 | 0.134 | ENR+CV-4 | Prim1 |
| Rpn2l | 0.688 | 0.462434667 | 0.376 | 0.729 | 0.281 | ENR+CV-4 | Rpn2 |
| Ywhab1 | 0.688 | 0.436761422 | 0.376 | 0.775 | 0.32 | ENR+CV-4 | Ywhab |
| Arpc1b1 | 0.688 | 0.429200112 | 0.376 | 0.789 | 0.337 | ENR+CV-4 | Arpc1b |
| Eif4e2l | 0.688 | 0.399667237 | 0.376 | 0.596 | 0.169 | ENR+CV-4 | Eif4e2 |
| Stub1 | 0.688 | 0.399146024 | 0.376 | 0.688 | 0.242 | ENR+CV-4 | Stub1 |
| Cct7l | 0.688 | 0.38280246 | 0.376 | 0.798 | 0.317 | ENR+CV-4 | Cct7 |
| Rplp2l | 0.688 | 0.300647466 | 0.376 | 0.982 | 0.903 | ENR+CV-4 | Rplp2 |
| Vim2 | 0.687 | 0.647484535 | 0.374 | 0.495 | 0.103 | ENR+CV-4 | Vim |
| Aldh9a12 | 0.687 | 0.507380681 | 0.374 | 0.587 | 0.174 | ENR+CV-4 | Aldh9a1 |
| Cks1b | 0.687 | 0.472233625 | 0.374 | 0.541 | 0.133 | ENR+CV-4 | Cks1b |
| Tmpo | 0.687 | 0.471756886 | 0.374 | 0.651 | 0.228 | ENR+CV-4 | Tmpo |
| Bzw1l | 0.687 | 0.450499601 | 0.374 | 0.794 | 0.37 | ENR+CV-4 | Bzw1 |
| Bax1 | 0.687 | 0.430416376 | 0.374 | 0.679 | 0.24 | ENR+CV-4 | Bax |
| Racgap1 | 0.686 | 0.576320136 | 0.372 | 0.463 | 0.072 | ENR+CV-4 | Racgap1 |
| Acat1l | 0.686 | 0.524260928 | 0.372 | 0.555 | 0.152 | ENR+CV-4 | Acat1 |
| Hspa14 | 0.686 | 0.442468723 | 0.372 | 0.509 | 0.109 | ENR+CV-4 | Hspa14 |
| Hmgn5 | 0.686 | 0.41926084 | 0.372 | 0.546 | 0.134 | ENR+CV-4 | Hmgn5 |
| Eif3l1 | 0.686 | 0.412818114 | 0.372 | 0.697 | 0.256 | ENR+CV-4 | Eif3l |
| 0610011F06Rik1 | 0.686 | 0.398470295 | 0.372 | 0.619 | 0.192 | ENR+CV-4 | 0610011F06Rik |
| Ssr1 | 0.686 | 0.395891444 | 0.372 | 0.688 | 0.24 | ENR+CV-4 | Ssr1 |
| Lsm5 | 0.685 | 0.461503893 | 0.37 | 0.537 | 0.132 | ENR+CV-4 | Lsm5 |
| Slc38a2l | 0.685 | 0.448931396 | 0.37 | 0.619 | 0.201 | ENR+CV-4 | Slc38a2 |
| Hnrnpk2 | 0.685 | 0.387755388 | 0.37 | 0.913 | 0.493 | ENR+CV-4 | Hnrnpk |
| Rpn13 | 0.685 | 0.374525928 | 0.37 | 0.835 | 0.368 | ENR+CV-4 | Rpn1 |
| 1110004F10Rik1 | 0.684 | 0.488440002 | 0.368 | 0.615 | 0.209 | ENR+CV-4 | 1110004F10Rik |
| Glrx5l | 0.684 | 0.481875637 | 0.368 | 0.541 | 0.136 | ENR+CV-4 | Glrx5 |
| Dnm1l1 | 0.684 | 0.419269005 | 0.368 | 0.596 | 0.18 | ENR+CV-4 | Dnm1l |
| Psmc5l | 0.684 | 0.40838474 | 0.368 | 0.638 | 0.21 | ENR+CV-4 | Psmc5 |
| Ube2c | 0.684 | 0.394088235 | 0.368 | 0.661 | 0.224 | ENR+CV-4 | Ube2c |
| Gnb2l | 0.684 | 0.392787503 | 0.368 | 0.798 | 0.34 | ENR+CV-4 | Gnb2 |
| Ndufs2l | 0.684 | 0.391338527 | 0.368 | 0.766 | 0.311 | ENR+CV-4 | Ndufs2 |
| Txn2l | 0.684 | 0.389405913 | 0.368 | 0.688 | 0.248 | ENR+CV-4 | Txn2 |
| Atox12 | 0.684 | 0.383200454 | 0.368 | 0.817 | 0.349 | ENR+CV-4 | Atox1 |
| Nap1l1 | 0.684 | 0.332941693 | 0.368 | 0.706 | 0.245 | ENR+CV-4 | Nap1l1 |
| H2afx | 0.683 | 0.588749735 | 0.366 | 0.523 | 0.133 | ENR+CV-4 | H2afx |
| Ccna2 | 0.683 | 0.546191597 | 0.366 | 0.5 | 0.108 | ENR+CV-4 | Ccna2 |
| Ymel1l1 | 0.683 | 0.466398153 | 0.366 | 0.592 | 0.185 | ENR+CV-4 | Ymel1l |
| Ppa2l | 0.683 | 0.457064583 | 0.366 | 0.55 | 0.149 | ENR+CV-4 | Ppa2 |
| Csde1l | 0.683 | 0.453069275 | 0.366 | 0.725 | 0.312 | ENR+CV-4 | Csde1 |
| Ndufs62 | 0.683 | 0.364843302 | 0.366 | 0.867 | 0.41 | ENR+CV-4 | Ndufs6 |
| Rpl142 | 0.683 | 0.304363832 | 0.366 | 0.982 | 0.923 | ENR+CV-4 | Rpl14 |
| Esco2 | 0.682 | 0.563297615 | 0.364 | 0.459 | 0.075 | ENR+CV-4 | Esco2 |
| Picalm | 0.682 | 0.383090249 | 0.364 | 0.642 | 0.22 | ENR+CV-4 | Picalm |
| Ppp1ca1 | 0.682 | 0.377801654 | 0.364 | 0.853 | 0.398 | ENR+CV-4 | Ppp1ca |
| Ndufa121 | 0.682 | 0.36013752 | 0.364 | 0.812 | 0.348 | ENR+CV-4 | Ndufa12 |
| Suz12 | 0.681 | 0.525225803 | 0.362 | 0.55 | 0.156 | ENR+CV-4 | Suz12 |
| Impa1l | 0.681 | 0.457188219 | 0.362 | 0.569 | 0.167 | ENR+CV-4 | Impa1 |
| Usp1 | 0.681 | 0.439181801 | 0.362 | 0.578 | 0.17 | ENR+CV-4 | Usp1 |
| Rpl7l11 | 0.681 | 0.435875789 | 0.362 | 0.578 | 0.173 | ENR+CV-4 | Rpl7l1 |
| Eif1l | 0.681 | 0.42764852 | 0.362 | 0.849 | 0.429 | ENR+CV-4 | Eif1 |
| Sumo3l | 0.681 | 0.423602054 | 0.362 | 0.55 | 0.149 | ENR+CV-4 | Sumo3 |
| Mrpl522 | 0.681 | 0.414509131 | 0.362 | 0.844 | 0.429 | ENR+CV-4 | Mrpl52 |
| G3bp1l | 0.681 | 0.412770582 | 0.362 | 0.72 | 0.287 | ENR+CV-4 | G3bp1 |
| Aamp1 | 0.681 | 0.409554132 | 0.362 | 0.578 | 0.169 | ENR+CV-4 | Aamp |
| Mgst1l | 0.681 | 0.409091184 | 0.362 | 0.849 | 0.428 | ENR+CV-4 | Mgst1 |
| Nap1l41 | 0.681 | 0.407769615 | 0.362 | 0.624 | 0.207 | ENR+CV-4 | Nap1l4 |
| Atp5j2 | 0.681 | 0.400650181 | 0.362 | 0.917 | 0.69 | ENR+CV-4 | Atp5j |
| Ndufs81 | 0.681 | 0.342833689 | 0.362 | 0.789 | 0.334 | ENR+CV-4 | Ndufs8 |
| Calm13 | 0.681 | 0.317905921 | 0.362 | 0.995 | 0.872 | ENR+CV-4 | Calm1 |
| Hnrnpa0 | 0.68 | 0.497457147 | 0.36 | 0.67 | 0.248 | ENR+CV-4 | Hnrnpa0 |
| Ctsb2 | 0.68 | 0.436616519 | 0.36 | 0.775 | 0.353 | ENR+CV-4 | Ctsb |
| Naa50l | 0.68 | 0.4225512 | 0.36 | 0.624 | 0.214 | ENR+CV-4 | Naa50 |
| Psmd15 | 0.68 | 0.395012363 | 0.36 | 0.596 | 0.185 | ENR+CV-4 | Psmd1 |
| Fkbp42 | 0.68 | 0.392997644 | 0.36 | 0.849 | 0.401 | ENR+CV-4 | Fkbp4 |
| Aimp21 | 0.68 | 0.345814134 | 0.36 | 0.546 | 0.139 | ENR+CV-4 | Aimp2 |
| Hist1h2ae | 0.679 | 0.669743134 | 0.358 | 0.417 | 0.05 | ENR+CV-4 | Hist1h2ae |
| Kif1l | 0.679 | 0.53354431 | 0.358 | 0.463 | 0.084 | ENR+CV-4 | Kif1l |
| Rab5c1 | 0.679 | 0.458426524 | 0.358 | 0.509 | 0.121 | ENR+CV-4 | Rab5c |
| Eif3b1 | 0.679 | 0.441008052 | 0.358 | 0.596 | 0.19 | ENR+CV-4 | Eif3b |
| Ppil1l | 0.679 | 0.432546972 | 0.358 | 0.518 | 0.127 | ENR+CV-4 | Ppil1 |

TABLE 1-continued

Derived gene list of the top defining genes from in vivo ileal
small intestine PCs and EECs captured on the Seq-Well platform

| | | | | | | | |
|---|---|---|---|---|---|---|---|
| Psmd21 | 0.679 | 0.414754014 | 0.358 | 0.564 | 0.161 | ENR+CV-4 | Psmd2 |
| Bzw21 | 0.679 | 0.411195205 | 0.358 | 0.72 | 0.289 | ENR+CV-4 | Bzw2 |
| Oat1 | 0.679 | 0.398524766 | 0.358 | 0.844 | 0.405 | ENR+CV-4 | Oat |
| Hnrnpl1 | 0.679 | 0.381470976 | 0.358 | 0.702 | 0.269 | ENR+CV-4 | Hnrnpl |
| Pebp11 | 0.679 | 0.378758007 | 0.358 | 0.812 | 0.358 | ENR+CV-4 | Pebp1 |
| Snrpf2 | 0.679 | 0.377138937 | 0.358 | 0.794 | 0.343 | ENR+CV-4 | Snrpf |
| Mt12 | 0.679 | 0.321424366 | 0.358 | 0.995 | 0.654 | ENR+CV-4 | Mt1 |
| Spc24 | 0.678 | 0.538749784 | 0.356 | 0.482 | 0.103 | ENR+CV-4 | Spc24 |
| Ctsz1 | 0.678 | 0.407610891 | 0.356 | 0.619 | 0.208 | ENR+CV-4 | Ctsz |
| Srrt | 0.678 | 0.390679604 | 0.356 | 0.601 | 0.189 | ENR+CV-4 | Srrt |
| Tomm72 | 0.678 | 0.377267316 | 0.356 | 0.908 | 0.535 | ENR+CV-4 | Tomm7 |
| Supt16 | 0.678 | 0.374746583 | 0.356 | 0.67 | 0.247 | ENR+CV-4 | Supt16 |
| Phlda12 | 0.678 | 0.372820616 | 0.356 | 0.771 | 0.317 | ENR+CV-4 | Phlda1 |
| Dnajc9 | 0.678 | 0.367789891 | 0.356 | 0.546 | 0.145 | ENR+CV-4 | Dnajc9 |
| 2700094K13Rik | 0.678 | 0.361214845 | 0.356 | 0.674 | 0.248 | ENR+CV-4 | 2700094K13Rik |
| Rrm2 | 0.677 | 0.567249607 | 0.354 | 0.459 | 0.086 | ENR+CV-4 | Rrm2 |
| Sbno11 | 0.677 | 0.406792464 | 0.354 | 0.583 | 0.183 | ENR+CV-4 | Sbno1 |
| Lyar | 0.677 | 0.363496725 | 0.354 | 0.587 | 0.179 | ENR+CV-4 | Lyar |
| 2810004N23Rik1 | 0.677 | 0.358848834 | 0.354 | 0.55 | 0.153 | ENR+CV-4 | 2810004N23Rik |
| Slc25a39 | 0.677 | 0.332106275 | 0.354 | 0.665 | 0.239 | ENR+CV-4 | Slc25a39 |
| Rfc31 | 0.676 | 0.50841338 | 0.352 | 0.505 | 0.126 | ENR+CV-4 | Rfc3 |
| Pold21 | 0.676 | 0.504831998 | 0.352 | 0.468 | 0.094 | ENR+CV-4 | Pold2 |
| Hjurp | 0.676 | 0.450388798 | 0.352 | 0.578 | 0.183 | ENR+CV-4 | Hjurp |
| Cldn71 | 0.676 | 0.386197609 | 0.352 | 0.95 | 0.605 | ENR+CV-4 | Cldn7 |
| Akr7a51 | 0.676 | 0.338961386 | 0.352 | 0.619 | 0.203 | ENR+CV-4 | Akr7a5 |
| Snrnp271 | 0.675 | 0.472384797 | 0.35 | 0.546 | 0.164 | ENR+CV-4 | Snrnp27 |
| G3bp21 | 0.675 | 0.407529673 | 0.35 | 0.647 | 0.234 | ENR+CV-4 | G3bp2 |
| Cct81 | 0.675 | 0.397739545 | 0.35 | 0.729 | 0.309 | ENR+CV-4 | Cct8 |
| Ranbp11 | 0.675 | 0.384827397 | 0.35 | 0.894 | 0.523 | ENR+CV-4 | Ranbp1 |
| Rnaseh2c | 0.675 | 0.378244713 | 0.35 | 0.596 | 0.191 | ENR+CV-4 | Rnaseh2c |
| Por2 | 0.675 | 0.374010234 | 0.35 | 0.56 | 0.16 | ENR+CV-4 | Por |
| Lbr | 0.675 | 0.371026739 | 0.35 | 0.606 | 0.197 | ENR+CV-4 | Lbr |
| Pdha11 | 0.675 | 0.364468925 | 0.35 | 0.702 | 0.269 | ENR+CV-4 | Pdha1 |
| Dhx151 | 0.675 | 0.358426136 | 0.35 | 0.683 | 0.261 | ENR+CV-4 | Dhx15 |
| Ncl | 0.675 | 0.330352866 | 0.35 | 0.995 | 0.798 | ENR+CV-4 | Ncl |
| Ubc2 | 0.674 | 0.427396604 | 0.348 | 0.908 | 0.559 | ENR+CV-4 | Ubc |
| Comt1 | 0.674 | 0.388351131 | 0.348 | 0.569 | 0.177 | ENR+CV-4 | Comt |
| Ndufa13 | 0.674 | 0.337217893 | 0.348 | 0.807 | 0.367 | ENR+CV-4 | Ndufa1 |
| Spc25 | 0.673 | 0.602127954 | 0.346 | 0.427 | 0.067 | ENR+CV-4 | Spc25 |
| Tomm40 | 0.673 | 0.399390899 | 0.346 | 0.537 | 0.15 | ENR+CV-4 | Tomm40 |
| Smc6 | 0.673 | 0.384299371 | 0.346 | 0.55 | 0.163 | ENR+CV-4 | Smc6 |
| Aldh21 | 0.673 | 0.384069443 | 0.346 | 0.55 | 0.161 | ENR+CV-4 | Aldh2 |
| Psmd41 | 0.673 | 0.383602955 | 0.346 | 0.619 | 0.217 | ENR+CV-4 | Psmd4 |
| Ddb1 | 0.673 | 0.378845678 | 0.346 | 0.624 | 0.216 | ENR+CV-4 | Ddb1 |
| Canx1 | 0.673 | 0.377972804 | 0.346 | 0.89 | 0.499 | ENR+CV-4 | Canx |
| Gars1 | 0.673 | 0.365836801 | 0.346 | 0.665 | 0.249 | ENR+CV-4 | Gars |
| Cyb5b1 | 0.673 | 0.362914761 | 0.346 | 0.651 | 0.24 | ENR+CV-4 | Cyb5b |
| Ddx1 | 0.673 | 0.292593178 | 0.346 | 0.628 | 0.212 | ENR+CV-4 | Ddx1 |
| Sgta1 | 0.672 | 0.481633307 | 0.344 | 0.5 | 0.125 | ENR+CV-4 | Sgta |
| Fbln11 | 0.672 | 0.469946715 | 0.344 | 0.445 | 0.08 | ENR+CV-4 | Fbln1 |
| Mfge81 | 0.672 | 0.392437381 | 0.344 | 0.569 | 0.175 | ENR+CV-4 | Mfge8 |
| Tspo1 | 0.672 | 0.391762902 | 0.344 | 0.546 | 0.156 | ENR+CV-4 | Tspo |
| Eif4g11 | 0.672 | 0.375141201 | 0.344 | 0.821 | 0.388 | ENR+CV-4 | Eif4g1 |
| Bclaf1 | 0.672 | 0.363969595 | 0.344 | 0.725 | 0.304 | ENR+CV-4 | Bclaf1 |
| St13 | 0.672 | 0.347987605 | 0.344 | 0.739 | 0.309 | ENR+CV-4 | St13 |
| Ndufa111 | 0.672 | 0.344076857 | 0.344 | 0.72 | 0.298 | ENR+CV-4 | Ndufa11 |
| Tspan32 | 0.672 | 0.329849744 | 0.344 | 0.683 | 0.259 | ENR+CV-4 | Tspan3 |
| Eif2b5 | 0.671 | 0.481397833 | 0.342 | 0.445 | 0.083 | ENR+CV-4 | Eif2b5 |
| Wbp111 | 0.671 | 0.446031616 | 0.342 | 0.514 | 0.139 | ENR+CV-4 | Wbp11 |
| Cops61 | 0.671 | 0.39214168 | 0.342 | 0.638 | 0.24 | ENR+CV-4 | Cops6 |
| Scd22 | 0.671 | 0.382561947 | 0.342 | 0.917 | 0.524 | ENR+CV-4 | Scd2 |
| H3f3b1 | 0.671 | 0.376600549 | 0.342 | 0.963 | 0.724 | ENR+CV-4 | H3f3b |
| Hopx1 | 0.671 | 0.374512746 | 0.342 | 0.725 | 0.306 | ENR+CV-4 | Hopx |
| Snrpb21 | 0.671 | 0.368533644 | 0.342 | 0.541 | 0.156 | ENR+CV-4 | Snrpb2 |
| Slc25a52 | 0.671 | 0.364943967 | 0.342 | 0.959 | 0.762 | ENR+CV-4 | Slc25a5 |
| Rbm25 | 0.671 | 0.338002175 | 0.342 | 0.784 | 0.36 | ENR+CV-4 | Rbm25 |
| Ghitm1 | 0.671 | 0.320764319 | 0.342 | 0.789 | 0.342 | ENR+CV-4 | Ghitm |
| Epcam1 | 0.671 | 0.313293746 | 0.342 | 0.991 | 0.808 | ENR+CV-4 | Epcam |
| Acot12 | 0.67 | 0.544185825 | 0.34 | 0.45 | 0.093 | ENR+CV-4 | Acot1 |
| Lig1 | 0.67 | 0.496093386 | 0.34 | 0.477 | 0.113 | ENR+CV-4 | Lig1 |
| Mrps51 | 0.67 | 0.42478924 | 0.34 | 0.509 | 0.137 | ENR+CV-4 | Mrps5 |
| Ctsa1 | 0.67 | 0.422422193 | 0.34 | 0.537 | 0.155 | ENR+CV-4 | Ctsa |
| Ddx391 | 0.67 | 0.398607796 | 0.34 | 0.55 | 0.167 | ENR+CV-4 | Ddx39 |
| Dctn31 | 0.67 | 0.371238139 | 0.34 | 0.523 | 0.143 | ENR+CV-4 | Dctn3 |
| Pcbp21 | 0.67 | 0.355994415 | 0.34 | 0.821 | 0.39 | ENR+CV-4 | Pcbp2 |
| Sdhc1 | 0.67 | 0.352881727 | 0.34 | 0.624 | 0.219 | ENR+CV-4 | Sdhc |
| Mcm71 | 0.67 | 0.348554368 | 0.34 | 0.528 | 0.145 | ENR+CV-4 | Mcm7 |

TABLE 1-continued

Derived gene list of the top defining genes from in vivo ileal
small intestine PCs and EECs captured on the Seq-Well platform

| Gene | Val1 | Val2 | Val3 | Val4 | Val5 | Group | Gene2 |
|---|---|---|---|---|---|---|---|
| Eif1ax1 | 0.67 | 0.348506425 | 0.34 | 0.647 | 0.242 | ENR+CV-4 | Eif1ax |
| Etfb1 | 0.67 | 0.325328403 | 0.34 | 0.803 | 0.374 | ENR+CV-4 | Etfb |
| Rars1 | 0.67 | 0.322727933 | 0.34 | 0.711 | 0.283 | ENR+CV-4 | Rars |
| Ldha2 | 0.67 | 0.321681419 | 0.34 | 0.977 | 0.683 | ENR+CV-4 | Ldha |
| Nedd81 | 0.67 | 0.321469076 | 0.34 | 0.807 | 0.366 | ENR+CV-4 | Nedd8 |
| Pet1001 | 0.67 | 0.31110172 | 0.34 | 0.573 | 0.177 | ENR+CV-4 | Pet100 |
| Hnrnpm1 | 0.67 | 0.276863019 | 0.34 | 0.757 | 0.303 | ENR+CV-4 | Hnrnpm |
| Casc5 | 0.669 | 0.55165573 | 0.338 | 0.427 | 0.072 | ENR+CV-4 | Casc5 |
| Knstrn | 0.669 | 0.521565055 | 0.338 | 0.417 | 0.066 | ENR+CV-4 | Knstrn |
| Ncln1 | 0.669 | 0.474508215 | 0.338 | 0.472 | 0.111 | ENR+CV-4 | Ncln |
| Nrtn1 | 0.669 | 0.465891402 | 0.338 | 0.436 | 0.079 | ENR+CV-4 | Nrtn |
| Arhgef261 | 0.669 | 0.42612713 | 0.338 | 0.518 | 0.145 | ENR+CV-4 | Arhgef26 |
| Timm441 | 0.669 | 0.409921028 | 0.338 | 0.514 | 0.14 | ENR+CV-4 | Timm44 |
| Dctpp11 | 0.669 | 0.40605455 | 0.338 | 0.578 | 0.192 | ENR+CV-4 | Dctpp1 |
| Eif4h | 0.669 | 0.362656218 | 0.338 | 0.688 | 0.283 | ENR+CV-4 | Eif4h |
| Stip11 | 0.669 | 0.341191781 | 0.338 | 0.661 | 0.256 | ENR+CV-4 | Stip1 |
| Psmd71 | 0.669 | 0.33805473 | 0.338 | 0.638 | 0.236 | ENR+CV-4 | Psmd7 |
| Dpy30 | 0.669 | 0.337090127 | 0.338 | 0.642 | 0.237 | ENR+CV-4 | Dpy30 |
| Psma6 | 0.669 | 0.294017699 | 0.338 | 0.812 | 0.36 | ENR+CV-4 | Psma6 |
| Kif15 | 0.668 | 0.502452402 | 0.336 | 0.445 | 0.088 | ENR+CV-4 | Kif15 |
| Ide1 | 0.668 | 0.492597526 | 0.336 | 0.459 | 0.101 | ENR+CV-4 | Ide |
| Carhsp11 | 0.668 | 0.385790101 | 0.336 | 0.514 | 0.139 | ENR+CV-4 | Carhsp1 |
| Smarcc11 | 0.668 | 0.384019789 | 0.336 | 0.615 | 0.223 | ENR+CV-4 | Smarcc1 |
| Tuba1a1 | 0.668 | 0.345153033 | 0.336 | 0.606 | 0.208 | ENR+CV-4 | Tuba1a |
| Hes61 | 0.668 | 0.342067577 | 0.336 | 0.601 | 0.204 | ENR+CV-4 | Hes6 |
| Mrpl331 | 0.668 | 0.338280194 | 0.336 | 0.812 | 0.38 | ENR+CV-4 | Mrpl33 |
| Arhgdia | 0.668 | 0.324823416 | 0.336 | 0.674 | 0.262 | ENR+CV-4 | Arhgdia |
| Pa2g4 | 0.668 | 0.306366224 | 0.336 | 0.936 | 0.485 | ENR+CV-4 | Pa2g4 |
| Psmb41 | 0.668 | 0.30187197 | 0.336 | 0.761 | 0.324 | ENR+CV-4 | Psmb4 |
| Psmd141 | 0.668 | 0.286164247 | 0.336 | 0.638 | 0.229 | ENR+CV-4 | Psmd14 |
| Psmd131 | 0.667 | 0.43333474 | 0.334 | 0.505 | 0.137 | ENR+CV-4 | Psmd13 |
| Pin1 | 0.667 | 0.424940607 | 0.334 | 0.514 | 0.146 | ENR+CV-4 | Pin1 |
| Npepps1 | 0.667 | 0.419532386 | 0.334 | 0.528 | 0.157 | ENR+CV-4 | Npepps |
| Rfc1 | 0.667 | 0.414046306 | 0.334 | 0.56 | 0.182 | ENR+CV-4 | Rfc1 |
| Cdx11 | 0.667 | 0.406475313 | 0.334 | 0.578 | 0.196 | ENR+CV-4 | Cdx1 |
| Ccdc1071 | 0.667 | 0.399580727 | 0.334 | 0.514 | 0.145 | ENR+CV-4 | Ccdc107 |
| Sf3b5 | 0.667 | 0.348984526 | 0.334 | 0.734 | 0.323 | ENR+CV-4 | Sf3b5 |
| Eif3c1 | 0.667 | 0.337190612 | 0.334 | 0.862 | 0.445 | ENR+CV-4 | Eif3c |
| Tmco11 | 0.667 | 0.330055073 | 0.334 | 0.583 | 0.194 | ENR+CV-4 | Tmco1 |
| Uqcrh2 | 0.667 | 0.32903571 | 0.334 | 0.954 | 0.638 | ENR+CV-4 | Uqcrh |
| Rpl311 | 0.667 | 0.305974834 | 0.334 | 0.78 | 0.335 | ENR+CV-4 | Rpl31 |
| Ddost1 | 0.667 | 0.305101451 | 0.334 | 0.729 | 0.302 | ENR+CV-4 | Ddost |
| Rfc4 | 0.666 | 0.383628619 | 0.332 | 0.482 | 0.116 | ENR+CV-4 | Rfc4 |
| Ran1 | 0.666 | 0.365371443 | 0.332 | 0.817 | 0.435 | ENR+CV-4 | Ran |
| Cdkn1b | 0.666 | 0.35750126 | 0.332 | 0.523 | 0.149 | ENR+CV-4 | Cdkn1b |
| Ngfrap11 | 0.666 | 0.357227422 | 0.332 | 0.587 | 0.197 | ENR+CV-4 | Ngfrap1 |
| Pls11 | 0.666 | 0.355594668 | 0.332 | 0.573 | 0.19 | ENR+CV-4 | Pls1 |
| Cox5a1 | 0.666 | 0.308717492 | 0.332 | 0.899 | 0.47 | ENR+CV-4 | Cox5a |
| Nsun21 | 0.666 | 0.307194659 | 0.332 | 0.606 | 0.211 | ENR+CV-4 | Nsun2 |
| Zfp911 | 0.666 | 0.297064785 | 0.332 | 0.592 | 0.2 | ENR+CV-4 | Zfp91 |
| Hist1h2an | 0.665 | 0.674177812 | 0.33 | 0.381 | 0.044 | ENR+CV-4 | Hist1h2an |
| Cenpa | 0.665 | 0.527590739 | 0.33 | 0.482 | 0.125 | ENR+CV-4 | Cenpa |
| Nup85 | 0.665 | 0.478868801 | 0.33 | 0.445 | 0.093 | ENR+CV-4 | Nup85 |
| Ncaph2 | 0.665 | 0.475306267 | 0.33 | 0.463 | 0.111 | ENR+CV-4 | Ncaph2 |
| Tmem91 | 0.665 | 0.47132724 | 0.33 | 0.445 | 0.096 | ENR+CV-4 | Tmem9 |
| Prpf191 | 0.665 | 0.391973919 | 0.33 | 0.56 | 0.183 | ENR+CV-4 | Prpf19 |
| Qdpr1 | 0.665 | 0.369867851 | 0.33 | 0.528 | 0.158 | ENR+CV-4 | Qdpr |
| Set1 | 0.665 | 0.368414125 | 0.33 | 0.775 | 0.37 | ENR+CV-4 | Set |
| Cdh171 | 0.665 | 0.365892163 | 0.33 | 0.633 | 0.233 | ENR+CV-4 | Cdh17 |
| Aprt1 | 0.665 | 0.346532541 | 0.33 | 0.683 | 0.281 | ENR+CV-4 | Aprt |
| Tmem1601 | 0.665 | 0.344773789 | 0.33 | 0.592 | 0.205 | ENR+CV-4 | Tmem160 |
| Ywhaz1 | 0.665 | 0.324580771 | 0.33 | 0.807 | 0.376 | ENR+CV-4 | Ywhaz |
| Xrn21 | 0.665 | 0.273027946 | 0.33 | 0.67 | 0.259 | ENR+CV-4 | Xrn2 |
| Gspt1 | 0.665 | 0.27249459 | 0.33 | 0.628 | 0.227 | ENR+CV-4 | Gspt1 |
| Atp6v0b | 0.665 | 0.259646371 | 0.33 | 0.61 | 0.207 | ENR+CV-4 | Atp6v0b |
| 1700021F05Rik1 | 0.664 | 0.444897122 | 0.328 | 0.431 | 0.085 | ENR+CV-4 | 1700021F05Rik |
| Blvrb1 | 0.664 | 0.433514098 | 0.328 | 0.431 | 0.083 | ENR+CV-4 | Blvrb |
| Psip1 | 0.664 | 0.408994978 | 0.328 | 0.491 | 0.131 | ENR+CV-4 | Psip1 |
| Psat1 | 0.664 | 0.395386713 | 0.328 | 0.537 | 0.167 | ENR+CV-4 | Psat1 |
| Gm102691 | 0.664 | 0.388027645 | 0.328 | 0.821 | 0.435 | ENR+CV-4 | Gm10269 |
| Sdc4 | 0.664 | 0.346407997 | 0.328 | 0.67 | 0.265 | ENR+CV-4 | Sdc4 |
| Polr2i1 | 0.664 | 0.340054242 | 0.328 | 0.514 | 0.145 | ENR+CV-4 | Polr2i |
| Fus | 0.664 | 0.33650456 | 0.328 | 0.734 | 0.314 | ENR+CV-4 | Fus |
| Snrnp70 | 0.664 | 0.311268886 | 0.328 | 0.683 | 0.272 | ENR+CV-4 | Snrnp70 |
| Ndufs41 | 0.664 | 0.260943989 | 0.328 | 0.739 | 0.312 | ENR+CV-4 | Ndufs4 |
| Raly1 | 0.663 | 0.4305928 | 0.326 | 0.514 | 0.156 | ENR+CV-4 | Raly |
| Snord1181 | 0.663 | 0.41644523 | 0.326 | 0.463 | 0.115 | ENR+CV-4 | Snord118 |

TABLE 1-continued

Derived gene list of the top defining genes from in vivo ileal
small intestine PCs and EECs captured on the Seq-Well platform

| | | | | | | |
|---|---|---|---|---|---|---|
| Lonpl1 | 0.663 | 0.41193122 | 0.326 | 0.546 | 0.179 ENR+CV-4 | Lonp1 |
| Ipo5l | 0.663 | 0.410223746 | 0.326 | 0.537 | 0.174 ENR+CV-4 | Ipo5 |
| Prmt5l | 0.663 | 0.386239988 | 0.326 | 0.482 | 0.124 ENR+CV-4 | Prmt5 |
| Rrm1 | 0.663 | 0.375063397 | 0.326 | 0.537 | 0.166 ENR+CV-4 | Rrm1 |
| Tma7l | 0.663 | 0.37238474 | 0.326 | 0.606 | 0.229 ENR+CV-4 | Tma7 |
| Actn4 | 0.663 | 0.37189973 | 0.326 | 0.688 | 0.289 ENR+CV-4 | Actn4 |
| Tra2b1 | 0.663 | 0.350145825 | 0.326 | 0.628 | 0.237 ENR+CV-4 | Tra2b |
| Tkt2 | 0.663 | 0.347075619 | 0.326 | 0.862 | 0.457 ENR+CV-4 | Tkt |
| Pfdn2l | 0.663 | 0.343968577 | 0.326 | 0.491 | 0.127 ENR+CV-4 | Pfdn2 |
| Adiporl1 | 0.663 | 0.343461264 | 0.326 | 0.583 | 0.201 ENR+CV-4 | Adipor1 |
| Dap3l | 0.663 | 0.336510256 | 0.326 | 0.564 | 0.186 ENR+CV-4 | Dap3 |
| Rpl35 2 | 0.663 | 0.334997231 | 0.326 | 0.917 | 0.712 ENR+CV-4 | Rpl35 |
| Cct5l | 0.663 | 0.319237694 | 0.326 | 0.881 | 0.455 ENR+CV-4 | Cct5 |
| Fam96a1 | 0.663 | 0.293036299 | 0.326 | 0.596 | 0.206 ENR+CV-4 | Fam96a |
| Snrpb | 0.663 | 0.285354559 | 0.326 | 0.748 | 0.316 ENR+CV-4 | Snrpb |
| Nelfe | 0.662 | 0.493177825 | 0.324 | 0.45 | 0.105 ENR+CV-4 | Nelfe |
| Nsmce4a | 0.662 | 0.423956768 | 0.324 | 0.468 | 0.117 ENR+CV-4 | Nsmce4a |
| Lrig1l | 0.662 | 0.413099113 | 0.324 | 0.491 | 0.135 ENR+CV-4 | Lrig1 |
| Ap2s1l | 0.662 | 0.405875761 | 0.324 | 0.583 | 0.213 ENR+CV-4 | Ap2s1 |
| Nmt1l | 0.662 | 0.365337437 | 0.324 | 0.505 | 0.143 ENR+CV-4 | Nmt1 |
| Taf9 | 0.662 | 0.329318874 | 0.324 | 0.587 | 0.207 ENR+CV-4 | Taf9 |
| Tbcb1 | 0.662 | 0.325513208 | 0.324 | 0.518 | 0.152 ENR+CV-4 | Tbcb |
| Snd1l | 0.662 | 0.313870014 | 0.324 | 0.578 | 0.196 ENR+CV-4 | Snd1 |
| Gpi1 2 | 0.662 | 0.273270071 | 0.324 | 0.821 | 0.379 ENR+CV-4 | Gpi1 |
| Chchd3 | 0.662 | 0.261629411 | 0.324 | 0.587 | 0.197 ENR+CV-4 | Chchd3 |
| Bcas2 | 0.662 | 0.25859773 | 0.324 | 0.615 | 0.217 ENR+CV-4 | Bcas2 |
| Wdr45b1 | 0.661 | 0.43660642 | 0.322 | 0.436 | 0.093 ENR+CV-4 | Wdr45b |
| Cdca3 | 0.661 | 0.422887863 | 0.322 | 0.495 | 0.139 ENR+CV-4 | Cdca3 |
| Arl3l | 0.661 | 0.41129259 | 0.322 | 0.468 | 0.117 ENR+CV-4 | Arl3 |
| Sqle1 | 0.661 | 0.36010356 | 0.322 | 0.532 | 0.164 ENR+CV-4 | Sqle |
| Ndufa9l | 0.661 | 0.350362278 | 0.322 | 0.514 | 0.153 ENR+CV-4 | Ndufa9 |
| Thoc7l | 0.661 | 0.349914795 | 0.322 | 0.771 | 0.377 ENR+CV-4 | Thoc7 |
| Hadh1 | 0.661 | 0.335702471 | 0.322 | 0.711 | 0.31 ENR+CV-4 | Hadh |
| Rbm34l | 0.661 | 0.331056316 | 0.322 | 0.486 | 0.131 ENR+CV-4 | Rbm34 |
| Vps29l | 0.661 | 0.323156892 | 0.322 | 0.573 | 0.198 ENR+CV-4 | Vps29 |
| Rbbp4 | 0.661 | 0.318181265 | 0.322 | 0.729 | 0.319 ENR+CV-4 | Rbbp4 |
| Dtymk | 0.661 | 0.309774069 | 0.322 | 0.647 | 0.25 ENR+CV-4 | Dtymk |
| Rbbp7 | 0.661 | 0.298779579 | 0.322 | 0.697 | 0.286 ENR+CV-4 | Rbbp7 |
| Gltscr2l | 0.661 | 0.296856439 | 0.322 | 0.697 | 0.291 ENR+CV-4 | Gltscr2 |
| Rad23a | 0.66 | 0.436342186 | 0.32 | 0.491 | 0.142 ENR+CV-4 | Rad23a |
| Marcksl1l | 0.66 | 0.381017759 | 0.32 | 0.546 | 0.179 ENR+CV-4 | Marcksl1 |
| Glg1l | 0.66 | 0.354697737 | 0.32 | 0.482 | 0.128 ENR+CV-4 | Glg1 |
| H2afz | 0.66 | 0.329041963 | 0.32 | 0.72 | 0.329 ENR+CV-4 | H2afz |
| Hsd17b10l | 0.66 | 0.318234529 | 0.32 | 0.583 | 0.2 ENR+CV-4 | Hsd17b10 |
| Cyb5r3 | 0.66 | 0.315552655 | 0.32 | 0.523 | 0.157 ENR+CV-4 | Cyb5r3 |
| Eif2s2 | 0.66 | 0.314523627 | 0.32 | 0.849 | 0.422 ENR+CV-4 | Eif2s2 |
| Hsp90b1l | 0.66 | 0.314338717 | 0.32 | 0.968 | 0.704 ENR+CV-4 | Hsp90b1 |
| Wdr61l | 0.66 | 0.30452697 | 0.32 | 0.587 | 0.207 ENR+CV-4 | Wdr61 |
| Chmp4b | 0.66 | 0.278630038 | 0.32 | 0.615 | 0.226 ENR+CV-4 | Chmp4b |
| Vaultrc5 2 | 0.66 | 0.274522775 | 0.32 | 0.67 | 0.289 ENR+CV-4 | Vaultrc5 |
| Cuta | 0.659 | 0.426885337 | 0.318 | 0.5 | 0.15 ENR+CV-4 | Cuta |
| Smn1l | 0.659 | 0.416343615 | 0.318 | 0.44 | 0.1 ENR+CV-4 | Smn1 |
| Hdac3l | 0.659 | 0.408327897 | 0.318 | 0.472 | 0.126 ENR+CV-4 | Hdac3 |
| Acadl1 | 0.659 | 0.38732077 | 0.318 | 0.468 | 0.12 ENR+CV-4 | Acadl |
| Aes1 | 0.659 | 0.352588746 | 0.318 | 0.633 | 0.249 ENR+CV-4 | Aes |
| Aars | 0.659 | 0.345477055 | 0.318 | 0.509 | 0.15 ENR+CV-4 | Aars |
| Mapk1 | 0.659 | 0.344281155 | 0.318 | 0.523 | 0.162 ENR+CV-4 | Mapk1 |
| Mdh1l | 0.659 | 0.327696381 | 0.318 | 0.775 | 0.369 ENR+CV-4 | Mdh1 |
| Psmb5l | 0.659 | 0.325334211 | 0.318 | 0.628 | 0.245 ENR+CV-4 | Psmb5 |
| Suclg1l | 0.659 | 0.323715253 | 0.318 | 0.739 | 0.335 ENR+CV-4 | Suclg1 |
| Eif3i | 0.659 | 0.322553597 | 0.318 | 0.872 | 0.454 ENR+CV-4 | Eif3i |
| Knop1 | 0.659 | 0.322148937 | 0.318 | 0.56 | 0.187 ENR+CV-4 | Knop1 |
| Atp5a1 | 0.659 | 0.321714912 | 0.318 | 0.963 | 0.609 ENR+CV-4 | Atp5a1 |
| Pgp | 0.659 | 0.318621881 | 0.318 | 0.601 | 0.221 ENR+CV-4 | Pgp |
| Rab7l | 0.659 | 0.310240022 | 0.318 | 0.518 | 0.156 ENR+CV-4 | Rab7 |
| Ddx24l | 0.659 | 0.29598459 | 0.318 | 0.518 | 0.154 ENR+CV-4 | Ddx24 |
| Tubb2b1 | 0.658 | 0.490899035 | 0.316 | 0.385 | 0.057 ENR+CV-4 | Tubb2b |
| Gsk3b1 | 0.658 | 0.377728897 | 0.316 | 0.514 | 0.161 ENR+CV-4 | Gsk3b |
| Bdh1l | 0.658 | 0.366430564 | 0.316 | 0.463 | 0.117 ENR+CV-4 | Bdh1 |
| Utp11l1 | 0.658 | 0.358442054 | 0.316 | 0.495 | 0.145 ENR+CV-4 | Utp11l |
| Eno1l | 0.658 | 0.351410015 | 0.316 | 0.739 | 0.346 ENR+CV-4 | Eno1 |
| Lima1l | 0.658 | 0.324186996 | 0.316 | 0.628 | 0.246 ENR+CV-4 | Lima1 |
| D17Wsu104e1 | 0.658 | 0.320708608 | 0.316 | 0.592 | 0.216 ENR+CV-4 | D17Wsu104e |
| Nars1 | 0.658 | 0.303894844 | 0.316 | 0.867 | 0.475 ENR+CV-4 | Nars |
| Timm13 | 0.658 | 0.301216754 | 0.316 | 0.849 | 0.43 ENR+CV-4 | Timm13 |
| Lamtor2l | 0.658 | 0.300294284 | 0.316 | 0.569 | 0.195 ENR+CV-4 | Lamtor2 |
| Hspa9 | 0.658 | 0.298288996 | 0.316 | 0.83 | 0.425 ENR+CV-4 | Hspa9 |

TABLE 1-continued

Derived gene list of the top defining genes from in vivo ileal
small intestine PCs and EECs captured on the Seq-Well platform

| Gene | | | | | | |
|---|---|---|---|---|---|---|
| Sugt1 | 0.658 | 0.293433354 | 0.316 | 0.573 | 0.199 | ENR+CV-4 Sugt1 |
| Naa15 | 0.658 | 0.290739735 | 0.316 | 0.573 | 0.2 | ENR+CV-4 Naa15 |
| Vps35 | 0.658 | 0.289579422 | 0.316 | 0.518 | 0.156 | ENR+CV-4 Vps35 |
| Cd2ap1 | 0.658 | 0.25309638 | 0.316 | 0.688 | 0.279 | ENR+CV-4 Cd2ap |
| Ccnb2 | 0.657 | 0.506270205 | 0.314 | 0.427 | 0.094 | ENR+CV-4 Ccnb2 |
| Copz11 | 0.657 | 0.37751331 | 0.314 | 0.546 | 0.189 | ENR+CV-4 Copz1 |
| Wwp11 | 0.657 | 0.36461092 | 0.314 | 0.454 | 0.113 | ENR+CV-4 Wwp1 |
| Oxct1 | 0.657 | 0.325542426 | 0.314 | 0.523 | 0.165 | ENR+CV-4 Oxct1 |
| Gmnn | 0.657 | 0.322284332 | 0.314 | 0.546 | 0.181 | ENR+CV-4 Gmnn |
| Ptms1 | 0.657 | 0.310908679 | 0.314 | 0.587 | 0.211 | ENR+CV-4 Ptms |
| Eif5b1 | 0.657 | 0.293408437 | 0.314 | 0.739 | 0.331 | ENR+CV-4 Eif5b |
| Cope1 | 0.657 | 0.268315803 | 0.314 | 0.72 | 0.307 | ENR+CV-4 Cope |
| Trim371 | 0.656 | 0.504794996 | 0.312 | 0.413 | 0.086 | ENR+CV-4 Trim37 |
| Plk1 | 0.656 | 0.484687109 | 0.312 | 0.39 | 0.063 | ENR+CV-4 Plk1 |
| U2af11 | 0.656 | 0.419056701 | 0.312 | 0.491 | 0.151 | ENR+CV-4 U2af1 |
| Hdac11 | 0.656 | 0.402622666 | 0.312 | 0.5 | 0.154 | ENR+CV-4 Hdac1 |
| Got21 | 0.656 | 0.401793178 | 0.312 | 0.468 | 0.129 | ENR+CV-4 Got2 |
| Laptm4b1 | 0.656 | 0.392263258 | 0.312 | 0.495 | 0.148 | ENR+CV-4 Laptm4b |
| Mpzl11 | 0.656 | 0.364314028 | 0.312 | 0.45 | 0.113 | ENR+CV-4 Mpzl1 |
| Rab141 | 0.656 | 0.346738193 | 0.312 | 0.523 | 0.171 | ENR+CV-4 Rab14 |
| Oaz12 | 0.656 | 0.337712242 | 0.312 | 0.904 | 0.615 | ENR+CV-4 Oaz1 |
| Calm31 | 0.656 | 0.33274162 | 0.312 | 0.693 | 0.301 | ENR+CV-4 Calm3 |
| Celf1 | 0.656 | 0.320510115 | 0.312 | 0.528 | 0.173 | ENR+CV-4 Celf1 |
| Lta4h1 | 0.656 | 0.317683966 | 0.312 | 0.537 | 0.178 | ENR+CV-4 Lta4h |
| Insig11 | 0.656 | 0.311534947 | 0.312 | 0.518 | 0.161 | ENR+CV-4 Insig1 |
| Sec61a11 | 0.656 | 0.308315291 | 0.312 | 0.619 | 0.24 | ENR+CV-4 Sec61a1 |
| Smarca5 | 0.656 | 0.300646863 | 0.312 | 0.628 | 0.245 | ENR+CV-4 Smarca5 |
| Arpc21 | 0.656 | 0.297653526 | 0.312 | 0.826 | 0.427 | ENR+CV-4 Arpc2 |
| Tuba1b | 0.656 | 0.287366402 | 0.312 | 0.798 | 0.386 | ENR+CV-4 Tuba1b |
| Dut | 0.656 | 0.281011027 | 0.312 | 0.628 | 0.245 | ENR+CV-4 Dut |
| C1qbp | 0.656 | 0.275817378 | 0.312 | 0.734 | 0.325 | ENR+CV-4 C1qbp |
| Gstm51 | 0.656 | 0.272042667 | 0.312 | 0.61 | 0.23 | ENR+CV-4 Gstm5 |
| Clic1 | 0.656 | 0.251339406 | 0.312 | 0.679 | 0.276 | ENR+CV-4 Clic1 |
| RP23-45G16.5 | 0.655 | 0.525111377 | 0.31 | 0.399 | 0.075 | ENR+CV-4 RP23-45G16.5 |
| Lrrc591 | 0.655 | 0.422416486 | 0.31 | 0.445 | 0.11 | ENR+CV-4 Lrrc59 |
| Rps252 | 0.655 | 0.350670548 | 0.31 | 0.881 | 0.547 | ENR+CV-4 Rps25 |
| 2700029M09Rik | 0.655 | 0.344425997 | 0.31 | 0.514 | 0.163 | ENR+CV-4 2700029M09Rik |
| Ptges3 | 0.655 | 0.325497707 | 0.31 | 0.665 | 0.283 | ENR+CV-4 Ptges3 |
| Ptp4a21 | 0.655 | 0.319278718 | 0.31 | 0.734 | 0.339 | ENR+CV-4 Ptp4a2 |
| Capzb1 | 0.655 | 0.297157062 | 0.31 | 0.665 | 0.278 | ENR+CV-4 Capzb |
| Smc1a | 0.655 | 0.285733326 | 0.31 | 0.587 | 0.218 | ENR+CV-4 Smc1a |
| Ndufb101 | 0.655 | 0.285449848 | 0.31 | 0.615 | 0.234 | ENR+CV-4 Ndufb10 |
| Fdps | 0.655 | 0.282166933 | 0.31 | 0.683 | 0.287 | ENR+CV-4 Fdps |
| Phb21 | 0.655 | 0.253274434 | 0.31 | 0.693 | 0.286 | ENR+CV-4 Phb2 |
| Rbm471 | 0.654 | 0.399486726 | 0.308 | 0.583 | 0.227 | ENR+CV-4 Rbm47 |
| Fam104a1 | 0.654 | 0.377863575 | 0.308 | 0.482 | 0.143 | ENR+CV-4 Fam104a |
| Atp5g3 | 0.654 | 0.365539154 | 0.308 | 0.881 | 0.471 | ENR+CV-4 Atp5g3 |
| Pes11 | 0.654 | 0.354694951 | 0.308 | 0.468 | 0.129 | ENR+CV-4 Pes1 |
| Tcerg1 | 0.654 | 0.34846106 | 0.308 | 0.495 | 0.15 | ENR+CV-4 Tcerg1 |
| Mtf2 | 0.654 | 0.327385761 | 0.308 | 0.45 | 0.113 | ENR+CV-4 Mtf2 |
| Uchl5 | 0.654 | 0.320014681 | 0.308 | 0.5 | 0.153 | ENR+CV-4 Uchl5 |
| Eif3f1 | 0.654 | 0.298586472 | 0.308 | 0.83 | 0.431 | ENR+CV-4 Eif3f |
| Hook11 | 0.654 | 0.293398393 | 0.308 | 0.853 | 0.447 | ENR+CV-4 Hook1 |
| Vcp1 | 0.654 | 0.28900104 | 0.308 | 0.628 | 0.247 | ENR+CV-4 Vcp |
| Letm1 | 0.653 | 0.416450408 | 0.306 | 0.422 | 0.096 | ENR+CV-4 Letm1 |
| Abcf2 | 0.653 | 0.406890248 | 0.306 | 0.417 | 0.092 | ENR+CV-4 Abcf2 |
| Tsc22d41 | 0.653 | 0.406703039 | 0.306 | 0.431 | 0.103 | ENR+CV-4 Tsc22d4 |
| Ccdc124 | 0.653 | 0.388477874 | 0.306 | 0.459 | 0.124 | ENR+CV-4 Ccdc124 |
| Asna11 | 0.653 | 0.374130817 | 0.306 | 0.431 | 0.102 | ENR+CV-4 Asna1 |
| Dsg21 | 0.653 | 0.373507085 | 0.306 | 0.541 | 0.193 | ENR+CV-4 Dsg2 |
| Rnf187 | 0.653 | 0.370080349 | 0.306 | 0.491 | 0.149 | ENR+CV-4 Rnf187 |
| Pnkd1 | 0.653 | 0.359091487 | 0.306 | 0.454 | 0.118 | ENR+CV-4 Pnkd |
| Blmh1 | 0.653 | 0.344989542 | 0.306 | 0.454 | 0.118 | ENR+CV-4 Blmh |
| Aup11 | 0.653 | 0.335521837 | 0.306 | 0.514 | 0.165 | ENR+CV-4 Aup1 |
| Sod1 | 0.653 | 0.312546785 | 0.306 | 0.917 | 0.547 | ENR+CV-4 Sod1 |
| Cox171 | 0.653 | 0.294958314 | 0.306 | 0.656 | 0.276 | ENR+CV-4 Cox17 |
| Atp511 | 0.653 | 0.29075963 | 0.306 | 0.601 | 0.226 | ENR+CV-4 Atp5l |
| Bsg3 | 0.653 | 0.270281931 | 0.306 | 0.986 | 0.727 | ENR+CV-4 Bsg |
| Hadha1 | 0.653 | 0.263995424 | 0.306 | 0.638 | 0.258 | ENR+CV-4 Hadha |
| Slc7a5 | 0.652 | 0.501041268 | 0.304 | 0.381 | 0.065 | ENR+CV-4 Slc7a5 |
| Agmat1 | 0.652 | 0.464331078 | 0.304 | 0.376 | 0.061 | ENR+CV-4 Agmat |
| Ralgps21 | 0.652 | 0.412204816 | 0.304 | 0.417 | 0.092 | ENR+CV-4 Ralgps2 |
| Ssna1 | 0.652 | 0.41104223 | 0.304 | 0.445 | 0.116 | ENR+CV-4 Ssna1 |
| Lsm71 | 0.652 | 0.3889045 | 0.304 | 0.417 | 0.093 | ENR+CV-4 Lsm7 |
| Kras | 0.652 | 0.377256728 | 0.304 | 0.454 | 0.123 | ENR+CV-4 Kras |
| Stmn1 | 0.652 | 0.370176616 | 0.304 | 0.472 | 0.135 | ENR+CV-4 Stmn1 |
| Nlrp61 | 0.652 | 0.369772904 | 0.304 | 0.495 | 0.154 | ENR+CV-4 Nlrp6 |

TABLE 1-continued

Derived gene list of the top defining genes from in vivo ileal
small intestine PCs and EECs captured on the Seq-Well platform

| Gene | | | | | | | |
|---|---|---|---|---|---|---|---|
| Khdrbs11 | 0.652 | 0.344289978 | 0.304 | 0.532 | 0.185 | ENR+CV-4 | Khdrbs1 |
| Sec31a1 | 0.652 | 0.336512699 | 0.304 | 0.518 | 0.172 | ENR+CV-4 | Sec31a |
| Pak1ip1 | 0.652 | 0.322095467 | 0.304 | 0.518 | 0.171 | ENR+CV-4 | Pak1ip1 |
| Gale1 | 0.652 | 0.299572437 | 0.304 | 0.518 | 0.167 | ENR+CV-4 | Gale |
| Srsf1 | 0.652 | 0.298651007 | 0.304 | 0.5 | 0.152 | ENR+CV-4 | Srsf1 |
| Rabac11 | 0.652 | 0.274679278 | 0.304 | 0.528 | 0.174 | ENR+CV-4 | Rabac1 |
| Cbx5 | 0.652 | 0.273389267 | 0.304 | 0.56 | 0.198 | ENR+CV-4 | Cbx5 |
| Hnrnpdl | 0.652 | 0.254481355 | 0.304 | 0.661 | 0.267 | ENR+CV-4 | Hnrnpdl |
| Sgol1 | 0.651 | 0.494512586 | 0.302 | 0.362 | 0.051 | ENR+CV-4 | Sgol1 |
| Bex41 | 0.651 | 0.48055676 | 0.302 | 0.394 | 0.078 | ENR+CV-4 | Bex4 |
| Chchd6 | 0.651 | 0.47199616 | 0.302 | 0.372 | 0.058 | ENR+CV-4 | Chchd6 |
| Diap3 | 0.651 | 0.428296437 | 0.302 | 0.376 | 0.06 | ENR+CV-4 | Diap3 |
| Psenen1 | 0.651 | 0.424658466 | 0.302 | 0.385 | 0.069 | ENR+CV-4 | Psenen |
| Emc8 | 0.651 | 0.406808068 | 0.302 | 0.436 | 0.11 | ENR+CV-4 | Emc8 |
| Pmvk1 | 0.651 | 0.395181641 | 0.302 | 0.422 | 0.099 | ENR+CV-4 | Pmvk |
| Mrps91 | 0.651 | 0.363210172 | 0.302 | 0.445 | 0.117 | ENR+CV-4 | Mrps9 |
| Samm50 | 0.651 | 0.331921143 | 0.302 | 0.482 | 0.144 | ENR+CV-4 | Samm50 |
| Asns | 0.651 | 0.326679794 | 0.302 | 0.638 | 0.27 | ENR+CV-4 | Asns |
| Gsr1 | 0.651 | 0.315854328 | 0.302 | 0.532 | 0.182 | ENR+CV-4 | Gsr |
| Bri3bp1 | 0.651 | 0.306762595 | 0.302 | 0.463 | 0.128 | ENR+CV-4 | Bri3bp |
| Kcnq12 | 0.651 | 0.287192159 | 0.302 | 0.5 | 0.154 | ENR+CV-4 | Kcnq1 |
| Sc4mol | 0.651 | 0.277254499 | 0.302 | 0.592 | 0.227 | ENR+CV-4 | Sc4mol |
| Fkbp2 | 0.651 | 0.272084012 | 0.302 | 0.592 | 0.229 | ENR+CV-4 | Fkbp2 |
| Ptgr11 | 0.651 | 0.253972151 | 0.302 | 0.596 | 0.224 | ENR+CV-4 | Ptgr1 |
| Acot71 | 0.65 | 0.44480374 | 0.3 | 0.399 | 0.083 | ENR+CV-4 | Acot7 |
| Hbegf1 | 0.65 | 0.383581494 | 0.3 | 0.56 | 0.211 | ENR+CV-4 | Hbegf |
| Puf60 | 0.65 | 0.354611462 | 0.3 | 0.486 | 0.149 | ENR+CV-4 | Puf60 |
| M6pr1 | 0.65 | 0.347583988 | 0.3 | 0.509 | 0.171 | ENR+CV-4 | M6pr |
| Fbp21 | 0.65 | 0.281335781 | 0.3 | 0.564 | 0.206 | ENR+CV-4 | Fbp2 |
| Cnih4 | 0.65 | 0.254820446 | 0.3 | 0.555 | 0.195 | ENR+CV-4 | Cnih4 |
| Amn1 | 0.649 | 0.487246076 | 0.298 | 0.372 | 0.064 | ENR+CV-4 | Amn |
| Dgcr6 | 0.649 | 0.447758603 | 0.298 | 0.394 | 0.082 | ENR+CV-4 | Dgcr6 |
| Hmgb3 | 0.649 | 0.430737682 | 0.298 | 0.394 | 0.082 | ENR+CV-4 | Hmgb3 |
| Atad2 | 0.649 | 0.365116743 | 0.298 | 0.45 | 0.12 | ENR+CV-4 | Atad2 |
| Elf32 | 0.649 | 0.35012133 | 0.298 | 0.661 | 0.292 | ENR+CV-4 | Elf3 |
| Ilf3 | 0.649 | 0.341105762 | 0.298 | 0.454 | 0.125 | ENR+CV-4 | Ilf3 |
| Btg11 | 0.649 | 0.328845008 | 0.298 | 0.491 | 0.154 | ENR+CV-4 | Btg1 |
| Polr2m | 0.649 | 0.316870425 | 0.298 | 0.55 | 0.203 | ENR+CV-4 | Polr2m |
| Atp6v1a1 | 0.649 | 0.316281949 | 0.298 | 0.445 | 0.117 | ENR+CV-4 | Atp6v1a |
| Timm10b1 | 0.649 | 0.308898934 | 0.298 | 0.5 | 0.16 | ENR+CV-4 | Timm10b |
| Mrps17 | 0.649 | 0.279292265 | 0.298 | 0.509 | 0.164 | ENR+CV-4 | Mrps17 |
| Gipc2 | 0.649 | 0.27030012 | 0.298 | 0.532 | 0.184 | ENR+CV-4 | Gipc2 |
| Cox6c3 | 0.649 | 0.264944787 | 0.298 | 0.977 | 0.78 | ENR+CV-4 | Cox6c |
| Ssx2ip1 | 0.648 | 0.418476953 | 0.296 | 0.404 | 0.091 | ENR+CV-4 | Ssx2ip |
| Shmt2 | 0.648 | 0.403653756 | 0.296 | 0.463 | 0.139 | ENR+CV-4 | Shmt2 |
| Cox191 | 0.648 | 0.348052973 | 0.296 | 0.44 | 0.117 | ENR+CV-4 | Cox19 |
| Alkbh51 | 0.648 | 0.321180129 | 0.296 | 0.468 | 0.137 | ENR+CV-4 | Alkbh5 |
| Pgrmc21 | 0.648 | 0.320028984 | 0.296 | 0.468 | 0.137 | ENR+CV-4 | Pgrmc2 |
| Ppp5c | 0.648 | 0.307659006 | 0.296 | 0.459 | 0.129 | ENR+CV-4 | Ppp5c |
| Azin1 | 0.648 | 0.283431031 | 0.296 | 0.495 | 0.155 | ENR+CV-4 | Azin1 |
| Krtcap2 | 0.648 | 0.257736946 | 0.296 | 0.693 | 0.304 | ENR+CV-4 | Krtcap2 |
| Pmm1 | 0.647 | 0.512284826 | 0.294 | 0.367 | 0.064 | ENR+CV-4 | Pmm1 |
| Poc1a | 0.647 | 0.462857178 | 0.294 | 0.344 | 0.041 | ENR+CV-4 | Poc1a |
| Ddx19a | 0.647 | 0.435564391 | 0.294 | 0.39 | 0.079 | ENR+CV-4 | Ddx19a |
| Tfrc | 0.647 | 0.340402506 | 0.294 | 0.486 | 0.156 | ENR+CV-4 | Tfrc |
| Hnrnpab | 0.647 | 0.335725179 | 0.294 | 0.849 | 0.475 | ENR+CV-4 | Hnrnpab |
| Pcm1 | 0.647 | 0.324531997 | 0.294 | 0.546 | 0.203 | ENR+CV-4 | Pcm1 |
| Cox7c1 | 0.647 | 0.306604436 | 0.294 | 0.734 | 0.361 | ENR+CV-4 | Cox7c |
| Snrpc1 | 0.647 | 0.305153599 | 0.294 | 0.445 | 0.12 | ENR+CV-4 | Snrpc |
| Cnn31 | 0.647 | 0.296645683 | 0.294 | 0.583 | 0.229 | ENR+CV-4 | Cnn3 |
| Cd811 | 0.647 | 0.282818594 | 0.294 | 0.885 | 0.48 | ENR+CV-4 | Cd81 |
| Elof1 | 0.647 | 0.281811682 | 0.294 | 0.5 | 0.161 | ENR+CV-4 | Elof1 |
| Tsn1 | 0.647 | 0.281552658 | 0.294 | 0.523 | 0.182 | ENR+CV-4 | Tsn |
| Sf3b2 | 0.647 | 0.275565348 | 0.294 | 0.642 | 0.268 | ENR+CV-4 | Sf3b2 |
| 1110008F13Rik1 | 0.647 | 0.27453518 | 0.294 | 0.624 | 0.258 | ENR+CV-4 | 1110008F13Rik |
| Fam162a1 | 0.647 | 0.251895647 | 0.294 | 0.743 | 0.346 | ENR+CV-4 | Fam162a |
| Mecr1 | 0.646 | 0.388189363 | 0.292 | 0.404 | 0.092 | ENR+CV-4 | Mecr |
| Aqp41 | 0.646 | 0.314248957 | 0.292 | 0.436 | 0.115 | ENR+CV-4 | Aqp4 |
| Psmb31 | 0.646 | 0.309428359 | 0.292 | 0.624 | 0.266 | ENR+CV-4 | Psmb3 |
| Cpne31 | 0.646 | 0.289586674 | 0.292 | 0.518 | 0.183 | ENR+CV-4 | Cpne3 |
| Hist1h1e | 0.646 | 0.289497648 | 0.292 | 0.61 | 0.247 | ENR+CV-4 | Hist1h1e |
| Acaa21 | 0.646 | 0.279017327 | 0.292 | 0.537 | 0.192 | ENR+CV-4 | Acaa2 |
| Vps361 | 0.646 | 0.267004542 | 0.292 | 0.514 | 0.176 | ENR+CV-4 | Vps36 |
| Hspa8 | 0.646 | 0.265670461 | 0.292 | 0.986 | 0.77 | ENR+CV-4 | Hspa8 |
| Aurkb | 0.645 | 0.429339282 | 0.29 | 0.349 | 0.048 | ENR+CV-4 | Aurkb |
| Cryzl11 | 0.645 | 0.395189119 | 0.29 | 0.417 | 0.105 | ENR+CV-4 | Cryzl1 |
| Rpa2 | 0.645 | 0.391936206 | 0.29 | 0.372 | 0.067 | ENR+CV-4 | Rpa2 |

TABLE 1-continued

Derived gene list of the top defining genes from in vivo ileal
small intestine PCs and EECs captured on the Seq-Well platform

| | | | | | | |
|---|---|---|---|---|---|---|
| Spata24 | 0.645 | 0.385991762 | 0.29 | 0.372 | 0.067 ENR+CV-4 | Spata24 |
| Eif1ad | 0.645 | 0.380845021 | 0.29 | 0.394 | 0.085 ENR+CV-4 | Eif1ad |
| Gm45401 | 0.645 | 0.374922144 | 0.29 | 0.5 | 0.172 ENR+CV-4 | Gm4540 |
| Prkcsh1 | 0.645 | 0.321826641 | 0.29 | 0.5 | 0.169 ENR+CV-4 | Prkcsh |
| Xpo1 | 0.645 | 0.305477469 | 0.29 | 0.472 | 0.145 ENR+CV-4 | Xpo1 |
| Rnf7 | 0.645 | 0.294936033 | 0.29 | 0.537 | 0.198 ENR+CV-4 | Rnf7 |
| Nipsnap11 | 0.645 | 0.292274846 | 0.29 | 0.454 | 0.13 ENR+CV-4 | Nipsnap1 |
| Aig11 | 0.645 | 0.290184442 | 0.29 | 0.463 | 0.138 ENR+CV-4 | Aig1 |
| Pkn21 | 0.645 | 0.269646851 | 0.29 | 0.482 | 0.152 ENR+CV-4 | Pkn2 |
| Ppig | 0.645 | 0.266779213 | 0.29 | 0.564 | 0.218 ENR+CV-4 | Ppig |
| Cd91 | 0.645 | 0.25913769 | 0.29 | 0.615 | 0.25 ENR+CV-4 | Cd9 |
| Clybl1 | 0.644 | 0.443714733 | 0.288 | 0.376 | 0.076 ENR+CV-4 | Clybl |
| Sigmar11 | 0.644 | 0.376193874 | 0.288 | 0.399 | 0.092 ENR+CV-4 | Sigmar1 |
| Dpysl21 | 0.644 | 0.363250719 | 0.288 | 0.427 | 0.115 ENR+CV-4 | Dpysl2 |
| Gm102631 | 0.644 | 0.346429428 | 0.288 | 0.404 | 0.094 ENR+CV-4 | Gm10263 |
| Hells | 0.644 | 0.343949981 | 0.288 | 0.505 | 0.177 ENR+CV-4 | Hells |
| Mrps26 | 0.644 | 0.329273931 | 0.288 | 0.445 | 0.128 ENR+CV-4 | Mrps26 |
| Higd1a1 | 0.644 | 0.312609564 | 0.288 | 0.463 | 0.142 ENR+CV-4 | Higd1a |
| Zc3h15 | 0.644 | 0.293495979 | 0.288 | 0.55 | 0.212 ENR+CV-4 | Zc3h15 |
| Rad21 | 0.644 | 0.259092466 | 0.288 | 0.573 | 0.225 ENR+CV-4 | Rad21 |
| Fyttd11 | 0.644 | 0.258087343 | 0.288 | 0.495 | 0.166 ENR+CV-4 | Fyttd1 |
| Ckap2l | 0.643 | 0.465135799 | 0.286 | 0.349 | 0.053 ENR+CV-4 | Ckap2l |
| Ckap5 | 0.643 | 0.386945088 | 0.286 | 0.422 | 0.113 ENR+CV-4 | Ckap5 |
| Pla2g12a1 | 0.643 | 0.327545992 | 0.286 | 0.44 | 0.126 ENR+CV-4 | Pla2g12a |
| Cdk2ap21 | 0.643 | 0.32640794 | 0.286 | 0.477 | 0.154 ENR+CV-4 | Cdk2ap2 |
| Lrpprc | 0.643 | 0.311464662 | 0.286 | 0.427 | 0.113 ENR+CV-4 | Lrpprc |
| Psmd111 | 0.643 | 0.302071708 | 0.286 | 0.486 | 0.163 ENR+CV-4 | Psmd11 |
| Ldlr | 0.643 | 0.284014317 | 0.286 | 0.472 | 0.149 ENR+CV-4 | Ldlr |
| Cotl11 | 0.643 | 0.2760333 | 0.286 | 0.596 | 0.243 ENR+CV-4 | Cotl1 |
| Tomm70a1 | 0.643 | 0.271025126 | 0.286 | 0.596 | 0.25 ENR+CV-4 | Tomm70a |
| Aimp1 | 0.643 | 0.269813445 | 0.286 | 0.606 | 0.25 ENR+CV-4 | Aimp1 |
| Hmgn1 | 0.643 | 0.267159815 | 0.286 | 0.899 | 0.526 ENR+CV-4 | Hmgn1 |
| Hsd17b121 | 0.643 | 0.263909135 | 0.286 | 0.61 | 0.255 ENR+CV-4 | Hsd17b12 |
| Tnpo31 | 0.642 | 0.375753898 | 0.284 | 0.404 | 0.099 ENR+CV-4 | Tnpo3 |
| Prelid21 | 0.642 | 0.37147467 | 0.284 | 0.431 | 0.122 ENR+CV-4 | Prelid2 |
| H2-Ke2 | 0.642 | 0.336246352 | 0.284 | 0.422 | 0.112 ENR+CV-4 | H2-Ke2 |
| Tmem54 | 0.642 | 0.325901449 | 0.284 | 0.431 | 0.12 ENR+CV-4 | Tmem54 |
| Limd1 | 0.642 | 0.324653572 | 0.284 | 0.399 | 0.093 ENR+CV-4 | Limd1 |
| Tob1 | 0.642 | 0.295380327 | 0.284 | 0.468 | 0.147 ENR+CV-4 | Tob1 |
| Smchd1 | 0.642 | 0.28976823 | 0.284 | 0.45 | 0.131 ENR+CV-4 | Smchd1 |
| Pgd1 | 0.642 | 0.278687046 | 0.284 | 0.514 | 0.18 ENR+CV-4 | Pgd |
| Aurkaip1 | 0.642 | 0.261691729 | 0.284 | 0.5 | 0.169 ENR+CV-4 | Aurkaip1 |
| Psmb11 | 0.642 | 0.254217297 | 0.284 | 0.927 | 0.593 ENR+CV-4 | Psmb1 |
| Cab39l | 0.641 | 0.435081551 | 0.282 | 0.353 | 0.062 ENR+CV-4 | Cab39l |
| Thoc3 | 0.641 | 0.415211666 | 0.282 | 0.372 | 0.075 ENR+CV-4 | Thoc3 |
| Rtf1 | 0.641 | 0.385552494 | 0.282 | 0.408 | 0.105 ENR+CV-4 | Rtf1 |
| Dlat1 | 0.641 | 0.329664821 | 0.282 | 0.427 | 0.119 ENR+CV-4 | Dlat |
| Wdr431 | 0.641 | 0.323265599 | 0.282 | 0.532 | 0.204 ENR+CV-4 | Wdr43 |
| Rgcc1 | 0.641 | 0.321569094 | 0.282 | 0.706 | 0.368 ENR+CV-4 | Rgcc |
| Me21 | 0.641 | 0.318330371 | 0.282 | 0.468 | 0.152 ENR+CV-4 | Me2 |
| Drap11 | 0.641 | 0.300897032 | 0.282 | 0.468 | 0.148 ENR+CV-4 | Drap1 |
| Dera1 | 0.641 | 0.295782072 | 0.282 | 0.459 | 0.145 ENR+CV-4 | Dera |
| Smim20 | 0.641 | 0.279187454 | 0.282 | 0.431 | 0.119 ENR+CV-4 | Smim20 |
| Ube2k | 0.641 | 0.26692081 | 0.282 | 0.482 | 0.159 ENR+CV-4 | Ube2k |
| Mbnl11 | 0.641 | 0.264419375 | 0.282 | 0.532 | 0.195 ENR+CV-4 | Mbnl1 |
| Adk | 0.641 | 0.250804817 | 0.282 | 0.459 | 0.139 ENR+CV-4 | Adk |
| Aurka | 0.64 | 0.434979796 | 0.28 | 0.335 | 0.045 ENR+CV-4 | Aurka |
| Ppp1r7 | 0.64 | 0.357851734 | 0.28 | 0.404 | 0.103 ENR+CV-4 | Ppp1r7 |
| Tspan31 | 0.64 | 0.26835933 | 0.28 | 0.459 | 0.141 ENR+CV-4 | Tspan31 |
| 0610007P14Rik | 0.64 | 0.268159967 | 0.28 | 0.491 | 0.168 ENR+CV-4 | 0610007P14Rik |
| Fau | 0.64 | 0.260614206 | 0.28 | 0.633 | 0.276 ENR+CV-4 | Fau |
| Sox42 | 0.64 | 0.259866123 | 0.28 | 0.766 | 0.367 ENR+CV-4 | Sox4 |
| Mrpl151 | 0.64 | 0.252779889 | 0.28 | 0.624 | 0.271 ENR+CV-4 | Mrpl15 |
| Coro1c | 0.639 | 0.418711098 | 0.278 | 0.372 | 0.08 ENR+CV-4 | Coro1c |
| Rnd31 | 0.639 | 0.404849427 | 0.278 | 0.413 | 0.112 ENR+CV-4 | Rnd3 |
| Eif2b41 | 0.639 | 0.380142916 | 0.278 | 0.385 | 0.09 ENR+CV-4 | Eif2b4 |
| Yrdc1 | 0.639 | 0.377976245 | 0.278 | 0.39 | 0.092 ENR+CV-4 | Yrdc |
| Bub1 | 0.639 | 0.372410583 | 0.278 | 0.358 | 0.065 ENR+CV-4 | Bub1 |
| Hspa4l | 0.639 | 0.356310631 | 0.278 | 0.394 | 0.095 ENR+CV-4 | Hspa4l |
| Elovl11 | 0.639 | 0.334923395 | 0.278 | 0.404 | 0.104 ENR+CV-4 | Elovl1 |
| Zfp503 | 0.639 | 0.332192694 | 0.278 | 0.39 | 0.089 ENR+CV-4 | Zfp503 |
| Dhrs41 | 0.639 | 0.330226 | 0.278 | 0.541 | 0.217 ENR+CV-4 | Dhrs4 |
| Nop14 | 0.639 | 0.320161781 | 0.278 | 0.445 | 0.136 ENR+CV-4 | Nop14 |
| Ppm1g1 | 0.639 | 0.318595673 | 0.278 | 0.472 | 0.155 ENR+CV-4 | Ppm1g |
| Dkc11 | 0.639 | 0.31256963 | 0.278 | 0.509 | 0.189 ENR+CV-4 | Dkc1 |
| Rab1b | 0.639 | 0.31147767 | 0.278 | 0.422 | 0.117 ENR+CV-4 | Rab1b |
| Shmt11 | 0.639 | 0.293188027 | 0.278 | 0.427 | 0.118 ENR+CV-4 | Shmt1 |

TABLE 1-continued

Derived gene list of the top defining genes from in vivo ileal
small intestine PCs and EECs captured on the Seq-Well platform

| | | | | | | |
|---|---|---|---|---|---|---|
| Fam96b1 | 0.639 | 0.277888543 | 0.278 | 0.417 | 0.112 ENR+CV-4 | Fam96b |
| Gins2 | 0.638 | 0.396156237 | 0.276 | 0.372 | 0.081 ENR+CV-4 | Gins2 |
| Plk4 | 0.638 | 0.395800506 | 0.276 | 0.335 | 0.048 ENR+CV-4 | Plk4 |
| Xrcc1 | 0.638 | 0.365878926 | 0.276 | 0.353 | 0.064 ENR+CV-4 | Xrcc1 |
| Nfia1 | 0.638 | 0.365420315 | 0.276 | 0.427 | 0.126 ENR+CV-4 | Nfia |
| Fam111a | 0.638 | 0.353293738 | 0.276 | 0.353 | 0.064 ENR+CV-4 | Fam111a |
| Pole3 | 0.638 | 0.352143379 | 0.276 | 0.394 | 0.097 ENR+CV-4 | Pole3 |
| Mrto4 | 0.638 | 0.313130691 | 0.276 | 0.422 | 0.119 ENR+CV-4 | Mrto4 |
| Nsdhl1 | 0.638 | 0.301688834 | 0.276 | 0.39 | 0.093 ENR+CV-4 | Nsdhl |
| Eif4a11 | 0.638 | 0.293519513 | 0.276 | 0.803 | 0.481 ENR+CV-4 | Eif4a1 |
| Etf1 | 0.638 | 0.281849255 | 0.276 | 0.606 | 0.257 ENR+CV-4 | Etf1 |
| 1110001J03Rik1 | 0.638 | 0.273807218 | 0.276 | 0.555 | 0.222 ENR+CV-4 | 1110001J03Rik |
| Hist2h2bb | 0.637 | 0.458322705 | 0.274 | 0.335 | 0.051 ENR+CV-4 | Hist2h2bb |
| Mars | 0.637 | 0.385445323 | 0.274 | 0.394 | 0.102 ENR+CV-4 | Mars |
| Pisd1 | 0.637 | 0.336668131 | 0.274 | 0.431 | 0.131 ENR+CV-4 | Pisd |
| Cmc2 | 0.637 | 0.321446476 | 0.274 | 0.353 | 0.064 ENR+CV-4 | Cmc2 |
| 2310036O22Rik | 0.637 | 0.286697279 | 0.274 | 0.459 | 0.149 ENR+CV-4 | 2310036O22Rik |
| Atp13a3 | 0.637 | 0.267453223 | 0.274 | 0.445 | 0.137 ENR+CV-4 | Atp13a3 |
| Fdft1 | 0.637 | 0.256228886 | 0.274 | 0.477 | 0.161 ENR+CV-4 | Fdft1 |
| Vdac1 | 0.637 | 0.252143759 | 0.274 | 0.67 | 0.308 ENR+CV-4 | Vdac1 |
| Asf1b | 0.636 | 0.412320824 | 0.272 | 0.317 | 0.038 ENR+CV-4 | Asf1b |
| Rbm381 | 0.636 | 0.38500037 | 0.272 | 0.353 | 0.068 ENR+CV-4 | Rbm38 |
| Psmd3 | 0.636 | 0.309545626 | 0.272 | 0.431 | 0.129 ENR+CV-4 | Psmd3 |
| Slc6a61 | 0.636 | 0.308991754 | 0.272 | 0.427 | 0.126 ENR+CV-4 | Slc6a6 |
| Myb | 0.636 | 0.304971812 | 0.272 | 0.408 | 0.112 ENR+CV-4 | Myb |
| Cenpw | 0.636 | 0.277047868 | 0.272 | 0.431 | 0.128 ENR+CV-4 | Cenpw |
| Csnk2b | 0.636 | 0.272457299 | 0.272 | 0.477 | 0.163 ENR+CV-4 | Csnk2b |
| Fam32a1 | 0.636 | 0.266005911 | 0.272 | 0.472 | 0.16 ENR+CV-4 | Fam32a |
| Ddx211 | 0.636 | 0.261920255 | 0.272 | 0.665 | 0.322 ENR+CV-4 | Ddx21 |
| Ahcyl1 | 0.636 | 0.261350959 | 0.272 | 0.486 | 0.171 ENR+CV-4 | Ahcyl1 |
| Axin21 | 0.636 | 0.261145253 | 0.272 | 0.564 | 0.232 ENR+CV-4 | Axin2 |
| Asah1 | 0.636 | 0.252155347 | 0.272 | 0.459 | 0.146 ENR+CV-4 | Asah1 |
| Slc16a32 | 0.635 | 0.384191345 | 0.27 | 0.394 | 0.105 ENR+CV-4 | Slc16a3 |
| Mpnd2 | 0.635 | 0.368868069 | 0.27 | 0.385 | 0.096 ENR+CV-4 | Mpnd |
| Ndufs51 | 0.635 | 0.363296538 | 0.27 | 0.427 | 0.132 ENR+CV-4 | Ndufs5 |
| Rdh11 | 0.635 | 0.348329524 | 0.27 | 0.372 | 0.084 ENR+CV-4 | Rdh11 |
| Ap2a2 | 0.635 | 0.3126178 | 0.27 | 0.385 | 0.094 ENR+CV-4 | Ap2a2 |
| Hdac2 | 0.635 | 0.279240452 | 0.27 | 0.477 | 0.168 ENR+CV-4 | Hdac2 |
| Ppie1 | 0.635 | 0.276781613 | 0.27 | 0.408 | 0.113 ENR+CV-4 | Ppie |
| Ppp1cb1 | 0.635 | 0.265449714 | 0.27 | 0.56 | 0.228 ENR+CV-4 | Ppp1cb |
| Sarnp1 | 0.635 | 0.26461051 | 0.27 | 0.482 | 0.169 ENR+CV-4 | Sarnp |
| Emc10 | 0.635 | 0.26367078 | 0.27 | 0.454 | 0.147 ENR+CV-4 | Emc10 |
| Ctbp1 | 0.635 | 0.25236991 | 0.27 | 0.459 | 0.149 ENR+CV-4 | Ctbp1 |
| Fads11 | 0.634 | 0.358505812 | 0.268 | 0.404 | 0.115 ENR+CV-4 | Fads1 |
| Rell1 | 0.634 | 0.355626005 | 0.268 | 0.353 | 0.072 ENR+CV-4 | Rell1 |
| Hsd17b11 | 0.634 | 0.342172731 | 0.268 | 0.372 | 0.085 ENR+CV-4 | Hsd17b11 |
| Nudcd3 | 0.634 | 0.331748329 | 0.268 | 0.358 | 0.075 ENR+CV-4 | Nudcd3 |
| Itga61 | 0.634 | 0.312724988 | 0.268 | 0.468 | 0.164 ENR+CV-4 | Itga6 |
| Ywhag | 0.634 | 0.304427373 | 0.268 | 0.417 | 0.125 ENR+CV-4 | Ywhag |
| Polr2b | 0.634 | 0.298278882 | 0.268 | 0.408 | 0.114 ENR+CV-4 | Polr2b |
| Ccz11 | 0.634 | 0.296029121 | 0.268 | 0.39 | 0.099 ENR+CV-4 | Ccz1 |
| Zc3h13 | 0.634 | 0.293792914 | 0.268 | 0.413 | 0.118 ENR+CV-4 | Zc3h13 |
| Aldh18a11 | 0.634 | 0.283718003 | 0.268 | 0.454 | 0.154 ENR+CV-4 | Aldh18a1 |
| Ywhah | 0.634 | 0.282444 | 0.268 | 0.459 | 0.151 ENR+CV-4 | Ywhah |
| Pum2 | 0.634 | 0.272196661 | 0.268 | 0.427 | 0.127 ENR+CV-4 | Pum2 |
| Tspan7 | 0.634 | 0.264996807 | 0.268 | 0.431 | 0.132 ENR+CV-4 | Tspan7 |
| Lars22 | 0.634 | 0.256328028 | 0.268 | 0.927 | 0.604 ENR+CV-4 | Lars2 |
| Sgol2 | 0.633 | 0.450322004 | 0.266 | 0.312 | 0.038 ENR+CV-4 | Sgol2 |
| Cars | 0.633 | 0.396678823 | 0.266 | 0.376 | 0.094 ENR+CV-4 | Cars |
| Ncapg | 0.633 | 0.37222054 | 0.266 | 0.358 | 0.076 ENR+CV-4 | Ncapg |
| Srm1 | 0.633 | 0.321162388 | 0.266 | 0.408 | 0.117 ENR+CV-4 | Srm |
| Smarcd21 | 0.633 | 0.309664492 | 0.266 | 0.399 | 0.11 ENR+CV-4 | Smarcd2 |
| Gins1 | 0.633 | 0.306863377 | 0.266 | 0.427 | 0.132 ENR+CV-4 | Gins1 |
| Tipin | 0.633 | 0.295315981 | 0.266 | 0.417 | 0.124 ENR+CV-4 | Tipin |
| Stt3b1 | 0.633 | 0.282817896 | 0.266 | 0.5 | 0.192 ENR+CV-4 | Stt3b |
| Fkbp81 | 0.633 | 0.278250257 | 0.266 | 0.505 | 0.19 ENR+CV-4 | Fkbp8 |
| Capns1 | 0.633 | 0.26139724 | 0.266 | 0.477 | 0.17 ENR+CV-4 | Capns1 |
| mt-Ta | 0.632 | 0.52011571 | 0.264 | 0.298 | 0.03 ENR+CV-4 | mt-Ta |
| Bspry | 0.632 | 0.418086977 | 0.264 | 0.339 | 0.065 ENR+CV-4 | Bspry |
| Ppp3r1 | 0.632 | 0.343054494 | 0.264 | 0.376 | 0.095 ENR+CV-4 | Ppp3r1 |
| Ddx10 | 0.632 | 0.306047969 | 0.264 | 0.381 | 0.095 ENR+CV-4 | Ddx10 |
| Syngr2 | 0.632 | 0.305361182 | 0.264 | 0.468 | 0.167 ENR+CV-4 | Syngr2 |
| Scpep11 | 0.632 | 0.29936659 | 0.264 | 0.367 | 0.085 ENR+CV-4 | Scpep1 |
| Nubp11 | 0.632 | 0.280538742 | 0.264 | 0.399 | 0.11 ENR+CV-4 | Nubp1 |
| Usp101 | 0.632 | 0.265646459 | 0.264 | 0.427 | 0.13 ENR+CV-4 | Usp10 |
| Cdx21 | 0.632 | 0.260363808 | 0.264 | 0.417 | 0.123 ENR+CV-4 | Cdx2 |
| Eif2b1 | 0.632 | 0.25757233 | 0.264 | 0.436 | 0.139 ENR+CV-4 | Eif2b1 |

TABLE 1-continued

Derived gene list of the top defining genes from in vivo ileal
small intestine PCs and EECs captured on the Seq-Well platform

| | | | | | | |
|---|---|---|---|---|---|---|
| Ass1l | 0.631 | 0.430272833 | 0.262 | 0.312 | 0.044 ENR+CV-4 | Ass1 |
| Nomo1 | 0.631 | 0.30617481 | 0.262 | 0.408 | 0.122 ENR+CV-4 | Nomo1 |
| Iars | 0.631 | 0.30384173 | 0.262 | 0.422 | 0.132 ENR+CV-4 | Iars |
| Commd4 | 0.631 | 0.296226012 | 0.262 | 0.454 | 0.158 ENR+CV-4 | Commd4 |
| Nans | 0.631 | 0.286497408 | 0.262 | 0.422 | 0.131 ENR+CV-4 | Nans |
| Eif4e | 0.631 | 0.265640858 | 0.262 | 0.404 | 0.113 ENR+CV-4 | Eif4e |
| Net1l | 0.631 | 0.264027699 | 0.262 | 0.459 | 0.159 ENR+CV-4 | Net1 |
| Hn1l | 0.631 | 0.262887953 | 0.262 | 0.381 | 0.095 ENR+CV-4 | Hn1l |
| n-R5-8s1l | 0.63 | 0.472028508 | 0.26 | 0.312 | 0.044 ENR+CV-4 | n-R5-8s1 |
| Kif23 | 0.63 | 0.336091265 | 0.26 | 0.376 | 0.095 ENR+CV-4 | Kif23 |
| Rassf4l | 0.63 | 0.332438122 | 0.26 | 0.335 | 0.062 ENR+CV-4 | Rassf4 |
| Actn1l | 0.63 | 0.29816753 | 0.26 | 0.472 | 0.175 ENR+CV-4 | Actn1 |
| Hat1 | 0.63 | 0.266787855 | 0.26 | 0.417 | 0.127 ENR+CV-4 | Hat1 |
| Rps4y2l | 0.629 | 0.367340969 | 0.258 | 0.394 | 0.116 ENR+CV-4 | Rps4y2 |
| Ccnb1 | 0.629 | 0.330017227 | 0.258 | 0.339 | 0.067 ENR+CV-4 | Ccnb1 |
| Cdkn2aipnl1 | 0.629 | 0.293411053 | 0.258 | 0.394 | 0.113 ENR+CV-4 | Cdkn2aipnl |
| Eif2a1 | 0.629 | 0.265578565 | 0.258 | 0.468 | 0.171 ENR+CV-4 | Eif2a |
| Gar1l | 0.629 | 0.252312069 | 0.258 | 0.39 | 0.106 ENR+CV-4 | Gar1 |
| Acsl4 | 0.628 | 0.361873568 | 0.256 | 0.349 | 0.08 ENR+CV-4 | Acsl4 |
| Mcm5 | 0.628 | 0.36152962 | 0.256 | 0.367 | 0.094 ENR+CV-4 | Mcm5 |
| Rbbp8l | 0.628 | 0.337089067 | 0.256 | 0.358 | 0.086 ENR+CV-4 | Rbbp8 |
| Rbm22 | 0.628 | 0.327031707 | 0.256 | 0.367 | 0.092 ENR+CV-4 | Rbm22 |
| Hexim1l | 0.628 | 0.321477174 | 0.256 | 0.394 | 0.116 ENR+CV-4 | Hexim1 |
| Cetn2l | 0.628 | 0.287459197 | 0.256 | 0.404 | 0.122 ENR+CV-4 | Cetn2 |
| Utp14a1 | 0.628 | 0.287294189 | 0.256 | 0.417 | 0.134 ENR+CV-4 | Utp14a |
| Ogdh | 0.628 | 0.271497075 | 0.256 | 0.394 | 0.111 ENR+CV-4 | Ogdh |
| Gtf2f2 | 0.628 | 0.269606098 | 0.256 | 0.381 | 0.102 ENR+CV-4 | Gtf2f2 |
| Crip2 | 0.627 | 0.468832798 | 0.254 | 0.284 | 0.027 ENR+CV-4 | Crip2 |
| Rfc5 | 0.627 | 0.332928657 | 0.254 | 0.349 | 0.079 ENR+CV-4 | Rfc5 |
| Nudt19 | 0.627 | 0.30588313 | 0.254 | 0.404 | 0.126 ENR+CV-4 | Nudt19 |
| Ndfip2l | 0.627 | 0.282070888 | 0.254 | 0.399 | 0.118 ENR+CV-4 | Ndfip2 |
| Tmprss4l | 0.627 | 0.280667597 | 0.254 | 0.422 | 0.136 ENR+CV-4 | Tmprss4 |
| Abhd17a1 | 0.627 | 0.262663453 | 0.254 | 0.39 | 0.109 ENR+CV-4 | Abhd17a |
| Yes1 | 0.627 | 0.257371906 | 0.254 | 0.394 | 0.115 ENR+CV-4 | Yes1 |
| Gpa33l | 0.627 | 0.256744797 | 0.254 | 0.472 | 0.178 ENR+CV-4 | Gpa33 |
| mt-Tq2 | 0.626 | 0.507613601 | 0.252 | 0.298 | 0.041 ENR+CV-4 | mt-Tq |
| Haus3 | 0.626 | 0.408491992 | 0.252 | 0.289 | 0.032 ENR+CV-4 | Haus3 |
| Elovl6 | 0.626 | 0.379800454 | 0.252 | 0.358 | 0.093 ENR+CV-4 | Elovl6 |
| Fen1 | 0.626 | 0.36493647 | 0.252 | 0.335 | 0.071 ENR+CV-4 | Fen1 |
| Rpa1 | 0.626 | 0.357229408 | 0.252 | 0.33 | 0.067 ENR+CV-4 | Rpa1 |
| Fastkd2 | 0.626 | 0.341038691 | 0.252 | 0.326 | 0.063 ENR+CV-4 | Fastkd2 |
| Slc29a1 | 0.626 | 0.333677875 | 0.252 | 0.367 | 0.097 ENR+CV-4 | Slc29a1 |
| Cenph | 0.626 | 0.33274086 | 0.252 | 0.335 | 0.071 ENR+CV-4 | Cenph |
| Uaca | 0.626 | 0.321591416 | 0.252 | 0.367 | 0.096 ENR+CV-4 | Uaca |
| Elovl5l | 0.626 | 0.315432295 | 0.252 | 0.353 | 0.084 ENR+CV-4 | Elovl5 |
| Suclg2l | 0.626 | 0.311892372 | 0.252 | 0.394 | 0.121 ENR+CV-4 | Suclg2 |
| Bnip3l | 0.626 | 0.310358559 | 0.252 | 0.45 | 0.166 ENR+CV-4 | Bnip3 |
| 1-Jun | 0.626 | 0.287709687 | 0.252 | 0.849 | 0.537 ENR+CV-4 | Jun |
| Ruvbl2 | 0.626 | 0.277440729 | 0.252 | 0.376 | 0.101 ENR+CV-4 | Ruvbl2 |
| Hmga1l | 0.626 | 0.269209705 | 0.252 | 0.367 | 0.094 ENR+CV-4 | Hmga1 |
| Pigt1 | 0.625 | 0.347217637 | 0.25 | 0.353 | 0.087 ENR+CV-4 | Pigt |
| Pold3 | 0.625 | 0.341609002 | 0.25 | 0.353 | 0.089 ENR+CV-4 | Pold3 |
| Mrpl38 | 0.625 | 0.300642861 | 0.25 | 0.376 | 0.104 ENR+CV-4 | Mrpl38 |
| Gna11l | 0.625 | 0.288473003 | 0.25 | 0.394 | 0.12 ENR+CV-4 | Gna11 |
| Ipo7l | 0.625 | 0.276403818 | 0.25 | 0.413 | 0.136 ENR+CV-4 | Ipo7 |
| Hif1a | 0.625 | 0.252852129 | 0.25 | 0.381 | 0.105 ENR+CV-4 | Hif1a |
| Cep55 | 0.624 | 0.411824822 | 0.248 | 0.298 | 0.042 ENR+CV-4 | Cep55 |
| Lhpp1 | 0.624 | 0.368480228 | 0.248 | 0.326 | 0.065 ENR+CV-4 | Lhpp |
| Prps2 | 0.624 | 0.330792474 | 0.248 | 0.335 | 0.072 ENR+CV-4 | Prps2 |
| Dbf4 | 0.624 | 0.330519029 | 0.248 | 0.335 | 0.073 ENR+CV-4 | Dbf4 |
| Yif1a | 0.624 | 0.327090787 | 0.248 | 0.339 | 0.077 ENR+CV-4 | Yif1a |
| Irf2bp1 | 0.624 | 0.323781201 | 0.248 | 0.33 | 0.068 ENR+CV-4 | Irf2bp1 |
| Ckap2 | 0.624 | 0.296999071 | 0.248 | 0.335 | 0.072 ENR+CV-4 | Ckap2 |
| Pdcd5l | 0.624 | 0.270689529 | 0.248 | 0.463 | 0.176 ENR+CV-4 | Pdcd5 |
| Cnot6 | 0.624 | 0.250235558 | 0.248 | 0.399 | 0.122 ENR+CV-4 | Cnot6 |
| Usp5 | 0.623 | 0.296070093 | 0.246 | 0.349 | 0.085 ENR+CV-4 | Usp5 |
| Szrd1l | 0.623 | 0.294557625 | 0.246 | 0.39 | 0.12 ENR+CV-4 | Szrd1 |
| Rapgef6l | 0.623 | 0.282129135 | 0.246 | 0.362 | 0.098 ENR+CV-4 | Rapgef6 |
| Khsrp | 0.623 | 0.281588039 | 0.246 | 0.367 | 0.1 ENR+CV-4 | Khsrp |
| Sap30 | 0.623 | 0.274040743 | 0.246 | 0.344 | 0.08 ENR+CV-4 | Sap30 |
| Ergic1 | 0.623 | 0.272957798 | 0.246 | 0.417 | 0.141 ENR+CV-4 | Ergic1 |
| Rad50 | 0.623 | 0.264624691 | 0.246 | 0.381 | 0.111 ENR+CV-4 | Rad50 |
| Med10l | 0.623 | 0.255804697 | 0.246 | 0.362 | 0.096 ENR+CV-4 | Med10 |
| Sys1 | 0.623 | 0.250792429 | 0.246 | 0.394 | 0.122 ENR+CV-4 | Sys1 |
| Gps2 | 0.622 | 0.309477253 | 0.244 | 0.353 | 0.092 ENR+CV-4 | Gps2 |
| Asf1a | 0.622 | 0.259245481 | 0.244 | 0.381 | 0.113 ENR+CV-4 | Asf1a |
| Tex10 | 0.622 | 0.250514396 | 0.244 | 0.326 | 0.066 ENR+CV-4 | Tex10 |

TABLE 1-continued

Derived gene list of the top defining genes from in vivo ileal
small intestine PCs and EECs captured on the Seq-Well platform

| | | | | | | |
|---|---|---|---|---|---|---|
| Bub1b | 0.621 | 0.420436517 | 0.242 | 0.289 | 0.04 ENR+CV-4 | Bub1b |
| B3galtl1 | 0.621 | 0.415895288 | 0.242 | 0.312 | 0.061 ENR+CV-4 | B3galtl |
| Gm224261 | 0.621 | 0.393583924 | 0.242 | 0.294 | 0.045 ENR+CV-4 | Gm22426 |
| Pigs | 0.621 | 0.334602414 | 0.242 | 0.321 | 0.067 ENR+CV-4 | Pigs |
| Vrk1 | 0.621 | 0.333487514 | 0.242 | 0.335 | 0.079 ENR+CV-4 | Vrk1 |
| Grn1 | 0.621 | 0.325156479 | 0.242 | 0.344 | 0.087 ENR+CV-4 | Grn |
| Ing2 | 0.621 | 0.319572792 | 0.242 | 0.321 | 0.066 ENR+CV-4 | Ing2 |
| Psme3 | 0.621 | 0.296635304 | 0.242 | 0.339 | 0.081 ENR+CV-4 | Psme3 |
| Galm1 | 0.621 | 0.2669532 | 0.242 | 0.367 | 0.105 ENR+CV-4 | Galm |
| Exosc8 | 0.621 | 0.266145568 | 0.242 | 0.353 | 0.093 ENR+CV-4 | Exosc8 |
| Glyr1 | 0.621 | 0.257287166 | 0.242 | 0.427 | 0.151 ENR+CV-4 | Glyr1 |
| Ap3b1 | 0.621 | 0.252537964 | 0.242 | 0.413 | 0.139 ENR+CV-4 | Ap3b1 |
| Srd5a1 | 0.62 | 0.39435197 | 0.24 | 0.307 | 0.058 ENR+CV-4 | Srd5a1 |
| Thumpd1 | 0.62 | 0.367588858 | 0.24 | 0.335 | 0.081 ENR+CV-4 | Thumpd1 |
| Ift74 | 0.62 | 0.343265365 | 0.24 | 0.312 | 0.061 ENR+CV-4 | Ift74 |
| Cdc34 | 0.62 | 0.306463274 | 0.24 | 0.353 | 0.095 ENR+CV-4 | Cdc34 |
| 5830418K08Rik | 0.62 | 0.302865047 | 0.24 | 0.326 | 0.071 ENR+CV-4 | 5830418K08Rik |
| Crot | 0.62 | 0.282663514 | 0.24 | 0.353 | 0.095 ENR+CV-4 | Crot |
| Dnajb11 | 0.62 | 0.253627237 | 0.24 | 0.372 | 0.109 ENR+CV-4 | Dnajb11 |
| Kif4 | 0.619 | 0.347123971 | 0.238 | 0.294 | 0.046 ENR+CV-4 | Kif4 |
| Pde5a | 0.619 | 0.341161587 | 0.238 | 0.312 | 0.063 ENR+CV-4 | Pde5a |
| Vat11 | 0.619 | 0.338434089 | 0.238 | 0.312 | 0.064 ENR+CV-4 | Vat1 |
| Ttc1 | 0.619 | 0.3032868 | 0.238 | 0.349 | 0.094 ENR+CV-4 | Ttc1 |
| Tmx2 | 0.619 | 0.290595514 | 0.238 | 0.349 | 0.093 ENR+CV-4 | Tmx2 |
| Eftud2 | 0.619 | 0.28894147 | 0.238 | 0.362 | 0.105 ENR+CV-4 | Eftud2 |
| Gtf3c2 | 0.618 | 0.274717511 | 0.236 | 0.339 | 0.086 ENR+CV-4 | Gtf3c2 |
| Shoc2 | 0.618 | 0.274245318 | 0.236 | 0.367 | 0.108 ENR+CV-4 | Shoc2 |
| Prkag1 | 0.618 | 0.272555399 | 0.236 | 0.321 | 0.071 ENR+CV-4 | Prkag1 |
| Ppih | 0.618 | 0.261990744 | 0.236 | 0.349 | 0.094 ENR+CV-4 | Ppih |
| Tex9 | 0.617 | 0.383774176 | 0.234 | 0.28 | 0.039 ENR+CV-4 | Tex9 |
| Tsfm | 0.617 | 0.30071894 | 0.234 | 0.344 | 0.093 ENR+CV-4 | Tsfm |
| Rpia | 0.617 | 0.279474692 | 0.234 | 0.33 | 0.08 ENR+CV-4 | Rpia |
| Zfp7031 | 0.617 | 0.274955225 | 0.234 | 0.362 | 0.107 ENR+CV-4 | Zfp703 |
| Clic61 | 0.617 | 0.272257971 | 0.234 | 0.349 | 0.097 ENR+CV-4 | Clic6 |
| Cdc25a | 0.617 | 0.263242377 | 0.234 | 0.335 | 0.085 ENR+CV-4 | Cdc25a |
| Pola1 | 0.617 | 0.256622112 | 0.234 | 0.339 | 0.087 ENR+CV-4 | Pola1 |
| Snx21 | 0.617 | 0.250007402 | 0.234 | 0.381 | 0.123 ENR+CV-4 | Snx2 |
| Umps | 0.616 | 0.32148919 | 0.232 | 0.335 | 0.088 ENR+CV-4 | Umps |
| Mcm3 | 0.616 | 0.315931459 | 0.232 | 0.358 | 0.107 ENR+CV-4 | Mcm3 |
| Dhx40 | 0.616 | 0.309394901 | 0.232 | 0.326 | 0.08 ENR+CV-4 | Dhx40 |
| Dnaaf2 | 0.616 | 0.304305212 | 0.232 | 0.303 | 0.06 ENR+CV-4 | Dnaaf2 |
| Zcchc17 | 0.616 | 0.256421425 | 0.232 | 0.372 | 0.117 ENR+CV-4 | Zcchc17 |
| Stk11 | 0.616 | 0.250995595 | 0.232 | 0.349 | 0.097 ENR+CV-4 | Stk11 |
| Mrpl191 | 0.616 | 0.25063656 | 0.232 | 0.367 | 0.113 ENR+CV-4 | Mrpl19 |
| Snord49b1 | 0.615 | 0.369311634 | 0.23 | 0.284 | 0.046 ENR+CV-4 | Snord49b |
| A430005L14Rik | 0.615 | 0.32039217 | 0.23 | 0.317 | 0.073 ENR+CV-4 | A430005L14Rik |
| Rtfdc1 | 0.615 | 0.308006814 | 0.23 | 0.339 | 0.095 ENR+CV-4 | Rtfdc1 |
| Ntmt11 | 0.615 | 0.293681918 | 0.23 | 0.321 | 0.077 ENR+CV-4 | Ntmt1 |
| Mogs | 0.615 | 0.283989883 | 0.23 | 0.303 | 0.061 ENR+CV-4 | Mogs |
| Sephs21 | 0.615 | 0.250925623 | 0.23 | 0.399 | 0.14 ENR+CV-4 | Sephs2 |
| Atf32 | 0.614 | 0.358958947 | 0.228 | 0.518 | 0.255 ENR+CV-4 | Atf3 |
| Tceal81 | 0.614 | 0.323786018 | 0.228 | 0.353 | 0.107 ENR+CV-4 | Tceal8 |
| Fam98b | 0.614 | 0.310854215 | 0.228 | 0.33 | 0.089 ENR+CV-4 | Fam98b |
| Brd71 | 0.614 | 0.305282135 | 0.228 | 0.367 | 0.119 ENR+CV-4 | Brd7 |
| Nmt2 | 0.614 | 0.294021041 | 0.228 | 0.33 | 0.087 ENR+CV-4 | Nmt2 |
| Dpp8 | 0.614 | 0.293236292 | 0.228 | 0.33 | 0.087 ENR+CV-4 | Dpp8 |
| Cenpk | 0.614 | 0.275361044 | 0.228 | 0.289 | 0.051 ENR+CV-4 | Cenpk |
| Jagn1 | 0.614 | 0.274150281 | 0.228 | 0.372 | 0.12 ENR+CV-4 | Jagn1 |
| Stk381 | 0.614 | 0.270959938 | 0.228 | 0.335 | 0.09 ENR+CV-4 | Stk38 |
| Atic | 0.614 | 0.266512734 | 0.228 | 0.381 | 0.129 ENR+CV-4 | Atic |
| Naa35 | 0.614 | 0.265968033 | 0.228 | 0.349 | 0.103 ENR+CV-4 | Naa35 |
| Gnl3l | 0.614 | 0.260701927 | 0.228 | 0.349 | 0.101 ENR+CV-4 | Gnl3l |
| Hnrnpul1 | 0.614 | 0.257772384 | 0.228 | 0.367 | 0.119 ENR+CV-4 | Hnrnpul1 |
| D2Wsu81e | 0.613 | 0.368401553 | 0.226 | 0.303 | 0.067 ENR+CV-4 | D2Wsu81e |
| Cenpp | 0.613 | 0.317145041 | 0.226 | 0.284 | 0.048 ENR+CV-4 | Cenpp |
| Zak | 0.613 | 0.309756947 | 0.226 | 0.317 | 0.077 ENR+CV-4 | Zak |
| Mrpl4 | 0.613 | 0.283629564 | 0.226 | 0.349 | 0.104 ENR+CV-4 | Mrpl4 |
| Srsf9 | 0.613 | 0.25845922 | 0.226 | 0.335 | 0.092 ENR+CV-4 | Srsf9 |
| Prkar2a1 | 0.613 | 0.257638718 | 0.226 | 0.367 | 0.12 ENR+CV-4 | Prkar2a |
| Zc3h18 | 0.613 | 0.257334768 | 0.226 | 0.353 | 0.106 ENR+CV-4 | Zc3h18 |
| Slc31a11 | 0.613 | 0.254220284 | 0.226 | 0.367 | 0.119 ENR+CV-4 | Slc31a1 |
| Mpst1 | 0.612 | 0.340138084 | 0.224 | 0.294 | 0.06 ENR+CV-4 | Mpst |
| Agpat1 | 0.612 | 0.322153203 | 0.224 | 0.312 | 0.076 ENR+CV-4 | Agpat1 |
| Cdc42se2 | 0.612 | 0.286017471 | 0.224 | 0.307 | 0.071 ENR+CV-4 | Cdc42se2 |
| Lss | 0.612 | 0.284279086 | 0.224 | 0.326 | 0.087 ENR+CV-4 | Lss |
| Slc25a15 | 0.612 | 0.271353559 | 0.224 | 0.303 | 0.067 ENR+CV-4 | Slc25a15 |
| Sertad1 | 0.612 | 0.271337923 | 0.224 | 0.321 | 0.081 ENR+CV-4 | Sertad1 |

TABLE 1-continued

Derived gene list of the top defining genes from in vivo ileal
small intestine PCs and EECs captured on the Seq-Well platform

| Gene | | | | | | Gene |
|---|---|---|---|---|---|---|
| Eri1 | 0.612 | 0.267068661 | 0.224 | 0.321 | 0.082 ENR+CV-4 | Eri1 |
| Tnfaip1 | 0.612 | 0.255671673 | 0.224 | 0.326 | 0.086 ENR+CV-4 | Tnfaip1 |
| Ppp3ca | 0.612 | 0.253076048 | 0.224 | 0.339 | 0.097 ENR+CV-4 | Ppp3ca |
| Casp31 | 0.612 | 0.250496293 | 0.224 | 0.326 | 0.087 ENR+CV-4 | Casp3 |
| Gm246011 | 0.611 | 0.435601181 | 0.222 | 0.266 | 0.039 ENR+CV-4 | Gm24601 |
| Melk | 0.611 | 0.377722843 | 0.222 | 0.275 | 0.046 ENR+CV-4 | Melk |
| Ncapg2 | 0.611 | 0.330955973 | 0.222 | 0.28 | 0.05 ENR+CV-4 | Ncapg2 |
| Tmed1 | 0.611 | 0.320936223 | 0.222 | 0.284 | 0.054 ENR+CV-4 | Tmed1 |
| Tssc4 | 0.611 | 0.299007834 | 0.222 | 0.307 | 0.074 ENR+CV-4 | Tssc4 |
| Slc25a13 | 0.611 | 0.284516581 | 0.222 | 0.298 | 0.066 ENR+CV-4 | Slc25a13 |
| Acads1 | 0.611 | 0.256787714 | 0.222 | 0.33 | 0.092 ENR+CV-4 | Acads |
| Plod21 | 0.61 | 0.435768294 | 0.22 | 0.261 | 0.037 ENR+CV-4 | Plod2 |
| Blm | 0.61 | 0.414459228 | 0.22 | 0.252 | 0.029 ENR+CV-4 | Blm |
| Nuf2 | 0.61 | 0.37954463 | 0.22 | 0.266 | 0.041 ENR+CV-4 | Nuf2 |
| 2310011J03Rik | 0.61 | 0.302501514 | 0.22 | 0.298 | 0.067 ENR+CV-4 | 2310011J03Rik |
| C330027C09Rik | 0.61 | 0.287450981 | 0.22 | 0.289 | 0.057 ENR+CV-4 | C330027C09Rik |
| Efr3a1 | 0.61 | 0.277233886 | 0.22 | 0.344 | 0.106 ENR+CV-4 | Efr3a |
| Irf81 | 0.61 | 0.271948655 | 0.22 | 0.312 | 0.078 ENR+CV-4 | Irf8 |
| Wipi1 | 0.61 | 0.271457838 | 0.22 | 0.312 | 0.078 ENR+CV-4 | Wipi1 |
| Grb2 | 0.61 | 0.270873786 | 0.22 | 0.33 | 0.094 ENR+CV-4 | Grb2 |
| Cyp2j61 | 0.61 | 0.265117202 | 0.22 | 0.381 | 0.137 ENR+CV-4 | Cyp2j6 |
| Yipf1 | 0.61 | 0.251337274 | 0.22 | 0.326 | 0.089 ENR+CV-4 | Yipf1 |
| Kif20a | 0.609 | 0.364371068 | 0.218 | 0.28 | 0.054 ENR+CV-4 | Kif20a |
| Eefsec | 0.609 | 0.361513738 | 0.218 | 0.271 | 0.045 ENR+CV-4 | Eefsec |
| Shcbp1 | 0.609 | 0.340993964 | 0.218 | 0.261 | 0.037 ENR+CV-4 | Shcbp1 |
| Sympk | 0.609 | 0.311329566 | 0.218 | 0.303 | 0.073 ENR+CV-4 | Sympk |
| Kpna3 | 0.609 | 0.303616678 | 0.218 | 0.33 | 0.099 ENR+CV-4 | Kpna3 |
| Gtf2e2 | 0.609 | 0.280838174 | 0.218 | 0.326 | 0.093 ENR+CV-4 | Gtf2e2 |
| Alcam | 0.609 | 0.270193664 | 0.218 | 0.326 | 0.093 ENR+CV-4 | Alcam |
| Rad51ap1 | 0.608 | 0.351250973 | 0.216 | 0.261 | 0.039 ENR+CV-4 | Rad51ap1 |
| Tead21 | 0.608 | 0.311897227 | 0.216 | 0.307 | 0.08 ENR+CV-4 | Tead2 |
| Micu1 | 0.608 | 0.305973606 | 0.216 | 0.298 | 0.072 ENR+CV-4 | Micu1 |
| Asl | 0.608 | 0.302896244 | 0.216 | 0.284 | 0.058 ENR+CV-4 | Asl |
| D10Wsu102e1 | 0.608 | 0.300028757 | 0.216 | 0.303 | 0.076 ENR+CV-4 | D10Wsu102e |
| Afg3l1 | 0.608 | 0.293809122 | 0.216 | 0.298 | 0.071 ENR+CV-4 | Afg3l1 |
| Prmt7 | 0.608 | 0.292948387 | 0.216 | 0.298 | 0.071 ENR+CV-4 | Prmt7 |
| Mtap | 0.608 | 0.292469689 | 0.216 | 0.307 | 0.077 ENR+CV-4 | Mtap |
| Cited21 | 0.608 | 0.272663432 | 0.216 | 0.303 | 0.074 ENR+CV-4 | Cited2 |
| Srebf2 | 0.608 | 0.269659638 | 0.216 | 0.344 | 0.11 ENR+CV-4 | Srebf2 |
| Acp6 | 0.607 | 0.357136764 | 0.214 | 0.289 | 0.067 ENR+CV-4 | Acp6 |
| Kif18a | 0.607 | 0.332108695 | 0.214 | 0.248 | 0.029 ENR+CV-4 | Kif18a |
| Qsox2 | 0.607 | 0.287273561 | 0.214 | 0.289 | 0.064 ENR+CV-4 | Qsox2 |
| Yars | 0.607 | 0.268201161 | 0.214 | 0.326 | 0.094 ENR+CV-4 | Yars |
| Nob11 | 0.607 | 0.259556749 | 0.214 | 0.326 | 0.096 ENR+CV-4 | Nob1 |
| Lias | 0.607 | 0.251568136 | 0.214 | 0.289 | 0.064 ENR+CV-4 | Lias |
| Sapcd2 | 0.606 | 0.344509264 | 0.212 | 0.243 | 0.027 ENR+CV-4 | Sapcd2 |
| 3110082I17Rik | 0.606 | 0.319165232 | 0.212 | 0.266 | 0.047 ENR+CV-4 | 3110082I17Rik |
| Elovl7 | 0.606 | 0.271177344 | 0.212 | 0.298 | 0.074 ENR+CV-4 | Elovl7 |
| Dhrs7b | 0.606 | 0.269370767 | 0.212 | 0.317 | 0.088 ENR+CV-4 | Dhrs7b |
| Clic4 | 0.606 | 0.260096064 | 0.212 | 0.294 | 0.07 ENR+CV-4 | Clic4 |
| Arf3 | 0.606 | 0.257913189 | 0.212 | 0.303 | 0.077 ENR+CV-4 | Arf3 |
| Tnfrsf19 | 0.606 | 0.255708385 | 0.212 | 0.298 | 0.072 ENR+CV-4 | Tnfrsf19 |
| Tcf19 | 0.605 | 0.401346154 | 0.21 | 0.252 | 0.038 ENR+CV-4 | Tcf19 |
| Arhgap11a | 0.605 | 0.349102838 | 0.21 | 0.266 | 0.05 ENR+CV-4 | Arhgap11a |
| Apeh | 0.605 | 0.31415317 | 0.21 | 0.28 | 0.06 ENR+CV-4 | Apeh |
| Exosc2 | 0.605 | 0.305886006 | 0.21 | 0.289 | 0.068 ENR+CV-4 | Exosc2 |
| Ipo9 | 0.605 | 0.303488268 | 0.21 | 0.28 | 0.06 ENR+CV-4 | Ipo9 |
| Ppp1r35 | 0.605 | 0.302479141 | 0.21 | 0.266 | 0.048 ENR+CV-4 | Ppp1r35 |
| Camta11 | 0.605 | 0.266391661 | 0.21 | 0.28 | 0.059 ENR+CV-4 | Camta1 |
| Senp1 | 0.605 | 0.261566805 | 0.21 | 0.289 | 0.068 ENR+CV-4 | Senp1 |
| Prpf31 | 0.605 | 0.257009663 | 0.21 | 0.307 | 0.083 ENR+CV-4 | Prpf31 |
| Snrnp25 | 0.605 | 0.253226085 | 0.21 | 0.289 | 0.067 ENR+CV-4 | Snrnp25 |
| Gcdh | 0.604 | 0.36156399 | 0.208 | 0.261 | 0.048 ENR+CV-4 | Gcdh |
| Ptpro | 0.604 | 0.352918684 | 0.208 | 0.261 | 0.047 ENR+CV-4 | Ptpro |
| Tst1 | 0.604 | 0.301813014 | 0.208 | 0.275 | 0.059 ENR+CV-4 | Tst |
| Ankrd101 | 0.604 | 0.291383813 | 0.208 | 0.303 | 0.083 ENR+CV-4 | Ankrd10 |
| Nvl | 0.604 | 0.28641588 | 0.208 | 0.298 | 0.078 ENR+CV-4 | Nvl |
| Coro2a | 0.604 | 0.261692037 | 0.208 | 0.28 | 0.061 ENR+CV-4 | Coro2a |
| Cpox1 | 0.604 | 0.259814646 | 0.208 | 0.326 | 0.1 ENR+CV-4 | Cpox |
| Hist1h1d1 | 0.604 | 0.252042307 | 0.208 | 0.326 | 0.1 ENR+CV-4 | Hist1h1d |
| Trip13 | 0.603 | 0.302790032 | 0.206 | 0.248 | 0.036 ENR+CV-4 | Trip13 |
| Ncapd2 | 0.603 | 0.301622055 | 0.206 | 0.275 | 0.059 ENR+CV-4 | Ncapd2 |
| Zdhhc16 | 0.603 | 0.281306104 | 0.206 | 0.28 | 0.064 ENR+CV-4 | Zdhhc16 |
| Ythdf1 | 0.603 | 0.280808703 | 0.206 | 0.275 | 0.058 ENR+CV-4 | Ythdf1 |
| 9-Sep | 0.603 | 0.25856948 | 0.206 | 0.275 | 0.058 ENR+CV-4 | 9-Sep |
| Crlf11 | 0.602 | 0.324599888 | 0.204 | 0.243 | 0.034 ENR+CV-4 | Crlf1 |
| Wdr76 | 0.602 | 0.29817531 | 0.204 | 0.252 | 0.042 ENR+CV-4 | Wdr76 |

TABLE 1-continued

Derived gene list of the top defining genes from in vivo ileal
small intestine PCs and EECs captured on the Seq-Well platform

| | | | | | | | |
|---|---|---|---|---|---|---|---|
| Slc35a4 | 0.602 | 0.277903123 | 0.204 | 0.275 | 0.063 | ENR+CV-4 | Slc35a4 |
| Tdg | 0.601 | 0.307606777 | 0.202 | 0.252 | 0.044 | ENR+CV-4 | Tdg |
| Ssbp4 | 0.601 | 0.29747273 | 0.202 | 0.275 | 0.063 | ENR+CV-4 | Ssbp4 |
| Ndc1 | 0.601 | 0.272287224 | 0.202 | 0.252 | 0.044 | ENR+CV-4 | Ndc1 |
| Mtfp11 | 0.601 | 0.271952175 | 0.202 | 0.266 | 0.057 | ENR+CV-4 | Mtfp1 |
| Aqr | 0.601 | 0.266211331 | 0.202 | 0.307 | 0.093 | ENR+CV-4 | Aqr |
| Anln | 0.601 | 0.263897525 | 0.202 | 0.266 | 0.054 | ENR+CV-4 | Anln |
| Mrpl49 | 0.601 | 0.250560827 | 0.202 | 0.294 | 0.079 | ENR+CV-4 | Mrpl49 |
| Tmem120a | 0.601 | 0.250542084 | 0.202 | 0.275 | 0.062 | ENR+CV-4 | Tmem120a |
| Olfm41 | 0.81 | 1.226911976 | 0.62 | 0.862 | 0.273 | ENR-1 | Olfm4 |
| Cps12 | 0.783 | 0.788114568 | 0.566 | 0.922 | 0.343 | ENR-1 | Cps1 |
| Fabp2 | 0.743 | 0.511011373 | 0.486 | 0.9 | 0.383 | ENR-1 | Fabp2 |
| Pigr | 0.738 | 0.610489813 | 0.476 | 0.929 | 0.497 | ENR-1 | Pigr |
| Gm51604 | 0.736 | 0.614479498 | 0.472 | 0.81 | 0.282 | ENR-1 | Gm5160 |
| Gm94932 | 0.734 | 0.581927207 | 0.468 | 0.848 | 0.339 | ENR-1 | Gm9493 |
| Clca41 | 0.732 | 0.746235305 | 0.464 | 0.851 | 0.436 | ENR-1 | Clca4 |
| Ccl25 | 0.73 | 0.580549634 | 0.46 | 0.74 | 0.226 | ENR-1 | Ccl25 |
| Npm11 | 0.727 | 0.459468514 | 0.454 | 0.985 | 0.74 | ENR-1 | Npm1 |
| Hspd1 | 0.723 | 0.530228945 | 0.446 | 0.929 | 0.488 | ENR-1 | Hspd1 |
| Otc | 0.721 | 0.645007147 | 0.442 | 0.628 | 0.154 | ENR-1 | Otc |
| Gm10260 | 0.712 | 0.542083966 | 0.424 | 0.736 | 0.26 | ENR-1 | Gm10260 |
| Gm4968 | 0.711 | 0.540868382 | 0.422 | 0.706 | 0.232 | ENR-1 | Gm4968 |
| Rpl42 | 0.711 | 0.330994832 | 0.422 | 1 | 0.938 | ENR-1 | Rpl4 |
| Hook12 | 0.706 | 0.479315331 | 0.412 | 0.892 | 0.442 | ENR-1 | Hook1 |
| Lgals43 | 0.706 | 0.378396697 | 0.412 | 0.989 | 0.797 | ENR-1 | Lgals4 |
| Aldh1b12 | 0.705 | 0.491175323 | 0.41 | 0.81 | 0.335 | ENR-1 | Aldh1b1 |
| Rpsa-ps10 | 0.702 | 0.475830688 | 0.404 | 0.662 | 0.198 | ENR-1 | Rpsa-ps10 |
| C1qbp1 | 0.702 | 0.432385739 | 0.404 | 0.803 | 0.318 | ENR-1 | C1qbp |
| Plcb3 | 0.7 | 0.579716423 | 0.4 | 0.632 | 0.188 | ENR-1 | Plcb3 |
| Rps2-ps10 | 0.699 | 0.537995138 | 0.398 | 0.599 | 0.152 | ENR-1 | Rps2-ps10 |
| Amica11 | 0.699 | 0.448912034 | 0.398 | 0.725 | 0.256 | ENR-1 | Amica1 |
| Eef1b22 | 0.698 | 0.345420178 | 0.396 | 0.996 | 0.882 | ENR-1 | Eef1b2 |
| Phgr14 | 0.697 | 0.41170045 | 0.394 | 0.87 | 0.419 | ENR-1 | Phgr1 |
| Pycard | 0.696 | 0.473739525 | 0.392 | 0.736 | 0.276 | ENR-1 | Pycard |
| Gsto1 | 0.695 | 0.432865357 | 0.39 | 0.803 | 0.345 | ENR-1 | Gsto1 |
| Rps61 | 0.694 | 0.464066021 | 0.388 | 0.855 | 0.431 | ENR-1 | Rps6 |
| Gnb2l11 | 0.694 | 0.321098814 | 0.388 | 0.993 | 0.92 | ENR-1 | Gnb2l1 |
| Gm5619 | 0.693 | 0.498968076 | 0.386 | 0.572 | 0.139 | ENR-1 | Gm5619 |
| Mt2 | 0.692 | 0.430955838 | 0.384 | 0.933 | 0.509 | ENR-1 | Mt2 |
| Ncl1 | 0.692 | 0.382552891 | 0.384 | 0.993 | 0.796 | ENR-1 | Ncl |
| Lsm3 | 0.69 | 0.454639507 | 0.38 | 0.602 | 0.176 | ENR-1 | Lsm3 |
| Rpl13-ps3 | 0.688 | 0.425179545 | 0.376 | 0.74 | 0.287 | ENR-1 | Rpl13-ps3 |
| Hspe1 | 0.687 | 0.432319145 | 0.374 | 0.918 | 0.532 | ENR-1 | Hspe1 |
| Rps3a11 | 0.687 | 0.307529405 | 0.374 | 0.996 | 0.883 | ENR-1 | Rps3a1 |
| Mki671 | 0.686 | 0.560040298 | 0.372 | 0.691 | 0.299 | ENR-1 | Mki67 |
| Rpl9-ps1 | 0.686 | 0.418515475 | 0.372 | 0.599 | 0.169 | ENR-1 | Rpl9-ps1 |
| Rpsa | 0.685 | 0.395225063 | 0.37 | 0.963 | 0.631 | ENR-1 | Rpsa |
| Myb1 | 0.683 | 0.561335579 | 0.366 | 0.491 | 0.105 | ENR-1 | Myb |
| Gm87303 | 0.683 | 0.353463848 | 0.366 | 0.967 | 0.716 | ENR-1 | Gm8730 |
| Rps111 | 0.682 | 0.330472403 | 0.364 | 0.993 | 0.874 | ENR-1 | Rps11 |
| Gm65762 | 0.681 | 0.431941937 | 0.362 | 0.788 | 0.368 | ENR-1 | Gm6576 |
| Ppia2 | 0.681 | 0.409660487 | 0.362 | 0.877 | 0.49 | ENR-1 | Ppia |
| Lbr1 | 0.68 | 0.499493887 | 0.36 | 0.595 | 0.194 | ENR-1 | Lbr |
| Sfpq | 0.679 | 0.379030203 | 0.358 | 0.725 | 0.288 | ENR-1 | Sfpq |
| Gmnn1 | 0.678 | 0.529686811 | 0.356 | 0.565 | 0.177 | ENR-1 | Gmnn |
| Gm5786 | 0.678 | 0.447990342 | 0.356 | 0.587 | 0.181 | ENR-1 | Gm5786 |
| Ldha3 | 0.678 | 0.375459293 | 0.356 | 0.97 | 0.681 | ENR-1 | Ldha |
| Hsp90ab12 | 0.677 | 0.298716487 | 0.354 | 0.996 | 0.931 | ENR-1 | Hsp90ab1 |
| Gm7808 | 0.675 | 0.378422191 | 0.35 | 0.628 | 0.213 | ENR-1 | Gm7808 |
| Ivns1abp | 0.674 | 0.402223109 | 0.348 | 0.777 | 0.376 | ENR-1 | Ivns1abp |
| Rpa3 | 0.673 | 0.4066077 | 0.346 | 0.677 | 0.279 | ENR-1 | Rpa3 |
| Gstt2 | 0.672 | 0.490324512 | 0.344 | 0.498 | 0.127 | ENR-1 | Gstt2 |
| Rpl121 | 0.672 | 0.422347108 | 0.344 | 0.673 | 0.269 | ENR-1 | Rpl12 |
| Csrp2 | 0.672 | 0.421135636 | 0.344 | 0.565 | 0.179 | ENR-1 | Csrp2 |
| Pa2g41 | 0.672 | 0.417996373 | 0.344 | 0.855 | 0.485 | ENR-1 | Pa2g4 |
| Anp32b | 0.672 | 0.402906637 | 0.344 | 0.829 | 0.435 | ENR-1 | Anp32b |
| Tomm51 | 0.672 | 0.40230326 | 0.344 | 0.677 | 0.274 | ENR-1 | Tomm5 |
| Atp5a11 | 0.672 | 0.36600291 | 0.344 | 0.948 | 0.606 | ENR-1 | Atp5a1 |
| Rps10-ps11 | 0.672 | 0.352878057 | 0.344 | 0.888 | 0.477 | ENR-1 | Rps10-ps1 |
| Rpl21-ps4 | 0.671 | 0.418847992 | 0.342 | 0.572 | 0.178 | ENR-1 | Rpl21-ps4 |
| AI747448 | 0.67 | 0.652552706 | 0.34 | 0.454 | 0.097 | ENR-1 | AI747448 |
| Gm8225 | 0.67 | 0.401330178 | 0.34 | 0.602 | 0.205 | ENR-1 | Gm8225 |
| Hspa91 | 0.67 | 0.400450086 | 0.34 | 0.825 | 0.421 | ENR-1 | Hspa9 |
| Rpl10-ps32 | 0.67 | 0.347414958 | 0.34 | 0.706 | 0.289 | ENR-1 | Rpl10-ps3 |
| Pcbp1 | 0.67 | 0.345300966 | 0.34 | 0.743 | 0.312 | ENR-1 | Pcbp1 |
| Hspa81 | 0.67 | 0.317339776 | 0.34 | 0.985 | 0.768 | ENR-1 | Hspa8 |
| Tuba1b1 | 0.669 | 0.429958101 | 0.338 | 0.77 | 0.384 | ENR-1 | Tuba1b |

TABLE 1-continued

Derived gene list of the top defining genes from in vivo ileal
small intestine PCs and EECs captured on the Seq-Well platform

| | | | | | | |
|---|---|---|---|---|---|---|
| Fgfbp12 | 0.668 | 0.452645497 | 0.336 | 0.617 | 0.233 ENR-1 | Fgfbp1 |
| Xist3 | 0.668 | 0.397245425 | 0.336 | 0.922 | 0.668 ENR-1 | Xist |
| Sdc41 | 0.668 | 0.369889255 | 0.336 | 0.665 | 0.262 ENR-1 | Sdc4 |
| Gm81861 | 0.668 | 0.362123452 | 0.336 | 0.651 | 0.245 ENR-1 | Gm8186 |
| Slc25a53 | 0.668 | 0.341986244 | 0.336 | 0.981 | 0.759 ENR-1 | Slc25a5 |
| Tm4sf20 | 0.668 | 0.338504883 | 0.336 | 0.818 | 0.402 ENR-1 | Tm4sf20 |
| Mt13 | 0.668 | 0.28320989 | 0.336 | 0.974 | 0.652 ENR-1 | Mt1 |
| BX465866.1 | 0.667 | 0.433915498 | 0.334 | 0.487 | 0.118 ENR-1 | BX465866.1 |
| Fus1 | 0.667 | 0.356180534 | 0.334 | 0.725 | 0.311 ENR-1 | Fus |
| Gm102754 | 0.667 | 0.344343909 | 0.334 | 0.855 | 0.464 ENR-1 | Gm10275 |
| Pgk1 | 0.666 | 0.435093852 | 0.332 | 0.554 | 0.183 ENR-1 | Pgk1 |
| Ndufs7 | 0.665 | 0.348635098 | 0.33 | 0.688 | 0.29 ENR-1 | Ndufs7 |
| Gm64721 | 0.664 | 0.374146183 | 0.328 | 0.695 | 0.298 ENR-1 | Gm6472 |
| Slc12a21 | 0.664 | 0.364531809 | 0.328 | 0.881 | 0.491 ENR-1 | Slc12a2 |
| Atp5b3 | 0.664 | 0.330332862 | 0.328 | 0.97 | 0.722 ENR-1 | Atp5b |
| Rps71 | 0.664 | 0.301876888 | 0.328 | 0.97 | 0.801 ENR-1 | Rps7 |
| Smc3 | 0.663 | 0.40819151 | 0.326 | 0.572 | 0.204 ENR-1 | Smc3 |
| Mif3 | 0.663 | 0.36948123 | 0.326 | 0.877 | 0.497 ENR-1 | Mif |
| Top2a1 | 0.662 | 0.506413829 | 0.324 | 0.665 | 0.318 ENR-1 | Top2a |
| Eif4b | 0.662 | 0.36240463 | 0.324 | 0.721 | 0.332 ENR-1 | Eif4b |
| Snrpd11 | 0.662 | 0.358486456 | 0.324 | 0.743 | 0.347 ENR-1 | Snrpd1 |
| Cdca72 | 0.662 | 0.3575881 | 0.324 | 0.639 | 0.247 ENR-1 | Cdca7 |
| Nop58 | 0.661 | 0.345033957 | 0.322 | 0.773 | 0.376 ENR-1 | Nop58 |
| Hnrnpa2b11 | 0.661 | 0.319002237 | 0.322 | 0.959 | 0.717 ENR-1 | Hnrnpa2b1 |
| Sri | 0.66 | 0.326372167 | 0.32 | 0.643 | 0.255 ENR-1 | Sri |
| Tkt3 | 0.66 | 0.322378661 | 0.32 | 0.862 | 0.453 ENR-1 | Tkt |
| Gm8444 | 0.659 | 0.359255972 | 0.318 | 0.543 | 0.178 ENR-1 | Gm8444 |
| Banf11 | 0.659 | 0.33622482 | 0.318 | 0.818 | 0.427 ENR-1 | Banf1 |
| Hmgb21 | 0.658 | 0.423978338 | 0.316 | 0.836 | 0.479 ENR-1 | Hmgb2 |
| Sae12 | 0.657 | 0.410209832 | 0.314 | 0.561 | 0.205 ENR-1 | Sae1 |
| Eprs | 0.657 | 0.334116667 | 0.314 | 0.68 | 0.296 ENR-1 | Eprs |
| Tubb4b1 | 0.656 | 0.45617908 | 0.312 | 0.77 | 0.422 ENR-1 | Tubb4b |
| Cct6a | 0.656 | 0.371029052 | 0.312 | 0.755 | 0.38 ENR-1 | Cct6a |
| Myh9 | 0.656 | 0.348453619 | 0.312 | 0.762 | 0.382 ENR-1 | Myh9 |
| Mgam | 0.655 | 0.366801804 | 0.31 | 0.539 | 0.185 ENR-1 | Mgam |
| Ppp1r1b2 | 0.655 | 0.324269294 | 0.31 | 0.654 | 0.269 ENR-1 | Ppp1r1b |
| Vdac11 | 0.655 | 0.323905033 | 0.31 | 0.691 | 0.303 ENR-1 | Vdac1 |
| Rps27a1 | 0.655 | 0.31406595 | 0.31 | 0.792 | 0.404 ENR-1 | Rps27a |
| Aqp42 | 0.654 | 0.483930711 | 0.308 | 0.439 | 0.112 ENR-1 | Aqp4 |
| Isx | 0.654 | 0.449974563 | 0.308 | 0.398 | 0.071 ENR-1 | Isx |
| Smc41 | 0.654 | 0.4227726 | 0.308 | 0.617 | 0.268 ENR-1 | Smc4 |
| Rpl7a4 | 0.654 | 0.312469507 | 0.308 | 0.918 | 0.587 ENR-1 | Rpl7a |
| Crip13 | 0.654 | 0.269382773 | 0.308 | 0.818 | 0.393 ENR-1 | Crip1 |
| Gm98431 | 0.654 | 0.25822927 | 0.308 | 0.981 | 0.784 ENR-1 | Gm9843 |
| Gm21957 | 0.653 | 0.368238886 | 0.306 | 0.461 | 0.119 ENR-1 | Gm21957 |
| Eno12 | 0.653 | 0.339219386 | 0.306 | 0.721 | 0.343 ENR-1 | Eno1 |
| Ndufb5 | 0.653 | 0.31354239 | 0.306 | 0.796 | 0.406 ENR-1 | Ndufb5 |
| Rpl101 | 0.653 | 0.310938354 | 0.306 | 0.639 | 0.259 ENR-1 | Rpl10 |
| Rps23 | 0.653 | 0.261191332 | 0.306 | 0.993 | 0.932 ENR-1 | Rps2 |
| Rps26-ps1 | 0.652 | 0.283947704 | 0.304 | 0.58 | 0.212 ENR-1 | Rps26-ps1 |
| Snhg1 | 0.651 | 0.326347079 | 0.302 | 0.74 | 0.367 ENR-1 | Snhg1 |
| Rp91 | 0.651 | 0.313872741 | 0.302 | 0.569 | 0.214 ENR-1 | Rp9 |
| Rpl13a-ps11 | 0.651 | 0.303074859 | 0.302 | 0.721 | 0.34 ENR-1 | Rpl13a-ps1 |
| Cetn3 | 0.651 | 0.267908334 | 0.302 | 0.632 | 0.257 ENR-1 | Cetn3 |
| Nasp | 0.65 | 0.343166728 | 0.3 | 0.595 | 0.244 ENR-1 | Nasp |
| Mrpl18 | 0.65 | 0.333886645 | 0.3 | 0.61 | 0.257 ENR-1 | Mrpl18 |
| Btf31 | 0.65 | 0.330101253 | 0.3 | 0.807 | 0.444 ENR-1 | Btf3 |
| Ndufc2 | 0.65 | 0.294977597 | 0.3 | 0.84 | 0.488 ENR-1 | Ndufc2 |
| 2810417H13Rik1 | 0.649 | 0.441318779 | 0.298 | 0.572 | 0.237 ENR-1 | 2810417H13Rik |
| Serbp13 | 0.649 | 0.308088704 | 0.298 | 0.955 | 0.71 ENR-1 | Serbp1 |
| Anxa41 | 0.649 | 0.273304253 | 0.298 | 0.907 | 0.567 ENR-1 | Anxa4 |
| Hjurp1 | 0.648 | 0.326033972 | 0.296 | 0.52 | 0.182 ENR-1 | Hjurp |
| Cct3 | 0.648 | 0.320941303 | 0.296 | 0.706 | 0.341 ENR-1 | Cct3 |
| Rad211 | 0.648 | 0.288329432 | 0.296 | 0.576 | 0.222 ENR-1 | Rad21 |
| Lgals9 | 0.648 | 0.271388134 | 0.296 | 0.621 | 0.253 ENR-1 | Lgals9 |
| Rpl222 | 0.648 | 0.259854933 | 0.296 | 0.974 | 0.784 ENR-1 | Rpl22 |
| Eef24 | 0.648 | 0.257394821 | 0.296 | 0.974 | 0.845 ENR-1 | Eef2 |
| Eif4ebp1 | 0.647 | 0.354843341 | 0.294 | 0.539 | 0.206 ENR-1 | Eif4ebp1 |
| Ccnd11 | 0.647 | 0.352833112 | 0.294 | 0.513 | 0.181 ENR-1 | Ccnd1 |
| Nap1l11 | 0.647 | 0.344971346 | 0.294 | 0.595 | 0.246 ENR-1 | Nap1l1 |
| Gm16519 | 0.647 | 0.339888997 | 0.294 | 0.409 | 0.09 ENR-1 | Gm16519 |
| Pgp1 | 0.647 | 0.3240671 | 0.294 | 0.561 | 0.22 ENR-1 | Pgp |
| Gpx2 | 0.647 | 0.287687416 | 0.294 | 0.967 | 0.73 ENR-1 | Gpx2 |
| Hnf4a2 | 0.646 | 0.320348152 | 0.292 | 0.584 | 0.233 ENR-1 | Hnf4a |
| Srsf31 | 0.646 | 0.306726302 | 0.292 | 0.848 | 0.476 ENR-1 | Srsf3 |
| Ehf1 | 0.646 | 0.301988942 | 0.292 | 0.695 | 0.32 ENR-1 | Ehf |
| Gm10704 | 0.646 | 0.287726976 | 0.292 | 0.513 | 0.171 ENR-1 | Gm10704 |

TABLE 1-continued

Derived gene list of the top defining genes from in vivo ileal
small intestine PCs and EECs captured on the Seq-Well platform

| | | | | | | | |
|---|---|---|---|---|---|---|---|
| Cdca81 | 0.645 | 0.38096075 | 0.29 | 0.476 | 0.153 | ENR-1 | Cdca8 |
| Shmt21 | 0.645 | 0.365979259 | 0.29 | 0.457 | 0.136 | ENR-1 | Shmt2 |
| Usp11 | 0.645 | 0.35681899 | 0.29 | 0.498 | 0.17 | ENR-1 | Usp1 |
| Dut1 | 0.645 | 0.342085578 | 0.29 | 0.584 | 0.244 | ENR-1 | Dut |
| Rpl15 | 0.645 | 0.328011524 | 0.29 | 0.565 | 0.224 | ENR-1 | Rpl15 |
| Sdhd | 0.645 | 0.316089911 | 0.29 | 0.688 | 0.324 | ENR-1 | Sdhd |
| Dnajc2 | 0.645 | 0.315913549 | 0.29 | 0.599 | 0.255 | ENR-1 | Dnajc2 |
| Ranbp12 | 0.645 | 0.291501672 | 0.29 | 0.885 | 0.52 | ENR-1 | Ranbp1 |
| Cyc12 | 0.645 | 0.289124485 | 0.29 | 0.703 | 0.333 | ENR-1 | Cyc1 |
| Txn11 | 0.645 | 0.258663712 | 0.29 | 0.97 | 0.742 | ENR-1 | Txn1 |
| Gm9396 | 0.644 | 0.319678558 | 0.288 | 0.442 | 0.119 | ENR-1 | Gm9396 |
| Nucks11 | 0.644 | 0.27441388 | 0.288 | 0.677 | 0.309 | ENR-1 | Nucks1 |
| Rgcc2 | 0.643 | 0.383057267 | 0.286 | 0.688 | 0.365 | ENR-1 | Rgcc |
| Pcna | 0.643 | 0.349800646 | 0.286 | 0.625 | 0.284 | ENR-1 | Pcna |
| Cct21 | 0.643 | 0.286296153 | 0.286 | 0.788 | 0.407 | ENR-1 | Cct2 |
| Rrm11 | 0.642 | 0.420118982 | 0.284 | 0.48 | 0.166 | ENR-1 | Rrm1 |
| Cct4 | 0.642 | 0.299091989 | 0.284 | 0.725 | 0.366 | ENR-1 | Cct4 |
| Ckb2 | 0.642 | 0.289101867 | 0.284 | 0.636 | 0.28 | ENR-1 | Ckb |
| Tspan82 | 0.642 | 0.288455293 | 0.284 | 0.896 | 0.58 | ENR-1 | Tspan8 |
| Rpl310 | 0.642 | 0.253576604 | 0.284 | 0.981 | 0.757 | ENR-1 | Rpl3 |
| Oat2 | 0.642 | 0.253190029 | 0.284 | 0.803 | 0.403 | ENR-1 | Oat |
| Kpnb1 | 0.642 | 0.251126694 | 0.284 | 0.58 | 0.229 | ENR-1 | Kpnb1 |
| Gm20594 | 0.641 | 0.427031535 | 0.282 | 0.48 | 0.161 | ENR-1 | Gm20594 |
| Eif3e1 | 0.641 | 0.275593267 | 0.282 | 0.729 | 0.364 | ENR-1 | Eif3e |
| Sdha | 0.641 | 0.267501367 | 0.282 | 0.599 | 0.253 | ENR-1 | Sdha |
| G3bp12 | 0.641 | 0.2625822 | 0.282 | 0.651 | 0.287 | ENR-1 | G3bp1 |
| Zfp36l21 | 0.64 | 0.403068788 | 0.28 | 0.424 | 0.122 | ENR-1 | Zfp36l2 |
| Ewsr1 | 0.64 | 0.346328646 | 0.28 | 0.543 | 0.219 | ENR-1 | Ewsr1 |
| Lsm51 | 0.64 | 0.335376399 | 0.28 | 0.442 | 0.132 | ENR-1 | Lsm5 |
| Zfp292 | 0.64 | 0.319066818 | 0.28 | 0.55 | 0.226 | ENR-1 | Zfp292 |
| Pfkl1 | 0.64 | 0.312465906 | 0.28 | 0.491 | 0.171 | ENR-1 | Pfkl |
| Prdx4 | 0.64 | 0.300581795 | 0.28 | 0.569 | 0.234 | ENR-1 | Prdx4 |
| Idh3b | 0.64 | 0.291613703 | 0.28 | 0.543 | 0.212 | ENR-1 | Idh3b |
| Sdhb1 | 0.64 | 0.278080313 | 0.28 | 0.758 | 0.383 | ENR-1 | Sdhb |
| Baz1b | 0.64 | 0.272217475 | 0.28 | 0.55 | 0.216 | ENR-1 | Baz1b |
| Naca1 | 0.64 | 0.260990617 | 0.28 | 0.952 | 0.69 | ENR-1 | Naca |
| Uqcrfs1 | 0.64 | 0.259735004 | 0.28 | 0.695 | 0.332 | ENR-1 | Uqcrfs1 |
| Dhx9 | 0.64 | 0.257751695 | 0.28 | 0.625 | 0.267 | ENR-1 | Dhx9 |
| Idh3g | 0.639 | 0.296611246 | 0.278 | 0.517 | 0.192 | ENR-1 | Idh3g |
| Ssb | 0.639 | 0.281741475 | 0.278 | 0.836 | 0.477 | ENR-1 | Ssb |
| Hnrnpab1 | 0.639 | 0.261403714 | 0.278 | 0.84 | 0.472 | ENR-1 | Hnrnpab |
| Nolc1 | 0.638 | 0.306214591 | 0.276 | 0.532 | 0.211 | ENR-1 | Nolc1 |
| Cnbp1 | 0.638 | 0.289047293 | 0.276 | 0.87 | 0.576 | ENR-1 | Cnbp |
| Tmbim4 | 0.638 | 0.269731981 | 0.276 | 0.569 | 0.23 | ENR-1 | Tmbim4 |
| Ybx31 | 0.638 | 0.252539707 | 0.276 | 0.602 | 0.253 | ENR-1 | Ybx3 |
| Fh1 | 0.637 | 0.323621581 | 0.274 | 0.498 | 0.188 | ENR-1 | Fh1 |
| Cbx51 | 0.637 | 0.289384623 | 0.274 | 0.52 | 0.196 | ENR-1 | Cbx5 |
| Srsf6 | 0.637 | 0.270063014 | 0.274 | 0.628 | 0.285 | ENR-1 | Srsf6 |
| Rpl18a1 | 0.637 | 0.260388942 | 0.274 | 0.978 | 0.762 | ENR-1 | Rpl18a |
| Trap1 | 0.636 | 0.315986561 | 0.272 | 0.457 | 0.151 | ENR-1 | Trap1 |
| Gmds | 0.636 | 0.313941446 | 0.272 | 0.584 | 0.258 | ENR-1 | Gmds |
| Phb22 | 0.636 | 0.305145739 | 0.272 | 0.617 | 0.286 | ENR-1 | Phb2 |
| Bzw22 | 0.636 | 0.300870805 | 0.272 | 0.628 | 0.289 | ENR-1 | Bzw2 |
| Naa502 | 0.636 | 0.272737394 | 0.272 | 0.539 | 0.214 | ENR-1 | Naa50 |
| Mrpl42 | 0.636 | 0.254389379 | 0.272 | 0.68 | 0.324 | ENR-1 | Mrpl42 |
| Gdi2 | 0.636 | 0.250755394 | 0.272 | 0.699 | 0.347 | ENR-1 | Gdi2 |
| Gm4204 | 0.635 | 0.308685191 | 0.27 | 0.42 | 0.123 | ENR-1 | Gm4204 |
| Slc20a1 | 0.635 | 0.293038821 | 0.27 | 0.45 | 0.141 | ENR-1 | Slc20a1 |
| Lyar1 | 0.635 | 0.289249614 | 0.27 | 0.491 | 0.18 | ENR-1 | Lyar |
| Mrpl13 | 0.635 | 0.267662755 | 0.27 | 0.572 | 0.249 | ENR-1 | Mrpl13 |
| Pnn | 0.635 | 0.254946844 | 0.27 | 0.558 | 0.231 | ENR-1 | Pnn |
| Ndufb111 | 0.635 | 0.252808048 | 0.27 | 0.807 | 0.457 | ENR-1 | Ndufb11 |
| Cdca31 | 0.634 | 0.459009033 | 0.268 | 0.428 | 0.139 | ENR-1 | Cdca3 |
| Hist1h1e1 | 0.634 | 0.398016565 | 0.268 | 0.55 | 0.247 | ENR-1 | Hist1h1e |
| Ifngr1 | 0.634 | 0.370040438 | 0.268 | 0.465 | 0.168 | ENR-1 | Ifngr1 |
| Mcm72 | 0.634 | 0.369013081 | 0.268 | 0.439 | 0.146 | ENR-1 | Mcm7 |
| Pck2 | 0.634 | 0.330423604 | 0.268 | 0.435 | 0.137 | ENR-1 | Pck2 |
| Gm12728 | 0.634 | 0.301848003 | 0.268 | 0.472 | 0.161 | ENR-1 | Gm12728 |
| Tomm20 | 0.634 | 0.282951476 | 0.268 | 0.628 | 0.295 | ENR-1 | Tomm20 |
| Thyn1 | 0.634 | 0.269786332 | 0.268 | 0.457 | 0.154 | ENR-1 | Thyn1 |
| Pdss1 | 0.633 | 0.394521786 | 0.266 | 0.387 | 0.103 | ENR-1 | Pdss1 |
| Nlrp62 | 0.633 | 0.353986297 | 0.266 | 0.45 | 0.153 | ENR-1 | Nlrp6 |
| Ipo51 | 0.633 | 0.277911794 | 0.266 | 0.483 | 0.173 | ENR-1 | Ipo5 |
| Mrps28 | 0.633 | 0.257911504 | 0.266 | 0.461 | 0.154 | ENR-1 | Mrps28 |
| Rbbp71 | 0.633 | 0.255611373 | 0.266 | 0.625 | 0.286 | ENR-1 | Rbbp7 |
| Dek1 | 0.633 | 0.252701943 | 0.266 | 0.665 | 0.32 | ENR-1 | Dek |
| Tpr | 0.633 | 0.250504124 | 0.266 | 0.688 | 0.338 | ENR-1 | Tpr |

TABLE 1-continued

Derived gene list of the top defining genes from in vivo ileal
small intestine PCs and EECs captured on the Seq-Well platform

| | | | | | | |
|---|---|---|---|---|---|---|
| Ceacam1 | 0.632 | 0.356260706 | 0.264 | 0.387 | 0.1 ENR-1 | Ceacam1 |
| Tfam | 0.632 | 0.318779299 | 0.264 | 0.428 | 0.137 ENR-1 | Tfam |
| Clic62 | 0.632 | 0.316359452 | 0.264 | 0.375 | 0.093 ENR-1 | Clic6 |
| Psat11 | 0.632 | 0.29919317 | 0.264 | 0.468 | 0.167 ENR-1 | Psat1 |
| Ddx39b | 0.632 | 0.279836241 | 0.264 | 0.595 | 0.268 ENR-1 | Ddx39b |
| Dtymk1 | 0.631 | 0.265083873 | 0.262 | 0.572 | 0.25 ENR-1 | Dtymk |
| Prdx6 | 0.631 | 0.252793667 | 0.262 | 0.762 | 0.405 ENR-1 | Prdx6 |
| Pla2g4a | 0.63 | 0.443345474 | 0.26 | 0.335 | 0.063 ENR-1 | Pla2g4a |
| Tstd1 | 0.63 | 0.424007975 | 0.26 | 0.361 | 0.082 ENR-1 | Tstd1 |
| Cluh | 0.63 | 0.331570871 | 0.26 | 0.431 | 0.142 ENR-1 | Cluh |
| Cdk11 | 0.63 | 0.326736265 | 0.26 | 0.45 | 0.155 ENR-1 | Cdk1 |
| Cotl12 | 0.63 | 0.267261676 | 0.26 | 0.558 | 0.242 ENR-1 | Cotl1 |
| Syncrip | 0.63 | 0.256960384 | 0.26 | 0.532 | 0.219 ENR-1 | Syncrip |
| Mybbp1a1 | 0.63 | 0.255358253 | 0.26 | 0.535 | 0.223 ENR-1 | Mybbp1a |
| Cenpe1 | 0.629 | 0.424400928 | 0.258 | 0.416 | 0.138 ENR-1 | Cenpe |
| Tsix | 0.629 | 0.354774907 | 0.258 | 0.372 | 0.094 ENR-1 | Tsix |
| Gm10073 | 0.629 | 0.291463462 | 0.258 | 0.42 | 0.131 ENR-1 | Gm10073 |
| Alad | 0.629 | 0.290141073 | 0.258 | 0.472 | 0.176 ENR-1 | Alad |
| Pcna-ps2 | 0.628 | 0.376617835 | 0.256 | 0.394 | 0.116 ENR-1 | Pcna-ps2 |
| Slc35a3 | 0.628 | 0.314092412 | 0.256 | 0.398 | 0.12 ENR-1 | Slc35a3 |
| Orc5 | 0.627 | 0.315965573 | 0.254 | 0.576 | 0.272 ENR-1 | Orc5 |
| Uhrf1 | 0.626 | 0.261594985 | 0.252 | 0.398 | 0.12 ENR-1 | Uhrf1 |
| Ptbp1 | 0.626 | 0.255468863 | 0.252 | 0.476 | 0.181 ENR-1 | Ptbp1 |
| Rps3a3 | 0.626 | 0.252704803 | 0.252 | 0.487 | 0.187 ENR-1 | Rps3a3 |
| Smc21 | 0.625 | 0.417543003 | 0.25 | 0.446 | 0.171 ENR-1 | Smc2 |
| Zbtb38 | 0.625 | 0.389531928 | 0.25 | 0.349 | 0.087 ENR-1 | Zbtb38 |
| Ifi30 | 0.625 | 0.252448471 | 0.25 | 0.424 | 0.143 ENR-1 | Ifi30 |
| Hat11 | 0.624 | 0.366105231 | 0.248 | 0.394 | 0.125 ENR-1 | Hat1 |
| Farsb | 0.624 | 0.352945644 | 0.248 | 0.413 | 0.14 ENR-1 | Farsb |
| Mrps22 | 0.624 | 0.334874923 | 0.248 | 0.394 | 0.125 ENR-1 | Mrps22 |
| Mthfd2 | 0.624 | 0.30998256 | 0.248 | 0.409 | 0.136 ENR-1 | Mthfd2 |
| Orc6 | 0.624 | 0.29631237 | 0.248 | 0.431 | 0.153 ENR-1 | Orc6 |
| Taf15 | 0.624 | 0.287430524 | 0.248 | 0.457 | 0.173 ENR-1 | Taf15 |
| Lmnb11 | 0.624 | 0.273240544 | 0.248 | 0.431 | 0.15 ENR-1 | Lmnb1 |
| 2410004N09Rik | 0.624 | 0.273161599 | 0.248 | 0.442 | 0.158 ENR-1 | 2410004N09Rik |
| Smchd11 | 0.623 | 0.340895957 | 0.246 | 0.398 | 0.131 ENR-1 | Smchd1 |
| Gm16477 | 0.623 | 0.322625249 | 0.246 | 0.327 | 0.065 ENR-1 | Gm16477 |
| Tmem70 | 0.623 | 0.319533005 | 0.246 | 0.409 | 0.14 ENR-1 | Tmem70 |
| Mcm6 | 0.623 | 0.316644108 | 0.246 | 0.424 | 0.15 ENR-1 | Mcm6 |
| Kcne3 | 0.622 | 0.399945438 | 0.244 | 0.335 | 0.076 ENR-1 | Kcne3 |
| Ube2c1 | 0.622 | 0.386105811 | 0.244 | 0.502 | 0.227 ENR-1 | Ube2c |
| Dnmt1 | 0.622 | 0.265218687 | 0.244 | 0.424 | 0.147 ENR-1 | Dnmt1 |
| Dnajc91 | 0.621 | 0.305095217 | 0.242 | 0.416 | 0.148 ENR-1 | Dnajc9 |
| Gm23061 | 0.621 | 0.294862203 | 0.242 | 0.353 | 0.091 ENR-1 | Gm23061 |
| Nudcd2 | 0.621 | 0.265061999 | 0.242 | 0.476 | 0.193 ENR-1 | Nudcd2 |
| Prim11 | 0.62 | 0.329141152 | 0.24 | 0.398 | 0.137 ENR-1 | Prim1 |
| Atic1 | 0.62 | 0.31749315 | 0.24 | 0.387 | 0.126 ENR-1 | Atic |
| Eps8l3 | 0.62 | 0.277593248 | 0.24 | 0.387 | 0.122 ENR-1 | Eps8l3 |
| 2700029M09Rik1 | 0.62 | 0.272732307 | 0.24 | 0.435 | 0.164 ENR-1 | 2700029M09Rik |
| Mrpl47 | 0.62 | 0.255591746 | 0.24 | 0.379 | 0.117 ENR-1 | Mrpl47 |
| Naa38 | 0.62 | 0.254939564 | 0.24 | 0.465 | 0.186 ENR-1 | Naa38 |
| Lgr51 | 0.619 | 0.304444276 | 0.238 | 0.439 | 0.17 ENR-1 | Lgr5 |
| Cftr1 | 0.619 | 0.282925861 | 0.238 | 0.405 | 0.141 ENR-1 | Cftr |
| Kcnq13 | 0.619 | 0.259810417 | 0.238 | 0.424 | 0.154 ENR-1 | Kcnq1 |
| Tpx21 | 0.618 | 0.416123253 | 0.236 | 0.338 | 0.091 ENR-1 | Tpx2 |
| Aldh9a13 | 0.618 | 0.267660465 | 0.236 | 0.446 | 0.177 ENR-1 | Aldh9a1 |
| Cldn15 | 0.618 | 0.260919111 | 0.236 | 0.435 | 0.164 ENR-1 | Cldn15 |
| Nudt191 | 0.618 | 0.258782806 | 0.236 | 0.383 | 0.124 ENR-1 | Nudt19 |
| Hist1h1b1 | 0.617 | 0.398288984 | 0.234 | 0.413 | 0.16 ENR-1 | Hist1h1b |
| Ppp1r14d | 0.617 | 0.340373465 | 0.234 | 0.375 | 0.12 ENR-1 | Ppp1r14d |
| Cth | 0.617 | 0.337156072 | 0.234 | 0.379 | 0.123 ENR-1 | Cth |
| Shmt12 | 0.617 | 0.305092778 | 0.234 | 0.372 | 0.118 ENR-1 | Shmt1 |
| Atad3a1 | 0.617 | 0.277127157 | 0.234 | 0.413 | 0.15 ENR-1 | Atad3a |
| Gm15013 | 0.617 | 0.263283977 | 0.234 | 0.342 | 0.087 ENR-1 | Gm15013 |
| Ddx392 | 0.617 | 0.258776088 | 0.234 | 0.435 | 0.169 ENR-1 | Ddx39 |
| Tardbp | 0.617 | 0.251972117 | 0.234 | 0.472 | 0.198 ENR-1 | Tardbp |
| Hells1 | 0.616 | 0.311683278 | 0.232 | 0.442 | 0.177 ENR-1 | Hells |
| Mpp6 | 0.616 | 0.27534406 | 0.232 | 0.353 | 0.102 ENR-1 | Mpp6 |
| Ccna21 | 0.615 | 0.36865724 | 0.23 | 0.357 | 0.111 ENR-1 | Ccna2 |
| Gm1123 | 0.615 | 0.294352836 | 0.23 | 0.368 | 0.114 ENR-1 | Gm1123 |
| Gm26384 | 0.615 | 0.289628944 | 0.23 | 0.32 | 0.074 ENR-1 | Gm26384 |
| Ces2e | 0.615 | 0.264393442 | 0.23 | 0.361 | 0.107 ENR-1 | Ces2e |
| Cenpw1 | 0.615 | 0.254500541 | 0.23 | 0.383 | 0.127 ENR-1 | Cenpw |
| Mcm2 | 0.614 | 0.300638904 | 0.228 | 0.342 | 0.098 ENR-1 | Mcm2 |
| Ppif | 0.614 | 0.274205035 | 0.228 | 0.338 | 0.093 ENR-1 | Ppif |
| Nudt21 | 0.613 | 0.277498277 | 0.226 | 0.383 | 0.132 ENR-1 | Nudt21 |
| Sfxn12 | 0.613 | 0.257158425 | 0.226 | 0.446 | 0.185 ENR-1 | Sfxn1 |

TABLE 1-continued

Derived gene list of the top defining genes from in vivo ileal
small intestine PCs and EECs captured on the Seq-Well platform

| Gene | | | | | | | |
|---|---|---|---|---|---|---|---|
| AC102758.1 | 0.612 | 0.314790527 | 0.224 | 0.297 | 0.06 | ENR-1 | AC102758.1 |
| Mrpl192 | 0.612 | 0.281890511 | 0.224 | 0.353 | 0.111 | ENR-1 | Mrpl19 |
| Zfp326 | 0.612 | 0.279228361 | 0.224 | 0.349 | 0.107 | ENR-1 | Zfp326 |
| Whsc1 | 0.611 | 0.273424152 | 0.222 | 0.383 | 0.137 | ENR-1 | Whsc1 |
| Bdh12 | 0.611 | 0.264436491 | 0.222 | 0.361 | 0.119 | ENR-1 | Bdh1 |
| Tk1 | 0.61 | 0.404265379 | 0.22 | 0.305 | 0.076 | ENR-1 | Tk1 |
| Mcm51 | 0.61 | 0.321610611 | 0.22 | 0.327 | 0.093 | ENR-1 | Mcm5 |
| 4-Sep | 0.61 | 0.311020966 | 0.22 | 0.323 | 0.091 | ENR-1 | 4-Sep |
| Noxo1 | 0.61 | 0.308469986 | 0.22 | 0.331 | 0.094 | ENR-1 | Noxo1 |
| Cks2 | 0.61 | 0.270850368 | 0.22 | 0.372 | 0.129 | ENR-1 | Cks2 |
| Mlxipl | 0.61 | 0.265959441 | 0.22 | 0.368 | 0.123 | ENR-1 | Mlxipl |
| Spc241 | 0.609 | 0.266983333 | 0.218 | 0.342 | 0.106 | ENR-1 | Spc24 |
| Usp102 | 0.608 | 0.270835083 | 0.216 | 0.368 | 0.13 | ENR-1 | Usp10 |
| Tyms1 | 0.607 | 0.291261675 | 0.214 | 0.431 | 0.19 | ENR-1 | Tyms |
| Rad501 | 0.607 | 0.272187207 | 0.214 | 0.342 | 0.111 | ENR-1 | Rad50 |
| Gm5277 | 0.607 | 0.265545355 | 0.214 | 0.32 | 0.09 | ENR-1 | Gm5277 |
| Ppip5k2 | 0.607 | 0.256774763 | 0.214 | 0.368 | 0.132 | ENR-1 | Ppip5k2 |
| Kif151 | 0.606 | 0.359126054 | 0.212 | 0.316 | 0.091 | ENR-1 | Kif15 |
| Kif231 | 0.606 | 0.341872716 | 0.212 | 0.32 | 0.095 | ENR-1 | Kif23 |
| Ncapg1 | 0.606 | 0.283457176 | 0.212 | 0.301 | 0.076 | ENR-1 | Ncapg |
| Larp1 | 0.606 | 0.259656167 | 0.212 | 0.327 | 0.099 | ENR-1 | Larp1 |
| Topbp1 | 0.605 | 0.333514036 | 0.21 | 0.32 | 0.096 | ENR-1 | Topbp1 |
| Pbk1 | 0.605 | 0.303729342 | 0.21 | 0.331 | 0.104 | ENR-1 | Pbk |
| Atf5 | 0.605 | 0.29322935 | 0.21 | 0.335 | 0.105 | ENR-1 | Atf5 |
| Aadac | 0.605 | 0.278947227 | 0.21 | 0.283 | 0.061 | ENR-1 | Aadac |
| Igfbp4 | 0.605 | 0.252429489 | 0.21 | 0.368 | 0.135 | ENR-1 | Igfbp4 |
| Suclg22 | 0.604 | 0.28045907 | 0.208 | 0.349 | 0.121 | ENR-1 | Suclg2 |
| Iars1 | 0.604 | 0.253578975 | 0.208 | 0.361 | 0.132 | ENR-1 | Iars |
| Kcnn4 | 0.603 | 0.337667044 | 0.206 | 0.264 | 0.05 | ENR-1 | Kcnn4 |
| Kif20b1 | 0.603 | 0.328995429 | 0.206 | 0.338 | 0.118 | ENR-1 | Kif20b |
| Vdr | 0.603 | 0.316247425 | 0.206 | 0.301 | 0.082 | ENR-1 | Vdr |
| Pvrl3 | 0.603 | 0.273691265 | 0.206 | 0.375 | 0.148 | ENR-1 | Pvrl3 |
| Stat6 | 0.603 | 0.268186966 | 0.206 | 0.346 | 0.121 | ENR-1 | Stat6 |
| Mrps31 | 0.603 | 0.266483653 | 0.206 | 0.338 | 0.114 | ENR-1 | Mrps31 |
| Wwp12 | 0.602 | 0.291033289 | 0.204 | 0.335 | 0.116 | ENR-1 | Wwp1 |
| 1190007I07Rik | 0.602 | 0.282890167 | 0.204 | 0.327 | 0.107 | ENR-1 | 1190007I07Rik |
| Fut8 | 0.602 | 0.25580908 | 0.204 | 0.327 | 0.105 | ENR-1 | Fut8 |
| Hist1h1d2 | 0.601 | 0.347949629 | 0.202 | 0.312 | 0.099 | ENR-1 | Hist1h1d |
| Lgals44 | 0.699 | 0.501826029 | 0.398 | 0.935 | 0.778 | ENR-2 | Lgals4 |
| Olfm42 | 0.691 | 0.866124588 | 0.382 | 0.596 | 0.237 | ENR-2 | Olfm4 |
| mt-Co13 | 0.689 | 0.473587407 | 0.378 | 0.984 | 0.906 | ENR-2 | mt-Co1 |
| mt-Nd53 | 0.674 | 0.495547814 | 0.348 | 0.931 | 0.82 | ENR-2 | mt-Nd5 |
| Mt21 | 0.667 | 0.53344477 | 0.334 | 0.74 | 0.483 | ENR-2 | Mt2 |
| Phgr15 | 0.663 | 0.641090421 | 0.326 | 0.653 | 0.394 | ENR-2 | Phgr1 |
| Fabp21 | 0.658 | 0.554010839 | 0.316 | 0.63 | 0.358 | ENR-2 | Fabp2 |
| Ldha4 | 0.655 | 0.469817439 | 0.31 | 0.842 | 0.663 | ENR-2 | Ldha |
| Gm98432 | 0.655 | 0.429905094 | 0.31 | 0.86 | 0.778 | ENR-2 | Gm9843 |
| mt-Nd43 | 0.655 | 0.427437692 | 0.31 | 0.936 | 0.854 | ENR-2 | mt-Nd4 |
| Gm87304 | 0.654 | 0.484944949 | 0.308 | 0.817 | 0.709 | ENR-2 | Gm8730 |
| Mt14 | 0.649 | 0.336854409 | 0.298 | 0.851 | 0.627 | ENR-2 | Mt1 |
| Eef1b23 | 0.643 | 0.355242681 | 0.286 | 0.928 | 0.878 | ENR-2 | Eef1b2 |
| Cps13 | 0.64 | 0.631577696 | 0.28 | 0.572 | 0.327 | ENR-2 | Cps1 |
| Pigr1 | 0.639 | 0.515270596 | 0.278 | 0.67 | 0.484 | ENR-2 | Pigr |
| Gm94933 | 0.634 | 0.679133467 | 0.268 | 0.527 | 0.327 | ENR-2 | Gm9493 |
| Aldoa3 | 0.611 | 0.302710337 | 0.222 | 0.781 | 0.634 | ENR-2 | Aldoa |
| Gm102601 | 0.608 | 0.623963105 | 0.216 | 0.422 | 0.252 | ENR-2 | Gm10260 |
| Rps72 | 0.607 | 0.29763812 | 0.214 | 0.852 | 0.8 | ENR-2 | Rps7 |
| Ccl251 | 0.605 | 0.610584751 | 0.21 | 0.403 | 0.216 | ENR-2 | Ccl25 |
| Gm51605 | 0.601 | 0.594103232 | 0.202 | 0.437 | 0.278 | ENR-2 | Gm5160 |
| Aldob | 0.848 | 1.623037231 | 0.696 | 0.892 | 0.414 | ENR-3 | Aldob |
| Fabp12 | 0.845 | 2.384427893 | 0.69 | 0.789 | 0.187 | ENR-3 | Fabp1 |
| Fabp22 | 0.817 | 1.388857472 | 0.634 | 0.865 | 0.364 | ENR-3 | Fabp2 |
| Prap1 | 0.815 | 1.655418071 | 0.63 | 0.771 | 0.215 | ENR-3 | Prap1 |
| Mt15 | 0.81 | 1.023983132 | 0.62 | 0.962 | 0.639 | ENR-3 | Mt1 |
| Sis | 0.788 | 1.764132223 | 0.576 | 0.695 | 0.17 | ENR-3 | Sis |
| Mt22 | 0.784 | 0.934407414 | 0.568 | 0.892 | 0.495 | ENR-3 | Mt2 |
| Lgals45 | 0.773 | 0.667785349 | 0.546 | 0.97 | 0.79 | ENR-3 | Lgals4 |
| Phgr16 | 0.77 | 0.937737335 | 0.54 | 0.833 | 0.403 | ENR-3 | Phgr1 |
| 2210404O07Rik | 0.745 | 1.228859113 | 0.49 | 0.677 | 0.25 | ENR-3 | 2210404O07Rik |
| Ldha5 | 0.72 | 0.581090664 | 0.44 | 0.952 | 0.67 | ENR-3 | Ldha |
| mt-Co14 | 0.718 | 0.495052223 | 0.436 | 0.99 | 0.913 | ENR-3 | mt-Co1 |
| Ccl252 | 0.711 | 1.056012878 | 0.422 | 0.602 | 0.216 | ENR-3 | Ccl25 |
| mt-Nd22 | 0.707 | 0.425689812 | 0.414 | 0.99 | 0.922 | ENR-3 | mt-Nd2 |
| Reg1 | 0.706 | 2.261530152 | 0.412 | 0.448 | 0.045 | ENR-3 | Reg1 |
| Adh1 | 0.699 | 1.181060248 | 0.398 | 0.538 | 0.167 | ENR-3 | Adh1 |
| mt-Nd44 | 0.689 | 0.432937052 | 0.378 | 0.968 | 0.86 | ENR-3 | mt-Nd4 |
| Apoa1 | 0.677 | 1.597349307 | 0.354 | 0.388 | 0.038 | ENR-3 | Apoa1 |

TABLE 1-continued

Derived gene list of the top defining genes from in vivo ileal
small intestine PCs and EECs captured on the Seq-Well platform

| | | | | | | | |
|---|---|---|---|---|---|---|---|
| Khk | 0.676 | 1.099938046 | 0.352 | 0.46 | 0.132 | ENR-3 | Khk |
| Crip14 | 0.674 | 0.637244586 | 0.348 | 0.695 | 0.386 | ENR-3 | Crip1 |
| Olfm43 | 0.673 | 0.651208536 | 0.346 | 0.614 | 0.271 | ENR-3 | Olfm4 |
| Gm98433 | 0.672 | 0.432324038 | 0.344 | 0.9 | 0.783 | ENR-3 | Gm9843 |
| Pigr2 | 0.671 | 0.558387269 | 0.342 | 0.747 | 0.495 | ENR-3 | Pigr |
| mt-Nd54 | 0.671 | 0.413011431 | 0.342 | 0.944 | 0.829 | ENR-3 | mt-Nd5 |
| Gm94934 | 0.667 | 0.640979807 | 0.334 | 0.633 | 0.337 | ENR-3 | Gm9493 |
| Dak | 0.662 | 1.060434569 | 0.324 | 0.43 | 0.127 | ENR-3 | Dak |
| Txn12 | 0.66 | 0.399287767 | 0.32 | 0.894 | 0.739 | ENR-3 | Txn1 |
| Gsta1 | 0.659 | 1.284957561 | 0.318 | 0.394 | 0.083 | ENR-3 | Gsta1 |
| Pycard1 | 0.657 | 0.699920387 | 0.314 | 0.55 | 0.273 | ENR-3 | Pycard |
| Spink3 | 0.653 | 1.201322069 | 0.306 | 0.329 | 0.024 | ENR-3 | Spink3 |
| Tm4sf201 | 0.651 | 0.692000575 | 0.302 | 0.635 | 0.401 | ENR-3 | Tm4sf20 |
| Ces2e1 | 0.65 | 0.948245183 | 0.3 | 0.384 | 0.094 | ENR-3 | Ces2e |
| 2200002D01Rik | 0.65 | 0.773089545 | 0.3 | 0.494 | 0.216 | ENR-3 | 2200002D01Rik |
| Apoa4 | 0.647 | 1.447596801 | 0.294 | 0.319 | 0.027 | ENR-3 | Apoa4 |
| Gm87305 | 0.643 | 0.383652378 | 0.286 | 0.855 | 0.716 | ENR-3 | Gm8730 |
| Aldoa4 | 0.642 | 0.38898651 | 0.284 | 0.839 | 0.644 | ENR-3 | Aldoa |
| Oat3 | 0.636 | 0.637382252 | 0.272 | 0.612 | 0.403 | ENR-3 | Oat |
| mt-Co33 | 0.635 | 0.49603252 | 0.27 | 0.667 | 0.451 | ENR-3 | mt-Co3 |
| Slc5a11 | 0.634 | 0.937974442 | 0.268 | 0.39 | 0.143 | ENR-3 | Slc5a1 |
| Eno13 | 0.634 | 0.552498148 | 0.268 | 0.576 | 0.341 | ENR-3 | Eno1 |
| Apoc3 | 0.633 | 1.228218134 | 0.266 | 0.285 | 0.02 | ENR-3 | Apoc3 |
| Uqcrq3 | 0.631 | 0.333356592 | 0.262 | 0.902 | 0.751 | ENR-3 | Uqcrq |
| Gm64722 | 0.63 | 0.525151863 | 0.26 | 0.534 | 0.296 | ENR-3 | Gm6472 |
| Atpif1 | 0.629 | 0.330177413 | 0.258 | 0.892 | 0.79 | ENR-3 | Atpif1 |
| Rps112 | 0.629 | 0.2836447 | 0.258 | 0.942 | 0.874 | ENR-3 | Rps11 |
| Dbi4 | 0.627 | 0.376348252 | 0.254 | 0.914 | 0.816 | ENR-3 | Dbi |
| Tpi14 | 0.627 | 0.342440983 | 0.254 | 0.789 | 0.579 | ENR-3 | Tpi1 |
| Mttp | 0.624 | 0.847934898 | 0.248 | 0.331 | 0.094 | ENR-3 | Mttp |
| Mgam1 | 0.623 | 0.777260509 | 0.246 | 0.406 | 0.182 | ENR-3 | Mgam |
| Cps14 | 0.623 | 0.42542916 | 0.246 | 0.59 | 0.349 | ENR-3 | Cps1 |
| Gsto11 | 0.622 | 0.508334376 | 0.244 | 0.552 | 0.348 | ENR-3 | Gsto1 |
| AI7474481 | 0.621 | 0.801846827 | 0.242 | 0.331 | 0.093 | ENR-3 | AI747448 |
| Leap2 | 0.62 | 1.106124032 | 0.24 | 0.261 | 0.022 | ENR-3 | Leap2 |
| Cox7b2 | 0.62 | 0.340366475 | 0.24 | 0.843 | 0.717 | ENR-3 | Cox7b |
| Rps62 | 0.619 | 0.41840331 | 0.238 | 0.622 | 0.434 | ENR-3 | Rps6 |
| Cyb5 | 0.616 | 0.583760239 | 0.232 | 0.544 | 0.375 | ENR-3 | Cyb5 |
| Cyp4f14 | 0.614 | 0.951089623 | 0.228 | 0.255 | 0.029 | ENR-3 | Cyp4f14 |
| Rbp2 | 0.614 | 0.926216412 | 0.228 | 0.249 | 0.023 | ENR-3 | Rbp2 |
| Cox6b12 | 0.612 | 0.300429863 | 0.224 | 0.865 | 0.714 | ENR-3 | Cox6b1 |
| Sult1b1 | 0.61 | 0.933386812 | 0.22 | 0.255 | 0.038 | ENR-3 | Sult1b1 |
| Chchd102 | 0.608 | 0.556228058 | 0.216 | 0.49 | 0.31 | ENR-3 | Chchd10 |
| Gpi13 | 0.608 | 0.452768762 | 0.216 | 0.56 | 0.38 | ENR-3 | Gpi1 |
| Rps10-ps12 | 0.608 | 0.397633043 | 0.216 | 0.639 | 0.482 | ENR-3 | Rps10-ps1 |
| 2010001M06Rik | 0.607 | 0.745550688 | 0.214 | 0.285 | 0.076 | ENR-3 | 2010001M06Rik |
| Gm51606 | 0.607 | 0.447997513 | 0.214 | 0.496 | 0.288 | ENR-3 | Gm5160 |
| Mif4 | 0.607 | 0.338131266 | 0.214 | 0.681 | 0.499 | ENR-3 | Mif |
| Gm102602 | 0.606 | 0.484237543 | 0.212 | 0.458 | 0.266 | ENR-3 | Gm10260 |
| Slc25a54 | 0.605 | 0.263160706 | 0.21 | 0.855 | 0.762 | ENR-3 | Slc25a5 |
| AA467197 | 0.603 | 0.951083532 | 0.206 | 0.247 | 0.043 | ENR-3 | AA467197 |
| Maoa | 0.603 | 0.828195852 | 0.206 | 0.285 | 0.087 | ENR-3 | Maoa |
| Sult1d1 | 0.603 | 0.639520744 | 0.206 | 0.333 | 0.131 | ENR-3 | Sult1d1 |
| St3gal4 | 0.602 | 0.784461899 | 0.204 | 0.233 | 0.031 | ENR-3 | St3gal4 |
| Aadac1 | 0.602 | 0.759046337 | 0.204 | 0.255 | 0.054 | ENR-3 | Aadac |
| Otc1 | 0.602 | 0.582354235 | 0.204 | 0.353 | 0.159 | ENR-3 | Otc |
| Lypd8 | 0.602 | 0.529117096 | 0.204 | 0.48 | 0.31 | ENR-3 | Lypd8 |
| Rps2-ps101 | 0.601 | 0.555761639 | 0.202 | 0.351 | 0.156 | ENR-3 | Rps2-ps10 |
| Tubb4b2 | 0.601 | 0.396518633 | 0.202 | 0.586 | 0.424 | ENR-3 | Tubb4b |
| Spink45 | 0.874 | 1.424394711 | 0.748 | 0.994 | 0.746 | ENR-4 | Spink4 |
| Clps7 | 0.777 | 0.995852459 | 0.554 | 0.897 | 0.453 | ENR-4 | Clps |
| AY7611846 | 0.766 | 1.284747632 | 0.532 | 0.817 | 0.361 | ENR-4 | AY761184 |
| Gm152996 | 0.753 | 1.236197823 | 0.506 | 0.699 | 0.246 | ENR-4 | Gm15299 |
| Defa244 | 0.748 | 0.673622825 | 0.496 | 0.998 | 0.892 | ENR-4 | Defa24 |
| Defa176 | 0.711 | 0.43840216 | 0.422 | 0.992 | 0.708 | ENR-4 | Defa17 |
| Tff36 | 0.707 | 0.573615826 | 0.414 | 0.968 | 0.676 | ENR-4 | Tff3 |
| Fabp23 | 0.684 | 0.576616061 | 0.368 | 0.707 | 0.37 | ENR-4 | Fabp2 |
| Guca2a6 | 0.683 | 0.673396863 | 0.366 | 0.727 | 0.396 | ENR-4 | Guca2a |
| Defa266 | 0.682 | 0.764814463 | 0.364 | 0.626 | 0.276 | ENR-4 | Defa26 |
| Agr25 | 0.681 | 0.722478851 | 0.362 | 0.756 | 0.47 | ENR-4 | Agr2 |
| Gm148517 | 0.677 | 0.329003996 | 0.354 | 0.831 | 0.443 | ENR-4 | Gm14851 |
| Lgals46 | 0.662 | 0.378296127 | 0.324 | 0.94 | 0.789 | ENR-4 | Lgals4 |
| Mt16 | 0.66 | 0.344607346 | 0.32 | 0.899 | 0.639 | ENR-4 | Mt1 |
| Phgr17 | 0.659 | 0.571894559 | 0.318 | 0.691 | 0.41 | ENR-4 | Phgr1 |
| Olfm44 | 0.655 | 0.547471041 | 0.31 | 0.582 | 0.266 | ENR-4 | Olfm4 |
| Ldha6 | 0.655 | 0.34310918 | 0.31 | 0.899 | 0.67 | ENR-4 | Ldha |
| Fcgbp4 | 0.653 | 0.993083849 | 0.306 | 0.489 | 0.208 | ENR-4 | Fcgbp |

TABLE 1-continued

Derived gene list of the top defining genes from in vivo ileal
small intestine PCs and EECs captured on the Seq-Well platform

| | | | | | | | |
|---|---|---|---|---|---|---|---|
| Mt23 | 0.647 | 0.415319225 | 0.294 | 0.77 | 0.499 | ENR-4 | Mt2 |
| Klk1 | 0.632 | 1.036249612 | 0.264 | 0.297 | 0.034 | ENR-4 | Klk1 |
| Gm94935 | 0.63 | 0.517195173 | 0.26 | 0.562 | 0.338 | ENR-4 | Gm9493 |
| Prap11 | 0.625 | 0.419327727 | 0.25 | 0.489 | 0.235 | ENR-4 | Prap1 |
| Gm98434 | 0.625 | 0.302627001 | 0.25 | 0.885 | 0.782 | ENR-4 | Gm9843 |
| Gm87306 | 0.62 | 0.320970268 | 0.24 | 0.849 | 0.713 | ENR-4 | Gm8730 |
| Gm11231 | 0.619 | 0.77980094 | 0.238 | 0.331 | 0.101 | ENR-4 | Gm1123 |
| Aldob1 | 0.617 | 0.259787204 | 0.234 | 0.631 | 0.433 | ENR-4 | Aldob |
| Rps63 | 0.611 | 0.415852365 | 0.222 | 0.598 | 0.433 | ENR-4 | Rps6 |
| 2210404O07Rik1 | 0.609 | 0.463037112 | 0.218 | 0.464 | 0.265 | ENR-4 | 2210404O07Rik |
| Guca2b | 0.608 | 0.596105667 | 0.216 | 0.349 | 0.135 | ENR-4 | Guca2b |
| Pigr3 | 0.604 | 0.332644186 | 0.208 | 0.674 | 0.498 | ENR-4 | Pigr |
| Ifitm14 | 0.728 | 1.266514055 | 0.456 | 0.661 | 0.271 | ENR+CD-1 | Ifitm1 |
| S100a115 | 0.717 | 1.04296412 | 0.434 | 0.701 | 0.397 | ENR+CD-1 | S100a11 |
| Clu8 | 0.704 | 1.164798896 | 0.408 | 0.568 | 0.183 | ENR+CD-1 | Clu |
| Ifitm34 | 0.695 | 0.868364303 | 0.39 | 0.705 | 0.453 | ENR+CD-1 | Ifitm3 |
| Tmsb101 | 0.69 | 0.580472869 | 0.38 | 0.863 | 0.725 | ENR+CD-1 | Tmsb10 |
| Mmp77 | 0.678 | 0.402919101 | 0.356 | 0.893 | 0.512 | ENR+CD-1 | Mmp7 |
| D17H6S56E-54 | 0.677 | 0.931920895 | 0.354 | 0.651 | 0.413 | ENR+CD-1 | D17H6S56E-5 |
| S100a64 | 0.676 | 1.118626018 | 0.352 | 0.627 | 0.349 | ENR+CD-1 | S100a6 |
| Tmsb4x1 | 0.676 | 0.544945699 | 0.352 | 0.92 | 0.848 | ENR+CD-1 | Tmsb4x |
| Thbs14 | 0.667 | 0.905834032 | 0.334 | 0.541 | 0.242 | ENR+CD-1 | Thbs1 |
| Prdx11 | 0.658 | 0.401091653 | 0.316 | 0.931 | 0.876 | ENR+CD-1 | Prdx1 |
| Rdh10 | 0.653 | 1.038867978 | 0.306 | 0.41 | 0.123 | ENR+CD-1 | Rdh10 |
| Lrrc581 | 0.651 | 0.52230821 | 0.302 | 0.712 | 0.538 | ENR+CD-1 | Lrrc58 |
| Cfi | 0.65 | 0.955406446 | 0.3 | 0.43 | 0.141 | ENR+CD-1 | Cfi |
| S100a10 | 0.637 | 0.657620654 | 0.274 | 0.634 | 0.463 | ENR+CD-1 | S100a10 |
| Cd24a4 | 0.633 | 0.438901983 | 0.266 | 0.773 | 0.62 | ENR+CD-1 | Cd24a |
| Ctsl2 | 0.632 | 0.776789752 | 0.264 | 0.474 | 0.247 | ENR+CD-1 | Ctsl |
| Cldn43 | 0.63 | 0.668353449 | 0.26 | 0.533 | 0.312 | ENR+CD-1 | Cldn4 |
| Krt7 | 0.628 | 0.670919893 | 0.256 | 0.526 | 0.323 | ENR+CD-1 | Krt7 |
| Gpx1 | 0.627 | 0.433965819 | 0.254 | 0.741 | 0.615 | ENR+CD-1 | Gpx1 |
| Hsp90aa12 | 0.621 | 0.482215686 | 0.242 | 0.678 | 0.545 | ENR+CD-1 | Hsp90aa1 |
| Tpt14 | 0.617 | 0.300455932 | 0.234 | 0.878 | 0.747 | ENR+CD-1 | Tpt1 |
| Myl12a | 0.61 | 0.521781165 | 0.22 | 0.55 | 0.393 | ENR+CD-1 | Myl12a |
| Kitl | 0.605 | 0.774167138 | 0.21 | 0.328 | 0.128 | ENR+CD-1 | Kitl |
| Cxadr | 0.605 | 0.654634603 | 0.21 | 0.383 | 0.19 | ENR+CD-1 | Cxadr |
| Myl12b1 | 0.605 | 0.429834038 | 0.21 | 0.598 | 0.454 | ENR+CD-1 | Myl12b |
| Fxyd34 | 0.605 | 0.427737169 | 0.21 | 0.56 | 0.381 | ENR+CD-1 | Fxyd3 |
| Sbspon | 0.603 | 0.808834309 | 0.206 | 0.253 | 0.049 | ENR+CD-1 | Sbspon |
| Chgb6 | 0.845 | 0.840330017 | 0.69 | 0.965 | 0.418 | ENR+CD-2 | Chgb |
| Sct8 | 0.821 | 1.235777954 | 0.642 | 0.844 | 0.235 | ENR+CD-2 | Sct |
| Defa37 | 0.803 | 0.802828958 | 0.606 | 0.962 | 0.387 | ENR+CD-2 | Defa3 |
| Ang47 | 0.797 | 0.730641799 | 0.594 | 0.974 | 0.446 | ENR+CD-2 | Ang4 |
| Mmp78 | 0.796 | 0.773345323 | 0.592 | 0.977 | 0.492 | ENR+CD-2 | Mmp7 |
| Gm152846 | 0.79 | 0.631388586 | 0.58 | 0.998 | 0.691 | ENR+CD-2 | Gm15284 |
| Lyz17 | 0.788 | 0.600947747 | 0.576 | 0.995 | 0.654 | ENR+CD-2 | Lyz1 |
| Itln17 | 0.786 | 0.651103542 | 0.572 | 0.998 | 0.743 | ENR+CD-2 | Itln1 |
| Defa217 | 0.783 | 0.776202788 | 0.566 | 0.884 | 0.339 | ENR+CD-2 | Defa21 |
| Defa227 | 0.782 | 0.765089831 | 0.564 | 0.863 | 0.306 | ENR+CD-2 | Defa22 |
| Defa-rs17 | 0.777 | 0.663665047 | 0.554 | 0.95 | 0.427 | ENR+CD-2 | Defa-rs1 |
| Defa177 | 0.766 | 0.594762162 | 0.532 | 1 | 0.705 | ENR+CD-2 | Defa17 |
| Gm153157 | 0.752 | 0.703363896 | 0.504 | 0.816 | 0.287 | ENR+CD-2 | Gm15315 |
| Tff37 | 0.746 | 0.567941882 | 0.492 | 0.982 | 0.672 | ENR+CD-2 | Tff3 |
| Defa245 | 0.742 | 0.474196376 | 0.484 | 1 | 0.891 | ENR+CD-2 | Defa24 |
| Gm148518 | 0.739 | 0.446583792 | 0.478 | 0.894 | 0.433 | ENR+CD-2 | Gm14851 |
| Clu9 | 0.734 | 0.965368487 | 0.468 | 0.64 | 0.164 | ENR+CD-2 | Clu |
| Ifitm15 | 0.728 | 0.783309944 | 0.456 | 0.708 | 0.255 | ENR+CD-2 | Ifitm1 |
| Cck4 | 0.721 | 1.020507077 | 0.442 | 0.65 | 0.224 | ENR+CD-2 | Cck |
| S100a65 | 0.717 | 0.711435596 | 0.434 | 0.731 | 0.328 | ENR+CD-2 | S100a6 |
| Gcg3 | 0.711 | 1.006429421 | 0.422 | 0.565 | 0.149 | ENR+CD-2 | Gcg |
| Fxyd35 | 0.71 | 0.726447178 | 0.42 | 0.734 | 0.354 | ENR+CD-2 | Fxyd3 |
| Reg3b4 | 0.706 | 0.801648267 | 0.412 | 0.603 | 0.195 | ENR+CD-2 | Reg3b |
| Thbs15 | 0.706 | 0.796785646 | 0.412 | 0.636 | 0.222 | ENR+CD-2 | Thbs1 |
| AY7611857 | 0.704 | 0.551190274 | 0.408 | 0.76 | 0.329 | ENR+CD-2 | AY761185 |
| Chga4 | 0.7 | 0.679396712 | 0.4 | 0.592 | 0.185 | ENR+CD-2 | Chga |
| Mptx21 | 0.696 | 0.754335025 | 0.392 | 0.545 | 0.144 | ENR+CD-2 | Mptx2 |
| S100a116 | 0.693 | 0.673927124 | 0.386 | 0.715 | 0.388 | ENR+CD-2 | S100a11 |
| Tm4sf41 | 0.672 | 0.695786283 | 0.344 | 0.568 | 0.228 | ENR+CD-2 | Tm4sf4 |
| Clps9 | 0.67 | 0.28795985 | 0.34 | 0.826 | 0.46 | ENR+CD-2 | Clps |
| D17H6S56E-55 | 0.668 | 0.577220844 | 0.336 | 0.687 | 0.402 | ENR+CD-2 | D17H6S56E-5 |
| Guca2a7 | 0.666 | 0.436541828 | 0.332 | 0.733 | 0.394 | ENR+CD-2 | Guca2a |
| Cd24a5 | 0.662 | 0.424451845 | 0.324 | 0.822 | 0.61 | ENR+CD-2 | Cd24a |
| Tac14 | 0.66 | 0.51582336 | 0.32 | 0.492 | 0.167 | ENR+CD-2 | Tac1 |
| Ifitm35 | 0.656 | 0.476562816 | 0.312 | 0.724 | 0.444 | ENR+CD-2 | Ifitm3 |
| Cpe | 0.653 | 0.768488569 | 0.306 | 0.42 | 0.107 | ENR+CD-2 | Cpe |
| Scg2 | 0.65 | 0.909979206 | 0.3 | 0.381 | 0.077 | ENR+CD-2 | Scg2 |

TABLE 1-continued

Derived gene list of the top defining genes from in vivo ileal
small intestine PCs and EECs captured on the Seq-Well platform

| | | | | | | |
|---|---|---|---|---|---|---|
| Gm101046 | 0.65 | 0.486952231 | 0.3 | 0.536 | 0.208 | ENR+CD-2 | Gm10104 |
| Cfi1 | 0.645 | 0.699855748 | 0.29 | 0.429 | 0.134 | ENR+CD-2 | Cfi |
| Ctsl3 | 0.644 | 0.636553795 | 0.288 | 0.511 | 0.237 | ENR+CD-2 | Ctsl |
| Cldn44 | 0.644 | 0.499420163 | 0.288 | 0.585 | 0.3 | ENR+CD-2 | Cldn4 |
| Agr26 | 0.643 | 0.297331723 | 0.286 | 0.754 | 0.469 | ENR+CD-2 | Agr2 |
| Gm15293 | 0.638 | 0.537476239 | 0.276 | 0.414 | 0.123 | ENR+CD-2 | Gm15293 |
| Ghrl | 0.634 | 0.271791802 | 0.268 | 0.421 | 0.14 | ENR+CD-2 | Ghrl |
| Ly6e1 | 0.631 | 0.560375359 | 0.262 | 0.505 | 0.252 | ENR+CD-2 | Ly6e |
| Cst31 | 0.629 | 0.434601539 | 0.258 | 0.687 | 0.461 | ENR+CD-2 | Cst3 |
| Defa267 | 0.626 | 0.348255978 | 0.252 | 0.566 | 0.282 | ENR+CD-2 | Defa26 |
| Defa-rs71 | 0.625 | 0.470261981 | 0.25 | 0.424 | 0.155 | ENR+CD-2 | Defa-rs7 |
| Reg3g1 | 0.62 | 0.47864056 | 0.24 | 0.435 | 0.192 | ENR+CD-2 | Reg3g |
| Rdh101 | 0.618 | 0.600965297 | 0.236 | 0.364 | 0.122 | ENR+CD-2 | Rdh10 |
| Lect2 | 0.611 | 0.737151824 | 0.222 | 0.31 | 0.09 | ENR+CD-2 | Lect2 |
| Gadd45g | 0.61 | 0.53691856 | 0.22 | 0.376 | 0.158 | ENR+CD-2 | Gadd45g |
| Wbp56 | 0.61 | 0.353807258 | 0.22 | 0.689 | 0.486 | ENR+CD-2 | Wbp5 |
| Pcsk1 | 0.607 | 0.595290862 | 0.214 | 0.313 | 0.097 | ENR+CD-2 | Pcsk1 |
| Lamp22 | 0.607 | 0.440830518 | 0.214 | 0.482 | 0.282 | ENR+CD-2 | Lamp2 |
| Rnase42 | 0.607 | 0.417457058 | 0.214 | 0.548 | 0.347 | ENR+CD-2 | Rnase4 |
| Serpinb1a | 0.606 | 0.46729396 | 0.212 | 0.453 | 0.248 | ENR+CD-2 | Serpinb1a |
| Cyp2c55 | 0.605 | 0.475836171 | 0.21 | 0.382 | 0.172 | ENR+CD-2 | Cyp2c55 |
| Gm14850 | 0.605 | 0.333427165 | 0.21 | 0.385 | 0.153 | ENR+CD-2 | Gm14850 |
| Nupr11 | 0.603 | 0.328483346 | 0.206 | 0.444 | 0.223 | ENR+CD-2 | Nupr1 |
| Ttr | 0.601 | 0.691722383 | 0.202 | 0.331 | 0.133 | ENR+CD-2 | Ttr |
| Gm152847 | 0.911 | 1.417767489 | 0.822 | 1 | 0.677 | ENR+CD-3 | Gm15284 |
| Defa38 | 0.91 | 1.48438864 | 0.82 | 0.989 | 0.357 | ENR+CD-3 | Defa3 |
| Ang48 | 0.906 | 1.481959089 | 0.812 | 0.992 | 0.419 | ENR+CD-3 | Ang4 |
| Itln18 | 0.902 | 1.30581211 | 0.804 | 1 | 0.732 | ENR+CD-3 | Itln1 |
| Defa178 | 0.9 | 1.251411894 | 0.8 | 1 | 0.692 | ENR+CD-3 | Defa17 |
| Lyz18 | 0.899 | 1.379689576 | 0.798 | 0.999 | 0.638 | ENR+CD-3 | Lyz1 |
| Defa-rs18 | 0.893 | 1.30730474 | 0.786 | 0.988 | 0.397 | ENR+CD-3 | Defa-rs1 |
| Defa246 | 0.892 | 1.162558349 | 0.784 | 1 | 0.887 | ENR+CD-3 | Defa24 |
| Mmp79 | 0.882 | 1.300404782 | 0.764 | 0.983 | 0.469 | ENR+CD-3 | Mmp7 |
| Defa218 | 0.868 | 1.402843208 | 0.736 | 0.932 | 0.306 | ENR+CD-3 | Defa21 |
| Gm148519 | 0.862 | 1.309336088 | 0.724 | 0.95 | 0.403 | ENR+CD-3 | Gm14851 |
| Defa228 | 0.846 | 1.328756325 | 0.692 | 0.885 | 0.278 | ENR+CD-3 | Defa22 |
| Tff38 | 0.839 | 0.921100656 | 0.678 | 0.999 | 0.656 | ENR+CD-3 | Tff3 |
| Gm153158 | 0.816 | 1.235877475 | 0.632 | 0.828 | 0.262 | ENR+CD-3 | Gm15315 |
| AY7611858 | 0.808 | 1.152150262 | 0.616 | 0.834 | 0.297 | ENR+CD-3 | AY761185 |
| Clps10 | 0.772 | 0.827134581 | 0.544 | 0.872 | 0.435 | ENR+CD-3 | Clps |
| Chgb7 | 0.74 | 0.319575495 | 0.48 | 0.858 | 0.413 | ENR+CD-3 | Chgb |
| Spink47 | 0.737 | 0.379668581 | 0.474 | 0.981 | 0.736 | ENR+CD-3 | Spink4 |
| AY7611848 | 0.734 | 0.645499385 | 0.468 | 0.767 | 0.347 | ENR+CD-3 | AY761184 |
| Guca2a8 | 0.727 | 0.812298742 | 0.454 | 0.763 | 0.374 | ENR+CD-3 | Guca2a |
| Sct9 | 0.725 | 0.872798507 | 0.45 | 0.661 | 0.241 | ENR+CD-3 | Sct |
| Agr27 | 0.71 | 0.725107239 | 0.42 | 0.765 | 0.454 | ENR+CD-3 | Agr2 |
| Gm101047 | 0.708 | 0.952024661 | 0.416 | 0.582 | 0.186 | ENR+CD-3 | Gm10104 |
| Mptx22 | 0.7 | 1.409945284 | 0.4 | 0.513 | 0.132 | ENR+CD-3 | Mptx2 |
| Defa268 | 0.688 | 0.780710181 | 0.376 | 0.611 | 0.261 | ENR+CD-3 | Defa26 |
| Ifitm16 | 0.683 | 0.758241776 | 0.366 | 0.593 | 0.255 | ENR+CD-3 | Ifitm1 |
| Reg3b5 | 0.674 | 0.741838574 | 0.348 | 0.516 | 0.192 | ENR+CD-3 | Reg3b |
| Defa-rs72 | 0.668 | 0.966768154 | 0.336 | 0.455 | 0.137 | ENR+CD-3 | Defa-rs7 |
| S100a66 | 0.668 | 0.608871913 | 0.336 | 0.611 | 0.332 | ENR+CD-3 | S100a6 |
| Gm152931 | 0.659 | 1.003467707 | 0.318 | 0.416 | 0.11 | ENR+CD-3 | Gm15293 |
| Clu10 | 0.659 | 0.803118786 | 0.318 | 0.481 | 0.171 | ENR+CD-3 | Clu |
| Gm148501 | 0.653 | 0.846884672 | 0.306 | 0.428 | 0.135 | ENR+CD-3 | Gm14850 |
| Thbs16 | 0.653 | 0.752857526 | 0.306 | 0.503 | 0.227 | ENR+CD-3 | Thbs1 |
| Cck5 | 0.65 | 0.394319127 | 0.3 | 0.51 | 0.23 | ENR+CD-3 | Cck |
| Defa23 | 0.645 | 0.837081767 | 0.29 | 0.421 | 0.151 | ENR+CD-3 | Defa23 |
| S100a117 | 0.64 | 0.561318422 | 0.28 | 0.597 | 0.394 | ENR+CD-3 | S100a11 |
| Nupr12 | 0.638 | 0.82665142 | 0.276 | 0.451 | 0.212 | ENR+CD-3 | Nupr1 |
| D17H6S56E-56 | 0.633 | 0.525823846 | 0.266 | 0.598 | 0.405 | ENR+CD-3 | D17H6S56E-5 |
| Ifitm36 | 0.632 | 0.48982756 | 0.264 | 0.634 | 0.448 | ENR+CD-3 | Ifitm3 |
| Gcg4 | 0.631 | 0.443385283 | 0.262 | 0.411 | 0.158 | ENR+CD-3 | Gcg |
| Defa5 | 0.628 | 0.887931096 | 0.256 | 0.33 | 0.08 | ENR+CD-3 | Defa5 |
| Fxyd36 | 0.627 | 0.59934023 | 0.254 | 0.554 | 0.369 | ENR+CD-3 | Fxyd3 |
| Cd24a6 | 0.627 | 0.444065871 | 0.254 | 0.723 | 0.618 | ENR+CD-3 | Cd24a |
| Gm152997 | 0.626 | 0.457038003 | 0.252 | 0.499 | 0.259 | ENR+CD-3 | Gm15299 |
| Lyz2 | 0.621 | 0.810292369 | 0.242 | 0.339 | 0.108 | ENR+CD-3 | Lyz2 |
| Reg3g2 | 0.618 | 0.752320317 | 0.236 | 0.395 | 0.189 | ENR+CD-3 | Reg3g |
| Gm15292 | 0.613 | 0.781588719 | 0.226 | 0.323 | 0.109 | ENR+CD-3 | Gm15292 |
| Cldn45 | 0.612 | 0.506487127 | 0.224 | 0.489 | 0.304 | ENR+CD-3 | Cldn4 |
| Ghrl1 | 0.604 | 0.512540452 | 0.208 | 0.34 | 0.142 | ENR+CD-3 | Ghrl |
| Defa247 | 0.978 | 1.653810125 | 0.956 | 1 | 0.9 | ENR+CD-4 | Defa24 |
| Defa179 | 0.971 | 1.717509942 | 0.942 | 1 | 0.729 | ENR+CD-4 | Defa17 |
| Defa-rs19 | 0.969 | 1.915928136 | 0.938 | 1 | 0.466 | ENR+CD-4 | Defa-rs1 |
| Defa39 | 0.956 | 1.874812807 | 0.912 | 1 | 0.431 | ENR+CD-4 | Defa3 |

TABLE 1-continued

Derived gene list of the top defining genes from in vivo ileal
small intestine PCs and EECs captured on the Seq-Well platform

| | | | | | | | |
|---|---|---|---|---|---|---|---|
| Gm152848 | 0.948 | 1.894058904 | 0.896 | 1 | 0.715 | ENR+CD-4 | Gm15284 |
| AY7611859 | 0.944 | 1.735123513 | 0.888 | 0.986 | 0.354 | ENR+CD-4 | AY761185 |
| Itln19 | 0.94 | 1.683069674 | 0.88 | 1 | 0.763 | ENR+CD-4 | Itln1 |
| Ang49 | 0.926 | 1.830271754 | 0.852 | 0.991 | 0.487 | ENR+CD-4 | Ang4 |
| Gm153159 | 0.915 | 1.86256915 | 0.83 | 0.963 | 0.324 | ENR+CD-4 | Gm15315 |
| Lyz19 | 0.896 | 1.807121426 | 0.792 | 0.991 | 0.681 | ENR+CD-4 | Lyz1 |
| Clps11 | 0.893 | 1.472626516 | 0.786 | 0.986 | 0.482 | ENR+CD-4 | Clps |
| Defa219 | 0.892 | 1.733880333 | 0.784 | 0.981 | 0.378 | ENR+CD-4 | Defa21 |
| Mmp710 | 0.889 | 1.332678006 | 0.778 | 0.995 | 0.529 | ENR+CD-4 | Mmp7 |
| Gm1485110 | 0.888 | 1.893476735 | 0.776 | 0.991 | 0.466 | ENR+CD-4 | Gm14851 |
| Tff39 | 0.884 | 1.269128067 | 0.768 | 1 | 0.696 | ENR+CD-4 | Tff3 |
| Defa269 | 0.877 | 1.511985309 | 0.754 | 0.916 | 0.291 | ENR+CD-4 | Defa26 |
| Defa-rs73 | 0.867 | 1.553365651 | 0.734 | 0.846 | 0.16 | ENR+CD-4 | Defa-rs7 |
| Defa229 | 0.86 | 1.867440887 | 0.72 | 0.935 | 0.347 | ENR+CD-4 | Defa22 |
| AY7611849 | 0.848 | 1.603050723 | 0.696 | 0.935 | 0.39 | ENR+CD-4 | AY761184 |
| Gm152998 | 0.842 | 1.401888038 | 0.684 | 0.874 | 0.273 | ENR+CD-4 | Gm15299 |
| Gm101048 | 0.839 | 1.636002805 | 0.678 | 0.808 | 0.224 | ENR+CD-4 | Gm10104 |
| Guca2a9 | 0.829 | 1.263146743 | 0.658 | 0.907 | 0.414 | ENR+CD-4 | Guca2a |
| Spink48 | 0.825 | 1.128028718 | 0.65 | 0.995 | 0.764 | ENR+CD-4 | Spink4 |
| Defa231 | 0.819 | 1.298642496 | 0.638 | 0.78 | 0.169 | ENR+CD-4 | Defa23 |
| Gm148502 | 0.807 | 1.586456887 | 0.614 | 0.729 | 0.159 | ENR+CD-4 | Gm14850 |
| Gm152921 | 0.791 | 1.235848407 | 0.582 | 0.696 | 0.12 | ENR+CD-4 | Gm15292 |
| Nupr13 | 0.776 | 1.42316347 | 0.552 | 0.71 | 0.23 | ENR+CD-4 | Nupr1 |
| Gm152932 | 0.759 | 1.689396485 | 0.518 | 0.626 | 0.138 | ENR+CD-4 | Gm15293 |
| Lyz21 | 0.753 | 1.312597791 | 0.506 | 0.617 | 0.125 | ENR+CD-4 | Lyz2 |
| Agr28 | 0.746 | 0.904952546 | 0.492 | 0.846 | 0.488 | ENR+CD-4 | Agr2 |
| Defa51 | 0.739 | 1.427966915 | 0.478 | 0.565 | 0.1 | ENR+CD-4 | Defa5 |
| Gm9765 | 0.689 | 1.049917065 | 0.378 | 0.453 | 0.077 | ENR+CD-4 | Gm9765 |
| Ang2 | 0.685 | 1.029087335 | 0.37 | 0.439 | 0.068 | ENR+CD-4 | Ang2 |
| Gm6696 | 0.685 | 0.932998515 | 0.37 | 0.444 | 0.073 | ENR+CD-4 | Gm6696 |
| Pnliprp2 | 0.683 | 1.090192172 | 0.366 | 0.463 | 0.106 | ENR+CD-4 | Pnliprp2 |
| Gm7861 | 0.682 | 0.857146045 | 0.364 | 0.444 | 0.073 | ENR+CD-4 | Gm7861 |
| Defa25 | 0.667 | 0.916936303 | 0.334 | 0.388 | 0.051 | ENR+CD-4 | Defa25 |
| Guca2b1 | 0.665 | 0.784158582 | 0.33 | 0.477 | 0.146 | ENR+CD-4 | Guca2b |
| Rnase1 | 0.644 | 0.872333667 | 0.288 | 0.421 | 0.135 | ENR+CD-4 | Rnase1 |
| Rnase43 | 0.644 | 0.517518187 | 0.288 | 0.626 | 0.36 | ENR+CD-4 | Rnase4 |
| Gm21498 | 0.643 | 0.85822942 | 0.286 | 0.341 | 0.053 | ENR+CD-4 | Gm21498 |
| Ang6 | 0.641 | 0.855478261 | 0.282 | 0.341 | 0.059 | ENR+CD-4 | Ang6 |
| Cd24a7 | 0.639 | 0.379091879 | 0.278 | 0.846 | 0.627 | ENR+CD-4 | Cd24a |
| Ssr41 | 0.624 | 0.402782071 | 0.248 | 0.724 | 0.576 | ENR+CD-4 | Ssr4 |
| Selm2 | 0.622 | 0.541045922 | 0.244 | 0.486 | 0.249 | ENR+CD-4 | Selm |
| Ang5 | 0.619 | 0.749613346 | 0.238 | 0.294 | 0.054 | ENR+CD-4 | Ang5 |
| Cd632 | 0.618 | 0.368937721 | 0.236 | 0.715 | 0.512 | ENR+CD-4 | Cd63 |
| Tmed6 | 0.617 | 0.492982028 | 0.234 | 0.5 | 0.278 | ENR+CD-4 | Tmed6 |
| Ang | 0.616 | 0.593728014 | 0.232 | 0.36 | 0.128 | ENR+CD-4 | Ang |
| Serp1 | 0.616 | 0.437250688 | 0.232 | 0.565 | 0.352 | ENR+CD-4 | Serp1 |
| Mptx23 | 0.614 | 1.332002551 | 0.228 | 0.397 | 0.181 | ENR+CD-4 | Mptx2 |
| Muc2 | 0.607 | 0.701039035 | 0.214 | 0.276 | 0.061 | ENR+CD-4 | Muc2 |
| Habp2 | 0.606 | 0.5665122 | 0.212 | 0.276 | 0.06 | ENR+CD-4 | Habp2 |
| Vimp | 0.605 | 0.607806321 | 0.21 | 0.364 | 0.164 | ENR+CD-4 | Vimp |
| Sec11c | 0.605 | 0.390461867 | 0.21 | 0.542 | 0.345 | ENR+CD-4 | Sec11c |
| P4hb1 | 0.603 | 0.267765547 | 0.206 | 0.762 | 0.591 | ENR+CD-4 | P4hb |
| Fcgbp5 | 0.601 | 0.420617741 | 0.202 | 0.439 | 0.231 | ENR+CD-4 | Fcgbp |
| Muc13 | 0.601 | 0.408921351 | 0.202 | 0.491 | 0.289 | ENR+CD-4 | Muc13 |
| Cpe1 | 0.868 | 2.061769681 | 0.736 | 0.801 | 0.126 | Neuro-1 | Cpe |
| Chgb8 | 0.861 | 2.411534834 | 0.722 | 0.875 | 0.47 | Neuro-1 | Chgb |
| Chga5 | 0.858 | 1.923833184 | 0.716 | 0.838 | 0.216 | Neuro-1 | Chga |
| Neurod1 | 0.856 | 1.900034487 | 0.712 | 0.757 | 0.058 | Neuro-1 | Neurod1 |
| Serpinb1a1 | 0.825 | 1.52674678 | 0.65 | 0.809 | 0.259 | Neuro-1 | Serpinb1a |
| Tm4sf42 | 0.813 | 1.359021605 | 0.626 | 0.801 | 0.253 | Neuro-1 | Tm4sf4 |
| Pcsk11 | 0.81 | 1.645003246 | 0.62 | 0.706 | 0.108 | Neuro-1 | Pcsk1 |
| Sepp1 | 0.799 | 1.370027544 | 0.598 | 0.728 | 0.162 | Neuro-1 | Sepp1 |
| Hepacam2 | 0.781 | 1.464877563 | 0.562 | 0.632 | 0.077 | Neuro-1 | Hepacam2 |
| Hmgn3 | 0.78 | 1.564671978 | 0.56 | 0.61 | 0.052 | Neuro-1 | Hmgn3 |
| Ptprn2 | 0.776 | 1.330115601 | 0.552 | 0.61 | 0.059 | Neuro-1 | Ptprn2 |
| Scg5 | 0.765 | 1.399166134 | 0.53 | 0.574 | 0.043 | Neuro-1 | Scg5 |
| Fam183b | 0.765 | 1.373925491 | 0.53 | 0.588 | 0.061 | Neuro-1 | Fam183b |
| Sct10 | 0.754 | 1.905545228 | 0.508 | 0.728 | 0.294 | Neuro-1 | Sct |
| Scg21 | 0.747 | 2.097630337 | 0.494 | 0.566 | 0.1 | Neuro-1 | Scg2 |
| Rnf321 | 0.739 | 1.31568039 | 0.478 | 0.618 | 0.187 | Neuro-1 | Rnf32 |
| Ddc | 0.736 | 1.096785677 | 0.472 | 0.566 | 0.098 | Neuro-1 | Ddc |
| Prnp | 0.724 | 1.19680042 | 0.448 | 0.493 | 0.044 | Neuro-1 | Prnp |
| Tuba1a4 | 0.723 | 0.975817209 | 0.446 | 0.632 | 0.213 | Neuro-1 | Tuba1a |
| Sult1d11 | 0.722 | 1.059273546 | 0.444 | 0.574 | 0.138 | Neuro-1 | Sult1d1 |
| Fxyd37 | 0.721 | 0.89196613 | 0.442 | 0.757 | 0.388 | Neuro-1 | Fxyd3 |
| Cyp4b1 | 0.719 | 1.232809916 | 0.438 | 0.5 | 0.071 | Neuro-1 | Cyp4b1 |
| Cystm12 | 0.714 | 0.63886326 | 0.428 | 0.86 | 0.638 | Neuro-1 | Cystm1 |

TABLE 1-continued

Derived gene list of the top defining genes from in vivo ileal
small intestine PCs and EECs captured on the Seq-Well platform

| | | | | | | |
|---|---|---|---|---|---|---|
| Rab3c | 0.713 | 1.158868725 | 0.426 | 0.463 | 0.034 Neuro-1 | Rab3c |
| Lect21 | 0.712 | 1.534495074 | 0.424 | 0.515 | 0.105 Neuro-1 | Lect2 |
| Scgn | 0.712 | 1.443239579 | 0.424 | 0.456 | 0.033 Neuro-1 | Scgn |
| 5330417C22Rik | 0.711 | 0.96024513 | 0.422 | 0.522 | 0.097 Neuro-1 | 5330417C22Rik |
| Resp18 | 0.71 | 1.339151365 | 0.42 | 0.478 | 0.06 Neuro-1 | Resp18 |
| Cnot6l | 0.708 | 0.994980747 | 0.416 | 0.515 | 0.097 Neuro-1 | Cnot6l |
| Pcsk1n | 0.707 | 1.262864306 | 0.414 | 0.449 | 0.036 Neuro-1 | Pcsk1n |
| Ddx51 | 0.707 | 0.52010653 | 0.414 | 0.89 | 0.642 Neuro-1 | Ddx5 |
| Prkar1a | 0.706 | 0.794888222 | 0.412 | 0.647 | 0.254 Neuro-1 | Prkar1a |
| Hopx2 | 0.705 | 0.812314443 | 0.41 | 0.684 | 0.313 Neuro-1 | Hopx |
| Itm2c | 0.704 | 0.907713892 | 0.408 | 0.581 | 0.178 Neuro-1 | Itm2c |
| Map1b | 0.703 | 1.071367345 | 0.406 | 0.456 | 0.046 Neuro-1 | Map1b |
| Btg21 | 0.702 | 0.819592839 | 0.404 | 0.618 | 0.232 Neuro-1 | Btg2 |
| Cplx2 | 0.701 | 0.992904519 | 0.402 | 0.463 | 0.058 Neuro-1 | Cplx2 |
| Muc131 | 0.701 | 0.722582624 | 0.402 | 0.669 | 0.287 Neuro-1 | Muc13 |
| Cst32 | 0.698 | 0.765923639 | 0.396 | 0.765 | 0.48 Neuro-1 | Cst3 |
| Krt20 | 0.697 | 1.472795372 | 0.394 | 0.456 | 0.074 Neuro-1 | Krt20 |
| Slc18a1 | 0.696 | 0.99031306 | 0.392 | 0.441 | 0.044 Neuro-1 | Slc18a1 |
| Maged1 | 0.696 | 0.796949416 | 0.392 | 0.566 | 0.173 Neuro-1 | Maged1 |
| Gm609 | 0.693 | 0.847865386 | 0.386 | 0.449 | 0.056 Neuro-1 | Gm609 |
| Olfm1 | 0.692 | 0.984734604 | 0.384 | 0.412 | 0.024 Neuro-1 | Olfm1 |
| Gadd45g1 | 0.691 | 1.060556065 | 0.382 | 0.537 | 0.174 Neuro-1 | Gadd45g |
| Dpp4 | 0.69 | 1.078563799 | 0.38 | 0.478 | 0.109 Neuro-1 | Dpp4 |
| Arf51 | 0.689 | 0.694678628 | 0.378 | 0.632 | 0.267 Neuro-1 | Arf5 |
| Sis1 | 0.687 | 0.945039382 | 0.374 | 0.559 | 0.206 Neuro-1 | Sis |
| Cacna2d1 | 0.686 | 1.046893483 | 0.372 | 0.397 | 0.024 Neuro-1 | Cacna2d1 |
| Slc25a44 | 0.684 | 0.698704815 | 0.368 | 0.662 | 0.317 Neuro-1 | Slc25a4 |
| Ceacam10 | 0.683 | 1.237660611 | 0.366 | 0.404 | 0.039 Neuro-1 | Ceacam10 |
| Peg3 | 0.683 | 1.165933368 | 0.366 | 0.434 | 0.068 Neuro-1 | Peg3 |
| Bex2 | 0.683 | 0.99870905 | 0.366 | 0.426 | 0.06 Neuro-1 | Bex2 |
| Hk2 | 0.681 | 0.828213419 | 0.362 | 0.493 | 0.129 Neuro-1 | Hk2 |
| Gng12 | 0.681 | 0.715728427 | 0.362 | 0.529 | 0.159 Neuro-1 | Gng12 |
| Cd813 | 0.68 | 0.624985987 | 0.36 | 0.772 | 0.488 Neuro-1 | Cd81 |
| Pam | 0.679 | 1.058682168 | 0.358 | 0.419 | 0.064 Neuro-1 | Pam |
| Akap9 | 0.679 | 0.641135065 | 0.358 | 0.669 | 0.312 Neuro-1 | Akap9 |
| Syt13 | 0.678 | 0.969957383 | 0.356 | 0.382 | 0.025 Neuro-1 | Syt13 |
| Selm3 | 0.678 | 0.729440399 | 0.356 | 0.588 | 0.25 Neuro-1 | Selm |
| Rfx6 | 0.677 | 1.118582385 | 0.354 | 0.382 | 0.027 Neuro-1 | Rfx6 |
| Aplp1 | 0.677 | 0.985362262 | 0.354 | 0.39 | 0.035 Neuro-1 | Aplp1 |
| Txnip1 | 0.677 | 0.710016729 | 0.354 | 0.684 | 0.355 Neuro-1 | Txnip |
| Ubl3 | 0.676 | 0.729918323 | 0.352 | 0.493 | 0.133 Neuro-1 | Ubl3 |
| Selk | 0.676 | 0.660090551 | 0.352 | 0.588 | 0.248 Neuro-1 | Selk |
| Igfbp2 | 0.674 | 1.640894044 | 0.348 | 0.419 | 0.076 Neuro-1 | Igfbp2 |
| Gch1 | 0.674 | 0.839133061 | 0.348 | 0.419 | 0.067 Neuro-1 | Gch1 |
| Wbp57 | 0.674 | 0.513228435 | 0.348 | 0.794 | 0.502 Neuro-1 | Wbp5 |
| Tpm4 | 0.673 | 0.674267156 | 0.346 | 0.603 | 0.268 Neuro-1 | Tpm4 |
| Mien1 | 0.673 | 0.64287874 | 0.346 | 0.544 | 0.195 Neuro-1 | Mien1 |
| Tax1bp14 | 0.672 | 0.588102013 | 0.344 | 0.757 | 0.467 Neuro-1 | Tax1bp1 |
| Scg3 | 0.669 | 0.993218753 | 0.338 | 0.36 | 0.021 Neuro-1 | Scg3 |
| Spcs21 | 0.669 | 0.521967801 | 0.338 | 0.721 | 0.38 Neuro-1 | Spcs2 |
| Pla2g2f | 0.667 | 0.991923013 | 0.334 | 0.382 | 0.046 Neuro-1 | Pla2g2f |
| Phldb2 | 0.666 | 0.795150054 | 0.332 | 0.419 | 0.083 Neuro-1 | Phldb2 |
| Calm16 | 0.666 | 0.346774953 | 0.332 | 0.926 | 0.875 Neuro-1 | Calm1 |
| Ttr1 | 0.665 | 1.085323621 | 0.33 | 0.463 | 0.148 Neuro-1 | Ttr |
| Runx1t1 | 0.664 | 1.105954969 | 0.328 | 0.346 | 0.017 Neuro-1 | Runx1t1 |
| Cxxc5 | 0.664 | 0.847365801 | 0.328 | 0.397 | 0.068 Neuro-1 | Cxxc5 |
| Lgals3bp | 0.663 | 0.801567078 | 0.326 | 0.485 | 0.166 Neuro-1 | Lgals3bp |
| Ngfrap12 | 0.663 | 0.673121868 | 0.326 | 0.522 | 0.205 Neuro-1 | Ngfrap1 |
| Cd633 | 0.663 | 0.5234039 | 0.326 | 0.772 | 0.513 Neuro-1 | Cd63 |
| Tac15 | 0.662 | 2.258223311 | 0.324 | 0.478 | 0.197 Neuro-1 | Tac1 |
| Insm1 | 0.662 | 1.015476886 | 0.324 | 0.346 | 0.02 Neuro-1 | Insm1 |
| Oaz14 | 0.662 | 0.401184211 | 0.324 | 0.89 | 0.62 Neuro-1 | Oaz1 |
| Gm15200 | 0.661 | 1.021694868 | 0.322 | 0.368 | 0.045 Neuro-1 | Gm15200 |
| Marcks | 0.66 | 0.659513021 | 0.32 | 0.559 | 0.243 Neuro-1 | Marcks |
| St18 | 0.659 | 0.973607463 | 0.318 | 0.338 | 0.02 Neuro-1 | St18 |
| Camk2n1 | 0.658 | 0.802513074 | 0.316 | 0.412 | 0.098 Neuro-1 | Camk2n1 |
| Fgd2 | 0.657 | 0.842573313 | 0.314 | 0.338 | 0.022 Neuro-1 | Fgd2 |
| Scp2 | 0.657 | 0.600343936 | 0.314 | 0.551 | 0.232 Neuro-1 | Scp2 |
| Ddx6 | 0.657 | 0.584958973 | 0.314 | 0.588 | 0.274 Neuro-1 | Ddx6 |
| Nkx2-2 | 0.656 | 0.954889416 | 0.312 | 0.338 | 0.026 Neuro-1 | Nkx2-2 |
| Cacna1a | 0.654 | 0.777140018 | 0.308 | 0.346 | 0.034 Neuro-1 | Cacna1a |
| Etv1 | 0.653 | 1.00755855 | 0.306 | 0.324 | 0.017 Neuro-1 | Etv1 |
| Cpq | 0.653 | 0.798825882 | 0.306 | 0.375 | 0.066 Neuro-1 | Cpq |
| Tusc3 | 0.652 | 0.815489525 | 0.304 | 0.39 | 0.085 Neuro-1 | Tusc3 |
| Ets1 | 0.652 | 0.811009911 | 0.304 | 0.331 | 0.023 Neuro-1 | Ets1 |
| Btg12 | 0.652 | 0.69571158 | 0.304 | 0.463 | 0.159 Neuro-1 | Btg1 |
| Rph3al | 0.651 | 0.922069171 | 0.302 | 0.338 | 0.036 Neuro-1 | Rph3al |

TABLE 1-continued

Derived gene list of the top defining genes from in vivo ileal
small intestine PCs and EECs captured on the Seq-Well platform

| Mtch1 | 0.651 | 0.695188098 | 0.302 | 0.456 | 0.152 | Neuro-1 | Mtch1 |
|---|---|---|---|---|---|---|---|
| Plac82 | 0.651 | 0.688093339 | 0.302 | 0.735 | 0.59 | Neuro-1 | Plac8 |
| Prdx5 | 0.65 | 0.660838495 | 0.3 | 0.485 | 0.183 | Neuro-1 | Prdx5 |
| D4Wsu53e | 0.65 | 0.452838143 | 0.3 | 0.684 | 0.371 | Neuro-1 | D4Wsu53e |
| Nenf | 0.649 | 0.744694602 | 0.298 | 0.404 | 0.108 | Neuro-1 | Nenf |
| Ccnl1 | 0.648 | 0.484337397 | 0.296 | 0.588 | 0.274 | Neuro-1 | Ccnl1 |
| Ubb4 | 0.648 | 0.322781792 | 0.296 | 0.875 | 0.741 | Neuro-1 | Ubb |
| Rhob | 0.647 | 0.74053023 | 0.294 | 0.382 | 0.087 | Neuro-1 | Rhob |
| Atp6v1b2 | 0.647 | 0.738016702 | 0.294 | 0.397 | 0.101 | Neuro-1 | Atp6v1b2 |
| Eid1 | 0.646 | 0.673275145 | 0.292 | 0.39 | 0.092 | Neuro-1 | Eid1 |
| Rap1a | 0.644 | 0.623024799 | 0.288 | 0.456 | 0.167 | Neuro-1 | Rap1a |
| Gabarapl2 | 0.643 | 0.559841146 | 0.286 | 0.434 | 0.14 | Neuro-1 | Gabarapl2 |
| Clk1 | 0.643 | 0.485673461 | 0.286 | 0.5 | 0.196 | Neuro-1 | Clk1 |
| Calm21 | 0.643 | 0.408325971 | 0.286 | 0.794 | 0.582 | Neuro-1 | Calm2 |
| Gadd45a | 0.642 | 1.076853509 | 0.284 | 0.368 | 0.088 | Neuro-1 | Gadd45a |
| Ncald | 0.642 | 0.794960574 | 0.284 | 0.346 | 0.061 | Neuro-1 | Ncald |
| Lcorl | 0.642 | 0.786403022 | 0.284 | 0.382 | 0.095 | Neuro-1 | Lcorl |
| Phip | 0.642 | 0.627728651 | 0.284 | 0.434 | 0.147 | Neuro-1 | Phip |
| Acly | 0.642 | 0.545261691 | 0.284 | 0.5 | 0.213 | Neuro-1 | Acly |
| Nisch | 0.641 | 0.650495823 | 0.282 | 0.463 | 0.184 | Neuro-1 | Nisch |
| Gcc2 | 0.641 | 0.635252151 | 0.282 | 0.515 | 0.237 | Neuro-1 | Gcc2 |
| Hsbp11 | 0.641 | 0.503687612 | 0.282 | 0.588 | 0.311 | Neuro-1 | Hsbp1 |
| Ostc1 | 0.641 | 0.469101583 | 0.282 | 0.625 | 0.346 | Neuro-1 | Ostc |
| Laptm4a | 0.641 | 0.466806511 | 0.282 | 0.618 | 0.366 | Neuro-1 | Laptm4a |
| Hsp90b12 | 0.641 | 0.356420902 | 0.282 | 0.868 | 0.71 | Neuro-1 | Hsp90b1 |
| Celf3 | 0.64 | 0.703373457 | 0.28 | 0.301 | 0.018 | Neuro-1 | Celf3 |
| Atp2b1 | 0.64 | 0.549518999 | 0.28 | 0.507 | 0.216 | Neuro-1 | Atp2b1 |
| H3f3a2 | 0.64 | 0.403909324 | 0.28 | 0.757 | 0.473 | Neuro-1 | H3f3a |
| Wnt3 | 0.639 | 0.828878937 | 0.278 | 0.316 | 0.039 | Neuro-1 | Wnt3 |
| Ift20 | 0.639 | 0.623180713 | 0.278 | 0.434 | 0.157 | Neuro-1 | Ift20 |
| H2-D12 | 0.639 | 0.508253815 | 0.278 | 0.647 | 0.372 | Neuro-1 | H2-D1 |
| Gfra3 | 0.638 | 1.117930727 | 0.276 | 0.294 | 0.018 | Neuro-1 | Gfra3 |
| Rap1b | 0.638 | 0.754104706 | 0.276 | 0.382 | 0.112 | Neuro-1 | Rap1b |
| Afg3l2 | 0.638 | 0.685814481 | 0.276 | 0.412 | 0.136 | Neuro-1 | Afg3l2 |
| Mrfap1 | 0.638 | 0.44059393 | 0.276 | 0.61 | 0.324 | Neuro-1 | Mrfap1 |
| Tmem59 | 0.637 | 0.50045587 | 0.274 | 0.566 | 0.294 | Neuro-1 | Tmem59 |
| Gnai2 | 0.637 | 0.493258098 | 0.274 | 0.478 | 0.188 | Neuro-1 | Gnai2 |
| Ndufa14 | 0.637 | 0.450731142 | 0.274 | 0.669 | 0.376 | Neuro-1 | Ndufa1 |
| Serinc1 | 0.636 | 0.582311398 | 0.272 | 0.397 | 0.117 | Neuro-1 | Serinc1 |
| Sh3bgrl | 0.635 | 0.515924035 | 0.27 | 0.426 | 0.147 | Neuro-1 | Sh3bgrl |
| Ssr2 | 0.635 | 0.386689782 | 0.27 | 0.728 | 0.463 | Neuro-1 | Ssr2 |
| Tspan12 | 0.634 | 0.619319573 | 0.268 | 0.397 | 0.129 | Neuro-1 | Tspan12 |
| Clcn3 | 0.634 | 0.581409636 | 0.268 | 0.449 | 0.179 | Neuro-1 | Clcn3 |
| Morf4l2 | 0.634 | 0.535528125 | 0.268 | 0.441 | 0.164 | Neuro-1 | Morf4l2 |
| Bsg6 | 0.634 | 0.303402495 | 0.268 | 0.941 | 0.731 | Neuro-1 | Bsg |
| Fev | 0.632 | 0.86765879 | 0.264 | 0.287 | 0.022 | Neuro-1 | Fev |
| Bambi | 0.632 | 0.741238669 | 0.264 | 0.309 | 0.043 | Neuro-1 | Bambi |
| Slc35g2 | 0.632 | 0.733617229 | 0.264 | 0.294 | 0.029 | Neuro-1 | Slc35g2 |
| Ece1 | 0.632 | 0.721062527 | 0.264 | 0.338 | 0.075 | Neuro-1 | Ece1 |
| Tle1 | 0.632 | 0.706991013 | 0.264 | 0.353 | 0.09 | Neuro-1 | Tle1 |
| Cdkn1b1 | 0.632 | 0.658281295 | 0.264 | 0.419 | 0.157 | Neuro-1 | Cdkn1b |
| Impa12 | 0.632 | 0.502041566 | 0.264 | 0.449 | 0.175 | Neuro-1 | Impa1 |
| B2m | 0.632 | 0.442503547 | 0.264 | 0.706 | 0.428 | Neuro-1 | B2m |
| Krt71 | 0.632 | 0.39352623 | 0.264 | 0.618 | 0.335 | Neuro-1 | Krt7 |
| Sec61b3 | 0.632 | 0.33541501 | 0.264 | 0.801 | 0.594 | Neuro-1 | Sec61b |
| Dpysl22 | 0.631 | 0.603572304 | 0.262 | 0.382 | 0.12 | Neuro-1 | Dpysl2 |
| Surf4 | 0.631 | 0.528835041 | 0.262 | 0.449 | 0.185 | Neuro-1 | Surf4 |
| Ctsl4 | 0.631 | 0.439165318 | 0.262 | 0.537 | 0.261 | Neuro-1 | Ctsl |
| Neurog3 | 0.63 | 1.862919081 | 0.26 | 0.301 | 0.049 | Neuro-1 | Neurog3 |
| Vwa5b2 | 0.63 | 0.731717519 | 0.26 | 0.287 | 0.025 | Neuro-1 | Vwa5b2 |
| Jhdm1d | 0.63 | 0.645037441 | 0.26 | 0.316 | 0.053 | Neuro-1 | Jhdm1d |
| Tspan13 | 0.63 | 0.583500389 | 0.26 | 0.471 | 0.21 | Neuro-1 | Tspan13 |
| Calm32 | 0.63 | 0.522874254 | 0.26 | 0.551 | 0.31 | Neuro-1 | Calm3 |
| Gnb22 | 0.63 | 0.509441786 | 0.26 | 0.61 | 0.351 | Neuro-1 | Gnb2 |
| Baiap2l2 | 0.629 | 0.584108533 | 0.258 | 0.397 | 0.135 | Neuro-1 | Baiap2l2 |
| Kdelr2 | 0.629 | 0.466308675 | 0.258 | 0.566 | 0.308 | Neuro-1 | Kdelr2 |
| Arpc51 | 0.628 | 0.431600143 | 0.256 | 0.581 | 0.324 | Neuro-1 | Arpc5 |
| Eif5 | 0.628 | 0.331048493 | 0.256 | 0.757 | 0.506 | Neuro-1 | Eif5 |
| Gpr112 | 0.627 | 0.767151791 | 0.254 | 0.272 | 0.017 | Neuro-1 | Gpr112 |
| Atg3 | 0.627 | 0.509100865 | 0.254 | 0.382 | 0.119 | Neuro-1 | Atg3 |
| Nudt4 | 0.627 | 0.508601246 | 0.254 | 0.39 | 0.129 | Neuro-1 | Nudt4 |
| Atp6v0b1 | 0.627 | 0.500063354 | 0.254 | 0.478 | 0.216 | Neuro-1 | Atp6v0b |
| Rev3l | 0.627 | 0.499944614 | 0.254 | 0.382 | 0.118 | Neuro-1 | Rev3l |
| Nbea | 0.626 | 0.693383632 | 0.252 | 0.316 | 0.061 | Neuro-1 | Nbea |
| Gclm | 0.626 | 0.47904226 | 0.252 | 0.419 | 0.157 | Neuro-1 | Gclm |
| Rab11a | 0.626 | 0.464935682 | 0.252 | 0.478 | 0.217 | Neuro-1 | Rab11a |
| Cd164 | 0.626 | 0.45439964 | 0.252 | 0.434 | 0.166 | Neuro-1 | Cd164 |

TABLE 1-continued

Derived gene list of the top defining genes from in vivo ileal
small intestine PCs and EECs captured on the Seq-Well platform

| | | | | | | | |
|---|---|---|---|---|---|---|---|
| Uqcc2 | 0.626 | 0.364120338 | 0.252 | 0.654 | 0.39 | Neuro-1 | Uqcc2 |
| Pkdcc | 0.625 | 0.582903333 | 0.25 | 0.316 | 0.062 | Neuro-1 | Pkdcc |
| Rnf128 | 0.625 | 0.365771523 | 0.25 | 0.588 | 0.322 | Neuro-1 | Rnf128 |
| Hmgcr | 0.624 | 0.519532934 | 0.248 | 0.434 | 0.181 | Neuro-1 | Hmgcr |
| Ube2b | 0.624 | 0.434372908 | 0.248 | 0.522 | 0.266 | Neuro-1 | Ube2b |
| Itm2b1 | 0.624 | 0.352418292 | 0.248 | 0.699 | 0.46 | Neuro-1 | Itm2b |
| Atp6v0d1 | 0.623 | 0.501170413 | 0.246 | 0.324 | 0.071 | Neuro-1 | Atp6v0d1 |
| Sdcbp | 0.623 | 0.44728396 | 0.246 | 0.522 | 0.275 | Neuro-1 | Sdcbp |
| Snap25 | 0.622 | 0.733085499 | 0.244 | 0.265 | 0.019 | Neuro-1 | Snap25 |
| Gnptg | 0.622 | 0.684923176 | 0.244 | 0.309 | 0.065 | Neuro-1 | Gnptg |
| Jak1 | 0.622 | 0.529762102 | 0.244 | 0.397 | 0.15 | Neuro-1 | Jak1 |
| Tmed3 | 0.622 | 0.507178669 | 0.244 | 0.404 | 0.152 | Neuro-1 | Tmed3 |
| Tmem176b | 0.622 | 0.448540008 | 0.244 | 0.522 | 0.272 | Neuro-1 | Tmem176b |
| Pdap14 | 0.622 | 0.375444576 | 0.244 | 0.669 | 0.41 | Neuro-1 | Pdap1 |
| Htatsf1 | 0.621 | 0.641582192 | 0.242 | 0.382 | 0.145 | Neuro-1 | Htatsf1 |
| Etnk1 | 0.621 | 0.57604006 | 0.242 | 0.331 | 0.085 | Neuro-1 | Etnk1 |
| Msi2 | 0.621 | 0.55577455 | 0.242 | 0.397 | 0.151 | Neuro-1 | Msi2 |
| Rab3d1 | 0.621 | 0.517415086 | 0.242 | 0.382 | 0.134 | Neuro-1 | Rab3d |
| Atp6v1g1 | 0.621 | 0.440226679 | 0.242 | 0.5 | 0.255 | Neuro-1 | Atp6v1g1 |
| Fkbp1a | 0.621 | 0.434229581 | 0.242 | 0.537 | 0.267 | Neuro-1 | Fkbp1a |
| Ccnl2 | 0.62 | 0.578906158 | 0.24 | 0.441 | 0.197 | Neuro-1 | Ccnl2 |
| Fam135a | 0.62 | 0.556454682 | 0.24 | 0.353 | 0.109 | Neuro-1 | Fam135a |
| Prox11 | 0.62 | 0.537224344 | 0.24 | 0.368 | 0.121 | Neuro-1 | Prox1 |
| Pdia32 | 0.62 | 0.385565878 | 0.24 | 0.765 | 0.585 | Neuro-1 | Pdia3 |
| Tspan33 | 0.62 | 0.361026313 | 0.24 | 0.537 | 0.269 | Neuro-1 | Tspan3 |
| Arfl1 | 0.62 | 0.344187048 | 0.24 | 0.588 | 0.342 | Neuro-1 | Arf1 |
| Cdhr5 | 0.619 | 0.588085284 | 0.238 | 0.353 | 0.11 | Neuro-1 | Cdhr5 |
| Dgkd | 0.619 | 0.584670256 | 0.238 | 0.346 | 0.104 | Neuro-1 | Dgkd |
| Arl32 | 0.619 | 0.554441733 | 0.238 | 0.368 | 0.125 | Neuro-1 | Arl3 |
| Tecpr1 | 0.619 | 0.544698414 | 0.238 | 0.316 | 0.075 | Neuro-1 | Tecpr1 |
| Neb | 0.618 | 1.171075878 | 0.236 | 0.301 | 0.072 | Neuro-1 | Neb |
| Pafah1b1 | 0.618 | 0.443726027 | 0.236 | 0.463 | 0.224 | Neuro-1 | Pafah1b1 |
| Dad11 | 0.618 | 0.389491382 | 0.236 | 0.588 | 0.342 | Neuro-1 | Dad1 |
| Sqstm1 | 0.617 | 0.502684131 | 0.234 | 0.368 | 0.126 | Neuro-1 | Sqstm1 |
| Npdc1 | 0.617 | 0.502104728 | 0.234 | 0.346 | 0.106 | Neuro-1 | Npdc1 |
| Grcc10 | 0.617 | 0.458144986 | 0.234 | 0.485 | 0.252 | Neuro-1 | Grcc10 |
| Atp6v0e | 0.617 | 0.338596142 | 0.234 | 0.566 | 0.307 | Neuro-1 | Atp6v0e |
| Gripap1 | 0.616 | 0.607988443 | 0.232 | 0.287 | 0.052 | Neuro-1 | Gripap1 |
| Selt | 0.616 | 0.500239096 | 0.232 | 0.419 | 0.177 | Neuro-1 | Selt |
| Myo6 | 0.616 | 0.481571742 | 0.232 | 0.493 | 0.25 | Neuro-1 | Myo6 |
| Ddost2 | 0.615 | 0.397225476 | 0.23 | 0.544 | 0.313 | Neuro-1 | Ddost |
| Tcf25 | 0.615 | 0.361746655 | 0.23 | 0.507 | 0.261 | Neuro-1 | Tcf25 |
| Ica1 | 0.614 | 0.495387984 | 0.228 | 0.301 | 0.068 | Neuro-1 | Ica1 |
| Cyb5r31 | 0.614 | 0.478034094 | 0.228 | 0.397 | 0.165 | Neuro-1 | Cyb5r3 |
| Egr14 | 0.614 | 0.37889108 | 0.228 | 0.64 | 0.404 | Neuro-1 | Egr1 |
| Ankib1 | 0.613 | 0.607072595 | 0.226 | 0.287 | 0.059 | Neuro-1 | Ankib1 |
| Pim2 | 0.613 | 0.584781157 | 0.226 | 0.243 | 0.016 | Neuro-1 | Pim2 |
| D19Ertd737e | 0.613 | 0.577184167 | 0.226 | 0.309 | 0.08 | Neuro-1 | D19Ertd737e |
| Anapc5 | 0.613 | 0.326902542 | 0.226 | 0.485 | 0.238 | Neuro-1 | Anapc5 |
| Nktr | 0.612 | 0.451196678 | 0.224 | 0.39 | 0.16 | Neuro-1 | Nktr |
| Adh11 | 0.611 | 0.707180854 | 0.222 | 0.404 | 0.194 | Neuro-1 | Adh1 |
| Stxbp5l | 0.611 | 0.683170041 | 0.222 | 0.243 | 0.019 | Neuro-1 | Stxbp5l |
| Rimbp2 | 0.611 | 0.671794311 | 0.222 | 0.235 | 0.013 | Neuro-1 | Rimbp2 |
| Ccdc104 | 0.611 | 0.566216037 | 0.222 | 0.331 | 0.106 | Neuro-1 | Ccdc104 |
| Tmem661 | 0.611 | 0.520722237 | 0.222 | 0.353 | 0.126 | Neuro-1 | Tmem66 |
| Os9 | 0.611 | 0.475052482 | 0.222 | 0.426 | 0.2 | Neuro-1 | Os9 |
| Kif1b | 0.611 | 0.412591612 | 0.222 | 0.346 | 0.115 | Neuro-1 | Kif1b |
| Atrx | 0.611 | 0.3500952 | 0.222 | 0.61 | 0.372 | Neuro-1 | Atrx |
| Tpst2 | 0.61 | 0.611888595 | 0.22 | 0.265 | 0.046 | Neuro-1 | Tpst2 |
| Grtp1 | 0.61 | 0.604200286 | 0.22 | 0.324 | 0.103 | Neuro-1 | Grtp1 |
| Srrm21 | 0.61 | 0.372966321 | 0.22 | 0.713 | 0.47 | Neuro-1 | Srrm2 |
| Srsf5 | 0.61 | 0.349263651 | 0.22 | 0.566 | 0.352 | Neuro-1 | Srsf5 |
| Smpd3 | 0.609 | 0.618968949 | 0.218 | 0.324 | 0.106 | Neuro-1 | Smpd3 |
| Pbx1 | 0.609 | 0.511977577 | 0.218 | 0.316 | 0.094 | Neuro-1 | Pbx1 |
| Baz2b | 0.609 | 0.505153383 | 0.218 | 0.346 | 0.121 | Neuro-1 | Baz2b |
| Dnajc10 | 0.609 | 0.498149156 | 0.218 | 0.375 | 0.153 | Neuro-1 | Dnajc10 |
| Plscr1 | 0.609 | 0.493688786 | 0.218 | 0.346 | 0.124 | Neuro-1 | Plscr1 |
| Papss1 | 0.609 | 0.47358298 | 0.218 | 0.331 | 0.104 | Neuro-1 | Papss1 |
| Sfr12 | 0.609 | 0.442694651 | 0.218 | 0.426 | 0.2 | Neuro-1 | Sfr1 |
| 2700089E24Rik | 0.609 | 0.430347554 | 0.218 | 0.419 | 0.19 | Neuro-1 | 2700089E24Rik |
| Tmem208 | 0.609 | 0.345730582 | 0.218 | 0.471 | 0.235 | Neuro-1 | Tmem208 |
| Cdkn1c | 0.608 | 0.718787305 | 0.216 | 0.301 | 0.083 | Neuro-1 | Cdkn1c |
| Ids | 0.608 | 0.57633085 | 0.216 | 0.243 | 0.024 | Neuro-1 | Ids |
| Ginm1 | 0.608 | 0.557913003 | 0.216 | 0.316 | 0.095 | Neuro-1 | Ginm1 |
| Fndc3a | 0.608 | 0.511356955 | 0.216 | 0.324 | 0.102 | Neuro-1 | Fndc3a |
| Srp72 | 0.608 | 0.390566606 | 0.216 | 0.456 | 0.23 | Neuro-1 | Srp72 |
| Sdf4 | 0.608 | 0.371109666 | 0.216 | 0.426 | 0.198 | Neuro-1 | Sdf4 |

TABLE 1-continued

Derived gene list of the top defining genes from in vivo ileal
small intestine PCs and EECs captured on the Seq-Well platform

| | | | | | | | |
|---|---|---|---|---|---|---|---|
| Matr3 | 0.608 | 0.340711896 | 0.216 | 0.574 | 0.346 | Neuro-1 | Matr3 |
| Tpd521 | 0.608 | 0.310807678 | 0.216 | 0.654 | 0.428 | Neuro-1 | Tpd52 |
| Smim7 | 0.608 | 0.308843585 | 0.216 | 0.412 | 0.176 | Neuro-1 | Smim7 |
| Rab15 | 0.607 | 0.52109546 | 0.214 | 0.272 | 0.056 | Neuro-1 | Rab15 |
| Itfg1 | 0.607 | 0.51736313 | 0.214 | 0.316 | 0.101 | Neuro-1 | Itfg1 |
| Srp14 | 0.607 | 0.310416224 | 0.214 | 0.515 | 0.278 | Neuro-1 | Srp14 |
| Atf2 | 0.606 | 0.64125587 | 0.212 | 0.309 | 0.1 | Neuro-1 | Atf2 |
| Zbtb20 | 0.606 | 0.629224674 | 0.212 | 0.257 | 0.044 | Neuro-1 | Zbtb20 |
| Itpr1 | 0.606 | 0.593141036 | 0.212 | 0.257 | 0.043 | Neuro-1 | Itpr1 |
| Akap8l | 0.606 | 0.571486426 | 0.212 | 0.301 | 0.087 | Neuro-1 | Akap8l |
| Kit | 0.606 | 0.535581262 | 0.212 | 0.272 | 0.056 | Neuro-1 | Kit |
| Eif4g3 | 0.606 | 0.392281288 | 0.212 | 0.324 | 0.102 | Neuro-1 | Eif4g3 |
| Lrp11 | 0.605 | 0.470836804 | 0.21 | 0.235 | 0.024 | Neuro-1 | Lrp11 |
| Slc38a11 | 0.605 | 0.397030605 | 0.21 | 0.397 | 0.175 | Neuro-1 | Slc38a1 |
| Tmbim6 | 0.605 | 0.361225177 | 0.21 | 0.699 | 0.47 | Neuro-1 | Tmbim6 |
| Ufm1 | 0.605 | 0.31958869 | 0.21 | 0.404 | 0.175 | Neuro-1 | Ufm1 |
| Pfdn51 | 0.605 | 0.315328234 | 0.21 | 0.647 | 0.445 | Neuro-1 | Pfdn5 |
| Nefm | 0.604 | 1.056664137 | 0.208 | 0.221 | 0.013 | Neuro-1 | Nefm |
| Cldn46 | 0.604 | 0.404174506 | 0.208 | 0.544 | 0.327 | Neuro-1 | Cldn4 |
| Ywhab2 | 0.604 | 0.326678778 | 0.208 | 0.566 | 0.331 | Neuro-1 | Ywhab |
| Ssr42 | 0.604 | 0.317084171 | 0.208 | 0.728 | 0.578 | Neuro-1 | Ssr4 |
| Fryl | 0.603 | 0.497185124 | 0.206 | 0.309 | 0.098 | Neuro-1 | Fryl |
| Phyh | 0.603 | 0.45174218 | 0.206 | 0.324 | 0.111 | Neuro-1 | Phyh |
| Fam46a | 0.603 | 0.444230155 | 0.206 | 0.309 | 0.097 | Neuro-1 | Fam46a |
| Spcs11 | 0.603 | 0.432019153 | 0.206 | 0.559 | 0.35 | Neuro-1 | Spcs1 |
| Kdm1a | 0.603 | 0.421265714 | 0.206 | 0.324 | 0.112 | Neuro-1 | Kdm1a |
| Atp8b1 | 0.603 | 0.408418464 | 0.206 | 0.485 | 0.274 | Neuro-1 | Atp8b1 |
| Lamp23 | 0.603 | 0.373270994 | 0.206 | 0.507 | 0.3 | Neuro-1 | Lamp2 |
| Kmt2e | 0.603 | 0.367686215 | 0.206 | 0.404 | 0.186 | Neuro-1 | Kmt2e |
| Rock1 | 0.603 | 0.337299181 | 0.206 | 0.434 | 0.214 | Neuro-1 | Rock1 |
| Cryba2 | 0.602 | 0.722200536 | 0.204 | 0.221 | 0.016 | Neuro-1 | Cryba2 |
| Klhl7 | 0.602 | 0.574774143 | 0.204 | 0.235 | 0.03 | Neuro-1 | Klhl7 |
| Syp | 0.602 | 0.550937539 | 0.204 | 0.213 | 0.008 | Neuro-1 | Syp |
| Zmynd11 | 0.602 | 0.423387169 | 0.204 | 0.346 | 0.134 | Neuro-1 | Zmynd11 |
| Ypel3 | 0.601 | 0.604612464 | 0.202 | 0.235 | 0.033 | Neuro-1 | Ypel3 |
| Smim6 | 0.601 | 0.585922342 | 0.202 | 0.279 | 0.073 | Neuro-1 | Smim6 |
| Cdhr2 | 0.601 | 0.524211462 | 0.202 | 0.294 | 0.088 | Neuro-1 | Cdhr2 |
| Zfr | 0.601 | 0.485674276 | 0.202 | 0.36 | 0.156 | Neuro-1 | Zfr |
| Fyttd12 | 0.601 | 0.400754958 | 0.202 | 0.382 | 0.173 | Neuro-1 | Fyttd1 |
| Tulp4 | 0.601 | 0.384054255 | 0.202 | 0.287 | 0.078 | Neuro-1 | Tulp4 |
| Gfpt1 | 0.601 | 0.343263635 | 0.202 | 0.404 | 0.191 | Neuro-1 | Gfpt1 |
| Chgb9 | 0.917 | 2.327697706 | 0.834 | 0.989 | 0.472 | Neuro-2 | Chgb |
| Chga6 | 0.845 | 2.411948819 | 0.69 | 0.818 | 0.222 | Neuro-2 | Chga |
| Reg45 | 0.834 | 3.086108186 | 0.668 | 0.818 | 0.388 | Neuro-2 | Reg4 |
| Tac16 | 0.821 | 2.102281041 | 0.642 | 0.761 | 0.195 | Neuro-2 | Tac1 |
| Afp | 0.795 | 3.705224015 | 0.59 | 0.602 | 0.022 | Neuro-2 | Afp |
| Tph1 | 0.769 | 2.033817286 | 0.538 | 0.557 | 0.025 | Neuro-2 | Tph1 |
| Sepp11 | 0.76 | 1.6489138 | 0.52 | 0.636 | 0.168 | Neuro-2 | Sepp1 |
| Gstt1 | 0.708 | 1.648193654 | 0.416 | 0.466 | 0.072 | Neuro-2 | Gstt1 |
| S100a1 | 0.703 | 1.684653184 | 0.406 | 0.455 | 0.066 | Neuro-2 | S100a1 |
| Ldha12 | 0.701 | 0.544641379 | 0.402 | 0.932 | 0.691 | Neuro-2 | Ldha |
| Aldoa9 | 0.693 | 0.498704379 | 0.386 | 0.886 | 0.657 | Neuro-2 | Aldoa |
| Me22 | 0.681 | 1.381349324 | 0.362 | 0.466 | 0.159 | Neuro-2 | Me2 |
| Lgals411 | 0.681 | 0.425702026 | 0.362 | 0.932 | 0.804 | Neuro-2 | Lgals4 |
| Cystm13 | 0.677 | 0.666414217 | 0.354 | 0.807 | 0.64 | Neuro-2 | Cystm1 |
| Rab3c1 | 0.665 | 1.463902507 | 0.33 | 0.364 | 0.039 | Neuro-2 | Rab3c |
| mt-Nd56 | 0.656 | 0.330158111 | 0.312 | 0.943 | 0.838 | Neuro-2 | mt-Nd5 |
| Resp181 | 0.652 | 1.146002163 | 0.304 | 0.364 | 0.065 | Neuro-2 | Resp18 |
| Ddc1 | 0.649 | 1.078479392 | 0.298 | 0.386 | 0.105 | Neuro-2 | Ddc |
| Ucn3 | 0.64 | 1.539722718 | 0.28 | 0.284 | 0.005 | Neuro-2 | Ucn3 |
| Tpbg | 0.639 | 1.173945088 | 0.278 | 0.307 | 0.033 | Neuro-2 | Tpbg |
| Pigr8 | 0.637 | 0.48784511 | 0.274 | 0.716 | 0.514 | Neuro-2 | Pigr |
| Krt192 | 0.635 | 0.495719214 | 0.27 | 0.682 | 0.542 | Neuro-2 | Krt19 |
| Pcsk12 | 0.632 | 1.159855021 | 0.264 | 0.364 | 0.118 | Neuro-2 | Pcsk1 |
| Trpa1 | 0.63 | 1.170754886 | 0.26 | 0.261 | 0.002 | Neuro-2 | Trpa1 |
| Rgs2 | 0.629 | 1.236480896 | 0.258 | 0.295 | 0.042 | Neuro-2 | Rgs2 |
| Tm4sf5 | 0.629 | 0.722852056 | 0.258 | 0.477 | 0.26 | Neuro-2 | Tm4sf5 |
| Phgr112 | 0.629 | 0.400915035 | 0.258 | 0.693 | 0.436 | Neuro-2 | Phgr1 |
| Gng121 | 0.624 | 0.909339347 | 0.248 | 0.386 | 0.165 | Neuro-2 | Gng12 |
| Akr1c14 | 0.622 | 1.252444111 | 0.244 | 0.273 | 0.033 | Neuro-2 | Akr1c14 |
| Fam183b1 | 0.619 | 0.825344515 | 0.238 | 0.307 | 0.07 | Neuro-2 | Fam183b |
| mt-Co15 | 0.619 | 0.253087133 | 0.238 | 0.989 | 0.919 | Neuro-2 | mt-Co1 |
| Mt29 | 0.614 | 0.258638413 | 0.228 | 0.761 | 0.525 | Neuro-2 | Mt2 |
| Gm51607 | 0.613 | 0.383107503 | 0.226 | 0.534 | 0.302 | Neuro-2 | Gm5160 |
| Aldob5 | 0.612 | 0.33284222 | 0.224 | 0.636 | 0.452 | Neuro-2 | Aldob |
| 2810025M15Rik | 0.61 | 0.968354707 | 0.22 | 0.307 | 0.095 | Neuro-2 | 2810025M15Rik |
| Rasd1 | 0.608 | 0.95261514 | 0.216 | 0.261 | 0.05 | Neuro-2 | Rasd1 |

TABLE 1-continued

Derived gene list of the top defining genes from in vivo ileal
small intestine PCs and EECs captured on the Seq-Well platform

| | | | | | | | |
|---|---|---|---|---|---|---|---|
| Glud1 | 0.608 | 0.79062616 | 0.216 | 0.409 | 0.233 | Neuro-2 | Glud1 |
| Olfm410 | 0.606 | 0.461329406 | 0.212 | 0.511 | 0.297 | Neuro-2 | Olfm4 |
| S100a13 | 0.605 | 1.010102518 | 0.21 | 0.25 | 0.045 | Neuro-2 | S100a13 |
| Lmx1a | 0.605 | 0.744675128 | 0.21 | 0.216 | 0.006 | Neuro-2 | Lmx1a |
| Qdpr2 | 0.604 | 0.760405625 | 0.208 | 0.352 | 0.169 | Neuro-2 | Qdpr |
| Vim3 | 0.603 | 0.860395063 | 0.206 | 0.307 | 0.114 | Neuro-2 | Vim |
| Tm4sf204 | 0.603 | 0.479312866 | 0.206 | 0.568 | 0.418 | Neuro-2 | Tm4sf20 |

Table 1E. Results of ROC-test for Enteroendocrine-enriched marker
genes from all in vivo isolated small intestinal epithelial cells
(FIG. 5B EE InVivo)

| | myAUC | avg_diff | power | pct.1 | pct.2 | cluster | gene |
|---|---|---|---|---|---|---|---|
| Sct1 | 0.895 | 4.441579401 | 0.79 | 0.826 | 0.117 | 15 | Sct |
| Cpe | 0.791 | 2.49298151 | 0.582 | 0.584 | 0.004 | 15 | Cpe |
| Neurod1 | 0.768 | 2.390970023 | 0.536 | 0.537 | 0.002 | 15 | Neurod1 |
| Chgb | 0.747 | 4.217949736 | 0.494 | 0.5 | 0.009 | 15 | Chgb |
| Chga | 0.733 | 3.19332977 | 0.466 | 0.495 | 0.044 | 15 | Chga |
| Pyy | 0.724 | 3.902387734 | 0.448 | 0.458 | 0.015 | 15 | Pyy |
| Tm4sf410 | 0.704 | 1.072123268 | 0.408 | 0.621 | 0.258 | 15 | Tm4sf4 |
| Pcsk1 | 0.701 | 1.82008555 | 0.402 | 0.411 | 0.013 | 15 | Pcsk1 |
| Malat18 | 0.693 | 0.653493706 | 0.386 | 0.963 | 0.891 | 15 | Malat1 |
| Scg2 | 0.686 | 2.196639683 | 0.372 | 0.374 | 0.001 | 15 | Scg2 |
| Fam183b | 0.678 | 1.696400795 | 0.356 | 0.363 | 0.008 | 15 | Fam183b |
| Cck | 0.677 | 2.908997832 | 0.354 | 0.358 | 0.004 | 15 | Cck |
| Tuba1a1 | 0.674 | 1.338122488 | 0.348 | 0.363 | 0.016 | 15 | Tuba1a |
| Fxyd32 | 0.673 | 1.185527087 | 0.346 | 0.421 | 0.083 | 15 | Fxyd3 |
| Hepacam23 | 0.669 | 1.165044917 | 0.338 | 0.416 | 0.086 | 15 | Hepacam2 |
| Ddx56 | 0.661 | 0.623301847 | 0.322 | 0.716 | 0.565 | 15 | Ddx5 |
| Nts | 0.652 | 4.938667765 | 0.304 | 0.337 | 0.047 | 15 | Nts |
| Insm1 | 0.652 | 1.238734111 | 0.304 | 0.305 | 0.001 | 15 | Insm1 |
| Ptprn22 | 0.651 | 1.404630386 | 0.302 | 0.316 | 0.017 | 15 | Ptprn2 |
| Krt77 | 0.65 | 1.323938982 | 0.3 | 0.416 | 0.146 | 15 | Krt7 |
| Cplx2 | 0.649 | 1.240295575 | 0.298 | 0.3 | 0.003 | 15 | Cplx2 |
| Scgn | 0.647 | 1.540047379 | 0.294 | 0.295 | 0.001 | 15 | Scgn |
| Peg3 | 0.644 | 1.356044152 | 0.288 | 0.289 | 0.002 | 15 | Peg3 |
| Selm7 | 0.64 | 0.82025882 | 0.28 | 0.405 | 0.13 | 15 | Selm |
| Hopx7 | 0.638 | 0.926363644 | 0.276 | 0.389 | 0.135 | 15 | Hopx |
| Itm2c1 | 0.637 | 1.102633129 | 0.274 | 0.337 | 0.074 | 15 | Itm2c |
| Prnp | 0.634 | 1.303812979 | 0.268 | 0.274 | 0.006 | 15 | Prnp |
| Car82 | 0.633 | 1.529182238 | 0.266 | 0.305 | 0.049 | 15 | Car8 |
| Pam | 0.63 | 1.311657049 | 0.26 | 0.289 | 0.033 | 15 | Pam |
| Gch11 | 0.63 | 1.257519453 | 0.26 | 0.3 | 0.046 | 15 | Gch1 |
| Isl1 | 0.629 | 1.371287067 | 0.258 | 0.258 | 0.001 | 15 | Isl1 |
| Egr15 | 0.627 | 0.682695585 | 0.254 | 0.526 | 0.32 | 15 | Egr1 |
| Marcks4 | 0.626 | 0.940450751 | 0.252 | 0.347 | 0.111 | 15 | Marcks |
| Krt2011 | 0.626 | 0.523825991 | 0.252 | 0.779 | 0.664 | 15 | Krt20 |
| Maged1 | 0.624 | 1.065463701 | 0.248 | 0.268 | 0.022 | 15 | Maged1 |
| Rfx6 | 0.623 | 1.361875566 | 0.246 | 0.247 | 0.001 | 15 | Rfx6 |
| Resp18 | 0.621 | 1.452364039 | 0.242 | 0.242 | 0.001 | 15 | Resp18 |
| Cd817 | 0.62 | 0.872571881 | 0.24 | 0.4 | 0.195 | 15 | Cd81 |
| Ddc3 | 0.618 | 1.13237105 | 0.236 | 0.342 | 0.133 | 15 | Ddc |
| Ngfrap12 | 0.617 | 0.95111324 | 0.234 | 0.274 | 0.046 | 15 | Ngfrap1 |
| Hsp90ab19 | 0.617 | 0.31369222 | 0.234 | 0.842 | 0.726 | 15 | Hsp90ab1 |
| Pcsk1n | 0.615 | 1.344770047 | 0.23 | 0.232 | 0.001 | 15 | Pcsk1n |
| Scg3 | 0.613 | 1.10155346 | 0.226 | 0.226 | 0 | 15 | Scg3 |
| Gfra3 | 0.613 | 1.009603294 | 0.226 | 0.226 | 0.001 | 15 | Gfra3 |
| Gm6093 | 0.613 | 0.875441764 | 0.226 | 0.258 | 0.034 | 15 | Gm609 |
| Wbp510 | 0.611 | 0.699030828 | 0.222 | 0.384 | 0.186 | 15 | Wbp5 |
| Cnot6l | 0.608 | 0.880416395 | 0.216 | 0.258 | 0.046 | 15 | Cnot6l |
| 6-Jun | 0.607 | 0.552274824 | 0.214 | 0.595 | 0.477 | 15 | Jun |
| Gcg | 0.606 | 3.857236251 | 0.212 | 0.221 | 0.01 | 15 | Gcg |
| Vim | 0.605 | 1.356353586 | 0.21 | 0.216 | 0.006 | 15 | Vim |
| Scg5 | 0.605 | 0.989739316 | 0.21 | 0.211 | 0 | 15 | Scg5 |
| Fos5 | 0.605 | 0.396425334 | 0.21 | 0.716 | 0.596 | 15 | Fos |
| Aplp12 | 0.603 | 1.084201386 | 0.206 | 0.237 | 0.035 | 15 | Aplp1 |
| 5330417C22Rik3 | 0.603 | 0.83967063 | 0.206 | 0.263 | 0.062 | 15 | 5330417C22Rik |
| Myl7 | 0.602 | 1.38794983 | 0.204 | 0.221 | 0.019 | 15 | Myl7 |
| Pax6 | 0.602 | 1.042831316 | 0.204 | 0.205 | 0.001 | 15 | Pax6 |
| Cldn42 | 0.601 | 0.704209507 | 0.202 | 0.274 | 0.071 | 15 | Cldn4 |
| KCTD121 | 0.6 | 0.823319344 | 0.2 | 0.226 | 0.024 | 15 | KCTD12 |

TABLE 1-continued

Derived gene list of the top defining genes from in vivo ileal
small intestine PCs and EECs captured on the Seq-Well platform Table 1F. InVivo Cluster 11 (Paneth Cells) vs Top 200 ENR + CD-4
cells (FIG. 5C InVivo vs ENR + CD4)

| Gene | p_val | avg_diff | pct.1 | pct.2 |
| --- | --- | --- | --- | --- |
| Fabp6 | 6.89E−73 | 2.794414465 | 0.799 | 0 |
| Apoa1 | 1.28E−59 | 2.745285001 | 0.735 | 0.014 |
| Fabp2 | 9.49E−71 | 2.729962201 | 0.942 | 0.13 |
| Gm26924 | 4.31E−168 | 2.52809867 | 1 | 0.851 |
| Gm15564 | 1.07E−77 | 2.437318135 | 0.878 | 0.038 |
| Crip1 | 1.11E−65 | 2.201131282 | 0.894 | 0.096 |
| Zg16 | 1.25E−28 | 2.162302471 | 0.471 | 0.019 |
| Defa20 | 1.48E−44 | 2.046923898 | 0.635 | 0.024 |
| Ccl6 | 1.34E−60 | 1.987268927 | 0.905 | 0.192 |
| Olfm4 | 2.20E−31 | 1.74919956 | 0.434 | 0 |
| Clec2h | 8.09E−42 | 1.724494537 | 0.545 | 0 |
| Defa26 | 3.78E−87 | 1.661421348 | 0.995 | 0.909 |
| mmu-mir-6236 | 3.46E−46 | 1.656170899 | 0.587 | 0 |
| Lars2 | 4.38E−53 | 1.62324169 | 0.91 | 0.409 |
| Defa22 | 1.81E−90 | 1.597296473 | 1 | 0.923 |
| AY761184 | 1.80E−67 | 1.551528962 | 1 | 0.923 |
| Chd8 | 1.98E−14 | 1.547285814 | 0.36 | 0.072 |
| Sepp1 | 2.99E−23 | 1.504693501 | 0.524 | 0.087 |
| Spink3 | 1.31E−27 | 1.479284364 | 0.481 | 0.038 |
| Defa2 | 1.06E−35 | 1.47360816 | 0.508 | 0.005 |
| Gm1123 | 2.18E−39 | 1.425273122 | 0.73 | 0.106 |
| Gm15292 | 3.66E−65 | 1.404298385 | 0.952 | 0.692 |
| Gm21002 | 8.26E−32 | 1.403216059 | 0.466 | 0.005 |
| Reg4 | 9.70E−39 | 1.364094895 | 0.899 | 0.548 |
| Mptx1 | 1.12E−14 | 1.29579207 | 0.413 | 0.091 |
| Pnliprp2 | 3.57E−33 | 1.252964435 | 0.878 | 0.442 |
| Apoa4 | 3.00E−17 | 1.155744489 | 0.286 | 0.01 |
| Sis | 1.17E−16 | 1.154999476 | 0.439 | 0.072 |
| Cps1 | 7.87E−20 | 1.134883345 | 0.344 | 0.019 |
| Gm15308 | 3.15E−34 | 1.12386933 | 0.466 | 0 |
| Lbh | 1.19E−21 | 1.11711376 | 0.487 | 0.072 |
| St3gal4 | 9.40E−18 | 1.095313054 | 0.317 | 0.019 |
| Anpep | 4.23E−22 | 1.09277501 | 0.524 | 0.087 |
| Slc51a | 6.69E−19 | 1.024249548 | 0.28 | 0 |
| Mgam | 1.27E−15 | 0.999087463 | 0.402 | 0.067 |
| 2200002D01Rik | 2.83E−12 | 0.992108543 | 0.481 | 0.159 |
| Ccl25 | 1.86E−17 | 0.989852511 | 0.354 | 0.034 |
| Hpgd | 1.40E−19 | 0.968811329 | 0.439 | 0.053 |
| Mptx2 | 2.72E−13 | 0.949925415 | 0.788 | 0.423 |
| Ces2e | 6.56E−15 | 0.94678761 | 0.27 | 0.01 |
| Pycard | 7.85E−12 | 0.943278351 | 0.381 | 0.101 |
| Krt20 | 2.76E−13 | 0.908829291 | 0.36 | 0.072 |
| Bambi | 2.02E−14 | 0.901391979 | 0.37 | 0.053 |
| Ace2 | 8.63E−13 | 0.869654756 | 0.233 | 0.01 |
| Sult1d1 | 5.02E−17 | 0.868941062 | 0.36 | 0.034 |
| Clca3 | 6.45E−09 | 0.856399955 | 0.19 | 0.019 |
| Pigr | 2.86E−17 | 0.85359266 | 0.709 | 0.279 |
| Gm10104 | 4.05E−24 | 0.834585815 | 0.979 | 0.798 |
| Muc2 | 2.04E−16 | 0.832185644 | 0.661 | 0.245 |
| Slc5a1 | 3.20E−15 | 0.829348878 | 0.36 | 0.043 |
| Maoa | 5.22E−13 | 0.820182098 | 0.302 | 0.034 |
| Cdh17 | 1.55E−15 | 0.817891016 | 0.471 | 0.106 |
| Otc | 8.03E−13 | 0.799427168 | 0.228 | 0.01 |
| Krt19 | 5.26E−12 | 0.797610341 | 0.63 | 0.293 |
| Cyp4f14 | 2.15E−15 | 0.787921804 | 0.233 | 0 |
| Plb1 | 1.64E−13 | 0.787790121 | 0.206 | 0 |
| AI747448 | 3.14E−16 | 0.784452184 | 0.201 | 0.01 |
| Slc6a19 | 5.96E−11 | 0.782890249 | 0.169 | 0 |
| Atp5o | 6.03E−10 | 0.748647472 | 0.508 | 0.202 |
| Aoc1 | 8.16E−13 | 0.726366453 | 0.222 | 0.01 |
| Sord | 8.44E−11 | 0.723352746 | 0.365 | 0.082 |
| Mep1b | 4.62E−12 | 0.723175799 | 0.206 | 0.005 |
| Prap1 | 1.25E−13 | 0.720704557 | 0.317 | 0.038 |
| Mgst1 | 1.45E−12 | 0.717887883 | 0.481 | 0.144 |
| Gm7849 | 4.94E−09 | 0.717557393 | 0.386 | 0.12 |
| Enpep | 2.11E−12 | 0.708946078 | 0.19 | 0 |
| Atp1a1 | 7.56E−12 | 0.7036131 | 0.481 | 0.168 |
| Cndp2 | 5.70E−10 | 0.699939528 | 0.238 | 0.024 |
| Aldob | 4.07E−09 | 0.698437585 | 0.423 | 0.139 |
| Naaladl1 | 3.66E−11 | 0.694458684 | 0.212 | 0.014 |
| Fos | 5.76E−12 | 0.692995212 | 0.788 | 0.49 |
| Muc3 | 4.89E−12 | 0.689025992 | 0.185 | 0 |

TABLE 1-continued

Derived gene list of the top defining genes from in vivo ileal
small intestine PCs and EECs captured on the Seq-Well platform

| | | | | |
|---|---|---|---|---|
| 2210404O07Rik | 2.49E−11 | 0.668864299 | 0.418 | 0.13 |
| Dpep1 | 7.01E−10 | 0.666476273 | 0.153 | 0 |
| Oat | 5.12E−10 | 0.663503949 | 0.418 | 0.139 |
| Reg3g | 2.22E−10 | 0.662732291 | 0.608 | 0.274 |
| Dgat1 | 1.81E−11 | 0.66075657 | 0.259 | 0.024 |
| Pepd | 1.35E−06 | 0.652370213 | 0.228 | 0.053 |
| Uqcr10 | 3.69E−10 | 0.65050164 | 0.667 | 0.385 |
| Tob1 | 1.02E−10 | 0.650029355 | 0.328 | 0.062 |
| Cdx1 | 3.73E−07 | 0.645769015 | 0.354 | 0.144 |
| Plcb3 | 3.17E−10 | 0.640070365 | 0.228 | 0.024 |
| Lct | 7.94E−09 | 0.639932045 | 0.138 | 0 |
| Myo1a | 6.34E−08 | 0.636556999 | 0.217 | 0.038 |
| Pls1 | 1.26E−06 | 0.633128215 | 0.312 | 0.101 |
| Slc27a4 | 2.37E−09 | 0.632437472 | 0.169 | 0.01 |
| Guca2b | 1.81E−12 | 0.626285536 | 0.804 | 0.476 |
| Snord13 | 5.02E−09 | 0.621323384 | 0.402 | 0.125 |
| Slc9a3r1 | 6.25E−07 | 0.619366422 | 0.27 | 0.072 |
| Ckmt1 | 3.77E−09 | 0.614168327 | 0.296 | 0.067 |
| Slc15a1 | 2.41E−07 | 0.610956158 | 0.143 | 0.005 |
| Ggt1 | 2.36E−08 | 0.597187545 | 0.159 | 0.005 |
| Apob | 2.55E−06 | 0.59692589 | 0.206 | 0.062 |
| Gfpt1 | 1.91E−08 | 0.590343443 | 0.434 | 0.197 |
| Fbp2 | 6.63E−10 | 0.586392459 | 0.328 | 0.082 |
| Sgk1 | 7.18E−12 | 0.584589889 | 0.238 | 0.014 |
| Hpd | 5.68E−09 | 0.58229397 | 0.265 | 0.043 |
| Dpp4 | 4.71E−08 | 0.581900208 | 0.175 | 0.019 |
| Klf4 | 5.30E−09 | 0.574982296 | 0.233 | 0.029 |
| Hadha | 4.09E−07 | 0.571458506 | 0.291 | 0.096 |
| Cox5a | 7.87E−08 | 0.563300928 | 0.503 | 0.236 |
| Phgr1 | 5.25E−09 | 0.558407061 | 0.635 | 0.322 |
| Aldh1b1 | 8.06E−06 | 0.557440384 | 0.466 | 0.25 |
| Ace | 3.93E−08 | 0.554965613 | 0.127 | 0 |
| Tmigd1 | 3.55E−09 | 0.55155353 | 0.143 | 0 |
| Vil1 | 1.01E−06 | 0.551098465 | 0.45 | 0.216 |
| Sult1b1 | 4.49E−08 | 0.54573234 | 0.153 | 0.005 |
| Ccl5 | 8.68E−08 | 0.544612494 | 0.122 | 0 |
| Uqcrc1 | 4.05E−06 | 0.543715856 | 0.392 | 0.188 |
| Gm21498 | 3.24E−06 | 0.542339507 | 0.529 | 0.293 |
| Pdcd4 | 1.09E−10 | 0.538620646 | 0.312 | 0.067 |
| Hnf4g | 7.80E−07 | 0.533602425 | 0.185 | 0.024 |
| Agpat2 | 5.98E−07 | 0.533276832 | 0.175 | 0.024 |
| Xpnpep1 | 6.57E−07 | 0.531202684 | 0.206 | 0.038 |
| Rfk | 1.30E−05 | 0.525401438 | 0.36 | 0.144 |
| Maf | 8.88E−06 | 0.522184356 | 0.127 | 0.01 |
| Khk | 1.48E−05 | 0.519311747 | 0.153 | 0.024 |
| Car8 | 3.64E−08 | 0.519192064 | 0.354 | 0.106 |
| Nlrp6 | 1.10E−08 | 0.51574593 | 0.164 | 0.005 |
| Cdca7 | 2.96E−06 | 0.514361605 | 0.185 | 0.029 |
| Coro2a | 1.72E−07 | 0.509456294 | 0.138 | 0.01 |
| Xpnpep2 | 4.86E−05 | 0.508734097 | 0.106 | 0.005 |
| Apoc3 | 3.44E−06 | 0.507147645 | 0.18 | 0.034 |
| Tm4sf5 | 1.04E−05 | 0.506510188 | 0.265 | 0.111 |
| Agt | 1.36E−07 | 0.504633679 | 0.185 | 0.019 |
| 2010106E10Rik | 9.14E−06 | 0.504516033 | 0.148 | 0.019 |
| Gna11 | 1.82E−07 | 0.502564418 | 0.201 | 0.029 |
| Me2 | 3.26E−10 | 0.502447092 | 0.254 | 0.038 |
| Asph | 1.06E−07 | 0.498901513 | 0.386 | 0.135 |
| Slc51b | 3.93E−08 | 0.498893766 | 0.127 | 0 |
| Amn | 6.23E−07 | 0.497927062 | 0.138 | 0.005 |
| Rbp2 | 2.71E−07 | 0.493629472 | 0.143 | 0.005 |
| Gm10936 | 6.50E−11 | 0.489589605 | 0.196 | 0.01 |
| Ano6 | 1.78E−09 | 0.483434657 | 0.19 | 0.019 |
| Mttp | 3.42E−06 | 0.481033959 | 0.18 | 0.029 |
| Pabpc1 | 7.43E−08 | 0.480498931 | 0.841 | 0.606 |
| Mgst3 | 6.70E−07 | 0.47965119 | 0.333 | 0.13 |
| Creb3l3 | 9.95E−06 | 0.478757185 | 0.111 | 0.005 |
| Snord118 | 9.89E−07 | 0.478270728 | 0.296 | 0.091 |
| n-R5-8s1 | 2.60E−11 | 0.477213392 | 0.175 | 0 |
| Sel1l | 1.68E−11 | 0.475890045 | 0.339 | 0.077 |
| P4hb | 3.48E−11 | 0.473083977 | 0.889 | 0.75 |
| Sri | 7.54E−09 | 0.471992839 | 0.407 | 0.149 |
| B4galnt1 | 2.53E−07 | 0.466942661 | 0.206 | 0.038 |
| Aldh9a1 | 0.000635305 | 0.465621436 | 0.196 | 0.077 |
| Prlr | 5.87E−07 | 0.463002595 | 0.138 | 0.005 |
| Prr15 | 5.06E−11 | 0.462892291 | 0.392 | 0.115 |
| Ivns1abp | 1.10E−05 | 0.455338648 | 0.556 | 0.308 |
| Glod5 | 7.56E−07 | 0.450811522 | 0.132 | 0.005 |

TABLE 1-continued

Derived gene list of the top defining genes from in vivo ileal
small intestine PCs and EECs captured on the Seq-Well platform

| | | | | |
|---|---|---|---|---|
| Cox6a1 | 2.95E−05 | 0.450622885 | 0.656 | 0.447 |
| Mapk13 | 2.59E−05 | 0.448540988 | 0.243 | 0.072 |
| Atp5d | 3.76E−07 | 0.44814667 | 0.455 | 0.197 |
| Cd74 | 8.16E−05 | 0.445384695 | 0.101 | 0.005 |
| H2afv | 2.67E−05 | 0.443257922 | 0.365 | 0.159 |
| Ppp1r1b | 0.000298994 | 0.44020946 | 0.249 | 0.091 |
| Tmem59 | 1.50E−08 | 0.439241468 | 0.54 | 0.26 |
| Aqp1 | 6.71E−06 | 0.438238419 | 0.291 | 0.101 |
| Plac8 | 1.70E−06 | 0.438057927 | 0.693 | 0.481 |
| Psmb10 | 1.18E−05 | 0.434360989 | 0.243 | 0.082 |
| Ahnak | 1.37E−06 | 0.432900374 | 0.106 | 0.01 |
| Ppp1r14d | 3.94E−05 | 0.432278825 | 0.138 | 0.019 |
| Mep1a | 6.23E−07 | 0.431438692 | 0.138 | 0.005 |
| Klk1 | 0.00141784 | 0.430152287 | 0.122 | 0.024 |
| Man1a | 7.96E−07 | 0.429356647 | 0.275 | 0.072 |
| Ndufa3 | 8.27E−05 | 0.429296854 | 0.392 | 0.202 |
| Fam213b | 5.14E−08 | 0.429263379 | 0.148 | 0.005 |
| Map2k2 | 0.00043541 | 0.423775579 | 0.233 | 0.091 |
| Mogat2 | 9.12E−07 | 0.420208529 | 0.106 | 0 |
| Tmem120a | 1.97E−05 | 0.41751037 | 0.127 | 0.019 |
| Slc25a5 | 1.09E−06 | 0.416117714 | 0.746 | 0.572 |
| Lsm2 | 0.002495442 | 0.415462138 | 0.111 | 0.024 |
| Lgals4 | 7.47E−07 | 0.415061084 | 0.868 | 0.769 |
| Gpr128 | 8.64E−07 | 0.413486524 | 0.127 | 0.014 |
| Vdr | 7.63E−06 | 0.412339435 | 0.143 | 0.014 |
| Bcl2l15 | 8.37E−05 | 0.41126119 | 0.101 | 0.005 |
| Alpi | 1.98E−06 | 0.40984793 | 0.101 | 0 |
| Mdh2 | 6.10E−05 | 0.405836853 | 0.392 | 0.212 |
| Trp53inp1 | 2.98E−06 | 0.403353077 | 0.249 | 0.067 |
| Car4 | 1.98E−06 | 0.403314629 | 0.101 | 0 |
| Myo15b | 4.23E−06 | 0.398700241 | 0.222 | 0.058 |
| Hes1 | 0.001361387 | 0.397971035 | 0.228 | 0.087 |
| Hsd17b11 | 1.65E−05 | 0.397016358 | 0.153 | 0.058 |
| Golm1 | 1.64E−06 | 0.39487159 | 0.349 | 0.135 |
| Vdac1 | 1.33E−05 | 0.394491186 | 0.28 | 0.101 |
| Rbm47 | 2.33E−08 | 0.393474876 | 0.402 | 0.159 |
| Lrba | 3.11E−05 | 0.390948012 | 0.116 | 0.014 |
| Acsl5 | 8.38E−05 | 0.390765407 | 0.222 | 0.072 |
| Cs | 0.001253395 | 0.390576902 | 0.233 | 0.101 |
| Ms4a8a | 5.36E−05 | 0.390074254 | 0.143 | 0.029 |
| Klf5 | 0.001247316 | 0.389697895 | 0.222 | 0.091 |
| Gpd1 | 0.001098308 | 0.38945621 | 0.18 | 0.058 |
| Sult2b1 | 7.31E−05 | 0.389320415 | 0.101 | 0.005 |
| Cox7a1 | 3.30E−05 | 0.387585592 | 0.106 | 0.01 |
| Atp5b | 4.19E−07 | 0.385794895 | 0.741 | 0.51 |
| Chchd7 | 4.24E−05 | 0.385524129 | 0.291 | 0.115 |
| H2-Q2 | 0.000550478 | 0.381917811 | 0.175 | 0.048 |
| Vdac2 | 0.000600361 | 0.381917492 | 0.296 | 0.135 |
| Ubl3 | 9.37E−08 | 0.381413149 | 0.302 | 0.091 |
| Hspd1 | 0.003942912 | 0.380609278 | 0.349 | 0.202 |
| Acox1 | 0.000611774 | 0.379594091 | 0.201 | 0.072 |
| Atp5a1 | 1.18E−06 | 0.379498043 | 0.598 | 0.37 |
| Ramp1 | 3.48E−07 | 0.377749721 | 0.37 | 0.144 |
| Dusp1 | 9.55E−06 | 0.375874964 | 0.275 | 0.096 |
| Lad1 | 0.000861872 | 0.375757898 | 0.201 | 0.077 |
| Actn4 | 0.000120297 | 0.370280213 | 0.328 | 0.154 |
| Atp5k | 4.84E−08 | 0.3693736 | 0.524 | 0.255 |
| Taldo1 | 0.000205287 | 0.366870125 | 0.466 | 0.269 |
| 2410015M20Rik | 0.000101046 | 0.365838645 | 0.259 | 0.096 |
| Styk1 | 5.34E−07 | 0.364713415 | 0.212 | 0.043 |
| Mpp1 | 6.10E−05 | 0.364418368 | 0.148 | 0.034 |
| Mgat4c | 0.00012321 | 0.362713678 | 0.101 | 0.005 |
| Clrn3 | 0.00124897 | 0.360568958 | 0.111 | 0.019 |
| Gucy2c | 1.00E−05 | 0.360208647 | 0.212 | 0.058 |
| Slc12a2 | 1.30E−05 | 0.357673933 | 0.508 | 0.293 |
| Ell2 | 3.92E−07 | 0.35672579 | 0.254 | 0.072 |
| Reg3b | 0.000111213 | 0.356094204 | 0.561 | 0.356 |
| Prpsap1 | 0.00165382 | 0.355719227 | 0.148 | 0.053 |
| Faah | 0.002511093 | 0.354116242 | 0.111 | 0.024 |
| Hmgcl | 8.50E−05 | 0.353492089 | 0.132 | 0.038 |
| Ubxn2a | 4.70E−06 | 0.352849255 | 0.27 | 0.082 |
| Hadh | 8.14E−06 | 0.352437687 | 0.307 | 0.154 |
| Pnrc1 | 0.00328913 | 0.352271477 | 0.217 | 0.087 |
| Arf6 | 0.000338333 | 0.35191723 | 0.265 | 0.111 |
| Gsr | 5.42E−05 | 0.351862945 | 0.228 | 0.077 |
| Etfa | 1.75E−05 | 0.350637541 | 0.27 | 0.106 |
| Lgals3 | 0.001089262 | 0.349966881 | 0.127 | 0.029 |

TABLE 1-continued

Derived gene list of the top defining genes from in vivo ileal
small intestine PCs and EECs captured on the Seq-Well platform

| | | | | |
|---|---|---|---|---|
| Tstd1 | 9.12E−07 | 0.349108292 | 0.106 | 0 |
| Epcam | 4.96E−05 | 0.348739761 | 0.852 | 0.668 |
| Naip5 | 0.000158653 | 0.348352674 | 0.106 | 0.019 |
| Abhd17c | 0.000380818 | 0.347801117 | 0.132 | 0.034 |
| Mgat4a | 3.40E−06 | 0.347261458 | 0.175 | 0.038 |
| Fosb | 0.000748493 | 0.34637696 | 0.323 | 0.154 |
| Sptssa | 0.000443895 | 0.346066884 | 0.302 | 0.139 |
| Cftr | 0.000475678 | 0.344172836 | 0.122 | 0.019 |
| Rpl41 | 2.46E−06 | 0.343548269 | 0.825 | 0.774 |
| Efna1 | 0.000276603 | 0.342425524 | 0.164 | 0.043 |
| Samhd1 | 0.000716801 | 0.340224417 | 0.122 | 0.029 |
| Tmprss2 | 4.92E−05 | 0.340167759 | 0.439 | 0.236 |
| Uqcrc2 | 1.16E−05 | 0.339484562 | 0.312 | 0.13 |
| Sh3glb1 | 3.66E−07 | 0.339451718 | 0.328 | 0.13 |
| Sidt2 | 4.64E−05 | 0.338809612 | 0.106 | 0.005 |
| B2m | 2.18E−06 | 0.338709962 | 0.624 | 0.423 |
| Cobl | 1.85E−05 | 0.338053322 | 0.18 | 0.038 |
| Eps8l3 | 5.92E−06 | 0.336952586 | 0.233 | 0.067 |
| Cyc1 | 0.001210813 | 0.336024668 | 0.259 | 0.115 |
| Cryl1 | 0.000797843 | 0.335928912 | 0.101 | 0.019 |
| Pccb | 8.27E−08 | 0.334563979 | 0.238 | 0.058 |
| Tkt | 0.014546079 | 0.333591862 | 0.317 | 0.207 |
| Lypd8 | 2.62E−06 | 0.331319233 | 0.577 | 0.327 |
| Edem1 | 2.43E−05 | 0.329871174 | 0.243 | 0.072 |
| Hagh | 4.75E−06 | 0.329014544 | 0.212 | 0.053 |
| Lyz2 | 8.82E−05 | 0.326985506 | 0.804 | 0.601 |
| Dap | 0.000106582 | 0.326795179 | 0.312 | 0.135 |
| Sfxn1 | 0.009872151 | 0.325145567 | 0.201 | 0.087 |
| Myh14 | 0.008668194 | 0.324263927 | 0.159 | 0.058 |
| Smpdl3a | 0.000282998 | 0.324029974 | 0.175 | 0.053 |
| Fam174b | 0.00048122 | 0.323778232 | 0.222 | 0.077 |
| Gm24601 | 1.58E−09 | 0.323704332 | 0.148 | 0 |
| Misp | 0.010835316 | 0.323504586 | 0.175 | 0.082 |
| Zzef1 | 0.010032456 | 0.322700043 | 0.101 | 0.024 |
| Calm3 | 9.91E−05 | 0.322675306 | 0.317 | 0.139 |
| Fahd1 | 0.000241362 | 0.321598446 | 0.148 | 0.034 |
| Entpd7 | 1.89E−05 | 0.319727608 | 0.111 | 0.01 |
| Serpinb1a | 0.01616932 | 0.317900285 | 0.37 | 0.226 |
| Jup | 0.001389256 | 0.316634822 | 0.159 | 0.053 |
| Csrp2 | 0.000446077 | 0.316243516 | 0.169 | 0.053 |
| Pdha1 | 2.83E−06 | 0.316073056 | 0.339 | 0.144 |
| Cap1 | 0.025029824 | 0.31523349 | 0.19 | 0.096 |
| Ahcyl2 | 0.000303645 | 0.314865821 | 0.127 | 0.029 |
| Tulp4 | 0.000105189 | 0.314158504 | 0.243 | 0.087 |
| Gm10260 | 0.000202743 | 0.313419383 | 0.19 | 0.062 |
| 2-Mar | 8.63E−06 | 0.311646492 | 0.354 | 0.168 |
| Jun | 0.00193883 | 0.31094902 | 0.672 | 0.505 |
| Sppl2a | 1.28E−05 | 0.310946885 | 0.36 | 0.163 |
| Pgd | 0.004689561 | 0.308578277 | 0.148 | 0.053 |
| Zfyve21 | 0.000352105 | 0.3082869 | 0.138 | 0.029 |
| Slc13a1 | 1.98E−06 | 0.308020729 | 0.101 | 0 |
| Deptor | 3.04E−05 | 0.307090565 | 0.143 | 0.024 |
| Qsox1 | 7.84E−05 | 0.306665594 | 0.455 | 0.245 |
| Slc25a15 | 4.10E−06 | 0.304116641 | 0.122 | 0.014 |
| Tnfrsf1a | 0.004530766 | 0.302312236 | 0.127 | 0.043 |
| Cldn7 | 0.000579732 | 0.302041478 | 0.656 | 0.476 |
| Stk11 | 0.015440853 | 0.30139002 | 0.132 | 0.048 |
| Pxmp4 | 0.000212256 | 0.299765908 | 0.116 | 0.019 |
| Add3 | 0.012709722 | 0.299738578 | 0.153 | 0.072 |
| Tmbim6 | 1.30E−05 | 0.29957386 | 0.646 | 0.428 |
| Ndufa10 | 0.000210867 | 0.298526344 | 0.185 | 0.072 |
| Nadk | 0.005939395 | 0.298399624 | 0.143 | 0.048 |
| Tapbp | 0.000527405 | 0.294741343 | 0.138 | 0.058 |
| Ralgps2 | 0.000460055 | 0.294481536 | 0.127 | 0.024 |
| Cox4i1 | 0.004003242 | 0.293346203 | 0.778 | 0.678 |
| Mapk1 | 0.001303237 | 0.293271819 | 0.228 | 0.101 |
| Specc1l | 0.000406181 | 0.291989335 | 0.196 | 0.067 |
| Rmdn3 | 0.002273752 | 0.291531342 | 0.101 | 0.019 |
| Gng12 | 0.000615535 | 0.291180618 | 0.201 | 0.082 |
| Il17rc | 0.008351214 | 0.290611921 | 0.106 | 0.024 |
| Kcne3 | 0.035168848 | 0.290073745 | 0.159 | 0.067 |
| Perp | 0.000122508 | 0.289832559 | 0.228 | 0.096 |
| Arhgap21 | 0.002147713 | 0.289657036 | 0.116 | 0.024 |
| Glud1 | 0.003813991 | 0.289341641 | 0.275 | 0.144 |
| Pcmtd2 | 0.000133663 | 0.289334569 | 0.138 | 0.024 |
| Pdxdc1 | 0.000611179 | 0.289301238 | 0.275 | 0.12 |
| Syf2 | 0.000204932 | 0.287754737 | 0.159 | 0.062 |

TABLE 1-continued

Derived gene list of the top defining genes from in vivo ileal
small intestine PCs and EECs captured on the Seq-Well platform

| | | | | |
|---|---|---|---|---|
| Npepps | 0.000210932 | 0.287490999 | 0.164 | 0.048 |
| Ap2a2 | 5.77E−05 | 0.286049861 | 0.159 | 0.034 |
| Ceacam1 | 0.012558374 | 0.285711887 | 0.185 | 0.082 |
| Gm7861 | 5.09E−06 | 0.28566966 | 0.571 | 0.423 |
| Ndufv1 | 0.000731802 | 0.285654675 | 0.217 | 0.087 |
| Prodh | 9.12E−07 | 0.28536933 | 0.106 | 0 |
| Suclg1 | 0.001484541 | 0.284953462 | 0.296 | 0.154 |
| Atp5e | 2.01E−05 | 0.284538659 | 0.688 | 0.49 |
| Tm9sf2 | 0.000226493 | 0.284242333 | 0.333 | 0.163 |
| Azin1 | 0.000681563 | 0.28371138 | 0.228 | 0.091 |
| Casp1 | 0.0128346 | 0.281796158 | 0.138 | 0.048 |
| Cdhr2 | 0.001277173 | 0.281341383 | 0.217 | 0.087 |
| Tsc22d3 | 0.000336506 | 0.28111833 | 0.106 | 0.014 |
| Diap1 | 0.00036502 | 0.280817322 | 0.159 | 0.038 |
| Aldh6a1 | 0.000127747 | 0.280771928 | 0.153 | 0.034 |
| Ddx54 | 0.000262144 | 0.280593441 | 0.138 | 0.029 |
| Adk | 0.000427315 | 0.280112945 | 0.222 | 0.082 |
| Sema4a | 0.000836485 | 0.279603599 | 0.111 | 0.019 |
| Pum1 | 0.046348529 | 0.279046058 | 0.122 | 0.053 |
| Atg7 | 0.00773597 | 0.278616966 | 0.132 | 0.048 |
| Gipc2 | 0.001821273 | 0.278357685 | 0.159 | 0.053 |
| Bcar3 | 4.49E−05 | 0.278157211 | 0.132 | 0.024 |
| Mvp | 0.006999775 | 0.277281462 | 0.122 | 0.034 |
| Ifi30 | 0.006205503 | 0.277151701 | 0.116 | 0.038 |
| Rac1 | 1.45E−06 | 0.276928263 | 0.28 | 0.106 |
| Plekhb2 | 1.15E−07 | 0.276052595 | 0.201 | 0.043 |
| Iqgap2 | 0.0013389 | 0.275988331 | 0.116 | 0.029 |
| Lman1 | 6.25E−06 | 0.275922903 | 0.397 | 0.197 |
| Osr2 | 0.000621614 | 0.275671454 | 0.106 | 0.014 |
| Nucb2 | 0.000164379 | 0.274634584 | 0.386 | 0.197 |
| Ak2 | 0.00687328 | 0.274187748 | 0.312 | 0.178 |
| Atp5c1 | 0.002880814 | 0.274042138 | 0.513 | 0.389 |
| Gpa33 | 0.046607098 | 0.273985868 | 0.175 | 0.106 |
| Copa | 0.000526397 | 0.273955995 | 0.259 | 0.115 |
| Ndufb8 | 0.006740515 | 0.273190659 | 0.402 | 0.25 |
| Sdha | 0.005840515 | 0.272878213 | 0.265 | 0.135 |
| Riok3 | 0.002258585 | 0.272636128 | 0.153 | 0.053 |
| Clca4 | 0.002111404 | 0.272622559 | 0.291 | 0.149 |
| Rnf128 | 3.99E−07 | 0.271082123 | 0.503 | 0.274 |
| Camk2d | 0.000434015 | 0.270550821 | 0.132 | 0.029 |
| 2010107E04Rik | 0.001866922 | 0.270511937 | 0.619 | 0.428 |
| Hnf4a | 0.002383177 | 0.270376795 | 0.228 | 0.106 |
| Unc93b1 | 3.79E−05 | 0.270366067 | 0.111 | 0.01 |
| Cda | 0.013682109 | 0.268416519 | 0.101 | 0.024 |
| Wasl | 0.00196066 | 0.268014022 | 0.18 | 0.067 |
| Gne | 0.000210937 | 0.267730362 | 0.201 | 0.062 |
| Chchd3 | 0.002554413 | 0.266784765 | 0.222 | 0.101 |
| Bola3 | 0.132044858 | 0.266144467 | 0.122 | 0.058 |
| Ccdc107 | 0.002422551 | 0.265968784 | 0.122 | 0.048 |
| Akap8 | 0.008747812 | 0.265357404 | 0.116 | 0.038 |
| Hjurp | 0.178462987 | 0.264089732 | 0.111 | 0.058 |
| Lta4h | 0.036965722 | 0.264026193 | 0.175 | 0.082 |
| Tmem54 | 1.61E−05 | 0.263806428 | 0.18 | 0.062 |
| Ddx47 | 0.004818384 | 0.263691556 | 0.101 | 0.019 |
| Surf4 | 0.000298793 | 0.263678254 | 0.402 | 0.221 |
| Kit | 7.85E−08 | 0.263669741 | 0.28 | 0.091 |
| Sucla2 | 0.006604643 | 0.262674028 | 0.18 | 0.082 |
| Cep350 | 0.00096944 | 0.262051265 | 0.132 | 0.038 |
| Wnt3 | 0.000977386 | 0.26198011 | 0.217 | 0.087 |
| Pdcd6 | 0.007882918 | 0.25818866 | 0.222 | 0.115 |
| Pim3 | 3.35E−05 | 0.258174011 | 0.286 | 0.115 |
| Cldn15 | 0.000187162 | 0.257624763 | 0.349 | 0.192 |
| Itm2b | 0.000223028 | 0.257321318 | 0.571 | 0.375 |
| Slc31a1 | 0.004356272 | 0.257137521 | 0.169 | 0.062 |
| Vaultrc5 | 0.001619244 | 0.257017214 | 0.185 | 0.082 |
| Defa5 | 0.005601392 | 0.256972377 | 0.698 | 0.572 |
| Samd5 | 5.45E−08 | 0.256637806 | 0.143 | 0.01 |
| Aldh2 | 0.00066891 | 0.256489269 | 0.116 | 0.029 |
| Stat6 | 0.003478488 | 0.256235435 | 0.122 | 0.029 |
| Canx | 0.00040178 | 0.256007952 | 0.598 | 0.404 |
| Smim6 | 6.80E−08 | 0.255781064 | 0.296 | 0.096 |
| Vapa | 0.000226208 | 0.255554437 | 0.291 | 0.135 |
| Wdr1 | 0.004423034 | 0.255433876 | 0.201 | 0.096 |
| Mgst2 | 0.000188956 | 0.254791701 | 0.259 | 0.111 |
| Klf10 | 0.012020168 | 0.254344833 | 0.164 | 0.067 |
| Myb | 0.028335838 | 0.253500318 | 0.101 | 0.029 |
| Serpinb6a | 0.005531695 | 0.253468724 | 0.349 | 0.202 |

TABLE 1-continued

Derived gene list of the top defining genes from in vivo ileal small intestine PCs and EECs captured on the Seq-Well platform

| | | | | |
|---|---|---|---|---|
| Efcab4b | 0.002091294 | 0.252975069 | 0.127 | 0.029 |
| Tfrc | 0.000422437 | 0.251901024 | 0.127 | 0.043 |
| Ppard | 0.000896655 | 0.251380411 | 0.111 | 0.019 |
| Tfg | 1.95E−05 | 0.250724854 | 0.238 | 0.101 |
| Fam213a | 2.53E−09 | 0.250180706 | 0.407 | 0.163 |
| Cox7a2l | 0.017484589 | −0.252140376 | 0.27 | 0.322 |
| Srebf2 | 0.011510883 | −0.254567514 | 0.048 | 0.115 |
| Tubb5 | 0.129347951 | −0.259916799 | 0.275 | 0.341 |
| Gm5160 | 0.073566054 | −0.260849627 | 0.048 | 0.12 |
| Npm1 | 0.009802281 | −0.261222987 | 0.418 | 0.514 |
| Rps15a | 6.50E−07 | −0.261768917 | 0.725 | 0.856 |
| Cnn3 | 0.026069066 | −0.266341458 | 0.085 | 0.149 |
| Rpl11 | 0.02518531 | −0.275194507 | 0.079 | 0.13 |
| Rpl21 | 0.013458619 | −0.276391478 | 0.058 | 0.115 |
| Sec61g | 0.014267567 | −0.276477428 | 0.058 | 0.115 |
| Prdx4 | 0.031550414 | −0.280664075 | 0.069 | 0.12 |
| Ndufa6 | 0.000225184 | −0.281719307 | 0.545 | 0.649 |
| Polr2e | 0.058371858 | −0.282416849 | 0.116 | 0.173 |
| Gm10704 | 0.003253615 | −0.289029224 | 0.048 | 0.115 |
| Ythdc1 | 0.09564442 | −0.28958559 | 0.074 | 0.125 |
| Rps3 | 7.94E−11 | −0.289729383 | 0.868 | 0.928 |
| Nr2c2ap | 0.000588514 | −0.293271871 | 0.042 | 0.101 |
| Areg | 0.001281208 | −0.298928777 | 0.053 | 0.135 |
| Zfp36l1 | 0.000240351 | −0.29934516 | 0.085 | 0.144 |
| Maged1 | 0.003332676 | −0.30045974 | 0.048 | 0.101 |
| Tmem14c | 0.002306995 | −0.304323857 | 0.111 | 0.168 |
| Eef1d | 0.001371079 | −0.305433379 | 0.222 | 0.284 |
| Rpl23a | 0.062152778 | −0.305851719 | 0.069 | 0.135 |
| Pbdc1 | 0.025943464 | −0.306212432 | 0.042 | 0.106 |
| Orc5 | 0.056455039 | −0.30646476 | 0.116 | 0.192 |
| Irf2bp2 | 0.008329455 | −0.307736405 | 0.106 | 0.173 |
| Rps23 | 0.011739843 | −0.308446698 | 0.069 | 0.135 |
| Ten1 | 0.102160524 | −0.309709144 | 0.101 | 0.159 |
| Rpl13a-ps1 | 0.042009656 | −0.310152675 | 0.085 | 0.159 |
| Mif | 0.018013509 | −0.310948239 | 0.106 | 0.178 |
| Rpl21-ps4 | 0.000240118 | −0.311183162 | 0.042 | 0.115 |
| Sc4mol | 0.007711873 | −0.311224746 | 0.111 | 0.183 |
| Rpl37 | 0.008770113 | −0.3115343 | 0.365 | 0.462 |
| Polr2f | 0.000273658 | −0.312235393 | 0.228 | 0.293 |
| Rpl17 | 0.006815832 | −0.312820054 | 0.053 | 0.12 |
| 2310036O22Rik | 0.010330838 | −0.315652547 | 0.085 | 0.144 |
| Bri3 | 0.014926152 | −0.317141505 | 0.09 | 0.154 |
| Dbi | 0.001079677 | −0.317560635 | 0.54 | 0.611 |
| Fryl | 0.010593255 | −0.318541718 | 0.085 | 0.144 |
| Rps10-ps1 | 0.028097021 | −0.318863607 | 0.233 | 0.312 |
| U2surp | 0.027164055 | −0.319014849 | 0.111 | 0.173 |
| Smoc2 | 0.007238828 | −0.319778202 | 0.238 | 0.303 |
| Psmb7 | 0.006477049 | −0.320215106 | 0.037 | 0.13 |
| Gstp1 | 0.013296427 | −0.321690138 | 0.132 | 0.221 |
| Srp9 | 3.78E−05 | −0.322697933 | 0.333 | 0.385 |
| Tuba4a | 0.016637477 | −0.322905383 | 0.101 | 0.159 |
| Ifi27 | 0.015397997 | −0.322923537 | 0.042 | 0.106 |
| Tm2d1 | 0.05115425 | −0.325196427 | 0.079 | 0.135 |
| Gstm1 | 0.000230566 | −0.325940509 | 0.026 | 0.135 |
| Gm10288 | 0.016862232 | −0.32672543 | 0.058 | 0.139 |
| Eid1 | 0.004080842 | −0.327986425 | 0.063 | 0.12 |
| Nfib | 0.003840857 | −0.332070479 | 0.048 | 0.106 |
| Fkbp11 | 0.001702597 | −0.33457054 | 0.201 | 0.274 |
| Gadd45b | 0.005428897 | −0.335179663 | 0.053 | 0.115 |
| Gtf2i | 0.005136519 | −0.33667399 | 0.09 | 0.168 |
| Rpl19 | 0.011486209 | −0.338013065 | 0.143 | 0.236 |
| Timm13 | 0.001871889 | −0.338574841 | 0.265 | 0.327 |
| Itgb1 | 0.036462386 | −0.343180778 | 0.159 | 0.231 |
| Brk1 | 0.01403406 | −0.346372631 | 0.132 | 0.197 |
| Slc20a1 | 0.002705833 | −0.3488653 | 0.021 | 0.111 |
| Cxadr | 0.004298945 | −0.350462975 | 0.127 | 0.178 |
| Nhp2l1 | 0.00822258 | −0.352218539 | 0.021 | 0.101 |
| Phpt1 | 0.0029264 | −0.352720363 | 0.058 | 0.12 |
| Hsbp1 | 0.000823419 | −0.353008576 | 0.169 | 0.236 |
| Swi5 | 1.51E−05 | −0.354053685 | 0.212 | 0.264 |
| Tcp1 | 0.001071065 | −0.357264628 | 0.19 | 0.279 |
| Slirp | 0.027120843 | −0.359162885 | 0.201 | 0.26 |
| Tmem176b | 0.014638728 | −0.360250299 | 0.18 | 0.26 |
| Tsc22d1 | 0.000310827 | −0.362193796 | 0.185 | 0.25 |
| Rpl10 | 0.005810772 | −0.365229817 | 0.063 | 0.168 |
| Cldn3 | 0.000169145 | −0.3667166 | 0.423 | 0.486 |
| Snhg3 | 0.010138043 | −0.367572874 | 0.053 | 0.135 |

TABLE 1-continued

Derived gene list of the top defining genes from in vivo ileal
small intestine PCs and EECs captured on the Seq-Well platform

| | | | | |
|---|---|---|---|---|
| Nisch | 0.005919767 | −0.376326043 | 0.069 | 0.139 |
| Rps21 | 4.71E−07 | −0.376428799 | 0.725 | 0.837 |
| Rpl29 | 0.002651795 | −0.376516598 | 0.243 | 0.298 |
| Eif4g1 | 0.002722413 | −0.376609408 | 0.28 | 0.361 |
| Aplp2 | 0.000531071 | −0.378339699 | 0.132 | 0.202 |
| Avpi1 | 4.78E−05 | −0.379758207 | 0.048 | 0.106 |
| Nedd8 | 0.000377334 | −0.380703757 | 0.217 | 0.269 |
| Rpl35 | 0.000724596 | −0.381303013 | 0.508 | 0.625 |
| Krt23 | 0.000800174 | −0.38220357 | 0.074 | 0.159 |
| Rnf6 | 0.001260028 | −0.384243793 | 0.063 | 0.12 |
| Rpl32 | 2.57E−17 | −0.384437253 | 0.91 | 0.981 |
| Tmem57 | 0.000405747 | −0.386349148 | 0.053 | 0.125 |
| mt-Nd6 | 0.016053176 | −0.389263233 | 0.095 | 0.173 |
| Gm12728 | 0.000351127 | −0.389554075 | 0.021 | 0.106 |
| Ngfrap1 | 0.001609665 | −0.390367209 | 0.079 | 0.13 |
| Thyn1 | 0.008380408 | −0.39170097 | 0.032 | 0.101 |
| H3f3a | 0.004457828 | −0.392346385 | 0.18 | 0.269 |
| Ssb | 0.0001136 | −0.39357373 | 0.275 | 0.327 |
| Tecr | 0.000573426 | −0.393628314 | 0.138 | 0.226 |
| Wdr89 | 0.000939611 | −0.393703708 | 0.233 | 0.361 |
| Ttr | 0.003337606 | −0.395342766 | 0.026 | 0.101 |
| Ostc | 0.000377159 | −0.396743193 | 0.275 | 0.365 |
| Rpl13a | 7.09E−11 | −0.397237135 | 0.825 | 0.938 |
| Cpe | 9.63E−05 | −0.397741526 | 0.005 | 0.106 |
| Tpsg1 | 0.004260073 | −0.398698859 | 0.048 | 0.135 |
| Gm9843 | 2.85E−06 | −0.401098423 | 0.481 | 0.596 |
| 1110038B12Rik | 0.013164847 | −0.402047429 | 0.19 | 0.293 |
| Commd3 | 0.001200104 | −0.402077169 | 0.101 | 0.183 |
| Tmem205 | 0.004058066 | −0.402193663 | 0.101 | 0.197 |
| Calml4 | 0.000206327 | −0.40286878 | 0.328 | 0.385 |
| Tm4sf4 | 9.64E−07 | −0.403129844 | 0.376 | 0.433 |
| Rbx1 | 0.000414636 | −0.405344456 | 0.169 | 0.279 |
| Rpl31 | 0.012997575 | −0.406077236 | 0.106 | 0.212 |
| Pomp | 0.000173576 | −0.40754857 | 0.19 | 0.26 |
| Psat1 | 0.000502605 | −0.407965285 | 0.021 | 0.115 |
| Rgcc | 0.00096964 | −0.408602614 | 0.101 | 0.154 |
| Atf4 | 0.000403041 | −0.408615916 | 0.36 | 0.438 |
| Fundc2 | 0.007364425 | −0.409271455 | 0.09 | 0.183 |
| Strn3 | 0.000337646 | −0.409440929 | 0.111 | 0.168 |
| Eif4ebp1 | 0.000507077 | −0.409543936 | 0.132 | 0.183 |
| Gm9396 | 3.28E−06 | −0.409551355 | 0 | 0.101 |
| Atf5 | 3.28E−06 | −0.411534575 | 0 | 0.101 |
| Hn1 | 0.000806639 | −0.412677099 | 0.196 | 0.269 |
| Rpl14 | 3.91E−09 | −0.413504979 | 0.667 | 0.88 |
| D10Bwg1379e | 3.85E−06 | −0.41494752 | 0.069 | 0.135 |
| Hmgcr | 0.011028758 | −0.41849862 | 0.079 | 0.135 |
| Chchd2 | 1.85E−06 | −0.418713149 | 0.556 | 0.644 |
| Gm24146 | 4.45E−05 | −0.41888405 | 0.005 | 0.106 |
| Atox1 | 0.005490355 | −0.419855051 | 0.153 | 0.216 |
| Gstm5 | 0.000694529 | −0.420074174 | 0.079 | 0.163 |
| mt-Nd2 | 4.24E−07 | −0.420870803 | 0.683 | 0.837 |
| 2700060E02Rik | 0.000176909 | −0.421110265 | 0.185 | 0.279 |
| Gadd45g | 0.001950316 | −0.422570759 | 0.265 | 0.332 |
| Ndufa1 | 0.000579309 | −0.425214056 | 0.249 | 0.346 |
| Lect2 | 8.44E−07 | −0.425590616 | 0 | 0.111 |
| Prdx2 | 7.18E−05 | −0.427400479 | 0.307 | 0.385 |
| 0610009D07Rik | 0.000129747 | −0.431551957 | 0.122 | 0.221 |
| Echdc2 | 0.001345941 | −0.432901186 | 0.021 | 0.106 |
| Srp14 | 3.41E−05 | −0.434110934 | 0.169 | 0.236 |
| Lrrc26 | 0.000269847 | −0.43462566 | 0.106 | 0.192 |
| Ltn1 | 4.43E−05 | −0.43496069 | 0.074 | 0.173 |
| Tceb2 | 0.000549685 | −0.438016411 | 0.254 | 0.356 |
| Hist1h1c | 0.000416334 | −0.438205493 | 0.09 | 0.154 |
| Gm25911 | 0.000203714 | −0.4389797 | 0.021 | 0.13 |
| Rdh10 | 0.002218378 | −0.439024801 | 0.032 | 0.106 |
| Polr3k | 0.003914754 | −0.439369247 | 0.079 | 0.192 |
| Adh1 | 0.000947453 | −0.439537545 | 0.021 | 0.115 |
| Selm | 2.05E−06 | −0.439723493 | 0.418 | 0.476 |
| Prdx1 | 1.30E−06 | −0.440301939 | 0.709 | 0.784 |
| Mt2 | 0.00456606 | −0.440867663 | 0.079 | 0.163 |
| Eif3m | 4.93E−05 | −0.441195248 | 0.159 | 0.212 |
| Gm8420 | 7.29E−06 | −0.441299956 | 0.048 | 0.13 |
| Gm6139 | 4.26E−07 | −0.443757087 | 0 | 0.115 |
| Rps13 | 0.00057086 | −0.444545236 | 0.053 | 0.173 |
| Fdps | 0.002872595 | −0.44477163 | 0.048 | 0.154 |
| Gm9493 | 0.000158185 | −0.445937708 | 0.048 | 0.144 |
| Ywhaq | 0.000629845 | −0.448390041 | 0.127 | 0.24 |

TABLE 1-continued

Derived gene list of the top defining genes from in vivo ileal
small intestine PCs and EECs captured on the Seq-Well platform

| | | | | |
|---|---|---|---|---|
| Cd81 | 0.002047566 | −0.451319262 | 0.143 | 0.245 |
| Gas5 | 1.71E−05 | −0.454302947 | 0.455 | 0.635 |
| H2afz | 0.007854924 | −0.45441755 | 0.074 | 0.173 |
| Skp1a | 3.87E−06 | −0.455711713 | 0.37 | 0.423 |
| Ncl | 9.61E−07 | −0.457511022 | 0.577 | 0.639 |
| Hmgcs1 | 0.000290879 | −0.458974021 | 0.18 | 0.25 |
| Gm10132 | 7.44E−05 | −0.459725739 | 0.016 | 0.111 |
| Ranbp1 | 0.000528075 | −0.460830613 | 0.238 | 0.341 |
| Rps11 | 1.24E−06 | −0.46209607 | 0.593 | 0.74 |
| mt-Atp6 | 0.001240713 | −0.462281332 | 0.101 | 0.231 |
| Sec61b | 1.18E−07 | −0.462312239 | 0.646 | 0.736 |
| Taf1d | 0.013277287 | −0.462875628 | 0.116 | 0.192 |
| Grcc10 | 0.000332073 | −0.463270318 | 0.042 | 0.12 |
| Cfl1 | 1.94E−05 | −0.463334089 | 0.233 | 0.322 |
| Prom1 | 2.67E−05 | −0.463399463 | 0.143 | 0.236 |
| Rps17 | 0.00116106 | −0.464881009 | 0.058 | 0.173 |
| Ubl5 | 8.96E−05 | −0.464892598 | 0.291 | 0.38 |
| Rpl6 | 6.52E−05 | −0.465214038 | 0.196 | 0.332 |
| Hbegf | 0.000104344 | −0.466684197 | 0.106 | 0.183 |
| Dynll1 | 2.57E−07 | −0.46756004 | 0.27 | 0.394 |
| Btf3 | 0.000134943 | −0.467926409 | 0.185 | 0.284 |
| Sec11c | 1.02E−07 | −0.473369926 | 0.476 | 0.558 |
| Oaz1 | 8.09E−05 | −0.475982534 | 0.339 | 0.49 |
| Phgdh | 2.44E−05 | −0.481364965 | 0.016 | 0.125 |
| Psmb6 | 0.000319976 | −0.482323069 | 0.254 | 0.351 |
| Selk | 1.75E−07 | −0.482556045 | 0.296 | 0.394 |
| Rps9 | 7.39E−13 | −0.483566949 | 0.778 | 0.942 |
| Tomm20 | 0.000132435 | −0.490044399 | 0.063 | 0.202 |
| Lsr | 2.46E−05 | −0.491175809 | 0.27 | 0.375 |
| Atp5g1 | 8.08E−05 | −0.492013593 | 0.116 | 0.216 |
| Psmd8 | 6.76E−06 | −0.492661387 | 0.185 | 0.26 |
| Snrpg | 0.001572527 | −0.493223107 | 0.143 | 0.25 |
| Ptma | 8.07E−06 | −0.493817227 | 0.413 | 0.524 |
| Aldoa | 4.69E−07 | −0.493870974 | 0.265 | 0.322 |
| Rps27a | 6.85E−05 | −0.4972725 | 0.143 | 0.264 |
| Rpl23a-ps3 | 1.15E−06 | −0.500902127 | 0.005 | 0.139 |
| Rpl10a | 0.00028653 | −0.504079744 | 0.106 | 0.25 |
| Tmed6 | 2.07E−08 | −0.506835091 | 0.439 | 0.51 |
| Laptm4b | 1.64E−05 | −0.508853003 | 0.053 | 0.13 |
| Bud31 | 1.46E−06 | −0.509698976 | 0.127 | 0.197 |
| Gm6576 | 6.58E−05 | −0.510464331 | 0.085 | 0.25 |
| Hsp90aa1 | 0.000105567 | −0.511293723 | 0.217 | 0.37 |
| Hmgb2 | 0.00044436 | −0.512039439 | 0.159 | 0.226 |
| Rpl22l1 | 6.48E−06 | −0.513112107 | 0.471 | 0.596 |
| Atp6v0e | 4.01E−05 | −0.513115296 | 0.169 | 0.24 |
| Gm10269 | 5.18E−05 | −0.513419769 | 0.185 | 0.312 |
| Rpl10-ps3 | 7.01E−05 | −0.515446334 | 0.032 | 0.154 |
| Son | 6.18E−06 | −0.516770037 | 0.286 | 0.346 |
| Pkm | 0.00019381 | −0.521392815 | 0.19 | 0.341 |
| Rpl12 | 0.000101383 | −0.521536295 | 0.079 | 0.216 |
| Slc25a4 | 0.000186223 | −0.527207956 | 0.037 | 0.168 |
| 1810037I17Rik | 1.54E−05 | −0.529384464 | 0.212 | 0.269 |
| Pdgfa | 8.68E−05 | −0.532795772 | 0.063 | 0.178 |
| Ssr4 | 1.02E−11 | −0.533813325 | 0.661 | 0.712 |
| Tmem167 | 1.35E−06 | −0.536054534 | 0.164 | 0.245 |
| Gip | 4.57E−05 | −0.537319439 | 0.021 | 0.115 |
| Gng5 | 7.65E−06 | −0.538609306 | 0.164 | 0.279 |
| Nme1 | 8.52E−06 | −0.539926697 | 0.323 | 0.514 |
| Acta1 | 0.000254708 | −0.541387123 | 0.016 | 0.12 |
| Rps24 | 2.03E−21 | −0.545654318 | 0.852 | 0.962 |
| Nop10 | 5.91E−06 | −0.546337145 | 0.302 | 0.409 |
| Cdk4 | 1.20E−05 | −0.547122866 | 0.196 | 0.332 |
| Rps3a1 | 2.41E−10 | −0.547636784 | 0.603 | 0.788 |
| Rpl36al | 3.00E−07 | −0.552987884 | 0.434 | 0.596 |
| Pcna | 6.64E−06 | −0.557475861 | 0.032 | 0.178 |
| Rps27l | 1.29E−09 | −0.558161739 | 0.63 | 0.745 |
| Naca | 2.28E−06 | −0.559060194 | 0.365 | 0.514 |
| Cystm1 | 2.14E−05 | −0.560521007 | 0.27 | 0.49 |
| Eef1b2 | 5.73E−11 | −0.561211449 | 0.635 | 0.827 |
| Rps15 | 7.52E−09 | −0.563493746 | 0.571 | 0.707 |
| Gsta4 | 0.000376155 | −0.565132131 | 0.048 | 0.154 |
| Tpm4 | 1.18E−05 | −0.572677052 | 0.111 | 0.24 |
| Plk2 | 5.10E−07 | −0.575972557 | 0.016 | 0.13 |
| Atrx | 4.88E−06 | −0.577584592 | 0.169 | 0.264 |
| Rpl18 | 5.72E−07 | −0.577961954 | 0.291 | 0.471 |
| Pglyrp1 | 4.66E−08 | −0.580517035 | 0.286 | 0.447 |
| Rpl38 | 1.59E−08 | −0.58124534 | 0.54 | 0.673 |

TABLE 1-continued

Derived gene list of the top defining genes from in vivo ileal
small intestine PCs and EECs captured on the Seq-Well platform

| | | | | |
|---|---|---|---|---|
| mt-Nd5 | 3.08E−08 | −0.583013223 | 0.598 | 0.726 |
| Cstb | 2.54E−06 | −0.588440967 | 0.127 | 0.264 |
| Tnfrsf12a | 6.52E−06 | −0.593759924 | 0.026 | 0.159 |
| Rpl18a | 3.19E−08 | −0.594960202 | 0.376 | 0.587 |
| mt-Co1 | 4.09E−14 | −0.596199034 | 0.72 | 0.894 |
| Ftl1 | 1.25E−07 | −0.596348892 | 0.201 | 0.341 |
| Rpl27a | 2.96E−06 | −0.597795638 | 0.196 | 0.375 |
| Pebp1 | 1.11E−05 | −0.602051355 | 0.085 | 0.236 |
| Gm6472 | 1.11E−06 | −0.605115885 | 0.037 | 0.178 |
| Ubb | 8.67E−10 | −0.606892668 | 0.534 | 0.683 |
| Myl12a | 5.89E−05 | −0.607360494 | 0.233 | 0.375 |
| Rps2 | 1.55E−17 | −0.607915911 | 0.725 | 0.913 |
| Krt7 | 7.00E−08 | −0.608551206 | 0.185 | 0.327 |
| Tac1 | 1.32E−08 | −0.609466655 | 0 | 0.139 |
| Ccdc34 | 9.24E−07 | −0.610192214 | 0.148 | 0.245 |
| Nme2 | 4.16E−07 | −0.616087733 | 0.037 | 0.212 |
| Spcs1 | 1.98E−10 | −0.624977292 | 0.296 | 0.394 |
| Rpl5 | 3.14E−07 | −0.633252154 | 0.032 | 0.202 |
| mt-Cytb | 9.60E−18 | −0.633457589 | 0.878 | 0.947 |
| Gnb2l1 | 1.40E−16 | −0.634921488 | 0.725 | 0.851 |
| Gcg | 3.92E−07 | −0.636343125 | 0.016 | 0.168 |
| Hmgn1 | 2.55E−05 | −0.636993308 | 0.164 | 0.284 |
| Cd63 | 1.62E−14 | −0.637719602 | 0.593 | 0.721 |
| Rpl26 | 8.42E−17 | −0.638634723 | 0.735 | 0.923 |
| Rps5 | 5.27E−21 | −0.646605873 | 0.862 | 0.962 |
| Rps25 | 1.81E−07 | −0.652872931 | 0.228 | 0.423 |
| H3f3b | 1.69E−13 | −0.659838522 | 0.545 | 0.688 |
| Atp6v1f | 8.30E−07 | −0.664009401 | 0.169 | 0.312 |
| Ssr2 | 7.06E−09 | −0.664712565 | 0.354 | 0.476 |
| Atp6v1g1 | 4.97E−06 | −0.664760371 | 0.095 | 0.255 |
| Rps6 | 2.05E−07 | −0.665915434 | 0.063 | 0.274 |
| Rpl23 | 8.44E−10 | −0.669667798 | 0.429 | 0.668 |
| Cyp2c55 | 4.42E−07 | −0.674226292 | 0.005 | 0.144 |
| Pla2g1b | 8.84E−11 | −0.67953062 | 0 | 0.173 |
| Cst3 | 1.67E−11 | −0.682317075 | 0.339 | 0.438 |
| Gm26917 | 1.35E−05 | −0.683305761 | 0.048 | 0.178 |
| Romo1 | 1.54E−07 | −0.699449376 | 0.164 | 0.37 |
| Myl6 | 6.18E−09 | −0.69964038 | 0.106 | 0.288 |
| Ctsl | 1.33E−08 | −0.703093615 | 0.053 | 0.245 |
| Cyr61 | 1.00E−08 | −0.704444878 | 0.063 | 0.231 |
| Rpl30 | 1.25E−09 | −0.70998512 | 0.254 | 0.462 |
| Rnf32 | 5.41E−06 | −0.710130688 | 0.111 | 0.221 |
| Rplp1 | 3.38E−30 | −0.712756027 | 0.878 | 0.981 |
| Defa25 | 1.61E−10 | −0.715705986 | 0.185 | 0.399 |
| Ang6 | 5.79E−11 | −0.716221276 | 0.212 | 0.351 |
| Rpl13 | 2.27E−14 | −0.717649203 | 0.561 | 0.788 |
| Actg1 | 1.92E−10 | −0.724955082 | 0.063 | 0.269 |
| Rps16 | 3.84E−07 | −0.729478717 | 0.175 | 0.37 |
| Tuba1a | 2.94E−09 | −0.73434991 | 0.021 | 0.168 |
| Rps10 | 1.03E−18 | −0.737307591 | 0.614 | 0.827 |
| Rps8 | 5.48E−14 | −0.742402719 | 0.503 | 0.692 |
| Rpl3 | 2.14E−10 | −0.750557432 | 0.333 | 0.62 |
| Sox4 | 3.03E−08 | −0.760506904 | 0.069 | 0.245 |
| Fkbp3 | 8.56E−07 | −0.76976704 | 0.217 | 0.365 |
| 1810022K09Rik | 1.45E−08 | −0.787524184 | 0.138 | 0.337 |
| Chga | 1.32E−10 | −0.791039349 | 0.021 | 0.221 |
| Lrrc58 | 2.42E−10 | −0.792043496 | 0.222 | 0.476 |
| Rpsa | 6.39E−10 | −0.795078971 | 0.228 | 0.495 |
| Gm9765 | 2.36E−13 | −0.825289527 | 0.206 | 0.413 |
| mt-Nd1 | 8.58E−29 | −0.850345382 | 0.852 | 0.986 |
| Ifitm2 | 1.15E−12 | −0.865114602 | 0.228 | 0.418 |
| Cfi | 8.89E−13 | −0.876969132 | 0.016 | 0.226 |
| Ppia | 2.89E−12 | −0.893106102 | 0.058 | 0.337 |
| Cyp2e1 | 2.33E−10 | −0.918234535 | 0.026 | 0.231 |
| Eef1a1 | 1.44E−31 | −0.932185435 | 0.772 | 0.933 |
| Cck | 1.71E−13 | −0.956946027 | 0.016 | 0.269 |
| Fxyd3 | 1.64E−14 | −0.960305221 | 0.265 | 0.514 |
| Sct | 3.37E−09 | −0.969003141 | 0.196 | 0.433 |
| Ghrl | 1.83E−10 | −0.969586007 | 0 | 0.168 |
| Gm10275 | 2.62E−15 | −0.983530061 | 0.095 | 0.389 |
| Rps4x | 8.06E−17 | −0.985916347 | 0.228 | 0.567 |
| Scd2 | 9.20E−15 | −1.024887641 | 0.079 | 0.394 |
| Rpl7a | 1.27E−16 | −1.037579581 | 0.116 | 0.466 |
| Ang2 | 4.01E−18 | −1.051661404 | 0.132 | 0.438 |
| Gm8730 | 5.84E−19 | −1.059036053 | 0.206 | 0.606 |
| Thbs1 | 3.11E−17 | −1.062661826 | 0.217 | 0.442 |
| Rps20 | 2.28E−38 | −1.063543475 | 0.656 | 0.928 |

TABLE 1-continued

Derived gene list of the top defining genes from in vivo ileal
small intestine PCs and EECs captured on the Seq-Well platform

| | | | | |
|---|---|---|---|---|
| Rnase1 | 5.09E−13 | −1.06995887 | 0.164 | 0.428 |
| D17H6S56E-5 | 1.33E−15 | −1.099963647 | 0.185 | 0.476 |
| Rps7 | 4.89E−26 | −1.161473081 | 0.365 | 0.76 |
| Tmsb10 | 3.28E−25 | −1.199574969 | 0.333 | 0.683 |
| Clu | 4.67E−18 | −1.212913464 | 0.005 | 0.298 |
| S100a11 | 2.36E−20 | −1.226604206 | 0.053 | 0.438 |
| Uba52 | 4.77E−30 | −1.28447217 | 0.259 | 0.736 |
| Cldn4 | 5.51E−25 | −1.293526661 | 0.153 | 0.5 |
| Ifitm3 | 4.43E−22 | −1.306612102 | 0.048 | 0.452 |
| Gm23935 | 6.91E−34 | −1.326558771 | 0.762 | 0.913 |
| Malat1 | 1.04E−43 | −1.360749436 | 0.825 | 0.995 |
| Rpl7 | 1.59E−37 | −1.409066357 | 0.349 | 0.846 |
| Ifitm1 | 8.32E−28 | −1.434635185 | 0 | 0.404 |
| S100a6 | 5.28E−24 | −1.444056948 | 0.101 | 0.495 |
| Xist | 9.33E−33 | −1.583925327 | 0 | 0.462 |
| Tpt1 | 3.19E−48 | −1.661520782 | 0.286 | 0.798 |
| Chgb | 5.51E−36 | −1.908187675 | 0.011 | 0.519 |

TABLE 2

Reference gene lists used in single-cell analyses

| Wnt_KEGG | Reactome_Notch | Respiratory Electron Transport | Proteome Up 1-164 | Proteome Up 165-328 | Proteome Down 1-152 | Proteome Down 153-303 |
|---|---|---|---|---|---|---|
| APC | ADAM10 | COX1 | Ern2 | Cracr2a | Brwd3 | Esf1 |
| APC2 | ADAM17 | COX2 | Mecp2 | Mmp7 | Cd44 | Gnat3 |
| AXIN1 | APH1A | COX3 | Plcb1 | Fhdc1 | Ndufaf5 | Shank3 |
| AXIN2 | APH1B | COX4I1 | Pla2g1b | Mtus2 | Ppig | Srek1ip1 |
| BTRC | ARRB1 | COX5A | Ggh | Plb1 | Lrp2 | Srrm1 |
| CACYBP | ARRB2 | COX5B | Npc2 | Manf | Mllt6 | Prune2 |
| CAMK2A | ATP2A1 | COX6A1 | Pmfbp1 | Ang4 | Slfn9 | Mrpl43 |
| CAMK2B | ATP2A2 | COX6B1 | Cpq | Zbtb38 | Gm13251 | Cluh |
| CAMK2D | ATP2A3 | COX6C | Wif1 | Tmc5 | Ski | Scin |
| CAMK2G | B4GALT1 | COX7A2L | Lemd3 | Gsdma2 | Coro2a | Adck3 |
| CCND1 | CCNC | COX7B | Phf2 | Ush2A | Zcchc7 | Adck3 |
| CCND2 | CCND1 | COX7C | Insrr | Sct | Mylk | Dmbt1 |
| CCND3 | CDK8 | COX8A | Nupr1 | Lgals3bp | Zfp40 | Scarb1 |
| CER1 | CNTN1 | CYC1 | Ak1 | Clu | Ptprb | Mme |
| CHD8 | CREBBP | CYCS | Celsr2 | Eml1 | Cttnbp2 | Ces1e |
| CHP | CUL1 | CYTB | Hgfac | Cyp2e1 | Mgst1 | Fau |
| CHP2 | DLK1 | ETFA | Dnajc12 | Rcn1 | Fam151b | Hspe1 |
| CREBBP | DLL1 | ETFB | Ctsf | Smpd1 | Gm8973 | Ugt1a6 |
| CSNK1A1 | DLL4 | ETFDH | Dach1 | Scg2 | Olfm4 | Nqo1 |
| CSNK1A1L | DNER | LOC651820 | Pcsk1n | Hivep1 | Zranb2 | Ces2b |
| CSNK1E | DTX1 | LOC727947 | Dbn1 | Aplp1 | Ugt1a8 | Zfp677 |
| CSNK2A1 | DTX2 | MTND5P10 | Poll | Serpina1c | Bud31 | Clta |
| CSNK2A2 | DTX4 | ND1 | Dnaja4 | Cpe | AU019823 | L1cam |
| CSNK2B | E2F1 | ND2 | Pfn2 | Bmp1 | Ces2g | Rab35 |
| CTBP1 | E2F3 | ND3 | Cryba2 | Ang3 | Tstd1 | Dna2 |
| CTBP2 | EIF2C1 | ND4 | Cpn1 | Anpep | Khk | Wdr43 |
| CTNNB1 | EIF2C2 | ND4L | Herpud1 | S100a13 | Prss32 | Rps9 |
| CTNNBIP1 | EIF2C3 | ND5 | Ammecr1 | Serping1 | Nolc1 | Rps27 |
| CUL1 | EIF2C4 | ND6 | Slc9a3r2 | Serf2 | Ythdc1 | Rpl10 |
| CXXC4 | EP300 | NDUFA1 | Dpp7 | Cplx2 | Slc4a4 | Rpl35 |
| DAAM1 | FBXW7 | NDUFA10 | Gsdma | Nucb2 | Ddias | Rps27l |
| DAAM2 | FURIN | NDUFA11 | Maged2 | Ptprn2 | Nlrp6 | Rpl36 |
| DKK1 | HDAC1 | NDUFA12 | Fn3k | Evl | Atp4a | Brd2 |
| DKK2 | HDAC10 | NDUFA13 | Sgsh | Tbx3 | Wdhd1 | Eri1 |
| DKK4 | HDAC11 | NDUFA2 | Wbp5 | Pcsk1 | Ttll12 | Dek |
| DVL1 | HDAC2 | NDUFA3 | Gmpr | Ufm1 | Zfp709 | Gvin1 |
| DVL2 | HDAC3 | NDUFA4 | Crip2 | Cirbp | Dnajc19 | Nucks1 |
| DVL3 | HDAC4 | NDUFA5 | Hmgn3 | Dock4 | Zc3h18 | Lig3 |
| EP300 | HDAC5 | NDUFA6 | Srpr | Rnf216 | Dctd | Clic6 |
| FBXW11 | HDAC6 | NDUFA7 | AY761184 | Rp1 | Supt16 | Cdca8 |
| FOSL1 | HDAC7 | NDUFA8 | Cyp2c55 | Wfs1 | Gm4794 | Ces2e |
| FRAT1 | HDAC8 | NDUFA9 | Clca1 | Maz | Tcof1 | Gpr128 |
| FRAT2 | HDAC9 | NDUFAB1 | Prss23 | Kmt2a | Noc2l | Eif1ax |
| FZD1 | HES1 | NDUFB1 | Gabra4 | Gcg | Vdac3 | Kat6b |
| FZD10 | HES5 | NDUFB10 | Cep83 | Gck | Pbld1 | Pisd |
| FZD2 | HEY1 | NDUFB2 | Nts | Hrsp12 | Arg2 | Maob |
| FZD3 | HEY2 | NDUFB3 | Zswim7 | Ccl9 | Reg3a | Clic5 |
| FZD4 | HEYL | NDUFB4 | Mansc1 | S100a11 | Chek1 | Tbc1d4 |
| FZD5 | HIF1A | NDUFB5 | Clps | Gip | Fxn | Ncaph |

TABLE 2-continued

Reference gene lists used in single-cell analyses

| Wnt_KEGG | Reactome_Notch | Respiratory Electron Transport | Proteome Up 1-164 | Proteome Up 165-328 | Proteome Down 1-152 | Proteome Down 153-303 |
|---|---|---|---|---|---|---|
| FZD6 | JAG1 | NDUFB6 | Cuta | Prox1 | Aldh1a7 | Ttc22 |
| FZD7 | JAG2 | NDUFB7 | Ftl1 | Anxa5 | Rab33b | Cps1 |
| FZD8 | JUN | NDUFB8 | Sytl2 | Igfbp2 | Sdc4 | Ptcd1 |
| FZD9 | KAT2A | NDUFB9 | Sytl2 | Scg3 | Suv39h1 | Zim1 |
| GSK3B | KAT2B | NDUFC1 | Ddah2 | Ina | Aurkb | Yipf4 |
| JUN | LFNG | NDUFC2 | Sntb1 | Cdkn1b | Mpzl2 | Cwc22 |
| LEF1 | LOC441488 | NDUFS1 | Vmp1 | Plin2 | Fgfbp1 | Ccdc28a |
| LOC728622 | LOC728030 | NDUFS2 | Homer3 | Hist1h1a | Slc25a17 | Clasrp |
| LRP5 | MAML1 | NDUFS3 | Ly6e | Alox15 | Myo1a | Gnal |
| LRP6 | MAML2 | NDUFS4 | Pdia5 | Fbln2 | Papss2 | Rdh1 |
| MAP3K7 | MAML3 | NDUFS5 | Tor1aip1 | Thbs1 | Rdh7 | Cyp2d26 |
| MAPK10 | MAMLD1 | NDUFS6 | Bicd2 | Ahsg | Gmnn | Card11 |
| MAPK8 | MFNG | NDUFS7 | Sncb | Marcksl1 | Parp2 | Akr1c18 |
| MAPK9 | MIB1 | NDUFS8 | Dnah8 | Mt3 | Afp | Zg16 |
| MMP7 | MIB2 | NDUFV1 | Spats2l | Ets1 | Mt2 | Krtcap3 |
| MYC | MOV10 | NDUFV2 | Ugt2b38 | Chga | Mt1 | Tinf2 |
| NFAT5 | MYC | NDUFV3 | Scgn | Serpina1b | Tk1 | Cbr3 |
| NFATC1 | NCOR1 | SDHA | Plcb4 | Ang | Apoa4 | Itpka |
| NFATC2 | NCOR2 | SDHB | Oas3 | Cst3 | Ckm | Znf768 |
| NFATC3 | NCSTN | SDHC | Slc12a8 | Vim | Tyms | Plbd1 |
| NFATC4 | NEURL | SDHD | Selm | Muc13 | Ncl | Ak6 |
| NKD1 | NOTCH2 | UQCR11 | Pla2g15 | Nefh | Rrm2 | Ces1d |
| NKD2 | NOTCH3 | UQCRB | Gdap1l1 | Ctsd | Otc | Naa40 |
| NLK | NOTCH4 | UQCRBP1 | Gpld1 | Lyz1 | Atp1b1 | Lmcd1 |
| PLCB1 | NUMB | UQCRC1 | Sh3kbp1 | Wnt3 | Rpl27a | Ca9 |
| PLCB2 | POFUT1 | UQCRC2 | Ppp1r14c | Chgb | Rps16 | |
| PLCB3 | POGLUT1 | UQCRFS1 | Cd177 | Hmox1 | Srp14 | Impa2 |
| PLCB4 | PSEN1 | UQCRH | Ssbp1 | Map1b | Slc7a2 | Nifk |
| PORCN | PSEN2 | UQCRHL | Ctbs | Anxa6 | Dao | Nsmce2 |
| PPARD | PSENEN | UQCRQ | Hid1 | Scg5 | Tcea3 | Tipin |
| PPP2CA | RAB6A | | Pitpnc1 | Gusb | Rps2 | Depdc7 |
| PPP2CB | RBPJ | | Irak3 | Fn1 | Gna12 | Ces1f |
| PPP2R1A | RBX1 | | Pom121 | H1f0 | Rpl3 | St3gal4 |
| PPP2R1B | RFNG | | Dync2li1 | Anxa1 | Psmb9 | Aldob |
| PPP2R5A | RPS27A | | Habp2 | Nudt10 | Adssl1 | Smc1b |
| PPP2R5B | RPS27AP11 | | Aspm | Cck | Casp1 | Ddb2 |
| PPP2R5C | SEL1L | | Liph | Nefm | Hmgb2 | Nrf1 |
| PPP2R5D | SKP1 | | Celf3 | Nefl | Pou2f3 | Rsl24d1 |
| PPP2R5E | SNW1 | | Btbd7 | Sod1 | Chd1 | Gins4 |
| PPP3CA | ST3GAL3 | | Myt1 | Ttr | Vhl | Fars2 |
| PPP3CB | ST3GAL6 | | Kctd2 | Ctsl | Reg1 | Rnps1 |
| PPP3CC | TBL1X | | Lancl3 | Ada | Pla2g4a | Cdca3 |
| PPP3R1 | TBL1XR1 | | Nhlrc3 | Rnase1 | Rpia | Mrps18a |
| PPP3R2 | TFDP1 | | Cnst | Tcn2 | Vdr | Mrps5 |
| PRICKLE1 | TLE1 | | Gatsl2 | Lect2 | Brca1 | Mrpl16 |
| PRICKLE2 | TLE2 | | Rnase4 | Agr2 | Shmt1 | Acss1 |
| PRKACA | TLE3 | | Defa22 | Itln1 | Fabp6 | Aadac |
| PRKACB | TLE4 | | Parp12 | Tmem131 | Rpl9 | Mrpl15 |
| PRKACG | TMED2 | | Fgd2 | Snca | Plcb3 | Pno1 |
| PRKCA | TNRC6A | | Sgsm1 | Serpini1 | Efnb2 | Mrpl51 |
| PRKCB | TNRC6B | | Qsox1 | Anxa3 | Dmpk | Fam195a |
| PRKCG | TNRC6C | | Dzip1 | Ift81 | Fabp2 | Mrpl20 |
| PRKX | TP53 | | Hspa13 | Ptpn9 | Aqp4 | Rpl21 |
| PSEN1 | UBA52 | | Gskip | Cyp3a25 | Atp5e | Zwint |
| RAC1 | | | Gns | Reg3g | Cyb5a | Snx24 |
| RAC2 | | | Zc3hav1l | Lfng | Rps20 | Fam133b |
| RAC3 | | | Nfasc | Stxbp1 | Rab10 | Gemin7 |
| RBX1 | | | Topors | Cacna2d1 | Rpl27 | Mgme1 |
| RHOA | | | Thbs1 | Capn2 | Rpl37a | Cenpv |
| ROCK1 | | | Mtdh | Hk2 | Rnd3 | Mrps28 |
| ROCK2 | | | Cpm | Stim2 | Abat | Rpl15 |
| RUVBL1 | | | Slit1 | Ank3 | Timm8b | Cmss1 |
| SENP2 | | | Cadps | Ank3 | Rps7 | Lipt2 |
| SFRP1 | | | Tppp | Prom1 | Rps8 | Mrto4 |
| SFRP2 | | | Mroh2b | Mtss1 | Rps15a | Ube2c |
| SFRP4 | | | Slc39a4 | Gimap9 | Rps23 | Rpl34 |
| SFRP5 | | | Rph3al | Zfp407 | Rps18 | Zdhhc21 |
| SIAH1 | | | Syne1 | Sgsm3 | Hist1h4a | Msra |
| SKP1 | | | Tiam2 | Ktn1 | Rpl23 | Mrpl2 |
| SMAD2 | | | Atp8b3 | Pam | Rps24 | Ociad2 |
| SMAD3 | | | Sarm1 | D3Ertd254e | Rps25 | 1810009A15Rik |
| SMAD4 | | | Ttbk1 | Pcdhb12 | Rps26 | Knstrn |
| SOX17 | | | Crmp1 | Ccdc149 | Polr2l | 42627 |
| TBL1X | | | Zranb3 | Fcgbp | Rpl30 | Chmp2a |
| TBL1XR1 | | | Sphkap | Dnah1 | Rpl31 | Brix1 |

TABLE 2-continued

Reference gene lists used in single-cell analyses

| Wnt_KEGG | Reactome_Notch | Respiratory Electron Transport | Proteome Up 1-164 | Proteome Up 165-328 | Proteome Down 1-152 | Proteome Down 153-303 |
|---|---|---|---|---|---|---|
| TBL1Y | | | Styk1 | Abca14 | Rpl32 | |
| TCF7 | | | Fastkd1 | Cadps2 | Tra2b | Rmdn1 |
| TCF7L1 | | | Tbc1d30 | Thsd7a | Hmgb1 | L7rn6 |
| TCF7L2 | | | Pde1c | Arhgef37 | Sumo1 | Pycard |
| TP53 | | | Aga | Ryr2 | Rpl22 | Rbp7 |
| VANGL1 | | | Insm1 | Myof | Ugt1a2 | Nusap1 |
| VANGL2 | | | Arid3a | Tns1 | Rpl19 | Hemgn |
| WIF1 | | | Tff3 | Zfp945 | Hist1h3b | Ube3b |
| WNT1 | | | Sprr1a | Mcf2l | H3f3a | Icoslg |
| WNT10A | | | Pea15 | Dpysl3 | Csrp2 | Rangrf |
| WNT10B | | | Elavl4 | 9530053A07Rik | Khk | Pbk |
| WNT11 | | | Ktn1 | Klc3 | Rps3a | Rpl38 |
| WNT16 | | | Ktn1 | Pdia2 | Myo7a | Ap3b2 |
| WNT2 | | | Soat1 | Fam46a | Apoa1 | Neu3 |
| WNT2B | | | Cfi | Myo9a | Bche | Sult1b1 |
| WNT3 | | | Tmpo | Bicd2 | Rbp2 | Fbp1 |
| WNT3A | | | Tmpo | 2310045N01Rik | Ssrp1 | Slc5a1 |
| WNT4 | | | Lama5 | Mgll | Ces2f | Adh4 |
| WNT5A | | | Ptprn | Gm7849 | Slc7a1 | Suclg1 |
| WNT5B | | | Gm2a | Gm15293 | Prelid2 | Pde3a |
| WNT6 | | | Lrrk2 | Osbpl8 | Pdss1 | Mad2l1 |
| WNT7A | | | Pkdcc | Bicd1 | Dhrs11 | Atp12a |
| WNT7B | | | C2cd4cC2CD4 | Pls3 | Slc16a10 | Pck1 |
| WNT8A | | | Ang5 | Arhgap4 | Spc25 | Rab4b |
| WNT8B | | | Gm14851 | Vwa5b1 | Wdr19 | Gm12728 |
| WNT9A | | | Stxbp5l | Glt1d1 | Cks1brt | Gm3550 |
| WNT9B | | | Galns | Birc3 | Capn13 | Cluh |
| | | | Pnliprp2 | Map1a | Tbc1d9 | |
| | | | Hepacam2 | Bfsp1 | | |
| | | | Sez6l2 | Cntln | | |
| | | | Trp53i11 | Rap1gap | | |
| | | | Defa20 | Frmpd1 | | |
| | | | Chn2 | Npdc1 | | |
| | | | Heca | Kiaa1324 | | |
| | | | Ampd1 | Kiaa1324 | | |
| | | | Agt | Sytl1 | | |
| | | | Zfp941 | Ttc39a | | |
| | | | Peg3 | Tbc1d16 | | |
| | | | Vwa5b2 | Cdhr5 | | |
| | | | Pxdn | Aspg | | |

TABLE 3

Detected and quantified in vitro Proteome

Table 3A. (FIG. 3B Proteome)

| Accession Number | M1-1 Log2 Median Normalized | M1-2 Log2 Median Normalized | M2-1 Log2 Median Normalized | M2-2 Log2 Median Normalized | Average logFC | P.Value | adj.P.Val | change | Gene Symbol | Entry Name |
|---|---|---|---|---|---|---|---|---|---|---|
| Q9Z1S5 | 1.919 | 1.405 | 1.8885 | 1.833 | 1.833352 | 1.63E-06 | 0.000528463 | up | 42616 | Neuronal-specific septin-3 |
| Q9Z1B3 | 1.922 | 1.18 | 1.3575 | 2.007 | 1.616625 | 0.000542213 | 0.005190266 | up | Plcb1 | 1-phosphatidylinositol 4,5-bisphosphate phosphodiesterase beta-1 |
| Q9Z0Y2 | 3.79 | 3.377 | 3.9535 | 3.545 | 3.666375 | 9.91E-07 | 0.000496308 | up | Pla2g1b | Phospholipase A2 |
| Q9WVQ0 | 1.618 | 0.97 | 2.7755 | 1.716 | 1.713681 | 0.001071288 | 0.00723732 | up | Pnmbp1 | Polyamine-modulated factor 1-binding protein 1 |
| Q9WUA1 | 2.987 | 2.649 | 2.8515 | 2.698 | 2.796375 | 5.45E-07 | 0.000496308 | up | Wif1 | Wnt inhibitory factor 1 |
| Q9R013 | 2.399 | 2.243 | 2.1425 | 2.503 | 2.321875 | 1.62E-06 | 0.000528463 | up | Ctsf | Cathepsin F |
| Q9QXS6 | 1.932 | 1.914 | 2.2505 | 2.067 | 2.040875 | 2.28E-06 | 0.00058884 | up | Dbn1 | Drebrin |
| Q9JIV2 | 1.874 | 1.684 | 1.7955 | 1.925 | 1.819625 | 1.40E-06 | 0.000528463 | up | Pfn2 | Profilin-2 |
| Q9JIV1 | 2.127 | 1.298 | 2.4545 | 2.203 | 2.128054 | 1.87E-05 | 0.001261088 | up | Cryba2 | Beta-crystallin A2 |
| Q9JIN5 | 1.626 | 1.333 | 1.4785 | 2.041 | 1.619625 | 6.59E-05 | 0.002030382 | up | Cpn1 | Carboxypeptidase N catalytic chain |
| Q9EST1 | 2.424 | 2.069 | 2.3445 | 2.017 | 2.213625 | 5.70E-06 | 0.000861774 | up | Gsdma | Gasdermin-A |
| Q9ER67 | 1.351 | 1.54 | 1.7865 | 1.558 | 1.557372 | 7.50E-06 | 0.000936704 | up | Maged2 | Maged2 protein |
| Q9ER35 | 1.826 | 0.674 | 2.3155 | 2.445 | 1.829093 | 0.002378953 | 0.01135493 | up | Fn3k | Fructosamine-3-kinase |
| Q9DCB1 | 2.691 | 2.005 | 2.3475 | 1.98 | 2.255875 | 3.20E-05 | 0.00159398 | up | Hmgn3 | High mobility group nucleosome-binding domain-containing protein 3 |
| Q9D848 | 2.675 | 1.992 | 1.8715 | 0.311 | 1.873974 | 0.00102204 | 0.00774992 | up | AY761184 | CRS1C-3 |
| Q9D5R3 | 2.487 | 1.165 | 2.0435 | 1.588 | 1.820875 | 0.000920379 | 0.00671346 | up | Cep83 | Centrosomal protein of 83 kDa |
| Q9CWQ2 | 2.33 | 3.009 | 2.3595 | 3.382 | 2.770125 | 0.000103728 | 0.002461201 | up | Zswim7 | Zinc finger SWIM domain-containing protein 7 |
| Q9CR33 | 2.069 | 1.342 | 1.2615 | 2.246 | 1.729625 | 0.000986271 | 0.006963311 | up | Mansc1 | MANSC domain-containing protein 1 |
| Q9CQ89 | 2.206 | 1.342 | 1.5425 | 2.534 | 1.906125 | 0.000092097 | 0.006685812 | up | Cuta | Protein CutA |
| Q9CPX4 | 2.588 | 1.623 | 1.8175 | 2.291 | 2.079875 | 0.000190811 | 0.003192407 | up | Ftl1 | Ferritin |
| Q99N50-4 | 1.855 | 1.299 | 1.1175 | 1.8 | 1.517875 | 0.000437783 | 0.004711619 | up | Sytl2 | Isoform 4 of Synaptotagmin-like protein 2 |
| Q9JA5 | 2.204 | 2.403 | 2.0145 | 1.863 | 2.121125 | 9.16E-06 | 0.000991767 | up | Ly6e | Ly6e protein |
| Q921C5-2 | 2.114 | 1.381 | 1.7125 | 2.33 | 1.884375 | 0.000230276 | 0.003488521 | up | Bicd2 | Isoform 2 of Protein bicaudal D homolog 2 |
| Q91ZZ3 | 2.144 | 1.858 | 1.7555 | 1.529 | 1.821625 | 1.81E-05 | 0.001253109 | up | Sncb | Beta-synuclein |
| Q91XQ0 | 1.567 | 1.169 | 2.3695 | 2.239 | 1.836125 | 0.001115045 | 0.007397329 | up | Dnah8 | Dynein heavy chain 8, axonemal |
| Q91WD9 | 2.13 | 1.767 | 1.8935 | 2.339 | 2.032375 | 1.72E-05 | 0.001250999 | up | Scgn | Secretagogin |
| Q8R4S0 | 1.119 | 1.259 | 1.7095 | 1.989 | 1.519125 | 0.000576522 | 0.005337328 | up | Ppp1r14c | Protein phosphatase 1 regulatory subunit 14C |
| Q8R2S8 | 2.182 | 1.498 | 1.6015 | 1.344 | 1.600527 | 4.39E-05 | 0.001671268 | up | Cd177 | CD177 antigen |
| Q8R2K3 | 2.404 | 0.58 | 2.1815 | 2.104 | 2.1049 | 1.80E-05 | 0.001250999 | up | Ssbp1 | Single-stranded DNA-binding protein |
| Q8K329 | 1.744 | 1.808 | 1.7995 | 1.892 | 1.8078 | 5.21E-07 | 0.000496308 | up | Pom121 | Nuclear envelope pore membrane protein POM 121 |
| Q8K0T2 | 1.792 | 1.765 | 1.7145 | 1.934 | 1.791711 | 8.47E-07 | 0.000496308 | up | Dync2li1 | Cytoplasmic dynein 2 light intermediate chain 1 |
| Q8K0D2 | 2.456 | 2.167 | 2.0875 | 1.888 | 2.149625 | 5.38E-06 | 0.00085991 | up | Habp2 | Hyaluronan-binding protein 2 |
| Q8CJ27 | 0.845 | 2.7 | 2.1305 | 2.806 | 2.133999 | 0.001979196 | 0.01017514 | up | Aspm | Abnormal spindle-like microcephaly-associated protein homolog |
| Q8CIN6-2 | 2.314 | 2.198 | 2.4995 | 2.371 | 2.345625 | 5.20E-07 | 0.000496308 | up | Celf3 | Isoform 2 of CUGBP Elav-like family member 3 |
| Q8CFE5 | 1.153 | 2.342 | 3.0785 | 3.406 | 2.494875 | 0.002199176 | 0.01077274 | up | Btbd7 | BTB/POZ domain-containing protein 7 |
| Q8CFC2-3 | 1.935 | 1.067 | 1.9645 | 1.796 | 1.79679 | 1.55E-05 | 0.001188215 | up | Myt1 | Isoform 3 of Myelin transcription factor 1 |
| Q8CEZ0 | 1.842 | 1.162 | 1.5555 | 1.768 | 1.581875 | 8.81E-05 | 0.0022847 | up | Kctd2 | BTB/POZ domain-containing protein KCTD2 |
| Q8C7E4 | 2.488 | 1.585 | 2.1965 | 2.083 | 2.088125 | 3.99E-05 | 0.001671268 | up | Rnase4 | Ribonuclease 4 |
| Q8C1N8 | 2.168 | 1.5 | 2.5205 | 1.437 | 1.906375 | 0.00069737 | 0.005839835 | up | Defa22 | Alpha-defensin 22 |

TABLE 3-continued

Detected and quantified in vitro Proteome

| | | | | | | | |
|---|---|---|---|---|---|---|---|
| Q8BY35 | 1.523 | 1.046 | 1.5595 | 1.542 | 1.523108 | 1.78E-06 | 0.000528463 | Fgd2 | up | FYVE, RhoGEF and PH domain-containing protein 2 |
| Q8BND5-3 | 2.129 | 0.898 | 1.4425 | 1.827 | 1.574125 | 0.000178576 | 0.00765406 | Qsox1 | up | Isoform 3 of Sulfhydryl oxidase 1 |
| Q810U3 | 1.119 | 1.431 | 2.5695 | 2.421 | 1.885125 | 0.003135872 | 0.0134757 | Nfasc | up | Neurofascin |
| Q80YQ1 | 3.024 | 2.945 | 3.0295 | 2.119 | 2.945374 | 2.32E-07 | 0.000496308 | Thbs1 | up | Thrombospondin 1 |
| Q80TJ1-2 | 1.972 | 1.265 | 1.8515 | 1.851 | 1.851242 | 1.31E-06 | 0.000528463 | Cadps | up | Isoform 2 of Calcium-dependent secretion activator 1 |
| Q6ZPF3 | 1.633 | 0.847 | 2.1345 | 2.305 | 1.729875 | 0.001781463 | 0.009562387 | Tiam2 | up | T-lymphoma invasion and metastasis-inducing protein 2 |
| Q6PDS3-3 | 1.743 | 0.951 | 2.2335 | 2.359 | 1.821625 | 0.001228506 | 0.007844821 | Sarm1 | up | Isoform 3 of Sterile alpha and TIR motif-containing protein 1 |
| Q6NSW3-3 | 1.756 | 1.428 | 1.6805 | 1.984 | 1.712125 | 1.50E-05 | 0.001188215 | Sphkap | up | Isoform 3 of A-kinase anchor protein SPHKAP |
| Q69ZT9 | 2.226 | 0.801 | 1.1895 | 2.285 | 1.625375 | 0.006727622 | 0.02192564 | Tbc1d30 | up | TBC1 domain family member 30 |
| Q64191 | 2.453 | 1.297 | 1.9965 | 2.404 | 2.037625 | 0.000306477 | 0.004006703 | Aga | up | N(4)-(beta-N-acetylglucosaminyl)-L-asparaginase |
| Q632V0 | 1.483 | 1.774 | 1.9485 | 2.364 | 1.892375 | 7.58E-05 | 0.002167266 | Insm1 | up | Insulinoma-associated protein 1 |
| Q61129 | 1.748 | 1.679 | 1.9225 | 1.619 | 1.742125 | 2.52E-06 | 0.000617538 | Cfi | up | Complement factor I |
| Q60648 | 1.975 | 1.26 | 2.0995 | 1.811 | 1.812253 | 5.30E-05 | 0.001844081 | Gm2a | up | Ganglioside GM2 activator |
| Q5S006 | 1.581 | 1.441 | 2.0715 | 1.555 | 1.580585 | 4.75E-06 | 0.000841369 | Lrrk2 | up | Leucine-rich repeat serine/threonine-protein kinase 2 |
| Q5GAN1 | 3.593 | 3.129 | 2.6745 | 1.695 | 2.772875 | 0.000461621 | 0.000480339 | Ang5 | up | Angiogenin ribonuclease 5 |
| Q5ERJ0 | 2.4 | 1.913 | 1.6085 | 1.019 | 1.735125 | 0.000908599 | 0.006696628 | Gm14851 | up | CRS1C-2 |
| Q4VBW7 | 2.049 | 1.436 | 0.9165 | 1.902 | 1.575875 | 0.001119831 | 0.0074168 | Pnliprp2 | up | Pancreatic lipase-related protein 2 |
| Q4V9Z5-2 | 1.801 | 1.432 | 1.5445 | 2.096 | 1.718375 | 6.72E-05 | 0.002044753 | Sez6l2 | up | Isoform 2 of Seizure 6-like protein 2 |
| Q45VN2 | 2.747 | 2.301 | 2.6535 | 2.726 | 2.653932 | 3.29E-07 | 0.000496308 | Defa20 | up | Alpha-defensin 20 |
| Q3V1N5 | 1.377 | 2.635 | 1.1905 | 2.006 | 1.802125 | 0.001896275 | 0.009962234 | Heca | up | Protein Heca |
| Q3URU2 | 1.824 | 1.533 | 1.6705 | 1.936 | 1.740875 | 8.73E-06 | 0.000977434 | Peg3 | up | Paternally-expressed gene 3 protein |
| Q3UP38 | 1.74 | 1.162 | 1.2965 | 1.802 | 1.500125 | 0.000259438 | 0.003686409 | Cracr2a | up | EF-hand calcium-binding domain-containing protein 4B |
| Q3UN27 | 2.666 | 2.04 | 2.1545 | 1.868 | 2.15338 | 1.41E-05 | 0.00118665 | Mmp7 | up | Matrilysin |
| Q3TTY0 | 2.343 | 1.775 | 1.8565 | 1.701 | 1.855881 | 5.14E-06 | 0.000841369 | Plb1 | up | Phospholipase B1, membrane-associated |
| Q3TMQ6 | 3.144 | 3.114 | 2.3885 | 2.14 | 2.696625 | 0.000127357 | 0.002612217 | Ang4 | up | Angiogenin-4 |
| Q32M21 | 2.749 | 1.938 | 2.5425 | 1.916 | 2.286375 | 0.000120733 | 0.002566457 | Gsdma2 | up | Gasdermin-A2 |
| Q08535 | 3.103 | 1.116 | 2.2905 | 2.843 | 2.338125 | 0.001432842 | 0.008537397 | Sct | up | Secretin |
| Q06890 | 1.554 | 2.165 | 1.5055 | 0.541 | 1.507456 | 0.00093134 | 0.00675869 | Clu | up | Clusterin |
| Q05421 | 1.95 | 2.17 | 1.5755 | 1.804 | 1.874875 | 1.79E-06 | 0.001250999 | Cyp2e1 | up | Cytochrome P450 2E1 |
| Q03517 | 1.625 | 1.264 | 1.2065 | 1.911 | 1.501625 | 0.000240264 | 0.003559107 | Scg2 | up | Secretogranin-2 |
| Q00896 | 3.029 | 0.896 | 1.7315 | 1.817 | 1.814205 | 0.001750144 | 0.009452505 | Serpina1c | up | Alpha-1-antitrypsin 1-3 |
| Q00493 | 1.892 | 1.749 | 1.3295 | 1.305 | 1.568875 | 0.000152612 | 0.002821684 | Cpe | up | Carboxypeptidase E |
| P97802 | 3.593 | 3.129 | 2.7415 | 1.826 | 2.822375 | 0.000283149 | 0.000496308 | Ang3 | up | Angiogenin-3 |
| P84086 | 2.11 | 2.087 | 1.7845 | 2.232 | 2.087446 | 1.05E-06 | 0.000496308 | Cplx2 | up | Complexin-2 |
| P80560 | 1.842 | 1.788 | 1.7775 | 2.039 | 1.841682 | 9.66E-07 | 0.00116258 | Ptprn2 | up | Receptor-type tyrosine-protein phosphatase N2 |
| P63239 | 2.186 | 1.731 | 1.7185 | 1.875 | 1.874158 | 8.06E-06 | 0.000936704 | Pcsk1 | up | Neuroendocrine convertase 1 |
| P59764 | 1.344 | 1.328 | 1.7175 | 2.399 | 1.697125 | 0.000509312 | 0.005029437 | Dock4 | up | Dedicator of cytokinesis protein 4 |
| P58283-3 | 1.708 | 1.374 | 1.9535 | 1.623 | 1.664625 | 2.09E-05 | 0.001321066 | Rnf216 | up | Isoform 3 of E3 ubiquitin-protein ligase RNF216 |
| P55200 | 1.21 | 0.543 | 2.2865 | 2.379 | 1.604625 | 0.00152816 | 0.03369151 | Kmt2a | up | Histone-lysine N-methyltransferase 2A |
| P55095 | 1.867 | 1.775 | 1.3065 | 1.679 | 1.679789 | 1.28E-05 | 0.00116258 | Gcg | up | Glucagon |
| P48437 | 1.7 | 2.102 | 2.1305 | 1.95 | 1.970625 | 5.57E-06 | 0.00085901 | Prox1 | up | Prospero homeobox protein 1 |
| P47877 | 3.024 | 2.897 | 2.9265 | 2.995 | 2.960625 | 5.40E-08 | 0.000432658 | Igfbp2 | up | Insulin-like growth factor-binding protein 2 |
| P47867 | 2.941 | 2.542 | 3.0155 | 2.834 | 2.834798 | 8.82E-07 | 0.000496308 | Scg3 | up | Secretogranin-3 |
| P46660 | 1.608 | 1.399 | 1.7475 | 1.64 | 1.608475 | 3.38E-06 | 0.000727205 | Ina | up | Alpha-internexin |
| P39654 | 1.401 | 0.766 | 1.7575 | 2.077 | 1.500375 | 0.001679611 | 0.009272174 | Alox15 | up | Arachidonate 15-lipoxygenase |
| P37889 | 1.671 | 1.018 | 2.3635 | 1.531 | 1.645875 | 0.00066484 | 0.00567162 | Fbln2 | up | Fibulin-2 |
| P35441 | 3.046 | 2.909 | 3.0575 | 2.156 | 2.909724 | 1.12E-06 | 0.000500631 | Thbs1 | up | Thrombospondin-1 |
| P28667 | 1.53 | 0.543 | 2.2025 | 1.74 | 1.739012 | 2.49E-05 | 0.001435728 | Marcksl1 | up | MARCKS-related protein |
| P28184 | 2.777 | 1.595 | 1.6965 | 1.512 | 2.135875 | 0.000981534 | 0.006958876 | Mt3 | up | Metallothionein-3 |
| P27577 | 2.244 | 2.558 | 2.0385 | 2.909 | 2.165625 | 0.000287722 | 0.003868799 | Ets1 | up | Protein C-ets-1 |
| P26339 | 2.449 | 2.137 | 2.6225 | 2.555 | 2.449782 | 1.72E-06 | 0.000528463 | Chga | up | Chromogranin-A |

TABLE 3-continued

Detected and quantified in vitro Proteome

| | | | | | | | | |
|---|---|---|---|---|---|---|---|---|
| P22599 | 3.063 | 0.875 | 1.8055 | 2.069 | 1.953125 | 0.002738347 | 0.01237739 | up | Serpina1b | Alpha-1-antitrypsin 1-2 |
| P21570 | 2.195 | 1.555 | 1.7825 | 1.902 | 1.858625 | 2.06E-05 | 0.00131579 | up | Ang | Angiogenin |
| P21460 | 2.115 | 1.239 | 1.4025 | 1.775 | 1.632875 | 0.000321277 | 0.00404291 | up | Cst3 | Cystatin-C |
| P17897 | 2.927 | 1.667 | 2.2645 | 2.411 | 2.317375 | 0.000102461 | 0.00245844 | up | Lyz1 | Lysozyme C-1 |
| P17553 | 2.705 | 2.055 | 1.3575 | 1.691 | 1.952125 | 0.000563204 | 0.005287945 | up | Wnt3 | Proto-oncogene Wnt-3 |
| P16014 | 2.325 | 1.946 | 2.4405 | 2.366 | 2.325401 | 5.80E-07 | 0.000496308 | up | Chgb | Secretogranin-1 |
| P14873 | 2.39 | 2.04 | 2.3655 | 2.557 | 2.366088 | 1.03E-06 | 0.000496308 | up | Map1b | Microtubule-associated protein 1B |
| P14824 | 1.447 | 1.822 | 1.7405 | 1.364 | 1.593375 | 4.20E-05 | 0.00167268 | up | Anxa6 | Annexin A6 |
| P12961 | 1.893 | 1.303 | 1.4365 | 2.137 | 1.692375 | 0.000313666 | 0.00404438 | up | Scg5 | Neuroendocrine protein 7B2 |
| P12265 | 1.978 | 0.304 | 2.2855 | 1.948 | 1.948861 | 2.40E-05 | 0.001402557 | up | Gusb | Beta-glucuronidase |
| P11276 | 1.8 | 1.665 | 1.5365 | 1.802 | 1.700875 | 3.45E-06 | 0.000727205 | up | Fn1 | Fibronectin |
| P10107 | 1.937 | 2.608 | 2.6415 | 1.284 | 2.117625 | 0.0002677 | 0.006357335 | up | Anxa1 | Annexin A1 |
| P09240 | 2.26 | 0.481 | 1.4655 | 2.002 | 1.552125 | 0.005770574 | 0.01983078 | up | Cck | Cholecystokinin |
| P08553 | 1.584 | 1.357 | 1.5325 | 1.646 | 1.532958 | 3.63E-06 | 0.000728919 | up | Nefm | Neurofilament medium polypeptide |
| P08551 | 1.697 | 1.481 | 1.6825 | 1.788 | 1.682822 | 1.55E-06 | 0.000528463 | up | Nefl | Neurofilament light polypeptide |
| P08228 | 1.826 | 0.892 | 1.1695 | 2.321 | 1.552125 | 0.003743497 | 0.01523324 | up | Sod1 | Superoxide dismutase [Cu—Zn] |
| P06797 | 2.377 | 0.802 | 2.2995 | 1.808 | 1.821625 | 0.001780753 | 0.009562387 | up | Ctsl | Cathepsin L1 |
| P00683 | 2.99 | 2.203 | 2.7165 | 4.381 | 2.987052 | 0.000227931 | 0.003478735 | up | Rnase1 | Ribonuclease pancreatic |
| O88312 | 2.309 | 1.237 | 0.9115 | 1.981 | 1.609625 | 0.003576391 | 0.01478143 | up | Agr2 | Anterior gradient protein 2 homolog |
| O35684 | 1.863 | 1.077 | 1.8075 | 1.545 | 1.573125 | 0.000179541 | 0.003114218 | up | Serpini1 | Neuroserpin |
| O08399 | 1.813 | 1.126 | 1.5275 | 1.761 | 1.556875 | 0.000108367 | 0.002481296 | up | Stxbp1 | Syntaxin-binding protein 1 |
| F8VQA4 | 1.721 | 1.405 | 1.5215 | 2.077 | 1.681125 | 5.94E-06 | 0.001942086 | up | Pam | Peptidyl-glycine alpha-amidating monooxygenase |
| F6V035 | 1.704 | 1.098 | 1.5555 | 1.608 | 1.55601882 | 7.78E-06 | 0.000936704 | up | Ccdc149 | Protein Ccdc149 |
| E9Q8F8 | 2.503 | 0.663 | 3.0695 | 3.976 | 2.552875 | 0.006045857 | 0.020426433 | up | Abca14 | Protein Abca14 |
| E9Q835 | 1.838 | 1.662 | 2.1005 | 1.977 | 1.894375 | 6.57E-06 | 0.000907306 | up | Cadps2 | Calcium-dependent secretion activator 2 |
| E9Q6P0 | 2.347 | 1.477 | 2.0985 | 1.766 | 1.922125 | 0.000124875 | 0.002592615 | up | Thsd7a | Thrombospondin type-1 domain-containing protein 7A |
| E9Q0S6 | 0.944 | 1.445 | 2.2135 | 2.088 | 1.672625 | 0.001864277 | 0.009855092 | up | Tns1 | Protein Tns1 |
| E9PYM8 | 2.176 | 0.688 | 1.6965 | 2.47 | 1.757625 | 0.003075388 | 0.01332225 | up | Zfp945 | Protein Zfp945 |
| D3Z6P0 | 2.132 | 1.103 | 1.3525 | 2.061 | 1.662125 | 0.000126763 | 0.007993525 | up | Pdia2 | Protein disulfide-isomerase A2 |
| D3Z390 | 2.48 | 1.385 | 1.8445 | 2.432 | 2.035375 | 0.000428866 | 0.004669744 | up | Bicd2 | Bicaudal D homolog 2 (Drosophila ), isoform CRA_a |
| D3Z373 | 2.955 | 2.218 | 2.5985 | 1.87 | 2.410375 | 0.000102173 | 0.00245844 | up | 2310045N01Rik | Protein 2310045N01Rik |
| D3YYS6 | 1.648 | 1.052 | 1.2255 | 1.654 | 1.649334666 | 0.000111604 | 0.002493535 | up | Mgll | Monoglyceride lipase |
| D3YX03 | 2.165 | 2.033 | 1.8715 | 0.909 | 1.872684813 | 5.84E-05 | 0.001932826 | up | Gm7849 | Protein Gm7849 |
| B1AUY3 | 1.818 | 1.365 | 2.2695 | 2.992 | 2.111125 | 0.000935093 | 0.006763392 | up | Arhgap4 | Protein Arhgap4 |
| A9ZIV5 | 1.539 | 1.688 | 1.5255 | 2.014 | 1.68713745 | 0.001188215 | 0.001188215 | up | Vwa5b1 | von Willebrand factor A domain-containing protein 5B1 |
| A2ARP8 | 1.921 | 1.711 | 1.3865 | 1.08 | 1.524625 | 0.000329271 | 0.004078484 | up | Map1a | Microtubule-associated protein 1A |
| A2AMT1 | 1.593 | 0.651 | 2.1025 | 3.084 | 1.857625 | 0.007265371 | 0.023206332 | up | Bfsp1 | Filensin |
| A2AJ21 | 2.322 | 1.851 | 2.3395 | 2.486 | 2.322461069 | 0.000496308 | 0.000496308 | up | Npdc1 | Neural proliferation differentiation and control protein 1 |
| A0JNU3 | 2.302 | 1.857 | 3.2165 | 3.898 | 2.818375 | 0.001208178 | 0.00770736 | up | Aspg | 60 kDa lysophospholipase |
| A2ACP1 | 1.442 | 1.172 | 1.1125 | 0.996 | 1.171348084 | 3.75E-05 | 0.001639477 | up | Ttc39a | Tetratricopeptide repeat protein 39A |
| A2AFS3 | 1.738 | 1.764 | 1.1595 | 1.209 | 1.467625 | 0.000349563 | 0.00439781 | up | Kiaa1324 | UPF0577 protein KIAA1324 |
| A2AFS3-2 | 1.681 | 1.724 | 1.0495 | 1.089 | 1.385875 | 0.000737371 | 0.00598712 | up | Kiaa1324 | Isoform 2 of UPF0577 protein KIAA1324 |
| A2AHJ4 | -1.325 | -1.312 | -1.6885 | -1.8 | -1.531375 | 8.48E-05 | 0.002275515 | down | Brwd3 | Bromodomain and WD repeat-containing protein 3 |
| A2ALS5-3 | 1.428 | 1.017 | 1.1795 | 1.271 | 1.223875 | 3.48E-05 | 0.001614723 | up | Rap1gap | Isoform 3 of Rap1 GTPase-activating protein 1 |
| A2AM05 | 0.712 | 1.749 | 0.9975 | 2.238 | 1.424125 | 0.007701384 | 0.024193998 | up | Cntln | Centlein |
| A2APM2 | -1.843 | -1.042 | -1.9235 | -2.326 | -1.844546108 | 0.00013512 | 0.002680332 | down | Cd44 | CD44 antigen |
| A2AR02 | -1.642 | -0.589 | -0.8735 | -1.422 | -1.131625 | 0.004865676 | 0.017961089 | down | Ppig | Peptidyl-prolyl cis-trans isomerase G |
| A2ARV4 | -1.422 | 0.033 | -1.2255 | -1.188 | -1.188635091 | 8.70E-05 | 0.0022847 | up | Lrp2 | Low-density lipoprotein receptor-related protein 2 |
| A2CGA5 | 0.6 | 1.467 | 1.1335 | 1.508 | 1.177125 | 0.001431007 | 0.008532994 | up | Birc3 | Baculoviral IAP repeat-containing protein 3 |
| B1AR10 | -1.932 | -0.948 | -2.3265 | -3.084 | -2.072625 | 0.002417885 | 0.011458858 | down | Mllt6 | Protein Mllt6 |
| B1ARD6 | -1.624 | -0.756 | -0.8195 | -1.569 | -1.192125 | 0.004058816 | 0.01600755 | down | Slfn9 | Protein Slfn9 |

TABLE 3-continued

Detected and quantified in vitro Proteome

| | | | | | | | | |
|---|---|---|---|---|---|---|---|---|
| B1ASD8 | -1.151 | -0.693 | -0.6625 | -2.146 | -1.148345484 | 0.008969669 | 0.026852047 | Gm13251 | down | Protein Gm13251 |
| B1AVH5 | -1.404 | -1.422 | -1.7495 | -1.134 | -1.421153941 | 3.43E-05 | 0.001614723 | Coro2a | down | Coronin |
| B1AX39 | -1.151 | -2.339 | -1.3705 | -1.88 | -1.685125 | 0.001071961 | 0.00723732 | Zcche7 | down | Zinc finger CCHC domain-containing protein 7 |
| B1BID3 | -1.69 | -0.307 | -1.2965 | -2.86 | -1.538375 | 0.015394521 | 0.038918513 | Zfp40 | down | Protein Zfp40 |
| B2KG46 | 1.226 | 1.158 | 1.4615 | 1.248 | 1.247704648 | 6.46E-06 | 0.000907306 | Bicd1 | up | Protein bicaudal D homolog 1 |
| B2RU80 | -1.888 | -1.404 | -2.2815 | -2.537 | -2.027625 | 0.000281594 | 0.000384147 | Ptprb | down | Receptor-type tyrosine-protein phosphatase beta |
| B9EJ86 | 1.242 | 1.864 | 1.0905 | 0.802 | 1.240341508 | 0.000930338 | 0.00675869 | Osbpl8 | up | Oxysterol-binding protein |
| B9EJA2 | -1.439 | -1.031 | -0.9535 | -1.2 | -1.155875 | 0.000116764 | 0.00252203 | Cttnbp2 | down | Cortactin-binding protein 2 |
| D3YU60 | -1.514 | -0.88 | -2.0875 | -0.38 | -1.215375 | 0.015984588 | 0.03996895 | Mgst1 | down | Microsomal glutathione S-transferase 1 |
| D3YUE4 | -0.678 | -1.053 | -1.3175 | -1.611 | -1.164875 | 0.001290203 | 0.008102551 | Fam151b | down | Protein Fam151b |
| D3YX02 | 1.354 | 1.275 | 1.1975 | 1.386 | 1.303125 | 5.09E-06 | 0.000841369 | Gm15293 | up | Protein Gm15293 |
| D3YX71 | -0.602 | -2.402 | -1.3475 | -3.186 | -1.884375 | 0.015728602 | 0.039526188 | Gm8973 | down | Uncharacterized protein |
| D3YYD0 | -2.58 | -1.045 | 1.8875 | -1.993 | -1.889730404 | 0.000485724 | 0.004937744 | Olfm4 | down | Olfactomedin-4 |
| D3Z3A8 | 1.271 | 2.016 | 1.5115 | 0.837 | 1.408875 | 0.001116807 | 0.007402891 | Myo9a | up | Unconventional myosin-IXa |
| D3Z4T9 | -1.692 | -1.338 | -1.4265 | -2.701 | -1.690333075 | 0.000329135 | 0.004078484 | Zranb2 | down | Zinc finger Ran-binding domain-containing protein 2 |
| D3Z710 | 1.511 | 1.04 | 1.3825 | 1.574 | 1.383384734 | 4.61E-05 | 0.001710782 | Klc3 | up | Kinesin light chain 3 |
| E0CX20 | -2.039 | -1.624 | -2.3525 | -2.74 | -2.188875 | 0.000145184 | 0.002763462 | Bud31 | down | Protein BUD31 homolog |
| E9PUQ3 | -1.916 | -1.183 | -1.5635 | -2.66 | -1.830625 | 0.00010224 | 0.007094039 | AU019823 | down | Protein AU019823 |
| E9PV38 | -1.433 | -1.225 | -1.5595 | -1.408 | -1.408493743 | 6.38E-06 | 0.000907306 | Ces2g | down | Protein Ces2g |
| E9PXE2 | 1.372 | 1.007 | 1.2045 | 1.385 | 1.242125 | 4.27E-05 | 0.001671268 | Mcf2l | up | Guanine nucleotide exchange factor DBS |
| E9PY03 | -1.832 | -1.927 | -1.9725 | -1.438 | -1.83263141 | 4.97E-05 | 0.000841369 | Tstd1 | down | Upstream stimulatory factor 1 |
| E9Q1Q9 | -1.228 | -2.256 | -1.4795 | -0.174 | -1.284375 | 0.012772242 | 0.034187291 | Khk | down | Ketohexokinase |
| E9Q390 | 1.279 | 1.429 | 0.8835 | 0.99 | 1.145375 | 0.000314204 | 0.00404438 | Myof | up | Myoferlin |
| E9Q409 | -1.155 | -0.943 | -1.4935 | -1.12 | -1.154318401 | 5.14E-05 | 0.001809458 | Prss32 | down | Protein Prss32 |
| E9Q5C9 | -1.968 | -1.821 | -1.5075 | -2.239 | -1.883875 | 3.52E-05 | 0.001614723 | Nolc1 | down | Protein Nolc1 |
| E9Q5K9 | -1.951 | -1.083 | -1.7955 | -2.091 | -1.796718589 | 6.16E-05 | 0.001952061 | Ythdc1 | down | YTH domain-containing protein 1 |
| E9QSR6 | 1.186 | 0.722 | 1.7735 | 0.904 | 1.146375 | 0.002170846 | 0.010666562 | Arhgef37 | up | Rho guanine nucleotide exchange factor 37 |
| E9Q8N8 | -1.359 | -0.987 | -1.7165 | -2.079 | -1.535375 | 0.000823844 | 0.006357335 | Slc4a4 | down | Electrogenic sodium bicarbonate cotransporter 1 |
| E9QQC6 | 1.523 | 0.778 | 0.9895 | 1.436 | 1.181625 | 0.001183899 | 0.007660319 | Fcgbp | up | Protein Fcgbp |
| E9QLR9 | -2.131 | -2.144 | -1.7675 | -2.046 | -2.046497064 | 1.34E-06 | 0.000528463 | Ddias | down | DNA damage-induced apoptosis suppressor protein |
| E9QNS0 | -1.517 | -1.262 | -1.3005 | -1.178 | -1.300054355 | 8.78E-06 | 0.000977434 | Nlrp6 | down | NACHT, LRR and PYD domains-containing protein 6 |
| E9QNX7 | -1.411 | -0.605 | -2.7825 | -2.921 | -1.929875 | 0.015107954 | 0.038448758 | Atp4a | down | Potassium-transporting ATPase alpha chain 1 |
| F2Z423 | -1.459 | -0.535 | -2.0165 | -0.743 | -1.188375 | 0.013748101 | 0.03598213 | Ttll12 | down | Tubulin-tyrosine ligase-like protein 12 |
| F6R4Z5 | -1.473 | -0.647 | -1.1325 | -1.652 | -1.226125 | 0.001668908 | 0.009264408 | Zfp709 | down | Protein Zfp709 |
| F6V243 | 0.958 | 0.871 | 1.1595 | 1.86 | 1.158156729 | 0.0006775 | 0.005715245 | Pcdhb12 | up | Protein Pcdhb12 |
| F8VQC7 | 1.447 | 1.452 | 1.2755 | 1.397 | 1.397896615 | 2.70E-06 | 0.000617538 | Ktn1 | up | Kinectin |
| F8WLA4 | 1.349 | 0.712 | 1.3545 | 1.411 | 1.349125974 | 3.64E-06 | 0.000728919 | Sgsm3 | up | Small G protein-signaling modulator 3 |
| G3X8T2 | -1.171 | -1.171 | -0.7325 | -1.289 | -1.170987 | 1.16E-05 | 0.001090211 | Zc3h18 | down | RIKEN cDNA 5830416A07, isoform CRA_c |
| G3X956 | -1.701 | -0.681 | -1.0595 | -1.804 | -1.311375 | 0.003855666 | 0.0155351 | Supt16 | down | FACT complex subunit SPT16 |
| G3X9H7 | 1.27 | 1.333 | 1.3185 | 1.878 | 1.332838 | 4.14E-06 | 0.000790475 | Mtss1 | up | Metastasis suppressor 1, isoform CRA_e |
| G5E904 | -1.362 | -1.619 | -2.9455 | -2.181 | -2.026875 | 0.001296975 | 0.008106338 | Gm4794 | down | Sulfotransferase |
| I1E4X8 | 1.149 | 1.163 | 1.4315 | 1.271 | 1.253625 | 1.45E-06 | 0.00118665 | Stim2 | up | Stromal interaction molecule 2 |
| J3QMG3 | -0.916 | -0.797 | -1.4855 | -1.663 | -1.215375 | 0.002277135 | 0.0110199 | Vdac3 | down | Voltage-dependent anion-selective channel protein 3 |
| K3W4L7 | -1.188 | -1.811 | -1.9375 | -0.883 | -1.454875 | 0.001977855 | 0.01017514 | Pbld1 | down | Phenazine biosynthesis-like domain-containing protein 1 |
| O08529 | 1.421 | 1.297 | 1.1725 | 1.347 | 1.309375 | 6.15E-06 | 0.000907306 | Capn2 | up | Calpain-2 catalytic subunit |
| O09010 | 1.443 | 1.37 | 1.4835 | 1.56 | 1.464125 | 2.24E-06 | 0.00058884 | Lfng | up | Beta-1,3-N-acetylglucosaminyltransferase lunatic fringe |
| O09037 | -1.64 | -2.141 | -1.5875 | -1.077 | -1.611375 | 0.000210039 | 0.000245954 | Reg3a | down | Regenerating islet-derived protein 3-alpha |
| O35280 | -1.09 | -1.001 | -1.4995 | -1.475 | -1.266375 | 0.000176264 | 0.003578677 | Chek1 | down | Serine/threonine-protein kinase Chk1 |
| O35594 | 0.817 | 1.152 | 1.1275 | 1.543 | 1.150998 | 0.002560222 | 0.001190766 | Ifft81 | up | Intraflagellar transport protein 81 homolog |
| O35943 | -0.813 | -0.849 | -1.3945 | -1.715 | -1.192875 | 0.000245954 | 0.003085355 | Fxn | down | Frataxin, mitochondrial |
| O35945 | -1.241 | -1.721 | -1.8345 | -0.518 | -1.328625 | 0.003926343 | 0.01565951 | Aldh1a7 | down | Aldehyde dehydrogenase, cytosolic 1 |

TABLE 3-continued

Detected and quantified in vitro Proteome

| | | | | | | | |
|---|---|---|---|---|---|---|---|
| O54864-2 | -1.557 | -1.413 | -1.3965 | -2.183 | -1.556204 | 2.90E-05 | 0.001546817 down | Suv39h1 | Isoform 2 of Histone-lysine N-methyltransferase SUV39H1 |
| O55042 | 1.666 | 1.165 | 1.2265 | 1.268 | 1.267636 | 1.03E-05 | 0.001045334 up | Snca | Alpha-synuclein |
| O70126 | -1.572 | -0.967 | -0.8395 | -1.281 | -1.164875 | 0.000734879 | 0.005979009 down | Aurkb | Aurora kinase B |
| O70472 | 1.419 | 0.87 | 1.3875 | 1.011 | 1.171875 | 0.000429715 | 0.004672636 up | Tmem131 | Transmembrane protein 131 |
| O70514 | -1.413 | -1.091 | -1.0895 | -1.216 | -1.202375 | 0.001486938 | 0.001488081 down | Fgfbp1 | Fibroblast growth factor-binding protein 1 |
| O88310 | 1.445 | 1.239 | 0.9545 | 1.175 | 1.203375 | 5.28E-05 | 0.001844081 up | Itln1 | Intelectin-1a |
| O88451 | -1.202 | -1.565 | -2.2355 | -0.662 | -1.416125 | 0.004075268 | 0.01602497 down | Rdh7 | Retinol dehydrogenase 7 |
| O88513 | -1.6 | -1.306 | -0.8435 | -1.599 | -1.337125 | 0.00039035 | 0.004430968 down | Gmnn | Geminin |
| O88554 | -1.403 | -0.933 | -1.4925 | -1.465 | -1.403376 | 0.000936704 | 0.000093681 down | Parp2 | Poly [ADP-ribose] polymerase 2 |
| O88803 | 1.692 | 1.063 | 1.4425 | 1.463 | 1.443242 | 2.35E-05 | 0.001402557 up | Lect2 | Leukocyte cell-derived chemotaxin-2 |
| P02772 | -1.616 | -1.696 | -1.1235 | -1.316 | -1.437875 | 0.000127121 | 0.002612217 down | Afp | Alpha-fetoprotein |
| P02798 | -2.904 | -2.907 | -2.2505 | -3.047 | -2.904342 | 1.91E-07 | 0.000496308 down | Mt2 | Metallothionein-2 |
| P02802 | -2.19 | -2.322 | -1.3715 | -1.016 | -1.724875 | 0.002557451 | 0.01190766 down | Mt1 | Metallothionein-1 |
| P03958 | 1.339 | 0.074 | 1.5985 | 1.501 | 1.340051 | 0.000235506 | 0.003521621 up | Ada | Adenosine deaminase |
| P04184 | -1.268 | -1.033 | -1.0175 | -1.428 | -1.186625 | 9.77E-05 | 0.002401232 down | Tk1 | Thymidine kinase, cytosolic |
| P06728 | -1.343 | -2.171 | -1.8605 | -0.907 | -1.570375 | 0.001819873 | 0.00967781 down | Apoa4 | Apolipoprotein A-IV |
| P07309 | 1.309 | 0.951 | 1.2255 | 1.511 | 1.249125 | 7.53E-05 | 0.002163145 up | Ttr | Transthyretin |
| P07310 | -1.418 | -3.14 | -2.0165 | -2.541 | -2.278875 | 0.000931913 | 0.00675869 down | Ckm | Creatine kinase M-type |
| P09405 | -1.377 | -0.807 | -1.0695 | -1.615 | -1.217125 | 0.000783546 | 0.006190813 down | Ncl | Nucleolin |
| P0C027 | 1.368 | 1.133 | 0.8135 | 1.192 | 1.133819 | 8.97E-05 | 0.002304862 up | Nudt10 | Diphosphoinositol polyphosphate phosphohydrolase 3-alpha |
| P11725 | -1.478 | -1.458 | -2.2695 | -1.132 | -1.477049 | 7.65E-05 | 0.002167266 down | Otc | Ornithine carbamoyltransferase, mitochondrial |
| P14115 | -1.536 | -1.734 | -0.8425 | -2.121 | -1.558375 | 0.000833707 | 0.006381402 down | Rpl27a | 60S ribosomal protein L27a |
| P18242 | 1.508 | 1.211 | 0.9875 | 1.479 | 1.296375 | 0.000138492 | 0.002700428 up | Ctsd | Cathepsin D |
| P18581-2 | -1.863 | -1.174 | -2.2475 | -3.161 | -2.111375 | 0.001677287 | 0.009272174 down | Slc7a2 | Isoform 2 of Low affinity cationic amino acid transporter 2 |
| P18894 | -1.222 | -1.706 | -1.8305 | -1.375 | -1.375875 | 0.001910795 | 0.009965945 down | Dao | D-amino-acid oxidase |
| P19246 | 1.432 | 1.357 | 1.1695 | 1.176 | 1.283625 | 1.86E-05 | 0.001261088 up | Nefh | Neurofilament heavy polypeptide |
| P19467 | 1.437 | 0.978 | 1.3955 | 0.984 | 1.198625 | 0.000300581 | 0.003962314 up | Muc13 | Mucin-13 |
| P23881 | -1.331 | -1.172 | -1.7775 | -1.12 | -1.329973 | 0.000104034 | 0.002461201 down | Tcea3 | Transcription elongation factor A protein 3 |
| P25444 | -1.207 | -1.264 | -1.1365 | -2.462 | -1.263604 | 2.14E-05 | 0.001337621 down | Rps2 | 40S ribosomal protein S2 |
| P27600 | -1.957 | -1.145 | -2.8495 | -2.827 | -2.194625 | 0.002022413 | 0.01030991 down | Gna12 | Guanine nucleotide-binding protein subunit alpha-12 |
| P27659 | -1.484 | -1.144 | -0.9115 | -1.972 | -1.377875 | 0.001166624 | 0.007619665 down | Rpl3 | 60S ribosomal protein L3 |
| P28650-2 | -1.408 | -0.831 | -1.4375 | -1.789 | -1.409128 | 0.000128476 | 0.002612217 down | Adssl1 | Isoform 2 of Adenylosuccinate synthetase isozyme 1 |
| P30681 | -1.316 | -1.094 | -1.2715 | -1.62 | -1.315261 | 3.18E-05 | 0.00159398 down | Hmgb2 | High mobility group protein B2 |
| P31362 | 1.567 | 1.082 | -2.3845 | 1.176 | -1.896875 | 0.002319706 | 0.01115185 up | Pou2f3 | POU domain, class 2, transcription factor 3 |
| P40338 | -1.026 | -1.492 | -1.5695 | -2.554 | -1.532625 | 0.000244704 | 0.003578573 down | Vhl | Von Hippel-Lindau disease tumor suppressor |
| P43137 | -2.092 | -3.168 | -4.1035 | -2.043 | -2.852125 | 0.001489254 | 0.008686232 down | Reg1 | Lithostathine-1 |
| P43883 | 1.328 | 1.122 | 0.9365 | 1.559 | 1.236375 | 0.000212153 | 0.003357025 up | Plin2 | Perilipin-2 |
| P47968 | -0.958 | -1.223 | -1.2935 | -1.827 | -1.292372 | 0.000180309 | 0.003114218 down | Rpia | Ribose-5-phosphate isomerase |
| P48036 | 1.196 | 1.332 | 1.1055 | 0.94 | 1.143375 | 4.26E-05 | 0.001671268 up | Anxa5 | Annexin A5 |
| P48281 | -1.589 | -1.441 | -1.0795 | -1.499 | -1.441549 | 1.11E-05 | 0.001083377 down | Vdr | Vitamin D3 receptor |
| P48756 | 1.21 | 0.504 | 1.2845 | 1.769 | 1.211741 | 0.001425305 | 0.00852239 up | Gip | Gastric inhibitory polypeptide |
| P50431 | -1.382 | -1 | -1.1875 | -1.08 | -1.162375 | 4.12E-05 | 0.001671268 down | Shmt1 | Serine hydroxymethyltransferase, cytosolic |
| P50543 | 1.371 | 1.475 | 1.4645 | 0.855 | 1.371501 | 1.44E-05 | 0.00118665 up | S100a11 | Protein S100-A11 |
| P51162 | -0.519 | -1.799 | -2.7635 | -1.209 | -1.572625 | 0.01221016 | 0.03311413 down | Fabp6 | Gastrotropin |
| P51432 | -1.261 | -1.255 | -1.1345 | -1.096 | -1.186625 | 9.15E-06 | 0.000991767 down | Plcb3 | 1-phosphatidylinositol 4,5-bisphosphate phosphodiesterase beta-3 |
| P52792 | 1.847 | 0.711 | 1.3025 | 0.805 | 1.166375 | 0.004637109 | 0.01733293 up | Gck | Glucokinase |
| P52800 | -0.883 | -1.258 | -1.7545 | -1.065 | -1.240125 | 0.000589978 | 0.005397356 down | Efnb2 | Ephrin-B2 |
| P55050 | -1.558 | -2.656 | -2.1955 | -0.474 | -1.720875 | 0.00858524 | 0.02568169 down | Fabp2 | Fatty acid-binding protein, intestinal |
| P55088-3 | -2.495 | -1.955 | -2.0905 | -3.021 | -2.390375 | 0.000108035 | 0.002481296 down | Aqp4 | Isoform 3 of Aquaporin-4 |

TABLE 3-continued

Detected and quantified in vitro Proteome

| ID | | | | | | Gene | Dir | | | Description |
|---|---|---|---|---|---|---|---|---|---|---|
| P56382 | -1.051 | -3.179 | -1.3955 | -3.924 | -2.387375 | 0.01622922 | 0.04041672 | Atp5e | down | ATP synthase subunit epsilon, mitochondrial |
| P56395 | -1.162 | -0.964 | -1.6925 | -1.71 | -1.382125 | 0.000772361 | 0.006143504 | Cyb5a | down | Cytochrome b5 |
| P56695 | 1.527 | 0.901 | 0.7335 | 1.433 | 1.148625 | 0.002098924 | 0.01049665 | Wfs1 | up | Wolframin |
| P56716 | 0.494 | 1.733 | 1.3015 | 1.329 | 1.302723 | 0.00032442 | 0.004068699 | Rp1 | up | Oxygen-regulated protein 1 |
| P60824 | 0.902 | 1.138 | 1.3145 | 1.267 | 1.155375 | 5.93E-05 | 0.001942086 | Cirbp | up | Cold-inducible RNA-binding protein |
| P61358 | -1.508 | -0.773 | -1.0115 | -2.267 | -1.389875 | 0.004942579 | 0.01806194 | Rpl27 | down | 60S ribosomal protein L27 |
| P61514 | -1.096 | -1.38 | -0.8275 | -1.528 | -1.207875 | 0.000481327 | 0.004920094 | Rpl37a | down | 60S ribosomal protein L37a |
| P61961 | 1.579 | 0.388 | 1.1535 | 1.335 | 1.155166 | 0.001572259 | 0.008987222 | Ufm1 | up | Ubiquitin-fold modifier 1 |
| P62082 | -1.274 | -0.974 | -1.0365 | -1.419 | -1.175875 | 0.000125912 | 0.002607376 | Rps7 | down | 40S ribosomal protein S7 |
| P62245 | -1.248 | -1.487 | -1.6535 | -2.486 | -1.651936 | 0.000247161 | 0.003581352 | Rps15a | down | 40S ribosomal protein S15a |
| P62267 | -0.983 | -2.038 | -0.8085 | -2.125 | -1.488625 | 0.007755257 | 0.023841 | Rps23 | down | 40S ribosomal protein S23 |
| P62270 | -1.433 | -1.873 | -1.1505 | -1.958 | -1.603625 | 0.000348729 | 0.004189781 | Rps18 | down | 40S ribosomal protein S18 |
| P62806 | -1.39 | -0.628 | -1.3305 | -1.477 | -1.331005 | 2.00E-05 | 0.001303913 | Hist1h4a | down | Histone H4 |
| P62830 | -1.36 | -1.128 | -1.1215 | -1.476 | -1.271375 | 4.92E-05 | 0.001760748 | Rpl23 | down | 60S ribosomal protein L23 |
| P62852 | -2.56 | -2.842 | -2.8515 | -4.104 | -2.850786 | 1.68E-06 | 0.000528463 | Rps25 | down | 40S ribosomal protein S25 |
| P62855 | -1.566 | -1.344 | -1.0195 | -2.026 | -1.488875 | 0.000462717 | 0.00480339 | Rps26 | down | 40S ribosomal protein S26 |
| P62876 | -1.008 | -0.747 | -1.2095 | -1.636 | -1.150125 | 0.000925224 | 0.006740675 | Polr2l | down | DNA-directed RNA polymerases I, II, and III subunit RPABC5 |
| P62889 | -1.84 | -0.669 | -1.4315 | -2.06 | -1.500125 | 0.002329107 | 0.01117023 | Rpl30 | down | 60S ribosomal protein L30 |
| P62900 | -1.746 | -1.364 | -1.5065 | -2.581 | -1.744279 | 0.000264424 | 0.003717712 | Rpl31 | down | 60S ribosomal protein L31 |
| P62911 | -1.244 | -0.959 | -0.6925 | -1.954 | -1.212375 | 0.003137717 | 0.0134757 | Rpl32 | down | 60S ribosomal protein L32 |
| P63158 | -1.875 | -1.062 | -1.2145 | -1.339 | -1.337887 | 0.000147143 | 0.00278147 | Hmgb1 | down | High mobility group protein B1 |
| P63166 | -1.207 | -1.094 | -1.7425 | -1.532 | -1.393875 | 0.000233255 | 0.003516544 | Sumo1 | down | Small ubiquitin-related modifier 1 |
| P67984 | -1.504 | -1.157 | -1.4345 | -1.242 | -1.334375 | 2.90E-05 | 0.001546817 | Rpl22 | down | 60S ribosomal protein L22 |
| P70429 | 1.275 | 1.519 | 1.2085 | 1.206 | 1.27464 | 7.74E-06 | 0.000936704 | Evl | up | Ena/VASP-like protein |
| P81117 | 1.736 | 1.385 | 1.0905 | 1.276 | 1.371875 | 8.84E-05 | 0.0022847 | Nucb2 | up | Nucleobindin-2 |
| P84099 | -1.093 | -0.396 | -1.3905 | -3.354 | -1.38699 | 0.01628257 | 0.04051181 | Rpl19 | down | 60S ribosomal protein L19 |
| P84102 | 1.517 | 0.63 | 2.2205 | 0.775 | 1.285625 | 0.01270342 | 0.03404856 | Serf2 | up | Small EDRK-rich factor 2 |
| P84228 | -1.226 | -0.594 | -1.0075 | -1.809 | -1.159125 | 0.002789439 | 0.01251655 | Hist1h3b | down | Histone H3.2 |
| P84244 | -1.002 | -0.645 | -1.1735 | -1.765 | -1.146375 | 0.001900587 | 0.00996347 | H3f3a | down | Histone H3.3 |
| P97290 | 1.362 | 1.123 | 1.2185 | 1.278 | 1.245375 | 7.88E-06 | 0.000936704 | Serping1 | up | Plasma protease C1 inhibitor |
| P97314 | -1.447 | -1.021 | -1.3045 | -1.045 | -1.204375 | 0.000114077 | 0.002510641 | Csrp2 | down | Cysteine and glycine-rich protein 2 |
| P97328 | -1.151 | -2.263 | -1.4115 | -0.12 | -1.236375 | 0.01650177 | 0.0408795 | Klk | down | Ketohexokinase |
| P97351 | -1.36 | -0.944 | -1.2445 | -1.603 | -1.287875 | 0.000133059 | 0.002658106 | Rps3a | down | 40S ribosomal protein S3a |
| P97449 | 1.246 | 1.528 | 1.2875 | 0.807 | 1.246894 | 9.00E-05 | 0.002304862 | Anpep | up | Aminopeptidase N |
| P97479 | -1.135 | -1.101 | -1.2195 | -1.191 | -1.161625 | 5.01E-06 | 0.000841369 | Myo7a | down | Unconventional myosin-VIIa |
| P98063 | 1.296 | 1.342 | 1.2215 | 1.383 | 1.310625 | 0.000727205 | 0.000727205 | Bmp1 | up | Bone morphogenetic protein 1 |
| Q00623 | -1.311 | -2.229 | -2.6175 | -1.952 | -2.027375 | 0.000332404 | 0.004091988 | Apoa1 | down | Apolipoprotein A-I |
| Q03157 | 1.177 | 0.671 | 1.2695 | 1.559 | 1.178316 | 0.000473947 | 0.004869505 | Aplp1 | up | Amyloid-like protein 1 |
| Q03172 | 0.832 | 1.656 | 1.2325 | 1.102 | 1.205625 | 0.000427038 | 0.004665286 | Hivep1 | up | Zinc finger protein 40 |
| Q03311 | -1.349 | -1.892 | -2.0655 | -1.665 | -1.742875 | 6.97E-05 | 0.002060325 | Bche | down | Cholinesterase |
| Q05186 | 1.602 | 1.092 | 1.0235 | 1.511 | 1.307125 | 0.00035060 | 0.004189781 | Rcn1 | up | Reticulocalbin-1 |
| Q07797 | 1.212 | 1.255 | 1.1065 | 1.011 | 1.146125 | 1.69E-05 | 0.001250999 | Lgals3bp | up | Galectin-3-binding protein |
| Q08652 | -1.364 | -2.41 | -1.7785 | -0.366 | -1.479625 | 0.008932341 | 0.02676029 | Rbp2 | down | Retinol-binding protein 2 |
| Q08943-2 | -2.098 | -0.891 | -1.6565 | -2.418 | -1.765875 | 0.001656867 | 0.009240863 | Ssrp1 | down | Isoform 2 of FACT complex subunit SSRP1 |
| Q08ED5 | -1.702 | -1.686 | -2.2885 | -1.679 | -1.701948 | 9.51E-07 | 0.000496308 | Ces2f | down | Protein Ces2f |
| Q2QI47-3 | 1.068 | 0.864 | 1.5445 | 2.117 | 1.398375 | 0.002682728 | 0.01228429 | Ush2A | up | Isoform 3 of Usherin |
| Q32NZ6 | 1.76 | 1.111 | 1.2165 | 1.252 | 1.251557 | 1.73E-05 | 0.001250999 | Tmc5 | up | Transmembrane channel-like protein 5 |
| Q33DR2 | -1.379 | -1.779 | -1.2185 | -1.389 | -1.388531 | 1.01E-05 | 0.001045334 | Pdss1 | down | Decaprenyl-diphosphate synthase subunit 1 |
| Q3TMX5 | 1.514 | 0.958 | 1.0245 | 1.141 | 1.140175 | 0.000100387 | 0.002445284 | Manf | up | Arginine-rich, mutated in early stage tumors, isoform CRA_b |
| Q3U0B3 | -1.054 | -1.691 | -1.5305 | -0.923 | -1.299625 | 0.00092088 | 0.00671346 | Dhrs11 | down | Dehydrogenase/reductase SDR family member 11 |

TABLE 3-continued

Detected and quantified in vitro Proteome

| | | | | | | | | |
|---|---|---|---|---|---|---|---|---|
| Q3U9N9 | -1.309 | -0.055 | -1.4695 | -2.424 | -1.314375 | 0.01582461 | Slc16a10 | down | Monocarboxylate transporter 10 |
| Q3UA16 | -1.924 | -0.747 | -1.8235 | -2.598 | -1.825917 | 0.000929435 | Spc25 | down | Kinetochore protein Spc25 |
| Q3UGF1 | -0.199 | -0.895 | -1.3115 | -2.206 | -1.152875 | 0.0220145 | Wdr19 | down | WD repeat-containing protein 19 |
| Q3UHD3 | 1.347 | 0.087 | 1.7985 | 2.649 | 1.470375 | 0.01980273 | Mtus2 | up | Microtubule-associated tumor suppressor candidate 2 homolog |
| Q3UQ28 | 1.157 | 1.486 | 1.3875 | 1.146 | 1.294125 | 4.09E-05 | Pxdn | up | Peroxidasin homolog |
| Q3UR50 | 1.678 | 1.171 | 1.6125 | 1.377 | 1.459625 | 6.14E-05 | Vwa5b2 | up | von Willebrand factor A domain-containing protein 5B2 |
| Q3UTR7 | 1.922 | 1.275 | 0.9175 | 1.671 | 1.446375 | 0.00093424 | Agt | up | Angiotensinogen |
| Q3UW68 | -1.402 | -1.492 | -1.0855 | -0.676 | -1.163875 | 0.001025725 | Capn13 | down | Calpain-13 |
| Q3UYK3 | -0.639 | -1.148 | -1.5035 | -1.709 | -1.249875 | 0.001952687 | Tbc1d9 | down | TBC1 domain family member 9 |
| Q3V1V3 | -1.45 | -0.805 | -0.9155 | -1.805 | -1.243875 | 0.002715757 | Esf1 | down | ESF1 homolog |
| Q3V2R3 | 1.307 | 0.981 | 1.2265 | 1.433 | 1.236875 | 0.01232664 | Chn2 | up | Beta-chimaerin |
| Q3V3I2 | -1.715 | -1.092 | -2.2685 | -2.719 | -1.948625 | 0.001671268 | Gnat3 | down | Guanine nucleotide-binding protein G(t) subunit alpha-3 |
| Q4ACU6 | -1.525 | -1.512 | -1.6745 | -1.835 | -1.636625 | 0.009259797 | Shank3 | down | SH3 and multiple ankyrin repeat domains protein 3 |
| Q4V9W2 | -1.902 | -0.824 | -1.2515 | -1.464 | -1.360375 | 6.84E-06 | Srek1ip1 | down | Protein SREK1IP1 |
| Q4VAH7 | 1.047 | 1.639 | 1.2475 | 1.739 | 1.418125 | 0.000870895 | Hepacam2 | up | HEPACAM family member 2 |
| Q52KI8 | -1.036 | -0.819 | -1.2825 | -1.437 | -1.143625 | 0.000338703 | Srrm1 | down | Serine/arginine repetitive matrix protein 1 |
| Q52KR3 | -2.118 | -0.268 | -1.3905 | -1.67 | -1.393319 | 0.000364985 | Prune2 | down | Protein prune homolog 2 |
| Q571E4 | 1.473 | 0.565 | 1.3465 | 1.206 | 1.207102 | 0.005328674 | Galns | up | N-acetylgalactosamine-6-sulfatase |
| Q5DQR4 | 1.316 | 0.966 | 1.1715 | 1.133 | 1.146625 | 0.000274726 | Stxbp5l | up | Syntaxin-binding protein 5-like |
| Q5HZI2 | 0.822 | 0.518 | 1.5305 | 1.762 | 1.158125 | 2.22E-05 | C2cd4cC2CD4 | up | C2 calcium-dependent domain-containing protein 4C |
| Q60604 | -1.236 | -2.062 | -1.8295 | -0.073 | -1.300125 | 0.009692916 | Scin | up | Adseverin |
| Q60673 | 1.189 | 1.249 | 0.8005 | 1.265 | 1.189341 | 0.02823665 | Ptprn | up | Receptor-type tyrosine-protein phosphatase-like N |
| Q60936 | -1.293 | -1.012 | -1.8255 | -1.133 | -1.291776 | 0.01779587 | Adck3 | down | Chaperone activity of bc1 complex-like, mitochondrial |
| Q60936-2 | -1.293 | -0.997 | -1.7905 | -1.133 | -1.291732 | 0.00116258 | Adck3 | down | Isoform 2 of Chaperone activity of bc1 complex-like, mitochondrial |
| Q60997 | -1.643 | -0.987 | -1.1555 | -1.543 | -1.332125 | 0.000242562 | Dmbt1 | down | Deleted in malignant brain tumors 1 protein |
| Q61263 | 1.563 | 2.15 | 1.0245 | 0.494 | 1.307875 | 0.000263845 | Soat1 | up | Sterol O-acyltransferase 1 |
| Q61391 | -0.83 | -1.694 | 1.3345 | -0.675 | -1.133375 | 0.000387772 | Mme | up | Neprilysin |
| Q61595- | 1.391 | 1.442 | 1.2765 | 1.384 | 1.384175 | 0.009386066 | Ktn1 | up | Isoform 11 of Kinectin |
| Q61595-5 | 1.485 | 1.462 | 1.2985 | 1.415 | 1.415329 | 0.003947765 | Ktn1 | up | Isoform 5 of Kinectin |
| Q62395 | 1.037 | 1.294 | 0.4235 | 1.984 | 1.184625 | 2.17E-06 | Tff3 | up | Trefoil factor 3 |
| Q62431 | 1.672 | 1.343 | 1.2465 | 0.741 | 1.250625 | 2.70E-06 | Arid3a | up | AT-rich interactive domain-containing protein 3A |
| Q64176 | -1.21 | -1.557 | -1.2065 | -1.062 | -1.209609 | 0.006637775 | Ces1e | up | Carboxylesterase 1E |
| Q642K5 | -1.384 | -1.443 | -1.4375 | -2.406 | -1.442913 | 0.000488858 | Fau | down | 40S ribosomal protein S30 |
| Q64338 | 0.73 | 0.722 | 1.3705 | 1.805 | 1.156875 | 1.36E-06 | Pde1c | down | Calcium/calmodulin-dependent 3',5'-cyclic nucleotide phosphodiesterase 1C |
| Q64469 | -1.603 | -2.001 | -1.5715 | -0.844 | -1.572746 | 2.62E-06 | Nqo1 | up | NAD(P)H dehydrogenase [quinone] 1 |
| Q6D186 | 1.46 | 1.066 | 1.4225 | 2.251 | 1.458857 | 0.00595713 | Fastkd1 | up | FAST kinase domain-containing protein 1 |
| Q6I9G1 | 1.631 | 1.194 | 0.7015 | 1.233 | 1.195311 | 0.000128653 | Styk1 | up | Tyrosine-protein kinase STYK1 |
| Q6PCN3 | 0.917 | 1.005 | 1.5695 | 1.711 | 1.300625 | 0.000148835 | Ttbk1 | up | Tau-tubulin kinase 1 |
| Q6PDB7 | -0.858 | -1.424 | -1.6495 | -1.282 | -1.303375 | 0.000441484 | Ces2b | down | MCG142671, isoform CRA_b |
| Q6PEP4 | -1.629 | -1.409 | -1.4465 | -1.416 | -1.446328 | 0.00133176 | Zfp677 | down | Protein Zfp677 |
| Q6PFA2 | -1.132 | -0.575 | -1.5885 | -2.599 | -1.473625 | 0.00260697 | Clta | down | Clathrin light chain A |
| Q6PGI3 | -1.156 | -1.255 | -1.2885 | -1.61 | -1.288063 | 2.11E-06 | L1cam | down | L1 cell adhesion molecule |
| Q6UQ17 | 1.126 | 1.134 | 1.7555 | 1.841 | 1.464125 | 0.00940258 | Atp8b3 | up | Phospholipid-transporting ATPase IK |
| Q6ZQL4 | -1.562 | -0.715 | -0.9435 | -1.351 | -1.142875 | 1.15E-05 | Wdr43 | down | WD repeat-containing protein 43 |
| Q6ZWN5 | -1.072 | -0.691 | -1.1845 | -2.085 | -1.182848 | 0.00158063 | Rps9 | down | 40S ribosomal protein S9 |
| Q6ZWR6 | 1.167 | 0.703 | 1.1985 | 1.566 | 1.168184 | 0.00033372 | Syne1 | up | Nesprin-1 |
| Q6ZWU9 | -1.679 | -1.427 | -1.6985 | -2.385 | -1.697752 | 1.68E-06 | Rps27 | down | 40S ribosomal protein S27 |
| Q6ZWV3 | -1.298 | -0.703 | -1.0565 | -1.537 | -1.148625 | 0.000878643 | Rpl10 | down | 60S ribosomal protein L10 |

TABLE 3-continued

Detected and quantified in vitro Proteome

| | | | | | | | | |
|---|---|---|---|---|---|---|---|---|
| Q6ZWV7 | -0.946 | -0.202 | -1.1305 | -2.526 | -1.127441 | 0.01909055 | 0.04529062 | down | Rpl35 | 60S ribosomal protein L35 |
| Q6ZWY3 | -1.59 | -1.286 | -1.4875 | -2.317 | -1.588919 | 7.65E-05 | 0.002167266 | down | Rps27l | 40S ribosomal protein S27-like |
| Q6ZWZ4 | -1.085 | -1.539 | -0.8265 | -2.058 | -1.377125 | 0.002574063 | 0.01194031 | down | Rpl36 | 60S ribosomal protein L36 |
| Q768S4 | 1.2 | 0.548 | 1.8455 | 1.859 | 1.363125 | 0.005000017 | 0.01819715 | up | Rph3al | Rab effector Noc2 |
| Q7JJ13 | -1.243 | -0.748 | -0.9235 | -1.666 | -1.145125 | 0.00159883 | 0.009055139 | down | Brd2 | Bromodomain-containing protein 2 |
| Q7TNV0 | -1.8 | -0.726 | -1.2915 | -1.861 | -1.419625 | 0.002021786 | 0.01030991 | down | Dek | Protein DEK |
| Q7TQD2 | 1.195 | 1.666 | 0.7645 | 1.337 | 1.240625 | 0.000541584 | 0.005190266 | up | Tppp | Tubulin polymerization-promoting protein |
| Q80SU7 | -1.279 | -0.758 | -1.2235 | -1.338 | -1.223929 | 0.000125099 | 0.001250999 | down | Gvin1 | Interferon-induced very large GTPase 1 |
| Q80TR4 | 1.316 | 1.587 | 1.2175 | 0.818 | 1.234625 | 1.74E-05 | 0.00672153 | up | Slit1 | Slit homolog 1 protein |
| Q80V42 | 1.517 | 1.383 | 1.3355 | 1.228 | 1.365875 | 0.000257518 | 0.003672153 | up | Cpm | Carboxypeptidase M |
| Q80XU3 | -1.892 | -0.72 | -1.5225 | -1.116 | -1.312625 | 6.51E-06 | 0.000907306 | up | Nucks1 | Nuclear ubiquitous casein and cyclin-dependent kinase substrate 1 |
| Q80Z37 | 1.31 | 0.914 | 1.7665 | 0.782 | 1.193125 | 0.002099592 | 0.01049665 | up | Topors | E3 ubiquitin-protein ligase Topors |
| Q80ZH7 | -1.437 | -0.415 | -1.3725 | -1.247 | -1.2478 | 0.000104265 | 0.002461201 | down | Lig3 | DNA ligase |
| Q8BHB9 | -1.576 | -1.245 | -1.3195 | -1.01 | -1.287625 | 6.39E-05 | 0.001993323 | down | Clic6 | Chloride intracellular channel protein 6 |
| Q8BK48 | -1.646 | -1.907 | -2.1625 | -1.046 | -1.690375 | 0.000420689 | 0.004631048 | down | Ces2e | Pyrethroid hydrolase Ces2e |
| Q8BM96 | -0.895 | -1.193 | -1.2285 | -1.142 | -1.142365 | 0.001175119 | 0.007115119 | down | Gpr128 | Probable G-protein coupled receptor 128 |
| Q8BPQ7 | 1.5 | 0.707 | 1.4015 | 1.339 | 1.339562 | 1.36E-05 | 0.001402557 | up | Sgsm1 | Small G protein signaling modulator 1 |
| Q8BRB7 | -0.966 | -1.077 | -1.3755 | -1.962 | -1.345125 | 2.35E-05 | 0.001402557 | down | Kat6b | Histone acetyltransferase KAT6B |
| Q8BW75 | -0.94 | -1.056 | -1.8625 | -1.177 | -1.176056 | 0.000929521 | 0.00675869 | down | Maob | Amine oxidase [flavin-containing] B |
| Q8BZ20 | 1.138 | 0.69 | 1.1465 | 1.295 | 1.184418 | 0.000201809 | 0.003273883 | up | Parp12 | Poly [ADP-ribose] polymerase 12 |
| Q8C159 | -0.633 | -1.446 | -1.1765 | -1.271 | -1.177491 | 0.000193952 | 0.003206267 | down | Ttc22 | Tetratricopeptide repeat protein 22 |
| Q8C196 | -1.302 | -0.76 | -1.9525 | -0.825 | -1.209875 | 0.004336344 | 0.01660381 | up | Cps1 | Carbamoyl-phosphate synthase [ammonia], mitochondrial |
| Q8C2E4 | -1.411 | -1.637 | -1.8825 | -2.231 | -1.790375 | 0.000103319 | 0.002461201 | down | Ptcd1 | Pentatricopeptide repeat-containing protein 1, mitochondrial |
| Q8C393 | -1.644 | -1.003 | -1.1485 | -2.908 | -1.640816 | 0.004385833 | 0.01669742 | down | Zim1 | Protein Zim1 |
| Q8C407-2 | -1.553 | -0.796 | -1.7055 | -2.059 | -1.554821 | 0.000542507 | 0.005190266 | down | Yipf4 | Isoform 2 of Protein YIPF4 |
| Q8C5N3 | -1.581 | -0.922 | -0.9735 | -1.648 | -1.281125 | 0.001318049 | 0.008181909 | down | Cwc22 | Pre-mRNA-splicing factor CWC22 homolog |
| Q8CAB8 | 1.555 | 0.678 | 1.5715 | 1.494 | 1.294305 | 4.88E-05 | 0.00084136 | up | Gats12 | GATS-like protein 2 |
| Q8CFC7 | -1.219 | -0.633 | -0.8625 | -1.84 | -1.138625 | 0.004300742 | 0.01651693 | down | Clasrp | CLK4-associating serine/arginine rich protein |
| Q8CGK7 | -1.028 | -1.1 | -1.4805 | -1.82 | -1.357125 | 0.000583835 | 0.005353383 | down | Gnal | Guanine nucleotide-binding protein G(olf) subunit alpha |
| Q8CIV3 | 1.6 | 0.988 | 0.9025 | 1.225 | 1.178875 | 0.000434819 | 0.00471144 | up | Liph | Lipase member H |
| Q8K023 | -1.063 | -0.99 | -1.9945 | -1.758 | -1.451375 | 0.002113455 | 0.01051355 | down | Akr1c18 | Aldo-keto reductase family 1 member C18 |
| Q8K1K3 | -1.095 | -0.395 | -1.5935 | -1.813 | -1.224125 | 0.007199488 | 0.02306023 | down | Tinf2 | TERF1-interacting nuclear factor 2 |
| Q8K354 | -1.154 | -1.435 | -1.8555 | -0.441 | -1.221375 | 0.004436258 | 0.01681909 | down | Cbr3 | Carbonyl reductase [NADPH] |
| Q8K4B2 | 1.448 | 0.943 | 1.1955 | 1.204 | 1.197625 | 4.16E-05 | 0.001671268 | up | Irak3 | Interleukin-1 receptor-associated kinase 3 |
| Q8K4R4 | 1.072 | 0.913 | 1.6335 | 1.321 | 1.234875 | 0.00466991 | 0.004530039 | up | Pitpnc1 | Cytoplasmic phosphatidylinositol transfer protein 1 |
| Q8R0T2 | -1.662 | -0.647 | -0.8366 | -2.825 | -1.492625 | 0.01850904 | 0.04426219 | down | Znf768 | Zinc finger protein 768 |
| Q8R550 | 1.738 | 1.082 | 1.8435 | 1.303 | 1.491625 | 0.000409113 | 0.004547344 | up | Sh3kbp1 | SH3 domain-containing kinase-binding protein 1 |
| Q8VCI0 | -1.187 | -1.193 | -1.4105 | -0.754 | -1.187606 | 4.06E-05 | 0.001671268 | down | Plbd1 | Phospholipase B-like 1 |
| Q8VCT4 | -1.923 | -1.965 | -2.3285 | -1.001 | -1.924169 | 4.73E-05 | 0.001721365 | down | Ces1d | Carboxylesterase 1D |
| Q8VE10 | -1.74 | -0.906 | -0.8235 | -1.246 | -1.178285 | 0.001494738 | 0.0086887 | down | Naa40 | N-alpha-acetyltransferase 40 |
| Q8VE33 | 2.102 | 0.932 | 1.1705 | 1.609 | 1.453375 | 0.001660036 | 0.009251413 | up | Gdap1l1 | Ganglioside-induced differentiation-associated protein 1-like 1 |
| Q8VEE1 | -1.327 | -1.525 | -1.0345 | -1.145 | -1.257875 | 8.60E-05 | 0.002281069 | down | Lmcd1 | LIM and cysteine-rich domains protein 1 |
| Q8VHB5 | -1.611 | -1.401 | -1.7625 | -1.754 | -1.632125 | 8.58E-06 | 0.000977434 | down | Ca9 | Carbonic anhydrase 9 |
| Q8VHC3 | 1.688 | 1.48 | 1.1495 | 1.521 | 1.480691 | 1.53E-05 | 0.001188215 | up | Selm | Selenoprotein M |
| Q8VI93 | 1.378 | 0.979 | 1.6325 | 1.853 | 1.460625 | 0.000350804 | 0.004189781 | up | Oas3 | 2'-5'-oligoadenylate synthase 3 |
| Q8WUR0 | -0.949 | -1.798 | -1.4995 | -1.811 | -1.514375 | 0.000333673 | 0.004094465 | down | | Protein C19orf12 homolog |
| Q91UZ1 | 1.324 | 1.664 | 1.3895 | 1.329 | 1.389173 | 4.77E-06 | 0.00084136 | up | Plcb4 | Phosphoinositide phospholipase C |
| Q91VE6 | -1.492 | -1.242 | -1.0275 | -1.884 | -1.411375 | 0.000379021 | 0.004362831 | down | Nifk | MKI67 FHA domain-interacting nucleolar phosphoprotein |

TABLE 3-continued

| | | | | | | Detected and quantified in vitro Proteome | | |
|---|---|---|---|---|---|---|---|---|
| Q91WA1 | -1.929 | -0.883 | -1.5765 | -2.303 | -1.672875 | 0.001338945 | 0.00822481 | Tipin | down | TIMELESS-interacting protein |
| Q91WU0 | -1.5 | -1.991 | -2.4445 | -0.456 | -1.597875 | 0.00675493 | 0.02198782 | Ces1f | down | Expressed sequence AU018778 |
| Q91Y74 | -0.783 | -1.258 | -1.9425 | -0.946 | -1.232375 | 0.002374948 | 0.01134257 | St3gal4 | down | CMP-N-acetylneuraminate-beta-galactosamide-alpha-2,3-sialyltransferase 4 |
| Q920F6 | -1.931 | -0.989 | -2.1915 | -1.967 | -1.931734 | 1.03E-05 | 0.001045334 | Smc1b | down | Structural maintenance of chromosomes protein 1B |
| Q921T2 | 1.233 | 1.176 | 1.0935 | 1.365 | 1.216875 | 1.09E-05 | 0.001077527 | Tor1aip1 | up | Torsin-1A-interacting protein 1 |
| Q921X9 | 1.535 | 1.138 | 1.0115 | 1.523 | 1.301875 | 0.000241925 | 0.003568078 | Pdia5 | up | Protein disulfide-isomerase A5 |
| Q99IP6-2 | 1.14 | 1.24 | 1.2235 | 0.76 | 1.140479 | 2.75E-05 | 0.001497233 | Homer3 | up | Isoform 2 of Homer protein homolog 3 |
| Q99K73 | -1.189 | -0.97 | -1.1925 | -1.663 | -1.19191 | 3.94E-05 | 0.001660769 | Nrf1 | down | Nrf1 protein |
| Q99LD8 | 1.314 | 1.577 | 1.1265 | 1.14 | 1.289375 | 5.78E-05 | 0.001920568 | Ddah2 | up | N(G),N(G)-dimethylarginine dimethylaminohydrolase 2 |
| Q99LZ3 | -1.61 | -1.013 | -0.7435 | -1.481 | -1.211875 | 0.001699239 | 0.009334681 | Gins4 | down | DNA replication complex GINS protein SLD5 |
| Q99M01 | -0.869 | -0.578 | -1.7495 | -1.486 | -1.170625 | 0.006575054 | 0.021567553 | Fars2 | down | Phenylalanine--tRNA ligase, mitochondrial |
| Q99M54 | -1.383 | -1.488 | -0.4185 | -1.548 | -1.383657 | 0.006660769 | 0.021660769 | Cdca3 | down | Cell division cycle-associated protein 3 |
| Q99N50-2 | 1.685 | 1.299 | 1.0465 | 1.663 | 1.423375 | 0.000239004 | 0.003546996 | Sytl2 | up | Isoform 2 of Synaptotagmin-like protein 2 |
| Q99PG0 | -1.606 | -1.392 | -2.1105 | -1.558 | -1.60531 | 1.43E-05 | 0.001118665 | Aadac | down | Arylacetamide deacetylase |
| Q9CPS7 | -1.383 | -1.226 | -0.9215 | -1.327 | -1.22672 | 4.08E-05 | 0.001671268 | Pno1 | down | RNA-binding protein PNO1 |
| Q9CPY1 | -0.801 | -0.766 | -2.0015 | -1.543 | -1.277875 | 0.006835104 | 0.02217673 | Mrpl51 | down | 39S ribosomal protein L51, mitochondrial |
| Q9CQM8 | -1.227 | -1.156 | -0.7795 | -1.716 | -1.219625 | 0.000506438 | 0.005016799 | Rpl21 | down | 60S ribosomal protein L21 |
| Q9CQU5 | -1.159 | -0.699 | -1.1625 | -1.13 | -1.130129 | 8.04E-06 | 0.000936704 | Zwint | down | ZW10 interactor |
| Q9CV12 | -1.385 | -1.072 | -1.0115 | -1.275 | -1.185875 | 6.50E-05 | 0.002009755 | Fam133b | down | Protein FAM133B |
| Q9CWY4 | -0.742 | -0.855 | -1.6895 | -1.387 | -1.168375 | 0.003069459 | 0.013318166 | Gemin7 | down | Gem-associated protein 7 |
| Q9CXC3 | -1.486 | -0.854 | -1.7905 | -1.7 | -1.487435 | 0.000245296 | 0.003578677 | Mgme1 | down | Mitochondrial genome maintenance exonuclease 1 |
| Q9CXS4 | -1.106 | -1.141 | -0.9445 | -1.649 | -1.1404 | 5.35E-05 | 0.001847242 | Cenpv | down | Centromere protein V |
| Q9CY16 | -1.217 | -0.431 | -1.1285 | -1.28 | -1.129101 | 6.80E-05 | 0.002044753 | Mrps28 | down | 28S ribosomal protein S28, mitochondrial |
| Q9CZM2 | -1.509 | -1.064 | -0.9865 | -2.686 | -1.50632 | 0.003373831 | 0.014163317 | Rpl15 | down | 60S ribosomal protein L15 |
| Q9CZT6 | -1.275 | -0.965 | -0.8705 | -1.413 | -1.130875 | 0.000363681 | 0.004285573 | Cmss1 | down | Protein CMSS1 |
| Q9D009 | -0.836 | -2.401 | -2.1745 | -2.621 | -2.176266 | 0.000153481 | 0.002827569 | Lipt2 | down | Putative lipoyltransferase 2, mitochondrial |
| Q9D018 | -1.405 | -0.874 | -1.2445 | -1.908 | -1.357875 | 0.000630576 | 0.00555018 | Mrto4 | down | mRNA turnover protein 4 homolog |
| Q9D1C1 | -1.316 | -0.925 | -1.1505 | -1.63 | -1.255375 | 0.000241261 | 0.003567274 | Ube2c | down | Ubiquitin-conjugating enzyme E2 C |
| Q9D1R9 | -1.153 | -1.229 | -1.5795 | -4.242 | -1.577598 | 0.001508024 | 0.008732383 | Rpl34 | down | 60S ribosomal protein L34 |
| Q9D3P9 | 1.731 | 0.439 | 0.8595 | 2.111 | 1.285125 | 0.01757603 | 0.04276185 | Nts | up | Neurotensin/neuromedin N |
| Q9D6F4 | 0.695 | 0.98 | 1.4175 | 1.959 | 1.262875 | 0.003901759 | 0.01564194 | Gabra4 | up | Gamma-aminobutyric acid receptor subunit alpha-4 |
| Q9D6X6 | 1.521 | 1.393 | 0.7475 | 1.055 | 1.179125 | 0.000893457 | 0.006630399 | Prss23 | up | Serine protease 23 |
| Q9D816 | 0.664 | 1.318 | 0.5735 | 1.971 | 1.131625 | 0.01282542 | 0.03424754 | Cyp2c55 | up | Cytochrome P450 2C55 |
| Q9D8W7 | -0.573 | -1.182 | -1.9045 | -1.927 | -1.396625 | 0.00575519 | 0.01980477 | Ociad2 | down | OCIA domain-containing protein 2 |
| Q9D937 | -2.074 | -1.942 | -1.0675 | -2.286 | -1.943261 | 5.62E-05 | 0.001896735 | 1810009A15Rik | down | MCG127334 |
| Q9D9Z1 | -1.473 | -0.579 | -0.8635 | -1.605 | -1.130125 | 0.005324851 | 0.01890712 | Knstrn | down | Small kinetochore-associated protein |
| Q9DA9 | -0.99 | -1.148 | -0.7465 | -2.635 | -1.146583 | 0.001509696 | 0.008755526 | 14-Sep | down | Septin-14 |
| Q9DBG7 | 1.346 | 1.118 | 0.9025 | 1.401 | 1.191875 | 0.000150065 | 0.002816442 | Srpr | up | Signal recognition particle receptor subunit alpha |
| Q9DCS2 | -0.849 | -0.662 | -1.6145 | -1.557 | -1.170625 | 0.004879838 | 0.01797906 | | down | UPF0585 protein C16orf13 homolog |
| Q9DCT8 | 1.983 | 1.517 | 0.9975 | 1.047 | 1.386125 | 0.001339267 | 0.00822481 | Crip2 | up | Cysteine-rich protein 2 |
| Q9DD24 | 1.266 | 0.97 | 1.6605 | 1.153 | 1.262375 | 0.000169716 | 0.003015752 | Wbp5 | up | WW domain-binding protein 5 |
| Q9EPC5 | -2.063 | -2.064 | -2.2365 | -2.196 | -2.139875 | 5.65E-07 | 0.000496308 | Rbp7 | down | Retinoid-binding protein 7 |
| Q9EQ08 | 1.356 | 0.64 | 2.0045 | 1.075 | 1.268875 | 0.003329005 | 0.01402663 | Sgsh | up | Heparan N-sulfatase |
| Q9ERH4 | -1.354 | -0.911 | -1.2565 | -1.536 | -1.264375 | 0.000110527 | 0.002493535 | Nusap1 | down | Nucleolar and spindle-associated protein 1 |
| Q9ERZ0 | -1.833 | -1.41 | -1.0155 | -1.185 | -1.360875 | 0.000349173 | 0.004189781 | Hemgn | down | Hemogen |
| Q9ET22 | 1.451 | 1.159 | 1.3455 | 1.153 | 1.277125 | 2.51E-05 | 0.001438314 | Dpp7 | up | Dipeptidyl peptidase 2 |
| Q9JHJ8-2 | -1.805 | -1.83 | -2.0845 | -2.229 | -1.987125 | 9.49E-06 | 0.001014302 | Icoslg | down | Isoform 2 of ICOS ligand |
| Q9JHT5 | 1.463 | 1.751 | 1.5015 | 0.056 | 1.46377 | 0.001945377 | 0.01721365 | Ammecr1 | up | AMME syndrome candidate gene 1 protein homolog |
| Q9JIB0 | -1.2 | -1.555 | -1.6355 | -1.315 | -1.426375 | 4.75E-05 | 0.001721365 | Rangrf | down | Ran guanine nucleotide release factor |
| Q9JJ78 | -1.497 | -0.959 | -0.7695 | -1.442 | -1.166875 | 0.001339328 | 0.00822481 | Pbk | down | Lymphokine-activated killer T-cell-originated protein |

TABLE 3-continued

Detected and quantified in vitro Proteome

| | M1-1 Log2 Median Normalized | | M1-2 Log2 Median Normalized | | | | | |
|---|---|---|---|---|---|---|---|---|
| Q9JJI8 | -1.888 | -1.3975 | -2.169 | -1.700875 | 0.000327819 | 0.004078484 | down | Rpl38 | 60S ribosomal protein L38 kinase |
| Q9JJK5 | 1.863 | 1.1435 | 2.005 | 1.444375 | 0.003924183 | 0.01565951 | up | Herpud1 | Homocysteine-responsive endoplasmic reticulum-resident ubiquitin-like domain member 1 protein |
| Q9JMC3 | 1.758 | 1.3105 | 1.67 | 1.385875 | 0.00085966 | 0.006487114 | up | Dnaja4 | DnaJ homolog subfamily A member 4 |
| Q9JME5 | -1.059 | -1.1945 | -1.459 | -1.255625 | 3.35E-05 | 0.001610318 | down | Ap3b2 | AP-3 complex subunit beta-2 |
| Q9JMH7 | -1.209 | -1.8685 | -1.601 | -1.609875 | 5.68E-05 | 0.001896735 | down | Neu3 | Sialidase-3 |
| Q9QWG7 | -1.032 | -1.8475 | -0.115 | -1.142375 | 0.01815782 | 0.04367251 | down | Sult1b1 | Sulfotransferase family cytosolic 1B member 1 |
| Q9QXD6 | -1.892 | -2.2475 | -0.495 | -1.894604 | 0.001240745 | 0.007891529 | down | Fbp1 | Fructose-1,6-bisphosphatase 1 |
| Q9QXE2 | 0.861 | 1.4485 | 2.093 | 1.477875 | 0.000597171 | 0.005425997 | up | Pol1 | DNA polymerase lambda |
| Q9QXI6 | -0.837 | -1.4195 | -1.306 | -1.307123 | 0.000160715 | 0.002914586 | down | Slc5a1 | SGLT1 protein |
| Q9QXV0 | 1.444 | 1.5975 | 1.172 | 1.274125 | 0.000377612 | 0.004361008 | up | Pesk1n | ProSAAS |
| Q9QYB2 | 0.838 | 1.3505 | 1.402 | 1.286461 | 1.53E-05 | 0.001188215 | up | Dach1 | Dachshund homolog 1 |
| Q9QYY9 | -1.109 | -2.0305 | -0.87 | -1.653875 | 0.007753165 | 0.02430902 | down | Adh4 | Alcohol dehydrogenase 4 |
| Q9R022 | 1.573 | 0.6885 | 1.141 | 1.153625 | 0.000527425 | 0.00512337 | up | Dnajc12 | DnaJ homolog subfamily C member 12 |
| Q9R098 | 1.864 | 0.7445 | 1.669 | 1.366375 | 0.000141273 | 0.01059924 | up | Hgfac | Hepatocyte growth factor activator |
| Q9R0M0 | 1.297 | 1.2135 | 1.732 | 1.229375 | 0.000821301 | 0.006349624 | up | Celsr2 | Cadherin EGF LAG seven-pass G-type receptor 2 |
| Q9R0Y5-2 | 1.269 | 1.5015 | 0.887 | 1.269655 | 3.24E-05 | 0.00159398 | up | Ak1 | Isoform 2 of Adenylate kinase isoenzyme 1 |
| Q9WU40-2 | 1.383 | 1.4435 | 1.027 | 1.383821 | 3.67E-05 | 0.001639477 | up | Lemd3 | Isoform 2 of Inner nuclear membrane protein Man1 |
| Q9WVJ3 | 1.348 | 0.2215 | 1.67 | 1.351154 | 0.009321278 | 0.02760315 | up | Cpq | Carboxypeptidase Q |
| Q9Z0L8 | 1.579 | 1.347 | 0.9735 | 1.555 | 1.363625 | 0.000123141 | 0.002582605 | up | Ggh | Gamma-glutamyl hydrolase |
| Q9Z0X4 | -1.365 | -1.4205 | -1.014 | -1.277643 | 2.32E-05 | 0.001402557 | down | Pde3a | cGMP-inhibited 3',5'-cyclic phosphodiesterase A |
| Q9Z1W8 | -1.809 | -2.8885 | -3.388 | -2.437625 | 0.001836613 | 0.009721674 | down | Atp12a | Potassium-transporting ATPase alpha chain 2 |
| Q9Z2D6-2 | 1.46 | 1.3535 | 1.962 | 1.466713 | 3.97E-06 | 0.000776465 | up | Mecp2 | Isoform B of Methyl-CpG-binding protein 2 |
| Q9Z2V4 | -0.756 | -2.0085 | -1.158 | -1.375875 | 0.002520321 | 0.01180471 | down | Pck1 | Phosphoenolpyruvate carboxykinase, cytosolic [GTP] |
| V9GX31 | -0.954 | -1.1615 | -1.904 | -1.159861 | 0.001335846 | 0.00822481 | down | Gm12728 | Uncharacterized protein |

Table 3B. (FIG. 7A Paneth & EE InVivo TF)

| | M1-1 Log2 Median Normalized | M1-2 Log2 Median Normalized | M2-1 Log2 Median Normalized | M2-2 Log2 Median Normalized | Average log FC |
|---|---|---|---|---|---|
| TF PC | | | | | |
| Nupr1 | 1.12 | 0.44 | 1.37 | 1.15 | 1.02 |
| Foxa3 | 0.15 | 0.09 | 1.09 | 1.42 | 0.69 |
| Tcf12 | 0.22 | 0.45 | 0.67 | 0.58 | 0.48 |
| Lbh | 0.38 | 0.41 | 0.45 | 0.47 | 0.43 |
| Sox9 | -0.04 | 0.36 | 0.31 | -0.04 | 0.15 |
| TF EEC | | | | | |
| Ets1 | 2.24 | 1.47 | 2.04 | 2.91 | 2.17 |
| Insm1 | 1.48 | 1.77 | 1.95 | 2.36 | 1.89 |
| Peg3 | 1.82 | 1.53 | 1.67 | 1.94 | 1.74 |
| Maged1 | 0.67 | 0.61 | 1.16 | 0.86 | 0.83 |
| Jun | 0.35 | 0.22 | 0.34 | 0.21 | 0.28 |
| Junb | -0.07 | -0.16 | 0.13 | -0.17 | -0.07 |

TABLE 4

Enrichments for gene ontology (GO) terms generated with the ENR+CD-enriched and ENR-enriched proteomes on a background of all identified proteins, performed in DAVID 6.8

Table 4A. ENR+CD BP
ENR+CD-enriched
Biological Process

| Count | % | Proteins | log2(Fold Enrichment) | -log10(FDR) | Term |
|---|---|---|---|---|---|
| 18 | 8.0 | Q9R013, Q3UN27, Q9JJN5, P97449, Q80V42, Q8K0D2, Q00493, P06797, Q9ET22, Q9WV13, Q64191, O08529, Q61129, P63239, P98063, Q9D6X6, Q9R098, P18242 | 1.37 | 2.07 | proteolysis |
| 18 | 8.0 | P17553, P21570, P46660, P97449, Q9WUA1, Q9QXS6, Q8CFE5, Q03172, Q8K0T2, Q9QYB2, P97802, Q80TR4, Q9R0M0, Q63ZV0, O35594, O09010, P98063, P48437 | 1.14 | 1.31 | multicellular organism development |
| 14 | 6.2 | Q3UN27, Q9Z0L8, Q05421, Q80YQ1, P08228, P21460, P47877, P48756, F8VQA4, P03958, P43883, O55042, P35441, Q76854, P10107 | 1.45 | 1.56 | response to drug |
| 14 | 6.2 | P17553, Q8K4B2, Q64338, D3Z3A8, B1AUY3, P47877, Q3V2R3, Q6ZPF3, Q03172, Q8R4S0, Q9Z1B3, Q8K4R4, Q9R0M0, P10107 | 0.82 | 0.23 | signal transduction |
| 13 | 5.8 | P21570, P46660, P27577, P97449, Q9QXS6, Q6J9G1, P97802, Q80TR4, Q63ZV0, O35594, Q5S006, P84086, P98063 | 0.74 | 0.11 | cell differentiation |
| 12 | 5.3 | P09240, P27577, Q80YQ1, P21460, P11276, Q3UTR7, Q06890, Q63ZV0, Q9DCT8, P35441, Q3TMQ6, P48437, P28667 | 1.28 | 0.82 | positive regulation of cell proliferation |
| 10 | 4.4 | E9PXE2, Q9Z1B3, P56716, Q03517, D3Z3A8, Q5S006, Q91UZ1, E9Q0S6, Q3V2R3, Q6ZPF3 | 0.89 | 0.11 | intracellular signal transduction |
| 9 | 4.0 | P08551, O08599, Q3UTR7, P56695, Q08535, O55042, P28184, Q91ZZ3, P08228 | 2.19 | 1.95 | negative regulation of neuron apoptotic process |
| 7 | 3.1 | D3YYS6, A0JNU3, Q9Z1B3, Q8CIV3, Q9Z0Y2, Q91UZ1, Q3TTY0 | 2.15 | 1.15 | lipid catabolic process |
| 7 | 3.1 | P56695, Q80YQ1, Q9JIK5, P61961, P35441, Q921X9, P39654, D3Z6P0 | 2.15 | 1.15 | response to endoplasmic reticulum stress |
| 7 | 3.1 | P21570, P03958, F8VQA4, O08529, P27577, P28184, P21460 | 1.54 | 0.38 | response to hypoxia |
| 7 | 3.1 | Q3UN27, P03958, Q3UTR7, P97290, O55042, P08228, P47877 | 1.50 | 0.35 | aging |
| 6 | 2.7 | Q9Z1B3, P52792, O08599, P63239, Q5S006, P55095, P48756 | 3.14 | 2.14 | regulation of insulin secretion |
| 6 | 2.7 | Q9Z1B3, P08551, Q00896, P22599, P10107, P48756 | 2.65 | 1.43 | response to peptide hormone |
| 5 | 2.2 | P08553, P08551, P19246, P46660, P08228 | 4.34 | 3.05 | neurofilament cytoskeleton organization |
| 5 | 2.2 | Q9D848, P21460, Q8C1N8, Q5ER10, D3YX03 | 3.34 | 1.72 | defense response |
| 5 | 2.2 | O88312, Q80YQ1, P35441, P39654, Q9QXS6, P37889 | 3.34 | 1.72 | positive regulation of cell-substrate adhesion |
| 5 | 2.2 | P52792, Q06890, Q63ZV0, P10107, P48756 | 3.09 | 1.43 | endocrine pancreas development |
| 5 | 2.2 | Q00896, O35684, P97290, P21460, P22599 | 2.88 | 1.19 | negative regulation of peptidase activity |
| 5 | 2.2 | Q9ER67, Q3UTR7, P27577, P47877, P48756 | 2.53 | 0.82 | female pregnancy |
| 5 | 2.2 | Q3UN27, P17897, P21570, Q9Z0Y2, P26339 | 2.53 | 0.82 | defense response to Gram-positive bacterium |
| 5 | 2.2 | Q9JJN5, P63239, Q80V42, Q00493, P06797 | 2.39 | 0.68 | protein processing |
| 5 | 2.2 | Q3UN27, P17897, Q8C1N8, D3YX02, Q3TMQ6 | 2.21 | 0.52 | defense response to bacterium |
| 5 | 2.2 | A2AFS3, Q5S006, E9Q835, Q8C7E4, P06797 | 2.17 | 0.49 | cellular response to starvation |
| 5 | 2.2 | F8VQA4, P27577, P21460, P47877, P10107 | 1.91 | 0.30 | response to estradiol |
| 5 | 2.2 | O08599, Q5DQR4, P84086, E9Q835, Q76854 | 1.67 | 0.16 | exocytosis |

TABLE 4-continued

Enrichments for gene ontology (GO) terms generated with the ENR+CD-enriched and ENR-enriched proteomes on a background of all identified proteins, performed in DAVID 6.8

| | | | | |
|---|---|---|---|---|
| 5 | 2.2 | P08553, P08551, P14873, P19246, A2ARP8 | 1.53 | microtubule cytoskeleton organization |
| 4 | 1.8 | P21570, Q9Z0Y2, Q45VN2, Q3TMQ6 | 3.70 | antibacterial humoral response |
| 4 | 1.8 | F8VQA4, Q9JJN5, Q80V42, Q00493 | 3.56 | peptide metabolic process |
| 4 | 1.8 | A0JNU3, Q9Z0Y2, O55042, Q3TTY0 | 3.21 | phospholipid metabolic process |
| 4 | 1.8 | Q3UTR7, P27577, Q80YQ1, P35441, P48437 | 2.93 | positive regulation of endothelial cell migration |
| 4 | 1.8 | Q8K4B2, P27577, O55042, P10107 | 2.77 | response to interleukin-1 |
| 4 | 1.8 | Q3UN27, P08228, P21460, P48437 | 2.77 | response to nutrient levels |
| 4 | 1.8 | Q5S006, O55042, P28184, P26339 | 2.43 | negative regulation of neuron death |
| 4 | 1.8 | F8VQA4, Q9JJN5, P47877, P06797 | 2.43 | response to glucocorticoid |
| 4 | 1.8 | P08551, Q80TR4, Q06890, Q5S006 | 2.06 | neuron projection morphogenesis |
| 4 | 1.8 | O09010, Q5S006, Q9JJK5, P55095 | 1.85 | positive regulation of protein binding |
| 3 | 1.3 | P08553, P08551, P19246 | 5.02 | neurofilament bundle assembly |
| 3 | 1.3 | P09240, P55095, P81117 | 4.60 | negative regulation of appetite |
| 3 | 1.3 | P63239, Q9QXV0, P12961 | 4.60 | peptide hormone processing |
| 3 | 1.3 | I1E4X8, P56695, Q3UP38 | 4.28 | positive regulation of calcium ion transport |
| 3 | 1.3 | P08553, P08551, P19246 | 4.28 | intermediate filament bundle assembly |
| 3 | 1.3 | P08553, P08551, P19246 | 4.02 | axon development |
| 3 | 1.3 | Q3UN27, P27577, P10107 | 4.02 | estrous cycle |
| 3 | 1.3 | Q5S006, P55200, P48756 | 3.60 | exploration behavior |
| 3 | 1.3 | P56695, Q5S006, Q9JJK5 | 3.60 | negative regulation of endoplasmic reticulum stress-induced intrinsic apoptotic signaling pathway |
| 3 | 1.3 | Q80YQ1, P35441, P10107, P11276 | 3.60 | peptide cross-linking |
| 3 | 1.3 | B9EJ86, P21570, P28184 | 3.43 | activation of protein kinase B activity |
| 3 | 1.3 | Q06890, Q5S006, O55042 | 3.43 | regulation of neuron death |
| 3 | 1.3 | Q8CJ27, Q08535, P48437 | 3.28 | neuronal stem cell population maintenance |
| 3 | 1.3 | P08553, P19246, P46660 | 3.14 | intermediate filament cytoskeleton organization |
| 3 | 1.3 | P21570, P52792, Q80YQ1, P35441 | 3.02 | positive regulation of phosphorylation |
| 3 | 1.3 | O55042, Q91ZZ3, Q810U3 | 2.80 | synapse organization |
| 3 | 1.3 | D3YYS6, Q9D816, P39654 | 2.80 | arachidonic acid metabolic process |
| 3 | 1.3 | P56716, P14873, A2ARP8 | 2.70 | negative regulation of microtubule depolymerization |
| 3 | 1.3 | Q9WVJ3, P97449, Q00493 | 2.60 | peptide catabolic process |
| 3 | 1.3 | Q3UN27, P17897, P26339 | 2.60 | defense response to Gram-negative bacterium |
| 3 | 1.3 | Q3UTR7, P28184, P08228 | 2.52 | positive regulation of catalytic activity |
| 2 | 0.9 | P08551, P19246 | 5.02 | response to sodium arsenite |
| 2 | 0.9 | B2KG46, D3Z390 | 5.02 | minus-end-directed organelle transport along microtubule |

TABLE 4-continued

Enrichments for gene ontology (GO) terms generated with the ENR+CD-enriched and ENR-enriched proteomes on a background of all identified proteins, performed in DAVID 6.8

| Count | % | Proteins | | | Term |
|---|---|---|---|---|---|
| 2 | 0.9 | Q9Z1B3, Q3TTY0 | 5.02 | 0.19 | positive regulation of acrosome reaction |
| 2 | 0.9 | P08553 | 5.02 | 0.19 | intermediate filament polymerization or depolymerization |
| 2 | 0.9 | P08553, P08551 | 5.02 | 0.19 | regulation of axon diameter |
| 2 | 0.9 | P21460, P11276 | 5.02 | 0.19 | cell activation |
| 2 | 0.9 | B2KG46, D3Z390 | 5.02 | 0.19 | microtubule anchoring at microtubule organizing center |
| 2 | 0.9 | O55042, P10107 | 5.02 | 0.19 | negative regulation of exocytosis |
| 2 | 0.9 | P84086, P26339 | 5.02 | 0.19 | mast cell degranulation |
| 2 | 0.9 | P70429, Q9JIV2 | 4.43 | 0.11 | negative regulation of ruffle assembly |
| 2 | 0.9 | I1F4X8, Q3UP38 | 4.43 | 0.11 | store-operated calcium entry |
| 2 | 0.9 | P10107, P12961 | 4.43 | 0.11 | regulation of hormone secretion |
| 2 | 0.9 | P21570, Q3UTR7 | 4.43 | 0.11 | activation of phospholipase C activity |
| 2 | 0.9 | Q5S006, Q9JIV2 | 4.43 | 0.11 | regulation of synaptic vesicle exocytosis |
| 2 | 0.9 | Q5S006, O55042 | 4.43 | 0.11 | regulation of locomotion |
| 2 | 0.9 | Q03157, P81117 | 4.43 | 0.11 | negative regulation of cAMP biosynthetic process |
| 2 | 0.9 | Q80TR4, Q5S006 | 4.43 | 0.11 | tangential migration from the subventricular zone to the olfactory bulb |
| 2 | 0.9 | P80560, Q60673 | 4.43 | 0.11 | insulin secretion involved in cellular response to glucose stimulus |
| 2 | 0.9 | E9Q0S6, P11276 | 4.43 | 0.11 | cell-substrate junction assembly |

Table 4B. ENR+CD CC
ENR+CD-enriched
Cellular Component

| Count | % | Proteins | log2(Fold Enrichment) | −log10(FDR) | Term |
|---|---|---|---|---|---|
| 66 | 29.3 | P21570, Q9JIN5, Q9Z0Y2, P46660, Q80YQ1, P97449, P12265, P48036, P17897, Q62395, O88312, P50543, P22599, P26339, P07309, P55095, P18242, Q8VI93, P17553, Q45VN2, Q9Z0L8, P08228, P06797, P11276, Q9WVJ3, Q64191, O35684, P63239, Q9D848, P35441, Q07797, Q8C1N8, D3YX03, Q9R013, Q00896, Q03517, P09240, P47877, P48756, F8VQA4, Q80TR4, Q8CIV3, Q3UTR7, Q06890, O55042, Q3UQ28, P28184, Q3TMX5, Q5ERJ0, Q9R098, Q3UN27, P97290, Q9QXV0, P19467, P21460, Q80V42, Q00493, E9PXE2, P03958, Q61129, Q08535, P98063, Q3TMQ6, P10107 | 2.48 | 30.31 | extracellular space |
| 65 | 28.9 | P21570, E9Q390, Q80YQ1, Q32NZ6, P97449, P12265, Q6ZPF3, P48036, P17897, Q9Z1B3, Q62395, O88310, O08529, Q8R258, P50543, Q9JIV2, Q22599, P07309, P18242, Q9CQ89, A2AFS3, Q9Z0L8, E9Q9C6, P08228, P06797, P11276, Q8R2K3, Q9WVJ3, Q64191, O08599, Q571E4, O35684, P61961, P35441, P47877, A2AM05, F8VQA4, Q9DBG7, Q3UTR7, P81117, P37889, Q9R013, Q00896, Q60648, Q9EQ08, P14824, P47877, Q9DBG7, Q3UTR7, Q06890, P00683, Q5S006, Q3UQ28, Q3UN27, P97290, Q9QXV0, P19467, P21460, Q80V42, Q00493, Q9ET22, Q61129, Q9LD8, Q8C7E4, Q810U3, P10107 | 0.41 | 0.97 | extracellular exosome |
| 60 | 26.7 | P21570, Q9JIN5, Q9Z0Y2, Q80YQ1, A9Z1V5, P17897, Q62395, O88310, O88312, P22599, P26339, P07309, P55095, P18242, P17553, Q9Z0L8, P08228, P11276, Q9WVJ3, O35684, P35441, Q9D6X6, Q07797, Q8C1N8, P37889, P81117, Q9R013, Q00896, Q03517, P09240, P47877, Q8K0D2, P48756, Q80TR4, Q8CIV3, Q06890, P16014, P00683, O55042, Q61129, Q9LD8, Q8C7E4, Q810U3, P10107 | 2.61 | 29.37 | extracellular region |

TABLE 4-continued

Enrichments for gene ontology (GO) terms generated with the ENR+CD-enriched and ENR-enriched proteomes on a background of all identified proteins, performed in DAVID 6.8

| | | | | |
|---|---|---|---|---|
| 45 | 20.0 | Q3UQ28, Q3TMX5, O88803, Q9R098, Q3UN27, Q91WD9, P97290, Q9QXV0, P19467, Q9WUA1, P21460, P47867, Q00493, P12961, Q9ET22, P97802, Q9D3P9, Q61129, Q08535, P98063, Q8C7E4, Q3TMQ6, P10107 A2AMT1, E9Q390, Q32M21, P59764, Q9DQR4, Q03157, Q9QXS6, Q69ZT9, Q6UQ17, Q5HZI2, P48036, Q9Z1B3, Q6J9G1, F8VQA4, O88310, O08529, Q8CIV3, I1E4X8, Q5S006, O55042, P28184, Q8R2S8, Q8VI93, Q9EST1, Q9D6F4, Q8BY35, P14873, A2AFS3, Q60673, P19467, P08228, Q80V42, Q3TTY0, E9PXE2, P03958, O08599, D3Z390, Q9R0M0, P43883, Q991A5, P39654, Q76854, Q810U3, P10107, P28667 | 0.38 | plasma membrane |
| 30 | 13.3 | Q00896, Q80YQ1, P12265, Q6UQ17, Q61263, P48036, B9EJ86, Q9DBG7, F8VQC7, O08529, I1E4X8, O88312, Q06890, Q5S006, Q3UQ28, P22599, Q3TMX5, Q8K329, D3Z6P0, P56695, Q05421, P21460, Q8VHC3, Q9WVJ3, Q64191, Q9D816, Q9JJK5, P35441, Q921X9, Q05186, P81117 | 0.81 | endoplasmic reticulum |
| 28 | 12.4 | P21570, Q8BPQ7, Q8R550, E9Q390, E9Q835, P47877, Q6UQ17, F8VQA4, Q06890, P80560, Q5S006, P26339, Q91WD9, B2KG46, Q60673, P08228, P47867, Q00493, P06797, Q9ET22, P03958, P97802, Q9D3P9, D3Z390, P63239, Q76854, Q3TMQ6, P10107 | 1.57 | cytoplasmic vesicle |
| 27 | 12.0 | Q8BPQ7, Q4VAH7, Q00896, Q912Z3, Q03157, Q6ZWR6, Q6UQ17, O08529, O09010, Q5S006, O55042, Q3UP38, P22599, Q62431, B2KG46, Q60673, A2AFS3, Q9QXV0, B1AUY3, Q00493, Q8VHC3, Q9ET22, Q9WVJ3, D3Z390, Q9D5R3, P98063, P81117 | 0.64 | Golgi apparatus |
| 19 | 8.4 | Q03517, Q9Z0Y2, Q60673, Q9QXV0, Q80YQ1, Q5DQR4, P08228, P06797, P12961, Q00493, P17897, F8VQA4, P52792, Q62395, P16014, P80560, P35441, Q76854, P26339, Q3TMQ6 | 3.60 | secretory granule |
| 17 | 7.6 | Q9R013, A2AFS3, Q9Z0L8, Q9EQ08, Q60648, P08228, P12265, P21460, P06797, Q9ET22, Q9WVJ3, P03958, Q64191, O08529, Q571F4, Q5S006, P18242 | 1.71 | lysosome |
| 17 | 7.6 | P21570, P09240, Q64338, P14873, Q60673, Q912Z3, P08228, P21460, Q90XS6, Q00493, P48756, P48036, F8VQA4, P03958, Q9D3P9, Q5S006, P84086 | 1.36 | neuronal cell body |
| 14 | 6.2 | Q9D6F4, Q91WD9, Q8R550, P14873, Q60673, P19246, Q60673, Q912Z3, Q3V2R3, D3YYS6, P80560, Q5S006, P84086, O55042, Q9Z1S5 | 1.38 | synapse |
| 11 | 4.9 | P48036, P08553, F8VQA4, P09240, P14873, P19246, Q60673, Q5S006, Q00493, P06797, P81117 | 2.73 | perikaryon |
| 11 | 4.9 | D3YYS6, P08553, P08551, P09240, P14873, P19246, Q5S006, O55042, P28184, P21460, Q810U3 | 1.17 | axon |
| 11 | 4.9 | P08553, F8VQA4, Q8R550, Q91WD9, P08551, Q06890, Q5S006, P08228, P06797, Q9Z1S5, D3Z710 | 0.91 | neuron projection |
| 10 | 4.4 | P17553, Q3UN27, Q62395, Q80TR4, E9Q9C6, Q3UQ28, P98063, Q07797, P11276, P37889 | 2.67 | proteinaceous extracellular matrix |
| 10 | 4.4 | P21570, P08551, Q06890, P14873, Q5S006, O55042, B1AUY3, Q912Z3, Q9QXS6, Q6ZPF3 | 1.86 | growth cone |
| 10 | 4.4 | Q3UN27, Q06890, Q9DCT8, Q80YQ1, P35441, Q3UQ28, P08228, Q07797, P11276, P37889, P18242 | 1.52 | extracellular matrix |
| 9 | 4.0 | Q9Z1B3, P08553, P08551, O08599, P19246, P46660, Q7TQD2, P08228, Q810U3 | 0.99 | myelin sheath |
| 8 | 3.6 | O08599, P09240, P80560, Q5S006, P84086, O55042, Q912Z3, Q9JJV2 | 2.50 | terminal bouton |
| 7 | 3.1 | F8VQA4, Q91WD9, Q60673, Q76S84, P26339, P47867, Q00493 | 3.99 | transport vesicle membrane |
| 7 | 3.1 | P17553, P17897, P80560, P63239, Q921X9, D3Z6P0, Q05186 | 1.85 | endoplasmic reticulum lumen |
| 7 | 3.1 | Q8K0T2, P56716, Q64338, O35594, Q91XQ0, Q69ZT9, P10107 | 1.46 | cilium |
| 6 | 2.7 | Q8BPQ7, Q8R550, E9Q390, O55042, E9Q835, P10107 | 1.77 | cytoplasmic vesicle membrane |

TABLE 4-continued

Enrichments for gene ontology (GO) terms generated with the ENR+CD-enriched and ENR-enriched proteomes on a background of all identified proteins, performed in DAVID 6.8

| | | | | | |
|---|---|---|---|---|---|
| 6 | 2.7 | P48036, Q60673, Q5S006, O55042, E9Q835, P28184 | 1.67 | 0.40 | synaptic vesicle |
| 5 | 2.2 | P48036, Q9D3P9, Q60673, O55042, Q91ZZ3 | 2.36 | 0.75 | axon terminus |
| 5 | 2.2 | Q3UTR7, Q06890, P97290, Q07797, P11276 | 2.15 | 0.55 | blood microparticle |
| 5 | 2.2 | P08553, A2AMT1, P08551, P19246, P46660 | 1.92 | 0.38 | intermediate filament |
| 5 | 2.2 | P48036, P03958, Q80YQ1, P35441, P97449, P06797 | 1.76 | 0.27 | external side of plasma membrane |
| 4 | 1.8 | P08553, P08551, P19246, P46660 | 4.67 | 2.43 | neurofilament |
| 4 | 1.8 | O88310, Q99JA5, Q8R2S8, Q80V42 | 3.09 | 0.90 | anchored component of membrane |
| 4 | 1.8 | F8VQA4, P80560, Q768S4, Q00493 | 3.09 | 0.90 | secretory granule membrane |
| 4 | 1.8 | Q5S006, O55042, P28184, Q91ZZ3 | 2.99 | 0.82 | inclusion body |
| 3 | 1.3 | P63239, P55095, P48756 | 4.99 | 1.44 | secretory granule lumen |
| 3 | 1.3 | Q03517, P08228, Q00493 | 4.58 | 1.15 | dense core granule |
| 3 | 1.3 | P08553, Q06890, P19246 | 4.58 | 1.15 | neurofibrillary tangle |
| 3 | 1.3 | P84086, P26339, P10107 | 3.99 | 0.79 | mast cell granule |
| 3 | 1.3 | P03958, Q5S006, P08228 | 3.26 | 0.41 | dendrite cytoplasm |
| 3 | 1.3 | O55042, Q6ZWR6, P81117 | 3.26 | 0.41 | nuclear outer membrane |
| 2 | 0.9 | Q06890, P26339 | 4.99 | 0.25 | chromaffin granule |

TABLE 4-continued

Enrichments for gene ontology (GO) terms generated with the ENR+CD-enriched and ENR-enriched proteomes on a background of all identified proteins, performed in DAVID 6.8

Table 4C. ENR+CD MF
ENR+CD-enriched
Molecular Function

| Count | % | Proteins | log2(Fold Enrichment) | −log10(FDR) | Term |
|---|---|---|---|---|---|
| 39 | 17.3 | Q9R013, P21570, Q9JIN5, Q64338, Q9Z0Y2, Q60648, P97449, P12265, Q8K0D2, Q6UQ17, P17897, Q9Z1B3, A0JNU3, O08529, Q8CIV3, P80560, P00683, Q9R098, P18242, Q3UN27, Q9Z0L8, Q80V42, Q3TTY0, Q00493, P06797, D3YYS6, Q9WVJ3, Q9ET22, P03958, Q64191, P97802, Q61129, Q571E4, Q99LD8, P63239, Q9D6X6, P98063, Q8C7E4, Q3TMQ6 | 0.63 | 1.19 | hydrolase activity |
| 24 | 10.7 | Q9Z0Y2, Q80YQ1, Q91UZ1, Q91ZZ3, P14824, Q8K0D2, Q5HZI2, P48036, Q9Z1B3, F8VQA4, O08529, I1E4X8, Q80TR4, O55042, P50543, Q3UP38, Q91WD9, Q9R0M0, P35441, Q768S4, P98063, P10107, Q05186, P81117, P37889 | 1.99 | 6.48 | calcium ion binding |
| 19 | 8.4 | Q9R013, Q3UN27, Q9JIN5, Q9Z0L8, P97449, Q80V42, Q8K0D2, Q00493, P06797, Q9ET22, Q9WVJ3, Q64191, O08529, Q61129, P63239, P98063, Q9D6X6, Q9R098, P18242 | 1.61 | 3.23 | peptidase activity |
| 17 | 7.6 | P08551, Q00896, Q8CAB8, P27577, G3X9H7, P08228, Q03157, P21460, P11276, P17897, O08599, Q5S006, O55042, P55200, P22599, P07309, O88803 | 0.69 | 0.25 | identical protein binding |
| 12 | 5.3 | P21570, P14873, D3Z3A8, Q5S006, A2ARP8, G3X9H7, E9Q0S6, P70429, Q9JIV2, Q9QXS6, Q6ZWR6, P28667 | 1.07 | 0.50 | actin binding |
| 11 | 4.9 | Q9Z1B3, Q8BPQ7, F8WIA4, D3Z3A8, P59764, Q5S006, Q5DQR4, B1AUY3, Q3V2R3, Q69ZT9, Q6ZPF3 | 1.40 | 0.96 | GTPase activator activity |
| 11 | 4.9 | P17553, P21570, P08553, Q6J9G1, Q9Z0Y2, Q80TR4, Q08535, G3X9H7, P12265, Q6ZWR6, P48756 | 1.30 | 0.77 | receptor binding |
| 8 | 3.6 | D3YYS6, E9PXE2, B9EJ86, Q8K4R4, E9Q835, P39654, P14824, D3Z6P0 | 1.05 | 0.14 | lipid binding |
| 7 | 3.1 | Q3UN27, P21570, Q8CIV3, Q80TR4, Q80YQ1, P35441, Q03157, P11276 | 2.91 | 2.45 | heparin binding |
| 7 | 3.1 | Q9WVJ3, Q3UN27, Q9JIN5, P97449, P98063, Q80V42, Q00493 | 2.11 | 1.16 | metallopeptidase activity |
| 7 | 3.1 | Q8BPQ7, F8WIA4, B2KG46, D3Z390, Q5DQR4, Q768S4, Q69ZT9 | 1.31 | 0.23 | Rab GTPase binding |
| 6 | 2.7 | Q3UTR7, P09240, Q08535, P07309, P55095, P48756 | 3.84 | 3.30 | hormone activity |
| 6 | 2.7 | Q00896, Q3UTR7, O35684, P97290, Q9QXV0, P22599 | 3.06 | 2.08 | serine-type endopeptidase inhibitor activity |
| 6 | 2.7 | P21570, F8VQA4, Q9CQ89, O55042, P28184, P08228 | 2.94 | 1.91 | copper ion binding |
| 6 | 2.7 | Q9ET22, Q61129, P63239, Q9D6X6, Q8K0D2, Q9R098 | 2.60 | 1.44 | serine-type peptidase activity |
| 6 | 2.7 | Q3UN27, Q61129, P63239, Q9D6X6, Q8K0D2, Q9R098 | 2.56 | 1.38 | serine-type endopeptidase activity |
| 6 | 2.7 | P21570, P97802, P00683, Q5GAN1, Q8C7E4, Q3TMQ6 | 2.18 | 0.91 | endonuclease activity |
| 6 | 2.7 | P08553, A2AMT1, P08551, P19246, P46660, P10107 | 1.45 | 0.21 | structural molecule activity |
| 5 | 2.2 | P21570, P97802, Q5GAN1, Q8C7E4, Q3TMQ6 | 3.47 | 1.95 | ribonuclease activity |
| 5 | 2.2 | Q00896, O35684, P97290, P21460, P22599 | 2.92 | 1.30 | peptidase inhibitor activity |
| 5 | 2.2 | P56695, P84086, P50543, P14824, P10107 | 2.47 | 0.83 | calcium-dependent protein binding |
| 4 | 1.8 | Q9ET22, Q9JIN5, Q80V42, Q00493 | 4.06 | 1.74 | serine-type carboxypeptidase activity |

TABLE 4-continued

Enrichments for gene ontology (GO) terms generated with the ENR+CD-enriched and ENR-enriched proteomes on a background of all identified proteins, performed in DAVID 6.8

| Count | % | Proteins | log2(Fold Enrichment) | −log10(FDR) | Term |
|---|---|---|---|---|---|
| 4 | 1.8 | Q00896, Q9QXV0, P21460, P22599 | 3.74 | 1.44 | endopeptidase inhibitor activity |
| 4 | 1.8 | Q9WVJ3, Q9JJN5, Q80V42, Q00493 | 3.47 | 1.20 | carboxypeptidase activity |
| 4 | 1.8 | P48036, P14824, P10107, Q5HZI2 | 2.97 | 0.78 | calcium-dependent phospholipid binding |
| 4 | 1.8 | Q9WVJ3, Q9ET22, P97449, P06797 | 2.36 | 0.36 | aminopeptidase activity |
| 4 | 1.8 | P08551, P19246, P10107, A2AM05 | 1.85 | 0.12 | protein binding, bridging |
| 3 | 1.3 | Q9JJN5, Q80V42, Q00493 | 4.32 | 0.96 | metallocarboxypeptidase activity |
| 3 | 1.3 | Q9ZIB3, Q9ZIT2, Q6ZWR6 | 3.32 | 0.42 | lamin binding |
| 3 | 1.3 | O08599, Q5S006, P84086 | 2.74 | 0.19 | syntaxin-1 binding |
| 3 | 1.3 | Q61263, B9EJ86, P14824 | 2.64 | 0.16 | cholesterol binding |
| 3 | 1.3 | A2CGA5, O55042, P28184 | 2.47 | 0.12 | cysteine-type endopeptidase inhibitor activity involved in apoptotic process |

Table 4D. ENR BP
ENR-enriched
Biological Process

| Count | % | Proteins | log2(Fold Enrichment) | −log10(FDR) | Term |
|---|---|---|---|---|---|
| 30 | 14.9 | P62270, P27659, P61514, Q6ZWZ4, Q9CPY1, Q9D1R9, P61358, P62900, Q6ZWV3, Q642K5, Q9CQM8, Q6ZWN5, Q99M01, P84099, Q6ZWU9, P62267, P62855, P62830, P62245, P67984, P62911, Q9CZM2, P62082, P14115, Q6ZWY3, P97351, Q9JJI8, P62889, Q6ZWV7, P25444 | 2.08 | 9.12 | translation |
| 11 | 5.4 | Q8BW75, P30681, Q8C196, Q9Z0X4, Q8VHB5, P11725, D3YU60, Q03311, E9QNX7, P27600, Q00623 | 1.27 | 0.66 | response to drug |
| 8 | 4.0 | Q8BHB9, Q9Z1W8, E9Q8N8, J3QMG3, Q9QXI6, P56382, O35943, E9QNX7 | 1.39 | 0.40 | ion transport |
| 7 | 3.5 | Q8CGK7, P51432, Q8BM96, Q3V3I2, Q8K023, P27600, Q00623 | 2.38 | 1.50 | G-protein coupled receptor signaling pathway |
| 5 | 2.5 | Q6ZWZ4, D3YX71, P67984, P62900, Q9CZM2 | 3.05 | 1.38 | cytoplasmic translation |
| 5 | 2.5 | P84244, Q7JI13, P62806, P84228, Q8BRB7 | 2.38 | 0.68 | nucleosome assembly |
| 4 | 2.0 | P06728, Q08652, Q9QYY9, Q00623 | 3.60 | 1.25 | retinoid metabolic process |
| 4 | 2.0 | Q6ZWU9, P25444, Q6ZWY3, P62852 | 3.10 | 0.82 | ribosomal small subunit assembly |
| 4 | 2.0 | Q9Z1W8, E9Q8N8, Q9QXI6, E9QNX7 | 2.79 | 0.59 | sodium ion transport |
| 3 | 1.5 | P43137, Q8C196, P11725 | 5.18 | 1.47 | midgut development |

TABLE 4-continued

Enrichments for gene ontology (GO) terms generated with the ENR+CD-enriched and ENR-enriched proteomes on a background of all identified proteins, performed in DAVID 6.8

| | | | | |
|---|---|---|---|---|
| 3 | 1.5 | P06728, Q99PG0, Q00623 | 4.18 | 0.82 | positive regulation of triglyceride catabolic process |
| 3 | 1.5 | P84244, P62806, P84228 | 3.96 | 0.69 | positive regulation of gene expression, epigenetic |
| 3 | 1.5 | P84244, P62806, P84228 | 3.96 | 0.69 | DNA methylation on cytosine |
| 3 | 1.5 | P02802, Q9Z1W8, P02798 | 3.96 | 0.69 | response to metal ion |
| 3 | 1.5 | Q8C196, P06728, Q00623 | 3.31 | 0.37 | triglyceride catabolic process |
| 3 | 1.5 | O35280, Q99LZ3, Q60997 | 3.18 | 0.32 | inner cell mass cell proliferation |
| 3 | 1.5 | Q9QXI6, P55050, P48281 | 3.07 | 0.27 | intestinal absorption |
| 3 | 1.5 | Q9CQU5, Q9D9Z1, Q9ERH4 | 2.77 | 0.17 | mitotic sister chromatid segregation |
| 3 | 1.5 | P43137, P62889, P62911 | 2.68 | 0.14 | liver regeneration |
| 3 | 1.5 | P27659, Q6ZWV3, Q9D0I8 | 2.60 | 0.12 | ribosomal large subunit assembly |
| 3 | 1.5 | Q33DR2, P62806, P84228 | 2.60 | 0.12 | protein heterotetramerization |
| 3 | 1.5 | P97328, E9Q1Q9, Q8C196, P11725 | 2.52 | 0.10 | response to zinc ion |
| 2 | 1.0 | P02802, P02798 | 5.18 | 0.23 | nitric oxide mediated signal transduction |
| 2 | 1.0 | Q8C196, P11725 | 5.18 | 0.23 | anion homeostasis |
| 2 | 1.0 | P06728, Q00623 | 5.18 | 0.23 | regulation of intestinal cholesterol absorption |
| 2 | 1.0 | Q91WU0, Q8VCT4 | 5.18 | 0.23 | short-chain fatty acid catabolic process |
| 2 | 1.0 | P06728, Q00623 | 5.18 | 0.23 | very-low-density lipoprotein particle remodeling |
| 2 | 1.0 | P06728, Q00623 | 5.18 | 0.23 | high-density lipoprotein particle assembly |
| 2 | 1.0 | Q9CXS4, P84244 | 4.60 | 0.14 | pericentric heterochromatin assembly |

TABLE 4-continued

Enrichments for gene ontology (GO) terms generated with the ENR+CD-enriched and ENR-enriched proteomes on a background of all identified proteins, performed in DAVID 6.8

| | | | | | |
|---|---|---|---|---|---|
| 2 | 1.0 | Q8C196, Q9Z2V4 | 4.60 | 0.14 | cellular response to glucagon stimulus |
| 2 | 1.0 | P02772, Q8K023 | 4.60 | 0.14 | progesterone metabolic process |
| 2 | 1.0 | E9QNS0, D3YYD0 | 4.60 | 0.14 | negative regulation of immune response |

Table 4E. ENR CC
ENR-enriched
Cellular Component

| Count | % | Proteins | log2(Fold Enrichment) | −log10(FDR) | Term |
|---|---|---|---|---|---|
| 33 | 16.3 | P62270, Q3UYK3, P27659, P61514, Q6ZWZ4, B1ARD6, P62900, Q9CQM8, F6R4Z5, Q6ZWN5, P84099, B1ASD8, P62267, Q3UW68, Q8K023, B1B1D3, P51432, P55050, P67984, P62911, Q9CZM2, P62082, P14115, Q6ZWY3, P97351, P27600, Q6PEP4, Q9JJI8, P62889, Q8C393, Q9D0I8, Q60997, Q9JME5 | 0.84 | 1.83 | intracellular |
| 27 | 13.4 | P27659, Q6ZWZ4, Q9D1R9, O88554, Q6ZQL4, P62900, Q9CQM8, Q6ZWN5, P84099, Q8C196, P62267, P62855, P62830, E9Q5C9, Q3V1V3, P62852, P30681, Q9CPS7, P63166, P62082, Q91VE6, P97351, P40338, P09405, Q9ERH4, B1AX39, Q9D0I8 | 0.71 | 0.82 | nucleolus |
| 26 | 12.9 | P62270, P27659, P61514, Q6ZWZ4, Q9CPY1, P62900, Q6ZWV3, Q642K5, Q9CQM8, Q6ZWN5, P84099, P62267, P62855, P62245, P62852, P67984, Q9CY16, P62911, Q9CZM2, P62082, P14115, Q6ZWY3, P97351, Q9JJI8, P62889, P25444 | 2.59 | 11.19 | ribosome |
| 26 | 12.9 | P43137, P07310, Q91WU0, P02772, Q8VCT4, P63158, Q642K5, Q8VEE1, Q8VC10, Q64176, E9PV38, O35280, Q3V1V3, P30681, P06728, Q03311, O70514, Q8K354, E9QNX7, A2ARV4, Q6PDB7, Q8BK48, Q60997, Q00623, D3YYD0, Q08ED5 | 1.32 | 3.40 | extracellular space |
| 24 | 11.9 | P62270, P27659, Q6ZWZ4, P61514, Q9CPY1, P61358, Q6ZWY3, P97351, Q9JJI8, P84099, P09405, P62889, P62267, P25444, P62852 | 1.65 | 4.64 | intracellular ribonucleoprotein complex |
| 20 | 9.9 | P62270, P27659, P61514, Q61391, P61358, P67984, P62900, P62082, Q6ZWN5, P97314, P97351, P27600, Q6PG13, P84099, Q9JJI8, P62889, P25444, P52800, A2APM2, P62830 | 1.44 | 2.79 | focal adhesion |
| 18 | 8.9 | P27659, Q6ZWZ4, P61514, Q9D1R9, P61358, P67984, P62900, Q9CQM8, Q6ZWV3, P62911, Q9CZM2, P14115, Q9JJI8, P84099, D3YX71, P62889, Q6ZWV7, P62830 | 3.60 | 12.49 | cytosolic large ribosomal subunit |
| 12 | 5.9 | P62270, Q6ZWU9, Q642K5, P62267, P62855, P62082, P25444, Q6ZWN5, P62245, P97351, Q6ZWY3, P62852 | 3.45 | 7.15 | cytosolic small ribosomal subunit |
| 12 | 5.9 | Q9CXS4, P30681, Q9CQU5, P63158, Q9D9Z1, Q9ERH4, G3X956, O70126, Q91VE6, Q3UA16, Q920F6, Q8K1K3 | 1.02 | 0.45 | chromosome |
| 11 | 5.4 | P62270, P62889, P61358, P67984, P62082, P62830, Q8VEE1, P62806, Q60997, P62245, P62852 | 1.85 | 1.96 | extracellular matrix |
| 7 | 3.5 | P62270, Q642K5, P62267, P62855, Q6ZWN5, P62852 | 3.41 | 3.36 | small ribosomal subunit |
| 5 | 2.5 | A2ARV4, Q60604, Q61391, Q9QXI6, B1AVH5 | 1.65 | 0.21 | brush border |
| 4 | 2.0 | P84244, P62806, P84228, Q8BRB7 | 2.94 | 0.78 | nucleosome |
| 4 | 2.0 | O35280, Q80ZH7, Q91VE6, Q920F6 | 2.33 | 0.36 | condensed nuclear chromosome |

TABLE 4-continued

Enrichments for gene ontology (GO) terms generated with the ENR+CD-enriched and ENR-enriched proteomes on a background of all identified proteins, performed in DAVID 6.8

| Count | % | Proteins | log2(Fold Enrichment) | -log10(FDR) | Term |
|---|---|---|---|---|---|
| 3 | 1.5 | P09405, Q6ZQL4, P63166 | 3.60 | 0.58 | fibrillar center |
| 3 | 1.5 | Q8CGK7, Q3V3I2, P27600 | 2.86 | 0.25 | heterotrimeric G-protein complex |

Table 4F. ENR MF
ENR-enriched
Molecular Function

| Count | % | Proteins | log2(Fold Enrichment) | -log10(FDR) | Term |
|---|---|---|---|---|---|
| 50 | 24.8 | P62270, Q9CVI2, P61514, Q6ZQL4, P61358, Q9CQM8, Q52KI8, P62267, G3X956, P62855, Q80XU3, G3X8T2, P62852, Q9CPS7, P67984, P62911, Q9CZM2, P14115, P97351, Q6ZWY3, P09405, Q9D0I8, P27659, Q6ZWZ4, Q7TNV0, P62900, Q642K5, Q6ZWV3, Q6ZWN5, P84099, Q64669, A2AR02, P62830, Q9CZT6, E9Q5K9, P62806, E9Q5C9, P6245, Q3V1V3, P3068I, Q9CY16, P63166, P62082, Q91VE6, Q8R0T2, P62889, Q6ZWV7, B1AX39, Q9ERH4, P25444 | 0.86 | 3.60 | poly(A) RNA binding |
| 31 | 15.3 | P62270, P27659, P61514, Q6ZWZ4, Q9CPY1, Q9D1R9, P61358, P62900, Q6ZWV3, Q642K5, Q9CQM8, Q6ZWN5, Q6ZWU9, P84099, D3YX71, P62267, Q9CY16, P62855, P62830, P62245, P62852, P67984, P62911, Q9CZM2, P62082, P14115, Q6ZWY3, P97351, Q9UI8, P62889, Q6ZWV7, P25444 | 2.82 | 15.74 | structural constituent of ribosome |
| 9 | 4.5 | Q91WU0, Q8VCT4, Q6PDB7, E9PV38, Q99PG0, Q03311, Q8BK48, Q64176, Q08ED5 | 3.08 | 4.00 | carboxylic ester hydrolase activity |
| 7 | 3.5 | E9Q8N8, P51162, Q3U9N9, Q9QXI6, P55050, Q08652, Q9EPC5 | 2.76 | 2.18 | transporter activity |
| 6 | 3.0 | P84244, P09405, Q7TNV0, G3X956, P62806, P84228 | 1.56 | 0.28 | histone binding |
| 4 | 2.0 | P84099, P61514, Q9D0I8, P62830 | 3.80 | 1.49 | large ribosomal subunit rRNA binding |
| 3 | 1.5 | Q08652, Q9QYY9, Q9EPC5 | 4.71 | 1.20 | retinol binding |
| 3 | 1.5 | Q9QYY9, O88451, Q8K023 | 3.90 | 0.71 | retinol dehydrogenase activity |
| 3 | 1.5 | Q8CGK7, Q3V3I2, P27600 | 3.25 | 0.39 | guanyl nucleotide binding |
| 3 | 1.5 | Q8CGK7, Q3V3I2, P27600 | 3.12 | 0.33 | G-protein beta/gamma-subunit complex binding |
| 2 | 1.0 | Q9Z1W8, E9QNX7 | 5.12 | 0.26 | hydrogen:potassium-exchanging ATPase activity |
| 2 | 1.0 | P06728, Q00623 | 5.12 | 0.26 | phosphatidylcholine-sterol O-acyltransferase activator activity |
| 2 | 1.0 | Q08652, Q9EPC5 | 4.54 | 0.16 | retinoid binding |

REFERENCES

1. Clevers H. Modeling Development and Disease with Organoids. Cell. Elsevier Inc.; 2016; 165:1586-97. Available from: dx.doi.org/10.1016/j.cell.2016.05.082
2. Prakadan S M, Shalek A K, Weitz D A. Scaling by shrinking: empowering single-cell "omics" with microfluidic devices. Nat. Rev. Genet. 2017; 18:345-61. Available from: www.nature.com/doifinder/10.1038/nrg.2017.15
3. Haber A L, Biton M, Rogel N, Herbst R H, Shekhar K, Smillie C, et al. A single-cell survey of the small intestinal epithelium. Nature. Nature Publishing Group; 2017; Available from: www.nature.com/doifinder/10.1038/nature24489
4. Grun D, Lyubimova A, Kester L, Wiebrands K, Basak O, Sasaki N, et al. Single-cell messenger RNA sequencing reveals rare intestinal cell types. Nature. 2015; 525:251-5. Available from: www.nature.com/doifinder/10.1038/nature14966
5. The HCA Consortium. The human cell atlas white paper. 2017;
6. Tanay A, Regev A. Scaling single-cell genomics from phenomenology to mechanism. Nature. 2017; 541:331-8. Available from: www.nature.com/doifinder/10.1038/nature21350
7. Satija R, Shalek A K. Heterogeneity in immune responses: From populations to single cells. Trends Immunol. Elsevier Ltd; 2014; 35:219-29. Available from: dx.doi.org/10.1016/j.it.2014.03.004
8. Foulke-Abel J, In J, Yin J, Zachos N C, Kovbasnjuk O, Estes M K, et al. Human Enteroids as a Model of Upper Small Intestinal Ion Transport Physiology and Pathophysiology. Gastroenterology. Elsevier, Inc; 2016; 150:638-649e8.
9. Moon C, VanDussen K L, Miyoshi H, Stappenbeck T S. Development of a primary mouse intestinal epithelial cell monolayer culture system to evaluate factors that modulate IgA transcytosis. Mucosal Immunol. Nature Publishing Group; 2013; 7:818-28. Available from: www.ncbi.nlm.nih.gov/pubmed/24220295
10. Basak O, Beumer J, Wiebrands K, Seno H, van Oudenaarden A, Clevers H. Induced Quiescence of Lgr5+ Stem Cells in Intestinal Organoids Enables Differentiation of Hormone-Producing Enteroendocrine Cells. Cell Stem Cell. Elsevier Inc.; 2017; 20:177-190.e4. Available from: linkinghub.elsevier.com/retrieve/pii/S1934590916303976
11. Schwank G, Koo B K, Sasselli V, Dekkers J F, Heo I, Demircan T, et al. Functional repair of CFTR by CRISPR/Cas9 in intestinal stem cell organoids of cystic fibrosis patients. Cell Stem Cell. Elsevier Inc.; 2013; 13:653-8. Available from: dx.doi.org/10.1016/j.stem.2013.11.002
12. Drost J, van Boxtel R, Blokzijl F, Mizutani T, Sasaki N, Sasselli V, et al. Use of CRISPR-modified human stem cell organoids to study the origin of mutational signatures in cancer. Science (80-.). 2017; 238:eaao3130. Available from: www.sciencemag.org/lookup/doi/10.1126/science.aao3130
13. Molodecky N a, Soon I S, Rabi D M, Ghali W a, Ferris M, Chernoff G, et al. Increasing incidence and prevalence of the inflammatory bowel diseases with time, based on systematic review. Gastroenterology. Elsevier Inc.; 2012 [cited 2014 May 27]; 142:46-54.e42; quiz e30. Available from: www.ncbi.nlm.nih.gov/pubmed/22001864
14. Wehkamp J, Salzman N H, Porter E, Nuding S, Weichenthal M, Petras R E, et al. Reduced Paneth cell α-defensins in ileal Crohn's disease. Proc. Natl. Acad. Sci. U.S.A 2005; 102:18129-34.
15. Ireland H, Houghton C, Howard L, Winton D J. Cellular inheritance of a Cre-activated reporter gene to determine Paneth cell longevity in the murine small intestine. Dev. Dyn. 2005; 233:1332-6.
16. Sato T, van Es J H, Snippert H J, Stange D E, Vries R G, van den Born M, et al. Paneth cells constitute the niche for Lgr5 stem cells in intestinal crypts. Nature. Nature Publishing Group; 2011; 469:415-8. Available from: www.pubmedcentral.nih.gov/articlerender.fcgi?artid=3547360&tool=pmcentrez&rendertype=ab stract
17. Clevers H C, Bevins C L. Paneth cells: maestros of the small intestinal crypts. Annu. Rev. Physiol. 2013 [cited 2014 May 28]; 75:289-311. Available from: www.ncbi.nlm.nih.gov/pubmed/23398152
18. Xavier R J, Podolsky D K. Unravelling the pathogenesis of inflammatory bowel disease. Nature. 2007 [cited 2014 May 24]; 448:427-34. Available from: www.ncbi.nlm.nih.gov/pubmed/17653185
19. Khor B, Gardet A, Xavier R J. Genetics and pathogenesis of inflammatory bowel disease. Nature. 2011 [cited 2014 May 23]; 474:307-17. Available from: www.pubmedcentral.nih.gov/articlerender.fcgi?artid=3204665&tool=pmcentrez&rendertype=ab stract
20. Liu T-C, Gurram B, Baldridge M T, Head R, Lam V, Luo C, et al. Paneth cell defects in Crohn's disease patients promote dysbiosis. JCI Insight. 2016; 1:1-15. Available from: https://insight.jci.org/articles/view/86907
21. Adolph T E, Tomczak M F, Niederreiter L, Ko H-J, Bock J, Martinez-Naves E, et al. Paneth cells as a site of origin for intestinal inflammation. Nature. 2013 [cited 2014 May 27]; 503:272-6. Available from: www.pubmedcentral.nih.gov/articlerender.fcgi?artid=3862182&tool=pmcentrez&rendertype=ab stract
22. Kobayashi K S, Chamaillard M, Ogura Y, Henegariu O, Inohara N, Nunez G, et al. Nod2-dependent regulation of innate and adaptive immunity in the intestinal tract. Science. 2005 [cited 2014 May 28]; 307:731-4. Available from: www.ncbi.nlm.nih.gov/pubmed/15692051
23. Kaser A, Blumberg R S. ATG16L1 Crohn's disease risk stresses the endoplasmic reticulum of Paneth cells. Gut. 2013 [cited 2014 May 28]; 2013-5. Available from: www.ncbi.nlm.nih.gov/pubmed/24304670
24. Kaser A, Lee A-H, Franke A, Glickman J N, Zeissig S, Tilg H, et al. XBP1 links ER stress to intestinal inflammation and confers genetic risk for human inflammatory bowel disease. Cell. 2008 [cited 2014 May 23]; 134:743-56. Available from: www.pubmedcentral.nih.gov/articlerender.fcgi?artid=2586148&tool=pmcentrez&rendertype=ab stract
25. Ayabe T, Satchell D P, Wilson C L, Parks W C, Selsted M E, Ouellette A J. Secretion of microbicidal α-defensins by intestinal Paneth cells in response to bacteria. Nat. Immunol. 2000; 1:113-8. Available from: www.nature.com/doifinder/10.1038/77783
26. Stockinger S, Albers T, Duerr C U, Menard S, PUtsep K, Andersson M, et al. Interleukin-13-mediated paneth cell degranulation and antimicrobial peptide release. J. Innate Immun. 2014; 6:530-41.
27. Tan G, Li R-H, Li C, Wu F, Zhao X-M, Ma J-Y, et al. Down-Regulation of Human Enteric Antimicrobial Pep- 28. Farin H F, Karthaus W R, Kujala P, Rakhshandehroo M, Schwank G, Vries R G J, et al. Paneth cell extrusion and release of antimicrobial products is directly controlled by immune cell-derived IFN-γ. J. Exp. Med. 2014; 211:1393-405. Available from: www.ncbi.nlm.nih.gov/pubmed/24980747
29. Wilson S S, Tocchi a, Holly M K, Parks W C, Smith J G. A small intestinal organoid model of non-invasive enteric pathogen-epithelial cell interactions. Mucosal Immunol. Nature Publishing Group; 2014; 8:1-10. Available from: www.ncbi.nlm.nih.gov/pubmed/25118165
30. Yin X, Farin H F, van Es J H, Clevers H, Langer R, Karp J M. Niche-independent high-purity cultures of Lgr5+ intestinal stem cells and their progeny. Nat. Methods. 2014 [cited 2014 May 23]; 11:106-12. Available from: www.ncbi.nlm.nih.gov/pubmed/24292484
31. Gierahn T$_M$, Wadsworth M H, Hughes T K, Bryson B D, Butler A, Satij a R, et al. Seq-Well: portable, low-cost RNA sequencing of single cells at high throughput. Nat. Methods. Nature Publishing Group; 2017; 14:1-8. Available from: www.nature.com/doifinder/10.1038/nmeth.4179
32. Yin X, Mead B E, Safaee H, Langer R, Karp J M, Levy O. Engineering Stem Cell Organoids. Cell Stem Cell. Elsevier Inc.; 2016; 18:25-38. Available from: linkinghub.elsevier.com/retrieve/pii/S 1934590915005500
33. McLean W J, Yin X, Lu L, Lenz D R, McLean D, Langer R, et al. Clonal Expansion of Lgr5-Positive Cells from Mammalian Cochlea and High-Purity Generation of Sensory Hair Cells. Cell Rep. The Author(s); 2017; 18:1917-29. Available from: dx.doi.org/10.1016/j.celrep 0.2017.01.066
34. van Es J H, Jay P, Gregorieff A, van Gijn M E, Jonkheer S, Hatzis P, et al. Wnt signalling induces maturation of Paneth cells in intestinal crypts. Nat. Cell Biol. 2005; 7:381-6. Available from: www.nature.com/doifinder/10.1038/ncb 1240
35. VanDussen K L, Carulli A J, Keeley T$_M$, Patel S R, Puthoff B J, Magness S T, et al. Notch signaling modulates proliferation and differentiation of intestinal crypt base columnar stem cells. Development. 2012; 139:488-97. Available from: dev.biologists.org/cgi/doi/10.1242/dev.070763
36. Tian H, Biehs B, Chiu C, Siebel C W, Wu Y, Costa M, et al. Opposing activities of notch and wnt signaling regulate intestinal stem cells and gut homeostasis. Cell Rep. The Authors; 2015; 11:33-42. Available from: dx.doi.org/10.1016/j.celrep0.2015.03.007
37. Buczacki S J a, Zecchini H I, Nicholson A M, Russell R, Vermeulen L, Kemp R, et al. Intestinal label-retaining cells are secretory precursors expressing Lgr5. Nature. Nature Publishing Group; 2013; 495:65-9. Available from: www.ncbi.nlm.nih.gov/pubmed/23446353
38. von Furstenberg R J, Gulati A S, Baxi A, Doherty J M, Stappenbeck T S, Gracz A D, et al. Sorting mouse jejunal epithelial cells with CD24 yields a population with characteristics of intestinal stem cells. AJP Gastrointest. Liver Physiol. 2011; 300:G409-17. Available from: ajpgi.physiology.org/cgi/doi/10.1152/ajpgi0.00453.2010
39. Subramanian A, Tamayo P, Mootha V K, Mukherjee S, Ebert B L, Gillette M A, et al. Gene set enrichment analysis: A knowledge-based approach for interpreting genome-wide expression profiles. Proc. Natl. Acad. Sci. 2005; 102:15545-50. Available from: www.pnas.org/cgi/doi/10.1073/pnas.0506580102
40. Mootha V K, Lindgren C M, Eriksson K-F, Subramanian A, Sihag S, Lehar J, et al. PGC-1α-responsive genes involved in oxidative phosphorylation are coordinately downregulated in human diabetes. Nat. Genet. 2003; 34:267-73. Available from: www.nature.com/doifinder/10.1038/nn1239
41. Xie X, Lu J, Kulbokas E J, Golub T R, Mootha V, Lindblad-Toh K, et al. Systematic discovery of regulatory motifs in human promoters and 3' UTRs by comparison of several mammals. Nature. 2005; 434:338-45.
42. Merico D, Isserlin R, Stueker O, Emili A, Bader G D. Enrichment map: A network-based method for gene-set enrichment visualization and interpretation. PLoS One. 2010; 5.
43. Shannon P, Markiel A, Ozier O, Baliga N S, Wang J T, Ramage D, et al. Cytoscape: a software environment for integrated models of biomolecular interaction networks. Genome Res. 2003; 13:2498-504. Available from: www.genome.org/cgi/doi/10.1101/gr.1239303
44. Stringari C, Edwards R A, Pate K T, Waterman M L, Donovan P J, Gratton E. Metabolic trajectory of cellular differentiation in small intestine by Phasor Fluorescence Lifetime Microscopy of NADH. Sci. Rep. 2012; 2:568. Available from: www.pubmedcentral.nih.gov/articlerender.fcgi?artid=3416911&tool=pmcentrez&rendertype=ab stract
45. Rodriguez-Colman M J, Schewe M, Meerlo M, Stigter E, Gerrits J, Pras-Raves M, et al. Interplay between metabolic identities in the intestinal crypt supports stem cell function. Nature. Nature Publishing Group; 2017; 1-13. Available from: www.nature.com/nature/journal/vaop/ncurrent/pdf/nature21673.pdf
46. Ayabe T, Satchell D P, Wilson C L, Parks W C, Selsted M E, Ouellette A J. Secretion of microbicidal alphadefensins by intestinal Paneth cells in response to bacteria. Nat. Immunol. 2000; 1:113-8. Available from: www.ncbi.nlm.nih.gov/pubmed/11248802
47. Kanamori M, Konno H, Osato N, Kawai J, Hayashizaki Y, Suzuki H. A genome-wide and nonredundant mouse transcription factor database. Biochem. Biophys. Res. Commun. 2004; 322:787-93.
48. Jia S N, Lin C, Chen D F, Li A Q, Dai L, Zhang L, et al. The transcription factor p8 regulates Autophagy in response to palmitic acid stress via a mammalian target of rapamycin (mTOR)-independent signaling pathway. J. Biol. Chem. 2016; 291:4462-72.
49. Grasso D, Bintz J, Lomberk G, Molej on MI, Loncle C, Garcia M N, et al. Pivotal Role of the Chromatin Protein Nupr1 in Kras-Induced Senescence and Transformation. Sci. Rep. Nature Publishing Group; 2015; 5:17549. Available from: www.nature.com/articles/srep17549
50. Cano C E, Hamidi T, Sandi M J, Iovanna J L. Nupr1: The Swiss-knife of cancer. J. Cell. Physiol. 2011; 226:1439-43.
51. Imielinski M, Baldassano R N, Griffiths A, Russell R K, Annese V, Dubinsky M, et al. Common variants at five new loci associated with early-onset inflammatory bowel disease. Nat. Genet. Nature Publishing Group; 2009; 41:1335-40. Available from: www.nature.com/doifinder/10.1038/ng.489
52. Santofimia-Castalio P, Rizzuti B, Pey A L, Soubeyran P, Vidal M, Urrutia R, et al. Intrinsically disordered chromatin protein NUPR1 binds to the C-terminal region of 53. Neira J L, Bintz J, Arruebo M, Rizzuti B, Bonacci T, Vega S, et al. Identification of a Drug Targeting an Intrinsically Disordered Protein Involved in Pancreatic Adenocarcinoma. Sci. Rep. Nature Publishing Group; 2017; 7:39732. Available from: www.nature.com/articles/srep39732
54. Wang X, Yamamoto Y, Wilson L H, Zhang T, Howitt B E, Farrow M a., et al. Cloning and variation of ground state intestinal stem cells. Nature. 2015; 522:173-8. Available from: www.nature.com/doifinder/10.1038/nature14484
55. VanDussen K L, Marinshaw J M, Shaikh N, Miyoshi H, Moon C, Tarr P I, et al. Development of an enhanced human gastrointestinal epithelial culture system to facilitate patient-based assays. Gut. 2015 [cited 2014 Jul 17]; 64:911-20. Available from: gut.bmj.com.ezp-prod1.hul.harvard.edu/content/early/2014/07/09/gutjnl-2013-306651.long
56. Mou H, Vinarsky V, Tata P R, Brazauskas K, Choi S H, Crooke A K, et al. Dual SMAD Signaling Inhibition Enables Long-Term Expansion of Diverse Epithelial Basal Cells. Cell Stem Cell. Elsevier Inc.; 2016; 19:217-31. Available from: dx.doi.org/10.1016/j.stem.2016.05.012
57. Gulati A S, Shanahan M T, Arthur J C, Grossniklaus E, von Furstenberg R J, Kreuk L, et al. Mouse background strain profoundly influences Paneth cell function and intestinal microbial composition. PLoS One. 2012 [cited 2014 May 28]; 7:e32403. Available from: www.pubmedcentral.nih.gov/articlerender.fcgi?artid=3288091&tool=pmcentrez&rendertype=ab stract
58. Bevins C L, Salzman N H. Paneth cells, antimicrobial peptides and maintenance of intestinal homeostasis. Nat. Rev. Microbiol. Nature Publishing Group; 2011 [cited 2014 May 23]; 9:356-68. Available from: www.ncbi.nlm.nih.gov/pubmed/21423246
59. Zhang Q, Pan Y, Yan R, Zeng B, Wang H, Zhang X, et al. Commensal bacteria direct selective cargo sorting to promote symbiosis. Nat. Immunol. Nature Publishing Group; 2015; 1-12. Available from: www.nature.com/doifinder/10.1038/ni.3233
60. Cunliffe R N, Rose F R, Keyte J, Abberley L, Chan W C, Mahida Y R. Human defensin 5 is stored in precursor form in normal Paneth cells and is expressed by some villous epithelial cells and by metaplastic Paneth cells in the colon in inflammatory bowel disease. Gut. 2001; 48:176-85.
61. Beumer J, Clevers H. Regulation and plasticity of intestinal stem cells during homeostasis and regeneration. Development. 2016; 143:3639-49.
62. Yan K S, Janda C Y, Chang J, Zheng G X Y, Larkin K A, Luca V C, et al. Non-equivalence of Wnt and R-spondin ligands during Lgr5+ intestinal stem-cell self-renewal. Nature. Nature Publishing Group; 2017; 1-18. Available from: www.nature.com/doifinder/10.1038/nature22313
63. Gjorevski N, Sachs N, Manfrin A, Giger S, Bragina M E, Ord??ez-Mor?n P, et al. Designer matrices for intestinal stem cell and organoid culture. Nature. Nature Publishing Group; 2016; 539:560-4. Available from: dx.doi.org/10.1038/nature20168
64. Sato T, Vries R G, Snippert H J, van de Wetering M, Barker N, Stange D E, et al. Single Lgr5 stem cells build crypt-villus structures in vitro without a mesenchymal niche. Nature. Nature Publishing Group; 2009 [cited 2014 May 23]; 459:262-5. Available from: www.ncbi.nlm.nih.gov/pubmed/19329995
65. Rudnick P A, Clauser K R, Kilpatrick L E, Tchekhovskoi D V, Neta P, Billheimer D D, et al. Performance Metrics for Evaluating Liquid Chromatography-Tandem Mass Spectrometry Systems in Shotgun Proteomics. Mol. Cell. Biol. 2009; 225-41.
66. Elias J E, Gygi S P. Target-Decoy Search Strategy for Mass Spectrometry-Based Proteomics. In: Hubbard S J, Jones A R, editors. Totowa, NJ: Humana Press; 2010. p. 55-71. Available from: link.springer.com/10.1007/978-1-60761-444-9
67. Nesvizhskii A I, Aebersold R. Interpretation of Shotgun Proteomic Data. Mol. Cell. Proteomics. 2005; 4:1419-40. Available from: www.mcponline.org/content/4/10/1419%5Cnwww.mcponline.org/content/4/10/1419.abstract %5 Cnwww.mcponline.org/content/4/10/1419.full.pdf
68. Phanstiel D H, Brumbaugh J, Wenger C D, Tian S, Probasco M D, Bailey D J, et al.
Proteomic and phosphoproteomic comparison of human ES and iPS cells. Nat. Methods. 2011; 8:821-7.
69. Smyth G K. Linear Models and Empirical Bayes Methods for Assessing Differential Expression in Microarray Experiments Linear Models and Empirical Bayes Methods for Assessing Differential Expression in Microarray Experiments. Stat. Appl. Genet. Mol. Biol. 2004; 3:1-26.
70. Benajmini Y, Hochberg Y. Controlling the False Discovery Rate: A Practical and Powerful Approach to Multiple Testing Author (s): Yoav Benjamini and Yosef Hochberg Source: Journal of the Royal Statistical Society. Series B (Methodological), Vol. 57, No. 1 Published by: J R Stat. Soc B. 1995; 57:289-300.
71. Oliveros J C. An interactive tool for comparing lists with Venn's diagrams. Venny. 2015. Available from: bioinfogp.cnb.csic.es/tools/venny/index.html
72. Huang D W, Sherman B T, Lempicki R a. Systematic and integrative analysis of large gene lists using DAVID bioinformatics resources. Nat. Protoc. 2009 [cited 2014 Jul 9]; 4:44-57. Available from: www.ncbi.nlm.nih.gov/pubmed/19131956
73. Huang D W, Sherman B T, Lempicki R A. Bioinformatics enrichment tools: Paths toward the comprehensive functional analysis of large gene lists. Nucleic Acids Res. 2009; 37:1-13.
74. Macosko E Z, Basu A, Satija R, Nemesh J, Shekhar K, Goldman M, et al. Highly Parallel Genome-wide Expression Profiling of Individual Cells Using Nanoliter Droplets. Cell. Elsevier; 2015; 161:1202-14. Available from: linkinghub.elsevier.com/retrieve/pii/S0092867415005498
75. Satij a R, Farrell J A, Gennert D, Schier A F, Regev A. Spatial reconstruction of single-cell gene expression data. Nat. Biotechnol. 2015; 33:495-502. Available from: www.nature.com/doifinder/10.1038/nbt.3192

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method of generating an in vitro cell-based system that faithfully recapitulates an in vivo phenotype of interest comprising:
   a) determining, using single cell RNA sequencing, gene expression for single cells in an initial in vitro cell-based system to computationally identify cell clusters of enteroendocrine Paneth cell types, wherein the initial in vitro cell-based system is an in vitro intestinal organoid cell-based system comprising Paneth cells, wherein the organoid cell-based system is obtained from an intestinal stem cell enriched organoid produced by enriching for murine LGR5+ intestinal stem cells in a scaffold and medium containing growth factors EGF (E), Noggin (N), R-spondin I (R), CHIR99021 (C), and valproic acid (V);
   b) identifying differences in the gene expression for single Paneth cells in the initial in vitro cell-based system by performing differential gene expression analysis for clusters of single Paneth enteroendocrine cell types and Paneth cells in the in vivo system having the phenotype of interest, wherein differential gene expression analysis comprises comparing a gene expression distribution as determined by single cell RNA sequencing of the initial in vitro cell-based system and a gene expression distribution as determined by single cell RNA sequencing in the Paneth cells in vivo system;
   c) identifying differential gene expression for Wnt and Notch pathways for Paneth cells identified in the initial in vitro cell-based system and the Paneth cell in vivo system in step (b); and
   d) modulating Wnt and/or Notch signaling in the initial in vitro cell-based system with one or more agents comprising a Wnt signaling activator and Notch signaling inhibitor to induce a shift that reduces the differences in gene expression for the Paneth cells between the initial in vitro cell-based system and the Paneth cell in vivo system, thereby generating the in vitro cell-based system that faithfully recapitulates the in vivo phenotype of interest,
   wherein the differential gene expression analysis comprises measuring a Euclidean distance, Pearson coefficient, Spearman coefficient, or any combination thereof, and
   wherein the differential gene expression analysis comprises 10 or more genes, 20 or more genes, 30 or more genes, 40 or more genes, 50 or more genes, 100 or more genes, 500 or more genes, or 1000 or more genes; or wherein the differential gene expression analysis comprises one or more cell pathways; or wherein the differential gene expression analysis comprises a transcriptome of the Paneth cell in vivo system.

2. The method of claim 1, wherein the shift that reduces the differences in gene expression for the Paneth cells in the initial cell-based in vitro system as compared to the target in vivo system is a statistically significant shift as measured by a P value of 0.05 or less in the gene expression distribution of the initial in vitro cell-based system toward that of the in vivo system.

3. The method of claim 1, wherein comparing a gene expression distribution comprises comparing only Paneth cells from the initial in vitro cell-based system with the lowest differences in gene expression as compared to the Paneth cells from the in vivo system and wherein the differences in gene expression are a statistically significant shift measured by a P value of 0.05 or less.

4. The method of claim 1, further comprising modulating the initial in vitro cell-based system to induce
- a gain of function by modulating expression of one or more genes, gene expression cassettes, or gene expression signatures associated with the gain of function, wherein the gain of function is in addition to and different from the in vivo phenotype of interest; or
- a loss of function by modulating expression of one or more genes, gene expression cassettes, or gene expression signatures associated with the loss of function, wherein the loss of function is in addition to and different from the in vivo phenotype of interest.

5. The method claim 1, wherein modulating comprises increasing or decreasing expression of one or more genes, gene expression cassettes, or gene expression signatures in the in vitro cell-based system; or
wherein modulating comprises activating or inhibiting one or more genes, gene expression cassettes, or gene expression signatures in the in vitro cell-based system.

6. The method of claim 1, wherein modulating Wnt and/or Notch signaling in the initial in vitro cell-based system with one or more agents comprising a Wnt signaling activator and Notch signaling inhibitor comprises delivering one or more modulating agents wherein the one or more modulating agents comprise one or more cytokines, growth factors, hormones, transcription factors, metabolites, synthetic ligands, or small molecules; or wherein the one or more modulating agents are comprise a genetic modifying agent or an epigenetic modifying agent.

7. The method of claim 6, wherein the genetic modifying agent comprises a CRISPR system, a zinc finger nuclease system, a TALEN, or a meganuclease; or
wherein the epigenetic modifying agent comprises a DNA methylation inhibitor, HDAC inhibitor, histone acetylation inhibitor, histone methylation inhibitor or histone demethylase inhibitor.

8. The method of claim 2, wherein the statistically significant shift having a P value of 0.05 or less is a shift that reduces the differences in the gene expression between the initial cell-based in vitro system and the in vivo system by at least a 10%.

9. The method of claim 1, further comprising step (e) performing single cell RNA sequencing on the modulated in vitro cell-based system to determine the shift in the gene expression distribution of the initial in vitro cell-based system toward that of the in vivo system, optionally, repeating step (d) to further modulate Wnt and/or Notch signaling.

10. The method of claim 1, wherein the Wnt signaling activator comprises 6-[[2-[[4-(2,4-Dichlorophenyl)-5-(5-methyl-1H-imidazol-2-yl)-2-pyrimidinyl]amino]ethyl]amino]-3-pyridinecarbonitrile (CHIR99021).

11. The method of claim 1, wherein the Notch signaling inhibitor comprises N-[N-(3,5-Difluorophenacetyl)-L-alanyl]-S-phenylglycine t-butyl ester (DAPT).

12. The method of claim 1, wherein modulating Wnt and/or Notch signaling in the initial in vitro cell-based system to induce a shift that reduces the differences in gene expression is temporally modulated to further reduce the differences in gene expression for the Paneth cells.

* * * * *

SEQUENCE LISTING

<160> NUMBER OF SEQ ID NOS: 8

<210> SEQ ID NO 1
<211> LENGTH: 107
<212> TYPE: PRT
<213> ORGANISM: Homo sapiens

<400> SEQUENCE: 1

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser
            100                 105

<210> SEQ ID NO 2
<211> LENGTH: 9
<212> TYPE: PRT
<213> ORGANISM: Homo sapiens

<400> SEQUENCE: 2

Ile Glu Val Met Tyr Pro Pro Pro Tyr
1               5

<210> SEQ ID NO 3
<211> LENGTH: 4
<212> TYPE: RNA
<213> ORGANISM: Artificial Seqence
<220> FEATURE:
<223> OTHER INFORMATION: Synthetic

<400> SEQUENCE: 3 ucuu                                                                    4

<210> SEQ ID NO 4
<211> LENGTH: 4
<212> TYPE: RNA
<213> ORGANISM: Artificial Sequence
<220> FEATURE:
<223> OTHER INFORMATION: Synthetic

<400> SEQUENCE: 4 uuuu                                                                    4

<210> SEQ ID NO 5
<211> LENGTH: 4
<212> TYPE: RNA
<213> ORGANISM: Artificial Sequence
<220> FEATURE:
<223> OTHER INFORMATION: Synthetic

<400> SEQUENCE: 5 uauu                                                                    4

```
<210> SEQ ID NO 6
<211> LENGTH: 4
<212> TYPE: RNA
<213> ORGANISM: Artificial Sequence
<220> FEATURE:
<223> OTHER INFORMATION: Synthetic

<400> SEQUENCE: 6 uguu                                                                        4

<210> SEQ ID NO 7
<211> LENGTH: 288
<212> TYPE: PRT
<213> ORGANISM: Artificial Sequence
<220> FEATURE:
<223> OTHER INFORMATION: Synthetic

<400> SEQUENCE: 7
```

Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
        35                  40                  45

Met Ser Arg Thr Arg Leu Pro Ser Pro Pro Ala Pro Ser Pro Ala Phe
    50                  55                  60

Ser Ala Asp Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
            100                 105                 110

Ala Ala Asp Ala Pro Pro Pro Thr Met Arg Val Ala Val Thr Ala Ala
        115                 120                 125

Arg Pro Pro Arg Ala Lys Pro Ala Pro Arg Arg Ala Ala Gln Pro
    130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175

Ala Gln His His Glu Ala Leu Val Gly His Gly Phe Thr His Ala His
            180                 185                 190

Ile Val Ala Leu Ser Gln His Pro Ala Ala Leu Gly Thr Val Ala Val
        195                 200                 205

Lys Tyr Gln Asp Met Ile Ala Ala Leu Pro Glu Ala Thr His Glu Ala
    210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
                245                 250                 255

Thr Gly Gln Leu Leu Lys Ile Ala Lys Arg Gly Gly Val Thr Ala Val
            260                 265                 270

Glu Ala Val His Ala Trp Arg Asn Ala Leu Thr Gly Ala Pro Leu Asn
        275                 280                 285

```
<210> SEQ ID NO 8
<211> LENGTH: 183
<212> TYPE: PRT
```

```
<213> ORGANISM: Artificial Sequence
<220> FEATURE:
<223> OTHER INFORMATION: Synthetic

<400> SEQUENCE: 8

Arg Pro Ala Leu Glu Ser Ile Val Ala Gln Leu Ser Arg Pro Asp Pro
 1               5                  10                  15

Ala Leu Ala Ala Leu Thr Asn Asp His Leu Val Ala Leu Ala Cys Leu
            20                  25                  30

Gly Gly Arg Pro Ala Leu Asp Ala Val Lys Lys Gly Leu Pro His Ala
        35                  40                  45

Pro Ala Leu Ile Lys Arg Thr Asn Arg Arg Ile Pro Glu Arg Thr Ser
    50                  55                  60

His Arg Val Ala Asp His Ala Gln Val Val Arg Val Leu Gly Phe Phe
65                  70                  75                  80

Gln Cys His Ser His Pro Ala Gln Ala Phe Asp Asp Ala Met Thr Gln
                85                  90                  95

Phe Gly Met Ser Arg His Gly Leu Leu Gln Leu Phe Arg Arg Val Gly
            100                 105                 110

Val Thr Glu Leu Glu Ala Arg Ser Gly Thr Leu Pro Pro Ala Ser Gln
        115                 120                 125

Arg Trp Asp Arg Ile Leu Gln Ala Ser Gly Met Lys Arg Ala Lys Pro
    130                 135                 140

Ser Pro Thr Ser Thr Gln Thr Pro Asp Gln Ala Ser Leu His Ala Phe
145                 150                 155                 160

Ala Asp Ser Leu Glu Arg Asp Leu Asp Ala Pro Ser Pro Met His Glu
                165                 170                 175

Gly Asp Gln Thr Arg Ala Ser
            180
```